(12) United States Patent
Shelton, IV

(10) Patent No.: US 8,800,838 B2
(45) Date of Patent: Aug. 12, 2014

(54) ROBOTICALLY-CONTROLLED CABLE-BASED SURGICAL END EFFECTORS

(75) Inventor: Frederick E. Shelton, IV, Hillsboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 70 days.

(21) Appl. No.: 13/369,629

(22) Filed: Feb. 9, 2012

(65) Prior Publication Data

US 2012/0138660 A1    Jun. 7, 2012

Related U.S. Application Data

(63) Continuation of application No. 13/118,278, filed on May 27, 2011, which is a continuation-in-part of application No. 11/711,979, filed on Feb. 28, 2007, now Pat. No. 8,317,070, which is a continuation-in-part of application No. 11/216,562, filed on Aug. 31, 2005, now Pat. No. 7,669,746.

(51) Int. Cl.
*A61B 17/068*    (2006.01)

(52) U.S. Cl.
USPC ............... 227/175.1; 227/176.1; 227/180.1

(58) Field of Classification Search
USPC ............ 227/175.1, 176.1, 180.1; 606/1, 130; 600/102
See application file for complete search history.

(56) References Cited

U.S. PATENT DOCUMENTS

| | | | |
|---|---|---|---|
| 66,052 A | 6/1867 | Smith | |
| 662,587 A | 11/1900 | Blake | |
| 951,393 A | 3/1910 | Hahn | |
| 2,037,727 A | 4/1936 | La Chapelle | |
| 2,132,295 A | 10/1938 | Hawkins | |
| 2,161,632 A | 6/1939 | Nattenheimer | |
| 2,211,117 A | 8/1940 | Hess | |
| 2,214,870 A | 9/1940 | West | |
| 2,441,096 A | 5/1948 | Happe | |
| 2,526,902 A | 10/1950 | Rublee | |
| 2,674,149 A | 4/1954 | Benson | |
| 2,804,848 A | 9/1957 | O'Farrell et al. | |
| 2,808,482 A | 10/1957 | Zanichkowsky et al. | |
| 2,853,074 A | 9/1958 | Olson | |
| 3,032,769 A | 5/1962 | Palmer | |
| 3,075,062 A | 1/1963 | Iaccarino | |
| 3,078,465 A | 2/1963 | Bobrov | |
| 3,166,072 A | 1/1965 | Sullivan, Jr. | |
| 3,266,494 A | 8/1966 | Brownrigg et al. | |
| 3,269,630 A | 8/1966 | Fleischer | |
| 3,357,296 A | 12/1967 | Lefever | |

(Continued)

FOREIGN PATENT DOCUMENTS

| CA | 2458946 A1 | 3/2003 |
|---|---|---|
| CA | 2512960 A1 | 1/2006 |

(Continued)

OTHER PUBLICATIONS

European Search Report, Application No. 08250668.4, dated May 4, 2009 (7 pages).

(Continued)

*Primary Examiner* — Alexandra Elve
*Assistant Examiner* — Nathaniel Chukwurah

(57) ABSTRACT

A cable-driven surgical tool configured to receive various control motions from a robotic system.

17 Claims, 163 Drawing Sheets

(56) References Cited

U.S. PATENT DOCUMENTS

| | | |
|---|---|---|
| 3,490,675 A | 1/1970 | Green et al. |
| 3,494,533 A | 2/1970 | Green et al. |
| 3,551,987 A | 1/1971 | Wilkinson |
| 3,598,943 A | 8/1971 | Barrett |
| 3,643,851 A | 2/1972 | Green et al. |
| 3,662,939 A | 5/1972 | Bryan |
| 3,717,294 A | 2/1973 | Green |
| 3,734,207 A | 5/1973 | Fishbein |
| 3,740,994 A | 6/1973 | DeCarlo, Jr. |
| 3,744,495 A | 7/1973 | Johnson |
| 3,746,002 A | 7/1973 | Haller |
| 3,751,902 A | 8/1973 | Kingsbury et al. |
| 3,819,100 A | 6/1974 | Noiles et al. |
| 3,821,919 A | 7/1974 | Knohl |
| 3,885,491 A | 5/1975 | Curtis |
| 3,892,228 A | 7/1975 | Mitsui |
| 3,894,174 A | 7/1975 | Cartun |
| 3,940,844 A | 3/1976 | Colby et al. |
| RE28,932 E | 8/1976 | Noiles et al. |
| 4,060,089 A | 11/1977 | Noiles |
| 4,129,059 A | 12/1978 | Van Eck |
| 4,213,562 A | 7/1980 | Garrett et al. |
| 4,250,436 A | 2/1981 | Weissman |
| 4,261,244 A | 4/1981 | Becht et al. |
| 4,272,662 A | 6/1981 | Simpson |
| 4,275,813 A | 6/1981 | Noiles |
| 4,289,133 A | 9/1981 | Rothfuss |
| 4,305,539 A | 12/1981 | Korolkov et al. |
| 4,317,451 A | 3/1982 | Cerwin et al. |
| 4,321,002 A | 3/1982 | Froehlich |
| 4,331,277 A | 5/1982 | Green |
| 4,340,331 A | 7/1982 | Savino |
| 4,347,450 A | 8/1982 | Colligan |
| 4,349,028 A | 9/1982 | Green |
| 4,353,371 A | 10/1982 | Cosman |
| 4,379,457 A | 4/1983 | Gravener et al. |
| 4,380,312 A | 4/1983 | Landrus |
| 4,383,634 A | 5/1983 | Green |
| 4,396,139 A | 8/1983 | Hall et al. |
| 4,402,445 A | 9/1983 | Green |
| 4,408,692 A | 10/1983 | Siegel et al. |
| 4,415,112 A | 11/1983 | Green |
| 4,428,376 A | 1/1984 | Mericle |
| 4,429,695 A | 2/1984 | Green |
| 4,434,796 A | 3/1984 | Karapetian et al. |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,475,679 A | 10/1984 | Fleury, Jr. |
| 4,485,816 A | 12/1984 | Krumme |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,548,202 A | 10/1985 | Duncan |
| 4,565,189 A | 1/1986 | Mabuchi |
| 4,566,620 A | 1/1986 | Green et al. |
| 4,573,469 A | 3/1986 | Golden et al. |
| 4,573,622 A | 3/1986 | Green et al. |
| 4,576,167 A | 3/1986 | Noiles et al. |
| 4,580,712 A | 4/1986 | Green |
| 4,589,416 A | 5/1986 | Green |
| 4,591,085 A | 5/1986 | Di Giovanni |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,632,290 A | 12/1986 | Green et al. |
| 4,633,874 A | 1/1987 | Chow et al. |
| 4,641,076 A | 2/1987 | Linden |
| 4,646,722 A | 3/1987 | Silverstein et al. |
| 4,655,222 A | 4/1987 | Florez et al. |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,671,445 A | 6/1987 | Barker et al. |
| 4,676,245 A | 6/1987 | Fukuda |
| 4,693,248 A | 9/1987 | Failla |
| 4,709,120 A | 11/1987 | Pearson |
| 4,715,520 A | 12/1987 | Roehr, Jr. et al. |
| 4,719,917 A | 1/1988 | Barrows et al. |
| 4,728,020 A | 3/1988 | Green et al. |
| 4,728,876 A | 3/1988 | Mongeon et al. |
| 4,729,260 A | 3/1988 | Dudden |
| 4,741,336 A | 5/1988 | Failla et al. |
| 4,752,024 A | 6/1988 | Green et al. |
| 4,754,909 A | 7/1988 | Barker et al. |
| 4,767,044 A | 8/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,844,068 A | 7/1989 | Arata et al. |
| 4,848,637 A | 7/1989 | Pruitt |
| 4,869,414 A | 9/1989 | Green et al. |
| 4,869,415 A | 9/1989 | Fox |
| 4,880,015 A | 11/1989 | Nierman |
| 4,890,613 A | 1/1990 | Golden et al. |
| 4,892,244 A | 1/1990 | Fox et al. |
| 4,915,100 A | 4/1990 | Green |
| 4,930,503 A | 6/1990 | Pruitt |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,978,049 A | 12/1990 | Green |
| 4,986,808 A | 1/1991 | Broadwin et al. |
| 4,988,334 A | 1/1991 | Hornlein et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,027,834 A | 7/1991 | Pruitt |
| 5,031,814 A | 7/1991 | Tompkins et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |
| 5,074,454 A | 12/1991 | Peters |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,106,008 A | 4/1992 | Tompkins et al. |
| 5,111,987 A | 5/1992 | Moeinzadeh et al. |
| 5,116,349 A | 5/1992 | Aranyi |

(56) References Cited

U.S. PATENT DOCUMENTS

| | | |
|---|---|---|
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,156,315 A | 10/1992 | Green et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,188,111 A | 2/1993 | Yates et al. |
| 5,190,517 A | 3/1993 | Zieve et al. |
| 5,195,968 A | 3/1993 | Lundquist et al. |
| 5,197,648 A | 3/1993 | Gingold |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,260,637 A | 11/1993 | Pizzi |
| 5,263,629 A | 11/1993 | Trumbull et al. |
| 5,263,973 A | 11/1993 | Cook |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,281,216 A | 1/1994 | Klicek |
| 5,282,806 A | 2/1994 | Haber et al. |
| 5,282,829 A | 2/1994 | Hermes |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,329 A | 5/1994 | Beaty et al. |
| 5,314,424 A | 5/1994 | Nicholas |
| 5,318,221 A | 6/1994 | Green et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,395 A | 8/1994 | Jarrett et al. |
| 5,342,396 A | 8/1994 | Cook |
| 5,344,060 A | 9/1994 | Gravener et al. |
| 5,350,400 A | 9/1994 | Esposito et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,003 A | 11/1994 | Williamson, IV |
| 5,366,134 A | 11/1994 | Green et al. |
| 5,366,479 A | 11/1994 | McGarry et al. |
| 5,368,015 A | 11/1994 | Wilk |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,312 A | 3/1995 | Desai |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,405,344 A | 4/1995 | Williamson et al. |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,415,334 A | 5/1995 | Williamson, IV et al. |
| 5,415,335 A | 5/1995 | Knodell, Jr. |
| 5,417,361 A | 5/1995 | Williamson, IV |
| 5,421,829 A | 6/1995 | Olichney et al. |
| 5,422,567 A | 6/1995 | Matsunaga |
| 5,423,809 A | 6/1995 | Klicek |
| 5,425,745 A | 6/1995 | Green et al. |
| 5,431,322 A | 7/1995 | Green et al. |
| 5,431,668 A | 7/1995 | Burbank, III et al. |
| 5,433,721 A | 7/1995 | Hooven et al. |
| 5,438,302 A | 8/1995 | Goble |
| 5,439,155 A | 8/1995 | Viola |
| 5,439,479 A | 8/1995 | Schichman et al. |
| 5,441,193 A | 8/1995 | Gravener |
| 5,441,494 A | 8/1995 | Ortiz |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,452,836 A | 9/1995 | Huitema et al. |
| 5,452,837 A | 9/1995 | Williamson, IV et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,470,006 A | 11/1995 | Rodak |
| 5,470,007 A | 11/1995 | Plyley et al. |
| 5,470,009 A | 11/1995 | Rodak |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |

(56) References Cited

U.S. PATENT DOCUMENTS

| | | |
|---|---|---|
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,553,675 A | 9/1996 | Pitzen et al. |
| 5,553,765 A | 9/1996 | Knodel et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,573,543 A | 11/1996 | Akopov et al. |
| 5,574,431 A | 11/1996 | McKeown et al. |
| 5,575,789 A | 11/1996 | Bell et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,450 A | 3/1997 | Zvenyatsky et al. |
| 5,609,285 A | 3/1997 | Grant et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,620,289 A | 4/1997 | Curry |
| 5,620,452 A | 4/1997 | Yoon |
| 5,624,452 A | 4/1997 | Yates |
| 5,626,587 A | 5/1997 | Bishop et al. |
| 5,628,446 A | 5/1997 | Geiste et al. |
| 5,628,743 A | 5/1997 | Cimino |
| 5,630,539 A | 5/1997 | Plyley et al. |
| 5,630,540 A | 5/1997 | Blewett |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,662,258 A | 9/1997 | Knodel et al. |
| 5,662,260 A | 9/1997 | Yoon |
| 5,662,662 A | 9/1997 | Bishop et al. |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |

(56) References Cited

U.S. PATENT DOCUMENTS

| | | |
|---|---|---|
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,693,042 A | 12/1997 | Boiarski et al. |
| 5,693,051 A | 12/1997 | Schulze et al. |
| 5,695,494 A | 12/1997 | Becker |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Costellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,811 A | 9/1998 | Yates et al. |
| 5,810,855 A | 9/1998 | Rayburn et al. |
| 5,813,813 A | 9/1998 | Daum et al. |
| 5,814,057 A | 9/1998 | Oi et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,132 A | 12/1998 | Ilvento |
| 5,846,254 A | 12/1998 | Schulze et al. |
| 5,849,011 A | 12/1998 | Jones et al. |
| 5,855,311 A | 1/1999 | Hamblin et al. |
| 5,855,583 A | 1/1999 | Wang et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,894,979 A | 4/1999 | Powell |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,948,030 A | 9/1999 | Miller et al. |
| 5,951,552 A | 9/1999 | Long et al. |
| 5,951,574 A | 9/1999 | Stefanchik et al. |
| 5,954,259 A | 9/1999 | Viola et al. |
| 5,964,774 A | 10/1999 | McKean et al. |
| 5,971,916 A | 10/1999 | Koren |
| 5,988,479 A | 11/1999 | Palmer |
| 6,003,517 A | 12/1999 | Sheffield et al. |
| 6,004,319 A | 12/1999 | Goble et al. |
| 6,010,054 A | 1/2000 | Johnson et al. |

(56) References Cited

U.S. PATENT DOCUMENTS

| | | | |
|---|---|---|---|
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,039,733 A | 3/2000 | Buysse et al. |
| 6,039,734 A | 3/2000 | Goble |
| 6,045,560 A | 4/2000 | McKean et al. |
| 6,050,472 A | 4/2000 | Shibata |
| 6,053,390 A | 4/2000 | Green et al. |
| 6,056,746 A | 5/2000 | Goble et al. |
| 6,063,097 A | 5/2000 | Oi et al. |
| 6,063,098 A | 5/2000 | Houser et al. |
| 6,066,132 A | 5/2000 | Chen et al. |
| 6,068,627 A | 5/2000 | Orszulak et al. |
| 6,071,233 A | 6/2000 | Ishikawa et al. |
| 6,074,386 A | 6/2000 | Goble et al. |
| 6,077,286 A | 6/2000 | Cuschieri et al. |
| 6,079,606 A | 6/2000 | Milliman et al. |
| 6,082,577 A | 7/2000 | Coates et al. |
| 6,083,234 A | 7/2000 | Nicholas et al. |
| 6,083,242 A | 7/2000 | Cook |
| 6,086,600 A | 7/2000 | Kortenbach |
| 6,090,106 A | 7/2000 | Goble et al. |
| 6,093,186 A | 7/2000 | Goble |
| 6,099,537 A | 8/2000 | Sugai et al. |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,120,433 A | 9/2000 | Mizuno et al. |
| 6,123,241 A | 9/2000 | Walter et al. |
| H1904 H | 10/2000 | Yates et al. |
| 6,126,058 A | 10/2000 | Adams et al. |
| 6,126,670 A | 10/2000 | Walker et al. |
| 6,131,789 A | 10/2000 | Schulze et al. |
| 6,132,368 A | 10/2000 | Cooper |
| 6,139,546 A | 10/2000 | Koenig et al. |
| 6,155,473 A | 12/2000 | Tompkins et al. |
| 6,156,056 A | 12/2000 | Kearns et al. |
| 6,159,146 A | 12/2000 | El Gazayerli |
| 6,159,200 A | 12/2000 | Verdura et al. |
| 6,162,208 A | 12/2000 | Hipps |
| 6,165,175 A | 12/2000 | Wampler et al. |
| 6,165,184 A | 12/2000 | Verdura et al. |
| 6,168,605 B1 | 1/2001 | Measamer et al. |
| 6,171,316 B1 | 1/2001 | Kovac et al. |
| 6,171,330 B1 | 1/2001 | Benchetrit |
| 6,174,308 B1 | 1/2001 | Goble et al. |
| 6,174,309 B1 | 1/2001 | Wrublewski et al. |
| 6,179,776 B1 | 1/2001 | Adams et al. |
| 6,181,105 B1 | 1/2001 | Cutolo et al. |
| 6,193,129 B1 | 2/2001 | Bittner et al. |
| 6,197,042 B1 | 3/2001 | Ginn et al. |
| 6,202,914 B1 | 3/2001 | Geiste et al. |
| 6,214,028 B1 | 4/2001 | Yoon et al. |
| 6,220,368 B1 | 4/2001 | Ark et al. |
| 6,223,835 B1 | 5/2001 | Habedank et al. |
| 6,228,081 B1 | 5/2001 | Goble |
| 6,228,084 B1 | 5/2001 | Kirwan, Jr. |
| 6,231,565 B1 | 5/2001 | Tovey et al. |
| 6,234,178 B1 | 5/2001 | Goble et al. |
| 6,241,139 B1 | 6/2001 | Milliman et al. |
| 6,241,723 B1 | 6/2001 | Heim et al. |
| 6,249,076 B1 | 6/2001 | Madden et al. |
| 6,250,532 B1 | 6/2001 | Green et al. |
| 6,258,107 B1 | 7/2001 | Balázs et al. |
| 6,261,286 B1 | 7/2001 | Goble et al. |
| 6,264,086 B1 | 7/2001 | McGuckin, Jr. |
| 6,264,087 B1 | 7/2001 | Whitman |
| 6,270,508 B1 | 8/2001 | Klieman et al. |
| 6,273,897 B1 | 8/2001 | Dalessandro et al. |
| 6,277,114 B1 | 8/2001 | Bullivant et al. |
| 6,293,942 B1 | 9/2001 | Goble et al. |
| 6,296,640 B1 | 10/2001 | Wampler et al. |
| 6,302,311 B1 | 10/2001 | Adams et al. |
| 6,306,134 B1 | 10/2001 | Goble et al. |
| 6,309,403 B1 | 10/2001 | Minor et al. |
| 6,315,184 B1 | 11/2001 | Whitman |
| 6,320,123 B1 | 11/2001 | Reimers |
| 6,324,339 B1 | 11/2001 | Hudson et al. |
| 6,325,799 B1 | 12/2001 | Goble |
| 6,325,810 B1 | 12/2001 | Hamilton et al. |
| 6,330,965 B1 | 12/2001 | Milliman et al. |
| 6,331,181 B1 | 12/2001 | Tierney et al. |
| 6,331,761 B1 | 12/2001 | Kumar et al. |
| 6,334,860 B1 | 1/2002 | Dorn |
| 6,336,926 B1 | 1/2002 | Goble |
| 6,338,737 B1 | 1/2002 | Toledano |
| 6,346,077 B1 | 2/2002 | Taylor et al. |
| 6,352,503 B1 | 3/2002 | Matsui et al. |
| 6,358,224 B1 | 3/2002 | Tims et al. |
| 6,364,877 B1 | 4/2002 | Goble et al. |
| 6,364,888 B1 | 4/2002 | Niemeyer et al. |
| 6,373,152 B1 | 4/2002 | Wang et al. |
| 6,387,113 B1 | 5/2002 | Hawkins et al. |
| 6,387,114 B2 | 5/2002 | Adams |
| 6,391,038 B2 | 5/2002 | Vargas et al. |
| 6,398,781 B1 | 6/2002 | Goble et al. |
| 6,398,797 B2 | 6/2002 | Bombard et al. |
| 6,406,440 B1 | 6/2002 | Stefanchik |
| 6,409,724 B1 | 6/2002 | Penny et al. |
| H2037 H | 7/2002 | Yates et al. |
| 6,416,486 B1 | 7/2002 | Wampler |
| 6,416,509 B1 | 7/2002 | Goble et al. |
| 6,419,695 B1 | 7/2002 | Gabbay |
| RE37,814 E | 8/2002 | Allgeyer |
| 6,436,097 B1 | 8/2002 | Nardella |
| 6,436,107 B1 | 8/2002 | Wang et al. |
| 6,436,122 B1 | 8/2002 | Frank et al. |
| 6,439,446 B1 | 8/2002 | Perry et al. |
| 6,440,146 B2 | 8/2002 | Nicholas et al. |
| 6,443,973 B1 | 9/2002 | Whitman |
| 6,450,391 B1 | 9/2002 | Kayan et al. |
| 6,468,275 B1 | 10/2002 | Wampler et al. |
| 6,471,106 B1 | 10/2002 | Reining |
| 6,482,200 B2 | 11/2002 | Shippert |
| 6,485,490 B2 | 11/2002 | Wampler et al. |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,543,456 B1 | 4/2003 | Freeman |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |

(56) References Cited

U.S. PATENT DOCUMENTS

| | | | |
|---|---|---|---|
| 6,588,643 B2 | 7/2003 | Bolduc et al. |
| 6,589,164 B1 | 7/2003 | Flaherty |
| 6,592,597 B2 | 7/2003 | Grant et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,605,078 B2 | 8/2003 | Adams |
| 6,605,669 B2 | 8/2003 | Awokola et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| 6,641,528 B2 | 11/2003 | Torii |
| 6,644,532 B2 | 11/2003 | Green et al. |
| 6,648,816 B2 | 11/2003 | Irion et al. |
| D484,243 S | 12/2003 | Ryan et al. |
| D484,595 S | 12/2003 | Ryan et al. |
| D484,596 S | 12/2003 | Ryan et al. |
| 6,656,193 B2 | 12/2003 | Grant et al. |
| 6,666,875 B1 | 12/2003 | Sakurai et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,692,507 B2 | 2/2004 | Pugsley et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,767,352 B2 | 7/2004 | Field et al. |
| 6,767,356 B2 | 7/2004 | Kanner et al. |
| 6,769,594 B2 | 8/2004 | Orban, III |
| 6,773,438 B1 | 8/2004 | Knodel et al. |
| 6,780,151 B2 | 8/2004 | Grabover et al. |
| 6,780,180 B1 | 8/2004 | Goble et al. |
| 6,783,524 B2 * | 8/2004 | Anderson et al. ............... 606/28 |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,821,273 B2 | 11/2004 | Mollenauer |
| 6,821,284 B2 | 11/2004 | Sturtz et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,843,403 B2 | 1/2005 | Whitman |
| 6,843,789 B2 | 1/2005 | Goble |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,913,608 B2 | 7/2005 | Liddicoat et al. |
| 6,913,613 B2 | 7/2005 | Schwarz et al. |
| 6,923,803 B2 | 8/2005 | Goble |
| 6,929,641 B2 | 8/2005 | Goble et al. |
| 6,931,830 B2 | 8/2005 | Liao |
| 6,936,042 B2 * | 8/2005 | Wallace et al. ............... 606/1 |
| 6,939,358 B2 | 9/2005 | Palacios et al. |
| 6,942,662 B2 | 9/2005 | Goble et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,851 B2 | 11/2005 | Heinrich |
| 6,959,852 B2 | 11/2005 | Shelton, IV et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,052,494 B2 | 5/2006 | Goble et al. |
| 7,055,730 B2 | 6/2006 | Ehrenfels et al. |

(56) References Cited

U.S. PATENT DOCUMENTS

| | | |
|---|---|---|
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,508 B2 | 6/2006 | Shelton, IV et al. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,070,083 B2 | 7/2006 | Jankowski |
| 7,070,559 B2 | 7/2006 | Adams et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,188,758 B2 | 3/2007 | Viola et al. |
| 7,189,207 B2 | 3/2007 | Viola |
| 7,195,627 B2 | 3/2007 | Amoah et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,208,005 B2 | 4/2007 | Frecker et al. |
| 7,210,609 B2 | 5/2007 | Leiboff et al. |
| 7,211,081 B2 | 5/2007 | Goble |
| 7,211,084 B2 | 5/2007 | Goble et al. |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,258,262 B2 | 8/2007 | Mastri et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,994 B2 | 10/2007 | Goble |
| 7,282,048 B2 | 10/2007 | Goble et al. |
| 7,295,907 B2 | 11/2007 | Lu et al. |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,556 B2 | 12/2007 | Metzger |
| 7,308,998 B2 | 12/2007 | Mastri et al. |
| 7,322,975 B2 | 1/2008 | Goble et al. |
| 7,324,572 B2 | 1/2008 | Chang |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,334,717 B2 | 2/2008 | Rethy et al. |
| 7,336,184 B2 | 2/2008 | Smith et al. |
| 7,338,513 B2 | 3/2008 | Lee et al. |
| 7,343,920 B2 | 3/2008 | Toby et al. |
| 7,348,763 B1 | 3/2008 | Reinhart et al. |
| 7,351,258 B2 | 4/2008 | Ricotta et al. |
| 7,354,447 B2 | 4/2008 | Shelton, IV et al. |
| 7,357,287 B2 | 4/2008 | Shelton, IV et al. |
| 7,364,060 B2 | 4/2008 | Milliman |
| 7,364,061 B2 | 4/2008 | Swayze et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,388,217 B2 | 6/2008 | Buschbeck et al. |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,439,354 B2 | 10/2008 | Lenges et al. |

(56) References Cited

U.S. PATENT DOCUMENTS

| | | |
|---|---|---|
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,473,253 B2 | 1/2009 | Dycus et al. |
| 7,479,608 B2 | 1/2009 | Smith |
| 7,481,347 B2 | 1/2009 | Roy |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,524,320 B2 | 4/2009 | Tierney et al. |
| 7,530,985 B2 | 5/2009 | Takemoto et al. |
| 7,546,940 B2 | 6/2009 | Milliman et al. |
| 7,547,312 B2 | 6/2009 | Bauman et al. |
| 7,549,563 B2 | 6/2009 | Mather et al. |
| 7,549,564 B2 | 6/2009 | Boudreaux |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,563,862 B2 | 7/2009 | Sieg et al. |
| 7,566,300 B2 | 7/2009 | Devierre et al. |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,615,003 B2 | 11/2009 | Stefanchik et al. |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,641,092 B2 | 1/2010 | Kruszynski et al. |
| 7,641,093 B2 | 1/2010 | Doll et al. |
| 7,644,848 B2 | 1/2010 | Swayze et al. |
| 7,651,498 B2 | 1/2010 | Shifrin et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,255 B2 | 3/2010 | Braun |
| 7,682,307 B2 | 3/2010 | Danitz et al. |
| 7,686,826 B2 | 3/2010 | Lee et al. |
| 7,688,028 B2 | 3/2010 | Phillips et al. |
| 7,691,098 B2 | 4/2010 | Wallace et al. |
| 7,699,204 B2 | 4/2010 | Viola |
| 7,699,859 B2 | 4/2010 | Bombard et al. |
| 7,708,180 B2 | 5/2010 | Murray et al. |
| 7,708,758 B2 | 5/2010 | Lee et al. |
| 7,714,239 B2 | 5/2010 | Smith |
| 7,717,312 B2 | 5/2010 | Beetel |
| 7,721,930 B2 | 5/2010 | McKenna et al. |
| 7,721,931 B2 | 5/2010 | Shelton, IV et al. |
| 7,721,934 B2 | 5/2010 | Shelton, IV et al. |
| 7,721,936 B2 | 5/2010 | Shalton, IV et al. |
| 7,722,610 B2 | 5/2010 | Viola et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,627 B2 | 6/2010 | Orban, III et al. |
| 7,753,245 B2 | 7/2010 | Boudreaux et al. |
| 7,753,904 B2 | 7/2010 | Shelton, IV et al. |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,774 B2 | 8/2010 | Mastri et al. |
| 7,770,775 B2 | 8/2010 | Shelton, IV et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,803,151 B2 | 9/2010 | Whitman |
| 7,806,891 B2 | 10/2010 | Nowlin et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,824,401 B2 | 11/2010 | Manzo et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,836,400 B2 | 11/2010 | May et al. |
| 7,837,080 B2 | 11/2010 | Schwemberger |
| 7,837,081 B2 | 11/2010 | Holsten et al. |
| 7,845,533 B2 | 12/2010 | Marczyk et al. |
| 7,845,534 B2 | 12/2010 | Viola et al. |
| 7,845,537 B2 | 12/2010 | Shelton, IV et al. |
| 7,846,149 B2 | 12/2010 | Jankowski |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,871,418 B2 | 1/2011 | Thompson et al. |
| 7,887,530 B2 | 2/2011 | Zemlok et al. |
| 7,891,532 B2 | 2/2011 | Mastri et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,909,191 B2 | 3/2011 | Baker et al. |

(56) References Cited

U.S. PATENT DOCUMENTS

| | | | |
|---|---|---|---|
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,376 B1 | 4/2011 | Knodel et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, IV et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,959,050 B2 | 6/2011 | Smith et al. |
| 7,959,051 B2 | 6/2011 | Smith et al. |
| 7,963,963 B2 | 6/2011 | Francischelli et al. |
| 7,966,799 B2 | 6/2011 | Morgan et al. |
| 7,967,180 B2 | 6/2011 | Scirica |
| 7,972,298 B2 | 7/2011 | Wallace et al. |
| 7,980,443 B2 | 7/2011 | Scheib et al. |
| 7,997,469 B2 | 8/2011 | Olson et al. |
| 8,002,795 B2 | 8/2011 | Beetel |
| 8,011,551 B2 | 9/2011 | Marczyk et al. |
| 8,011,553 B2 | 9/2011 | Mastri et al. |
| 8,011,555 B2 | 9/2011 | Tarinelli et al. |
| 8,020,742 B2 | 9/2011 | Marczyk |
| 8,020,743 B2 | 9/2011 | Shelton, IV |
| 8,025,199 B2 | 9/2011 | Whitman et al. |
| 8,028,883 B2 | 10/2011 | Stopek |
| 8,034,077 B2 | 10/2011 | Smith et al. |
| 8,038,045 B2 | 10/2011 | Bettuchi et al. |
| 8,038,046 B2 | 10/2011 | Smith et al. |
| 8,056,787 B2 | 11/2011 | Boudreaux et al. |
| 8,056,788 B2 | 11/2011 | Mastri et al. |
| 8,062,330 B2 | 11/2011 | Prommersberger et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 8,084,001 B2 | 12/2011 | Burns et al. |
| 8,091,756 B2 | 1/2012 | Viola |
| 8,097,017 B2 | 1/2012 | Viola |
| 8,108,072 B2 | 1/2012 | Zhao et al. |
| 8,113,410 B2 | 2/2012 | Hall et al. |
| 8,123,103 B2 | 2/2012 | Milliman |
| 8,136,712 B2 | 3/2012 | Zingman |
| 8,141,762 B2 | 3/2012 | Bedi et al. |
| 8,152,041 B2 | 4/2012 | Kostrzewski |
| 8,157,145 B2 | 4/2012 | Shelton, IV et al. |
| 8,157,152 B2 | 4/2012 | Holsten et al. |
| 8,157,153 B2 | 4/2012 | Shelton, IV et al. |
| 8,161,977 B2 | 4/2012 | Shelton, Iv et al. |
| 8,162,197 B2 | 4/2012 | Mastri et al. |
| 8,167,185 B2 | 5/2012 | Shelton, IV et al. |
| 8,167,895 B2 | 5/2012 | D'Agostino et al. |
| 8,172,124 B2 | 5/2012 | Shelton, IV et al. |
| 8,186,555 B2 | 5/2012 | Shelton, Iv et al. |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,205,781 B2 | 6/2012 | Baxter, III et al. |
| 8,210,411 B2 | 7/2012 | Yates et al. |
| 8,211,125 B2 | 7/2012 | Spivey |
| 8,215,531 B2 | 7/2012 | Shelton, IV et al. |
| 8,220,468 B2 | 7/2012 | Cooper et al. |
| 8,220,688 B2 | 7/2012 | Laurent et al. |
| 8,220,690 B2 | 7/2012 | Hess et al. |
| 8,225,799 B2 | 7/2012 | Bettuchi |
| 8,241,271 B2 | 8/2012 | Millman et al. |
| 8,245,898 B2 | 8/2012 | Smith et al. |
| 8,245,901 B2 | 8/2012 | Stopek |
| 8,256,654 B2 | 9/2012 | Bettuchi et al. |
| 8,257,391 B2 | 9/2012 | Orban, III et al. |
| 8,267,300 B2 | 9/2012 | Boudreaux |
| 8,272,553 B2 | 9/2012 | Mastri et al. |
| 8,292,155 B2 | 10/2012 | Shelton, IV et al. |
| 8,298,677 B2 | 10/2012 | Wiesner et al. |
| 8,308,040 B2 | 11/2012 | Huang et al. |
| 8,317,070 B2 | 11/2012 | Hueil et al. |
| 8,322,455 B2 | 12/2012 | Shelton, IV et al. |
| 8,322,589 B2 | 12/2012 | Boudreaux |
| 8,333,313 B2 | 12/2012 | Boudreaux et al. |
| 8,348,129 B2 | 1/2013 | Bedi et al. |
| 8,348,131 B2 | 1/2013 | Omaits et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,360,296 B2 | 1/2013 | Zingman |
| 8,360,297 B2 | 1/2013 | Shelton, IV et al. |
| 8,365,976 B2 | 2/2013 | Hess et al. |
| 8,371,491 B2 | 2/2013 | Huitema et al. |
| 8,372,094 B2 | 2/2013 | Bettuchi et al. |
| 8,453,912 B2 | 6/2013 | Mastri et al. |
| 2002/0022836 A1 | 2/2002 | Goble et al. |
| 2002/0029036 A1 | 3/2002 | Goble et al. |
| 2002/0072736 A1* | 6/2002 | Tierney et al. .............. 606/1 |
| 2002/0117534 A1 | 8/2002 | Green et al. |
| 2002/0134811 A1 | 9/2002 | Napier et al. |
| 2002/0165541 A1 | 11/2002 | Whitman |
| 2003/0093103 A1 | 5/2003 | Malackowski et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0030333 A1 | 2/2004 | Goble |
| 2004/0034357 A1 | 2/2004 | Beane et al. |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068307 A1 | 4/2004 | Goble |
| 2004/0070369 A1 | 4/2004 | Sakahibara |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |
| 2004/0101822 A1 | 5/2004 | Wiesner et al. |
| 2004/0108357 A1 | 6/2004 | Milliman et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0222268 A1 | 11/2004 | Bilotti et al. |
| 2004/0230214 A1 | 11/2004 | Donofrio et al. |
| 2004/0232201 A1 | 11/2004 | Wenchell et al. |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0006430 A1* | 1/2005 | Wales ...................... 227/175.1 |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |

(56) References Cited

U.S. PATENT DOCUMENTS

| | | |
|---|---|---|
| 2005/0070929 A1 | 3/2005 | Dalessandro et al. |
| 2005/0080454 A1 | 4/2005 | Drews et al. |
| 2005/0085693 A1 | 4/2005 | Belson et al. |
| 2005/0090817 A1 | 4/2005 | Phan |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0145675 A1 | 7/2005 | Hartwick et al. |
| 2005/0154258 A1 | 7/2005 | Tartaglia et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0184121 A1 | 8/2005 | Heinrich |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240222 A1 | 10/2005 | Shipp |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267455 A1 | 12/2005 | Eggers et al. |
| 2005/0274768 A1 | 12/2005 | Cummins et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079735 A1 | 4/2006 | Martone et al. |
| 2006/0085031 A1 | 4/2006 | Bettuchi |
| 2006/0085033 A1 | 4/2006 | Criscuolo et al. |
| 2006/0086032 A1 | 4/2006 | Valencic et al. |
| 2006/0100643 A1 | 5/2006 | Laufer et al. |
| 2006/0108393 A1 | 5/2006 | Heinrich et al. |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0173470 A1 | 8/2006 | Oray et al. |
| 2006/0180634 A1 | 8/2006 | Shelton, IV et al. |
| 2006/0200123 A1 | 9/2006 | Ryan |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0258904 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0023476 A1 | 2/2007 | Whitman et al. |
| 2007/0023477 A1 | 2/2007 | Whitman et al. |
| 2007/0027468 A1 | 2/2007 | Wales et al. |
| 2007/0027469 A1 | 2/2007 | Smith et al. |
| 2007/0034668 A1 | 2/2007 | Holsten et al. |
| 2007/0055219 A1 | 3/2007 | Whitman et al. |
| 2007/0070574 A1 | 3/2007 | Nerheim et al. |
| 2007/0073341 A1 | 3/2007 | Smith |
| 2007/0078484 A1 | 4/2007 | Talarico et al. |
| 2007/0083193 A1 | 4/2007 | Werneth et al. |
| 2007/0084897 A1 | 4/2007 | Shelton, IV et al. |
| 2007/0102472 A1 | 5/2007 | Shelton, IV |
| 2007/0106113 A1 | 5/2007 | Ravo |
| 2007/0106317 A1 | 5/2007 | Shelton, IV et al. |
| 2007/0114261 A1 | 5/2007 | Ortiz et al. |
| 2007/0118175 A1 | 5/2007 | Butler et al. |
| 2007/0129605 A1 | 6/2007 | Schaaf |
| 2007/0135803 A1 | 6/2007 | Belson |
| 2007/0158358 A1 | 7/2007 | Mason, II et al. |
| 2007/0170225 A1 | 7/2007 | Shelton, IV et al. |
| 2007/0173806 A1 | 7/2007 | Orszulak et al. |
| 2007/0173813 A1 | 7/2007 | Odom |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175955 A1 | 8/2007 | Shelton, IV et al. |
| 2007/0181632 A1 | 8/2007 | Milliman |
| 2007/0194079 A1 | 8/2007 | Hueil et al. |
| 2007/0194082 A1 | 8/2007 | Morgan et al. |
| 2007/0203510 A1 | 8/2007 | Bettuchi |
| 2007/0213750 A1 | 9/2007 | Weadock |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0239028 A1 | 10/2007 | Houser et al. |
| 2007/0246505 A1 | 10/2007 | Pace-Floridia et al. |
| 2007/0260278 A1 | 11/2007 | Wheeler et al. |
| 2007/0270784 A1 | 11/2007 | Smith et al. |
| 2007/0270884 A1 | 11/2007 | Smith et al. |
| 2007/0288044 A1 | 12/2007 | Jinno et al. |
| 2007/0299427 A1 | 12/2007 | Yeung et al. |
| 2008/0015598 A1 | 1/2008 | Prommersberger |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0030170 A1 | 2/2008 | Dacquay et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078802 A1 | 4/2008 | Hess et al. |
| 2008/0078803 A1 | 4/2008 | Shelton et al. |
| 2008/0082114 A1 | 4/2008 | McKenna et al. |
| 2008/0082125 A1 | 4/2008 | Murray et al. |

(56) References Cited

U.S. PATENT DOCUMENTS

| | | |
|---|---|---|
| 2008/0082126 A1 | 4/2008 | Murray et al. |
| 2008/0083813 A1 | 4/2008 | Zemlok et al. |
| 2008/0114385 A1 | 5/2008 | Byrum et al. |
| 2008/0129253 A1 | 6/2008 | Shiue et al. |
| 2008/0140115 A1 | 6/2008 | Stopek |
| 2008/0167522 A1 | 7/2008 | Giordano et al. |
| 2008/0167672 A1 | 7/2008 | Giordano et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0172087 A1 | 7/2008 | Fuchs et al. |
| 2008/0172088 A1 | 7/2008 | Smith et al. |
| 2008/0183193 A1 | 7/2008 | Omori et al. |
| 2008/0185419 A1 | 8/2008 | Smith et al. |
| 2008/0197167 A1 | 8/2008 | Viola et al. |
| 2008/0200835 A1 | 8/2008 | Monson et al. |
| 2008/0228029 A1 | 9/2008 | Mikkaichi et al. |
| 2008/0245841 A1 | 10/2008 | Smith et al. |
| 2008/0251568 A1 | 10/2008 | Zemlok et al. |
| 2008/0251569 A1 | 10/2008 | Smith et al. |
| 2008/0255413 A1 | 10/2008 | Zemlok et al. |
| 2008/0262654 A1 | 10/2008 | Omori et al. |
| 2008/0283570 A1 | 11/2008 | Boyden et al. |
| 2008/0287944 A1 | 11/2008 | Pearson et al. |
| 2008/0290134 A1 | 11/2008 | Bettuchi et al. |
| 2008/0296346 A1 | 12/2008 | Shelton, IV et al. |
| 2008/0308602 A1 | 12/2008 | Timm et al. |
| 2008/0308603 A1 | 12/2008 | Shelton, IV et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001124 A1 | 1/2009 | Hess et al. |
| 2009/0001130 A1 | 1/2009 | Hess et al. |
| 2009/0005807 A1 | 1/2009 | Hess et al. |
| 2009/0005808 A1 | 1/2009 | Hess et al. |
| 2009/0005809 A1 | 1/2009 | Hess et al. |
| 2009/0012534 A1 | 1/2009 | Madhani et al. |
| 2009/0012556 A1 | 1/2009 | Boudreaux et al. |
| 2009/0020958 A1 | 1/2009 | Soul |
| 2009/0054908 A1 | 2/2009 | Zand et al. |
| 2009/0057369 A1 | 3/2009 | Smith et al. |
| 2009/0078736 A1 | 3/2009 | Van Lue |
| 2009/0088774 A1 | 4/2009 | Swarup et al. |
| 2009/0090763 A1 | 4/2009 | Zemlok et al. |
| 2009/0093728 A1 | 4/2009 | Hyde et al. |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0143805 A1 | 6/2009 | Palmer et al. |
| 2009/0149871 A9 | 6/2009 | Kagan et al. |
| 2009/0157067 A1 | 6/2009 | Kane et al. |
| 2009/0206125 A1 | 8/2009 | Huitema et al. |
| 2009/0206126 A1 | 8/2009 | Huitema et al. |
| 2009/0206131 A1 | 8/2009 | Weisenburgh, II et al. |
| 2009/0206132 A1 | 8/2009 | Hueil et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0209946 A1 | 8/2009 | Swayze et al. |
| 2009/0209979 A1 | 8/2009 | Yates et al. |
| 2009/0209990 A1 | 8/2009 | Yates et al. |
| 2009/0213685 A1 | 8/2009 | Mak et al. |
| 2009/0218384 A1 | 9/2009 | Aranyi |
| 2009/0242610 A1 | 10/2009 | Shelton, IV et al. |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0292283 A1 | 11/2009 | Odom |
| 2009/0308907 A1 | 12/2009 | Nalagatla et al. |
| 2010/0012704 A1 | 1/2010 | Racenet et al. |
| 2010/0023024 A1 | 1/2010 | Zeiner et al. |
| 2010/0049084 A1 | 2/2010 | Nock et al. |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0089970 A1 | 4/2010 | Smith et al. |
| 2010/0096431 A1 | 4/2010 | Smith et al. |
| 2010/0108740 A1 | 5/2010 | Pastorelli et al. |
| 2010/0108741 A1 | 5/2010 | Hessler et al. |
| 2010/0127042 A1 | 5/2010 | Shelton, IV |
| 2010/0133317 A1 | 6/2010 | Shelton, IV et al. |
| 2010/0145146 A1 | 6/2010 | Melder |
| 2010/0147922 A1 | 6/2010 | Olson |
| 2010/0163598 A1 | 7/2010 | Belzer |
| 2010/0179382 A1 | 7/2010 | Shelton, IV et al. |
| 2010/0186219 A1 | 7/2010 | Smith |
| 2010/0193566 A1 | 8/2010 | Scheib et al. |
| 2010/0193567 A1 | 8/2010 | Scheib et al. |
| 2010/0193568 A1 | 8/2010 | Scheib et al. |
| 2010/0193569 A1 | 8/2010 | Yates et al. |
| 2010/0198220 A1 | 8/2010 | Boudreaux et al. |
| 2010/0200637 A1 | 8/2010 | Beetel |
| 2010/0213241 A1 | 8/2010 | Bedi et al. |
| 2010/0222901 A1 | 9/2010 | Swayze et al. |
| 2010/0224669 A1 | 9/2010 | Shelton, IV et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0243709 A1 | 9/2010 | Hess et al. |
| 2010/0258611 A1 | 10/2010 | Smith et al. |
| 2010/0264193 A1 | 10/2010 | Huang et al. |
| 2010/0276471 A1 | 11/2010 | Whitman |
| 2010/0294827 A1 | 11/2010 | Boyden et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0312261 A1 | 12/2010 | Suzuki et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0022032 A1 | 1/2011 | Zemlok et al. |
| 2011/0024477 A1 | 2/2011 | Hall et al. |
| 2011/0024478 A1 | 2/2011 | Shelton, IV |
| 2011/0024479 A1 | 2/2011 | Swensgard et al. |
| 2011/0036887 A1 | 2/2011 | Zemlok et al. |
| 2011/0042441 A1 | 2/2011 | Shelton, IV et al. |
| 2011/0060363 A1 | 3/2011 | Hess et al. |
| 2011/0068145 A1 | 3/2011 | Bedi et al. |
| 2011/0068148 A1 | 3/2011 | Hall et al. |
| 2011/0084112 A1 | 4/2011 | Kostrzewski |
| 2011/0087276 A1 | 4/2011 | Bedi et al. |
| 2011/0087279 A1 | 4/2011 | Shah et al. |
| 2011/0095068 A1 | 4/2011 | Patel |
| 2011/0101065 A1 | 5/2011 | Milliman |
| 2011/0114697 A1 | 5/2011 | Baxter, III et al. |
| 2011/0114700 A1 | 5/2011 | Baxter, III et al. |
| 2011/0118754 A1 | 5/2011 | Dachs, II et al. |
| 2011/0118761 A1 | 5/2011 | Baxter, III et al. |
| 2011/0125176 A1 | 5/2011 | Yates et al. |
| 2011/0125177 A1 | 5/2011 | Yates et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0144430 A1 | 6/2011 | Spivey et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155787 A1 | 6/2011 | Baxter, III et al. |
| 2011/0163147 A1 | 7/2011 | Laurent et al. |
| 2011/0174861 A1 | 7/2011 | Shelton, IV et al. |
| 2011/0174863 A1 | 7/2011 | Shelton, IV et al. |
| 2011/0178536 A1 | 7/2011 | Kostrzewski |
| 2011/0192882 A1 | 8/2011 | Hess et al. |

(56) References Cited

U.S. PATENT DOCUMENTS

| | | |
|---|---|---|
| 2011/0210156 A1 | 9/2011 | Smith et al. |
| 2011/0226837 A1 | 9/2011 | Baxter, III et al. |
| 2011/0275901 A1 | 11/2011 | Shelton, IV |
| 2011/0276083 A1 | 11/2011 | Shelton, IV et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0295242 A1 | 12/2011 | Spivey et al. |
| 2011/0295269 A1 | 12/2011 | Swensgard et al. |
| 2011/0295270 A1 | 12/2011 | Giordano et al. |
| 2011/0295295 A1 | 12/2011 | Shelton, IV et al. |
| 2012/0022523 A1 | 1/2012 | Smith et al. |
| 2012/0024934 A1 | 2/2012 | Shelton, IV et al. |
| 2012/0024935 A1 | 2/2012 | Shelton, IV et al. |
| 2012/0024936 A1 | 2/2012 | Baxter, III et al. |
| 2012/0029272 A1 | 2/2012 | Shelton, IV et al. |
| 2012/0029544 A1 | 2/2012 | Shelton, IV et al. |
| 2012/0029547 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0071866 A1 | 3/2012 | Kerr et al. |
| 2012/0074196 A1 | 3/2012 | Shelton, IV et al. |
| 2012/0074198 A1 | 3/2012 | Huitema et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080333 A1 | 4/2012 | Woodard, Jr. et al. |
| 2012/0080334 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080487 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0132450 A1 | 5/2012 | Timm et al. |
| 2012/0150192 A1 | 6/2012 | Dachs, II et al. |
| 2012/0160721 A1 | 6/2012 | Shelton, IV et al. |
| 2012/0175399 A1 | 6/2012 | Shelton et al. |
| 2012/0187179 A1 | 7/2012 | Gleiman |
| 2012/0199630 A1 | 8/2012 | Shelton, IV et al. |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211546 A1 | 8/2012 | Shelton, IV |
| 2012/0234890 A1 | 9/2012 | Aronhalt et al. |
| 2012/0234891 A1 | 9/2012 | Aronhalt et al. |
| 2012/0234892 A1 | 9/2012 | Aronhalt et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0234900 A1 | 9/2012 | Swayze |
| 2012/0238823 A1 | 9/2012 | Hagerty et al. |
| 2012/0238824 A1 | 9/2012 | Widenhouse et al. |
| 2012/0238826 A1 | 9/2012 | Yoo et al. |
| 2012/0238829 A1 | 9/2012 | Shelton, IV et al. |
| 2012/0239009 A1 | 9/2012 | Mollere et al. |
| 2012/0239010 A1 | 9/2012 | Shelton, IV et al. |
| 2012/0239012 A1 | 9/2012 | Laurent et al. |
| 2012/0239075 A1 | 9/2012 | Widenhouse et al. |
| 2012/0239082 A1 | 9/2012 | Shelton, IV et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Vasudevan et al. |
| 2012/0241497 A1 | 9/2012 | Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0265230 A1 | 10/2012 | Yates et al. |
| 2012/0273551 A1 | 11/2012 | Shelton, IV et al. |
| 2012/0283707 A1 | 11/2012 | Giordano et al. |
| 2012/0286019 A1 | 11/2012 | Hueil et al. |
| 2012/0292367 A1 | 11/2012 | Morgan et al. |
| 2012/0292370 A1 | 11/2012 | Hess et al. |
| 2012/0298719 A1 | 11/2012 | Shelton, IV et al. |
| 2013/0012931 A1 | 1/2013 | Spivey et al. |
| 2013/0012957 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0041371 A1 | 2/2013 | Yates et al. |
| 2013/0048697 A1 | 2/2013 | Shelton, IV et al. |
| 2013/0186936 A1 | 7/2013 | Shelton, IV |

FOREIGN PATENT DOCUMENTS

| | | |
|---|---|---|
| CA | 2514274 A1 | 1/2006 |
| CN | 2488482 Y | 5/2002 |
| CN | 1634601 A | 7/2005 |
| CN | 1868411 A | 11/2006 |
| CN | 1915180 A | 2/2007 |
| CN | 101011286 A | 8/2007 |
| CN | 101095621 A | 1/2008 |
| DE | 273689 C | 5/1914 |
| DE | 1775926 A | 1/1972 |
| DE | 3036217 A1 | 4/1982 |
| DE | 3210466 A1 | 9/1983 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0122046 A1 | 10/1984 |
| EP | 0070230 B1 | 10/1985 |

(56) References Cited

FOREIGN PATENT DOCUMENTS

| | | |
|---|---|---|
| EP | 0156774 A2 | 10/1985 |
| EP | 0387980 B1 | 10/1985 |
| EP | 0033548 B1 | 5/1986 |
| EP | 0129442 B1 | 11/1987 |
| EP | 0276104 A2 | 7/1988 |
| EP | 0178941 B1 | 1/1991 |
| EP | 0248844 B1 | 1/1993 |
| EP | 0545029 A1 | 6/1993 |
| EP | 0277959 B1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0653189 A2 | 5/1995 |
| EP | 0669104 A1 | 8/1995 |
| EP | 0511470 B1 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0708618 B1 | 3/1997 |
| EP | 0770355 A1 | 5/1997 |
| EP | 0503662 B1 | 6/1997 |
| EP | 0447121 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0843906 B1 | 3/2000 |
| EP | 0552050 B1 | 5/2000 |
| EP | 0833592 B1 | 5/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1090592 A1 | 4/2001 |
| EP | 1095627 A1 | 5/2001 |
| EP | 1256318 A1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1632191 A2 | 3/2006 |
| EP | 1065981 B1 | 5/2006 |
| EP | 1082944 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |

(56) References Cited

FOREIGN PATENT DOCUMENTS

| | | | |
|---|---|---|---|
| EP | 1045672 | B1 | 8/2006 |
| EP | 1617768 | B1 | 8/2006 |
| EP | 1693015 | A2 | 8/2006 |
| EP | 1400214 | B1 | 9/2006 |
| EP | 1702567 | A2 | 9/2006 |
| EP | 1129665 | B1 | 11/2006 |
| EP | 1400206 | B1 | 11/2006 |
| EP | 1721568 | A1 | 11/2006 |
| EP | 1256317 | B1 | 12/2006 |
| EP | 1285633 | B1 | 12/2006 |
| EP | 1728473 | A1 | 12/2006 |
| EP | 1728475 | A2 | 12/2006 |
| EP | 1479346 | B1 | 1/2007 |
| EP | 1484024 | B1 | 1/2007 |
| EP | 1754445 | A2 | 2/2007 |
| EP | 1759812 | A1 | 3/2007 |
| EP | 1767163 | A1 | 3/2007 |
| EP | 1769756 | A1 | 4/2007 |
| EP | 1769758 | A1 | 4/2007 |
| EP | 1581128 | B1 | 5/2007 |
| EP | 1780825 | A1 | 5/2007 |
| EP | 1785097 | A2 | 5/2007 |
| EP | 1790293 | A2 | 5/2007 |
| EP | 1800610 | A1 | 6/2007 |
| EP | 1300117 | B1 | 8/2007 |
| EP | 1813199 | A1 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1857057 | A2 | 11/2007 |
| EP | 1402821 | B1 | 12/2007 |
| EP | 1872727 | A1 | 1/2008 |
| EP | 1897502 | A1 | 3/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1990014 | A2 | 11/2008 |
| EP | 1693008 | B1 | 12/2008 |
| EP | 1759640 | B1 | 12/2008 |
| EP | 2000102 | A2 | 12/2008 |
| EP | 2008595 | A2 | 12/2008 |
| EP | 1736104 | B1 | 3/2009 |
| EP | 1749486 | B1 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 1550409 | A1 | 6/2009 |
| EP | 1550413 | B1 | 6/2009 |
| EP | 1745748 | B1 | 8/2009 |
| EP | 2090237 | A1 | 8/2009 |
| EP | 2090244 | A2 | 8/2009 |
| EP | 2090245 | A1 | 8/2009 |
| EP | 2090256 | A2 | 8/2009 |
| EP | 2095777 | A2 | 9/2009 |
| EP | 2110082 | A1 | 10/2009 |
| EP | 1813208 | B1 | 11/2009 |
| EP | 2116195 | A1 | 11/2009 |
| EP | 1607050 | B1 | 12/2009 |
| EP | 1815804 | B1 | 12/2009 |
| EP | 1566150 | B1 | 4/2010 |
| EP | 1813206 | B1 | 4/2010 |
| EP | 1769754 | B1 | 6/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 1627605 | B1 | 12/2010 |
| EP | 1813205 | B1 | 6/2011 |
| EP | 2090243 | B1 | 6/2011 |
| EP | 1785102 | B1 | 1/2012 |
| FR | 999646 | A | 2/1952 |
| FR | 1112936 | A | 3/1956 |
| FR | 2598905 | A1 | 11/1987 |
| FR | 2765794 | A | 1/1999 |
| GB | 939929 | A | 10/1963 |
| GB | 1210522 | A | 10/1970 |
| GB | 1217159 | A | 12/1970 |
| GB | 1339394 | A | 12/1973 |
| GB | 2109241 | A | 6/1983 |
| GB | 2272159 | A | 5/1994 |
| GB | 2284242 | A | 5/1995 |
| GB | 2336214 | A | 10/1999 |
| GB | 2425903 | A | 11/2006 |
| JP | 50-33988 | U | 4/1975 |
| JP | 58500053 | A | 1/1983 |
| JP | 61-98249 | A | 5/1986 |
| JP | 61502036 | A | 9/1986 |
| JP | 63-203149 | | 8/1988 |
| JP | 3-12126 | A | 1/1991 |
| JP | 05-084252 | A | 4/1993 |
| JP | 5-212039 | A | 8/1993 |
| JP | 6007357 | A | 1/1994 |
| JP | 7051273 | A | 2/1995 |
| JP | 7-124166 | A | 5/1995 |
| JP | 7-255735 | A | 10/1995 |
| JP | 8-33642 | A | 2/1996 |
| JP | 8033641 | A | 2/1996 |
| JP | 8-164141 | A | 6/1996 |
| JP | 8229050 | A | 9/1996 |
| JP | 2000033071 | A | 2/2000 |
| JP | 2000171730 | A | 6/2000 |
| JP | 2000287987 | A | 10/2000 |
| JP | 2000325303 | A | 11/2000 |
| JP | 2001-514541 | A | 9/2001 |
| JP | 2001-517473 | A | 10/2001 |
| JP | 2001286477 | A | 10/2001 |
| JP | 2002143078 | A | 5/2002 |
| JP | 2002369820 | A | 12/2002 |
| JP | 2003-500153 | A | 1/2003 |
| JP | 2003-521301 | A | 7/2003 |
| JP | 2004-329624 | A | 11/2004 |
| JP | 2004-344663 | | 12/2004 |
| JP | 2005-028149 | A | 2/2005 |
| JP | 2005505322 | T | 2/2005 |
| JP | 2005103293 | A | 4/2005 |
| JP | 2005131163 | A | 5/2005 |
| JP | 2005131164 | A | 5/2005 |
| JP | 2005131173 | A | 5/2005 |
| JP | 2005131211 | A | 5/2005 |
| JP | 2005131212 | A | 5/2005 |
| JP | 2005137423 | A | 6/2005 |
| JP | 2005152416 | A | 6/2005 |
| JP | 2005-523105 | A | 8/2005 |
| JP | 2005524474 | A | 8/2005 |
| JP | 2006-034975 | A | 2/2006 |
| JP | 2006-281405 | A | 10/2006 |
| RU | 2008830 | C1 | 3/1994 |
| RU | 2141279 | C1 | 11/1999 |
| RU | 2187249 | C2 | 8/2002 |
| RU | 2225170 | C2 | 3/2004 |
| SU | 189517 | A | 1/1967 |
| SU | 328636 | A | 9/1972 |
| SU | 886900 | A1 | 12/1981 |
| SU | 1009439 | A | 4/1983 |
| SU | 1333319 | A2 | 8/1987 |
| SU | 1377053 | A1 | 2/1988 |
| SU | 1561964 | A1 | 5/1990 |
| SU | 1708312 | A1 | 1/1992 |
| SU | 1722476 | A1 | 3/1992 |

(56) References Cited

FOREIGN PATENT DOCUMENTS

| | | |
|---|---|---|
| SU | 1752361 A1 | 8/1992 |
| WO | WO 82/02824 A1 | 9/1982 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/22378 A1 | 10/1994 |
| WO | WO 94/23659 A1 | 10/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/010482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 2003/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A1 | 1/2004 |
| WO | WO 2004/011037 A2 | 2/2004 |
| WO | WO 2004/019769 A1 | 3/2004 |
| WO | WO 2004/021868 A2 | 3/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |

(56) References Cited

FOREIGN PATENT DOCUMENTS

| | | | |
|---|---|---|---|
| WO | WO 2004/032763 A2 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/078050 A2 | 9/2004 |
| WO | WO 2004/078051 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A2 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/147439 A1 | 12/2007 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/070763 A1 | 6/2008 |
| WO | WO 2008/089404 A2 | 7/2008 |
| WO | WO 2008/109125 A1 | 9/2008 |
| WO | WO 2008/124748 A1 | 10/2008 |
| WO | WO 2010/063795 A1 | 6/2010 |
| WO | WO 2010/098871 A2 | 9/2010 |
| WO | WO 2012/021671 A1 | 2/2012 |
| WO | WO 2012/044844 A2 | 4/2012 |

OTHER PUBLICATIONS

Partial European Search Report, Application No. 08250661.9, dated May 7, 2009 (6 pages).
European Search Report, Application No. 08250667.6, dated May 14, 2009 (6 pages).
Partial European Search Report, Application No. 08250664.3, dated May 7, 2009 (6 pages).
European Search Report, Application No. 10178489.0, dated Nov. 29, 2010 (7 pages).
European Search Report, Application No. 10179946.8, dated Dec. 2, 2010 (7 pages).
European Search Report, Application 08250671.8, dated May 19, 2008 (9 pages).
European Search Report, Application 06254511.6, dated Jan. 24, 2007 (8 pages).
Examination Report for European Patent Application No. 06254511.6, dated Feb. 13, 2008 (5 pages).
European Search Report, Application No. 08250661.9, dated Jul. 28, 2009 (12 pages).
European Search Report, Application No. 11161037.4, dated Sep. 6, 2011 (9 pages).
European Examination Report, Application No. 08250661.9, dated Feb. 24, 2010 (6 pages).
European Examination Report, Application 08250664.3, dated Feb. 24, 2010 (6 pages).
European Search Report, Application No. 08250664.3, dated Jul. 28, 2009 (11 pages).
European Examination Report, Application 08250668.4, dated Dec. 10, 2009 (5 pages).
European Search Report, Application No. 11190802.6, dated Aug. 13, 2012 (8 pages).
International Search Report and Written Opinion for PCT/US2012/039134, Aug. 31, 2012 (11 pages).
Observations by a Third Party, European Application No. 06254511.6, dated Feb. 7, 2008 (4 pages).
European Examination Report for 08250671.8, dated Mar. 24, 2009 (6 pages).
European Examination Report for 08250671.8, dated Nov. 21, 2012 (5 pages).
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get The Lowdown On Ultracapacitors," Nov. 15, 2007; [online] URL: http://electronicdesign.conn/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
ASTM procedure D2240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
U.S. Appl. No. 12/031,542, filed Feb. 14, 2008.
U.S. Appl. No. 12/031,556, filed Feb. 14, 2008.
U.S. Appl. No. 12/031,573, filed Feb. 14, 2008.
U.S. Appl. No. 13/310,107, filed Dec. 2, 2011.
U.S. Appl. No. 13/369,629, filed Feb. 9, 2012.

(56) References Cited

OTHER PUBLICATIONS

U.S. Appl. No. 13/486,175, filed Jun. 1, 2012.
Covidien Brochure, "Endo GIA™ with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidient Brochure, "Endo GIA™ Black Reload with Tri-Staple™ Technology," (2012), 2 pages.
Covidient Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
U.S. Pat. Appl. No. 13/965,877, filed Aug. 13, 2013.
U.S. Pat. Appl. No. 13/967,388, filed Aug. 15, 2013.
U.S. Pat. Appl. No. 13/967,449, Aug. 15, 2013.
U.S. Pat. Appl. No. 13/967,716, Aug. 15, 2013.
U.S. Pat. Appl. No. 13/970,971, filed Aug. 20, 2013.
U.S. Pat. Appl. No. 13/971,006, filed Aug. 20, 2013.
U.S. Pat. Appl. No. 13/971,012, filed Aug. 20, 2013.
U.S. Pat. Appl. No. 13/971,022, filed Aug. 20, 2013.

\* cited by examiner

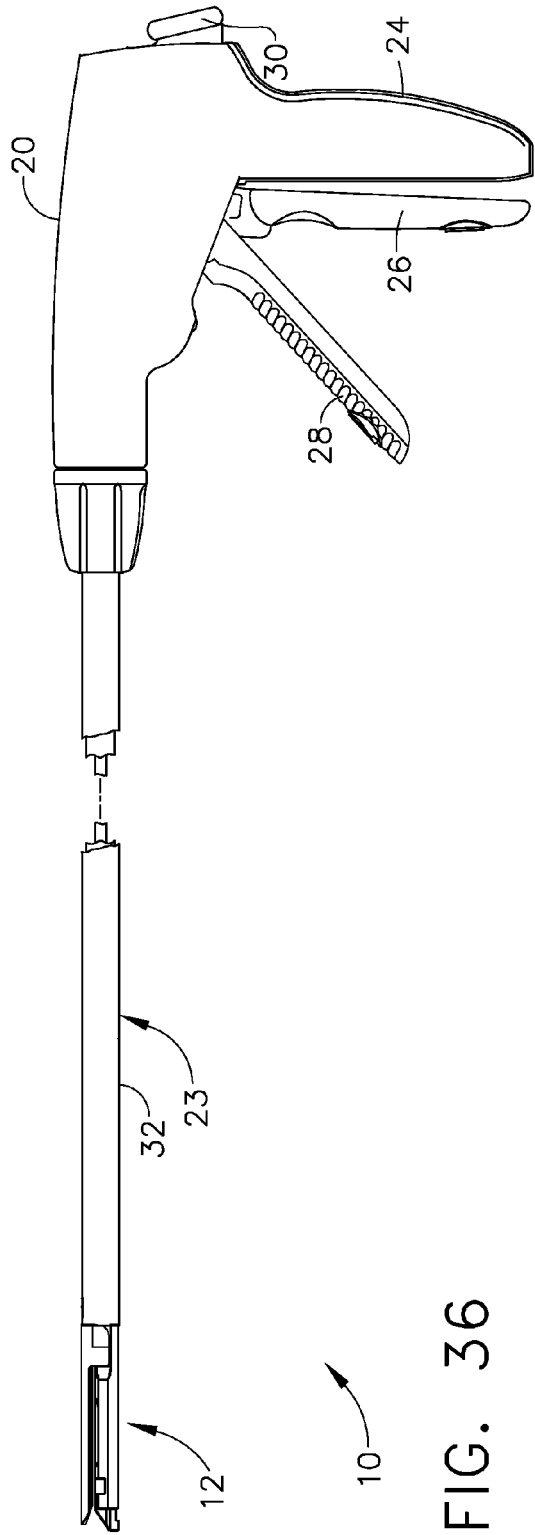
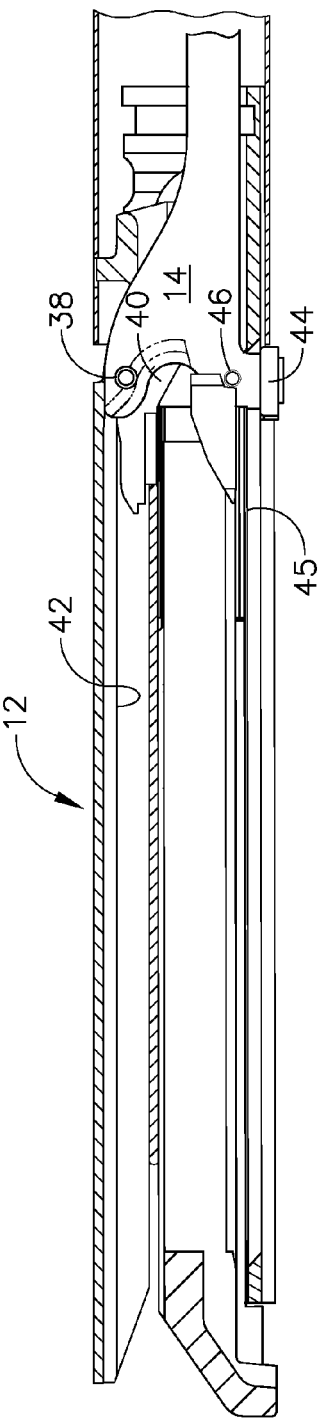
FIG. 36
FIG. 37

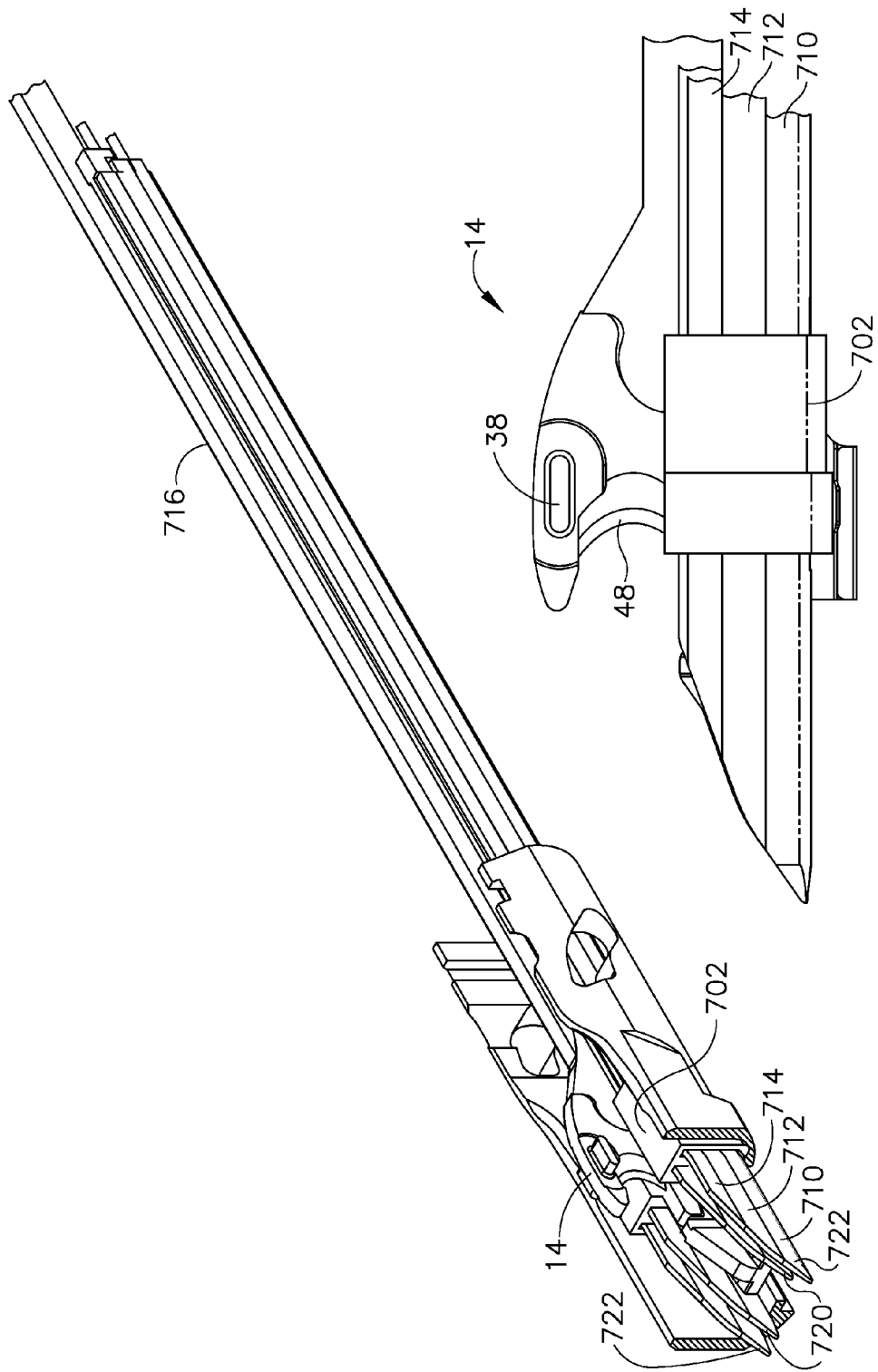

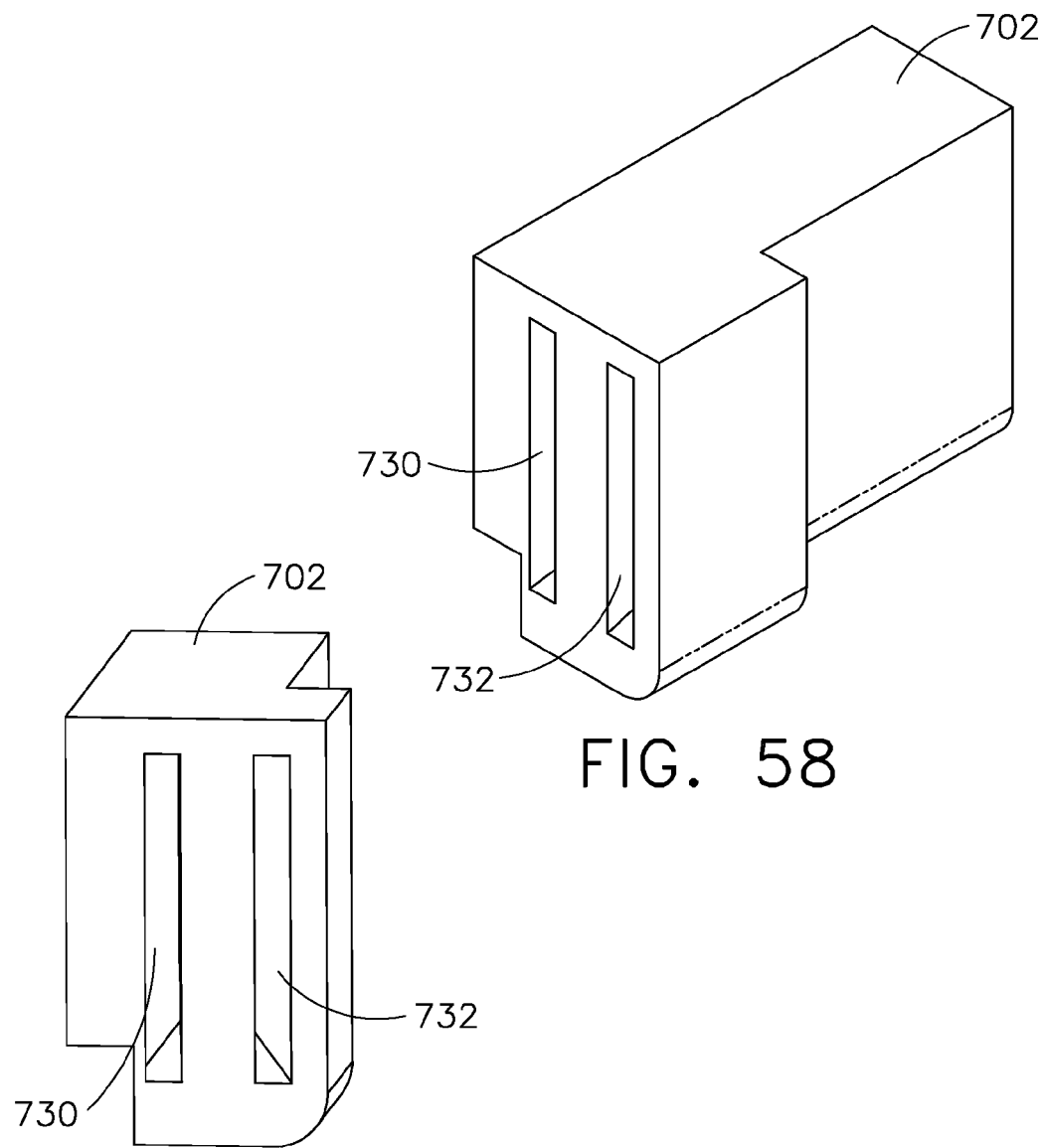
FIG. 58
FIG. 59
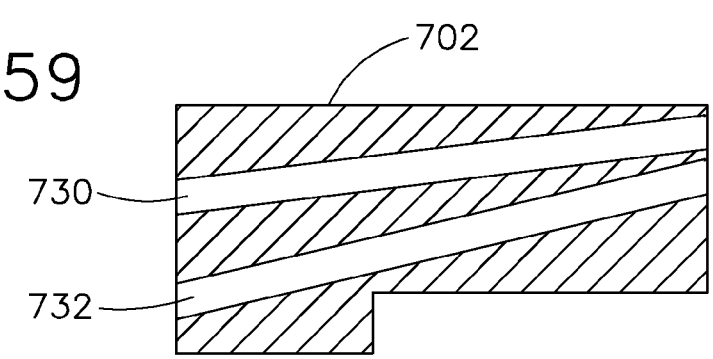
FIG. 60

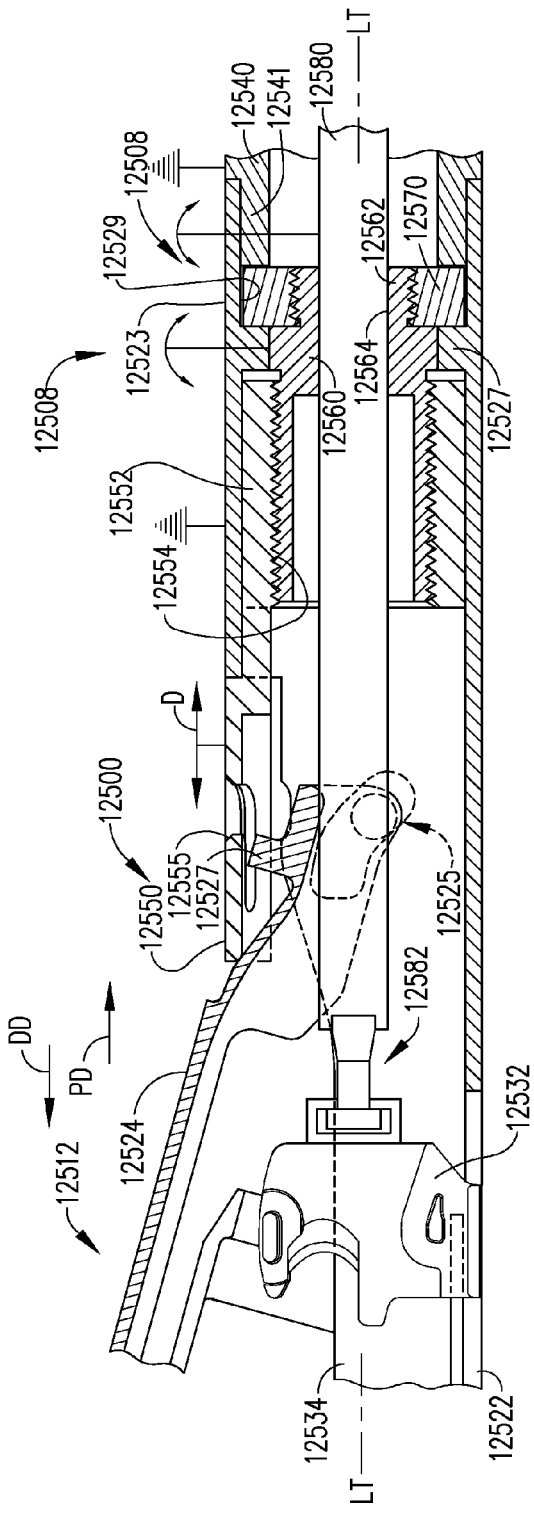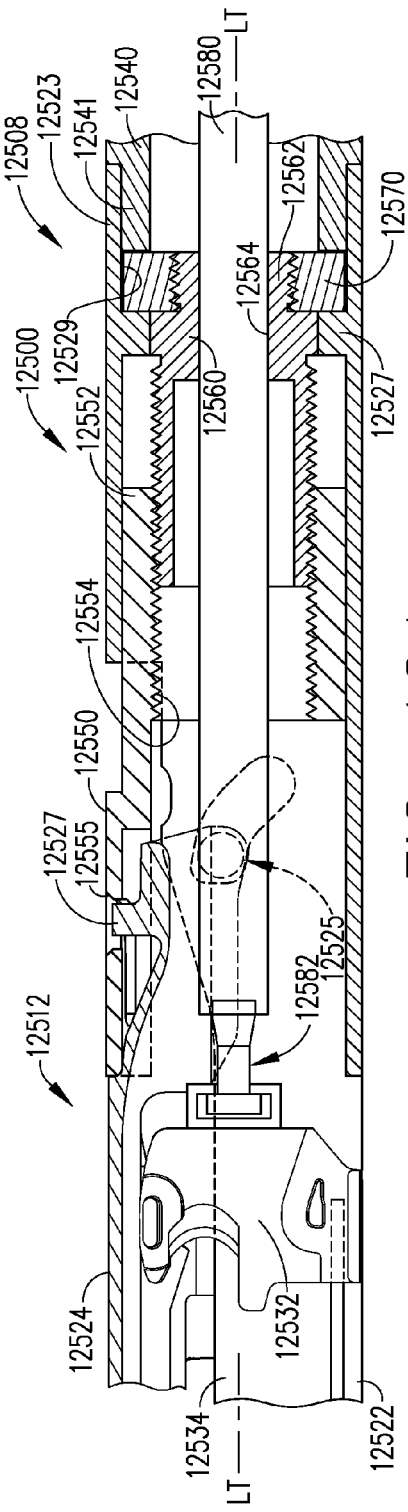

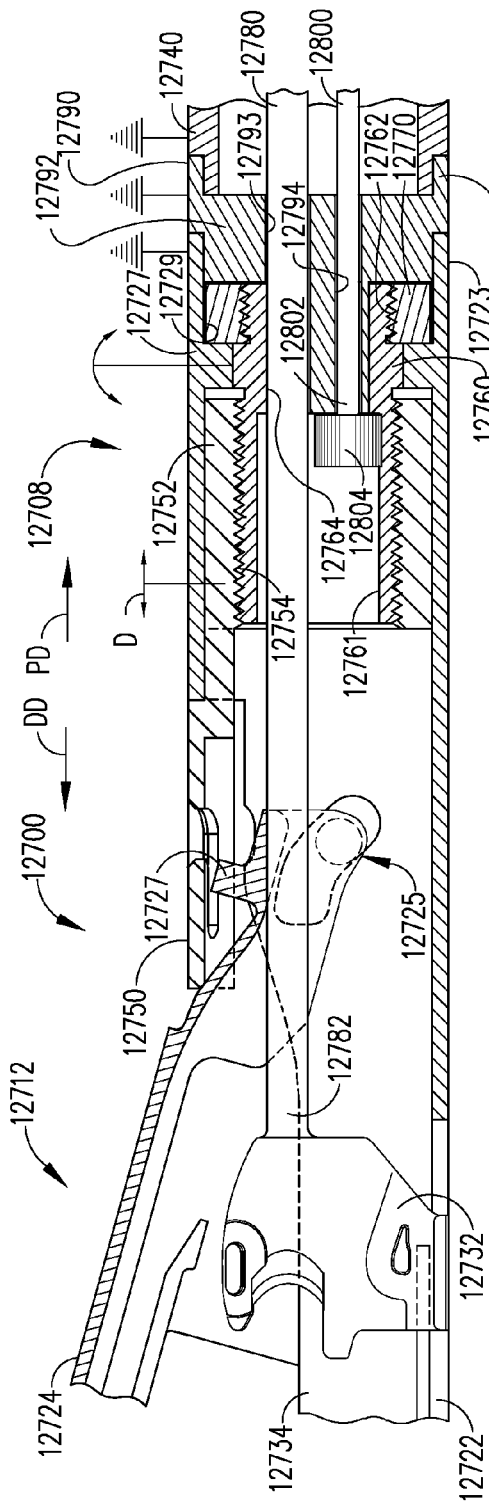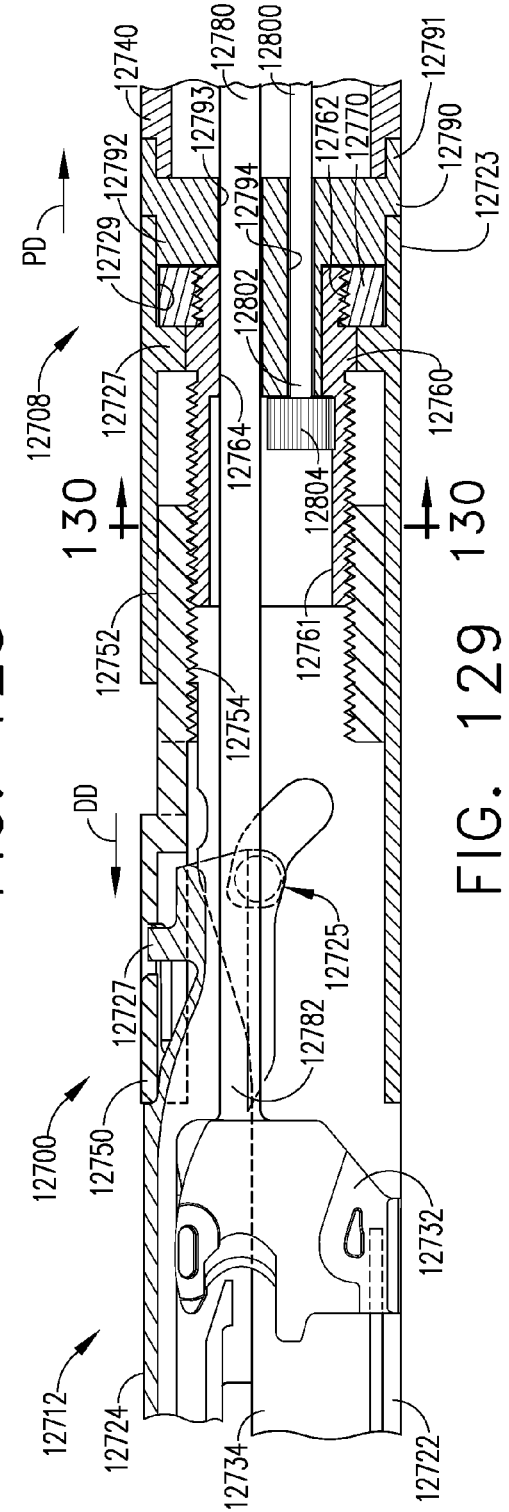

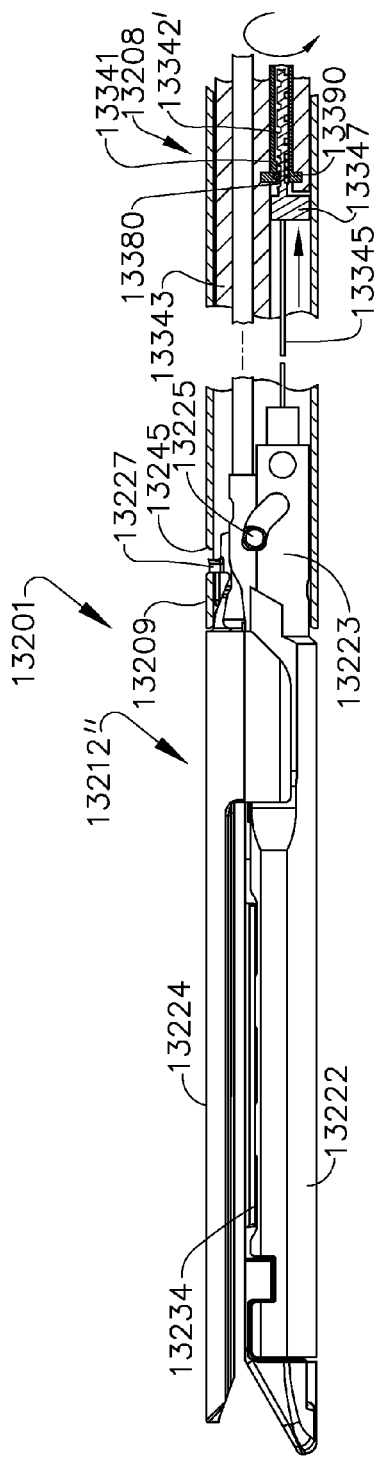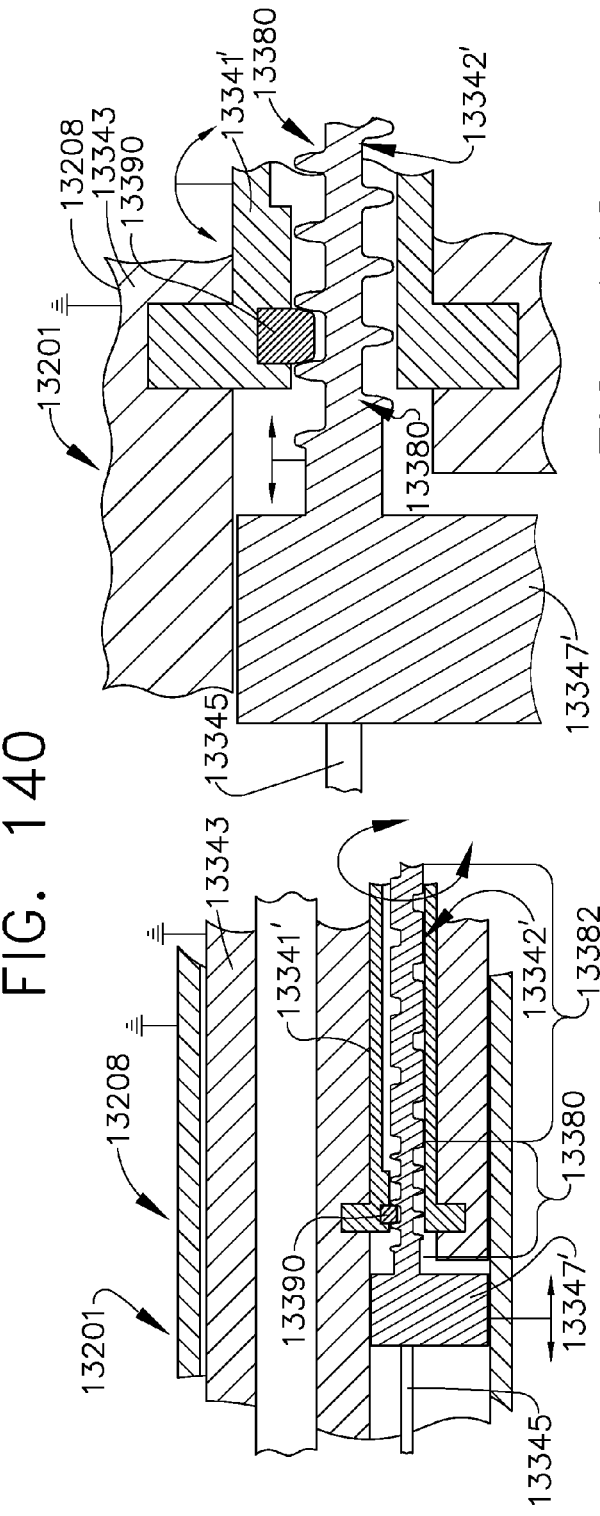

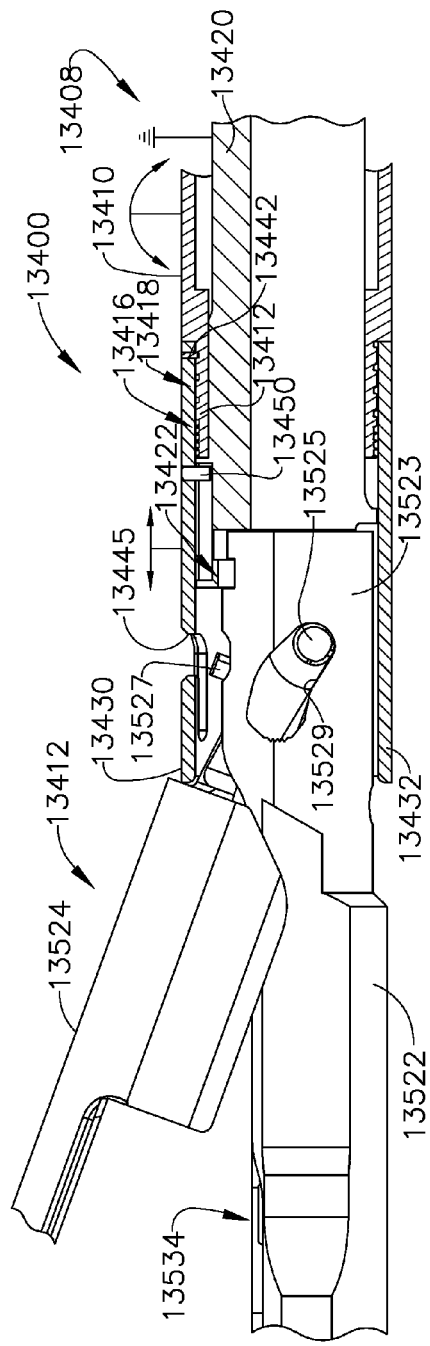
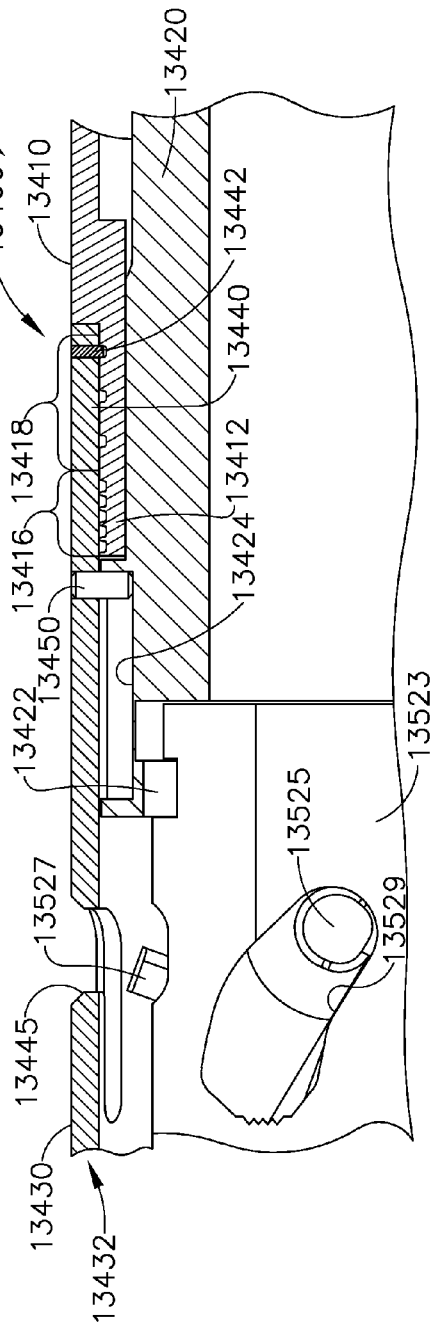

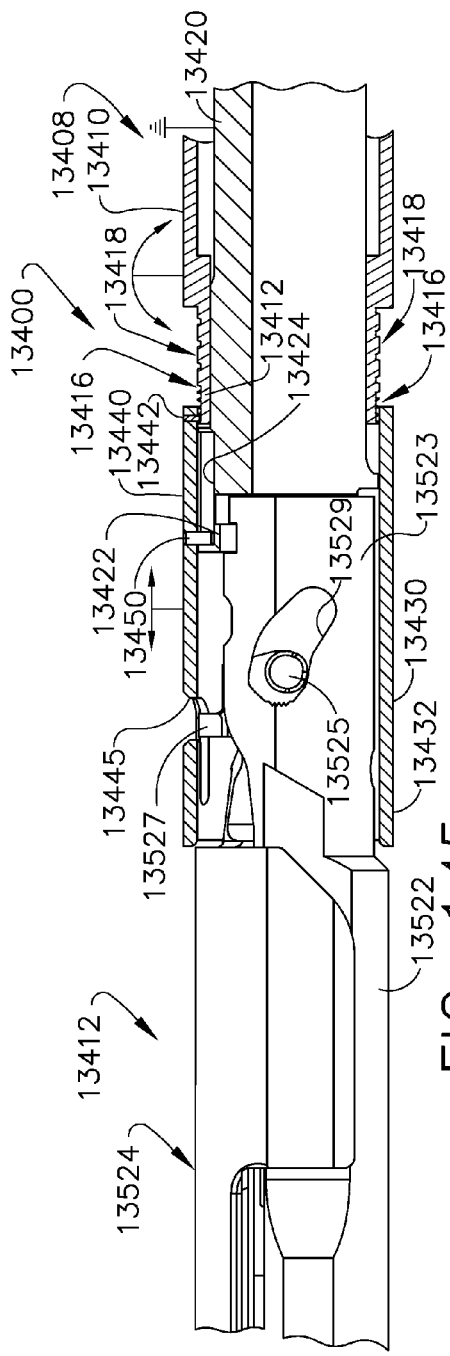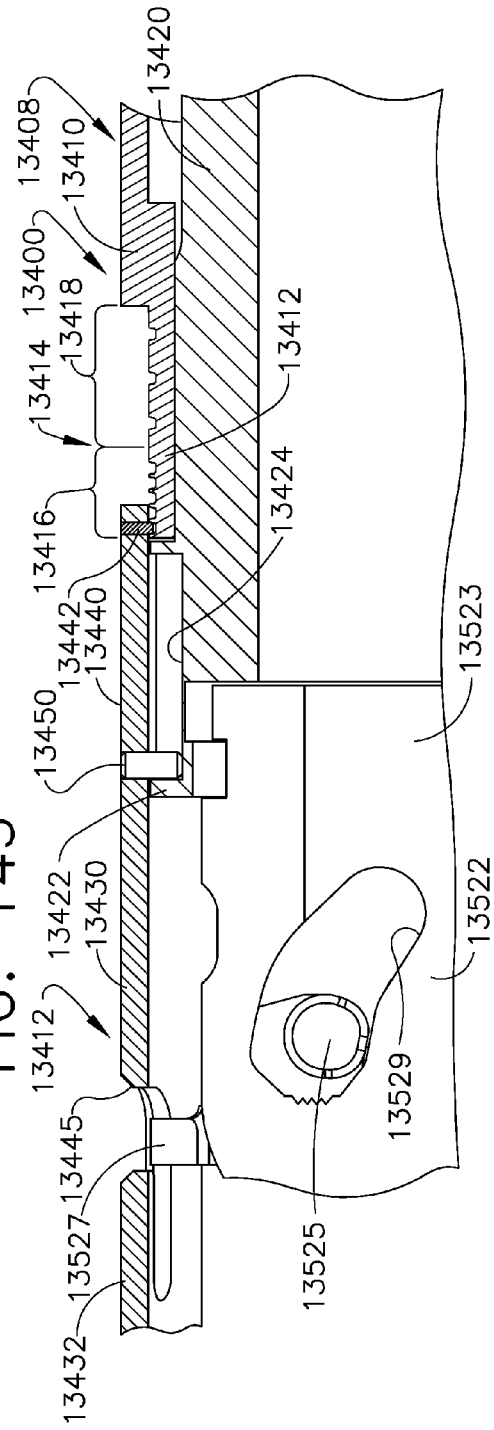

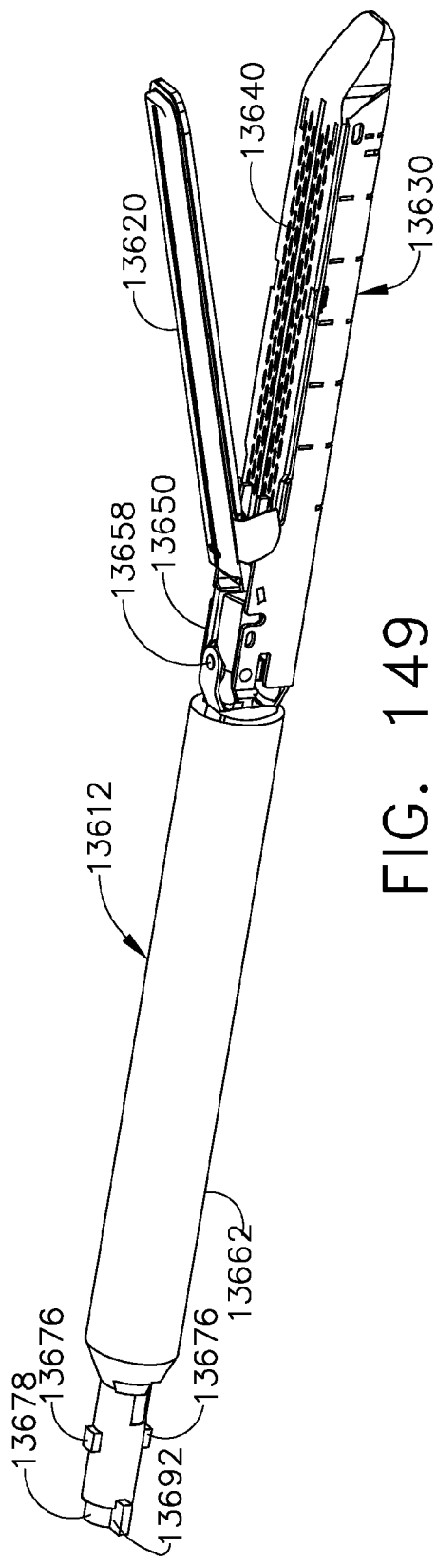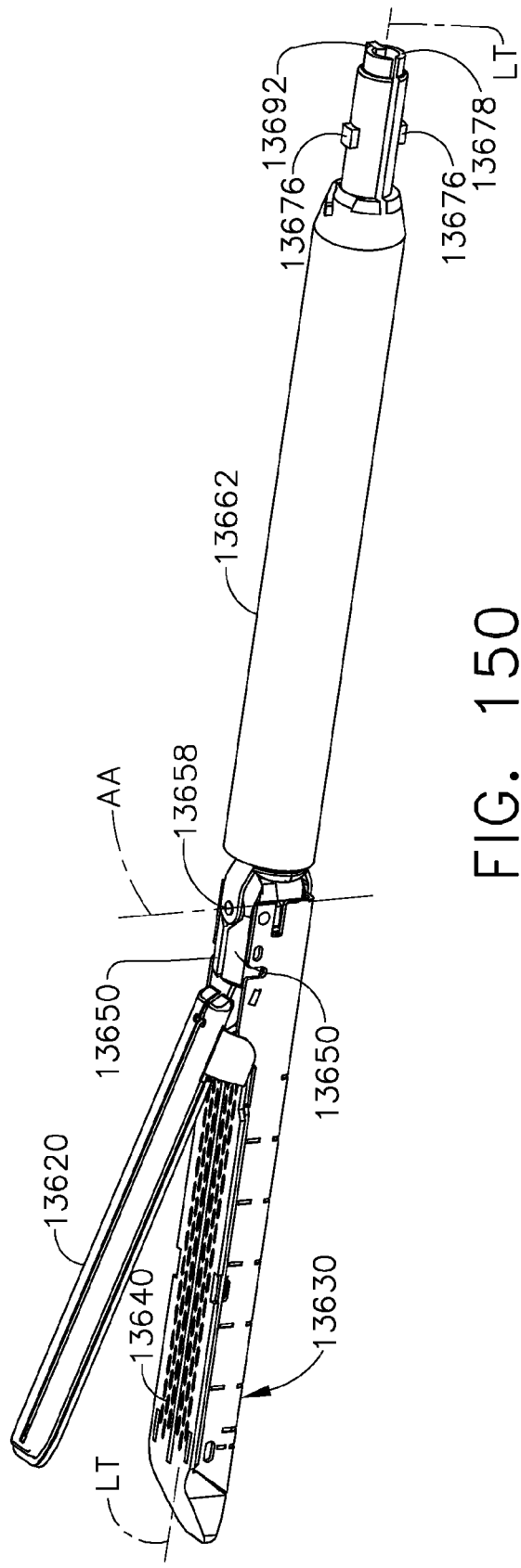
FIG. 149
FIG. 150

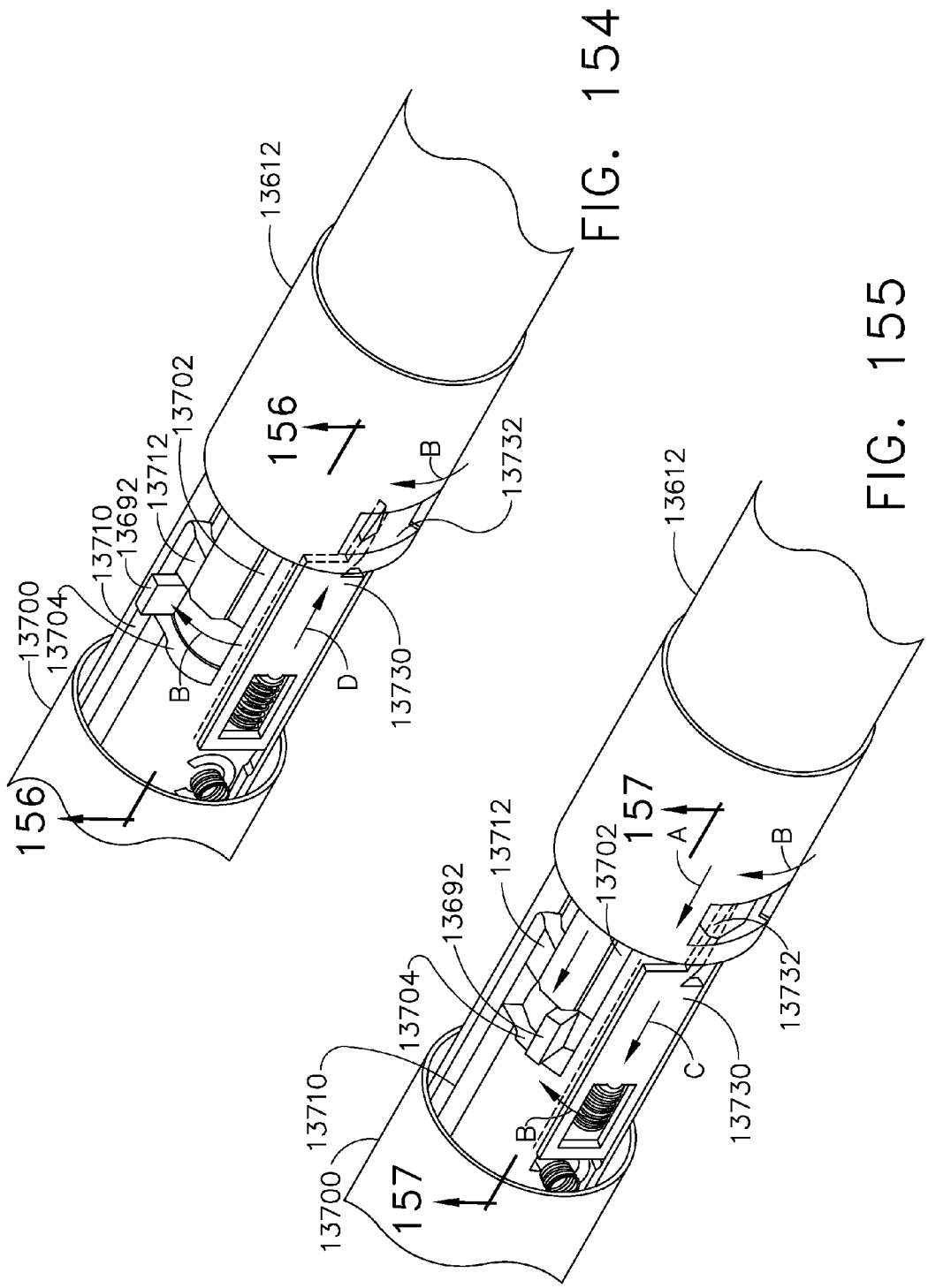

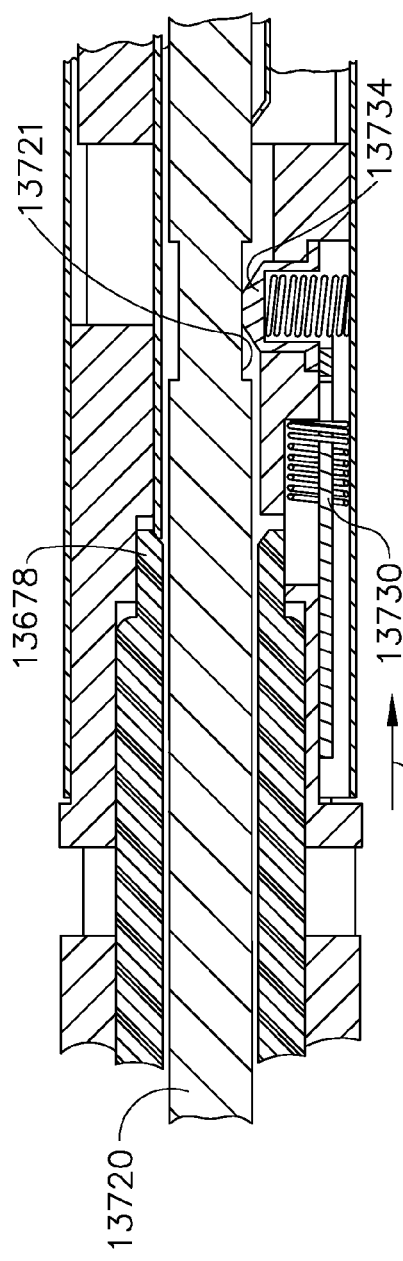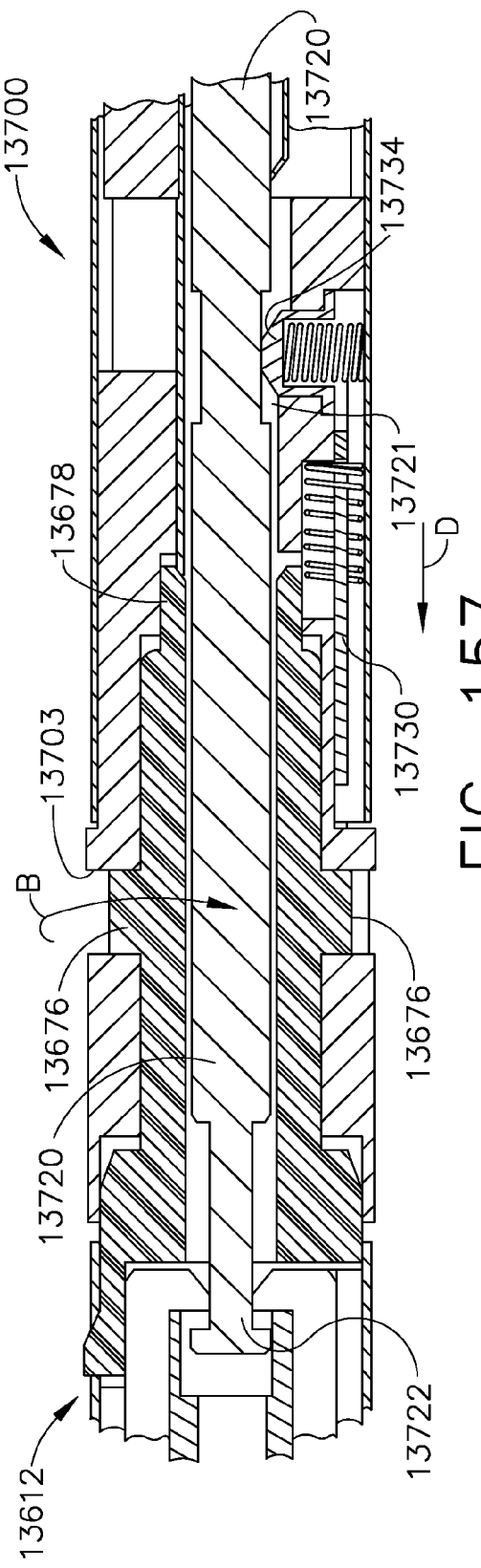

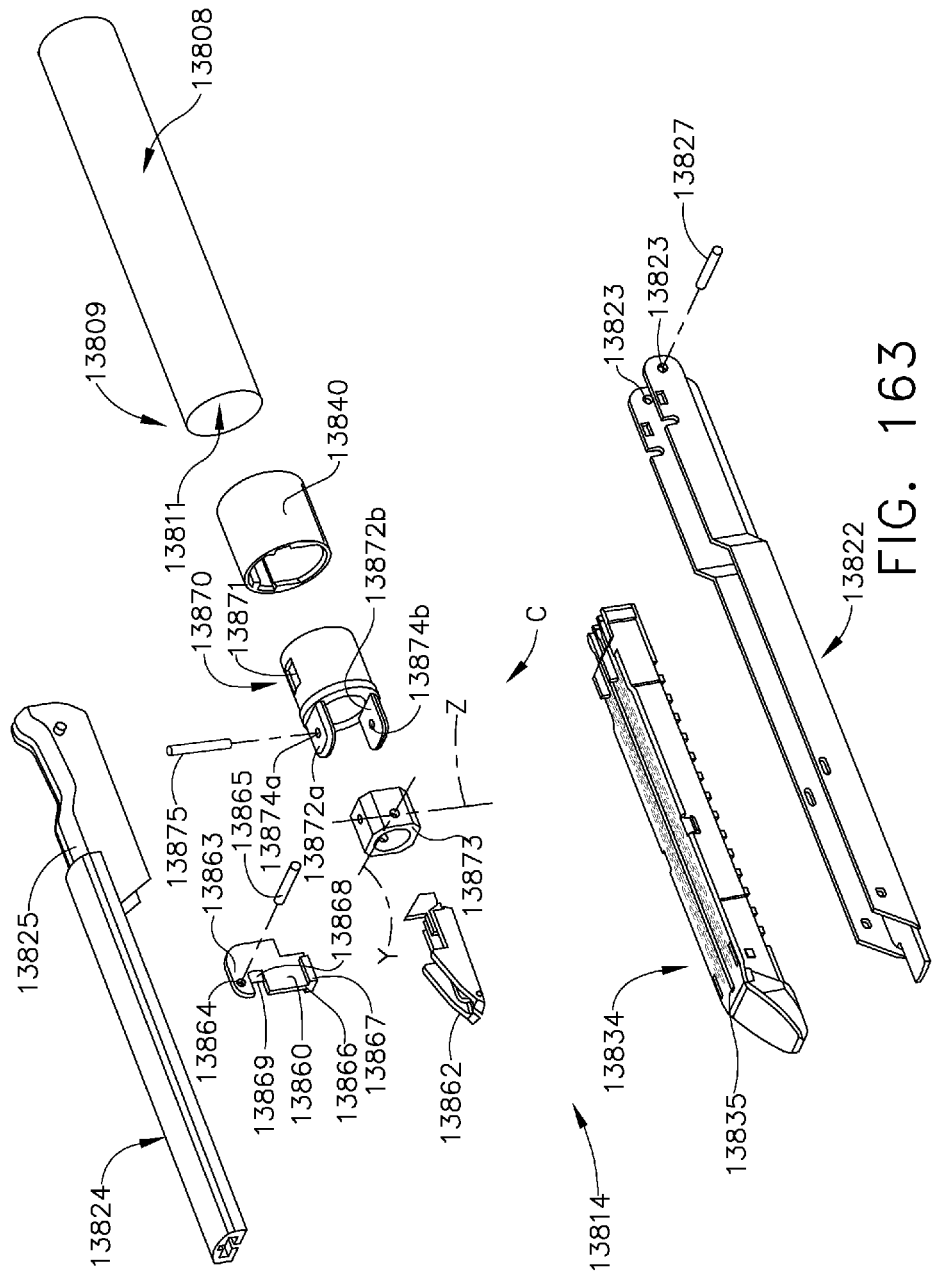

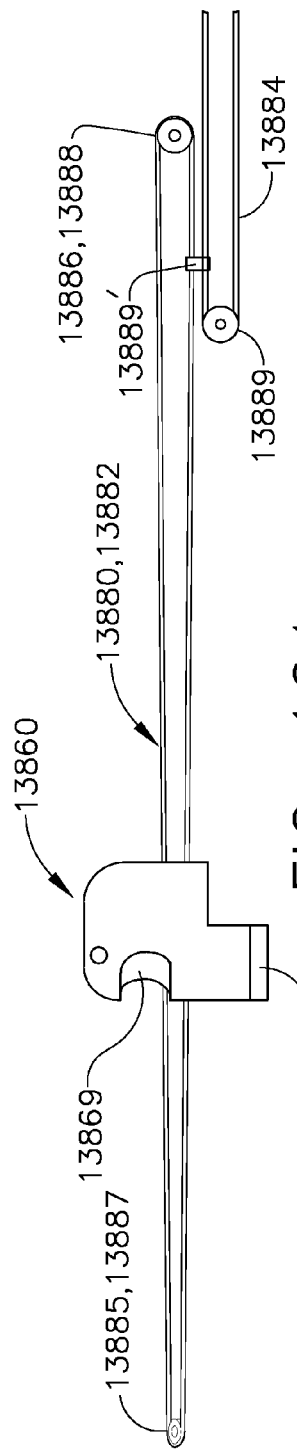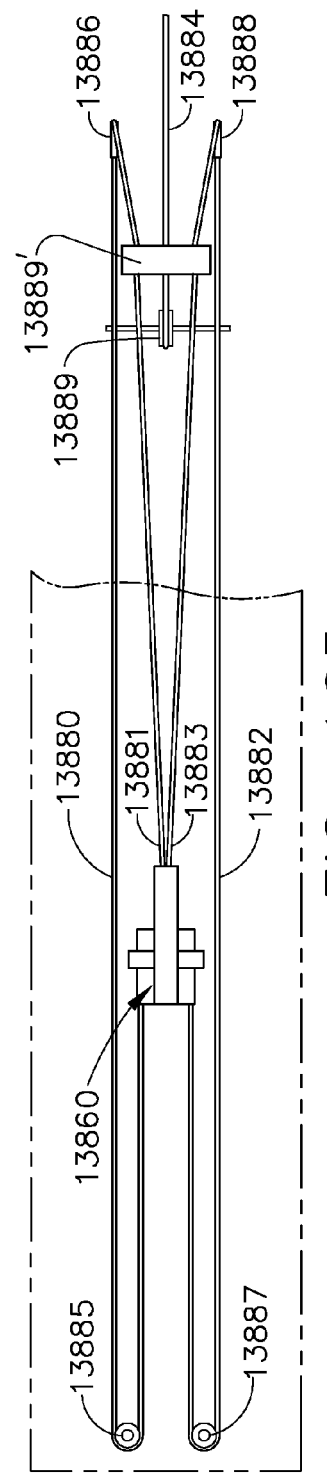

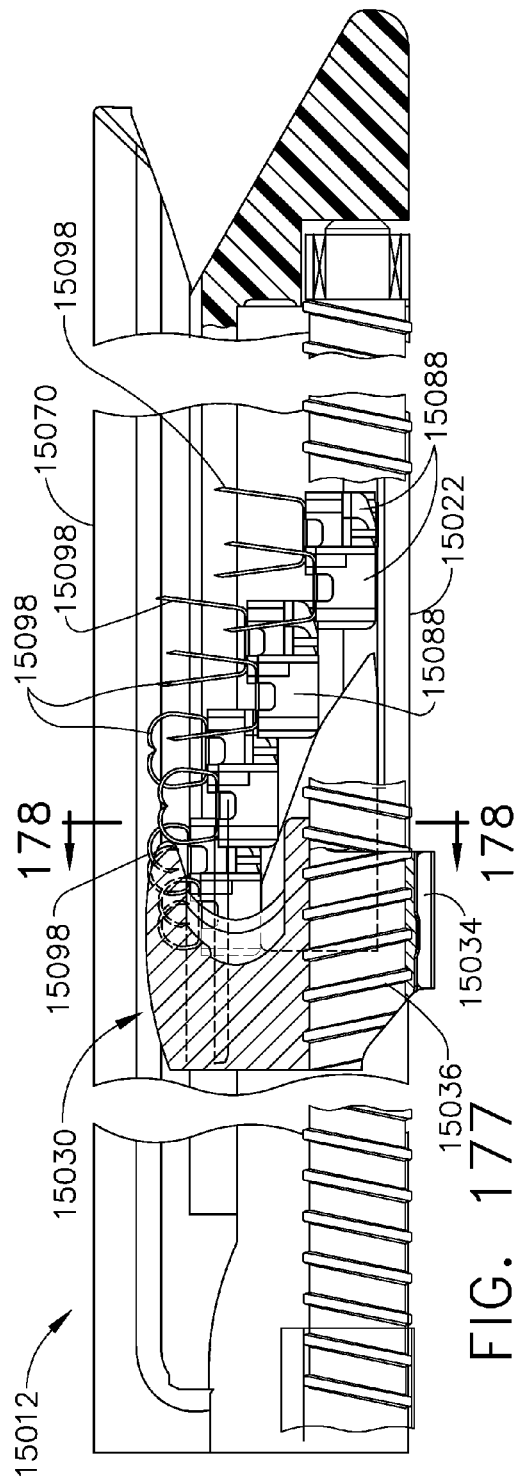
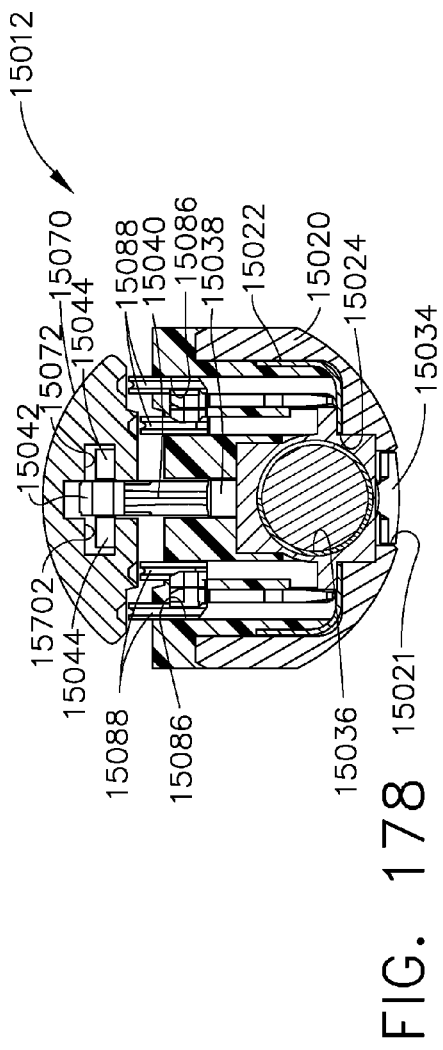
FIG. 177
FIG. 178

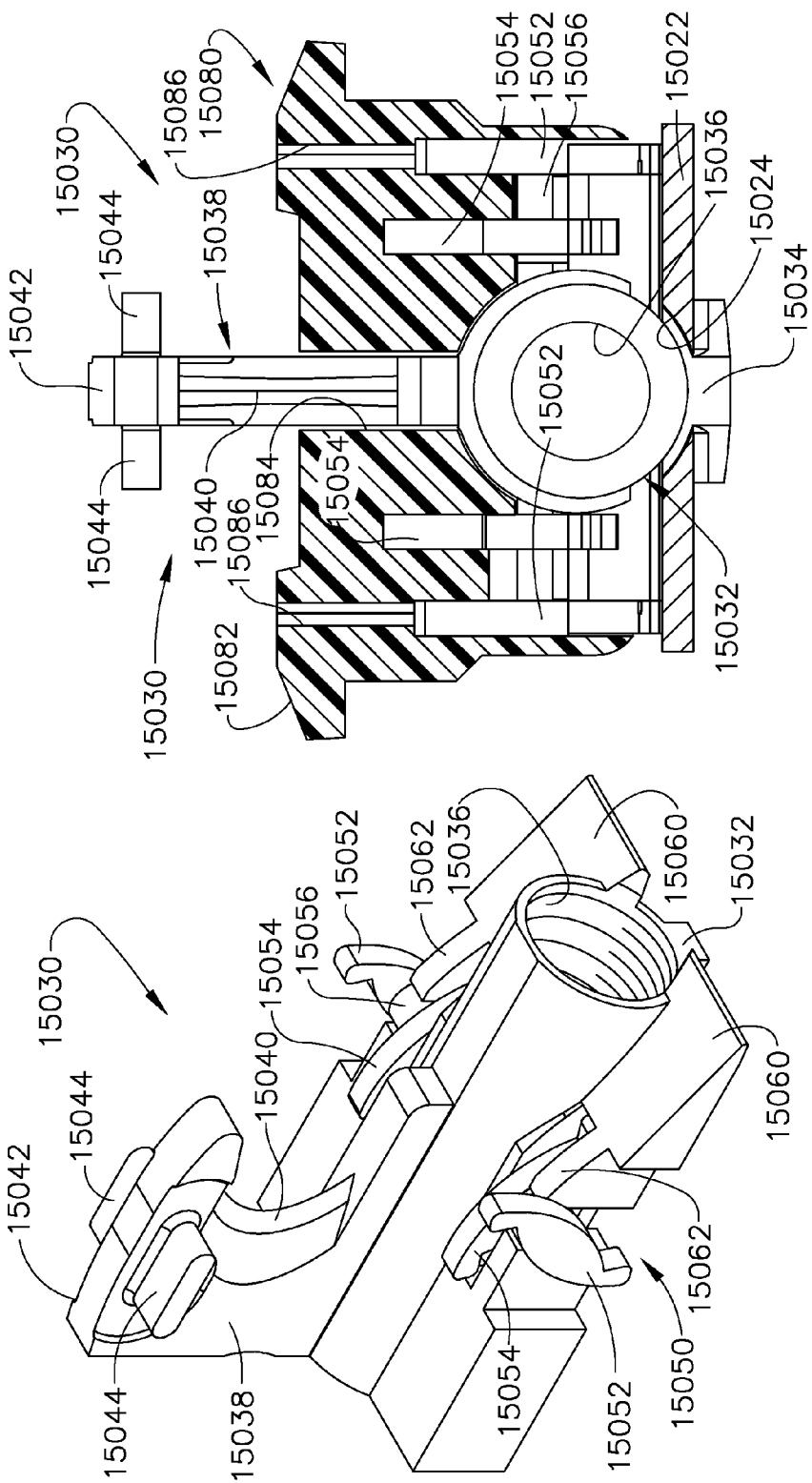

ROBOTICALLY-CONTROLLED CABLE-BASED SURGICAL END EFFECTORS

CROSS-REFERENCE TO RELATED APPLICATIONS

The present application is a continuation patent application and claims the benefit of U.S. patent application Ser. No. 13/118,278, filed May 27, 2011, entitled "Robotically-Controlled Surgical Stapling Devices That Produce Formed Staples Having Different Lengths", which is a continuation-in-part patent application of and claims the benefit of U.S. patent application Ser. No. 11/711,979, filed Feb. 28, 2007, entitled "Surgical Stapling devices That Produce Formed Staples Having Different Lengths" to Joseph C. Hueil, Jeffrey S. Swayze, and Frederick E. Shelton, IV, U.S. Patent Application Publication No. US 2007/0194081 A1, which is a continuation-in-part patent application under 35 U.S.C. §120 of and claims the benefit of U.S. patent application Ser. No. 11/216,562, filed Aug. 31, 2005, entitled "Staple Cartridges For Forming Staples Having Differing Formed Staple Heights," by F. Shelton, now U.S. Pat. No. 7,669,746, issued Mar. 2, 2010, the respective disclosures of which are all herein incorporated by reference in their respective entireties.

The present application is also related to the following, concurrently-filed U.S. patent applications, which are incorporated herein by reference:
(1) "Surgical Stapling Device With Staple Driver That Supports Multiple Wire Diameter Staples," by J. Swayze et al., U.S. patent application Ser. No. 11/711,977, now U.S. Pat. No. 7,673,781;
(2) "Surgical Stapling Device With Anvil Having Staple Forming Pockets Of Varying Depth," by J. Morgan et al., U.S. patent application Ser. No. 11/714,049, now U.S. Patent Publication No. 2007/0194082;
(3) "Surgical Stapling Device With Multiple Stacked Actuator Wedge Cams For Driving Staple Drivers," by J. Hueil et al., U.S. patent application Ser. No. 11/712,315, now U.S. Pat. No. 7,500,979;
(4) "Surgical Stapling Device With Staple Drivers Of Different Height," by J. Hueil et al., U.S. patent application Ser. No. 11/711,975, now U.S. Patent Publication No. 2007/0194079; and
(5) "Staple Cartridges For Forming Staples Having Differing Formed Staple Heights," by F. Shelton, IV, U.S. patent application Ser. No. 12/695,359, now U.S. Patent Publication No. 2010/0127042.

FIELD OF THE INVENTION

The present invention relates in general to stapling instruments that are capable of applying lines of staples and, more particularly, to improvements relating to staple cartridges for use with surgical stapling instruments that are capable of applying lines of staples having differing formed staple heights to tissue while simultaneously cutting the tissue.

BACKGROUND OF THE INVENTION

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges that, when driven distally, pass through openings in the staple cartridge and engage drivers supporting the staples to effect the firing of the staples toward the anvil.

An example of a surgical stapler suitable for endoscopic applications is described in U.S. Patent Application No. US 2004/0232196 A1, the disclosure of which is herein incorporated by reference in its entirety. In use, a clinician is able to close the jaw members of the stapler upon tissue to position the tissue prior to firing. Once the clinician has determined that the jaw members are properly gripping tissue, the clinician can then fire the surgical stapler, thereby severing and stapling the tissue. The simultaneous severing and stapling avoids complications that may arise when performing such actions sequentially with different surgical tools that respectively only sever or staple.

Whenever a transsection of tissue is across an area of varied tissue composition, it would be advantageous for the staples that are closest to the cut line to have one formed height that is less than the formed height of those staples that are farthest from the cut line. In practice, the rows of inside staples serve to provide a hemostatic barrier, while the outside rows of staples with larger formed heights provide a cinching effect where the tissue transitions from the tightly compressed hemostatic section to the non-compressed adjacent section. In other applications, it may be useful for the staples in a single line of staples to have differing formed heights. U.S. Pat. Nos. 4,941,623 and 5,027,834 to Pruitt disclose surgical stapler and cartridge arrangements that employ staples that have different prong lengths to ultimately achieve lines of staples that have differing formed heights. Likewise, WO 2003/094747A1 discloses a surgical stapler and cartridge that has six rows of staples wherein the outer two rows of staples comprise staples that are larger than the staples employed in the inner two rows and middle rows of staples. Thus, all of these approaches require the use of different sizes of staples in the same cartridge.

BRIEF SUMMARY OF THE INVENTION

In one general aspect, the present invention is directed to surgical stapling devices that are capable of producing staples of different formed lengths. For example, in such a device that also cuts the tissue being stapled, the inside rows of staples closest to the longitudinal incision line could have a formed height that is less than the formed height of the outer rows of staples. That way, the inside rows of staples may provide a hemostatic barrier, while the outside rows of staples with larger formed heights may provide a cinching effect where the tissue transitions from the tightly compressed hemostatic section to the non-compressed adjacent section.

According to various implementations, the staple cartridge may have staple drivers of different heights to product staples having different formed lengths. The staples driven by the shorter staple drivers would have longer formed lengths (assuming no other differences that would affect the formed heights of the staples). Also, the staple forming pockets in the anvil may have different depths. Staples formed in deeper pockets would tend to be longer than staples formed in shallow pockets. In addition, some of the staple forming pockets may be formed in compliant material portions of the anvil. Staples formed in such pockets would tend to be longer than staples formed in a non-compliant (or less compliant) portion of the anvil. Additionally, the channel may have internal steps that would produce staples having different formed heights.

Staples formed with staple drivers starting at a lower step would have a longer formed length that stapled formed with staple drivers starting at a higher step. Also, staples with different wire diameters may be used. Thicker staples would tend to produce staples with longer formed lengths. In that connection, embodiments of the present invention are directed to staple pushers that can accommodate staples of varying wire thicknesses. Also, staples of differing materials could be used. Staples made of stronger, less compliant materials, would tend to produce longer formed staples.

According to other embodiments, the surgical stapling device may comprise a plurality of stacked wedge band sets. Each stacked wedge band set may comprise a number of wedge bands stacked one on another. The wedge bands may be actuated in succession in order to drive the staples in successive stages. That is, for example, in an embodiment having three wedge bands in a stack, the first wedge band may be actuated first to partially deploy the staples, the second wedge band in stack may be actuated next to begin to form the staples, and the third wedge band in the stack may be actuated last to finish the formation of the staples. To produce staples having different formed heights, the heights of the stacks (corresponding to the cumulative height of the wedge bands in the stacks) may be different, for example.

The techniques used to create formed staples of different heights could be used in a variety of different surgical stapling devices. For example, the stapling devices could be devices that cut the clamped tissue or devices that include no cutting instrument. The surgical staplers may be, for example, endocutters, open linear stapler devices, or circular staplers.

In accordance with other general aspects of various embodiments of the present invention, there is provided a staple cartridge for use with a stapling device that has a robotically controlled actuator that is selectively actuatable in an axial direction and an anvil portion that is selectively movable between open and closed positions. In various embodiments, the staple cartridge comprises a cartridge body that is supportable within the stapling device for selective confronting relationship with the anvil portion thereof when in a closed position. The cartridge body is configured to axially receive a dynamic actuation member therein that is responsive to control motions applied thereto by the robotically controlled actuator. At least one first staple driver is movably supported within the cartridge body for contact by the dynamic actuation member such that, as the dynamic actuation member is axially advanced through the cartridge body when a first control motion is applied thereto by the robotically controlled actuator, the first staple drivers are driven in a direction toward the anvil when the anvil is in the closed position. Each first staple driver defines a first staple support cradle for supporting a staple thereon. The first staple support cradle is located a first staple forming distance from a corresponding portion of the closed anvil. At least one second staple driver is movably supported within the cartridge body for contact by the dynamic actuation member such that as the dynamic actuation member is axially advanced through the cartridge body, the second staple drivers are driven in the direction toward the closed anvil. Each of the second staple drivers define a second staple support cradle for supporting another staple thereon. The second staple support cradle is located a second staple forming distance from another portion of the closed anvil wherein the second staple forming distance differs from the first staple forming distance.

In accordance with other general aspects of various embodiments of the present invention, there is provided a surgical stapling device that includes a robotic system that is operable to produce a firing motion and a closing motion. The device further includes an implement portion that is responsive to the firing and closing motions from the robotic system. In various forms, the implement portion includes an elongate channel that is operably coupled to a portion of the robotic system and is configured to support a staple cartridge therein. An anvil is movably coupled to the elongate channel and has an anvil channel therein. The anvil is movable from an open position to a closed position upon application of the closing motion thereto from the robotic system. Various embodiments further include a firing device that includes a distally presented cutting edge that is longitudinally movable within the elongate channel and the anvil from a starting position to an ending position upon application of the firing motion thereto from the robotic system. The firing device has an upper portion for engaging the anvil channel and a lower portion for engaging the elongate channel during distal movement for firing. Various forms of the staple cartridge comprise a cartridge body that is sized to be supported within the elongate channel. The cartridge body has a longitudinally extending slot therein for receiving the firing device therein. The cartridge body has a non-planar deck surface that is configured to confront a staple forming portion of the anvil that has staple forming pockets therein when the anvil is in the closed position. A first plurality of inside staple drivers is axially aligned in a first row of inside staple drivers in a portion of the cartridge body that is adjacent a first side of the longitudinally extending slot. A second plurality of inside staple drivers is axially aligned in a second row of inside staple drivers in another portion of the cartridge body that is adjacent a second side of the longitudinally extending slot. The inside staple drivers are movably supported within the cartridge body for selective movement toward the anvil when the anvil is in a closed position. Each inside staple driver defines a first staple support cradle for supporting a staple thereon. Each first staple support cradle is located a first staple forming distance from a corresponding portion of the anvil when the anvil is in a closed position. A first plurality of outside staple drivers is axially aligned in a first row of outside staple drivers that are adjacent to the first row of the inside staple drivers. A second plurality of outside staple drivers is axially aligned in a second row of outside staple drivers and is adjacent to the second row of inside staple drivers. Each of the outside staple drivers is movably supported within the cartridge body for selective driving movement toward the anvil when the anvil is in the closed position. Each of the outside staple drivers define a second staple support cradle for supporting another staple thereon. Each second staple support cradle is located a second staple forming distance from another corresponding portion of the anvil when the anvil is in the closed position. The second staple forming distance differs in magnitude from the first staple forming distance. A wedge sled is supported within the cartridge body for driving contact by the firing device and actuating contact with the first and second pluralities of the inside staple drivers as well as the first and second pluralities of outside staple drivers such that, as the firing device moves within the elongated slot in the cartridge body in a first axial direction in response to the firing motion from the robotic system, the wedge sled drives each of the inside and outside drivers towards the anvil to bring the staples supported thereon into forming contact with the anvil when the anvil is in the closed position.

BRIEF DESCRIPTION OF THE FIGURES

The accompanying drawings, which are incorporated in and constitute a part of this specification, illustrate by way of example embodiments of the invention, and, together with the general description of the invention given above, and the detailed description of the embodiments given below, serve to explain the principles of the present invention, wherein:

FIG. 36 depicts a partially cut away side elevational view of the surgical stapling and severing instrument of FIG. 1 in the closed or clamped position according to various embodiments of the present invention;

FIG. 37 depicts a side elevation view of the surgical stapling and severing instrument of FIG. 1 in the closed or clamped position with tissue properly compressed according to various embodiments of the present invention;

FIGS. 51-62 depict aspects of a surgical stapling device having stacks of actuatable wedge bands according to various embodiments of the present invention;

FIG. 123 is a cross-sectional side view of a portion of the surgical end effector and elongated shaft assembly of the surgical tool embodiment of FIG. 122 with the anvil in the open position;

FIG. 124 is another cross-sectional side view of a portion of the surgical end effector and elongated shaft assembly of the surgical tool embodiment of FIG. 122 with the anvil in the closed position;

FIG. 128 is a cross-sectional side view of a portion of the surgical end effector and elongated shaft assembly of the surgical tool embodiment of FIG. 127 with the anvil in the open position;

FIG. 129 is another cross-sectional side view of a portion of the surgical end effector and elongated shaft assembly of the surgical tool embodiment of FIG. 128 with the anvil in the closed position;

FIG. 140 is a side view of a portion of another surgical end effector embodiment of a portion of a surgical tool embodiment of the present invention with some components thereof shown in cross-section;

FIG. 141 is an enlarged cross-sectional view of a portion of the end effector of FIG. 140;

FIG. 142 is another cross-sectional view of a portion of the end effector of FIGS. 140 and 141;

FIG. 143 is a cross-sectional side view of a portion of a surgical end effector and elongated shaft assembly of another surgical tool embodiment of the present invention with the anvil in the open position;

FIG. 144 is an enlarged cross-sectional side view of a portion of the surgical end effector and elongated shaft assembly of the surgical tool embodiment of FIG. 143;

FIG. 145 is another cross-sectional side view of a portion of the surgical end effector and elongated shaft assembly of FIGS. 143 and 144 with the anvil thereof in the closed position;

FIG. 146 is an enlarged cross-sectional side view of a portion of the surgical end effector and elongated shaft assembly of the surgical tool embodiment of FIGS. 143-145;

FIG. 149 is a front perspective view of a disposable loading unit arrangement that may be employed with various surgical tool embodiments of the present invention;

FIG. 150 is a rear perspective view of the disposable loading unit of FIG. 149;

FIG. 154 is a perspective view of a portion of a disposable loading unit and an elongated shaft assembly embodiment of a surgical tool embodiment of the present invention with the disposable loading unit in a first position;

FIG. 155 is another perspective view of a portion of the disposable loading unit and elongated shaft assembly of FIG. 154 with the disposable loading unit in a second position;

FIG. 156 is a cross-sectional view of a portion of the disposable loading unit and elongated shaft assembly embodiment depicted in FIGS. 154 and 154;

FIG. 157 is another cross-sectional view of the disposable loading unit and elongated shaft assembly embodiment depicted in FIGS. 154-156;

FIG. 158 is a partial exploded perspective view of a portion of another disposable loading unit embodiment and an elongated shaft assembly embodiment of a surgical tool embodiment of the present invention;

FIG. 159 is a partial exploded perspective view of a portion of another disposable loading unit embodiment and an elongated shaft assembly embodiment of a surgical tool embodiment of the present invention;

FIG. 160 is another partial exploded perspective view of the disposable loading unit embodiment and an elongated shaft assembly embodiment of FIG. 159;

FIG. 161 is a top view of another tool mounting portion embodiment of a surgical tool embodiment of the present invention;

FIG. 162 is a side view of another surgical tool embodiment of the present invention with some of the components thereof shown in cross-section and in relation to a robotic tool holder of a robotic system;

FIG. 163 is an exploded assembly view of a surgical end effector embodiment that may be used in connection with various surgical tool embodiments of the present invention;

FIG. 164 is a side view of a portion of a cable-driven system for driving a cutting instrument employed in various surgical end effector embodiments of the present invention;

FIG. 165 is a top view of the cable-driven system and cutting instrument of FIG. 164;

FIG. 166 is a top view of a cable drive transmission embodiment of the present invention in a closure position;

FIG. 167 is another top view of the cable drive transmission embodiment of FIG. 166 in a neutral position;

Figure 166:
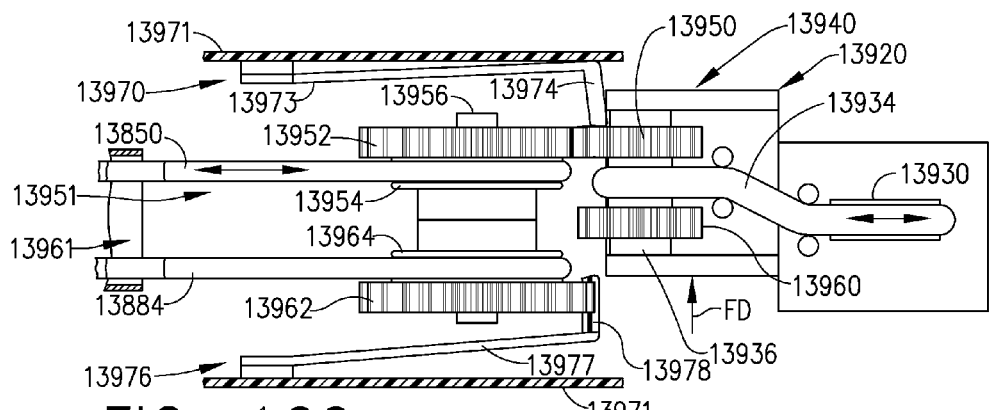
Figure 167:
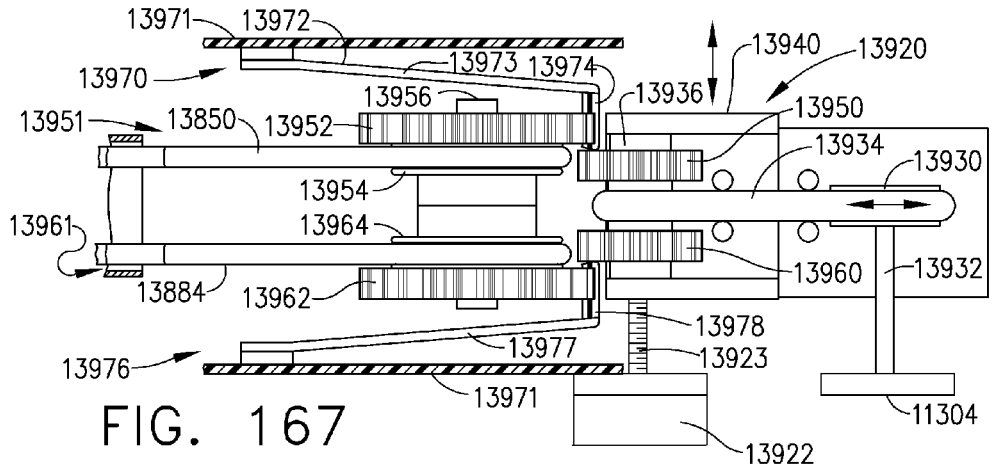
Figure 168:
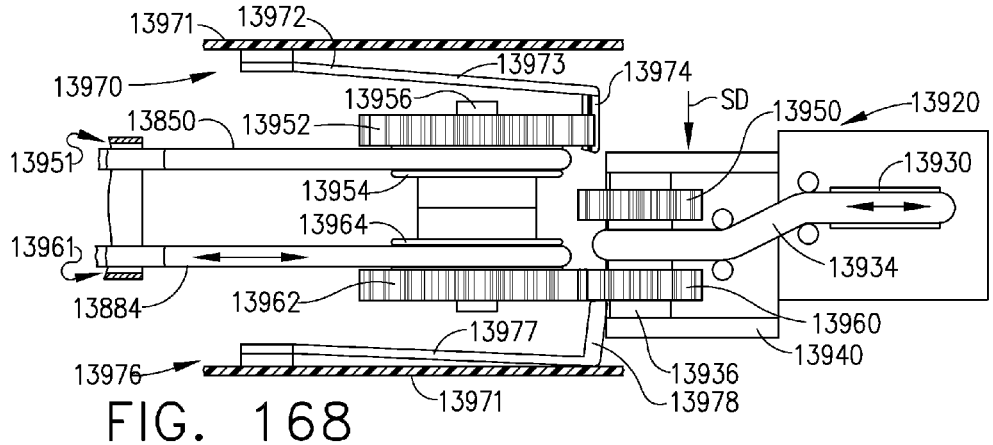
Figure 169:
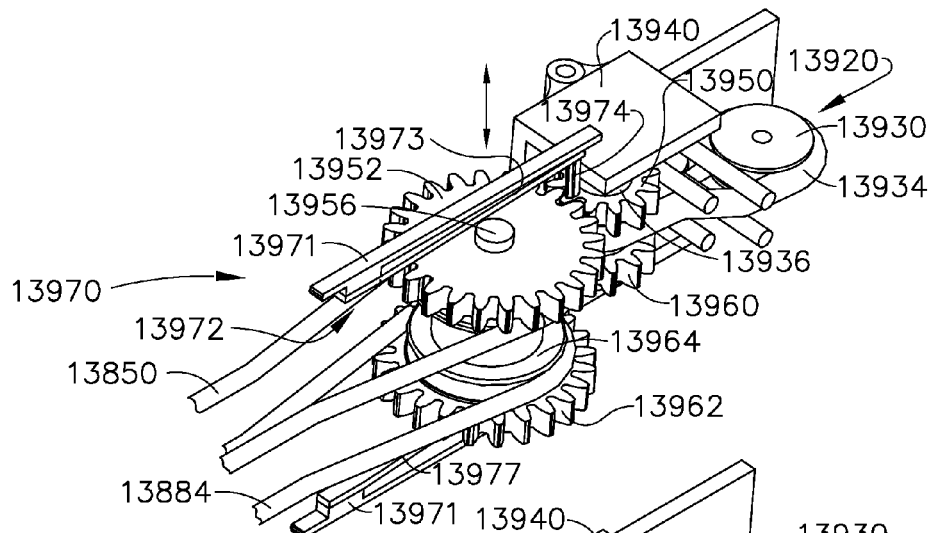
Figure 170:
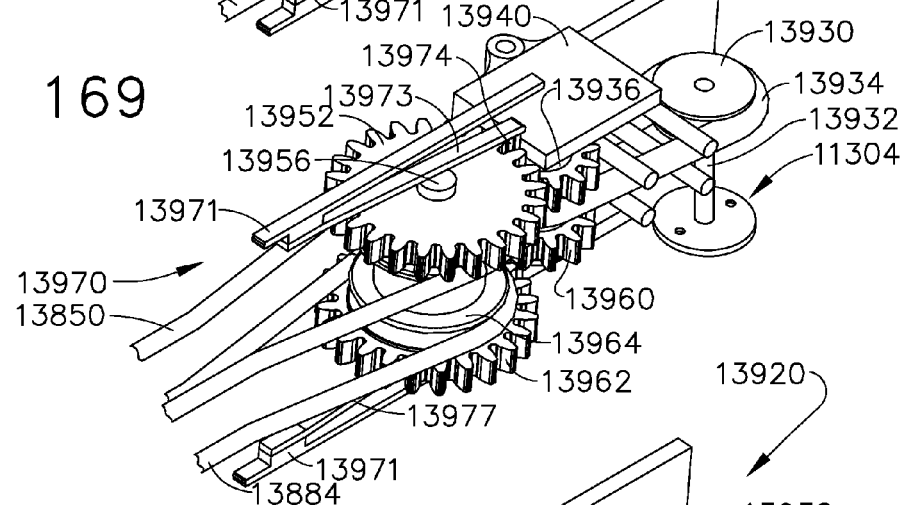
Figure 171:
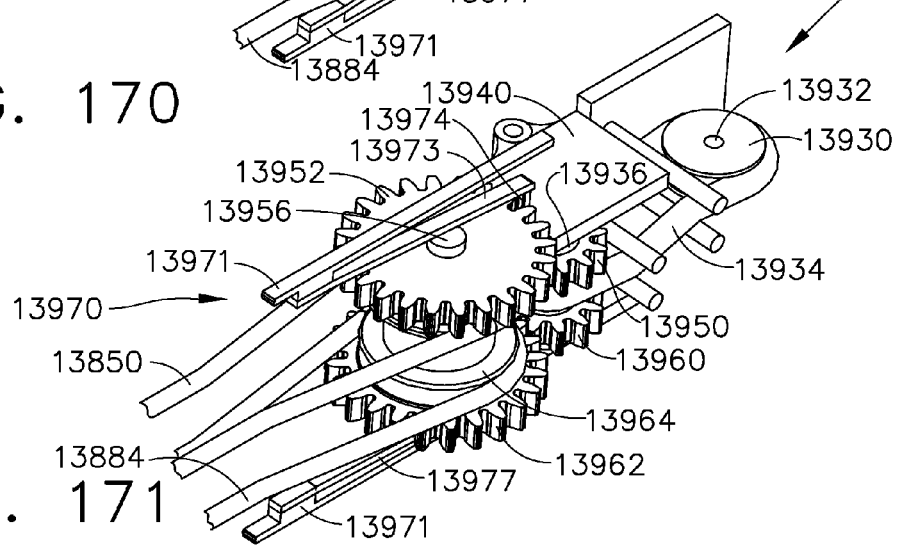
Figure 172:
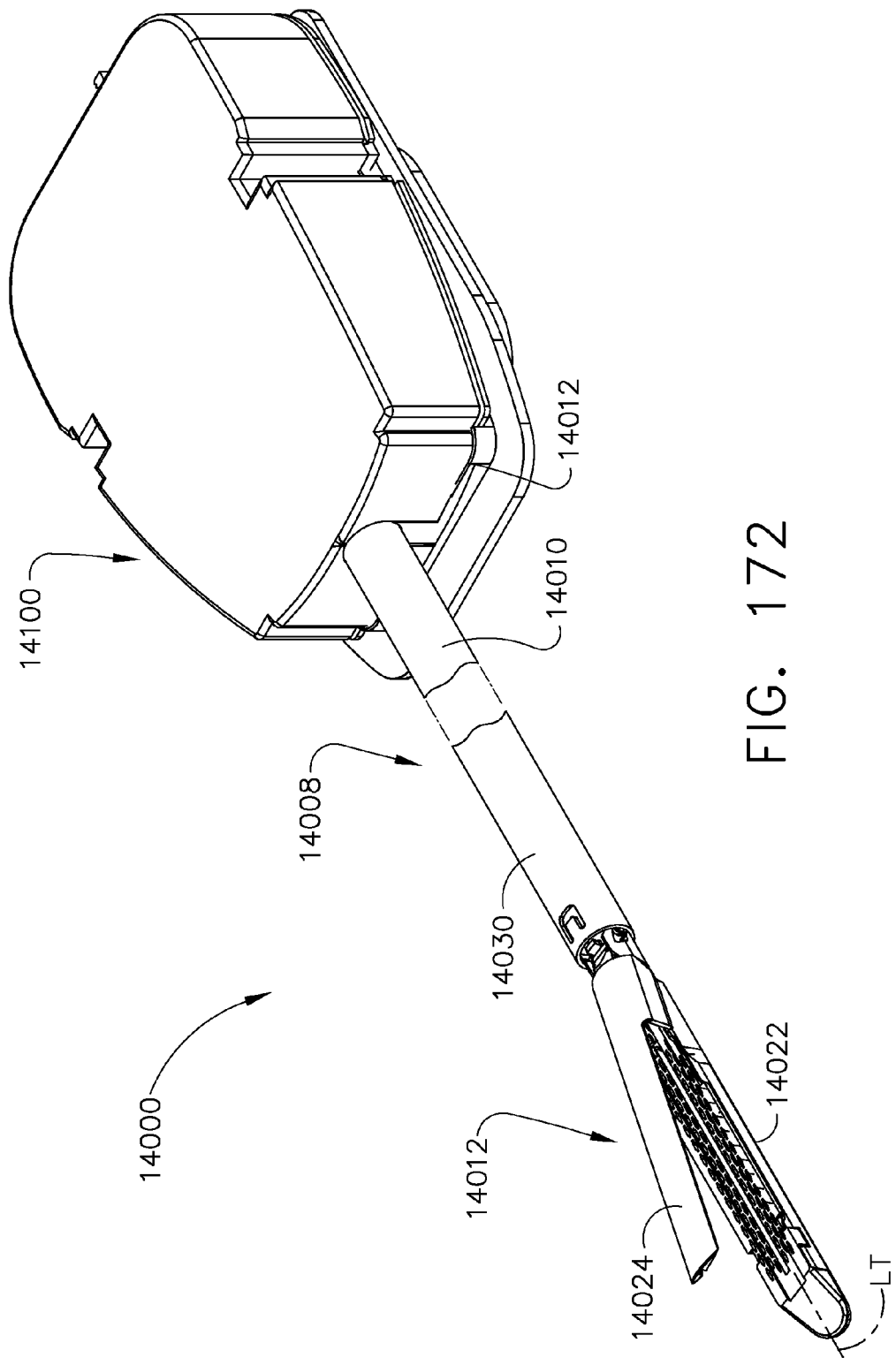
Figure 173:
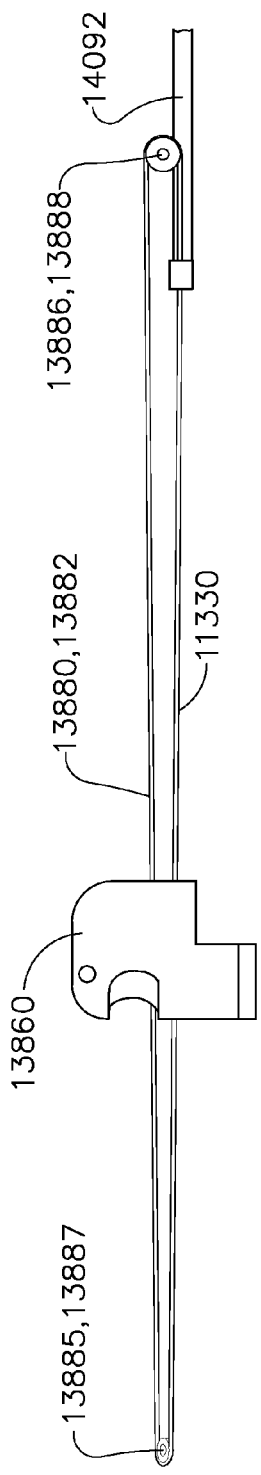
Figure 174:
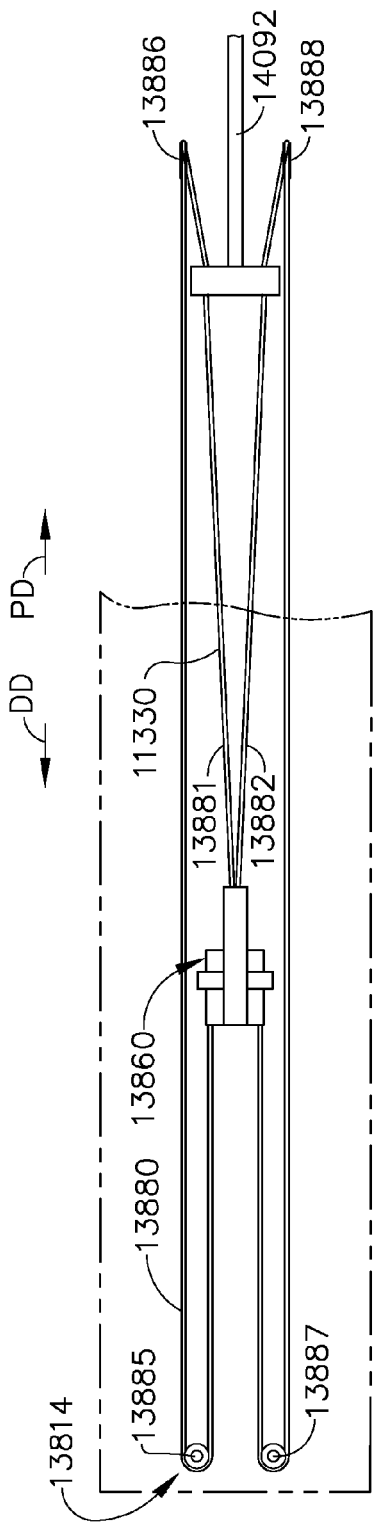
Figure 175:
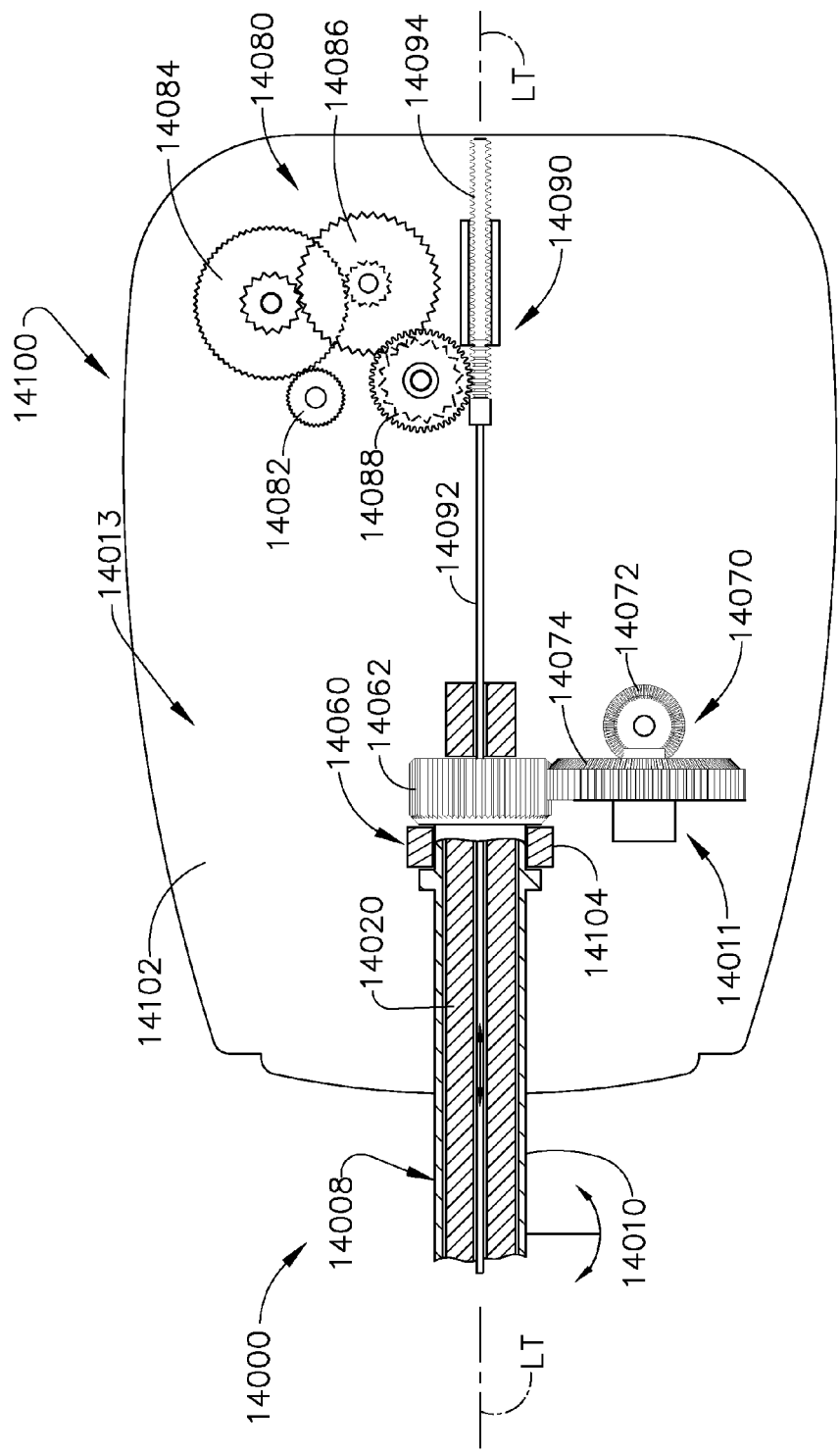
Figure 176:
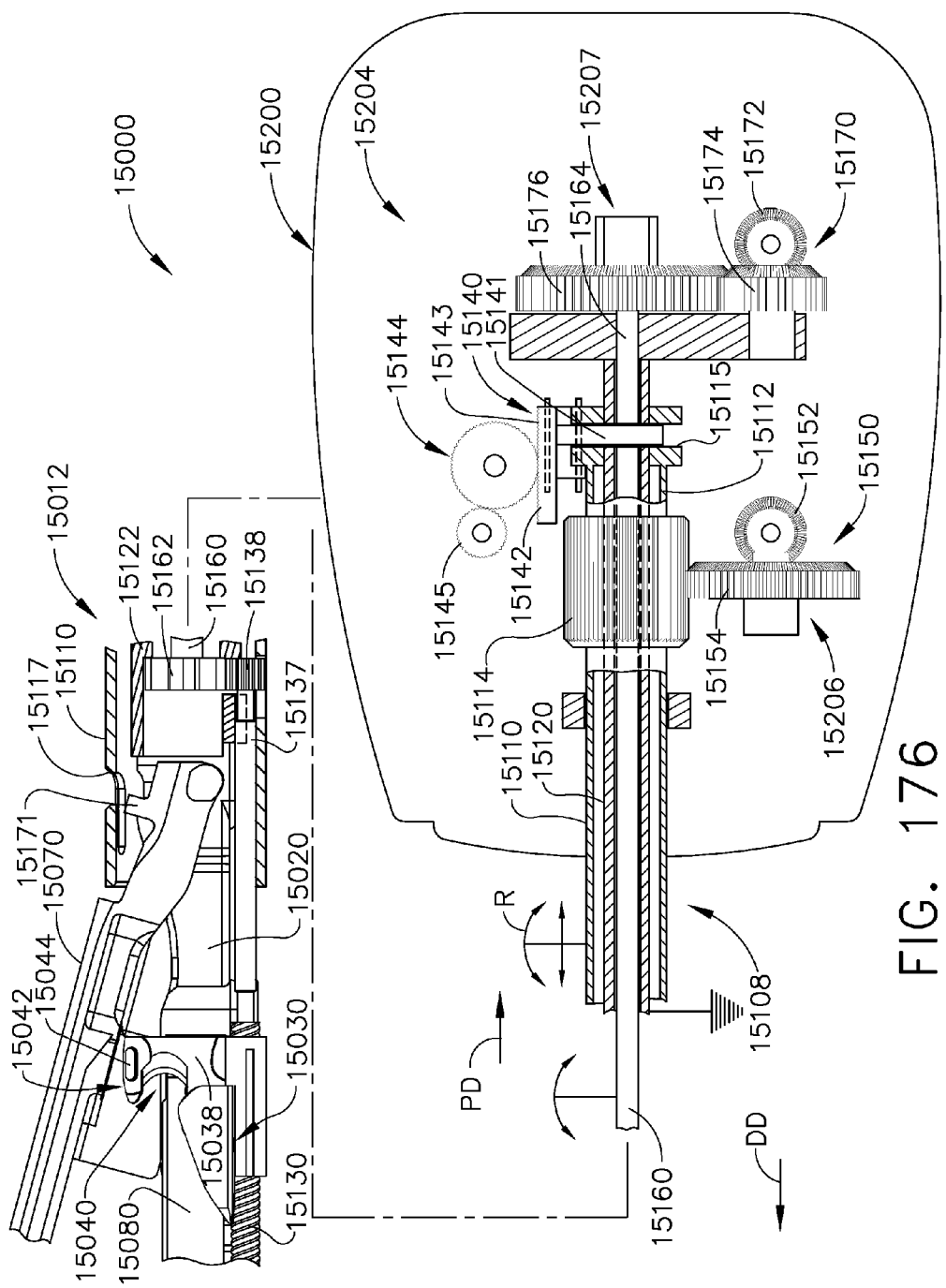
Figure 179:
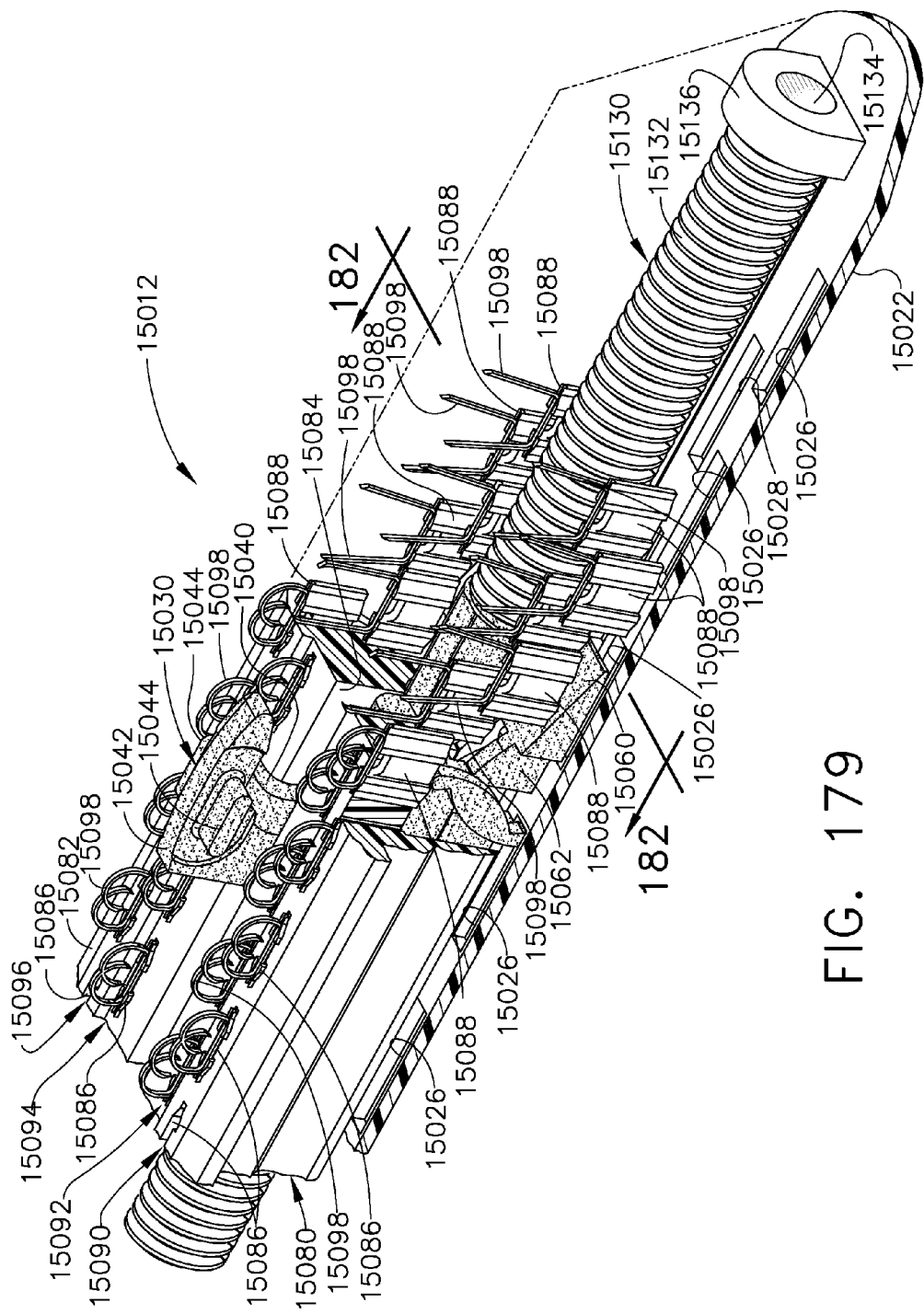
Figure 180:
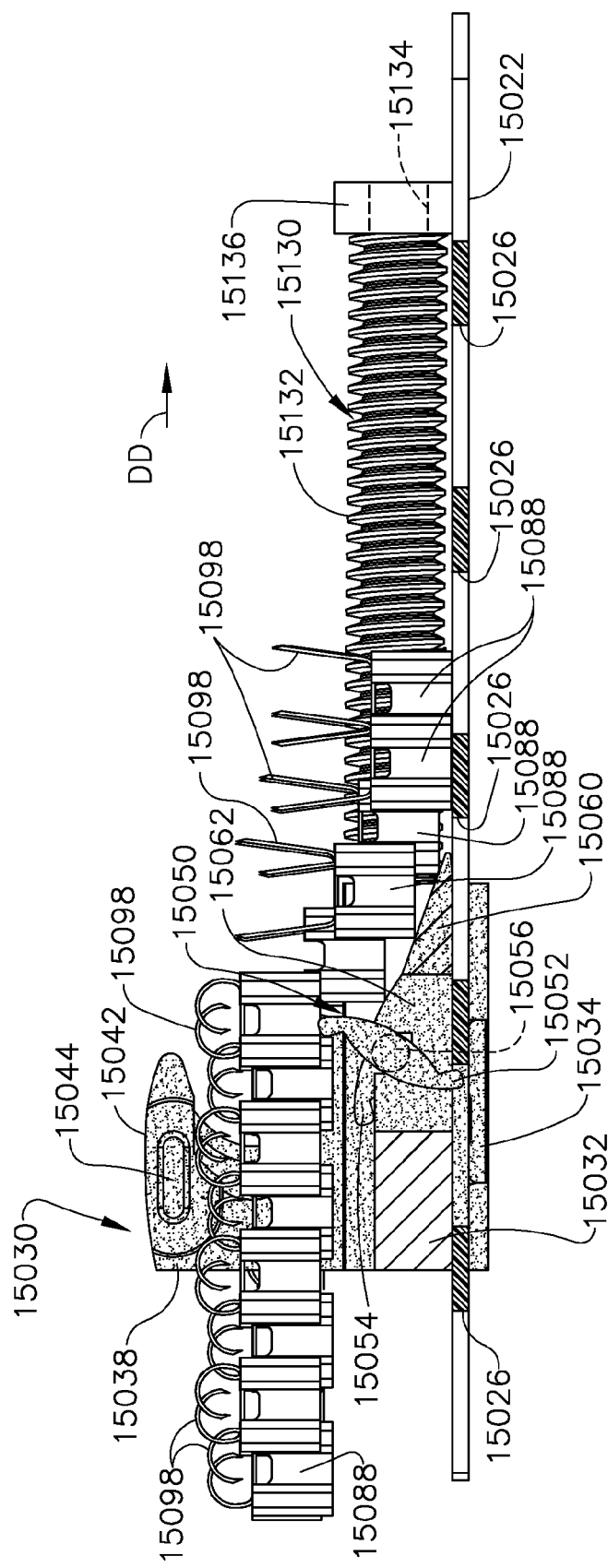
Figure 189:
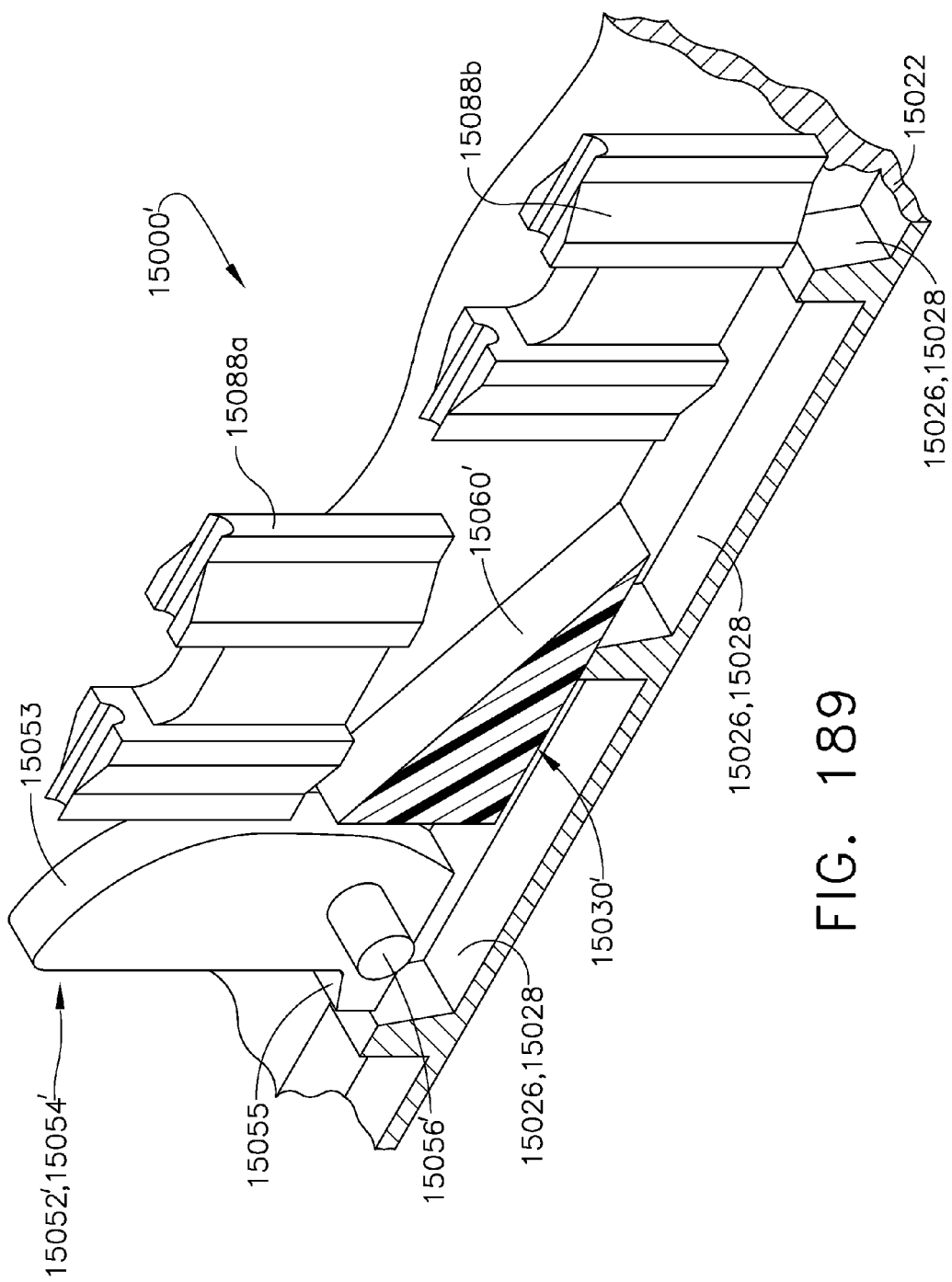
Figure 190:
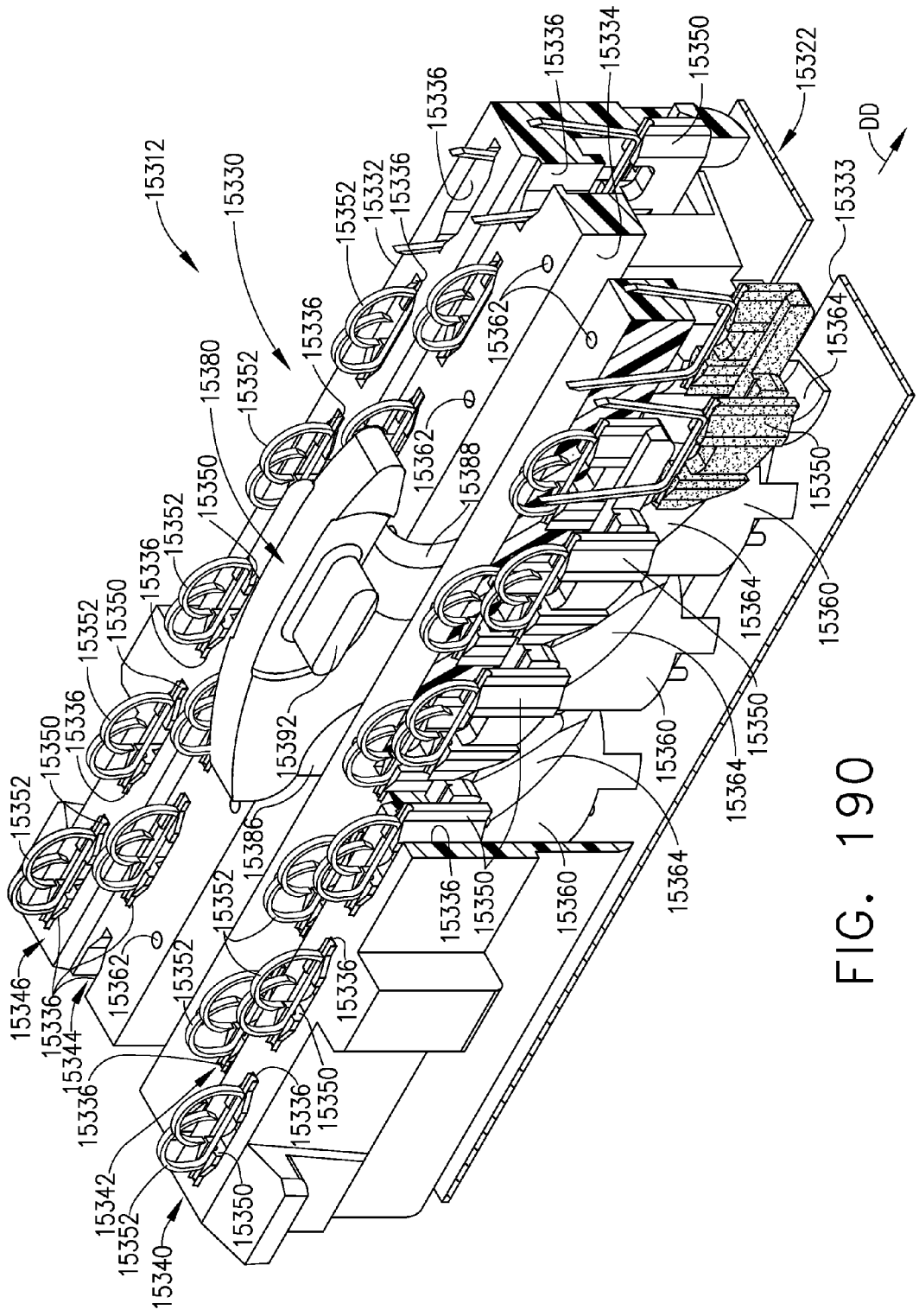
Figure 191:
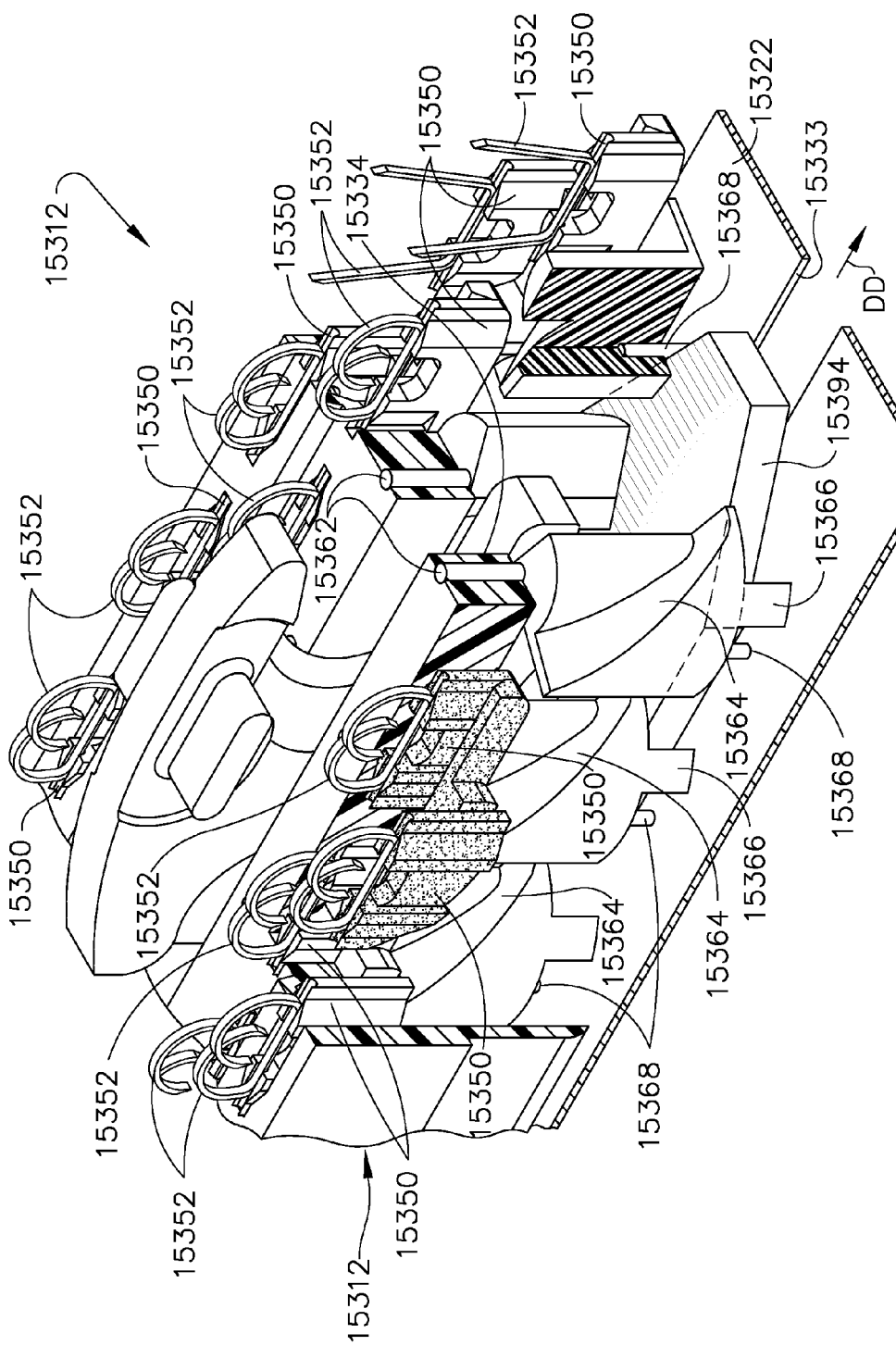
Figure 192:
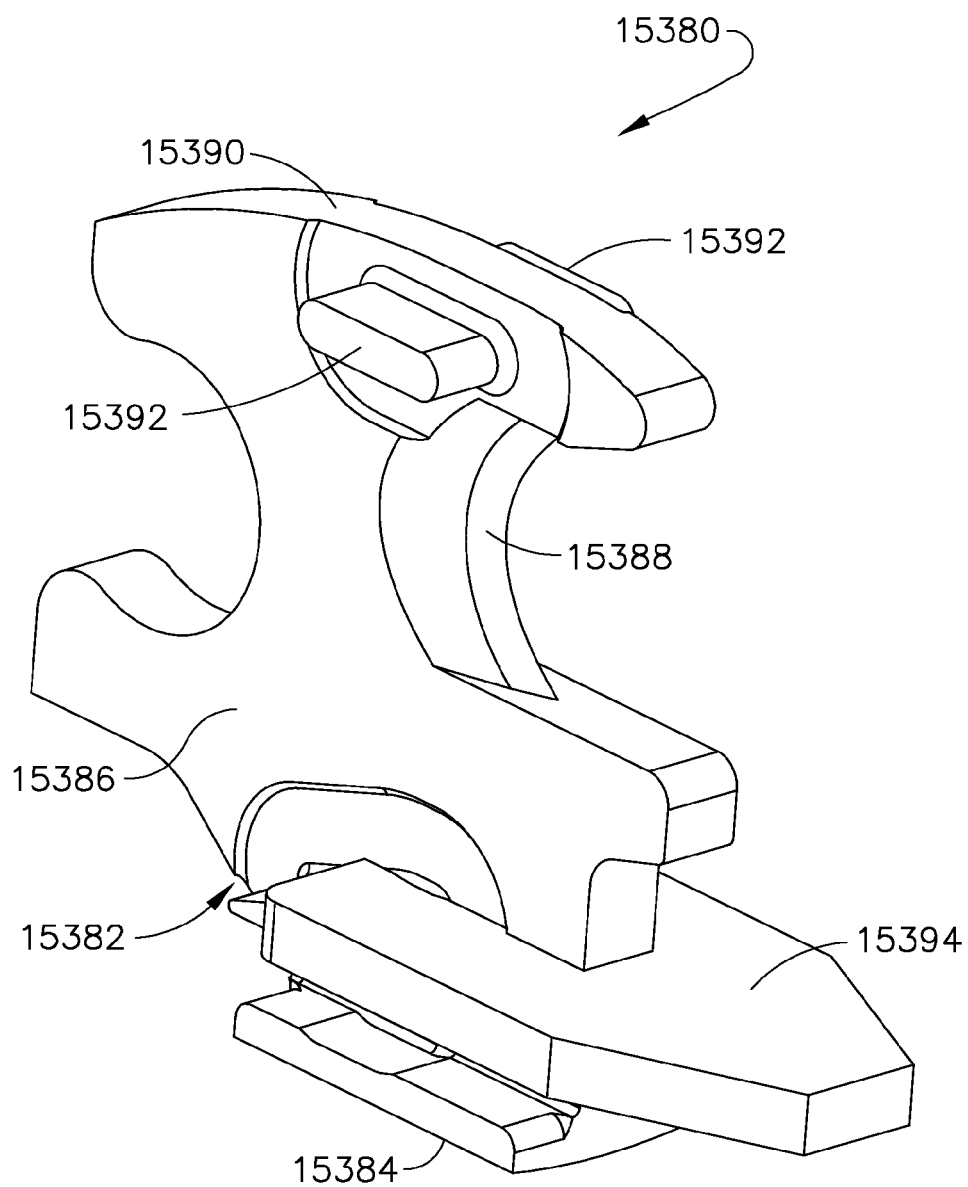
Figure 193:
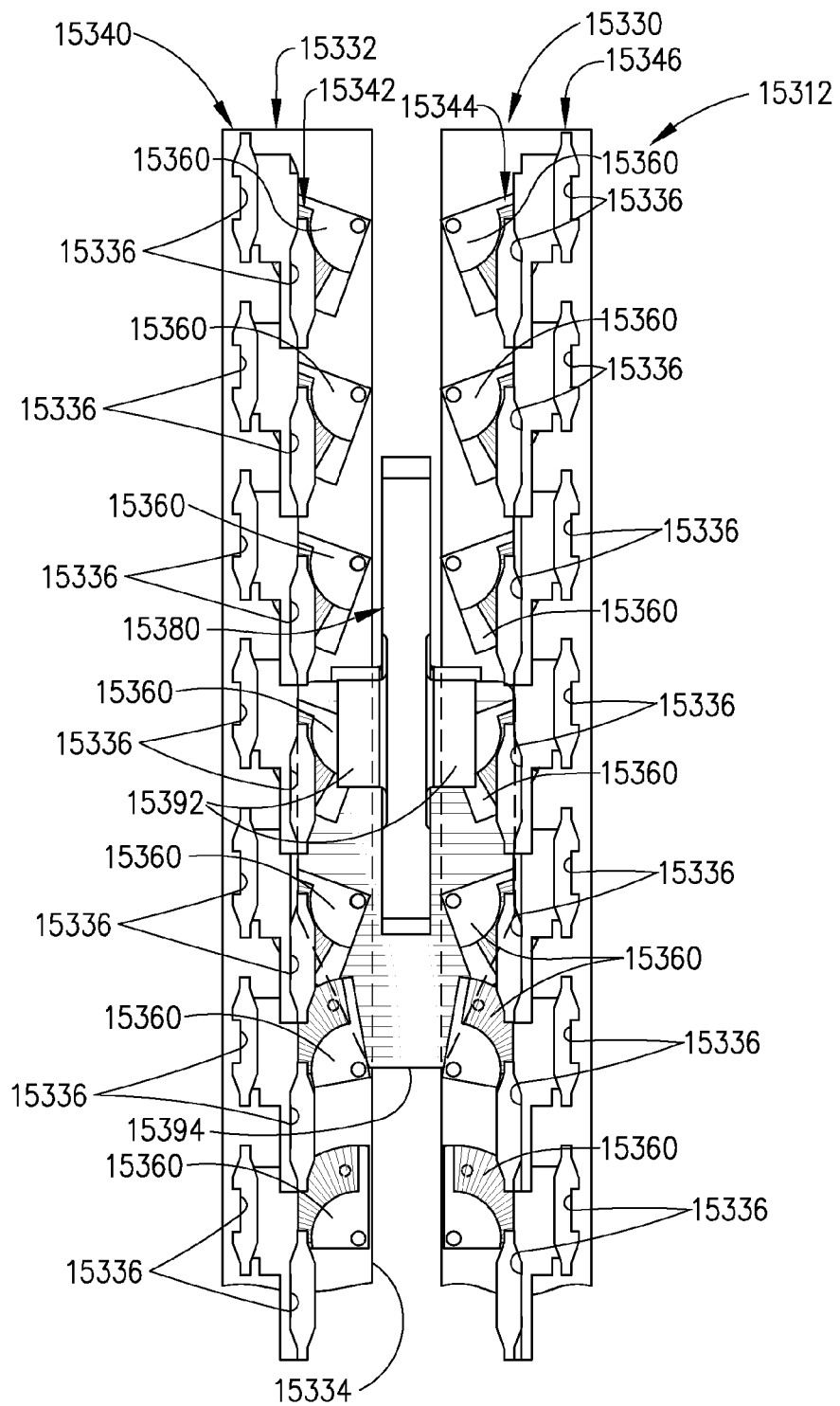
Figure 194:
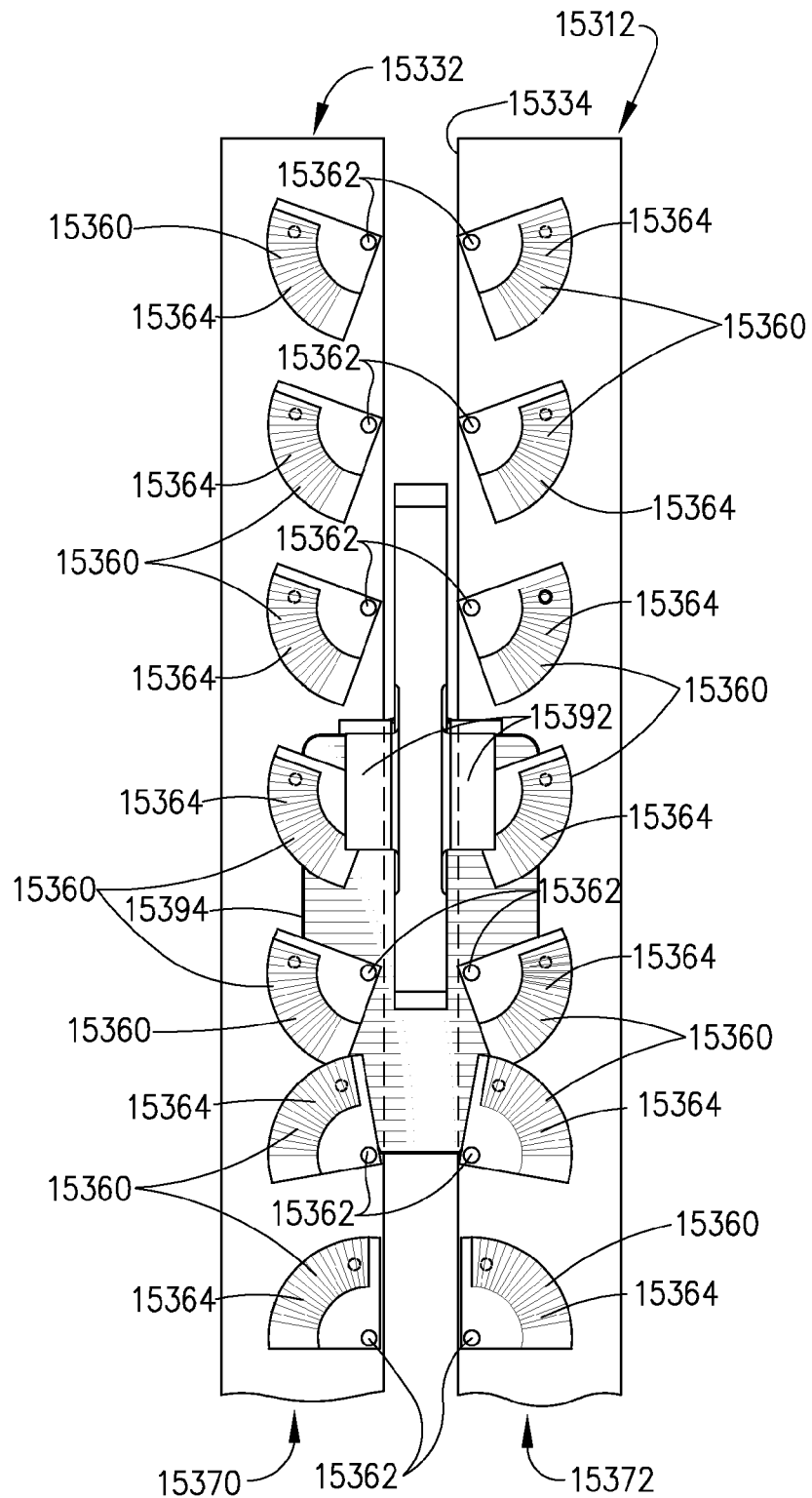
Figure 195:
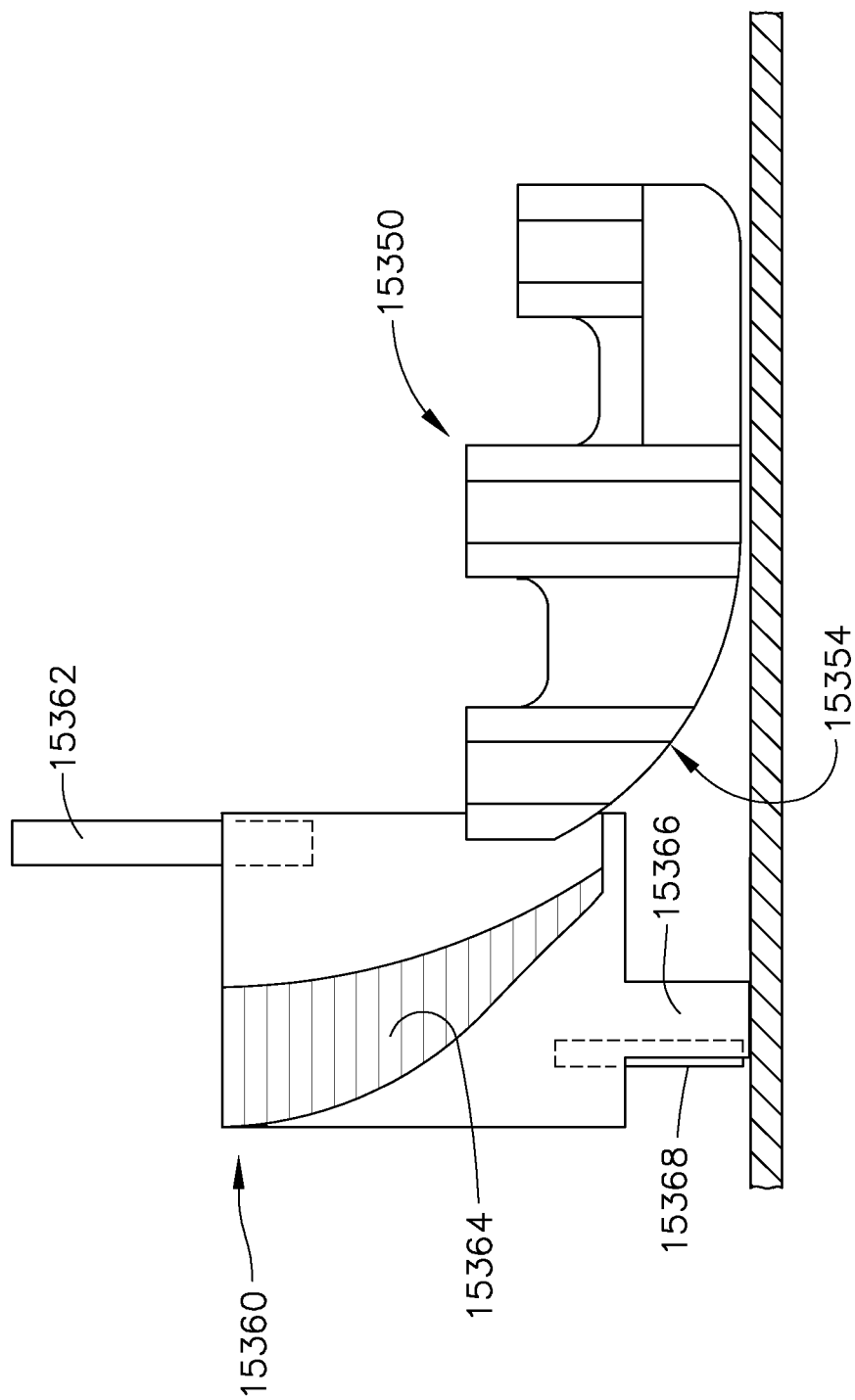
Figure 196:
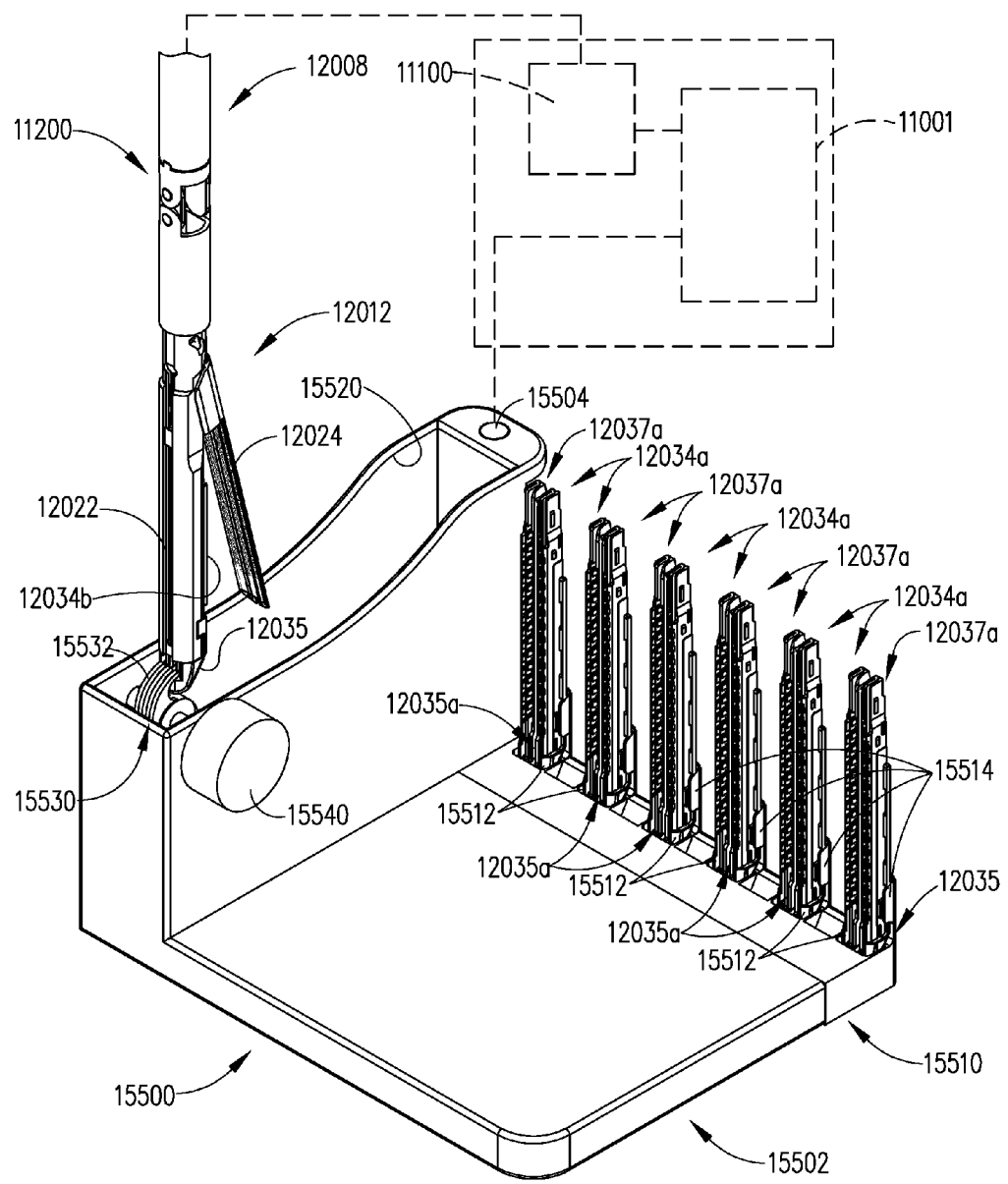
Figure 197:
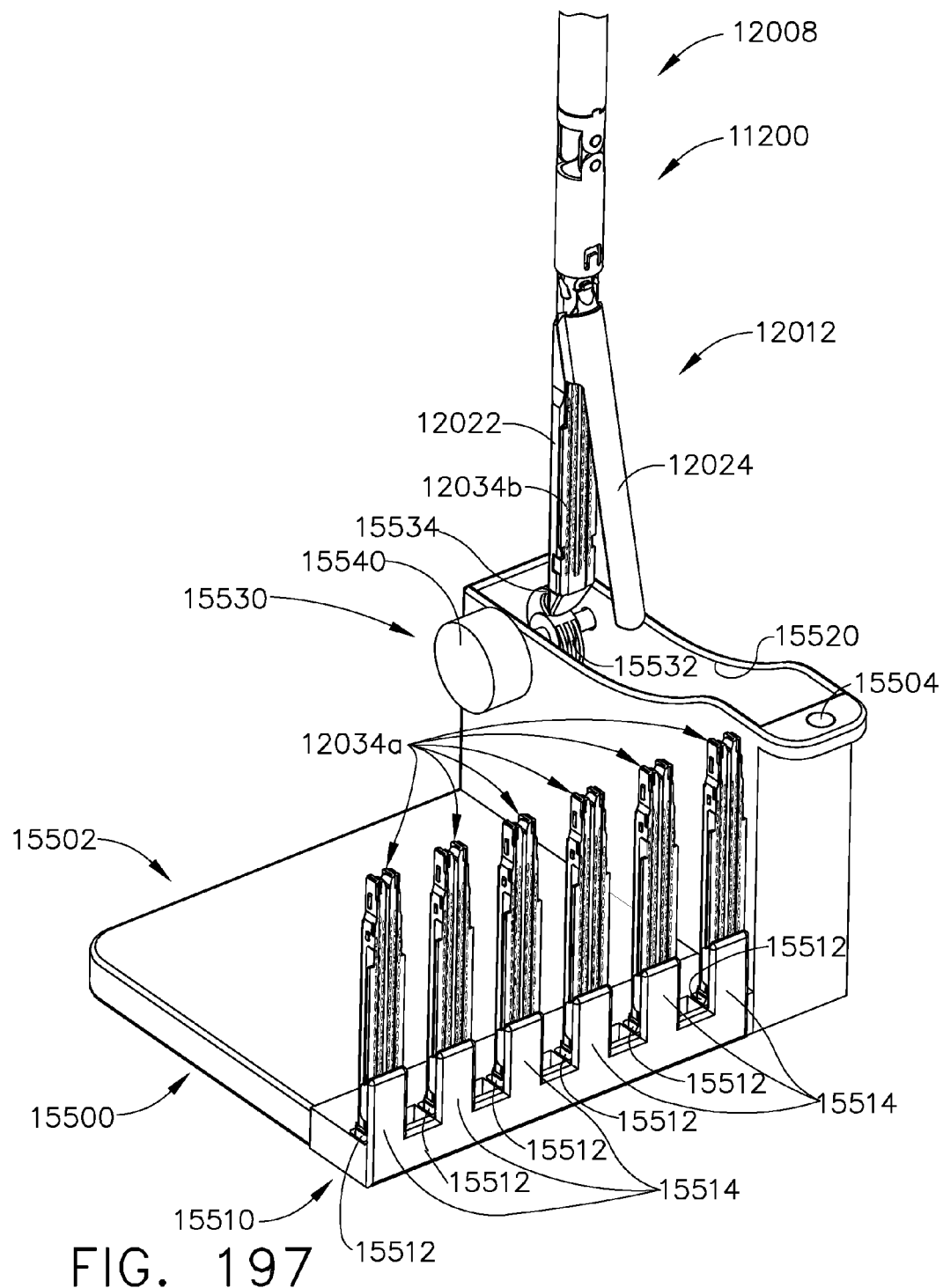
Figure 198:
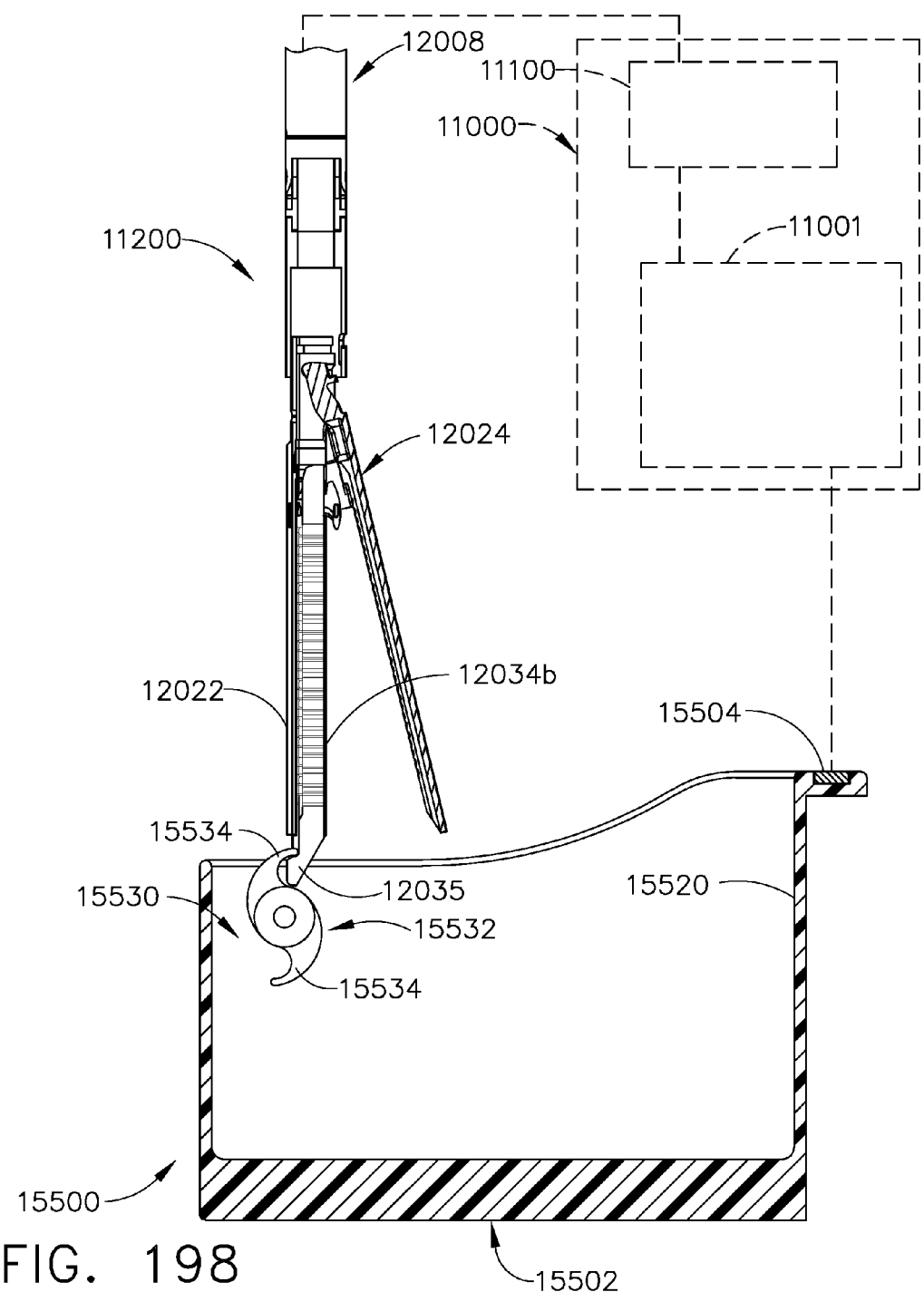
Figure 199:
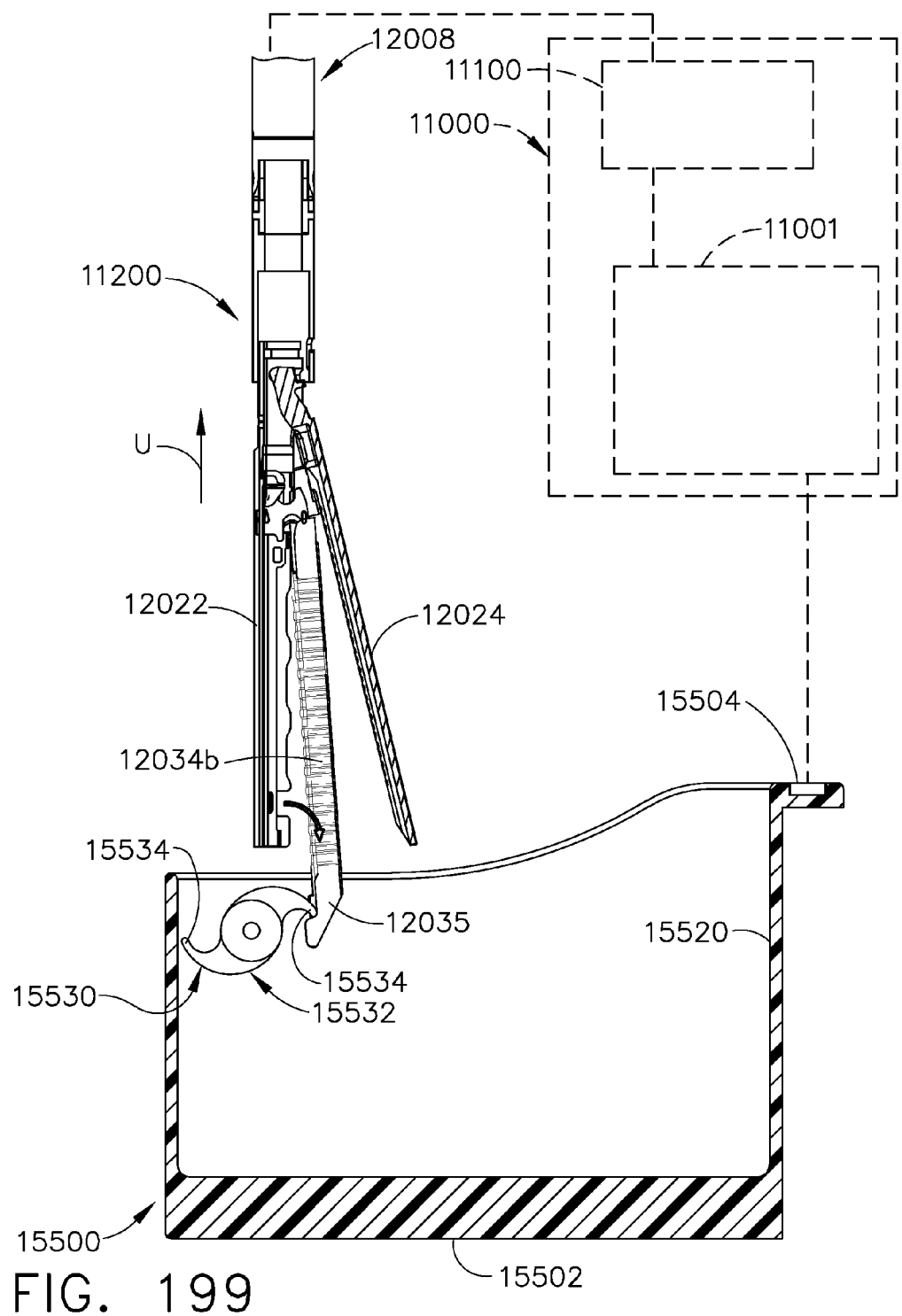
Figure 200:
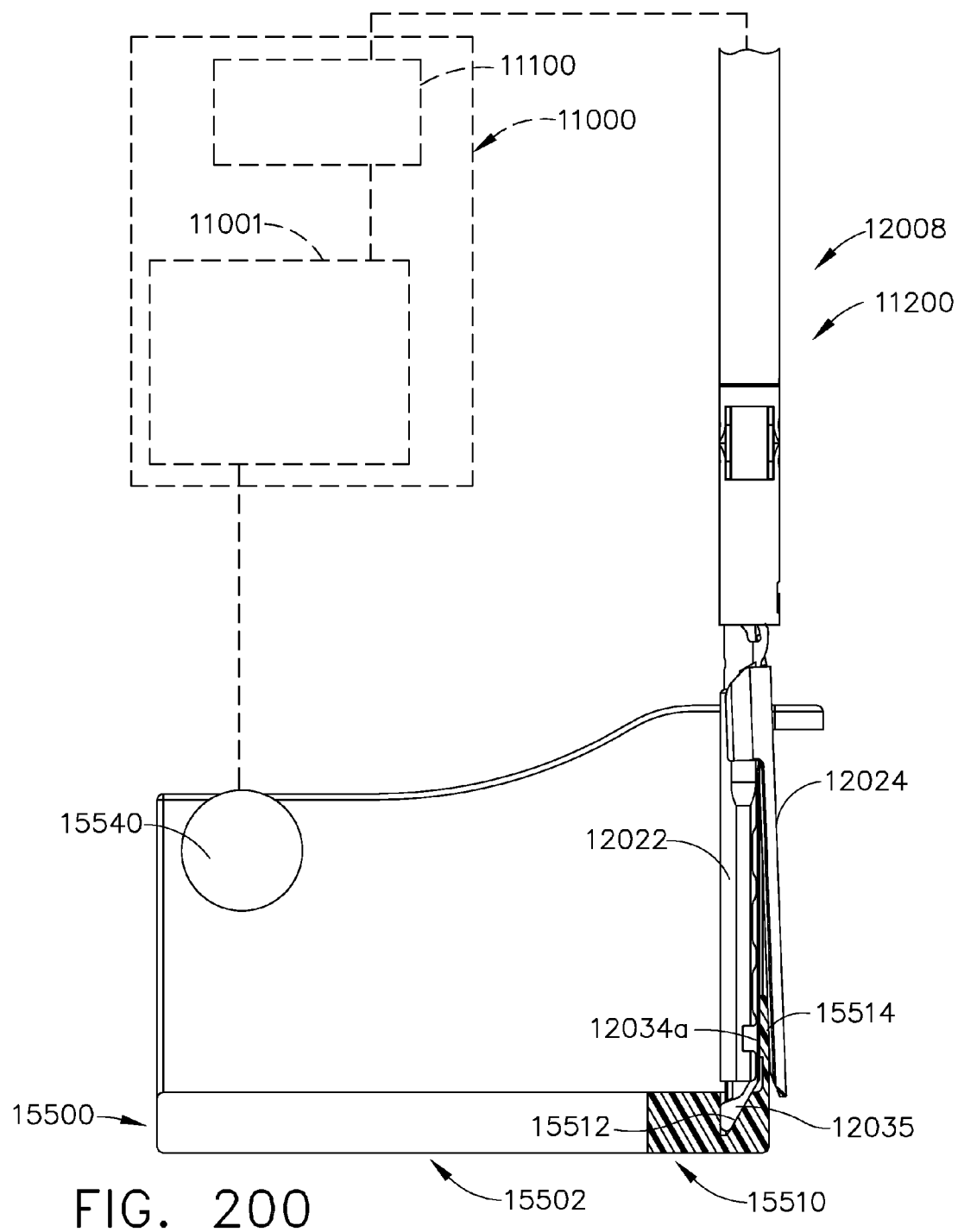
Figure 201:
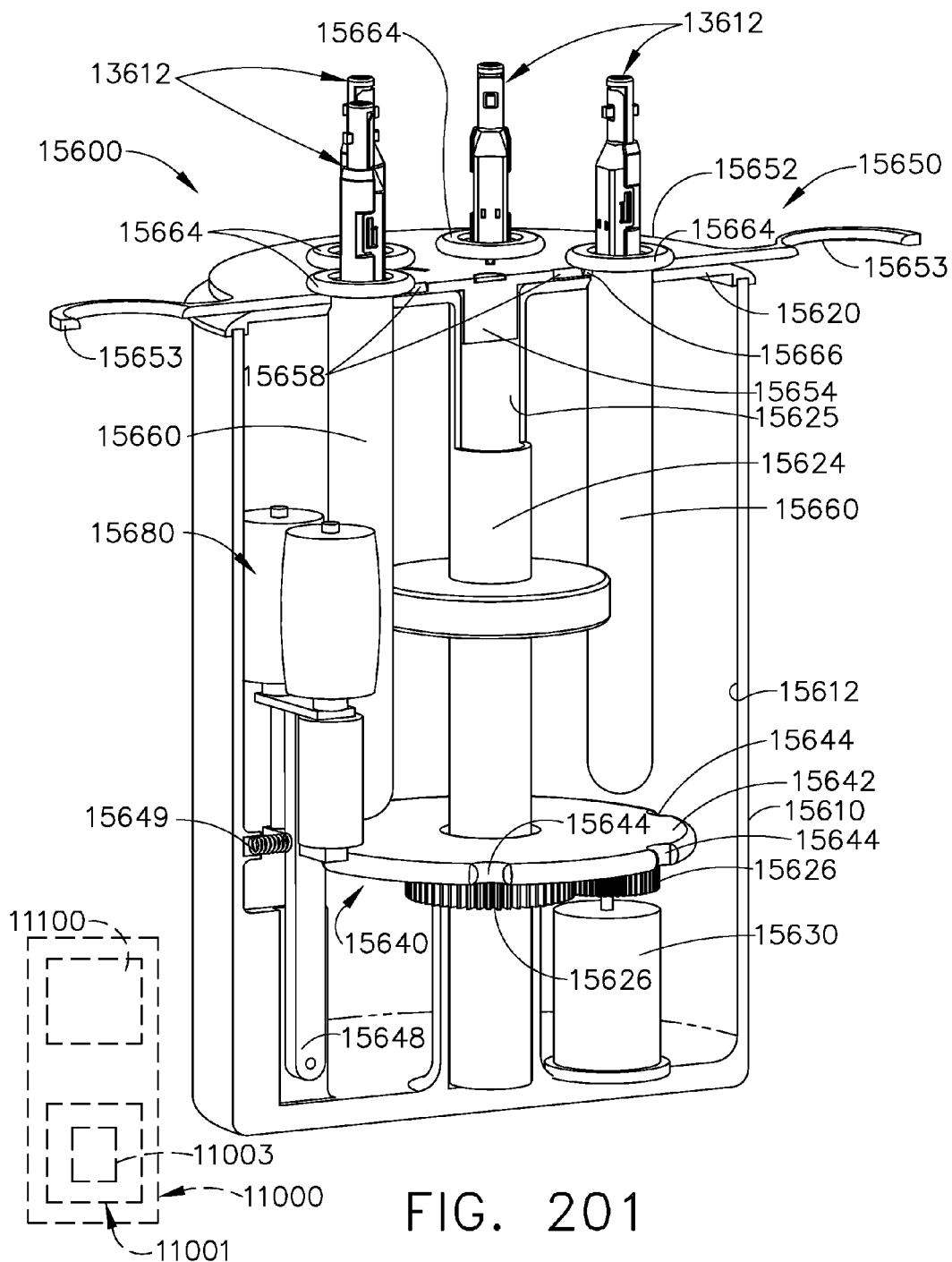
Figure 202:
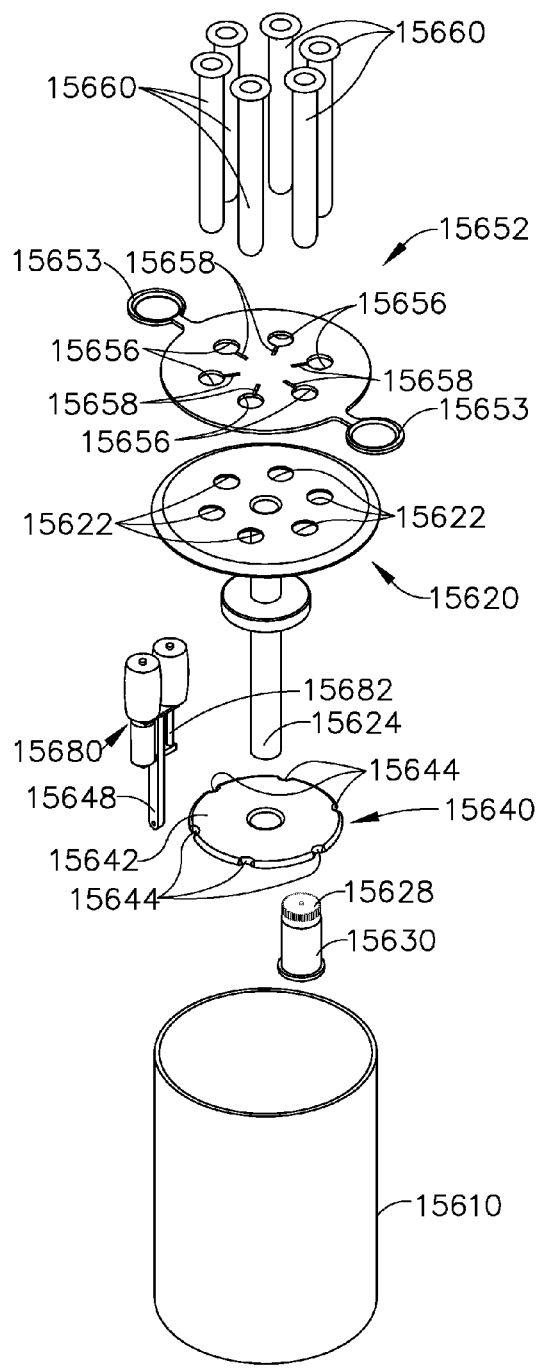
Figure 203:
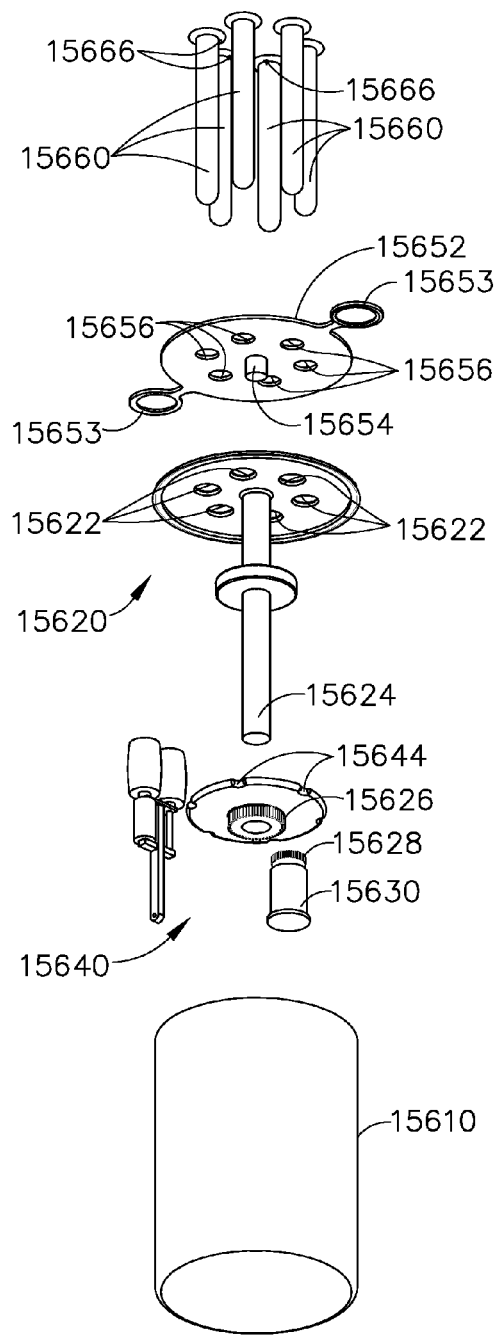
Figure 204:
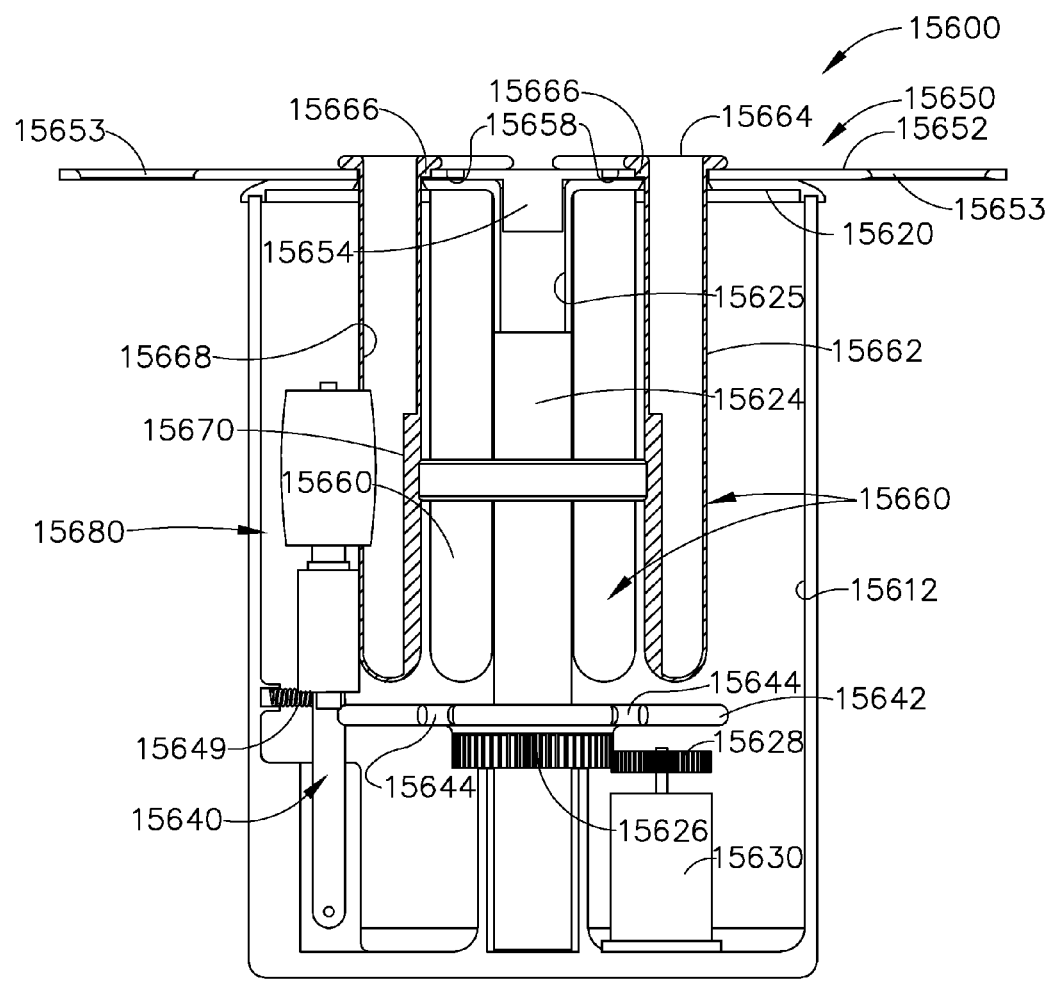
Figure 205:
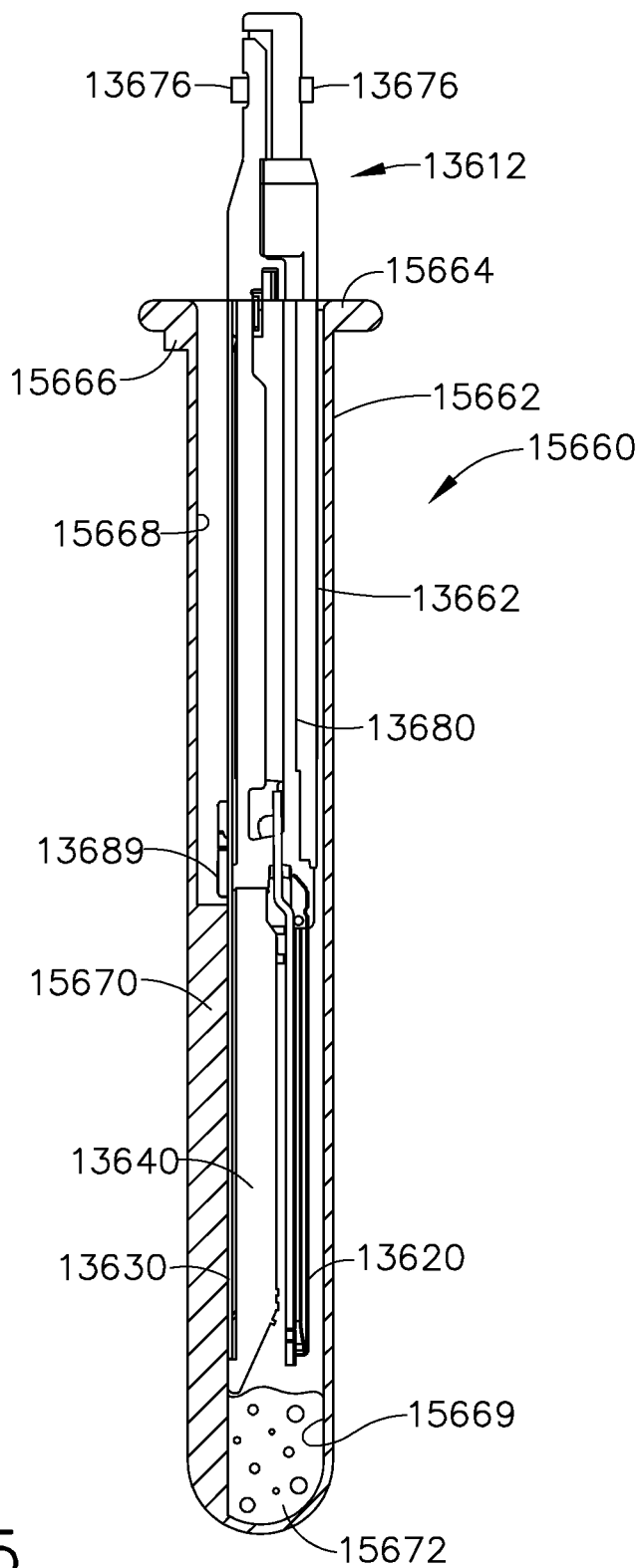
Figure 206:
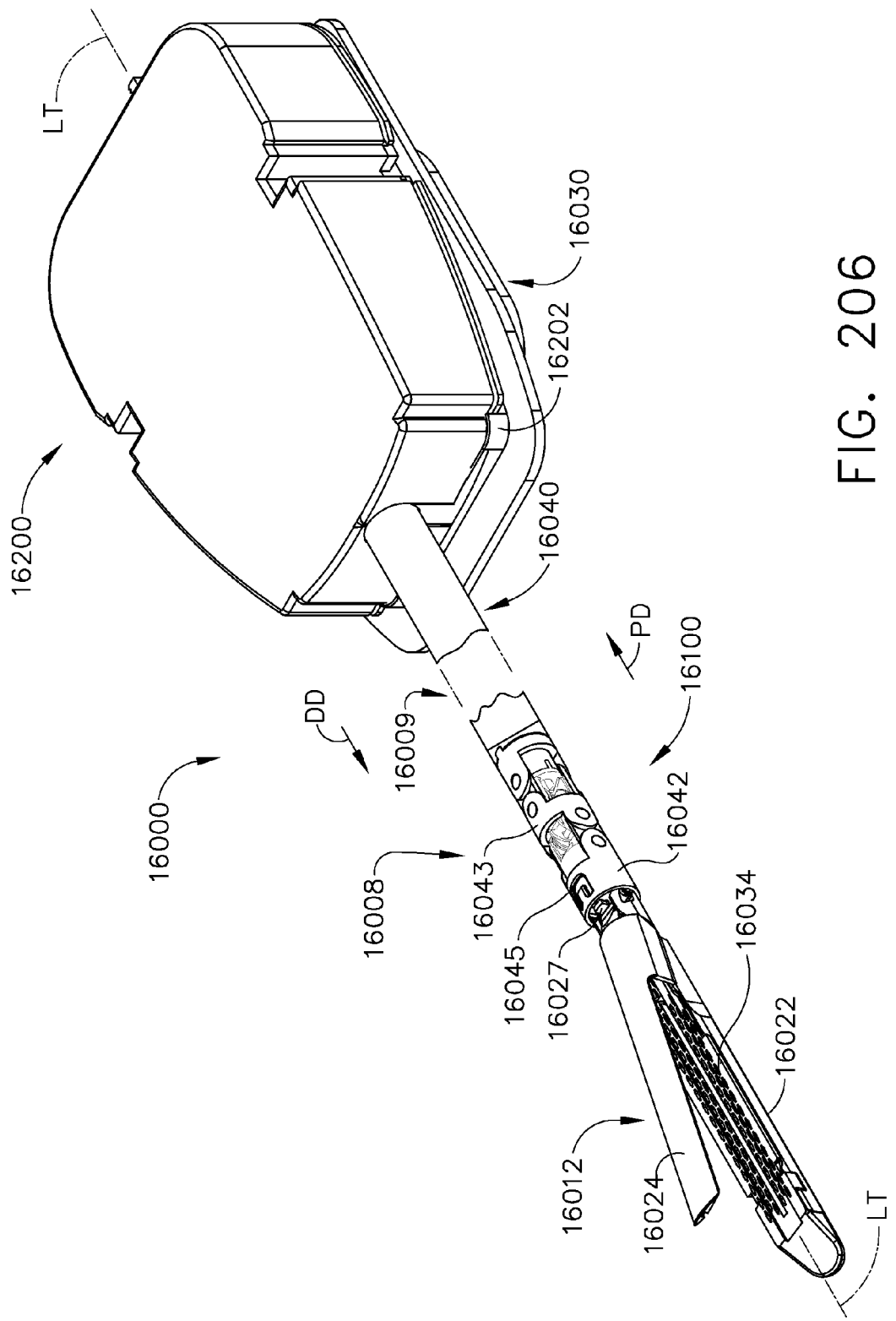
Figure 207:
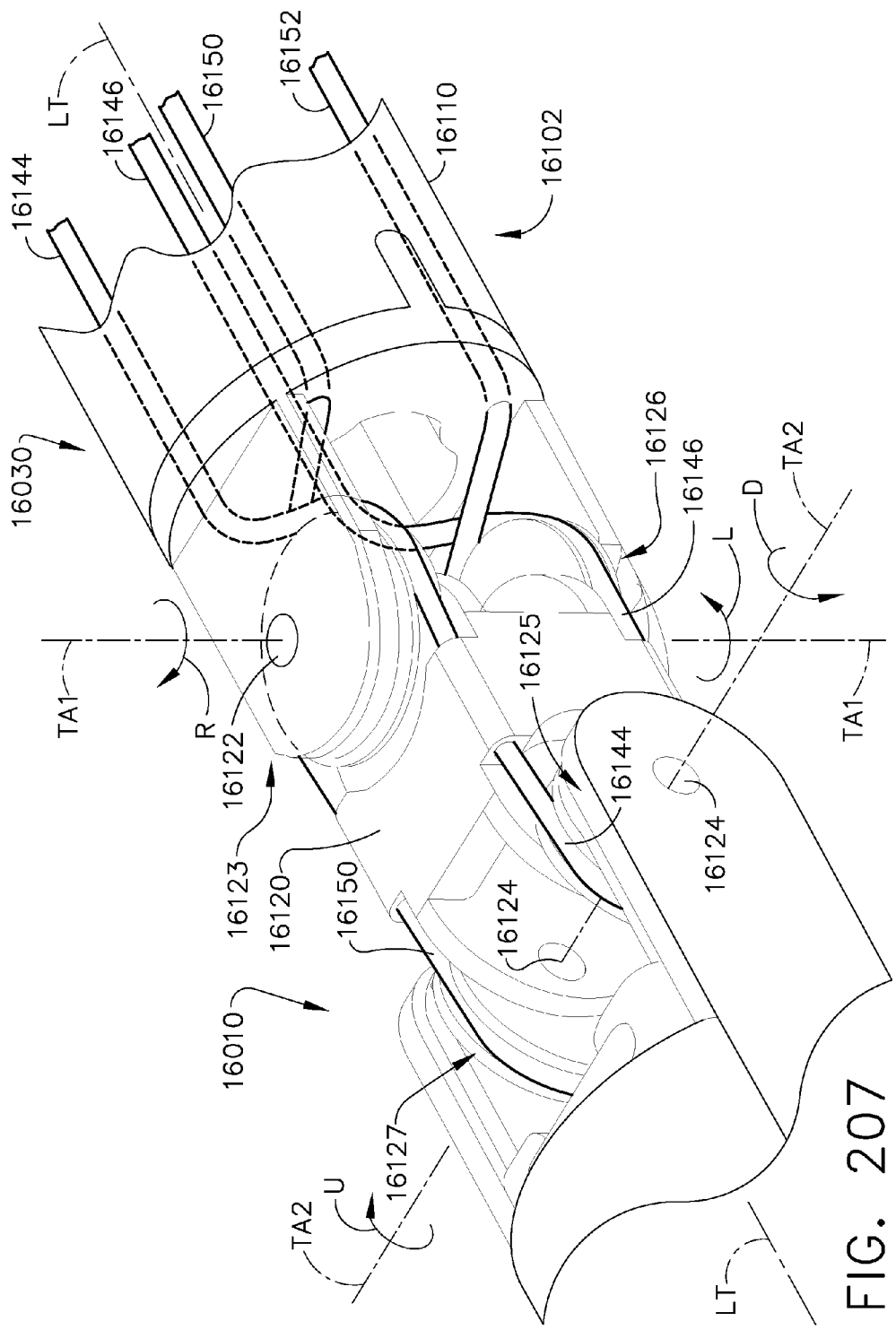
Figure 208:
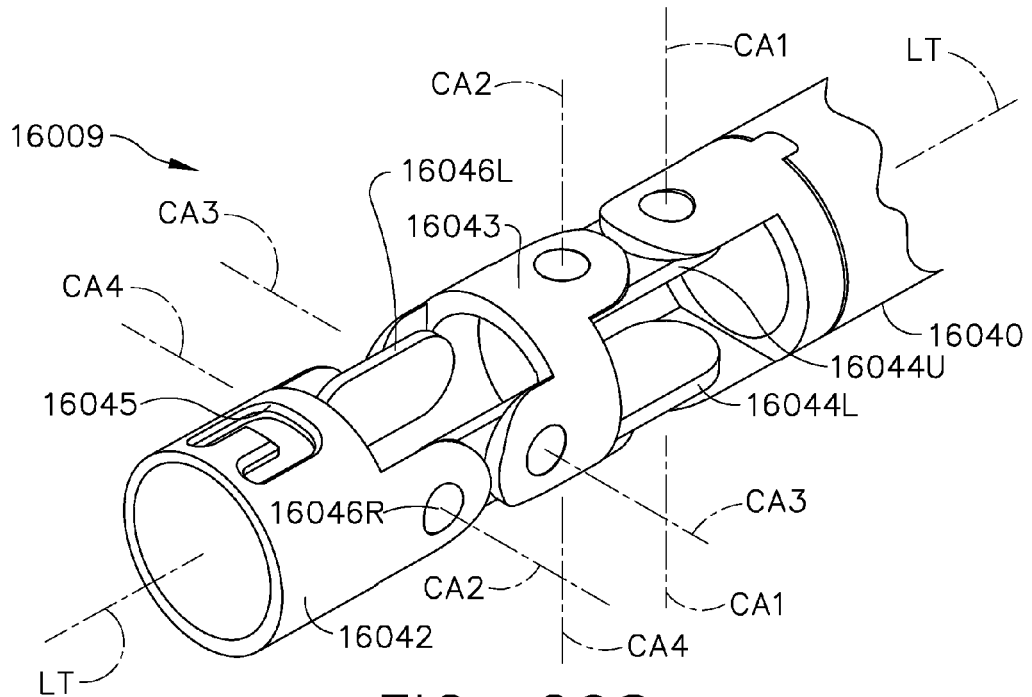
Figure 209:
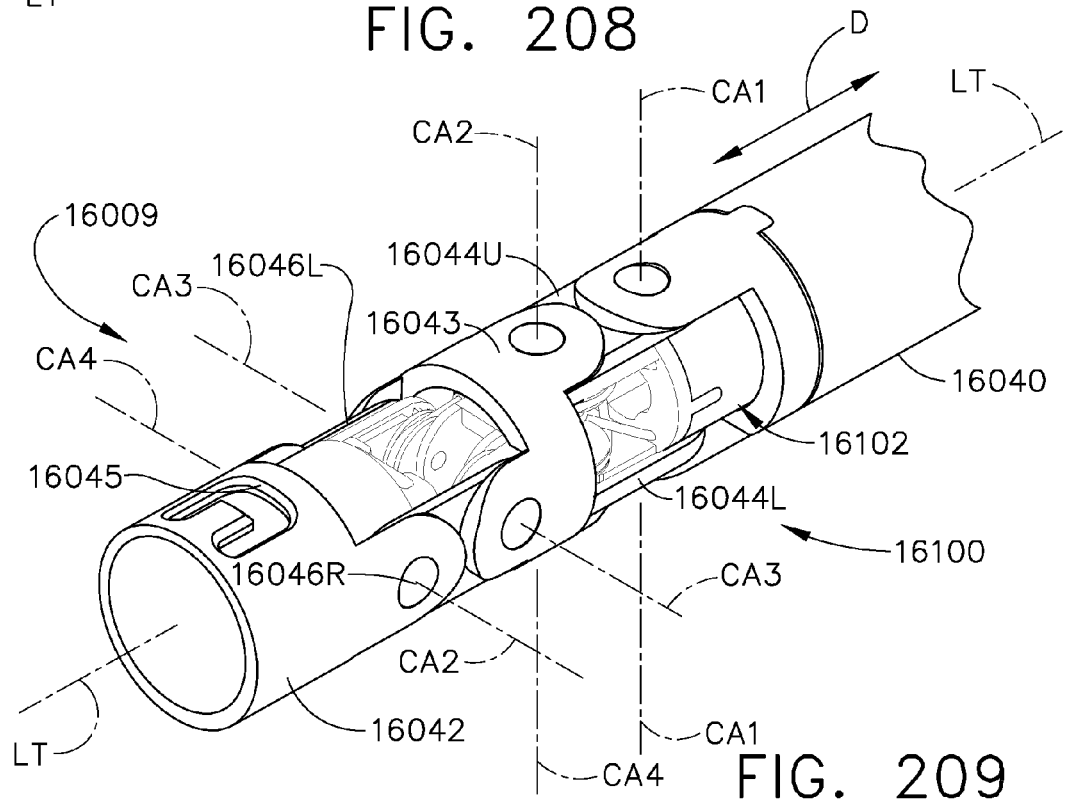
Figure 210:
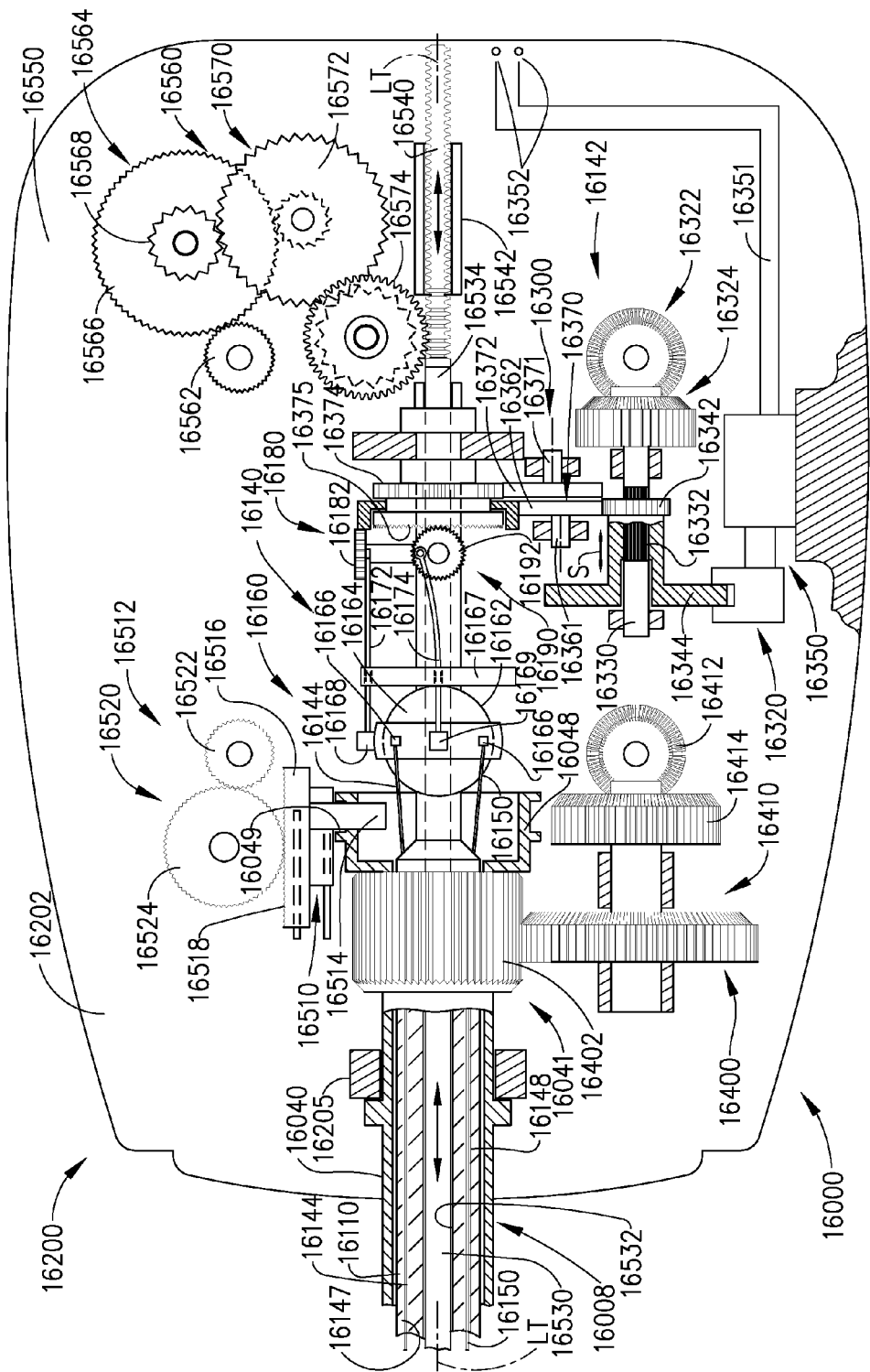
Figure 211:
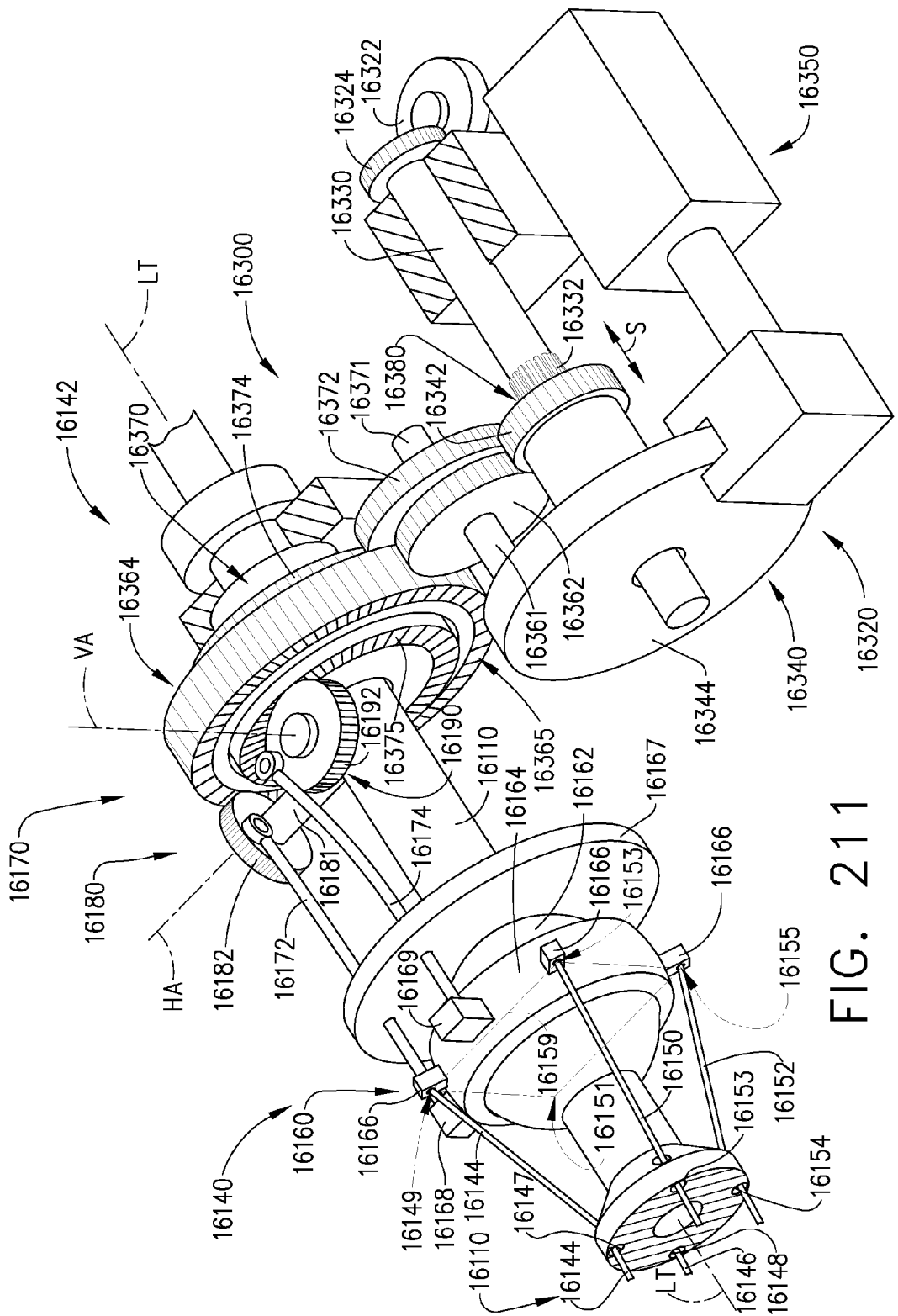
Figure 212:
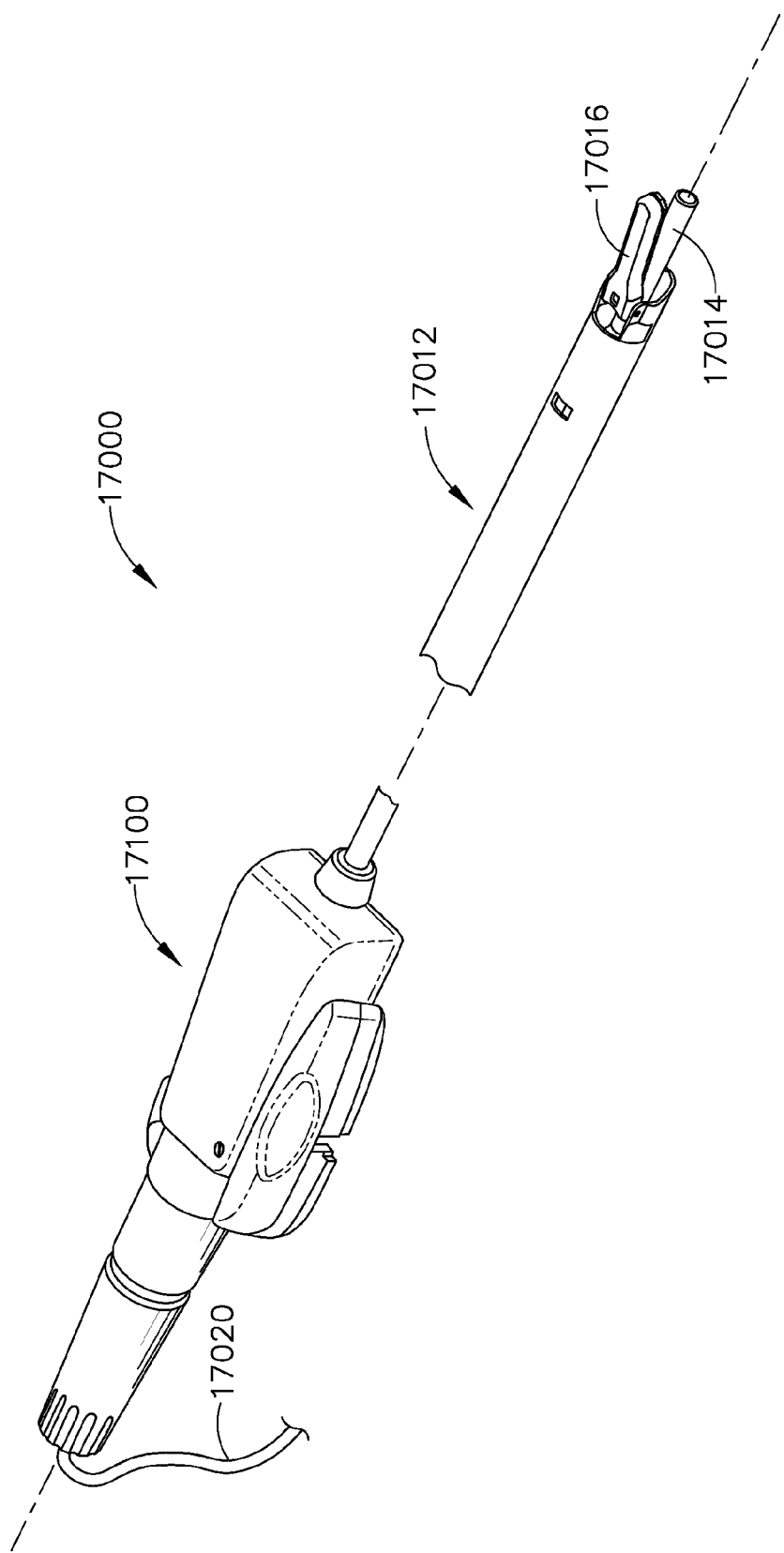
Figure 213:
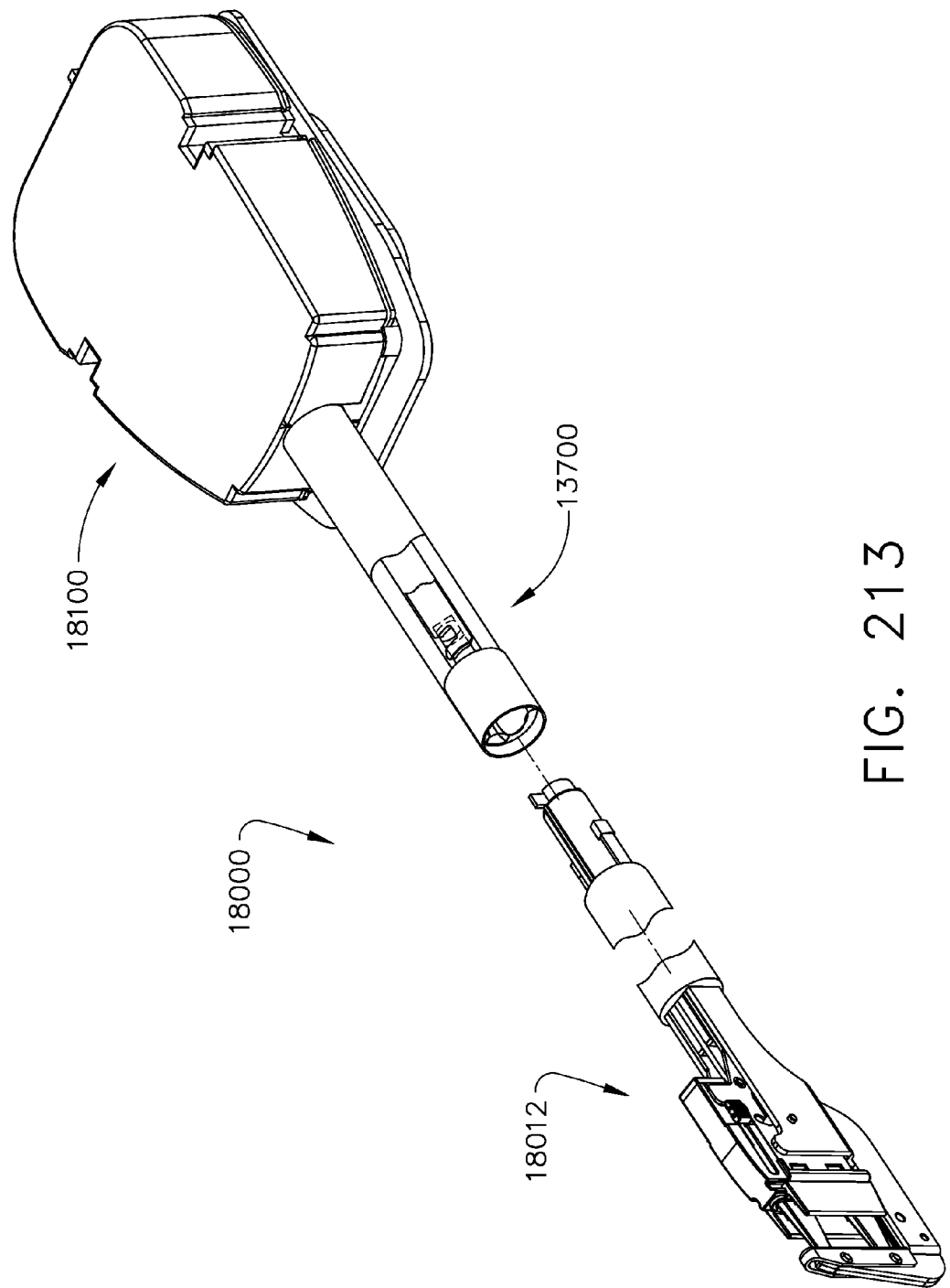

FIG. 168 is another top view of the cable drive transmission embodiment of FIGS. 166 and 167 in a firing position;

FIG. 169 is a perspective view of the cable drive transmission embodiment in the position depicted in FIG. 166;

FIG. 170 is a perspective view of the cable drive transmission embodiment in the position depicted in FIG. 167;

FIG. 171 is a perspective view of the cable drive transmission embodiment in the position depicted in FIG. 168;

FIG. 172 is a perspective view of another surgical tool embodiment of the present invention;

FIG. 173 is a side view of a portion of another cable-driven system embodiment for driving a cutting instrument employed in various surgical end effector embodiments of the present invention;

FIG. 174 is a top view of the cable-driven system embodiment of FIG. 173;

FIG. 175 is a top view of a tool mounting portion embodiment of another surgical tool embodiment of the present invention;

FIG. 176 is a top cross-sectional view of another surgical tool embodiment of the present invention;

FIG. 177 is a cross-sectional view of a portion of a surgical end effector embodiment of a surgical tool embodiment of the present invention;

FIG. 178 is a cross-sectional end view of the surgical end effector of FIG. 177 taken along line 178-178 in FIG. 177;

FIG. 179 is a perspective view of the surgical end effector of FIGS. 177 and 178 with portions thereof shown in cross-section;

FIG. 180 is a side view of a portion of the surgical end effector of FIGS. 177-179;

FIG. 181 is a perspective view of a sled assembly embodiment of various surgical tool embodiments of the present invention;

FIG. 182 is a cross-sectional view of the sled assembly embodiment of FIG. 181 and a portion of the elongated channel of FIG. 180;

FIGS. 183-188 diagrammatically depict the sequential firing of staples in a surgical tool embodiment of the present invention;

FIG. 189 is a partial perspective view of a portion of a surgical end effector embodiment of the present invention;

FIG. 190 is a partial cross-sectional perspective view of a portion of a surgical end effector embodiment of a surgical tool embodiment of the present invention;

FIG. 191 is another partial cross-sectional perspective view of the surgical end effector embodiment of FIG. 190 with a sled assembly axially advancing therethrough;

FIG. 192 is a perspective view of another sled assembly embodiment of another surgical tool embodiment of the present invention;

FIG. 193 is a partial top view of a portion of the surgical end effector embodiment depicted in FIGS. 190 and 191 with the sled assembly axially advancing therethrough;

FIG. 194 is another partial top view of the surgical end effector embodiment of FIG. 193 with the top surface of the surgical staple cartridge omitted for clarity;

FIG. 195 is a partial cross-sectional side view of a rotary driver embodiment and staple pusher embodiment of the surgical end effector depicted in FIGS. 190 and 191;

FIG. 196 is a perspective view of an automated reloading system embodiment of the present invention with a surgical end effector in extractive engagement with the extraction system thereof;

FIG. 197 is another perspective view of the automated reloading system embodiment depicted in FIG. 196;

FIG. 198 is a cross-sectional elevational view of the automated reloading system embodiment depicted in FIGS. 196 and 197;

FIG. 199 is another cross-sectional elevational view of the automated reloading system embodiment depicted in FIGS. 196-198 with the extraction system thereof removing a spent surgical staple cartridge from the surgical end effector;

FIG. 200 is another cross-sectional elevational view of the automated reloading system embodiment depicted in FIGS. 196-199 illustrating the loading of a new surgical staple cartridge into a surgical end effector;

FIG. 201 is a perspective view of another automated reloading system embodiment of the present invention with some components shown in cross-section;

FIG. 202 is an exploded perspective view of a portion of the automated reloading system embodiment of FIG. 201;

FIG. 203 is another exploded perspective view of the portion of the automated reloading system embodiment depicted in FIG. 202;

FIG. 204 is a cross-sectional elevational view of the automated reloading system embodiment of FIGS. 201-203;

FIG. 205 is a cross-sectional view of an orientation tube embodiment supporting a disposable loading unit therein;

FIG. 206 is a perspective view of another surgical tool embodiment of the present invention;

FIG. 207 is a partial perspective view of an articulation joint embodiment of a surgical tool embodiment of the present invention;

FIG. 208 is a perspective view of a closure tube embodiment of a surgical tool embodiment of the present invention;

FIG. 209 is a perspective view of the closure tube embodiment of FIG. 208 assembled on the articulation joint embodiment of FIG. 207;

FIG. 210 is a top view of a portion of a tool mounting portion embodiment of a surgical tool embodiment of the present invention;

FIG. 211 is a perspective view of an articulation drive assembly embodiment employed in the tool mounting portion embodiment of FIG. 210;

FIG. 212 is a perspective view of another surgical tool embodiment of the present invention; and FIG. 213 is a perspective view of another surgical tool embodiment of the present invention.

DETAILED DESCRIPTION

Applicant of the present application also owns the following patent applications that were filed on May 27, 2011 and which are each herein incorporated by reference in their respective entireties:

- U.S. patent application Ser. No. 13/118, 259, entitled "Surgical Instrument With Wireless Communication Between a Control Unit of a Robotic System and Remote Sensor";
- U.S. patent application Ser. No. 13/118,210, entitled "Robotically-Controlled Disposable Motor Driven Loading Unit";
- U.S. patent application Ser. No. 13/118,194, entitled "Robotically-Controlled Endoscopic Accessory Channel";
- U.S. patent application Ser. No. 13/118,253, entitled "Robotically-Controlled Motorized Surgical Instrument";
- U.S. patent application Ser. No. 13/118,190, entitled "Robotically-Controlled Motorized Cutting and Fastening Instrument";
- U.S. patent application Ser. No. 13/118,223, entitled "Robotically-Controlled Shaft Based Rotary Drive Systems For Surgical Instruments";
- U.S. patent application Ser. No. 13/118,263, entitled "Robotically-Controlled Surgical Instrument Having Recording Capabilities";
- U.S. patent application Ser. No. 13/118,272, entitled "Robotically-Controlled Surgical Instrument With Force Feedback Capabilities";
- U.S. patent application Ser. No. 13/118,246, entitled "Robotically-Driven Surgical Instrument With E-Beam Driver";
- U.S. patent application Ser. No. 13/118,241, entitled "Surgical Stapling Instruments With Rotatable Staple Deployment Arrangements".

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Uses of the phrases "in various embodiments," "in some embodiments," "in one embodiment", or "in an embodiment", or the like, throughout the specification are not necessarily all referring to the same embodiment. Furthermore, the particular features, structures, or characteristics of one or more embodiments may be combined in any suitable manner in one or more other embodiments. Such modifications and variations are intended to be included within the scope of the present invention.

Figure 1:
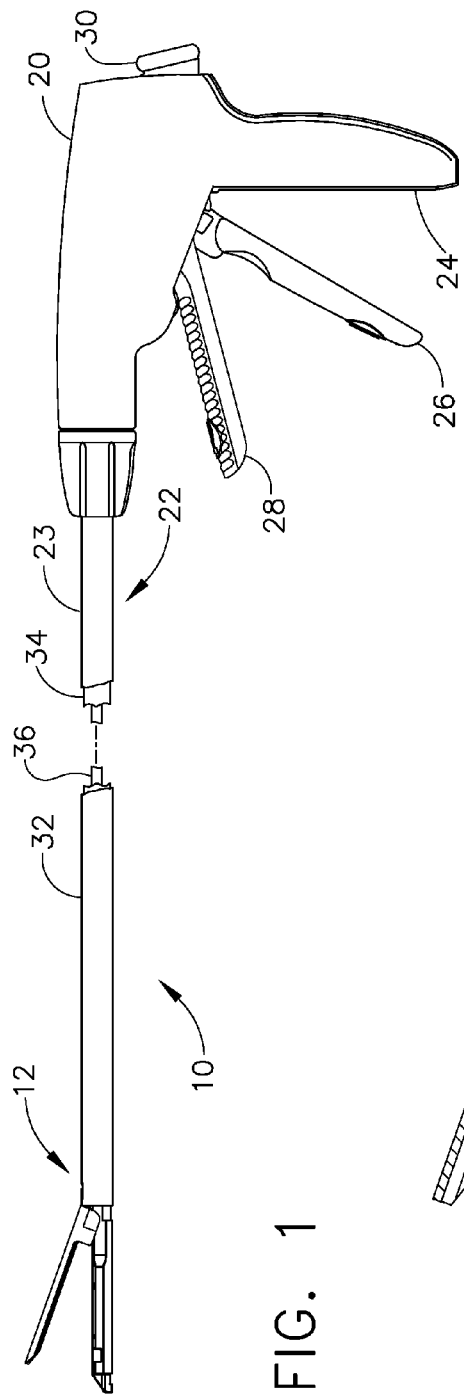
FIG. 1 depicts a partially cut away side elevation view of a surgical stapling and severing instrument in an open position according to various embodiments of the present invention.
Figure 2:
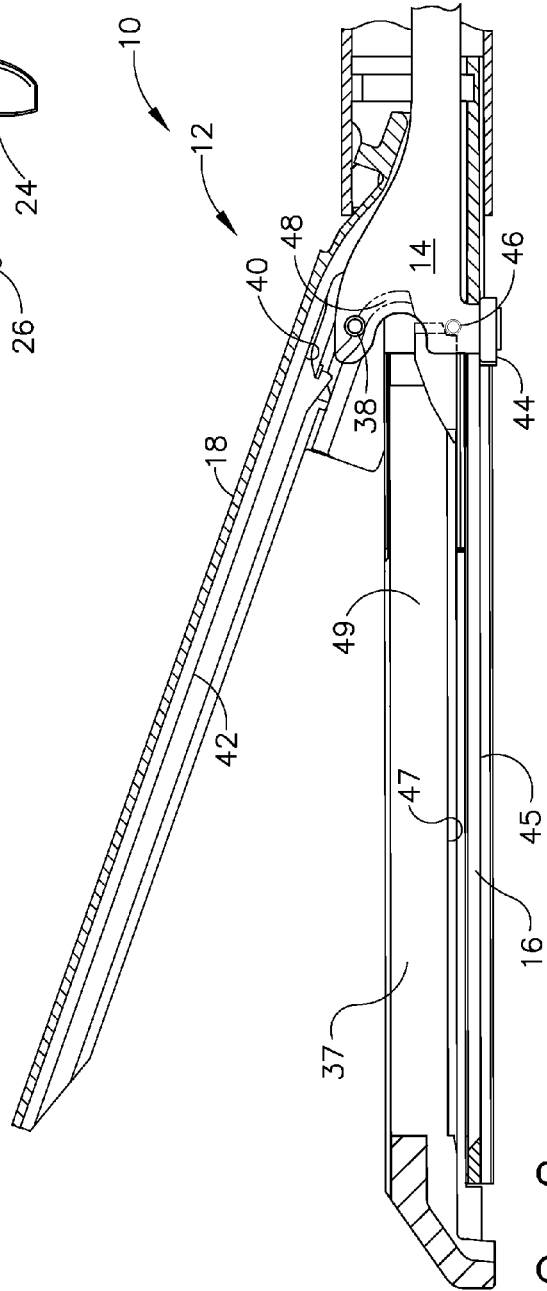
FIG. 2 depicts a cross-sectional side elevation detail view along the line 2-2 of FIG. 1 of an end effector of the surgical stapling and severing instrument according to various embodiments of the present invention.

Turning to the figures, wherein like numerals denote like components throughout the several views, FIGS. 1 and 2 depict one embodiment of a surgical stapling and severing instrument 10 that is capable of practicing the unique benefits of the present invention. It should be recognized, however, that the unique and novel aspects of the present invention may be advantageously employed in connection with a variety of other staplers and stapler instruments without departing from the spirit and scope of the present invention. Accordingly, the scope of protection afforded to the various embodiments of the present invention should not be limited to use only with the specific type of surgical stapling and severing instruments described herein.

As can be seen in FIGS. 1 and 2, the surgical stapling and severing instrument 10 incorporates an end effector 12 having an actuator or E-beam firing mechanism ("firing bar") 14 that advantageously controls the spacing of the end effector 12. In particular, an elongate channel 16 and a pivotally translatable anvil 18 are maintained at a spacing that assures effective stapling and severing. The problems are avoided associated with varying amounts of tissue being captured in the end effector 12.

It will be appreciated that the terms "proximal" and "distal" are used herein with reference to a clinician gripping a handle of an instrument. Thus, the end effector 12 is distal with respect to the more proximal handle portion 20. It will be further appreciated that for convenience and clarity, spatial terms such as "vertical" and "horizontal" are used herein with respect to the drawings. However, surgical instruments are used in many orientations and positions, and these terms are not intended to be limiting and absolute.

The surgical and stapling and severing instrument 10 includes a handle portion 20 that is connected to an implement portion 22, the latter further comprising a shaft 23 distally terminating in the end effector 12. The handle portion 20 includes a pistol grip 24 toward which a closure trigger 26 is pivotally drawn by the clinician to cause clamping, or closing, of the anvil 18 toward the elongate channel 16 of the end effector 12. A firing trigger 28 is farther outboard of the closure trigger 26 and is pivotally drawn by the clinician to cause the stapling and severing of clamped tissue in the end effector 12.

In practice, closure trigger 26 is actuated first. Once the clinician is satisfied with the positioning of the end effector 12, the clinician may draw back the closure trigger 26 to its fully closed, locked position proximate to the pistol grip 24. Then, the firing trigger 28 is actuated. The firing trigger 28 springedly returns when the clinician removes pressure. A release button 30 when depressed on the proximal end of the handle portion 20 releases any locked closure trigger 26.

A closure sleeve 32 encloses a frame 34, which in turn encloses a firing drive member 36 that is positioned by the firing trigger 28. The frame 34 connects the handle portion 20 to the end effector 12. With the closure sleeve 32 withdrawn proximally by the closure trigger 26 as depicted, the anvil 18 springedly opens, pivoting away from the elongate channel 16 and translating proximally with the closure sleeve 32. The elongate channel 16 receives a staple cartridge 37.

Figure 3:
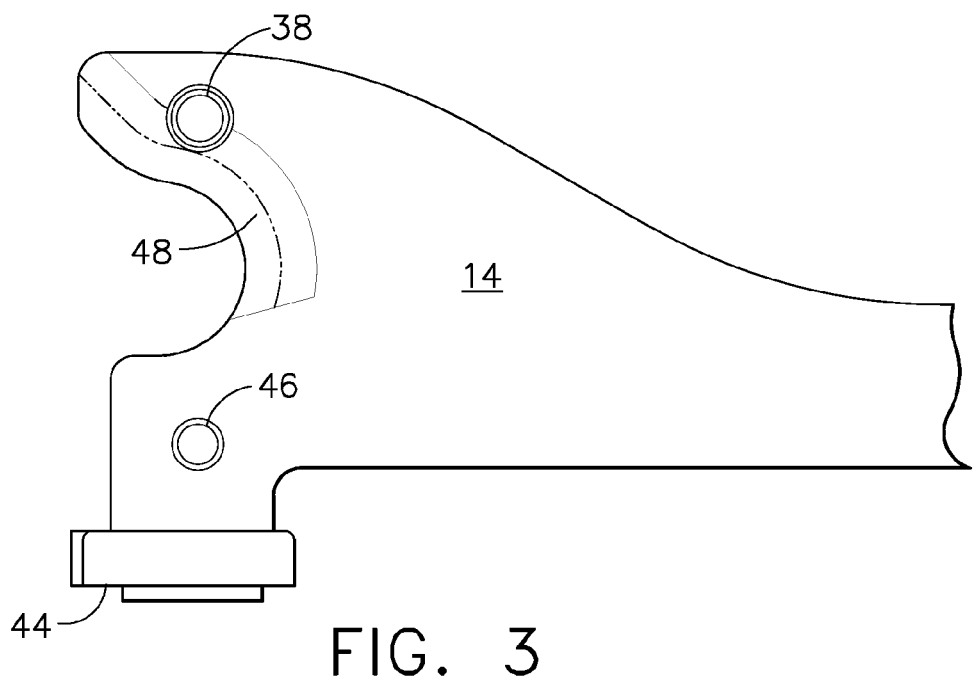
FIG. 3 depicts an enlarged side elevation view of the firing bar of the surgical stapling and severing instrument of FIG. 2 according to various embodiments of the present invention.
Figure 4:
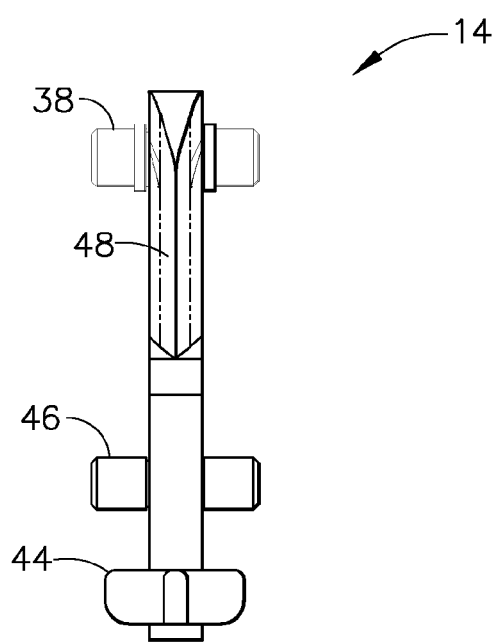
FIG. 4 depicts an enlarged front view of the firing bar of the surgical stapling and severing instrument of FIG. 2 according to various embodiments of the present invention.
Figure 5:
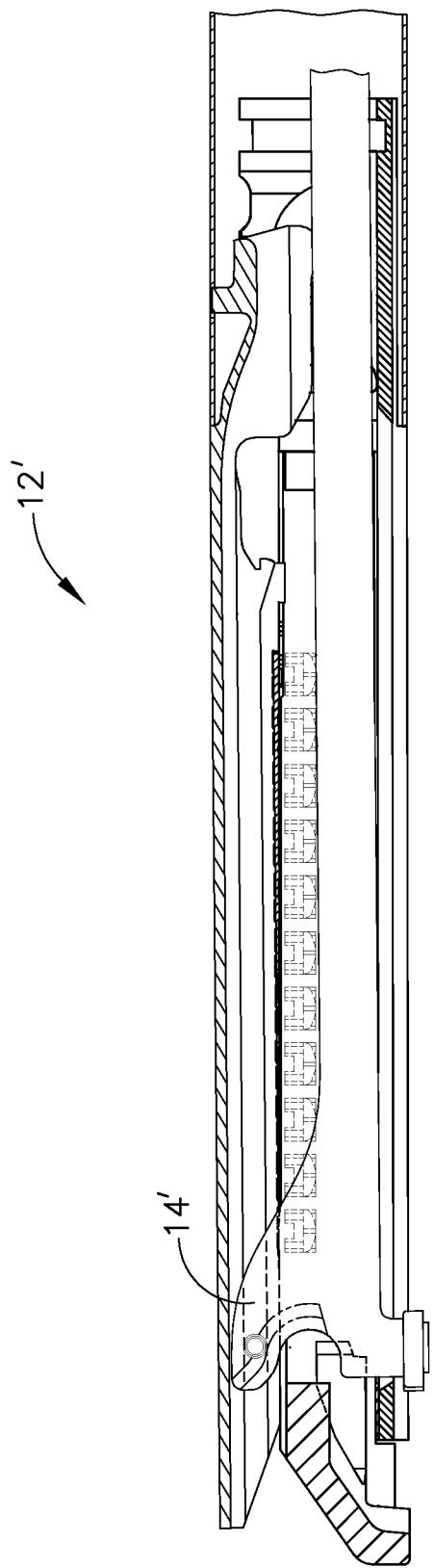
FIG. 5 depicts a cross-sectional side elevation detail view of an alternative end effector for the surgical stapling and severing instrument of FIG. 1, incorporating a firing bar that lacks a middle pin for preventing pinching of the end effector, according to various embodiments of the present invention.

With particular reference to FIGS. 2-4, the firing bar 14 includes three vertically spaced pins that control the spacing of the end effector 12 during firing. In particular, an upper pin 38 is staged to enter an anvil pocket 40 near the pivot between the anvil 18 and elongate channel 16. When fired with the anvil 18 closed, the upper pin 38 advances distally within a longitudinal anvil slot 42 extending distally through anvil 18. Any minor upward deflection in the anvil 18 is overcome by a downward force imparted by the upper pin 38. Firing bar 14 also includes a lowermost pin, or firing bar cap, 44 that upwardly engages a channel slot 45 in the elongate channel 16, thereby cooperating with the upper pin 38 to draw the anvil 18 and the elongate channel 16 slightly closer together in the event of excess tissue clamped therebetween. The firing bar 14 advantageously includes a middle pin 46 that passes through a firing drive slot 47 formed in a lower surface of the cartridge 300 and an upward surface of the elongate channel 16, thereby driving the staples therein as described below. The middle pin 46, by sliding against the elongate channel 16, advantageously resists any tendency for the end effector 12 to be pinched shut at its distal end. To illustrate an advantage of the middle pin 46, FIG. 5 depicts an alternative end effector 12' that lacks a middle pin on a firing bar 14'. In this depiction, the end effector 12' is allowed to pinch shut at its distal end, which tends to impair desired staple formation.

Returning to FIGS. 2-4, a distally presented cutting edge 48 between the upper and middle pins 38, 46 on the firing bar 14 traverses through a proximally presented, vertical slot 49 in the cartridge 37 to sever clamped tissue. The affirmative positioning of the firing bar 14 with regard to the elongate channel 16 and anvil 18 assure that an effective cut is performed. The affirmative vertical spacing provided by the E-Beam firing bar 14 is suitable for the limited size available for endoscopic devices. Moreover, the E-Beam firing bar 14 enables fabrication of an anvil 15 with a camber imparting a vertical deflection at its distal end, similar to the position depicted in FIG. 5. This cambered anvil 15 advantageously assists in achieving the desired gap in the end effector 12 even with an anvil 15 having a reduced thickness, which may be more suited to the size limitations of an endoscopic device.

With reference to FIGS. 6-9, the handle portion 20 is comprised of first and second base sections 50 and 52, which are molded from a polymeric material such as a glass-filled polycarbonate. The first base section 50 is provided with a plurality of cylindrically-shaped pins 54. The second base section 52 includes a plurality of extending members 56, each having a hexagonal-shaped opening 58. The cylindrically-shaped pins 54 are received within the hexagonal-shaped openings 58 and are frictionally held therein for maintaining the first and second base sections 50 and 52 in assembly.

A rotating knob 60 has a bore 62 extending completely through it for engaging and rotating the implement portion 22 about its longitudinal axis. The rotating knob 60 includes an inwardly protruding boss 64 extending along at least a portion of the bore 62. The protruding boss 64 is received within a longitudinal slot 66 formed at a proximal portion of the closure sleeve 32 such that rotation of the rotating knob 60 effects rotation of the closure sleeve 32. It will be appreciated that the boss 64 further extends through frame 34 and into contact with a portion of the firing drive member 36 to effect their rotation as well. Thus, the end effector 12 (not shown in FIGS. 6-9) rotates with the rotating knob 60.

A proximal end 68 of the frame 34 passes proximally through the rotating knob 60 and is provided with a circumferential notch 70 that is engaged by opposing channel securement members 72 extending respectively from the base sections 50 and 52. Only the channel securement member 72 of the second base section 52 is shown. The channel securement members 72, extending from the base sections 50, 52 serve to secure the frame 34 to the handle portion 20 such that the frame 34 does not move longitudinally relative to the handle portion 20.

The closure trigger 26 has a handle section 74, a gear segment section 76, and an intermediate section 78. A bore 80 extends through the intermediate section 78. A cylindrical support member 82 extending from the second base section 52 passes through the bore 80 for pivotably mounting the closure trigger 26 on the handle portion 20. A second cylindrical support member 83 extending from the second base section 52 passes through a bore 81 of firing trigger 28 for pivotally mounting on the handle portion 20. A hexagonal opening 84 is provided in the cylindrical support member 83 for receiving a securement pin (not shown) extending from the first base section 50.

A closure yoke 86 is housed within the handle portion 20 for reciprocating movement therein and serves to transfer motion from the closure trigger 26 to the closure sleeve 32. Support members 88 extending from the second base section 52 and securement member 72, which extends through a recess 89 in the yoke 86, support the yoke 86 within the handle portion 20.

A proximal end 90 of the closure sleeve 32 is provided with a flange 92 that is snap-fitted into a receiving recess 94 formed in a distal end 96 of the yoke 86. A proximal end 98 of the yoke 86 has a gear rack 100 that is engaged by the gear segment section 76 of the closure trigger 26. When the closure trigger 26 is moved toward the pistol grip 24 of the handle portion 20, the yoke 86 and, hence, the closure sleeve 32 move distally, compressing a spring 102 that biases the yoke 86 proximally. Distal movement of the closure sleeve 32 effects pivotal translation movement of the anvil 18 distally and toward the elongate channel 16 of the end effector 12 and proximal movement effects closing, as discussed below.

Figure 8:
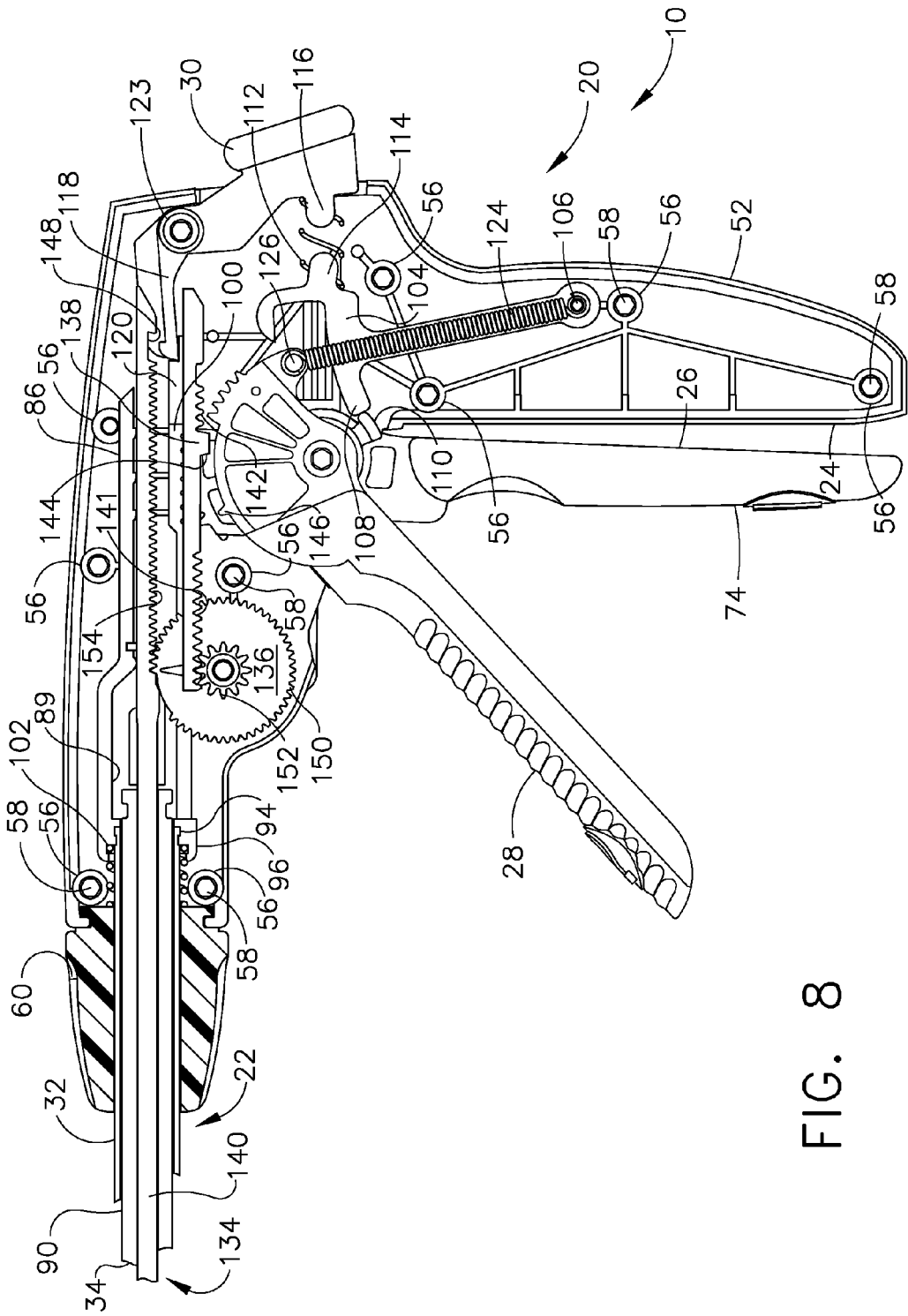
FIG. 8 depicts a side elevational view of the handle portion of the proximal end of the surgical stapling and severing instrument of FIG. 1 with the left side removed to expose interior parts in the closed ("clamped") position according to various embodiments of the present invention.

The closure trigger 26 is forward biased to an open position by a front surface 130 interacting with an engaging surface 128 of the firing trigger 28. Clamp first hook 104 that pivots top to rear in the handle portion 20 about a pin 106 restrains movement of the firing trigger 28 toward the pistol grip 24 until the closure trigger 26 is clamped to its closed position. Hook 104 restrains firing trigger 28 motion by engaging a lockout pin 107 in firing trigger 28. The hook 104 is also in contact with the closure trigger 26. In particular, a forward projection 108 of the hook 104 engages a member 110 on the intermediate section 78 of the closure trigger 26, the member 100 being outward of the bore 80 toward the handle section 74. Hook 104 is biased toward contact with member 110 of the closure trigger 26 and engagement with lockout pin 107 in firing trigger 28 by a release spring 112. As the closure trigger 26 is depressed, the hook 104 is moved top to rear, compressing the release spring 112 that is captured between a rearward projection 114 on the hook 104 and a forward projection 116 on the release button 30. As the yoke 86 moves distally in response to proximal movement of the closure trigger 26, an upper latch arm 118 of the release button 30 moves along an upper surface 120 on the yoke 86 until dropping into an upwardly presented recess 122 in a proximal, lower portion of the yoke 86. The release spring 112 urges the release button 30 outward, which pivots the upper latch arm 118 downwardly into engagement with the upwardly presented recess 122, thereby locking the closure trigger 26 in a tissue clamping position, such as depicted in FIG. 8.

The latch arm 118 can be moved out of the recess 122 to release the anvil 18 by pushing the release button 30 inward. Specifically, the upper latch arm 118 pivots upward about pin 123 of the second base section 52. The yoke 86 is then permitted to move proximally in response to return movement of the closure trigger 26.

A firing trigger return spring 124 is located within the handle portion 20 with one end attached to pin 106 of the second base section 52 and the other end attached to a pin 126 on the firing trigger 28. The firing return spring 124 applies a return force to the pin 126 for biasing the firing trigger 28 in a direction away from the pistol grip 24 of the handle portion 20. The closure trigger 26 is also biased away from pistol grip 24 by engaging surface 128 of firing trigger 28 biasing front surface 130 of closure trigger 26.

As the closure trigger 26 is moved toward the pistol grip 24, its front surface 130 engages with the engaging surface 128 on the firing trigger 28 causing the firing trigger 28 to move to its "firing" position. When in its firing position, the firing trigger 28 is located at an angle of approximately 45° to the pistol grip 24. After staple firing, the spring 124 causes the firing trigger 28 to return to its initial position. During the return movement of the firing trigger 28, its engaging surface 128 pushes against the front surface 130 of the closure trigger 26 causing the closure trigger 26 to return to its initial position. A stop member 132 extends from the second base section 52 to prevent the closure trigger 26 from rotating beyond its initial position.

The surgical stapling and severing instrument 10 additionally includes a reciprocating section 134, a multiplier 136 and a drive member 138. The reciprocating section 134 comprises a wedge sled in the implement portion 22 (not shown in FIGS. 6-9) and a metal drive rod 140. The drive member 138 includes first and second gear racks 141 and 142. A first notch 144 is provided on the drive member 138 intermediate the first and second gear racks 141, 142. During return movement of the firing trigger 28, a tooth 146 on the firing trigger 28 engages with the first notch 144 for returning the drive member 138 to its initial position after staple firing. A second notch 148 is located at a proximal end of the metal drive rod 140 for locking the metal drive rod 140 to the upper latch arm 118 of the release button 30 in its unfired position. The multiplier 136 comprises first and second integral pinion gears 150 and 152. The first integral pinion gear 150 is engaged with a first gear rack 154 provided on the metal drive rod 140. The second integral pinion gear 152 is engaged with the first gear rack 141 on the drive member 138. The first integral pinion gear 150 has a first diameter and the second integral pinion gear 152 has a second diameter which is smaller than the first diameter.

Figure 6:
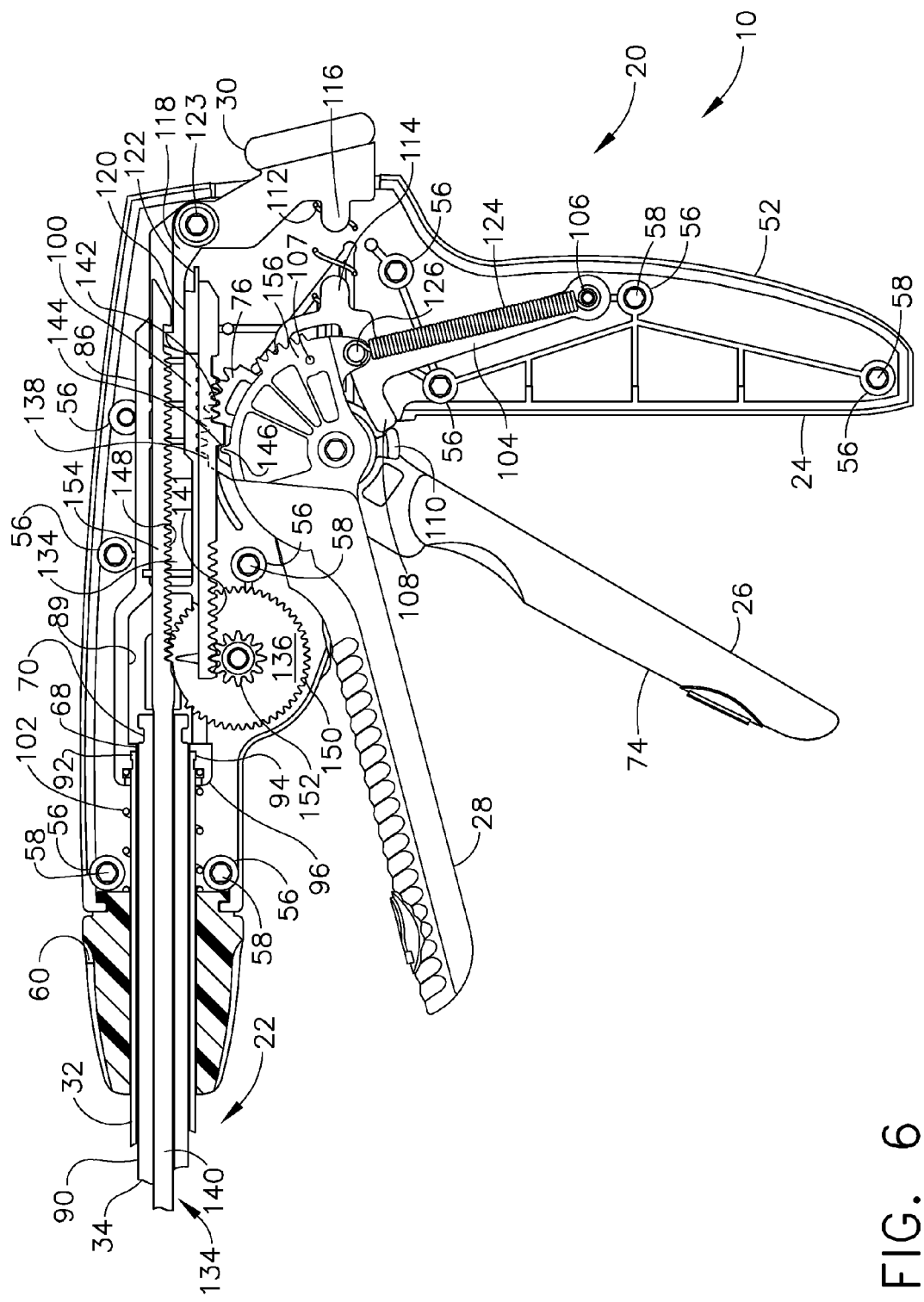
FIG. 6 depicts a side elevational view of a handle portion of a proximal end of the surgical stapling and severing instrument of FIG. 1 with a left side removed to expose interior parts in an unclamped, unfired ("start") position according to various embodiments of the present invention.
Figure 7:
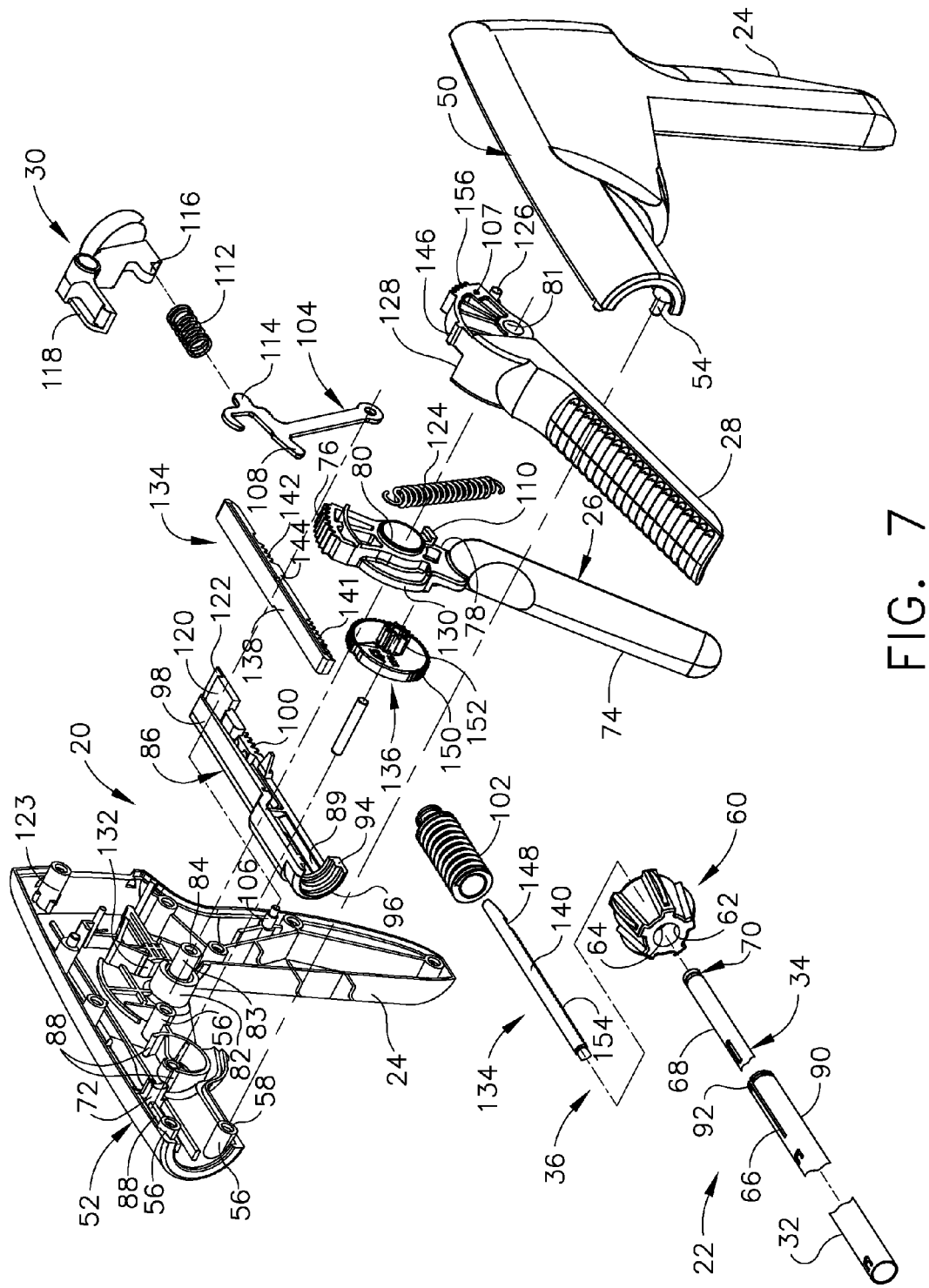
FIG. 7 depicts a perspective, exploded view of the handle portion of the proximal end of the surgical stapling and severing instrument of FIG. 1 according to various embodiments of the present invention.
Figure 9:
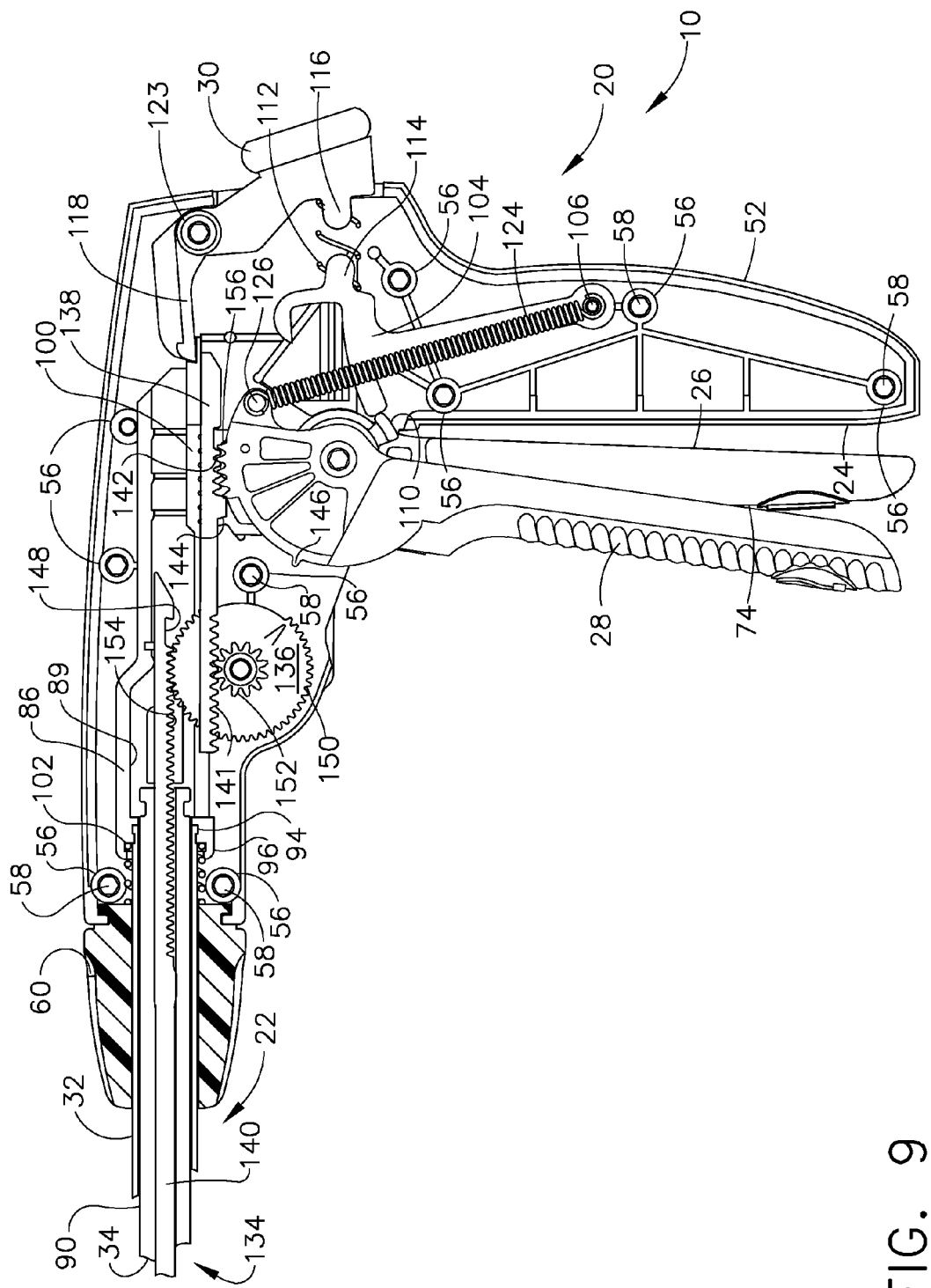
FIG. 9 depicts a side elevational view of the handle portion of proximal end of surgical stapling and severing instrument of FIG. 1 with the left side removed to expose interior parts in the stapled and severed ("fired") position according to various embodiments of the present invention.

FIGS. 6, 8 and 9 depict respectively the handle portion 20 in the start position (open and unfired), a clamped position (closed and unfired) and a fired position. The firing trigger 28 is provided with a gear segment section 156. The gear segment section 156 engages with the second gear rack 142 on the drive member 138 such that motion of the firing trigger 28 causes the drive member 138 to move back and forth between a first drive position, shown in FIG. 8, and a second drive position, shown in FIG. 9. In order to prevent staple firing before tissue clamping has occurred, the upper latch arm 118 on the release button 39 is engaged with the second notch 148 on the drive member 138 such that the metal drive rod 140 is locked in its proximal-most position, as depicted in FIG. 6. When the upper latch arm 118 falls into the recess 122, the upper latch arm 118 disengages with the second notch 148 to permit distal movement of the metal drive rod 140, as depicted in FIG. 9.

Because the first gear rack 141 on the drive member 138 and the gear rack 154 on the metal drive rod 140 are engaged with the multiplier 136, movement of the firing trigger 28 causes the metal drive rod 140 to reciprocate between a first reciprocating position, shown in FIG. 8, and a second reciprocating position, shown in FIG. 9. Since the diameter of the first pinion gear 150 is greater than the diameter of the second pinion gear 152, the multiplier 136 moves the reciprocating section 134 a greater distance than the drive member 138 is moved by the firing trigger 28. The diameters of the first and second pinion gears 150 and 152 may be changed to permit the length of the stroke of the firing trigger 28 and the force required to move it to be varied. It will be appreciated that the handle portion 20 is illustrative and that other actuation mechanisms may be employed. For instance, the closing and firing motions may be generated by automated means.

One embodiment of an end effector 12 of the surgical stapling and severing instrument 10 is depicted in further detail in FIGS. 18, 19, and 23-26. As described above, the handle portion 20 produces separate and distinct closing and firing motions that actuate the end effector 12. The end effector 12 advantageously maintains the clinical flexibility of this separate and distinct closing and firing (i.e., stapling and severing). In addition, the end effector 12 introduces the aforementioned ability to affirmatively maintain the closed spacing during firing after the clinician positions and clamps the tissue. Both features procedurally and structurally enhance the ability of the surgical stapling and severing instrument 10 by ensuring adequate spacing for instances where an otherwise inadequate amount of tissue is clamped and to enhance the clamping in instances where an otherwise excessive amount of tissue has been clamped.

Figure 10:
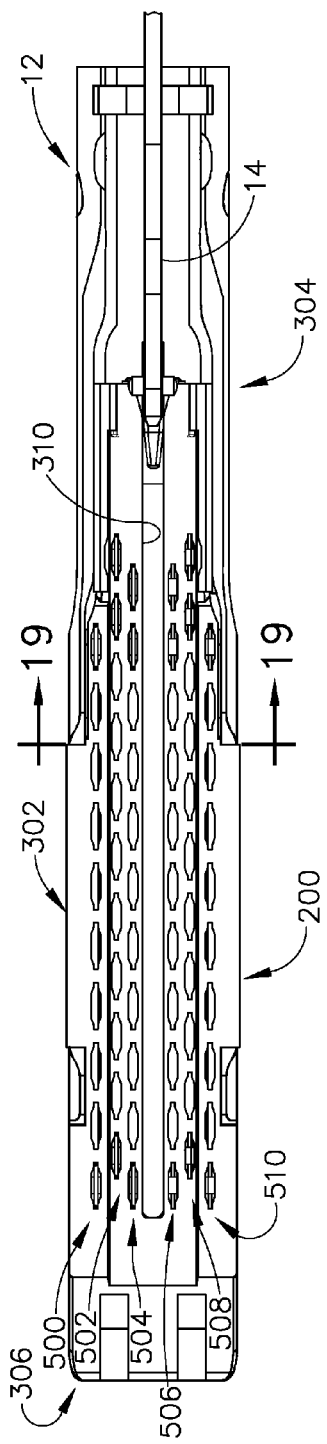
FIG. 10 depicts a plan view of a staple cartridge installed in an end effector according to various embodiments of the present invention.

FIG. 10 depicts a staple cartridge embodiment 300 of the present invention installed in the end effector 12 with the firing bar 14 in its unfired, proximal position. The staple cartridge 300 has a cartridge body 302 that is divided by an elongated slot 310 that extends from a proximal end 304 of the cartridge 300 towards a tapered outer tip 306. A plurality of staple-receiving channels 320a-320f are formed within the staple cartridge body 302 and are arranged in six laterally spaced longitudinal rows 500, 502, 504, 506, 508, 510, with three rows on each side of the elongated slot 310. Positioned within the staple-receiving channels 320a-320f are the staples 222. See FIGS. 10 and 11.

Figure 11:
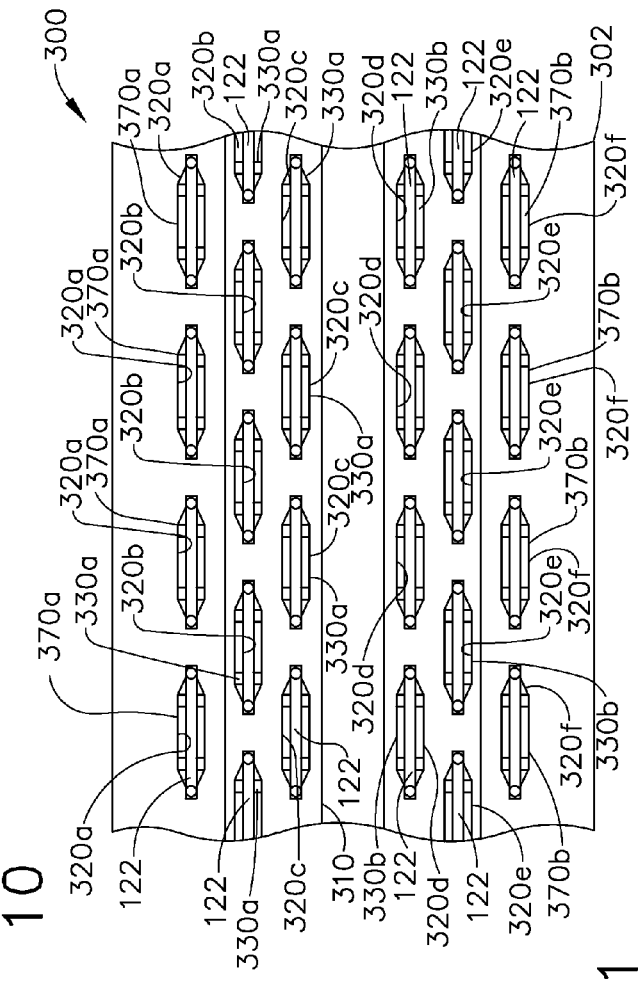
FIG. 11 is an enlarged plan view of a portion of a staple cartridge according to various embodiments of the present invention.

The cartridge 300 further includes four laterally spaced longitudinal rows of staple drivers 330a, 330b, 370a, and 370b as shown in FIG. 11. The "first" inside staple drivers 330a are slidably mounted within corresponding channels 320b and 320c such that each driver 330a supports two staples 222, one in a channel 320b and one in a channel 320c. Likewise, the "second" inside drivers 330b are slidably mounted within channels 320d and 320e such that each driver 330b supports two staples 222, one in a channel 320d and one in a channel 320e. The "outside" drivers 370a and 370b are slidably mounted within the staple-receiving channels 320a and 320f, respectively. Each of the outside drivers 370a and 370b supports a single staple 222. Drivers 370a are referred to herein as "first" outside drivers and drivers 370b are referred to herein as "second" outside drivers.

Figure 12:
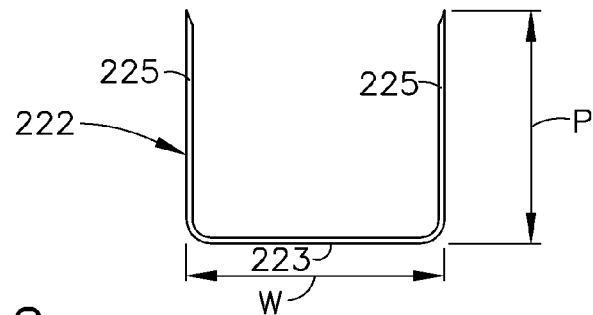
FIG. 12 is a side view of a staple that may be employed with various embodiments of the present invention.

FIG. 12 illustrates a staple 222 that may be used in connection with the various embodiments of the present invention. The staple 222 includes a main portion 223 and two prongs 225. The prongs 225 each have a length "P" and the main portion has a width "W". The reader will appreciate that a variety of different types of staples may be employed. For example, for a vascular staple, "P" may be approximately 0.102 inches; for a regular staple, "P" may be approximately 0.134 inches; and for a thick tissue staple, "P" may be approximately 0.160 inches. "W" may be approximately 0.012 inches. Other sizes of staples 222 may be employed in the manners discussed below.

The inside staple drivers 330a located on one side of the elongated slot 310 are referred to herein as "first" inside staple drivers and the inside staple drivers 330b located on the other side of the elongated slot 310 are referred to herein as "second" inside staple drivers. As will be discussed in further detail below, in one embodiment, the second inside staple drivers 330b are identical to the first inside staple drivers 330a, except for their orientation in their respective channels in the cartridge body 302.

Figure 14:
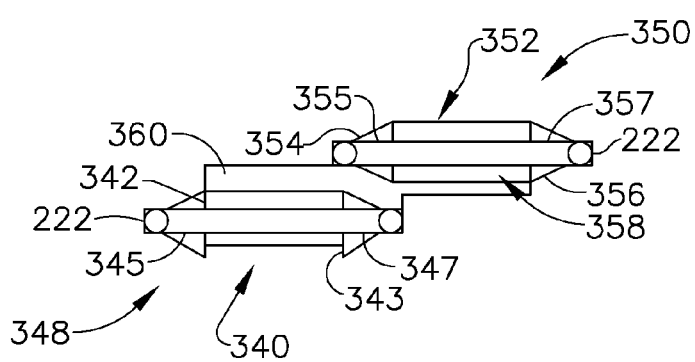
FIG. 14 is a top view of the inside double driver and staples of FIG. 13 according to various embodiments of the present invention.
Figure 13:
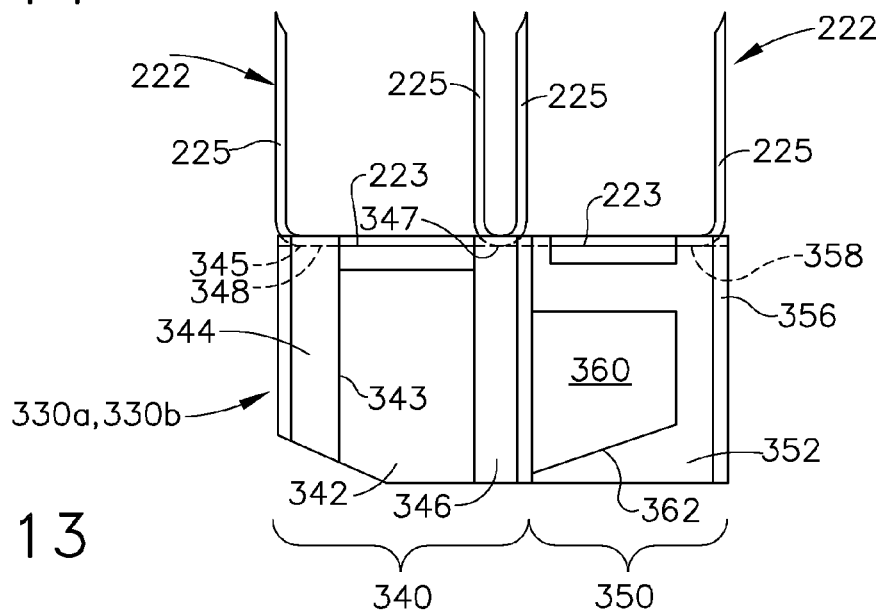
FIG. 13 is a front elevational view of one inside double driver supporting two staples thereon according to various embodiments of the present invention.
Figure 15:
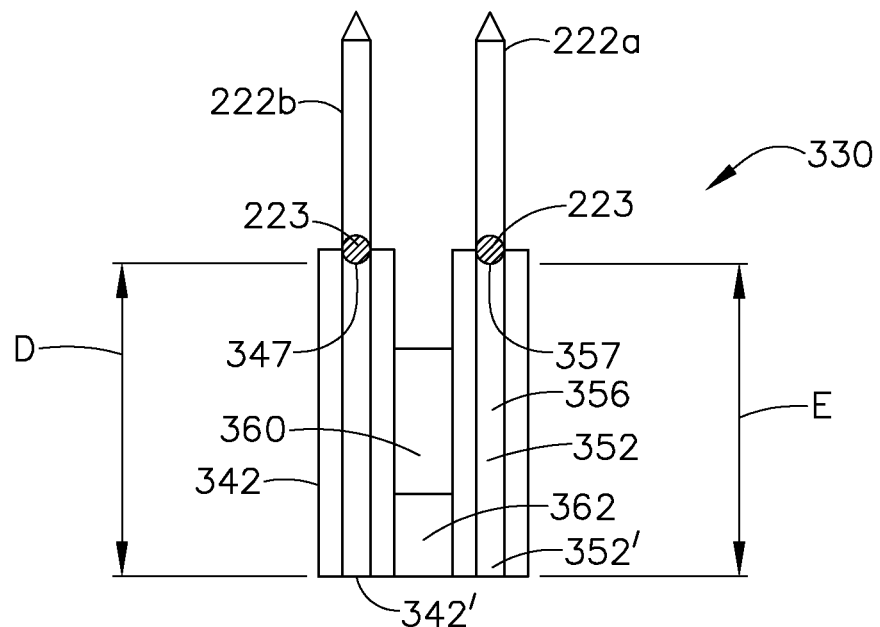
FIG. 15 is a right side elevational view of the inside double driver and staples of FIGS. 13 and 14 according to various embodiments of the present invention.

FIGS. 13-15 illustrate one embodiment of a "first" inside double driver 330a for supporting and driving staples 222. As can be seen in those Figures, the staple driver 330a has a primary driver portion 340 and a secondary driver portion 350 that is connected to the first primary portion 340 by a central base member 360. The primary driver portion 340 has a primary driver base 342 that has a groove 343 therein adapted to mate with a corresponding vertically extending tongue (not shown) in the cartridge body 302 for guiding and stabilizing the driver 330a as it moves within its respective channel. The primary driver portion 340 further has a first forward support column 344 and a first rearward support column 346 protruding upward from the first driver base 342. The first forward support column 344 has a first forward staple-receiving groove 345 therein and the first rearward support column 346 has a first rearwardly staple-receiving groove 347 therein. See FIGS. 13-15. The first forward support column 344 and the first rearward support column 346 are spaced from each other and collectively form a first staple cradle 348 for supporting the main portion 223 of the staple 222 therein in an upright position (i.e., prongs facing the anvil). Similarly, the secondary driver portion 350 has a secondary driver base 352 and a secondary forward support column 354 and a secondary rearward support column 356 protruding out from the second driver base 352. The secondary forward support column 354 has a secondary forward staple-receiving groove 355 therein and the secondary rearward support column 356 has a secondary rearward staple-receiving groove 357 therein. The secondary forward support column 354 and the secondary rearward support column 356 are spaced from each other and collectively form a secondary staple cradle 358 for supporting the main portion 223 of another staple 222 therein.

As can be seen in FIGS. 13 and 15, the central base member 360 has an angled rearwardly facing edge 362 adapted to be engaged by a corresponding sled cam as will be discussed in further detail below. As can be seen in FIGS. 13 and 14, in this embodiment, the secondary forward support column 354 of the secondary driver portion is oriented relative to the first rearward support column 346 such that the staple 222 that is supported in the secondary staple cradle 358 is longitudinally offset from the staple 222 in the first staple cradle 348. The reader will appreciate that the first inside drivers 330a are each installed in one orientation into a corresponding pair of channels 320b and 320c located on one side of the elongated slot 310 in the cartridge body 302. The second inside staple drivers 330b (located on the opposite side of the elongated slot 310 from the first inside staple drivers 330a) comprise inside drivers 330a rotated 180 degrees so that their respective angled surfaces 363 face towards the proximal end 304 of the cartridge 300 to enable them to be installed in pairs of corresponding channels 320d and 320e. Thus, in this embodiment, only one inside driver configuration is employed which thereby eliminates the need for two different inside staple driver configurations for channels on each side of the elongated slot 310.

Figure 17:
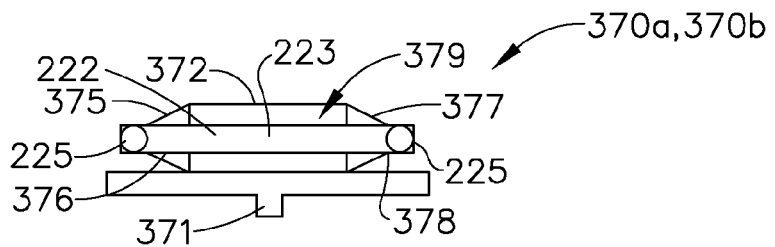
FIG. 17 is a top view of the outside single driver and staple of FIG. 16 according to various embodiments of the present invention.
Figure 16:
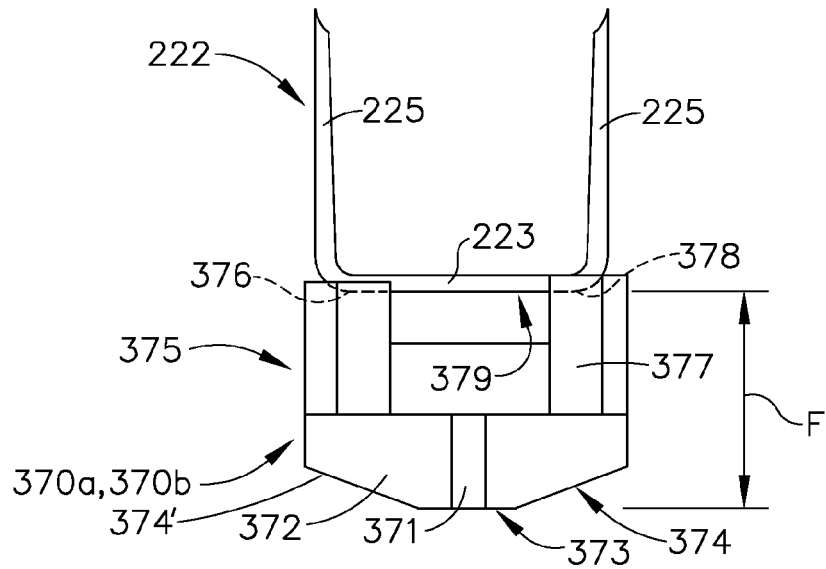
FIG. 16 is a front elevational view of one outside single driver supporting a staple thereon according to various embodiments of the present invention.

FIGS. 16 and 17 illustrate one embodiment of a "first" outside staple driver 370a. As can be seen in those Figures, a first outside staple driver 370a has a second base 372 that has an angled rearwardly facing portion 374. Protruding upward from the second base 372 is a second forward support column 375 that has a second forward staple-receiving groove 376 therein. A second rearward support column 377 also protrudes upward from the second base 372 in a spaced-apart relationship with respect to the second forward support column 375. The second rearward support column 377 has a second rearward staple-receiving groove 378 therein. The support columns 375, 377 collectively form a second staple cradle 379 that is configured to support a staple 222 therein in an upright position as illustrated in FIGS. 16 and 17. The staple drivers 370a also have a laterally protruding rib 371 which is received in a corresponding groove (not shown) in the cartridge body 302 for guiding and stabilizing the driver 370a as it moves within its respective channel.

Figure 19:
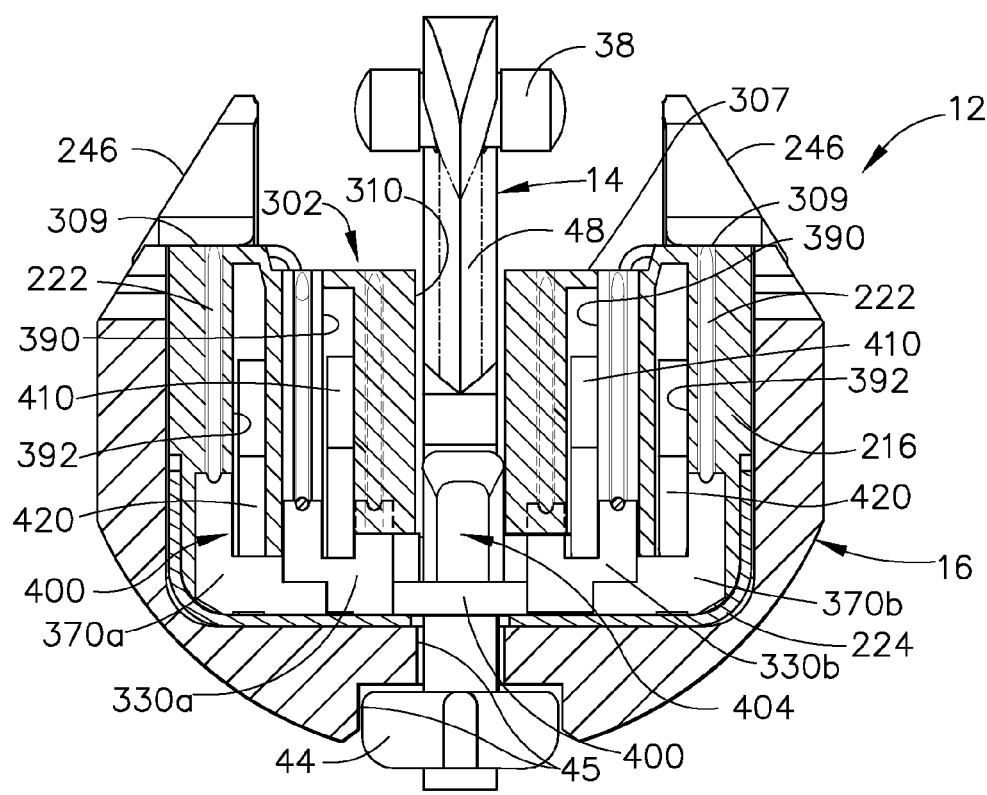
FIG. 19 is a section view taken along line 19-19 of FIG. 10 showing the cross-sectional relationship between the firing bar, elongate channel, wedge sled, staple drivers, staples and staple cartridge according to various embodiments of the present invention.
Figure 19A:
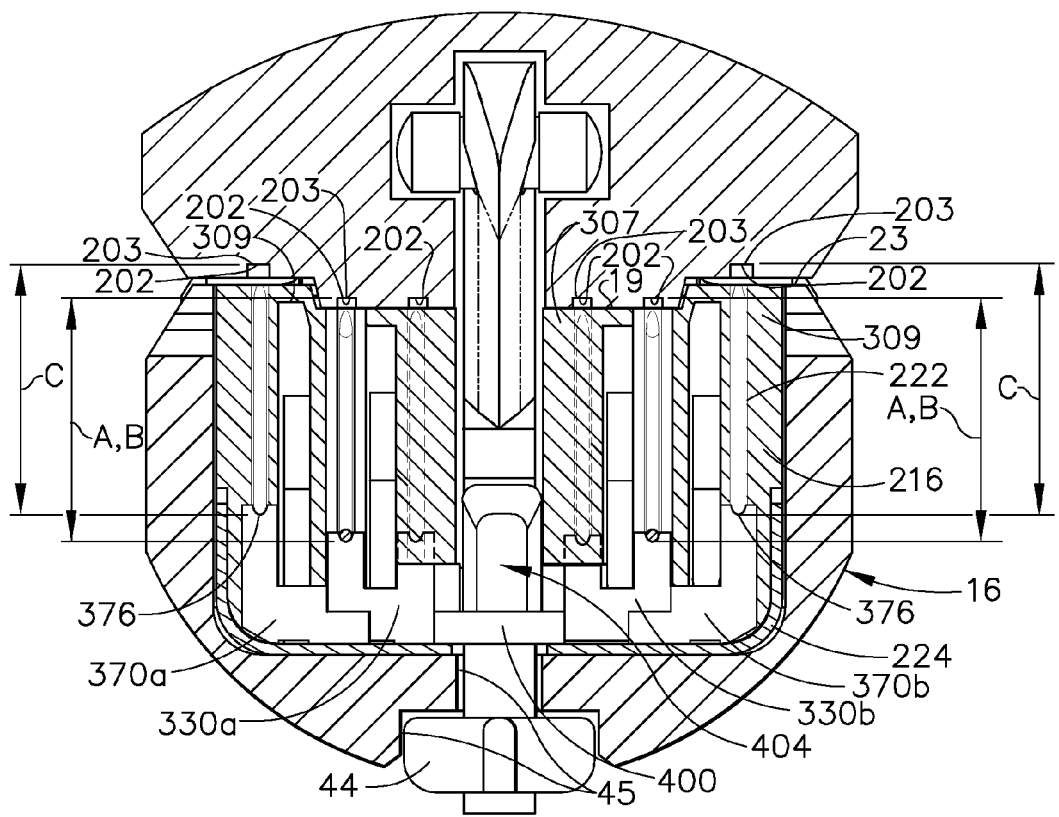
FIG. 19A is another cross-sectional view of an end effector showing the cross-sectional relationship between the firing bar, elongate channel, wedge sled, staple drivers, staples, staple cartridge and anvil according to various embodiments of the present invention.

The reader will appreciate that a first outside driver 370a is installed in one orientation into a corresponding channel 320a on one side of the elongated slot 310. A second outside staple driver 370b (to be located on the opposite side of the elongated slot 310 from the first outside staple drivers 370a) comprises an outside driver 370a rotated 180 degrees so that the angled surface 374' thereon faces toward the proximal end 304 of the cartridge 300 to enable it to be installed in a corresponding channel 320f in the cartridge body 302. Thus, in this embodiment, only one outside staple driver configuration is employed which avoids the need for two different outside staple driver configurations for channels on each side of the elongated slot 310. FIGS. 19 and 19A illustrate in cross-section one embodiment of a staple cartridge of the present invention mounted within one type of end effector 12. The end effector 12 in this embodiment employs a "stepped" anvil 18 of the type illustrated in FIGS. 23-25. In other embodiments, however, the bottom surface of the anvil is planar and not stepped. As can be seen in FIGS. 19A, and 23-25, the anvil 18 has a central portion 19 that is offset or not coplanar with the two lateral side portions 21, 23. Accordingly, in this embodiment, the upper surface 306 of the cartridge 300 is provided with a recessed central portion 307 and two lateral side portions 309 that are adapted to closely mate with the corresponding portions 19, 21, 23, respectively, of the anvil 18, when the anvil 18 is in the closed position. See FIG. 19A.

Figure 14A:
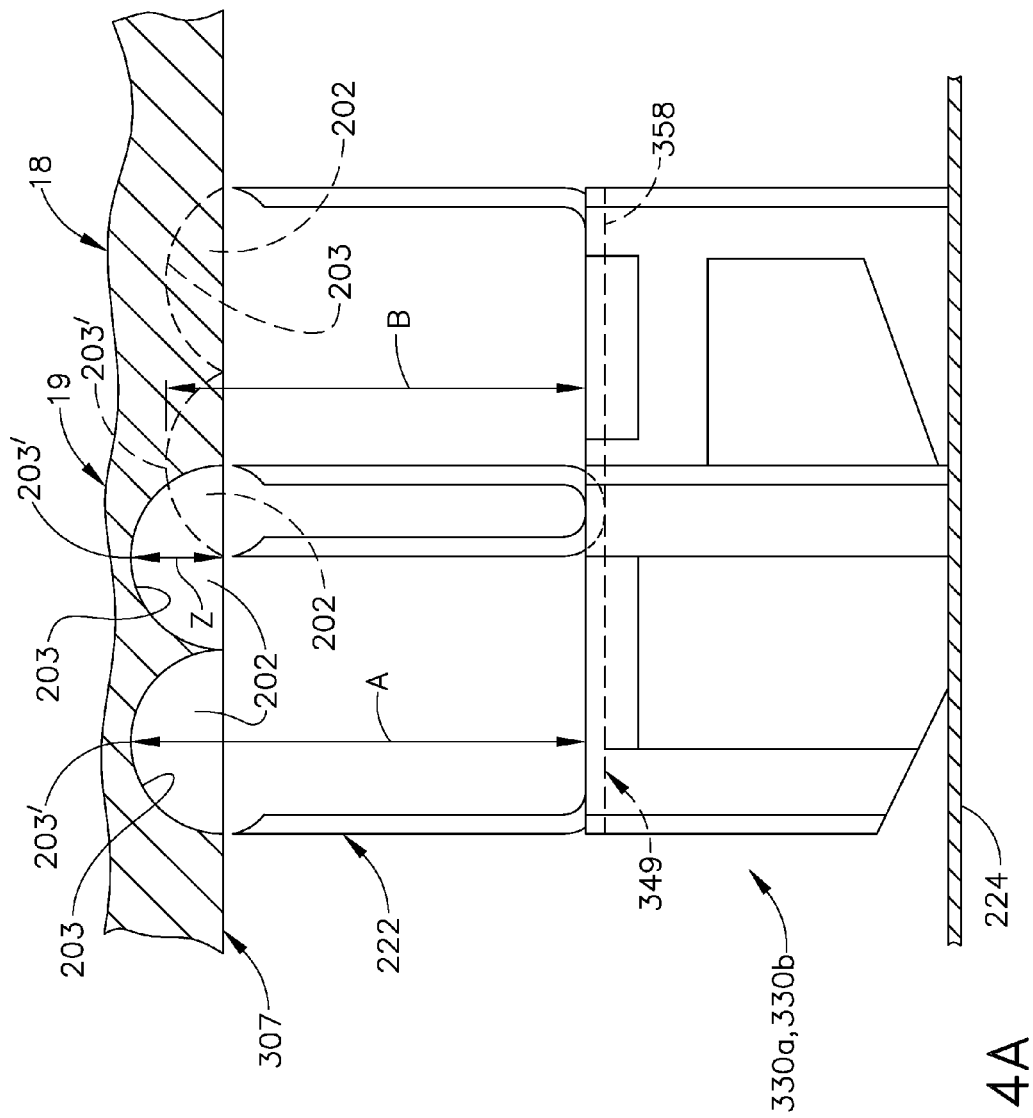
FIG. 14A is an elevational view of the inside double driver of FIG. 13 within a portion of a staple cartridge mounted in the end effector and also illustrating a corresponding portion of the anvil when in a closed position according to various embodiments of the present invention.
Figure 24:
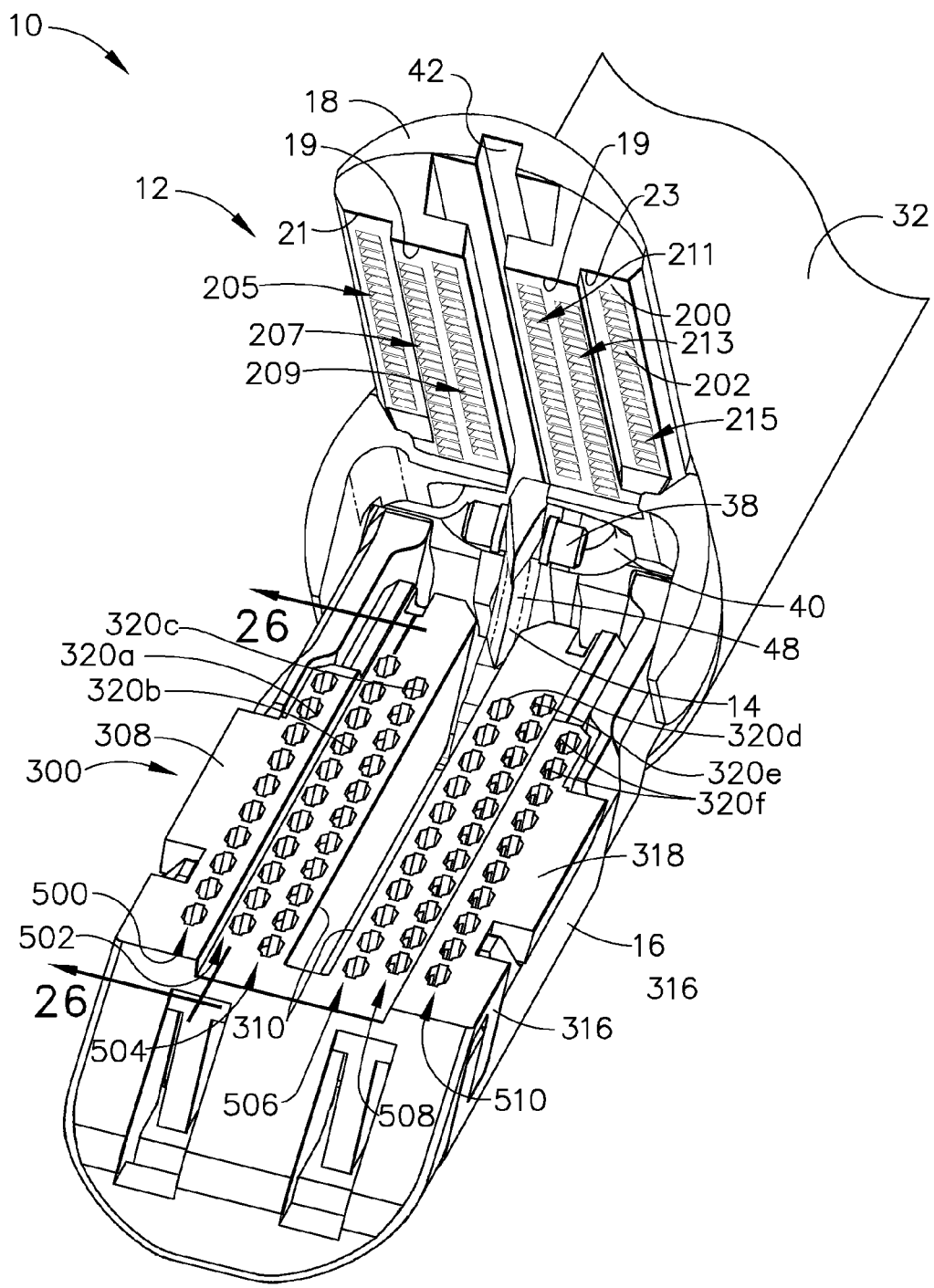
FIG. 24 is an isometric view of the end effector at the distal end of the surgical stapling and severing instrument of FIG. 1 with the anvil in the up or open position exposing the staple cartridge and cutting edge of the firing bar according to various embodiments of the present invention.

As can be seen in FIG. 24, in this embodiment, the under surfaces 200 of anvil 18 are provided with a series of forming pockets 202 that may be arranged in rows that correspond to the rows of channels in the cartridge 300. That is, row 205 of pockets 202 may correspond to channel row 500. Row 207 of pockets may correspond to channel row 502. Row 209 of pockets 202 may correspond to channel row 504. Row 211 of pockets 202 may correspond to channel row 506. Row 213 of pockets 202 may correspond to channel row 508. Row 215 of pockets 202 may correspond to channel row 510. Each pocket 202 has at least one forming surface 203 therein that is adapted to contact the ends of the staple prongs 225 being driven therein to thereby cause the prongs 225 to bend inwardly toward each other. In one embodiment, each pocket 202 has two intersecting arcuate forming surfaces 203 that are oriented as shown in FIG. 14A. Each arcuate forming surface has an apex 203' that defines a maximum pocket depth "Z". However other forming pocket configurations could be employed.

Returning to FIGS. 18 and 19, it can be seen that in one embodiment, the cartridge body 302 is mounted within the cartridge tray 224. As illustrated in FIG. 19, the cartridge body 302 is formed with two inside longitudinally extending slots 390 and two outside longitudinally extending slots 392. Slots 390 and 392 extend from the proximal end 304 of the cartridge to its tapered outer tip 306 (shown in FIG. 10). This embodiment further includes a wedge sled 400 that slidably supported on the cartridge tray 224. One wedge sled embodiment 400 includes a pair of inside sled cams 410, wherein one inside sled cam 410 corresponds to one of the inside longitudinally extending slots 390 and wherein the other inside sled cam 410 corresponds to the other inside longitudinally extending slot 390. See FIG. 19. The wedge sled 400 further includes a pair of outside sled cams 420, wherein one outside sled cam 420 corresponds to one of the outside longitudinally extending slots 392 and the other outside sled cam 420 corresponds to the other outside longitudinally extending slot 392 as shown in FIG. 19. When assembled, the cartridge tray 224 holds the wedge sled 400 and the drivers 330a, 330b, 370a, 370b inside the cartridge body 302.

Figure 18:
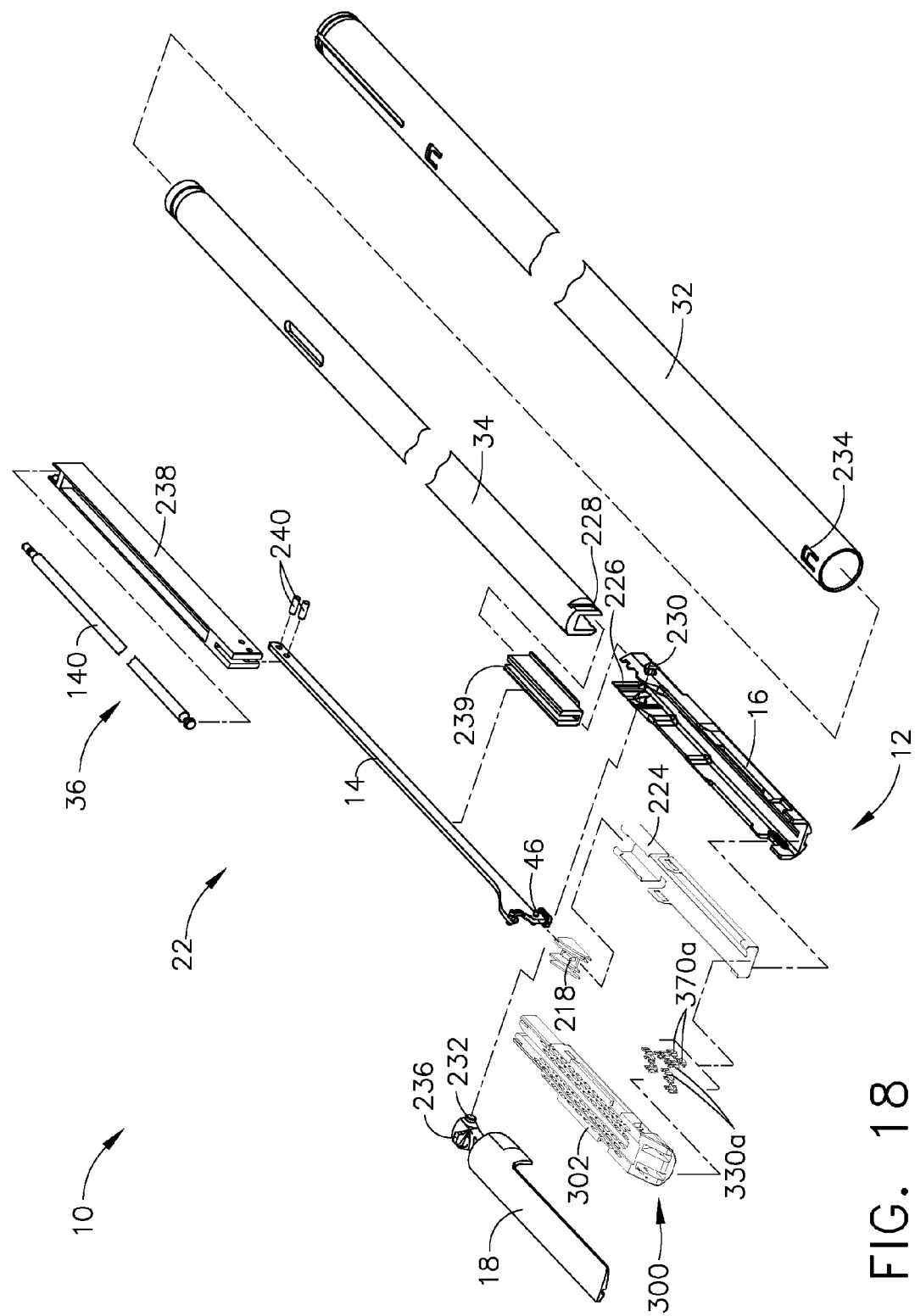
FIG. 18 is an isometric exploded view of the implement portion of the surgical stapling and severing instrument of FIG. 1 according to various embodiments of the present invention.

As can be seen in FIG. 18, the elongate channel 16 has a proximally placed attachment cavity 226 that receives a channel anchoring member 228 on the distal end of the frame 34 for attaching the end effector 12 to the handle portion 20. The elongate channel 16 also has an anvil cam slot 230 that pivotally receives an anvil pivot 232 of the anvil 18. The closure sleeve 32 that encompasses the frame 34 includes a distally presented tab 234 that engages an anvil feature 236 proximate but distal to the anvil pivot 232 on the anvil 18 to thereby effect opening and closing of the anvil 18. The firing drive member 36 is shown as being assembled from the firing bar 14 attached to a firing connector 238 by pins 240, which in turn is rotatingly and proximally attached to the metal drive rod 140. The firing bar 14 is guided at a distal end of the frame by a slotted guide 239 inserted therein.

Figure 20:
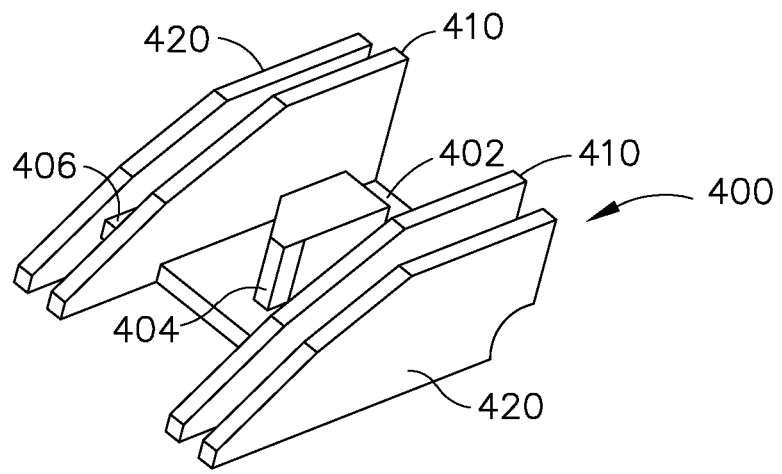
FIG. 20 is a perspective view of one wedge sled according to various embodiments of the present invention.
Figure 21:
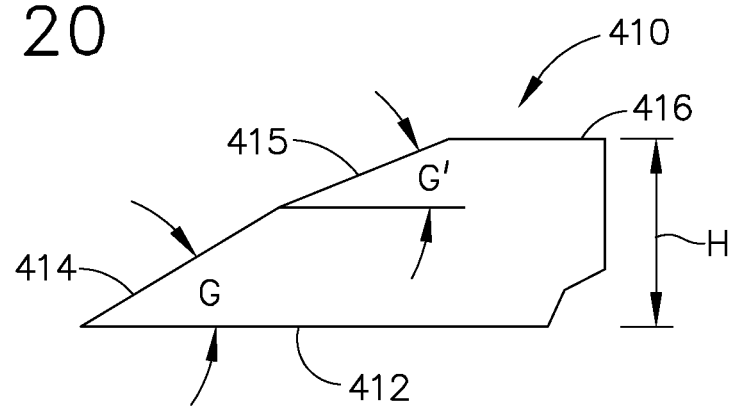
FIG. 21 is a side elevational view of an inside sled cam of the wedge sled depicted in FIG. 20 according to various embodiments of the present invention.
Figure 22:
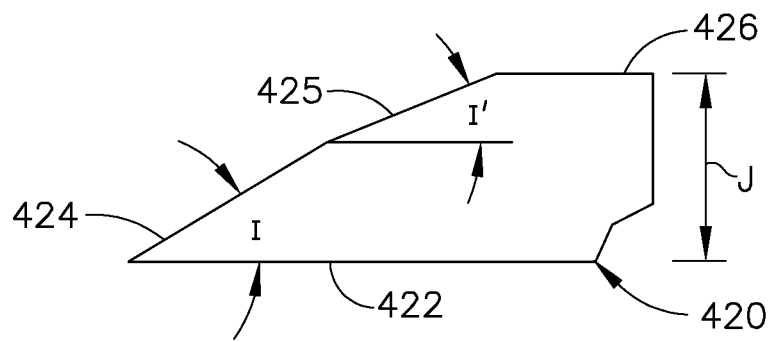
FIG. 22 is a side elevational view of an outside sled cam of the wedge sled depicted in FIG. 20 according to various embodiments of the present invention.
Figure 23:
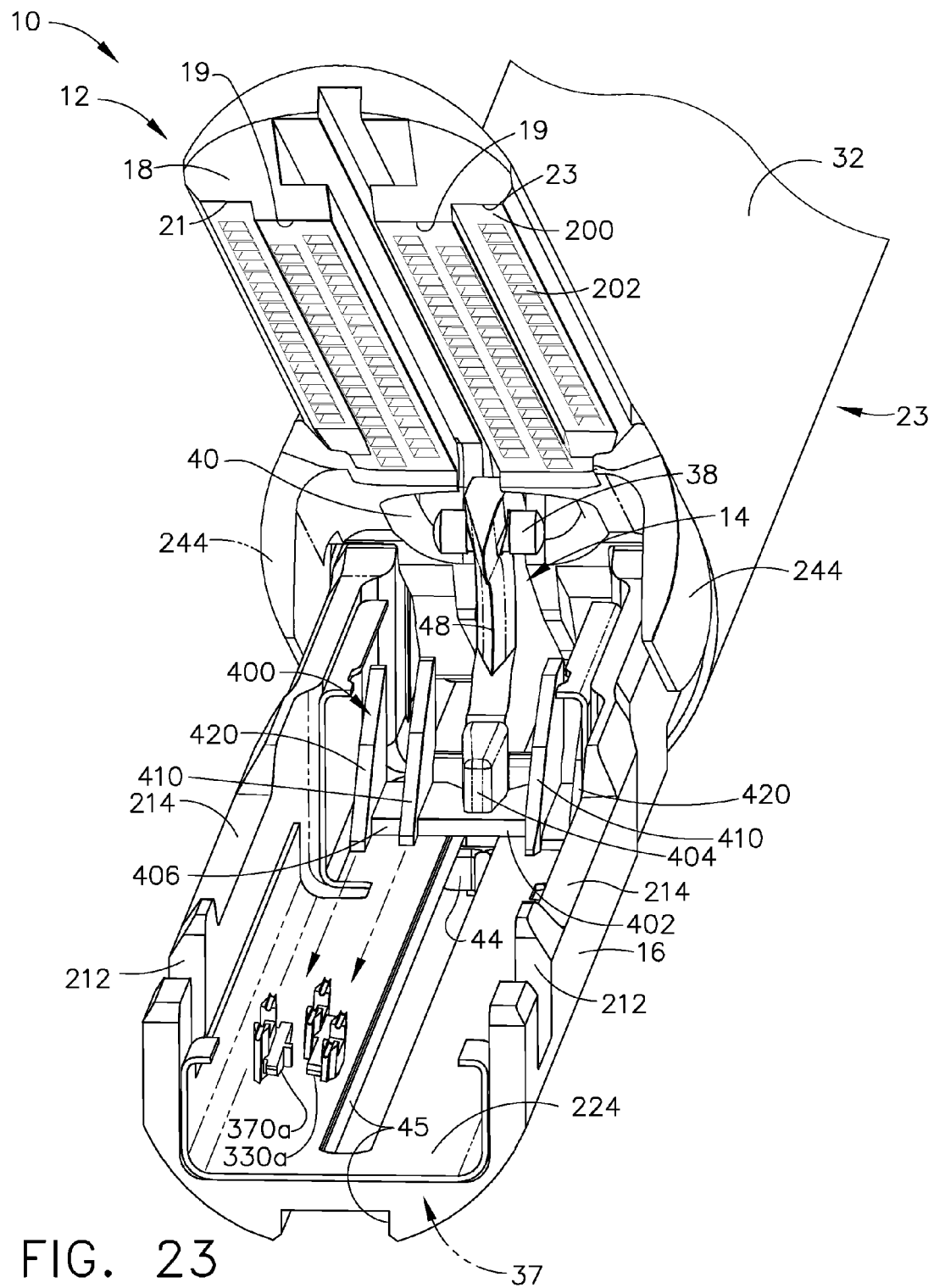
FIG. 23 is an isometric view of the end effector at the distal end of the surgical stapling and severing instrument of FIG. 1 with the anvil in the up or open position with the cartridge largely removed exposing a single staple driver and a double staple driver as exemplary and the wedge sled in its start position against a middle pin of the firing bar according to various embodiments of the present invention.

FIGS. 20-23 illustrate one embodiment of the wedge sled 400 of the present invention. As can be seen in FIGS. 20 and 23, the wedge sled 400 includes a central spacer portion 402 that extends between the inside sled cams 410. A pusher block 404 is formed on the central spacer portion 402 for engagement with the middle pin 46 of the firing bar 14. A side profile of one embodiment of an inside sled cam 410 is depicted in FIG. 21. As can be seen in that Figure, the inside sled cam 410 has a bottom surface 412, and a first camming surface 414 that forms an angle "G" with the bottom surface 412 and a second camming surface 415 that extends to a top surface 416. In one embodiment, for example, the angle "G" may be 35 degrees and the angle "G'" may be 20 degrees. The height of the inside sled cam 410 (the distance between the bottom surface 412 and the top surface 416) is represented as "first" sled cam height "H". In one embodiment, distance "H' is approximately 0.173 inches and the length of the top surface 416 may vary from embodiment to embodiment. As will be further evident as the present Detailed Description proceeds, the first sled cam height represents the vertical distance that the inside sled cams 410 will drive the corresponding inside drivers 330a, 330b toward the anvil 18 during operation.

The wedge sled 400 further comprises lateral spacer portions 406 that extend between the inside sled cams 410 and the outside sled cams 420 as shown in FIGS. 20 and 23. A side profile of one embodiment of an outside sled cam 420 is depicted in FIG. 22. In this embodiment, the outside sled cam 420 has a bottom surface 422 and a first camming surface 424 that forms an angle "I" with respect to the bottom surface 422 and a second camming surface 425 that to a top surface 426. In one embodiment, angle "I" may be approximately 35 degrees and angle "I'" may be approximately 20 degrees. The height of the outside sled cam 420 (the distance between the bottom surface 412 and the top surface 416) is represented as the "second" sled cam height "J". In one embodiment, distance "J' is approximately 0.163 inches. The second sled cam height represents the vertical distance that the outside sled cams 420 will drive the corresponding outside drivers 370a, 370b toward the anvil 18 during operation. The reader will understand that the above-recited dimensions are illustrative of one embodiment and may vary for other embodiments.

With particular reference to FIG. 23, a portion of the staple cartridge 300 is removed to expose portions of the elongate channel 16, such as recesses 212, 214 and to expose some components of the staple cartridge 300 in their unfired position. In particular, the cartridge body 302 (shown in FIG. 18) has been removed. The wedge sled 400 is shown at its proximal, unfired position with a pusher block 404 contacting the middle pin 46 (not shown in FIG. 23) of the firing bar 14. The wedge sled 400 is in longitudinal sliding contact upon the cartridge tray 224 and includes wedges sled cams 410, 420 that force upward the double drivers 330a, 330b and the single drivers 370b, 370b as the wedge sled 400 moves distally. Staples 222 (not shown in FIG. 23) resting upon the drivers 330a, 330b, 370a, 370b are thus also forced upward into contact with the anvil forming pockets 202 in anvil 18 to form closed staples. Also depicted is the channel slot 45 in the elongate channel 16 that is aligned with the elongated slot 310 in the staple cartridge 300.

FIG. 24 depicts the end effector 12, which is in an open position by a retracted closure sleeve 32, with a staple cartridge 300 installed in the elongate channel 16. The firing bar 14 is at its proximal position, with the upper pin 38 aligned in a non-interfering fashion with the anvil pocket 40. The anvil pocket 40 is shown as communicating with the longitudinal anvil slot 42 in the anvil 18. The distally presented cutting edge 48 of the firing bar 14 is aligned with and proximally from removed from the vertical slot 49 in the staple cartridge 300, thereby allowing removal of a spent cartridge and insertion of an unfired cartridge, which may be "snapfit" into the elongate channel 16. Specifically, in this embodiment, extension features 316, 318 of the staple cartridge 300 engage recesses 212, 214, respectively (shown in FIG. 23) of the elongate channel 16.

Figure 25:
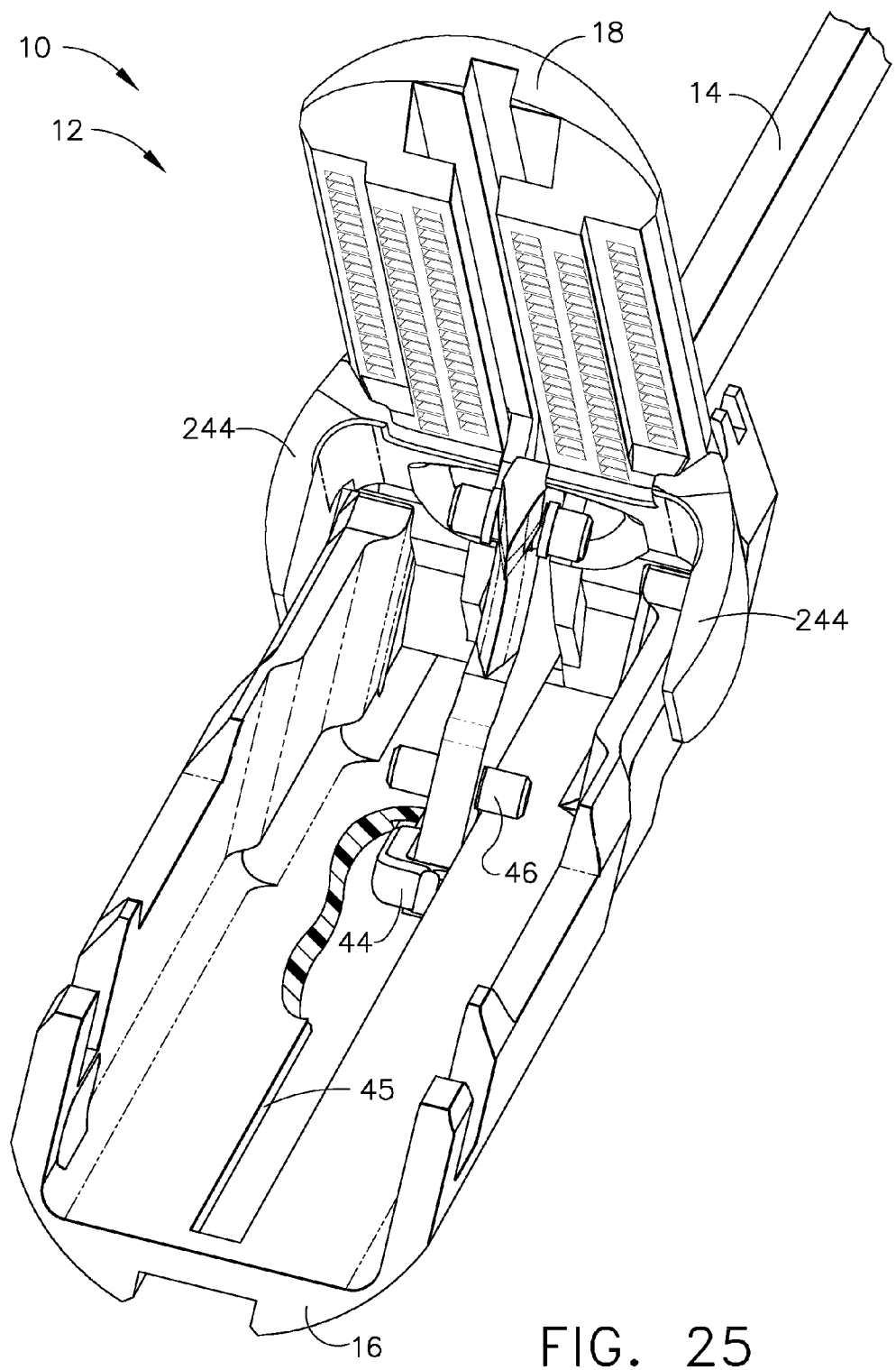
FIG. 25 is an isometric view of the distal end of the surgical stapling and severing instrument of FIG. 1 with the anvil in the up or open position with the staple cartridge completely removed and a portion of an elongate channel removed to expose a lowermost pin of the firing bar according to various embodiments of the present invention.
Figure 26:
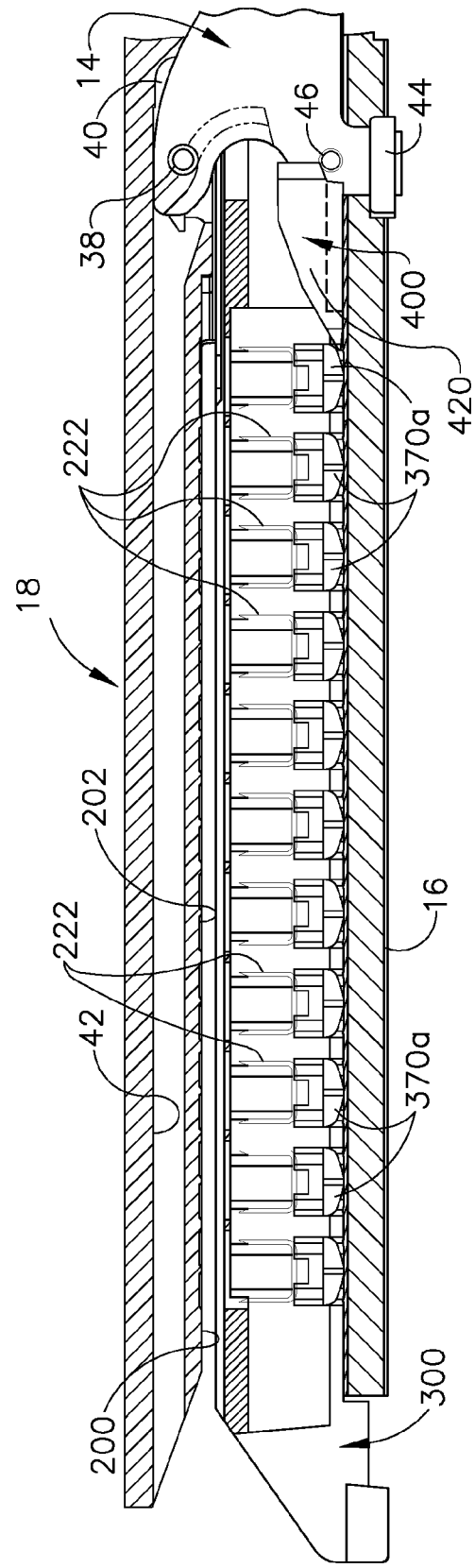
FIG. 26 is a side elevation view in section showing a mechanical relationship between the anvil, elongate channel, and staple cartridge in the closed position of the surgical stapling and severing instrument of FIG. 1, the section generally taken along lines 26-26 of FIG. 24 to expose wedge sled, staple drivers and staples but also depicting the firing bar along the longitudinal centerline according to various embodiments of the present invention.

FIG. 25 depicts the end effector 12 of FIG. 23 with all of the staple cartridge 300 removed to show the middle pin 46 of the firing bar 14 as well as portion of the elongate channel 16 removed adjacent to the channel slot 45 to expose the firing bar cap 44. In addition, portions of the shaft 23 are removed to expose a proximal portion of the firing bar 14. Projecting downward from the anvil 18 near the pivot is a pair of opposing tissue stops 244 which serve to prevent tissue from being positioned too far up into the end effector 12 during clamping. FIG. 26 depicts the end effector 12 in a closed position with the firing bar 14 in an unfired position. The upper pin 38 is in the anvil pocket 40 and is vertically aligned with the anvil slot 42 for distal longitudinal movement of the firing bar 14 during firing. The middle pin 46 is positioned to push the wedge sled 400 distally so that the sled cams 410, 420 contact and lift double drivers 330a, 330b and the single drivers 370a, 370b, respectively, to drive them upwardly toward the anvil 18.

Figure 15A:
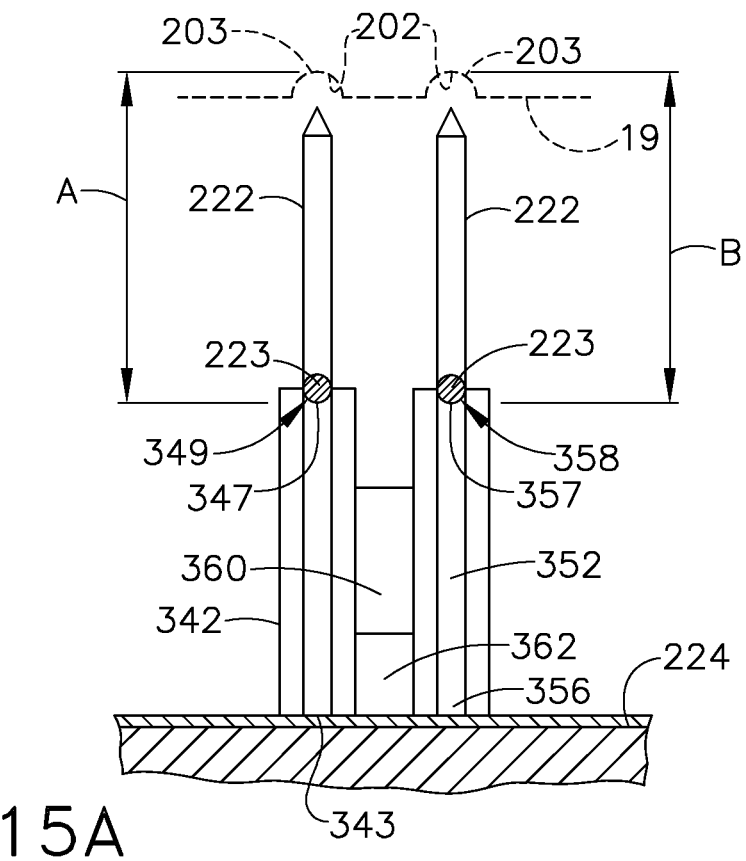
FIG. 15A is another side elevational view of the inside double driver of FIG. 15 wherein corresponding portions of the cartridge tray and anvil are illustrated in broken lines to depict the relationships therebetween according to various embodiments of the present invention.

As can be appreciated from reference to FIGS. 14A, 15A and 19A, in one embodiment of the present invention, the distance between the bottom of the first staple-receiving grooves 345, 347 forming the first staple cradle 349 and the apex 203' of forming surfaces 203 of the corresponding forming pocket 202 of anvil 18, when the anvil 18 is in the closed position and when the inside driver 330a, 330b is supported on the cartridge tray 224, is referred to herein as the first staple forming distance "A". The distance between the bottom of the secondary staple-receiving grooves 345, 347 forming the secondary staple cradle 349 and the apex 203' of the forming surface 203 of the corresponding forming pocket 202 in the anvil 18 when the anvil 18 is in the closed position and the inside driver 330a, 330b is supported on the cartridge tray 224 is referred to herein as the secondary staple forming distance "B". In one embodiment, the first staple forming distance "A" and the secondary staple forming distance "B" are substantially equal to each other. In other embodiments, those distances "A" and "B" may differ from each other.

Figure 16A:
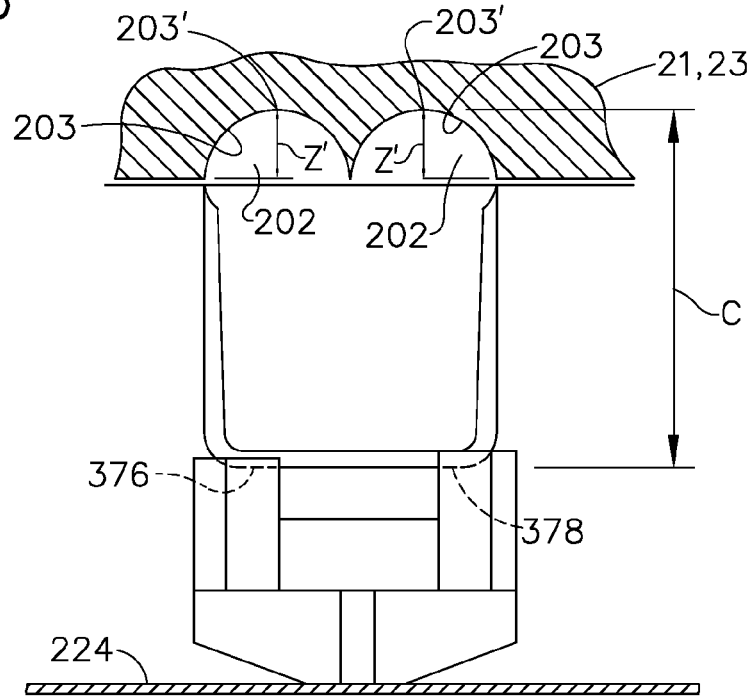
FIG. 16A is another front view of the outside single driver of FIG. 16 with portions of the cartridge tray and anvil shown to illustrate the relationships therebetween according to various embodiments of the present invention.

As illustrated in FIGS. 16A and 19A the distance between the bottom of the second staple-receiving grooves 376, 378 that form the second staple cradle 379 and the apex 203' of the forming surface 203 of a corresponding forming pocket 202 in anvil 18 when the anvil 18 is in the closed position and the outside drivers 370a, 370b are supported on the cartridge channel 224, is referred to herein as a "second" staple forming distance "C".

Figure 27:
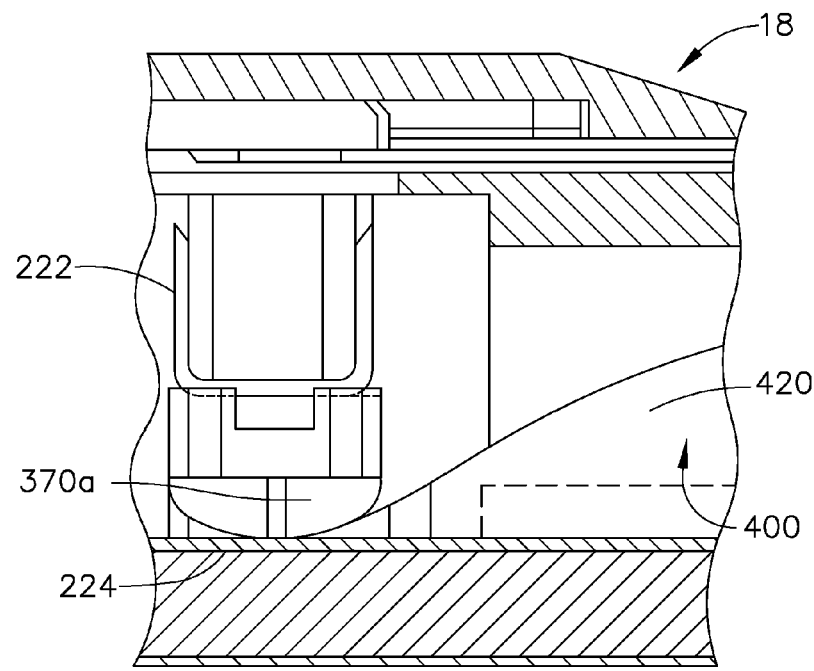
FIG. 27 is a cross-sectional view of a portion of a staple cartridge wherein an outside cam of a wedge is adjacent to an outside single driver according to various embodiments of the present invention.
Figure 28:
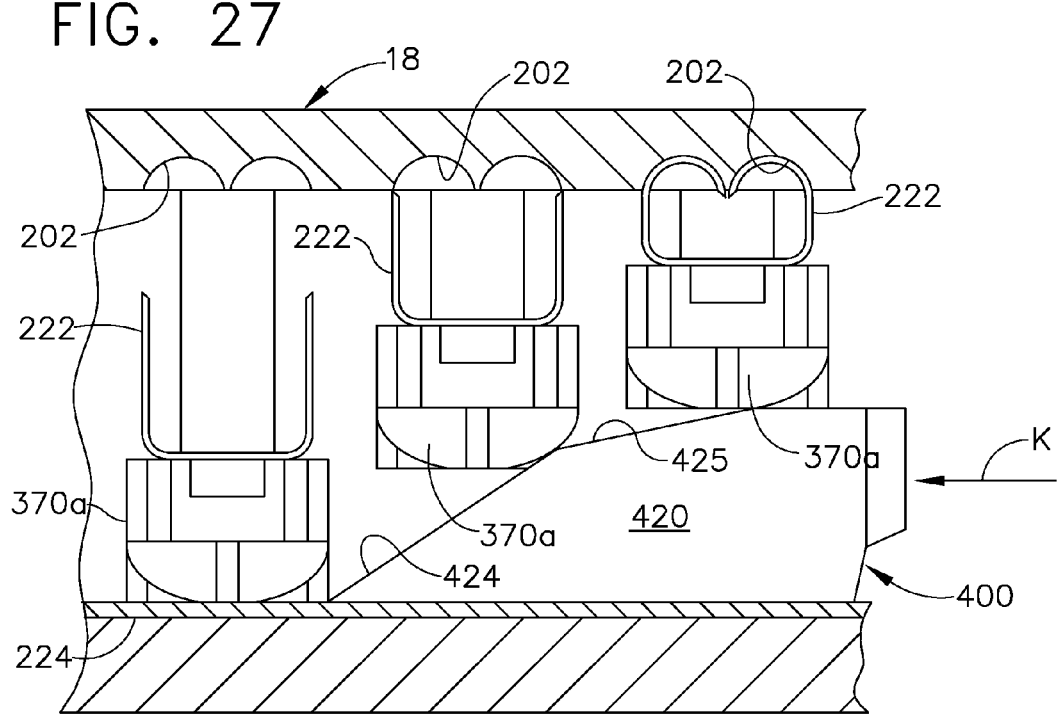
FIG. 28 is a cross-sectional view of a portion of a staple cartridge wherein an outside cam of a wedge sled is engaging three outside single drivers according to various embodiments of the present invention.

FIGS. 27 and 28 illustrate the forming of staples supported on some of the first outside drivers 370a. In FIG. 27, one of the outside sled cams 420 of the wedge sled 400 is initially contacting one of the outside drivers 370a. As the wedge sled 400 continues in the driving direction represented by arrow "K" in FIG. 28, the outside sled cam 420 causes the outside drivers 370a drive the staples 222 supported thereby into the staple forming pockets 202 in the anvil 18. Likewise, as the wedge sled 400 is driven in the driving direction "K", the inside sled cams 410 contact the inside drivers 330a, 330b and causes them to drive the staples 222 supported thereby into the corresponding staple forming pockets 202 in the anvil 18.

As indicated above, in some applications involving an area of varied tissue composition, it can be desirable to form rows of staples wherein the formed (final) heights of the staples in a row that is the farthest distance away from the cut line are greater than the formed (final) heights of those staples in the row that is closest to the cut line. In other applications, it may be desirable for the formed heights of the staples in a single row to increase (or decrease) from staple to staple. Another clinical benefit would be to have the formed heights of the staples in the outermost rows larger than formed heights of the staples in the inside rows. The various embodiments of the subject invention can provide these results while employing identical staples in all of the rows.

In the description to follow, those staples 222 in the outermost rows 520, 530 of staples (those staples formed using the outside staple drivers 370a, 370b) will be referred to hereinafter as staples 222' and those staples in the innermost rows 522, 524, 526, 528 of staples (those staples formed using the inside staple drivers 330a, 330b) will be referred to hereinafter as staples 222". It will be understood, however, that staples 222' and 222" are identical to each other prior to being formed by the various embodiments of the present invention. That is, staples 222' and 222" each have identical prong lengths "P" and widths "W". Returning to FIGS. 14A-16A and 21 and 22, the above desired effects may be attained by altering the staple forming distances "A", "B", and "C" relative to each other and/or the sled cam heights "H" and "J". In one embodiment of the subject invention, for example, the height "H" of each of the inside sled cams 410 is substantially equal to the sled height "J" of each of the outside sled cams 420. See FIGS. 21 and 22. In this embodiment, the staple forming distances "A" and "B" are substantially equal to each other, but distances "A" and "B" are less than the staple forming distance "C". The distance "D" between the bottoms of the first staple-receiving grooves 345, 347 and the bottom surface 342' of the primary driver base 342 is substantially equal to the distance "E" between the bottoms of the secondary staple-receiving grooves 356, 357 and the bottom surface 352' of the secondary driver base portion 352. See FIG. 15. Also in this embodiment, the distance "F" between the bottoms of the second staple-receiving grooves 376 and 378 and the bottom surface 373 of the third base 372 of the outside drivers 370a, 370b (FIG. 16) is less than distances "D" and "E" (FIG. 15). Because the forming distance "C" is greater than the forming distances "A" and "B", the staples 222 supported and formed by the outside drivers 370a, 370b are not compressed as much as the staples supported and formed by the inside drivers 330a, 330b. It will be understood that similar results may be attained on the opposite side of the elongated slot 310 and the cut line 600 formed in the tissue by using the same arrangements and sizes of inside drivers 330b and outside drivers 370b. In an alternative embodiment, the same effect may be achieved by altering the depths of the forming pockets 202 corresponding to the drivers 330a and 370b such that forming distance "C" is greater than the forming distances ""A" and "B". That is, the depth (distance "Z" in FIG. 16A) of the forming pockets 202 corresponding to the outside drivers 370a. 370b may be greater than the depth (distance "Z" in FIG. 14A) of the forming pockets 202 that correspond to the inside drivers 330a, 330b.

Figure 29:
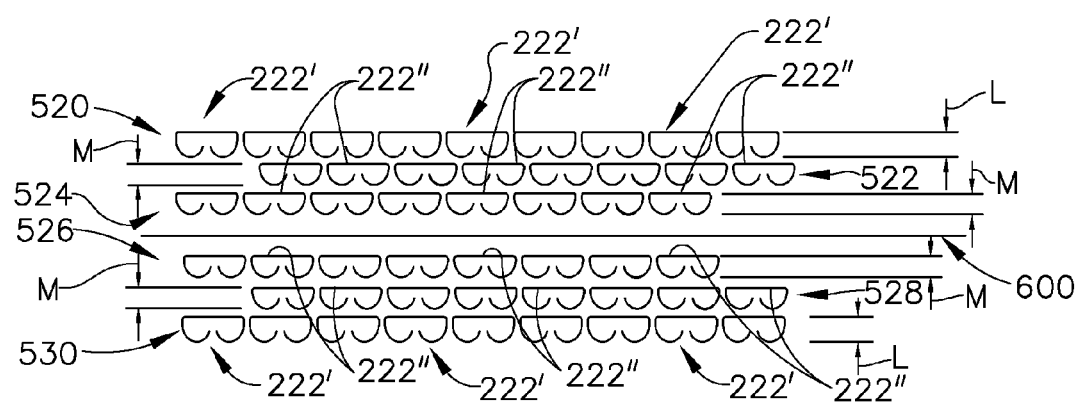
FIG. 29 is a diagrammatic representation of lines of staples installed on each side of a cut line using a surgical stapling and severing instrument according to various embodiments of the present invention.
Figure 31:
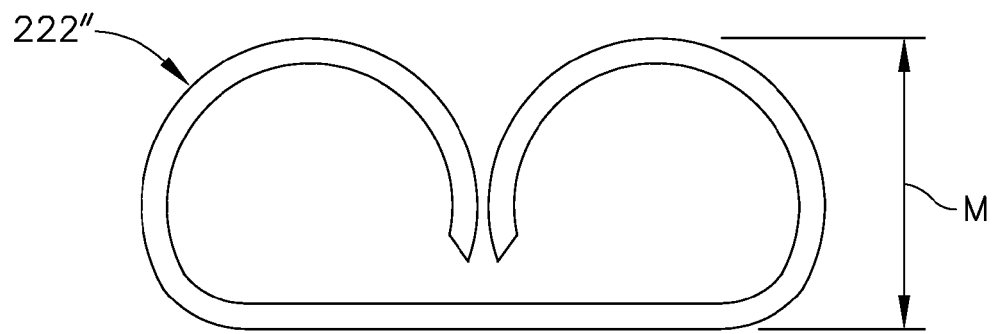
FIG. 31 depicts another staple formed by one outside driver according to various embodiments of the present invention.
Figure 30:
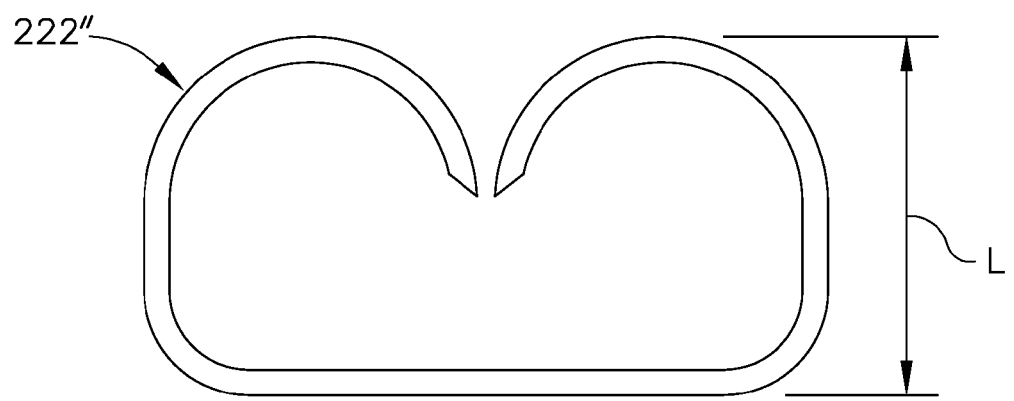
FIG. 30 depicts a staple formed by one inside driver according to various embodiments of the present invention.

FIG. 29 illustrates the rows of staples formed on each side of a cut line 600 utilizing this embodiment of the present invention wherein the forming distances "A" and "B" are equal to each other and the forming distance "C" is greater than the forming distances "A" and "B". For example, if forming distance "C" is 0.020" greater than forming distances "A" and "B", the formed height of the outside staples 222' (represented as dimension "L" in FIG. 30) in rows 520 and 530 would be 0.020 inches is greater than the formed height of the inside staples 222" (represented as dimension "M" in FIG. 31) in rows 522, 524, 526, 528.

The same result may be achieved by utilizing another embodiment of the present invention wherein the forming distances "A", "B" and "C" are essentially equal. In this embodiment, however, the height of each of the inside sled cams 410 (distance "H" in FIG. 21) is greater than the height of each of the outside sled cams 420 (distance "J" in FIG. 22). Thus, because the height "H" of the inside sled cams 410 is greater than the height "J'" of the outside sled cams 420, the inside sled cams 410 will drive the corresponding inside drivers 330a, 330b further towards the anvil than the outside sled cams 420 will drive the corresponding outside drivers 370a, 370b. Such driving action will cause the staples supported by the inside drivers 330a, 330b to be compressed to a greater extent than those staples supported by the outside drivers 370a, 370b. For example, if distance "H" is 0.020 inches greater than distance "J", the formed height of staples 222' in lines 520, 530 would be 0.020" greater than the formed height of staples 222" in lines 522, 524, 526, 528.

Figure 32:
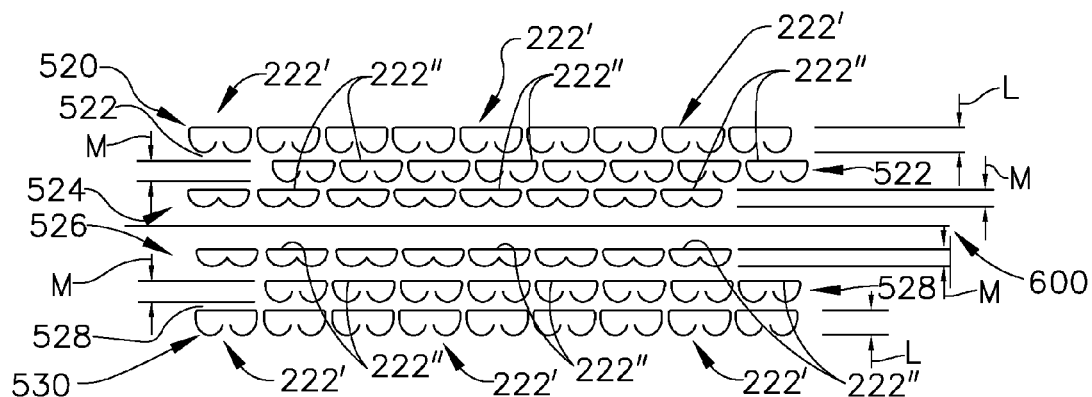
FIG. 32 is a diagrammatic representation of lines of staples installed on each side of a cut line using a surgical stapling and severing instrument according to various embodiments of the present invention.

When employing yet another embodiment of the present invention, the outside rows 520, 530 of staples 222' and the inside rows 522, 528 of staples 222" may be formed with heights that are greater than the formed heights of the staples 222" in the inside rows 524, 526. See FIG. 32. This result is achieved by making the forming distances "C" greater than the forming distance "A" and making forming distance "A" greater than secondary forming distance "B".

Figure 33:
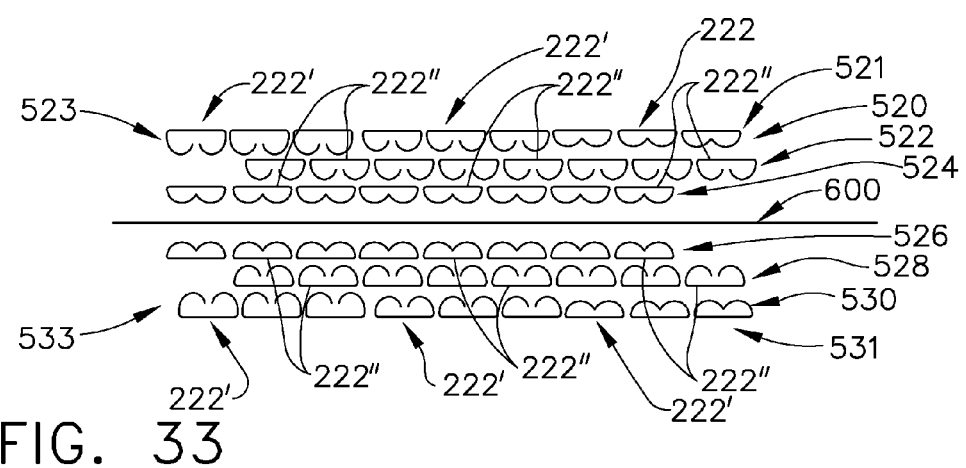
FIG. 33 is a diagrammatic representation of lines of staples installed on each side of a cut line using a surgical stapling and severing instrument according to various embodiments of the present invention.
Figure 34:
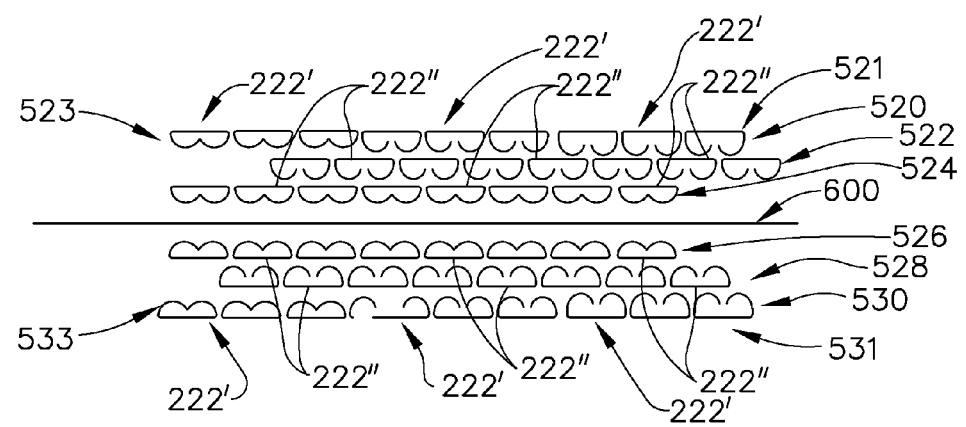
FIG. 34 is a diagrammatic representation of lines of staples installed on each side of a cut line using a surgical stapling and severing instrument according to various embodiments of the present invention.

Another embodiment of the present invention can be used to install staples where it is desirable for the formed heights of staples in a single row to vary. One such arrangement is depicted in FIG. 33. As can be seen in FIG. 33, the formed heights of the staples 222' in the outside rows 520, 530 increase when moving from the proximal ends 521, 531 of each row 520, 530, respectively to the distal ends 523, 533 of each row 520, 530, respectively. This effect may be accomplished by decreasing the forming distance "C" for each succeeding driver 370a, 370b. That is, the driver 370a closest the proximal end of the cartridge 300 would be sized to establish a forming distance "C" that is greater than the forming distance "C" achieved by the adjacent driver 370a and so on to achieve a condition wherein each succeeding staple 222' (moving in the direction from the proximal end to the distal end of the cartridge 300) would have larger formed heights. This result could also be attained in the staples 222" in rows 522, 524, 526, 528 by similarly altering the forming distances "A" and/or "B" attained by each driver 330a, 330b. Likewise, formed heights of the staples 222' in the outside rows 520, 530 could be made to decrease when moving from the proximal ends 521, 531 of each row 520, 530, respectively, to the distal ends 523, 533 of each row 520, 530, respectively. This result may be attained by increasing the forming distance of each succeeding driver 370a, 370b. That is, the driver 370a closest the proximal end of the cartridge 300 would have a forming distance "C" that is less than the forming distance "C" of the adjacent driver 370a and so on to achieve a condition wherein each succeeding staple 222' (moving in the direction from the proximal end to the distal end of the cartridge) would have smaller formed heights. See FIG. 34.

Figure 35:
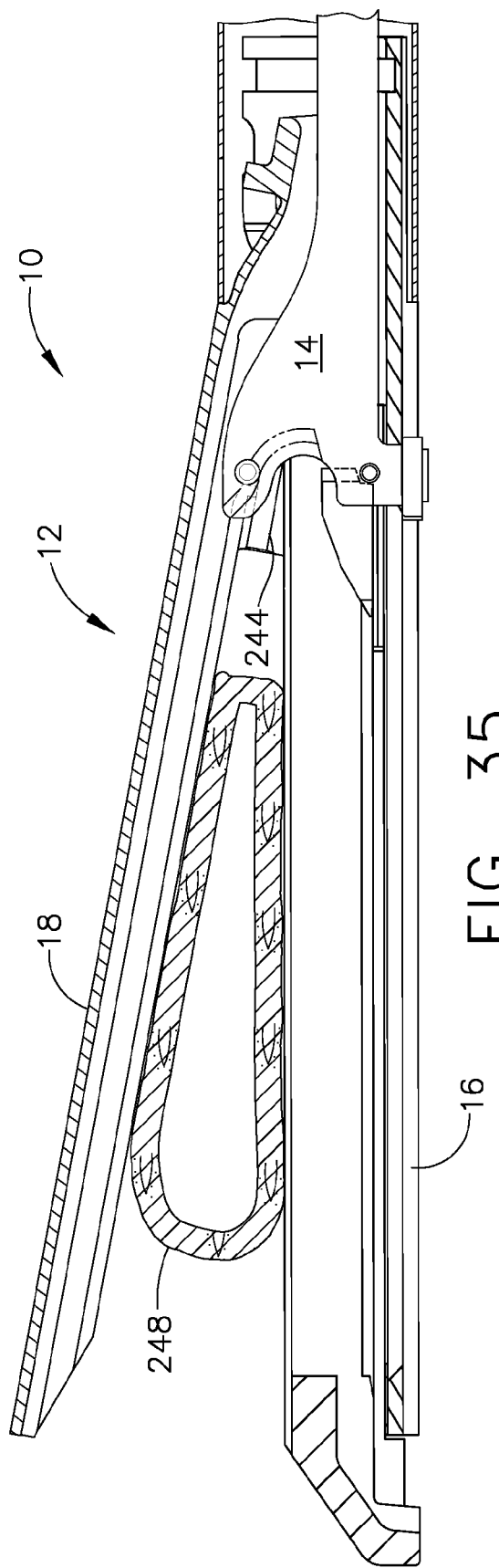
FIG. 35 is a side elevation section view of the surgical stapling and severing instrument of FIG. 1 taken along the longitudinal centerline of the end effector in a partially closed but unclamped position gripping tissue according to various embodiments of the present invention.

In use, the surgical stapling and severing instrument 10 is used as depicted in FIGS. 1-2 and 35-41. In FIGS. 1-2, the instrument 10 is in its start position, having had an unfired, fully loaded staple cartridge 300 snap-fitted into the distal end of the elongate channel 16. Both triggers 26, 28 are forward and the end effector 12 is open, such as would be typical after inserting the end effector 12 through a trocar or other opening into a body cavity. The instrument 10 is then manipulated by the clinician such that tissue 248 to be stapled and severed is positioned between the staple cartridge 300 and the anvil 18, as depicted in FIG. 35. With reference to FIGS. 36 and 37, the clinician then moves the closure trigger 26 proximally until positioned directly adjacent to the pistol grip 24, locking the handle portion 20 into the closed and clamped position. The retracted firing bar 14 in the end effector 12 does not impede the selective opening and closing of the end effector 12, but rather resides within the anvil pocket 40. With the anvil 18 closed and clamped, the E-beam firing bar 14 is aligned for firing through the end effector 12. In particular, the upper pin 38 is aligned with the anvil slot 42 and the elongate channel 16 is affirmatively engaged about the channel slot 45 by the middle pin 46 and the firing bar cap 44.

Figure 38:
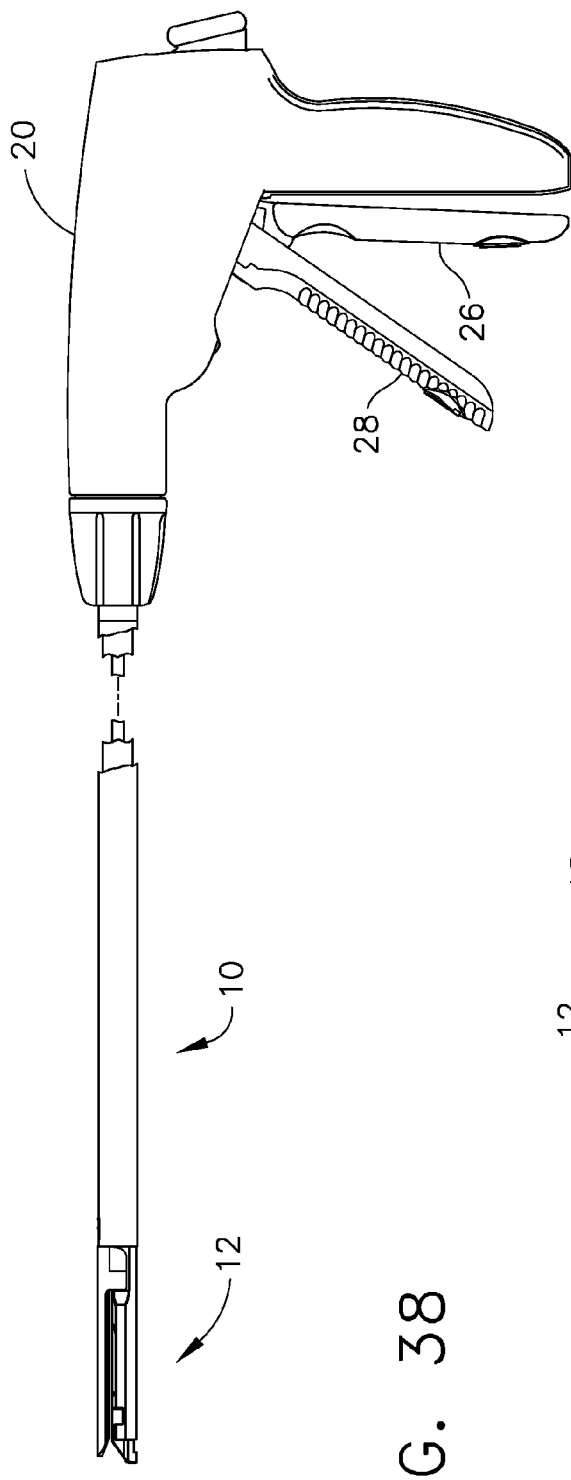
FIG. 38 depicts a view in centerline section of the distal end of the surgical stapling and severing instrument of FIG. 1 in a partially fired position according to various embodiments of the present invention.
Figure 39:
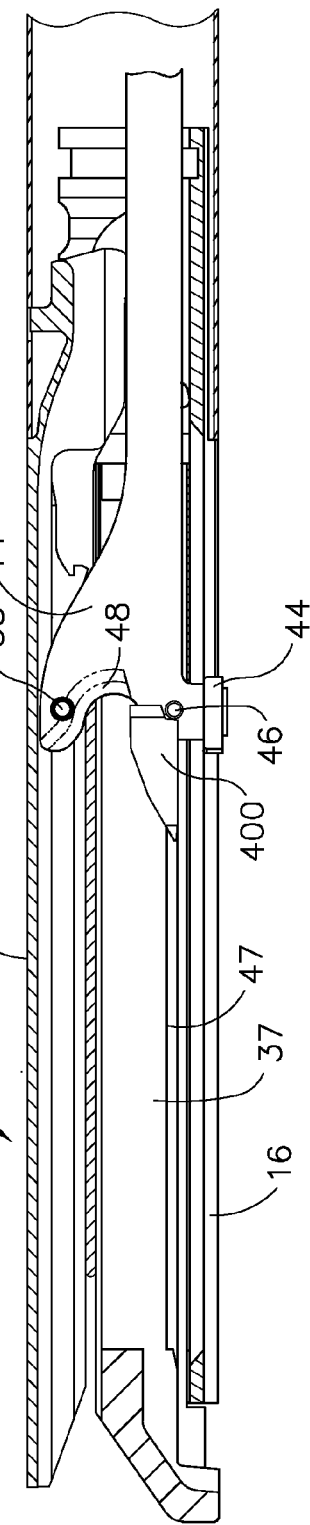
FIG. 39 depicts a partially cut away side elevation view of the surgical stapling and severing instrument of FIG. 1 in a partially fired position according to various embodiments of the present invention.

With reference to FIGS. 38 and 39, after tissue clamping has occurred, the clinician moves the firing trigger 28 proximally causing the firing bar 14 to move distally into the end effector 12. In particular, the middle pin 46 enters the staple cartridge 300 through the firing drive slot 47 to affect the firing of the staples 222 (not shown in FIGS. 38 and 39) via wedge sled 400 toward the anvil 18. The lowermost pin, or firing bar cap 44, cooperates with the middle pin 46 to slidingly position cutting edge 48 of the firing bar 14 to sever tissue. The two pins 44, 46 also position the upper pin 38 of the firing bar 14 within longitudinal anvil slot 42 of the anvil 18, affirmatively maintaining the spacing between the anvil 18 and the elongate channel 16 throughout its distal firing movement.

Figure 40:
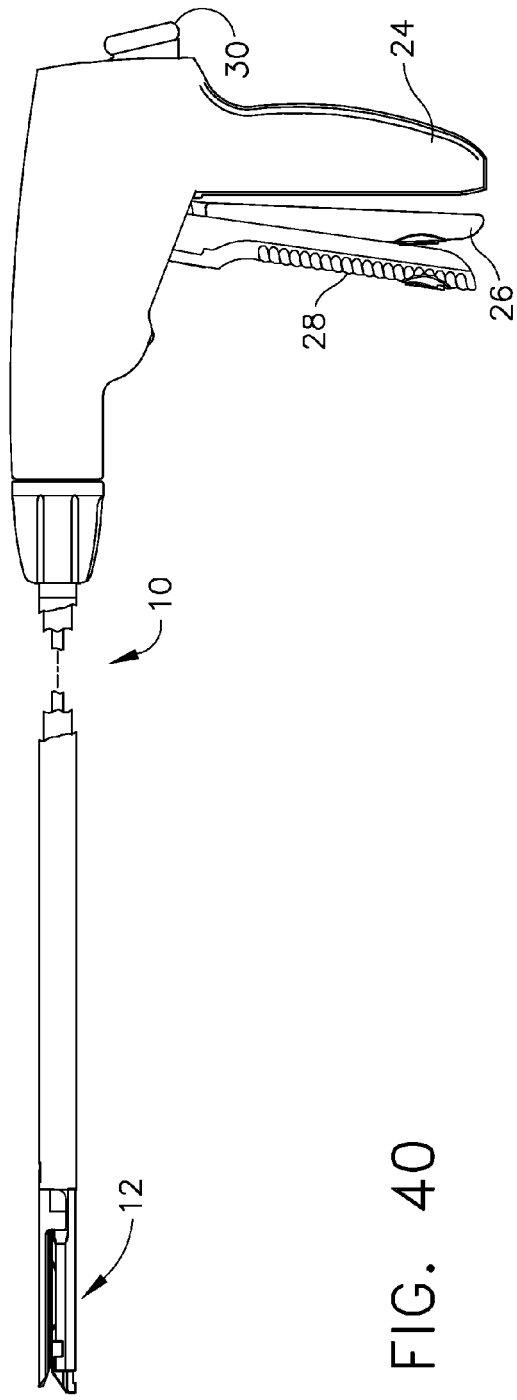
FIG. 40 depicts a view in centerline section of the distal end of the surgical stapling and severing instrument of FIG. 1 in a fully fired position according to various embodiments of the present invention.
Figure 41:
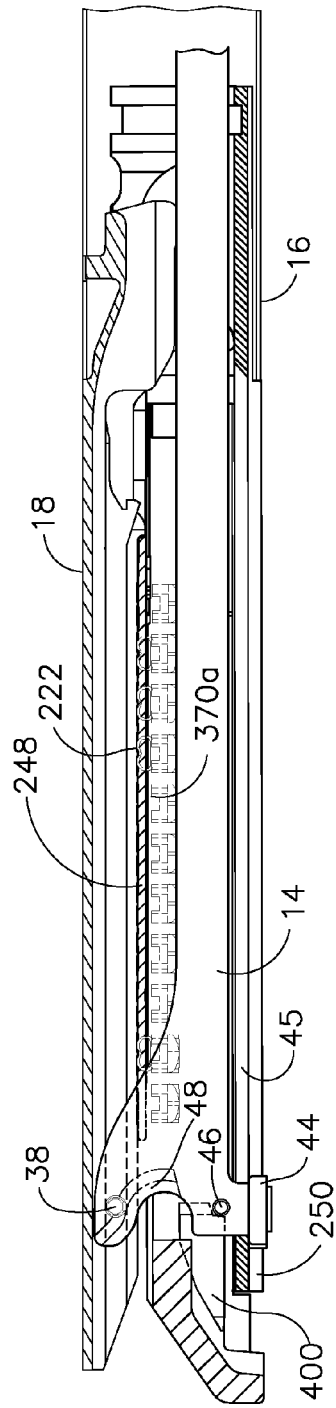
FIG. 41 is a partially cut-away side elevational view of the surgical stapling and severing instrument of FIG. 1 in a full fired position according to various embodiments of the present invention.

With reference to FIGS. 40 and 41, the clinician continues moving the firing trigger 28 until brought proximal to the closure trigger 26 and pistol grip 24. Thereby, all of the ends of the staples 222 are bent over as a result of their engagement with the anvil 18. The firing bar cap 44 is arrested against a firing bar stop 250 projecting toward the distal end of the channel slot 45. The cutting edge 48 has traversed completely through the tissue. The process is complete by releasing the firing trigger 28 and by then depressing the release button 30 while simultaneously squeezing the closure trigger 26 to open the end effector 12.

Figure 42:
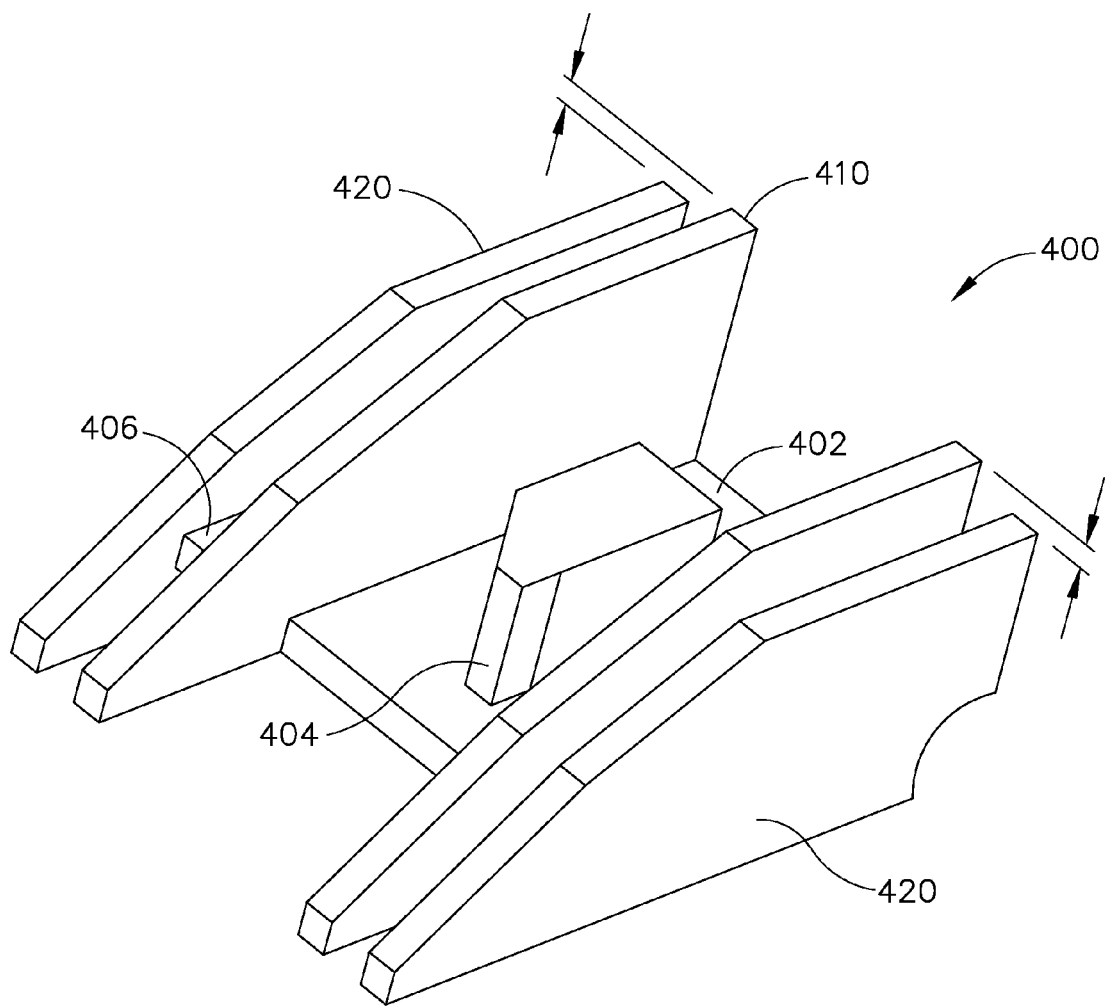
FIGS. 42-44 depict aspects of an end effector having a sled with multiple sled cams where one sled cam is taller than another according to various embodiments of the present invention.
Figure 43:
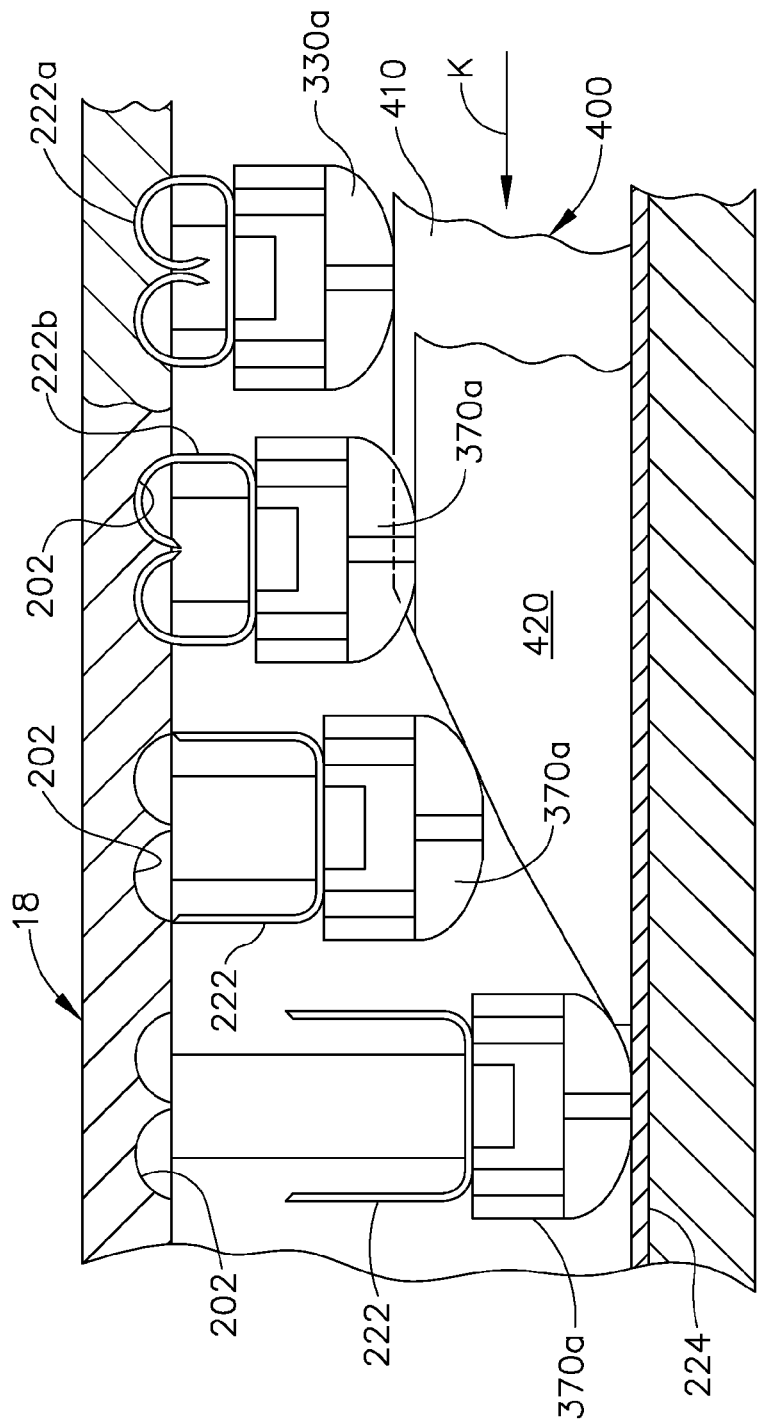

FIGS. 42-43 show the inside and outside sled cams 410, 420 of the sled 400 having different heights so that the staples, when formed, may have different formed heights. In particular, as shown in FIG. 42 the outside sled cam 420 may be shorter than the inside sled cam 410. That way, the outside staples may have a greater formed height than the inside staples. FIG. 42 is a perspective view of the sled 400 with the different heights for the inside and outside sled cams 410, 420. FIG. 43 is a side view of the end effector 12 showing various stages of driving the staples 222 with a sled 400 having different heights for the inside and outside sled cams 410, 420. As can be seen in FIG. 43, the formed staple 222b may have a greater formed height than the formed staple 222a because the staple 222b was driven by the outside cam sled 420 and the staple 222a was driven by the taller inside cam sled 410.

Figure 44:
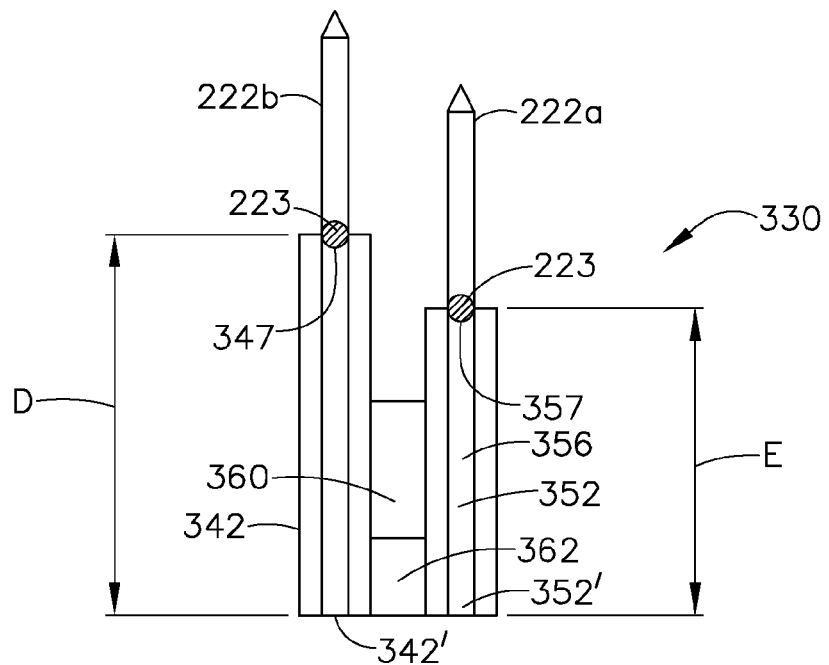

In another embodiment, as shown in FIG. 44, the heights of the driver portions 342, 352 of a double driver 330 may vary so that the staples, when formed, may have different heights. In particular, as shown in FIG. 44, the secondary driver portion 352 may be shorter (having height "E") than the primary driver portion 342 (having height "D"). That way, the staple 222a driven by the secondary driver portion 352 may have a greater formed height than the staple 222b driven by the primary driver portion 342. In various embodiments, some or all of the inside double drivers 330 could have primary and secondary driver portions 342 of different heights. Further, the heights differential need not be all the same. Different inside double drivers 330 could have different height differentials.

In addition, the height of the primary and secondary driver portions 342, 352 may be the same as or different from the height of the driver portions 372 of the outside staple drivers 370. That is, in various embodiments, the driver height of the outside staple driver portion 372 may be (1) different from the height of both driver portions 342, 352 of the inside double driver 330 when the driver portions 342, 352 are the same height, (2) different from the height of both driver portions 342, 352 when they are different heights, or (3) the same as the height for one of the driver portions 342, 352 when the driver portions 342, 352 have different heights. Also, the heights of the driver portions 372 of the outside staple drivers 370 need not be all the same. Different outside staple drivers 370 could have different heights.

Figure 45:
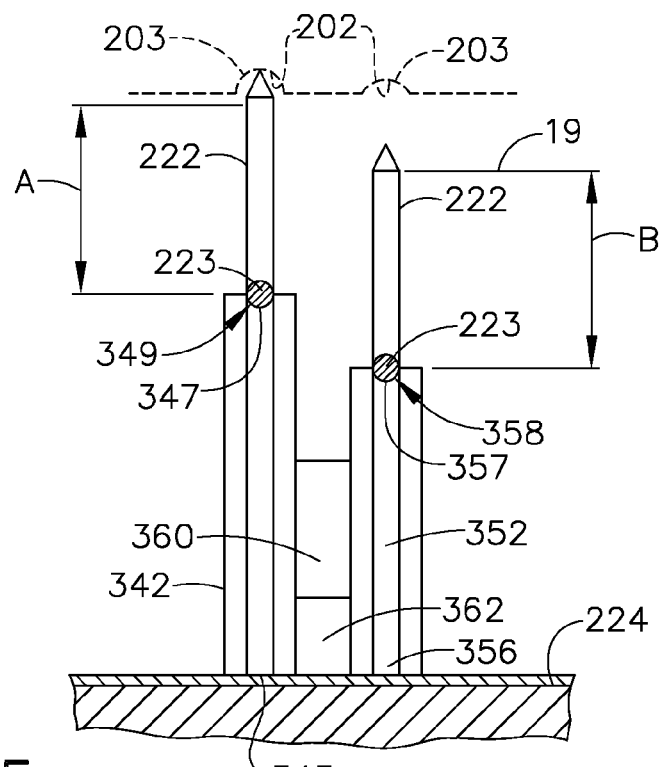
FIG. 45 depicts aspects of an end effector with staple forming pockets having varying depths according to various embodiments of the present invention.

FIG. 45 shows an embodiment having different height drivers (e.g., the primary driver portion 342 taller than the secondary driver portion 352) and with different depth anvil pockets 202. Varying the depth of the anvil pockets 202 can also affect the height of the formed staples. All things being equal, deeper pockets should result in longer formed staples. In the illustrated embodiment, the pockets 202 corresponding to the primary driver portion 342 are deeper than the pockets 202 corresponding to the secondary driver portion 352. Some or all of the pockets 202 for each staple row 500-510 could be deeper. Also, the depth differentials need not be the same. A multitude of different depths could be used in a single row 500-510 or across rows 500-510.

Figure 46:
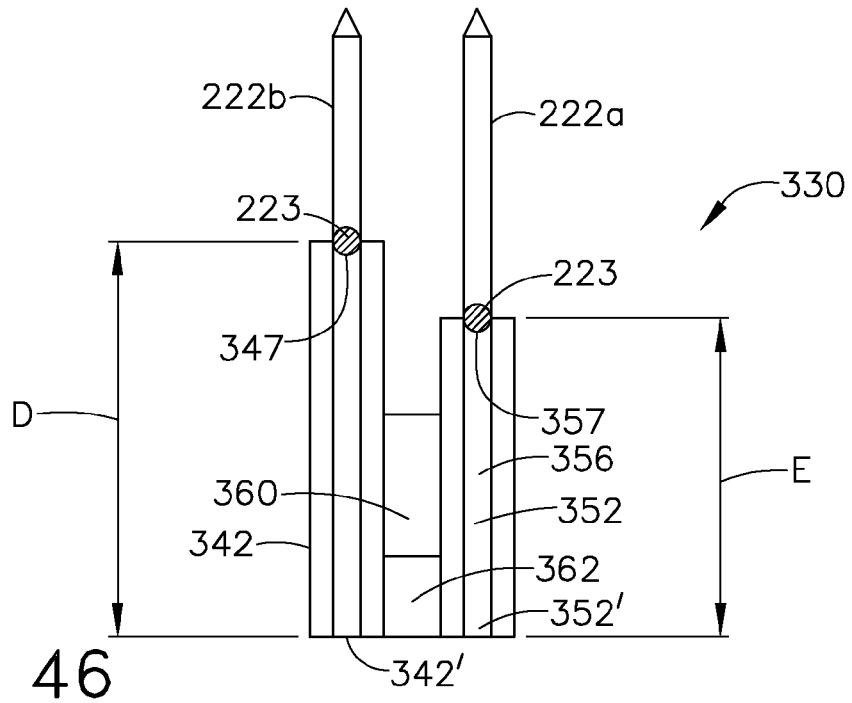
FIGS. 46-47 depict a double staple driver having staples of different pre-formation lengths according to various embodiments of the present invention.
Figure 47:
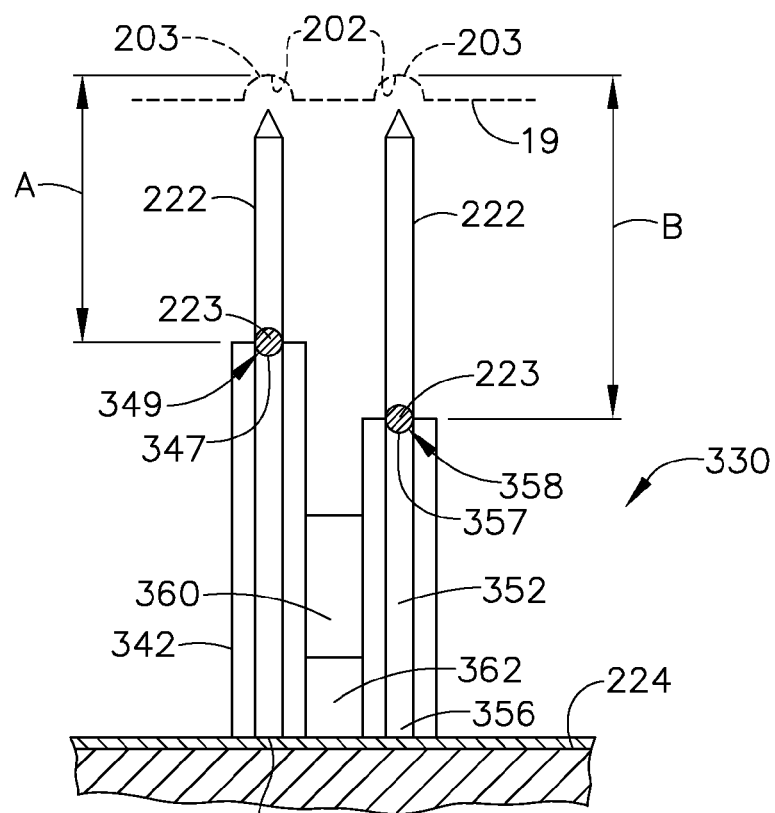

In addition, as shown in FIG. 46, staples 222 with differing pre-formation prong heights ("P") may be used. In the illustrated embodiment, the longer staple 222a is used with the shorter, secondary driver portion 352 of an inside double driver 330 in comparison with staple 222b driven by the primary driver portion 342. The pre-formation staple prong lengths may vary within a staple row 500-510 or across staple rows. That is, for example, all of the staples in the inside rows 504-506 could have the same pre-formation prong length x, all of the staples in the intermediate rows 502, 508 could be longer (e.g., a length 1.10x), and all of the staples in the outer rows 500, 510 could be still longer (e.g., a length of 1.20x). As shown in FIG. 47, the anvil pockets 202 could have the same depth. In other embodiments, varying anvil pocket depths could be used.

Figure 48:
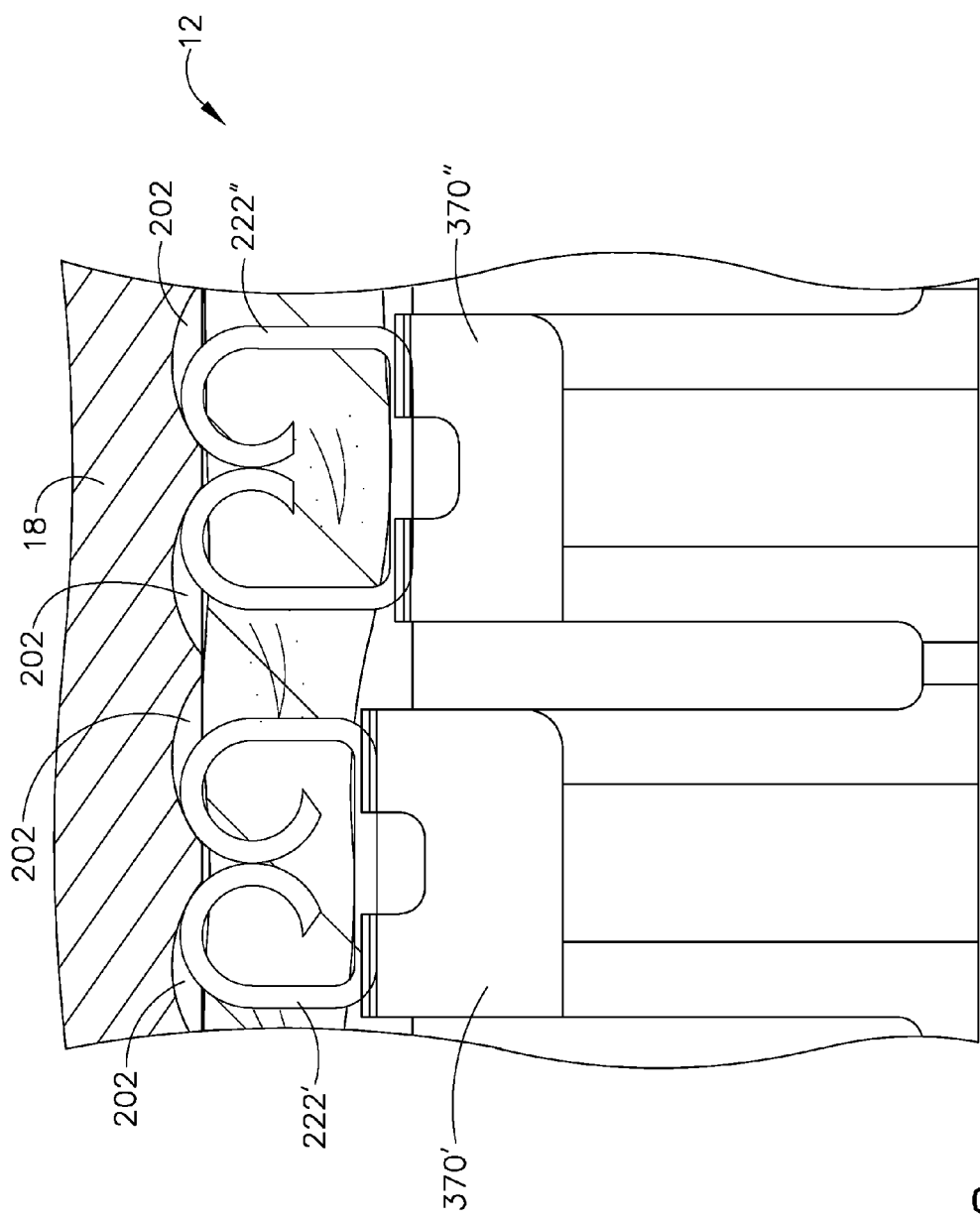
FIG. 48 depicts a side-view of an end effector having a double staple driver having different staple driver heights according to various embodiments of the present invention.

FIG. 48 is a side view of the end effector 12 in an embodiment where the outside staple drivers 370 have different heights. In particular, in the illustrated embodiment, the first staple driver 370' is taller than the second staple driver 370". In the illustrated embodiment, the staples 222 have the same pre-formation prong length and the corresponding anvil pockets 202 have the same depth. As such, the formed staple 222" formed with the second outside staple driver 370" is longer than the formed staple 222' formed with the first outside staple driver 370'.

Figure 49:
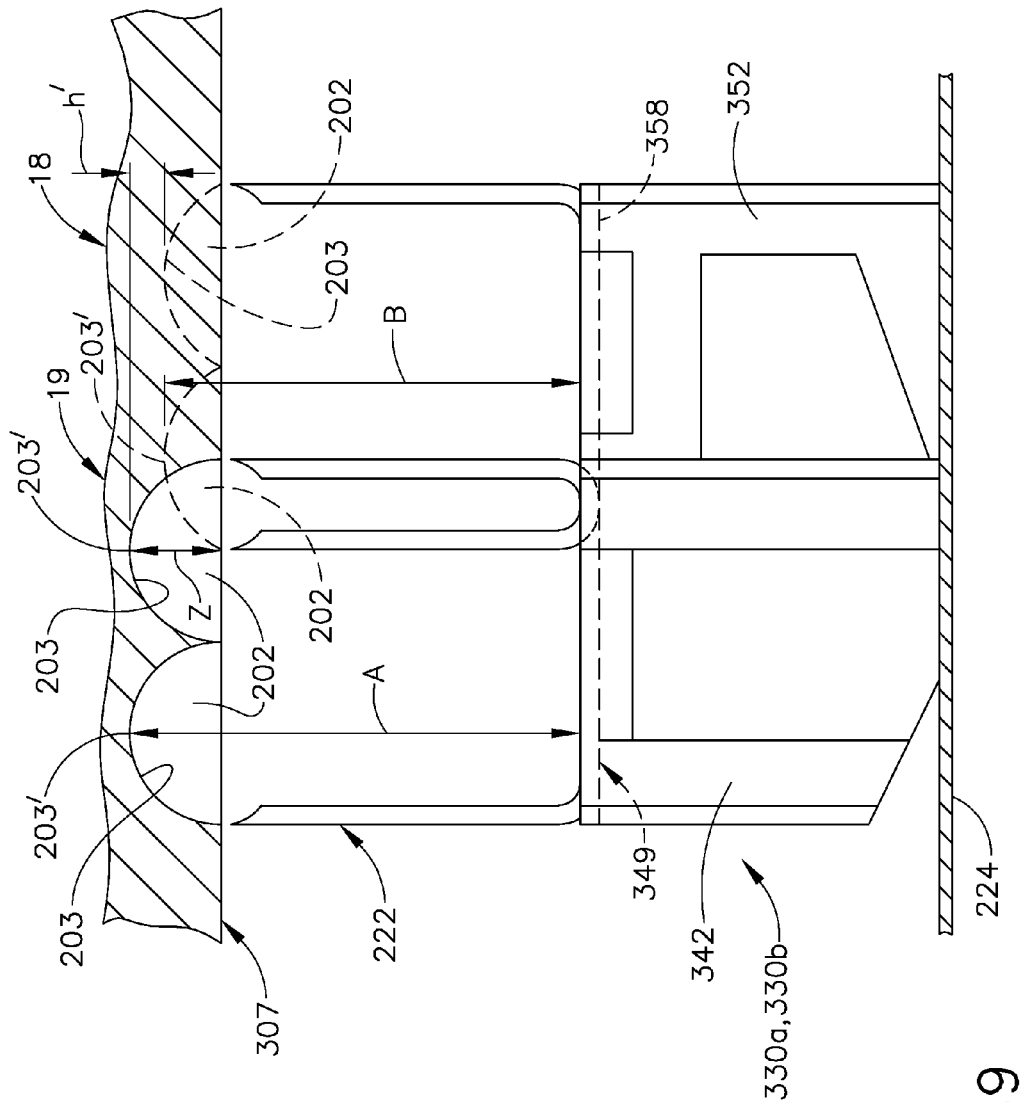
FIGS. 49-50 depict a side-view of an end effector having staple forming pockets of varying depths according to various embodiments of the present invention.
Figure 50:
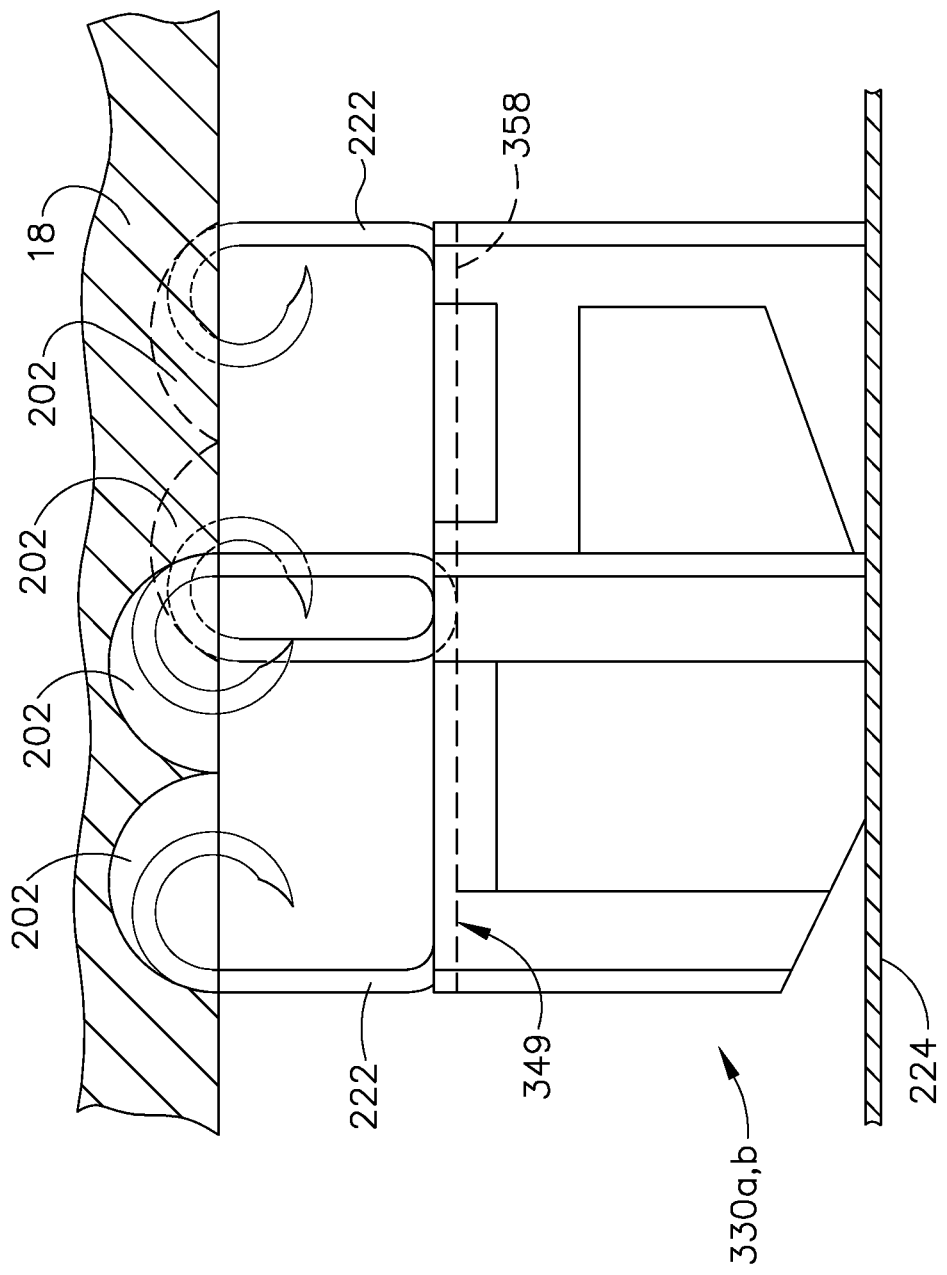

FIG. 49 is a side view of the end effector 12 where the anvil 18 has pockets 202 of different depth for the staples 222 driven by a inside double driver 330. In the illustrated embodiment, the pockets 202 corresponding to the primary driver portion 342 are deeper than the corresponding pockets 202 for the secondary driver portion 352. In this embodiment, the primary and secondary driver portions 342, 352 are the same height and the staples 222 have the same pre-formation prong length. The distance between the top of the primary driver portion 342 and the top of the corresponding anvil pockets 202 is height "A" and the corresponding height for the secondary portion 352 is height "B," where "A" is greater than "B" by a height differential "h". This should result in longer formed staples for the primary driver portion 342, as shown in FIG. 50.

Figure 51:
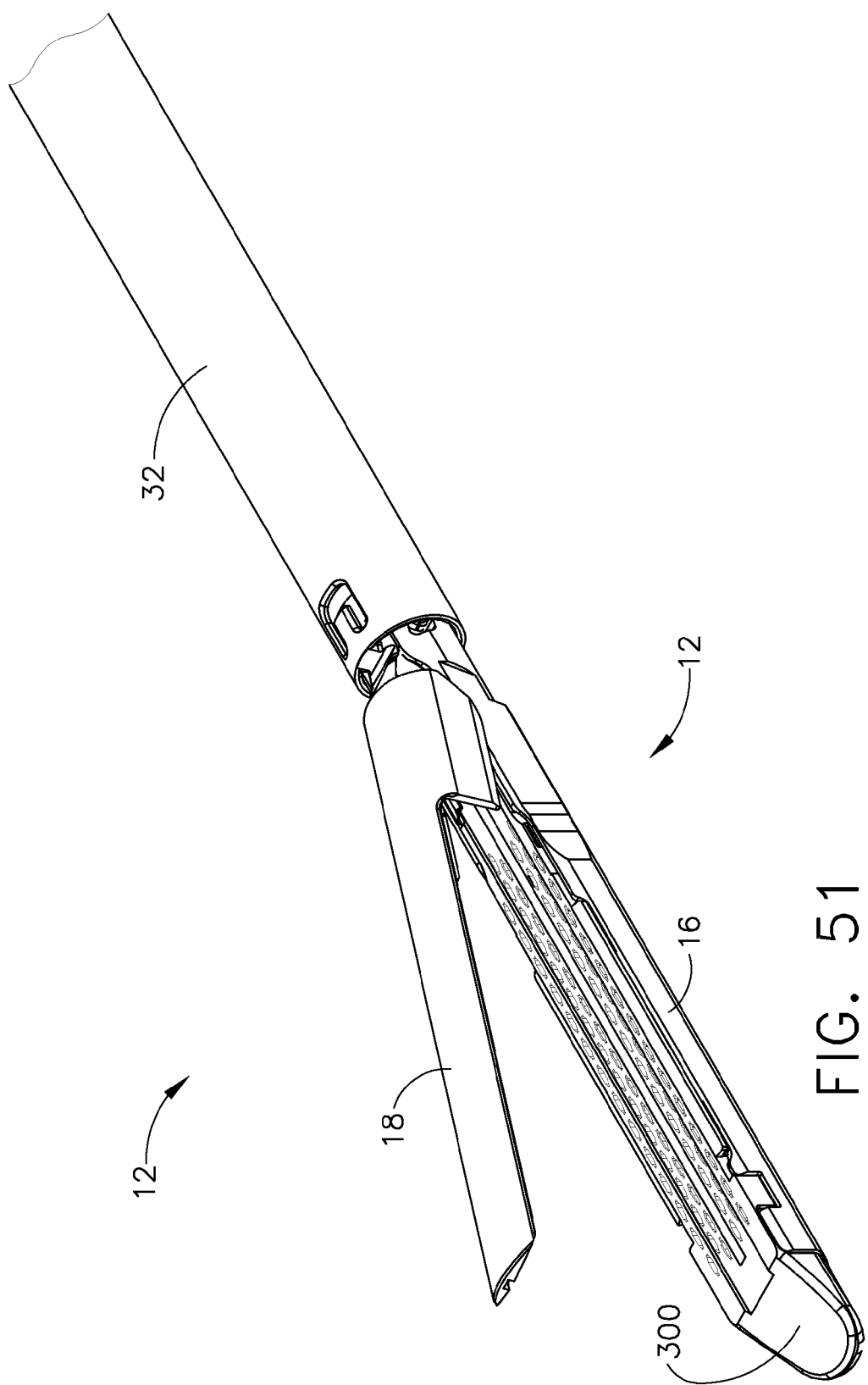
Figure 52:
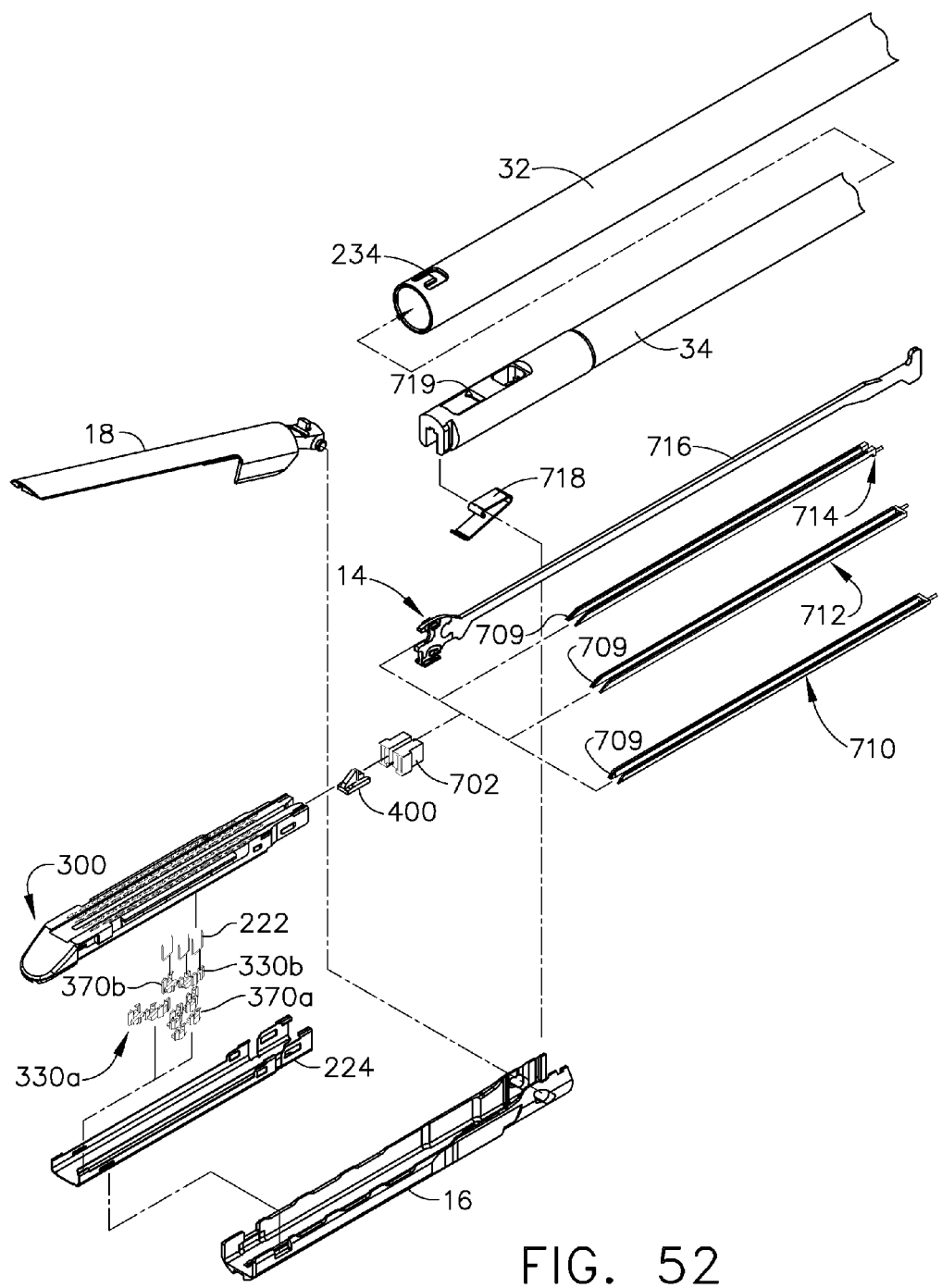
Figure 55:
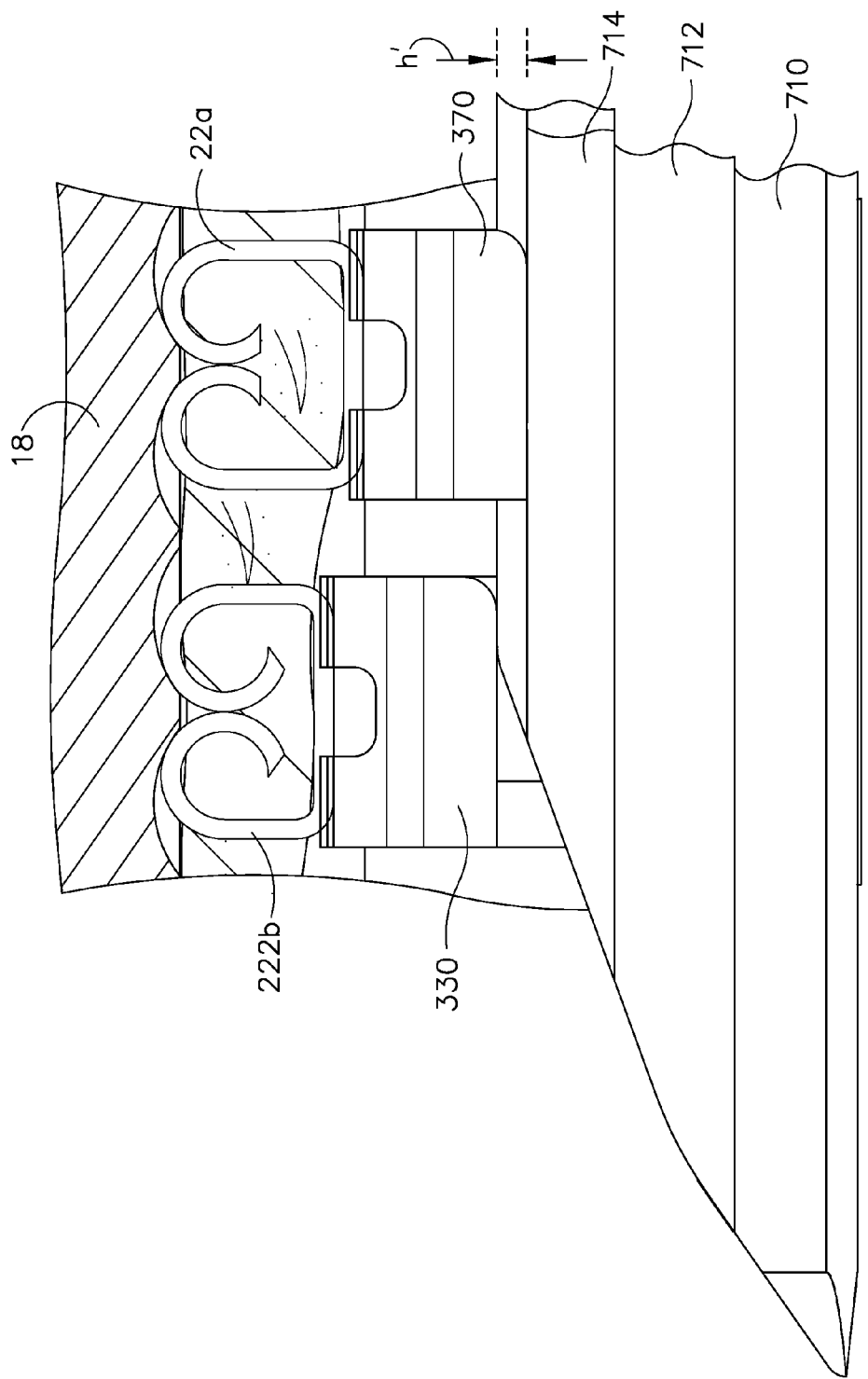
Figure 56:
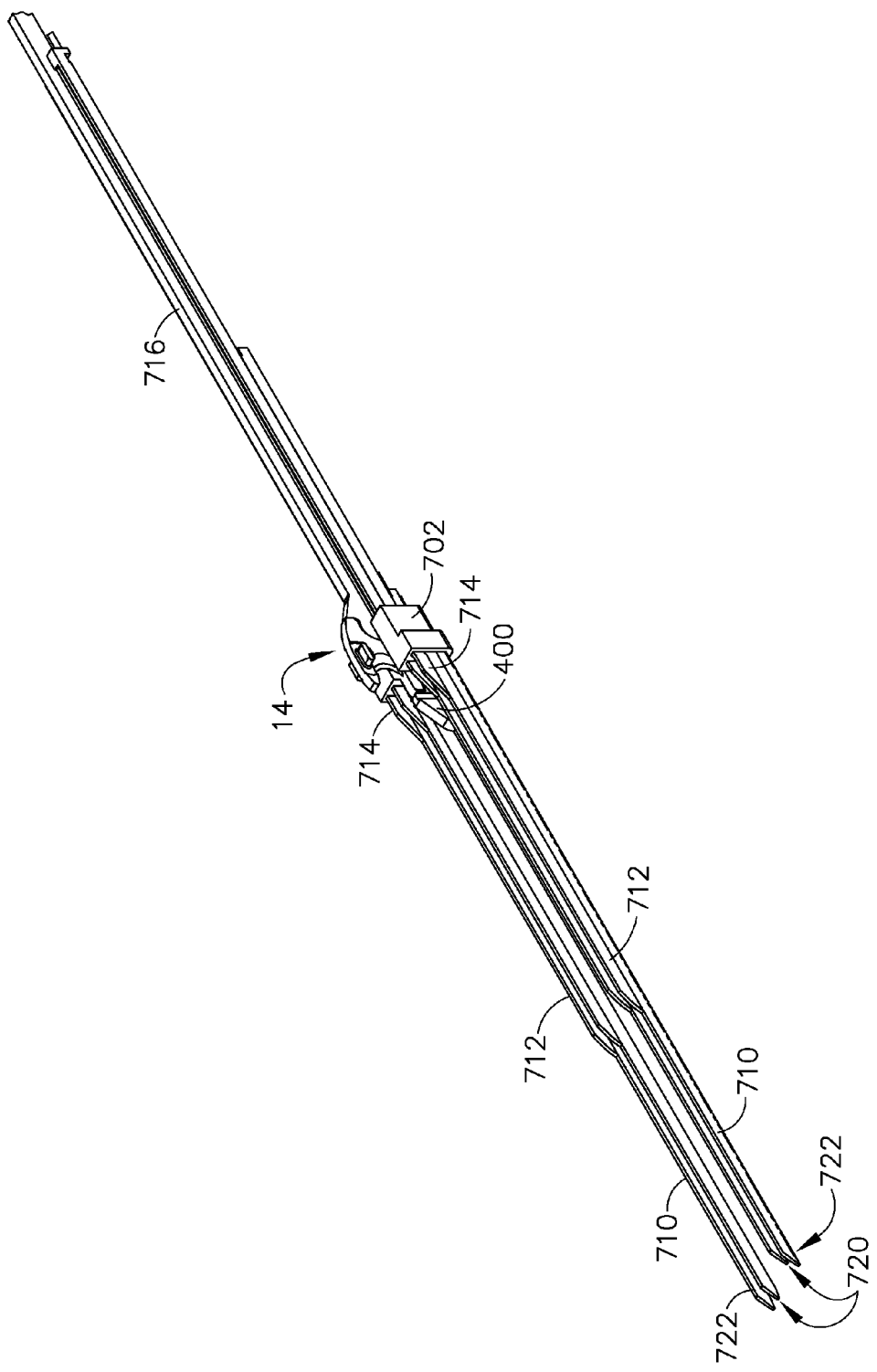
Figure 57:
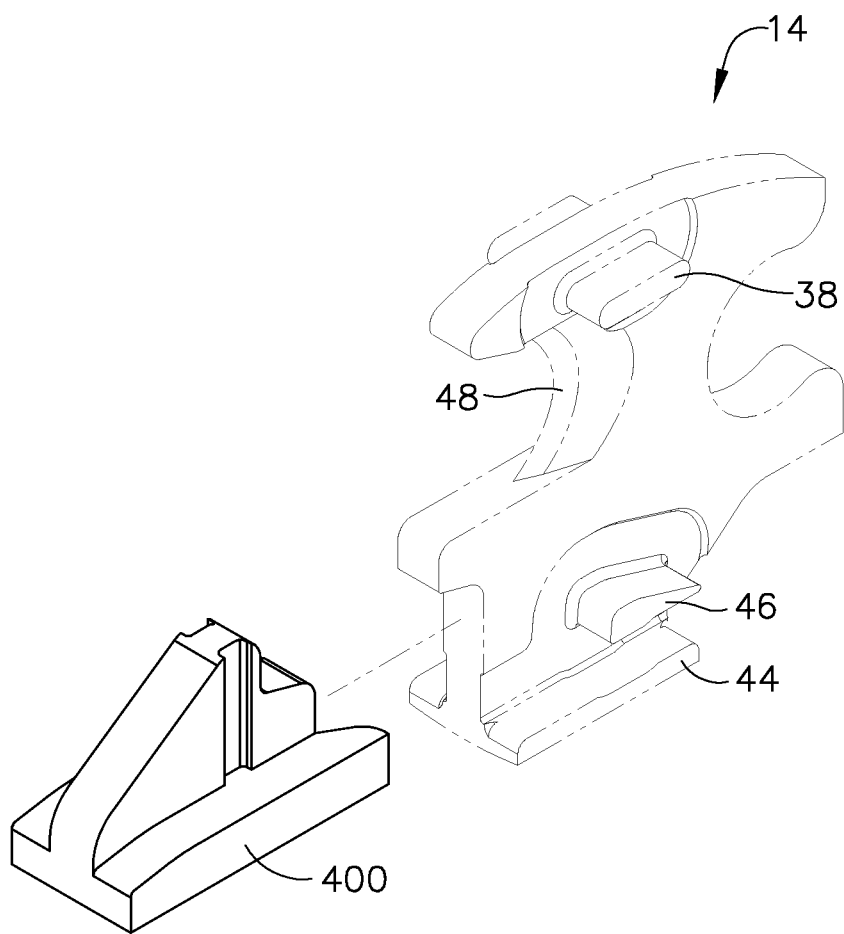

FIGS. 51 and 60 show aspects of an end effector 12 according to other embodiments that can be used to produce staples of different formed lengths. In the illustrated embodiment, the staple drivers 330, 370 are driven in stages by a plurality of actuator wedge cams 709 at the distal end of a plurality of wedge band sets 710, 712, 714. In the illustrated embodiment, each wedge band set comprise four wedge bands (shown best in FIG. 56); two 720 for actuating the inner drivers 330a,b and two 722 for actuating the outer drivers 370a,b. The wedge bands of the wedge band sets 710, 712, 714 may be actuated in serial order and may ride on top of one another in a stack to drive the staple drivers 330a,b, 370a,b (and hence the staples 222) in serial stages. For example, the wedge bands of the lowermost actuator wedge band set 710 may be fired (or actuated) first, and may partially deploy the staples 222. The middle wedge band set 712, which rides on top of the lowermost wedge band set 710 as shown in FIGS. 53-56, may be actuated next, which may have the effect of beginning to form the staples 222. Then the uppermost wedge band set 714, which rides on the middle wedge band set 712, may be actuated, which finishes the formation of the staples 222. FIG. 56 illustrates this operation. In FIG. 56, the lowermost wedge band sets 710 have been fired, the middle wedge band sets 712 have been partially fired, and the uppermost wedge band set 714 has not yet been fired. Thus, such an embodiment may comprise a plurality (in this case four) of stacked wedge band sets, each stack comprising a wedge band from the lowermost set 710, the middle set 712, and the uppermost set 714.

The firing bar 716, with the e-beam firing mechanism 14, may then be fired to cut the tissue clamped by the end effector 12. A hold down spring 718, which may be connected to the frame 34 at a crossbar 719, may engage and urge the firing bar 716 downward.

Figure 61:
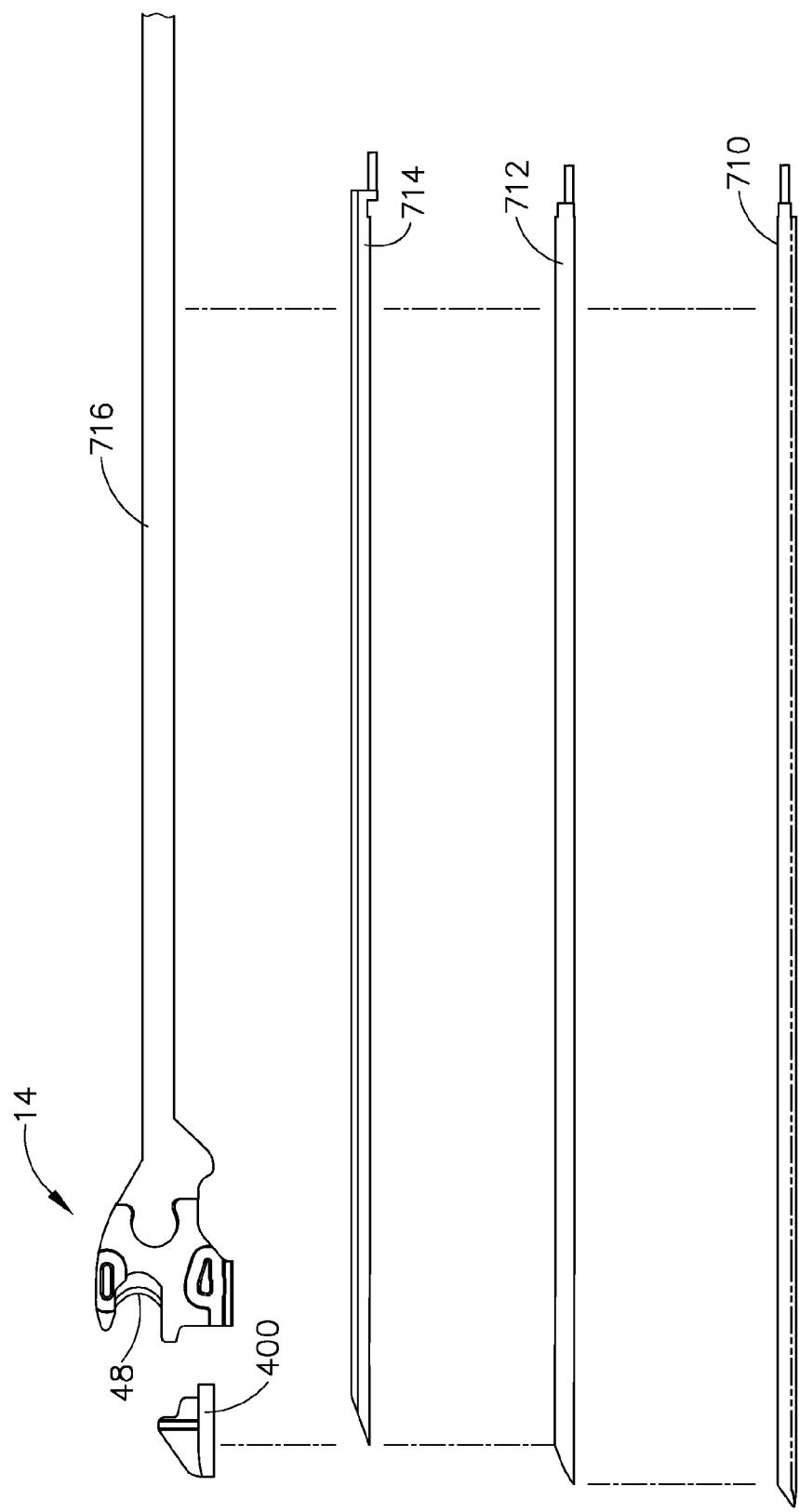

As can be seen best in FIGS. 54 and 56, the cumulative height of the wedge band stacks of inner row 720 or may be greater than the cumulative height of the wedge band stacks of the outer row 722 (by a height differential h'). That way, the outer row of staples may have a greater formed length than the inner row of formed staples, as shown in the example of FIG. 55, where the outer row staple 222a has a greater formed length than the inner row staple 222b. As shown the example of FIG. 61, according to one embodiment, the wedge bands of the lowermost and middle wedge bands sets 710, 712 may be the same height, and the height of the wedge bands for the outer row 722 of the uppermost wedge band set 714 may be less than the height of the wedge bands of the inner row 720 of the uppermost wedge band set 714 to provide the height differential for the different wedge band stacks.

The end effector 12 in such an embodiment may still comprise a sled 400, but without the sled cams 410, 420, to keep the firing mechanism 14 out of the lockout in the channel (see FIGS. 3-4 and related text).

The inner and outer wedge band stacks 720, 722 may be tightly spaced within the frame 34. Accordingly, the end effector 12 may further comprise an actuator wedge band respective guide 702 for spreading out the wedge band stacks 720, 722 when they enter the end effector 12 to align with the staple drivers 330, 370. The wedge band guide 702 may include wedge band channels for each of the inner and outer wedge band stacks 720, 722. That is, in the illustrated embodiment, the wedge band guide 702 may comprise four wedge band channels—two of the inner rows 720 and two for the outer rows 722. FIGS. 58-60 show one side of the wedge band guide 702 in more detail. As shown in FIG. 60, the wedge band channels 730, 732 may force the wedge band stacks 720, 722 outward as they enter the end effector 12. The inner wedge band channel 730 may direct the inner wedge band stack 720 so that the inner wedge band stack 720 aligns with the inner staple drivers 330 and the outer wedge band channel 732 may direct the outer row wedge band stack 722 so that the outer wedge band stack aligns with the outer staple drivers 370. In the illustrated embodiment, the channels 730, 732 are straight. In other embodiments, one or both of the channels 730, 732 may comprise curved portions.

Figure 62:
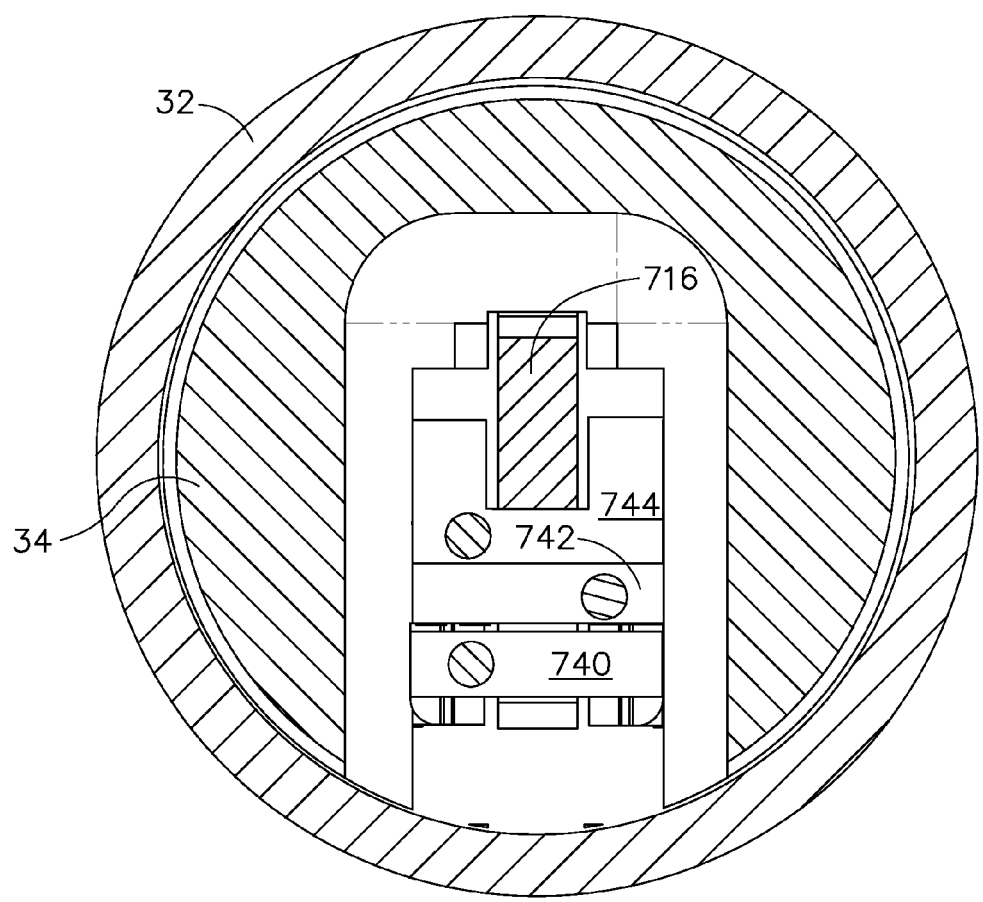
Figure 63:
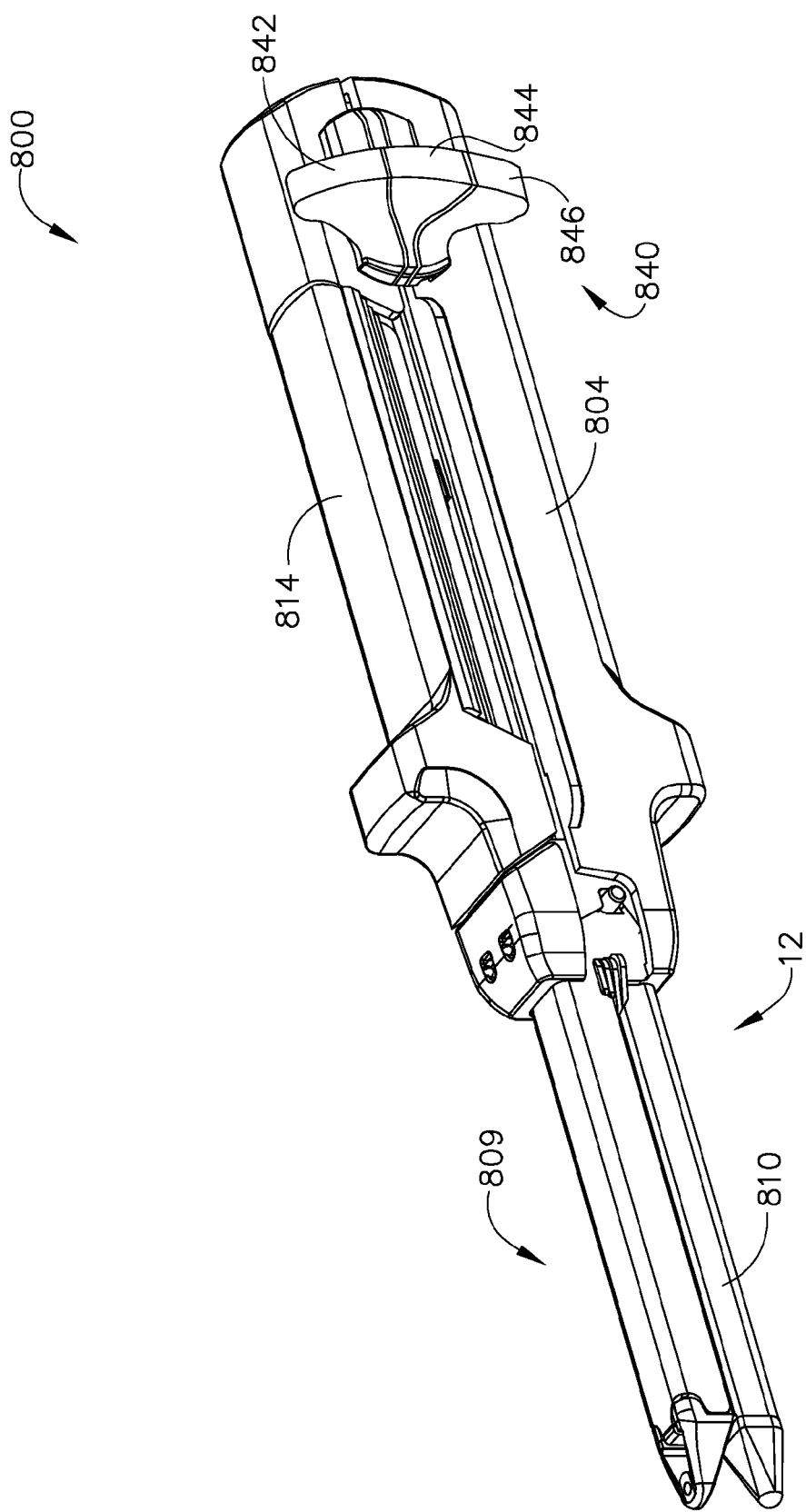
FIGS. 63-69 depict aspects of an open linear surgical stapling device according to various embodiments of the present invention.
Figure 64:
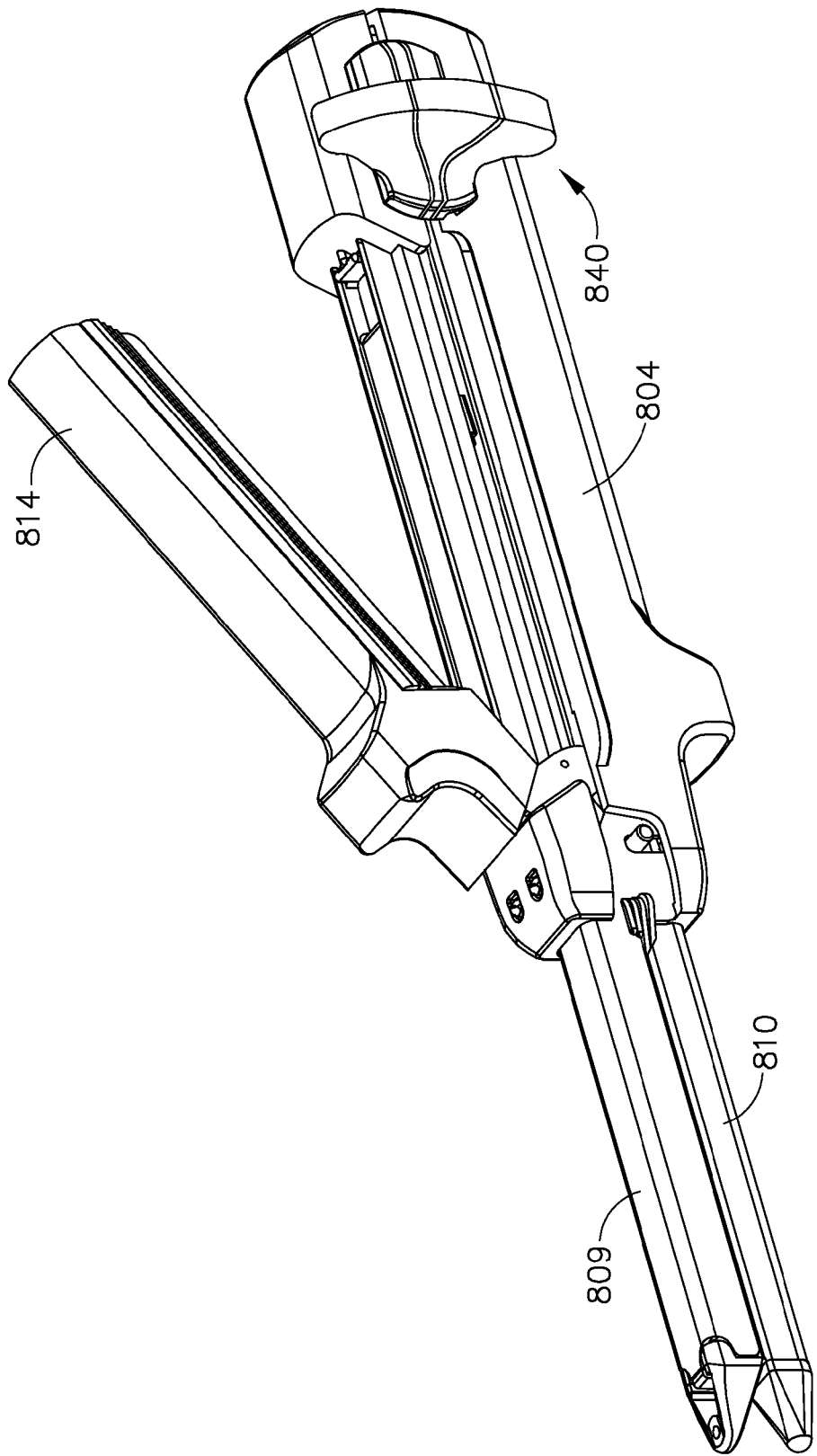
Figure 65:
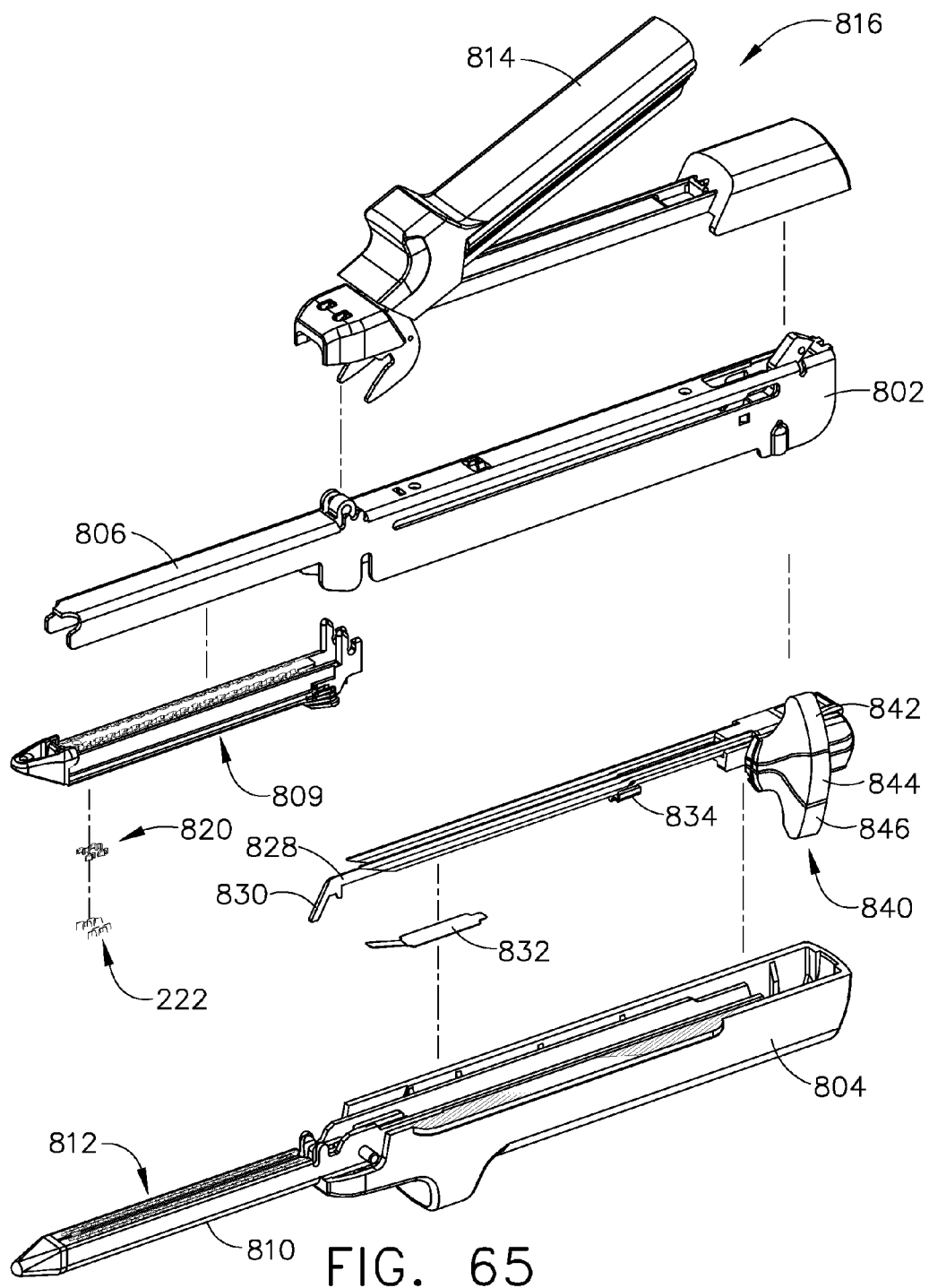

FIG. 62 is a cross-sectional view of the shaft assembly 10 according to such an embodiment. As shown in FIG. 62, each wedge band set 710-714 may have its own actuation (or firing) bar. The lowermost actuation bar 740 may actuate the wedge bands of the lowermost wedge band set 710, the middle actuation bar 742 may actuate the wedge bands of the middle wedge band set 712, and the uppermost actuation bar 744 may actuate the wedge bands of the uppermost wedge band set 714. The firing bar 716 for actuating the cutting instrument 14 may be connected to the uppermost wedge band set 714 so that the cutting instrument 14 is actuated with the uppermost (last) wedge band set 714. In other embodiments, the firing bar 716 may have its own actuation mechanism so that is may be actuated separately.

In practice, the clinician may choose (or select) to actuate less than all of the wedge band sets 710-714 before actuating the firing rod 716 to cut the tissue to thereby exercise some choice in the length of the staples to be formed. For example, in various embodiments, the clinician may select to actuate the lowermost and middle wedge band sets 710, 712—and not the uppermost wedge band set 714—before cutting.

FIGS. 63-69 illustrate an embodiment of an open linear stapling and cutting device 800 that may use multiple stacked wedge band sets to produce staples of different formed lengths. In the illustrated embodiment, the anvil 810 is below the channel 809. As such, the staples are driven down through tissue clamped in the end effector 12 as part of the stapling operation.

The device 800 may include an upper body piece 802 and a lower body piece 804. The upper body piece 802 may include a channel 806 in which the staple cartridge 809 is inserted. The anvil 810 may be connected to the lower body piece 804 and face the staple cartridge 809 so that the staples 222 can be formed against the staple forming surface 812 of the anvil 810. When the clinician is satisfied with the position of the tissue between the cartridge 809 and the anvil 810, the clinician may lock the device 800 using a clamp lever 814 of a clamp lever assembly 816 connected to the upper body piece 802.

The staple drivers 820 in the cartridge 809 may be actuated in stages using multiple staged wedge band stacks. Because the staples 222 are driven down in this embodiment, the wedge bands of the uppermost wedge band set 822 may be actuated first to partially deploy the staples 222. Next, the wedge bands of the middle wedge band set 824, which ride on the uppermost wedge band set 822, may be actuated to begin forming the staples 222. Then the wedge bands of the lowermost wedge band set 826, which ride on the middle wedge band set 824, may be actuated, which finishes the formation of the staples 222.

In the illustrated embodiment, the firing bar 828, with the knife 830 at is distal end, is connected to the lowermost wedge band set 826 and is fired with the lowermost wedge band set 826. A hold down spring 832 may engage and urge the firing bar 828 upward. A knife retainer 834 may retain the firing bar 828 with the lowermost wedge band set 826.

Figure 67:
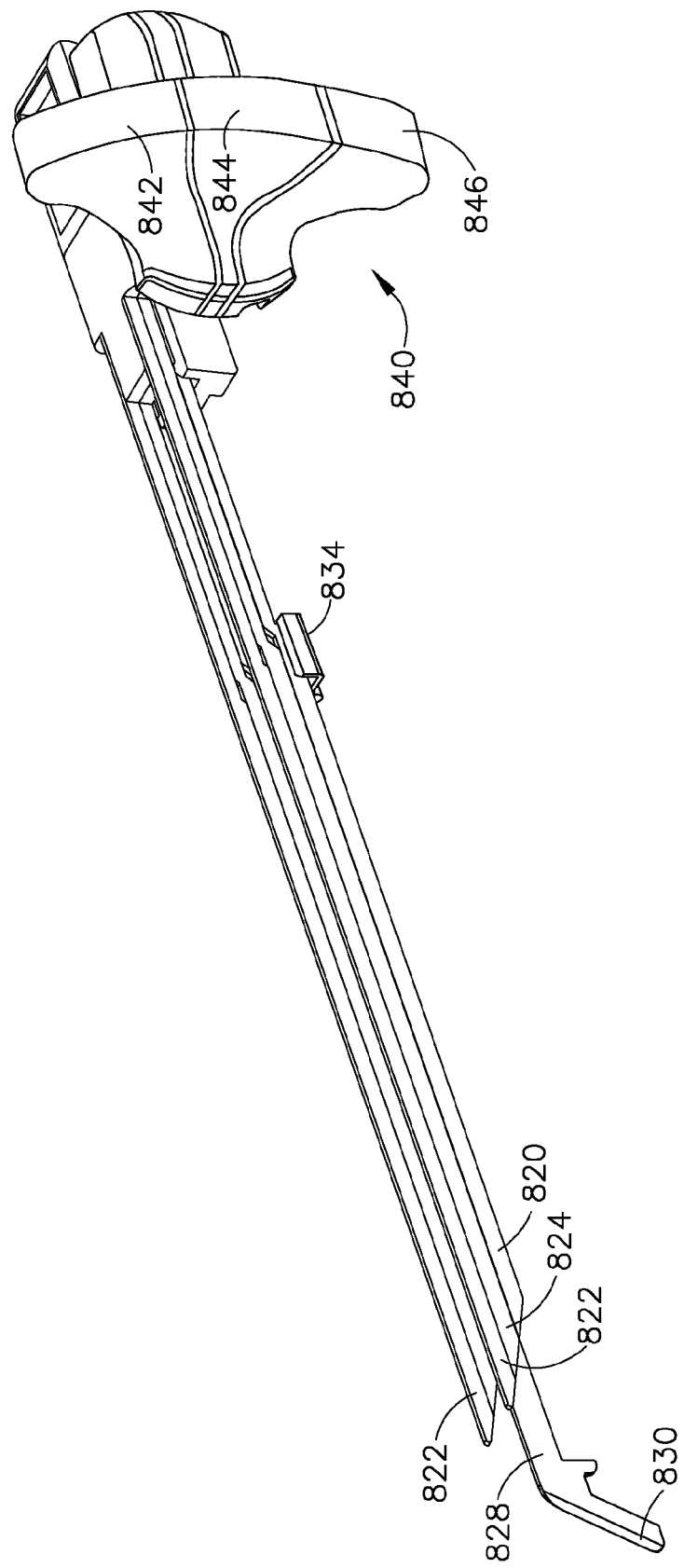
Figure 68:
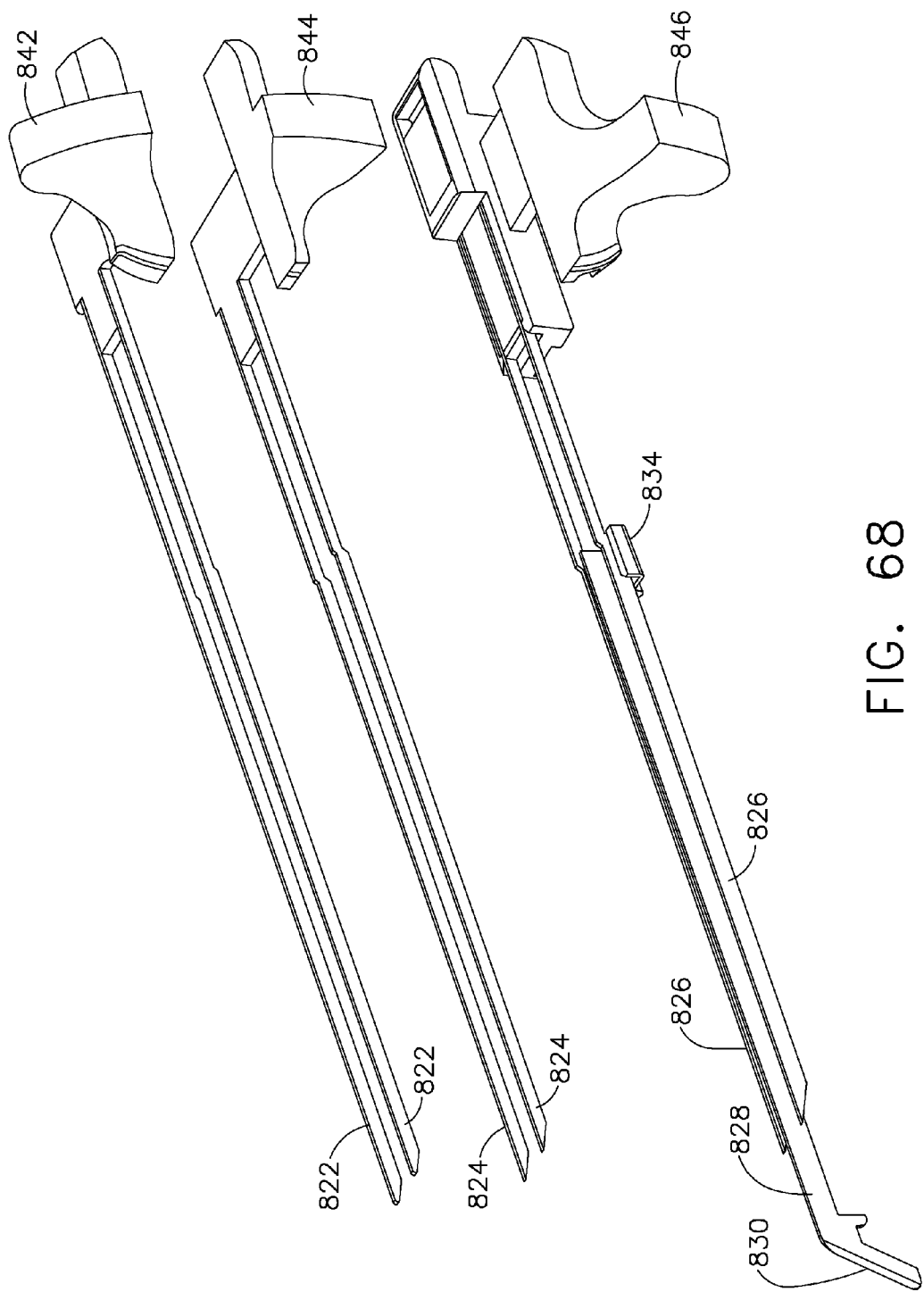
Figure 69:
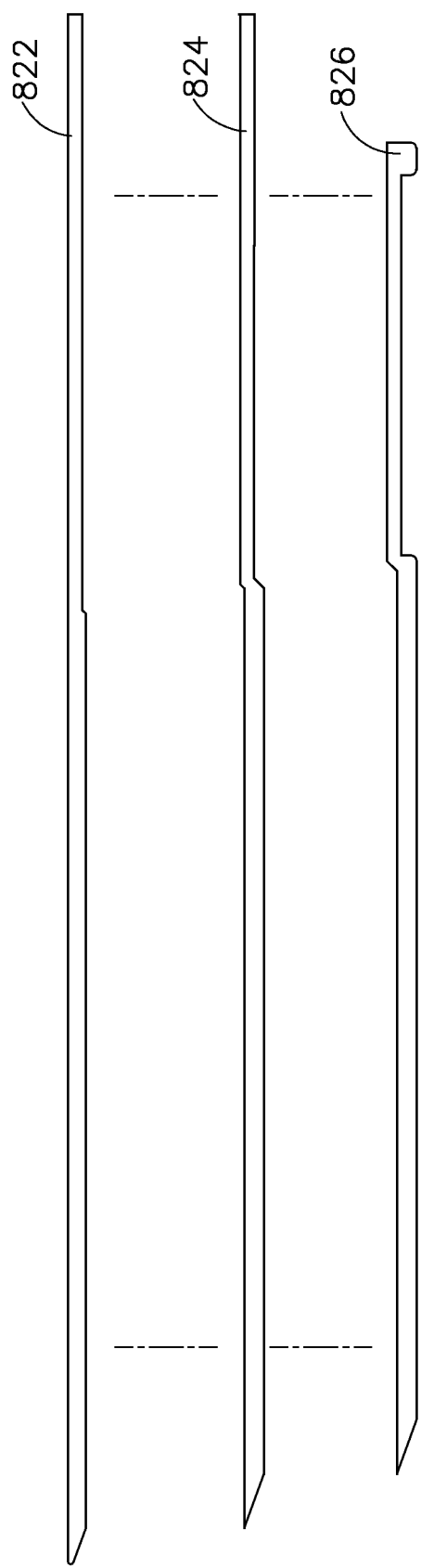

As best shown in FIGS. 67-68, the clinician may actuate the wedge band sets using a three-part actuation slide bar 840. The upper piece 842 may actuate the uppermost (initial) wedge band set 822. The middle piece 844 may actuate the middle wedge band set 824. The lower piece 846 may actuate the lowermost (last) wedge band set 826.

Figure 66:
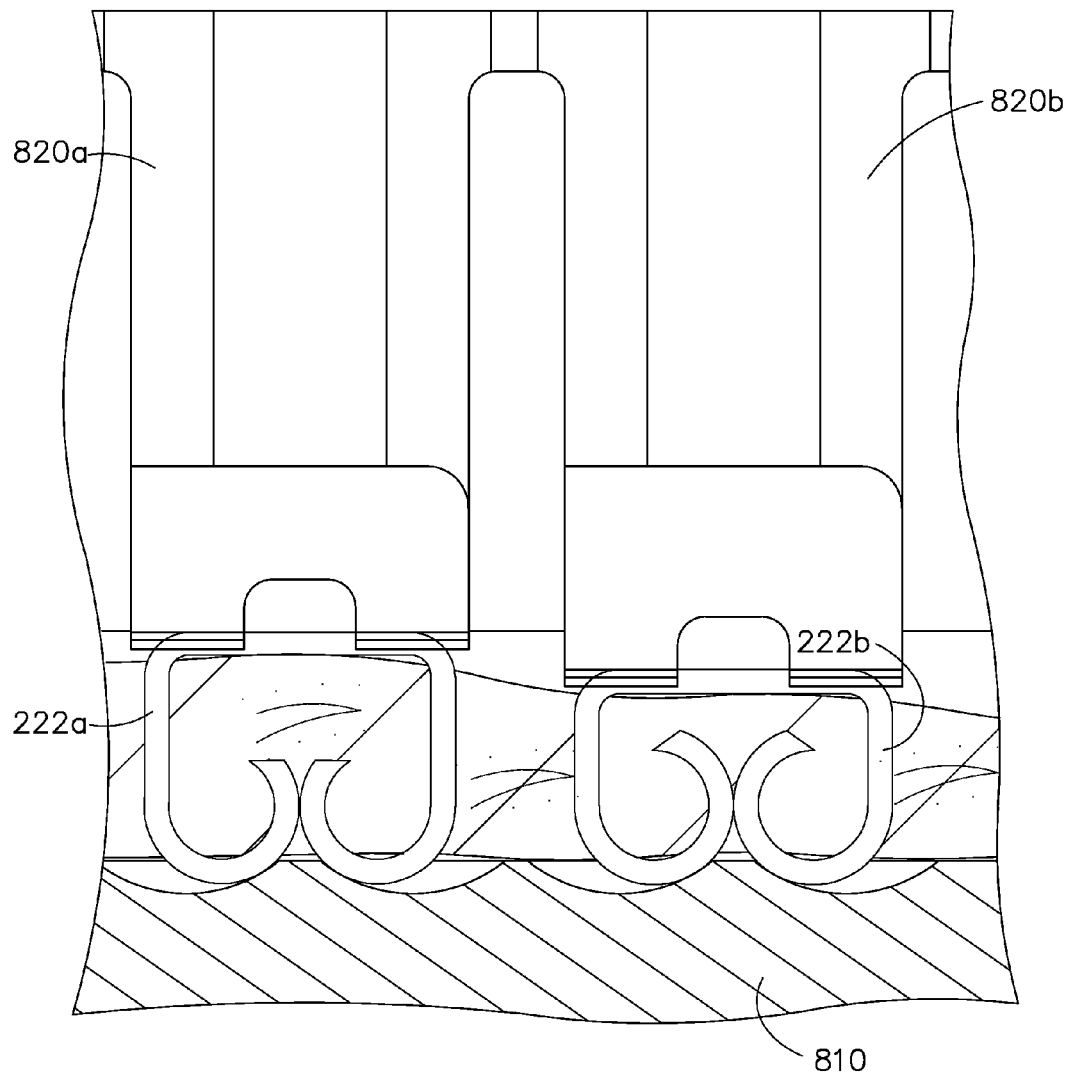

To form staples of different formed heights, the staple pushers 820 may have different heights. For example, as shown in FIG. 66, one set of staple pusher 820a could be shorter than another set of staple pushers 820b. As such, the formed staple 222a, produced by the shorter staple pusher 820a, may have a longer formed length than the formed staple 222b, formed by the longer staple pusher 820b. In other embodiments, the staples 222 may have different lengths or wire diameters to create different length formed staples, and/or the pockets 202 in the anvil 810 could have different depths to create different length formed staples. Also, the cumulative heights of the wedge band stacks could be different.

Figure 81:
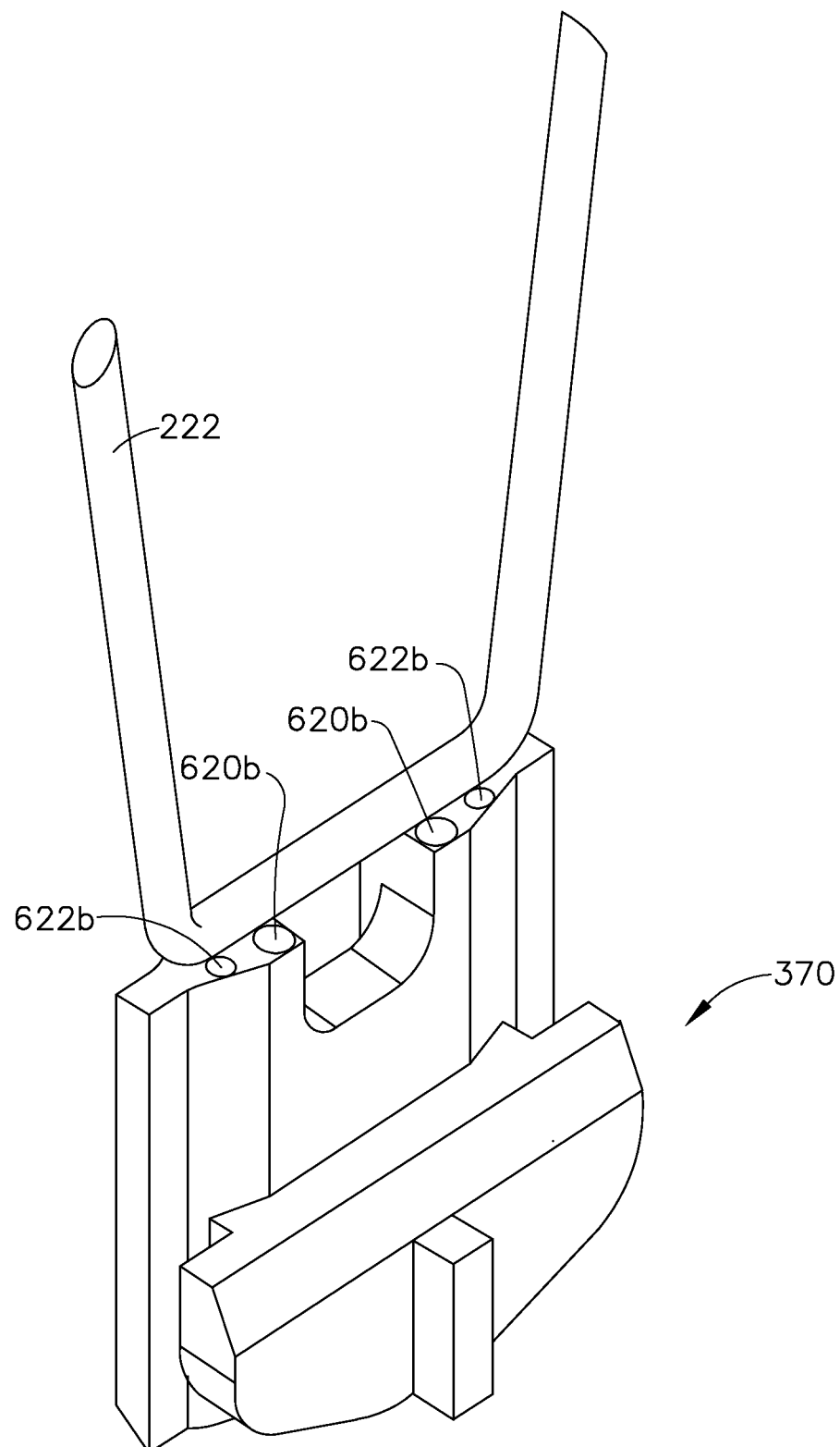
Figures 82, 83:
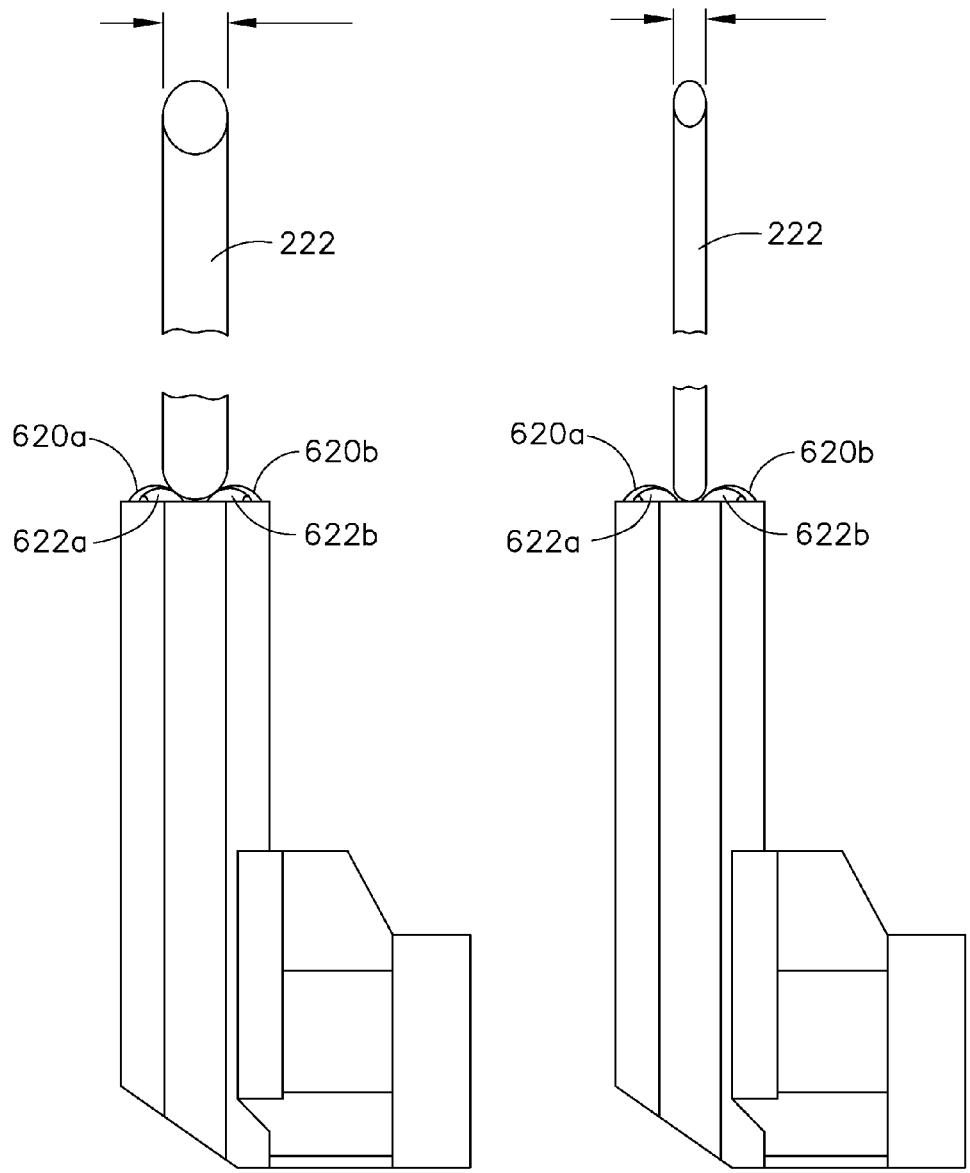

According to various embodiments of the present invention, the staple drivers could have a staple/driver interface that permits staples of varying wire diameter to be employed. For example, as shown in the embodiments of FIGS. 78-83, the outside staple drivers 370a,b may have a raised dimple configuration on its upper surface for supporting staples having differing wire diameters. The dimple configuration may comprise, as shown in the illustrated embodiment, two inner sets of outwardly protruding dimples (or convex bumps) 620a,b, and two outer sets of dimples 622a,b. Each set of dimples defines a receiving area where a staple 222 may sit in the upright position, as shown in FIGS. 81-83. The dimples of the inner sets 620a,b may be larger than the dimples of the outer dimple sets 622a,b so that the receiving area of the inner sets 620a,b is less than for the outer dimple sets 622a,b. Nevertheless, due to the convex nature of the dimples, staples 222 of varying wire thicknesses may be accommodated, as shown in FIGS. 82 and 83. For example, the dimples could be configured so that the staple drivers 370 can accommodate staples having a wire diameter of 0.006 inches to 0.012 inches, or some other range such as 0.004 inches to 0.008 inches or 0.006 inches to 0.008 inches, etc. As such, staples of different wire thicknesses could be used in a single cartridge 306. Differing wire diameters would produce different formed staple heights all other things being equal (e.g., same drive/ crush distance, same pocket depth, etc.). In addition, as shown best in FIG. 78, the staple cradles for the inside drivers 330 may include sharp points 624 that may injure the tissue that is being stapled. The dimple configurations on the outside staple drivers 370 lack such sharp points, which would tend to minimize the trauma on the tissue being stapled.

In the illustrated embodiment, the outer staple drivers 370a,b have the raised dimple configuration in order to accommodate staples of different wire diameters and the staple cradles of the inside staple drivers 342, 352 can only support upright staples of one general wire diameter. In other embodiments, the one or both of the inside staple drivers 342, 352 may also or alternatively have the raised dimple configuration. Also, rather than using the raised dimple configuration, a v-shaped staple channel 349, 379 may be used. Such a v-shaped channel may also accommodate staples having different wire diameters. Also, staple pushers with staple interfaces that accommodate different staple wire diameters could be used with other types of staple drivers than the inside double and outside single staple drivers shown in FIGS. 78-83.

FIGS. 70-77 are cross-sectional frontal views of the end effector 12 according to various embodiments of the present invention. In the embodiment shown in FIG. 70, the anvil 18 is stepped, having a central portion 19 that is offset relative to (or not coplanar with) the two lateral side portions 21, 23. Also, the upper surface 306 of the cartridge 300 has a recessed central portion 307 and two lateral side portions 309 (see FIG. 19A). All the staples 222 have the same pre-formation prong height and the corresponding anvil pockets 202 have the same depth. However, due to the stepped nature of the anvil 18, the pockets 202 on the two lateral side portions 21, 23 of the anvil 18 are offset from the pockets in the central portion 19 of the anvil. Offsetting the vertical position of the staple forming pockets 202 can affect the length of the formed staples 222. All other things being equal, staples formed by staple forming pockets that are elevated will have a longer formed length than staples formed with pockets that are not elevated. Also in this embodiment, the primary and secondary driver portions 342, 352 of the double inside drivers 330a,b are the same height, and the height of the driver portion 372 of the outside staple drivers 370a,b is greater than the height of the driver portions 342, 352 of the double inside staple drivers 330a,b. Also, the inside and outside sled cams 410, 4120 are the same height in this embodiment.

Figure 71:
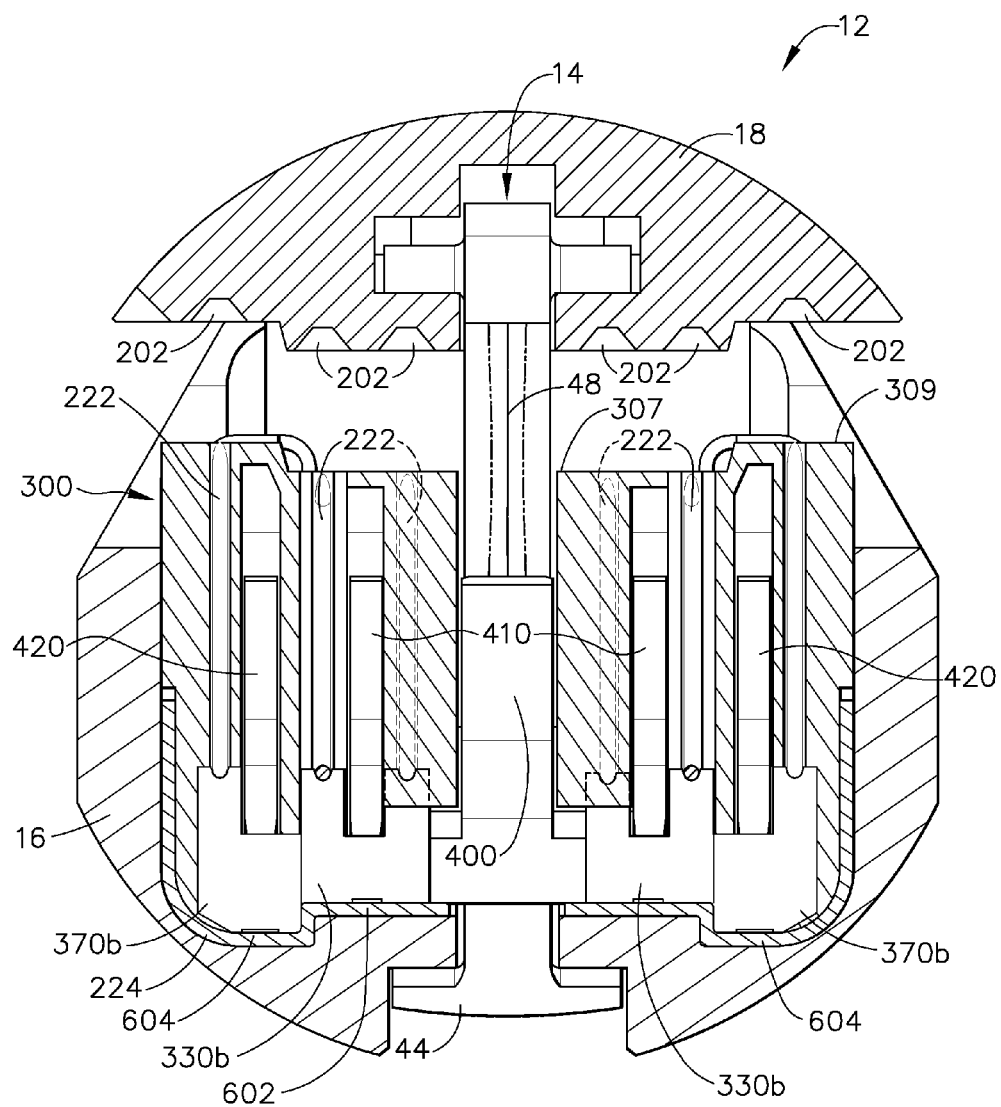

FIG. 71 shows an embodiment where the end effector 12 has a stepped cartridge tray 224 at the bottom of the cartridge 300 to match the steps in the channel 16. In particular, in the illustrated embodiment, the cartridge tray 224 has a central portion 602 on which the double inside staple drivers 330a,b rest and outer lateral portions 604 on which the outside staple drivers 370a,b rest. As can be seen in FIG. 71, the central portion 602 of the cartridge tray 224 is elevated above the lateral portions 604. As such, the sled 400 may be configured so that the outside sled cam 420 is positioned lower than the inside sled cam 410 so that the outside sled cam 420 can engage the lower outside driver portions 370a,b.

Figure 72:
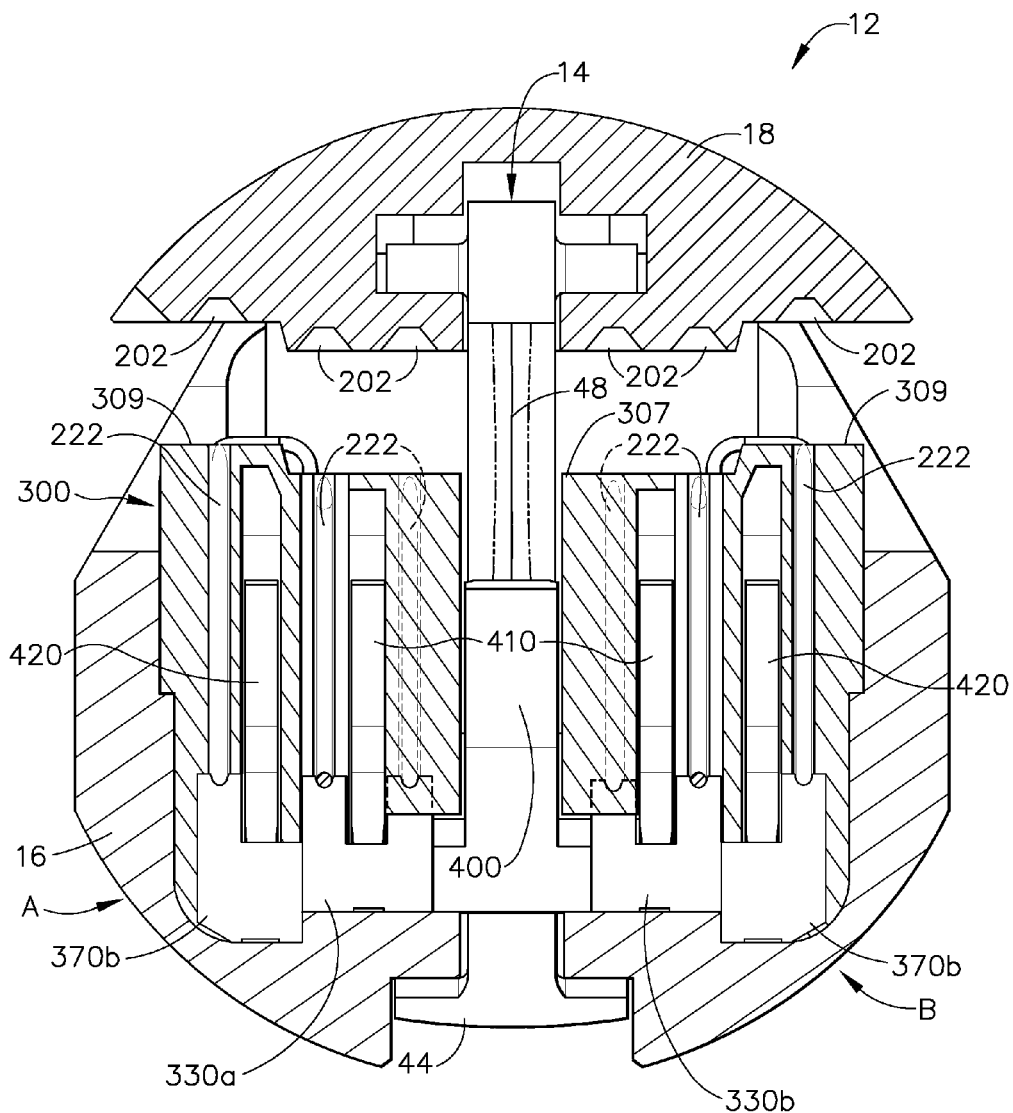

The embodiment illustrated in FIG. 72 is similar to that shown in FIG. 71 except that in FIG. 72 the cartridge 300 does not include the cartridge tray 224. Rather, the staple drivers 330, 370 rest directly on the channel 16. Such an embodiment may be beneficial because it may allow for more material (e.g., metal) in the channel 16 at points A and B than in a similar embodiment with the cartridge tray 224 (such as shown in FIG. 71).

Figure 73:
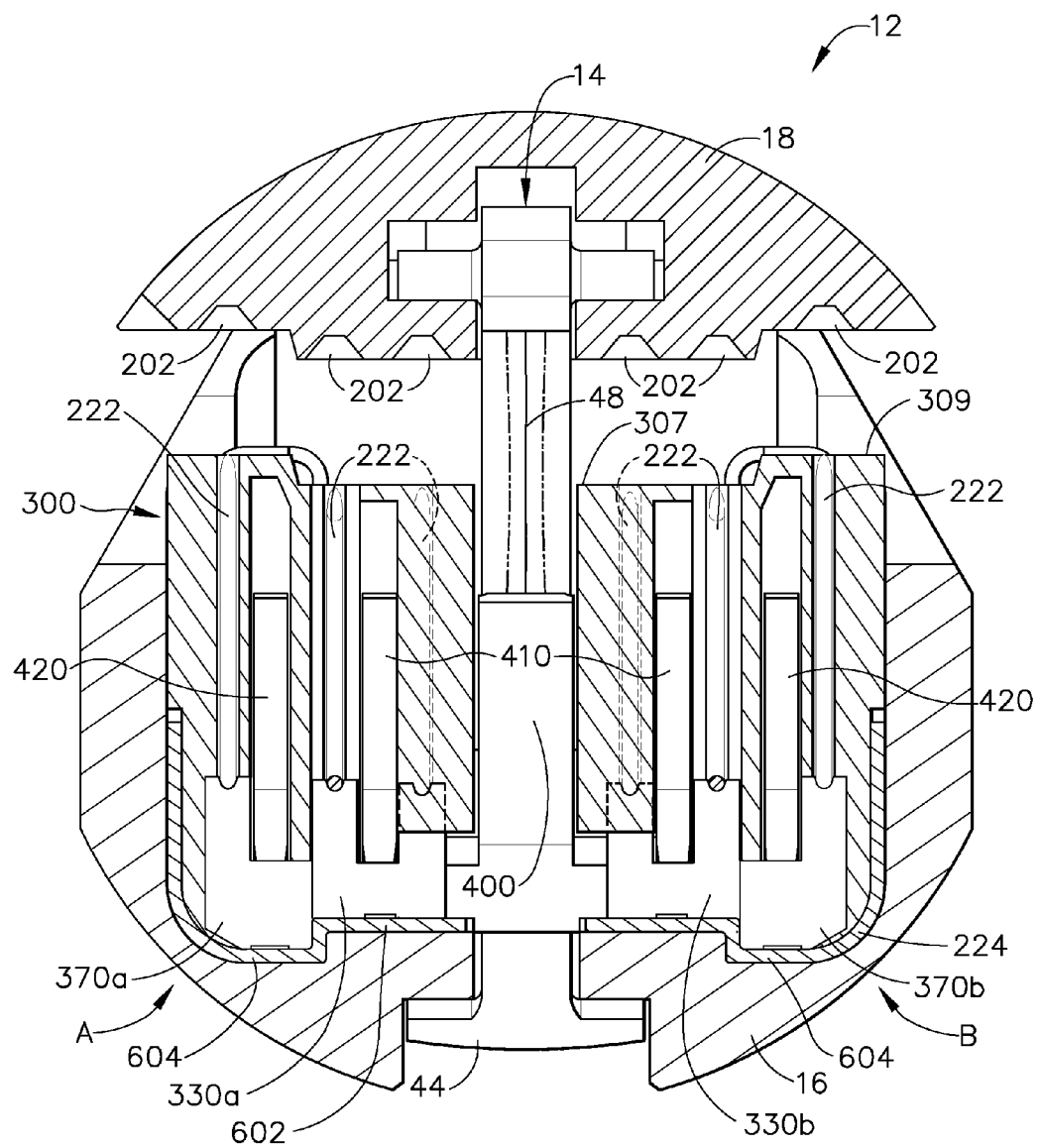

The embodiment illustrated in FIG. 73 is also similar to that shown in FIG. 71 except that in FIG. 73 the cartridge tray 224 is raised slightly relative to the bottom on the channel 16 in comparison with the embodiment shown in FIG. 71. Such an embodiment may also allow for more material (e.g., metal) in the channel 16 at points A and B than in the embodiment shown in FIG. 71. According to other embodiments, the height of the anvil 18 could be reduced to permit more material in the channel 16 at points A and B.

Figure 74:
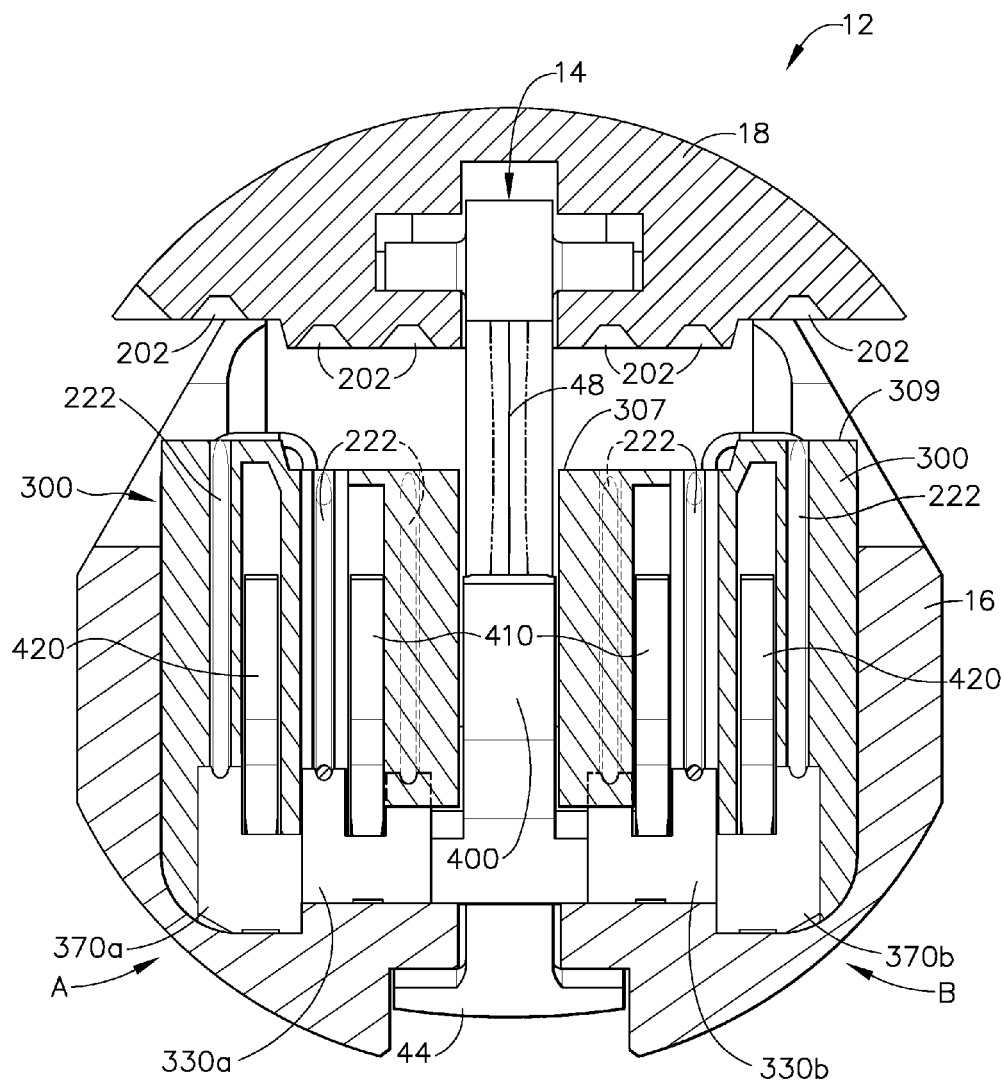

The embodiment of FIG. 74 is similar to that used in FIG. 73 except that no cartridge tray 224 is included in the embodiment of FIG. 74.

Figure 70:
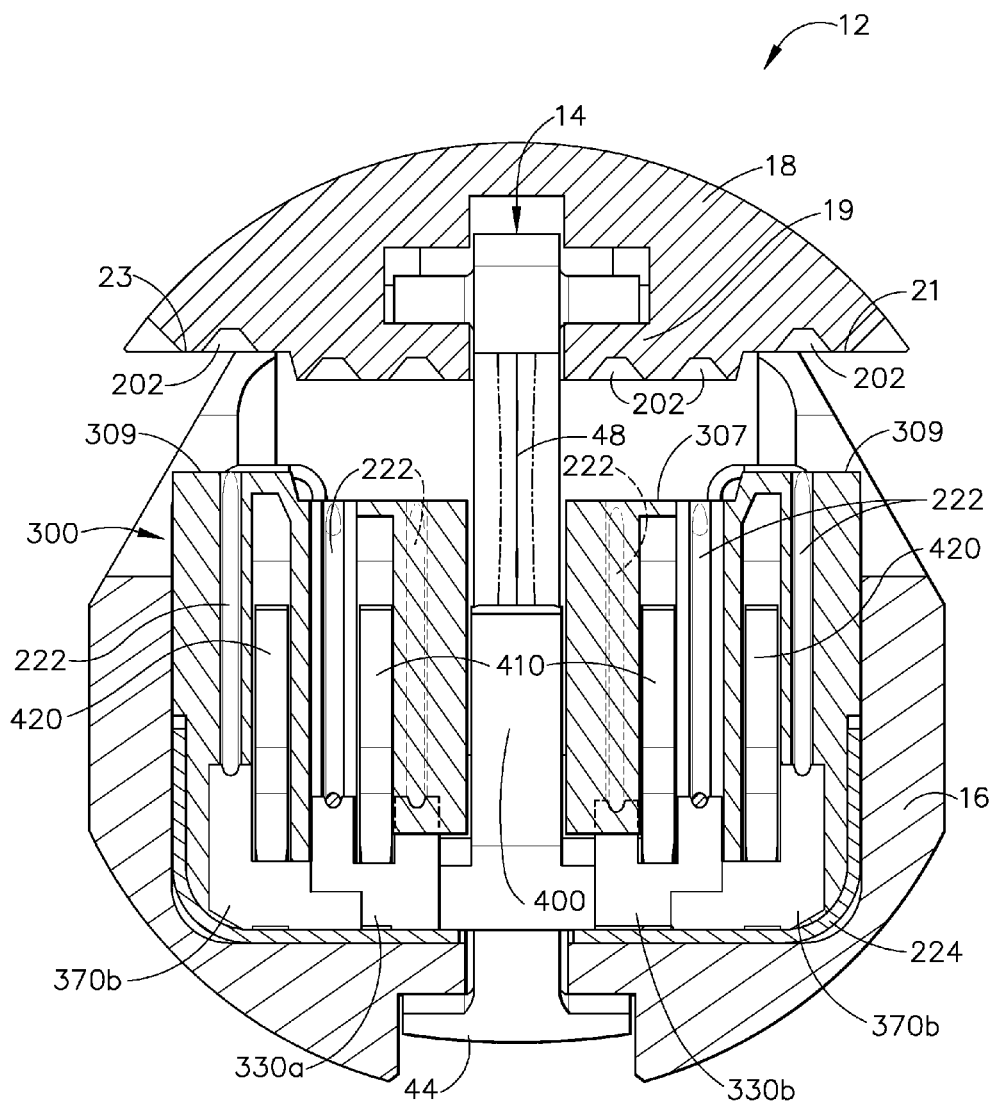
FIGS. 70-77 depicts cross-sectional front views of an end effector according to various embodiments of the present invention.
Figure 75:
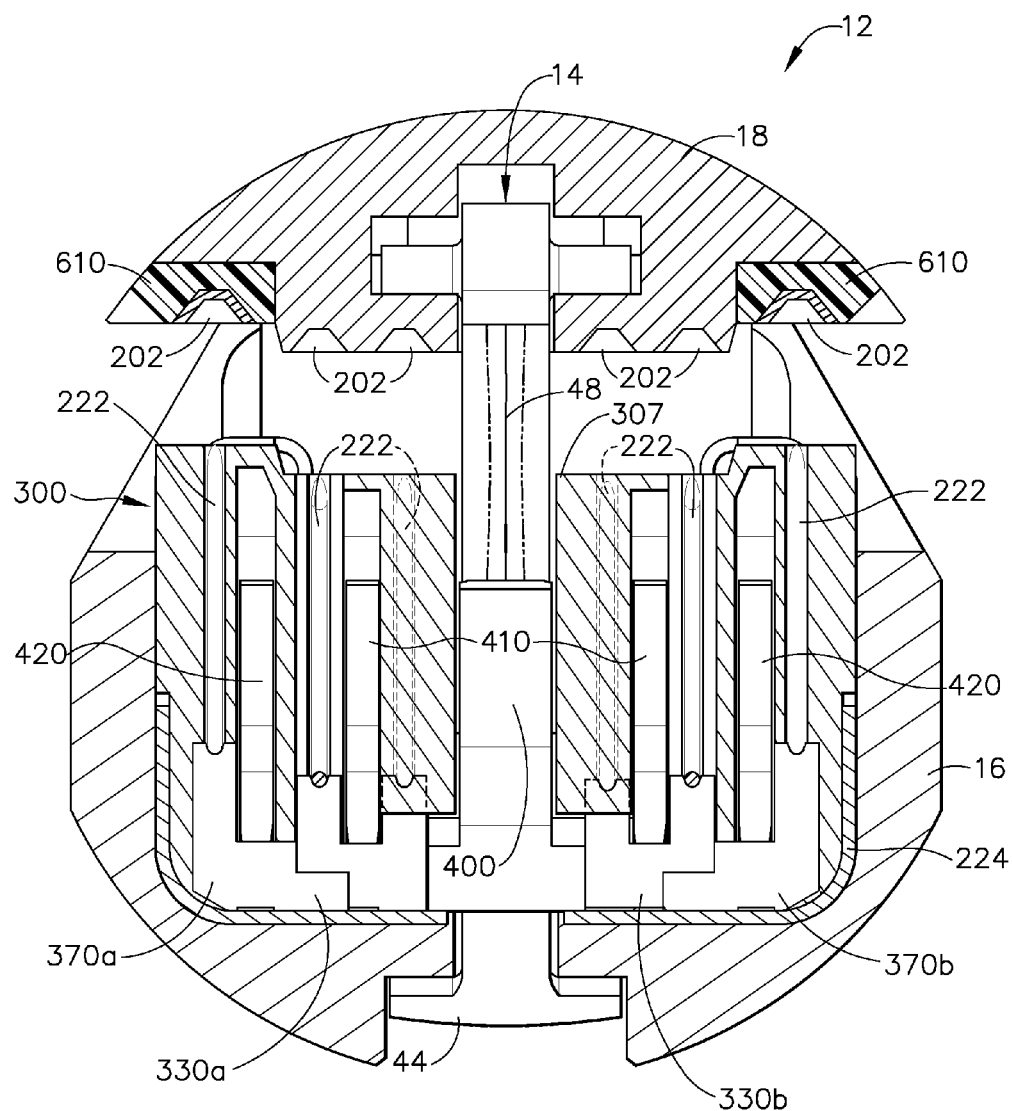

The embodiment of FIG. 75 is similar to that of FIG. 70 except than in FIG. 75 the outer rows of pockets 202 are formed in a compliant material portion 610 of the anvil 18. The compliant material portion 610 may be made from a material that is more compliant to the rest of the anvil 18. For example, the compliant material portion 610 may be made from plastic or a plastic composite material and the rest of the pockets may be defined in a less-compliant material, such as stainless steel, of the anvil 18. The less-compliant anvil portion is sometimes referred to herein as "non-compliant" to distinguish it from the compliant materials portion 610, although it should be recognized that the so-called non-compliant material portion would be somewhat compliant, just less compliant than the compliant material portion 610. All things being equal, staples formed with the outer pockets 202 formed in the compliant material portion 610 of the anvil 18 would be longer than stapled form in the non-compliant (e.g., metal) portion of the anvil 18 because the compliant material portion 610 would compress more during the staple formation process.

Figure 76:
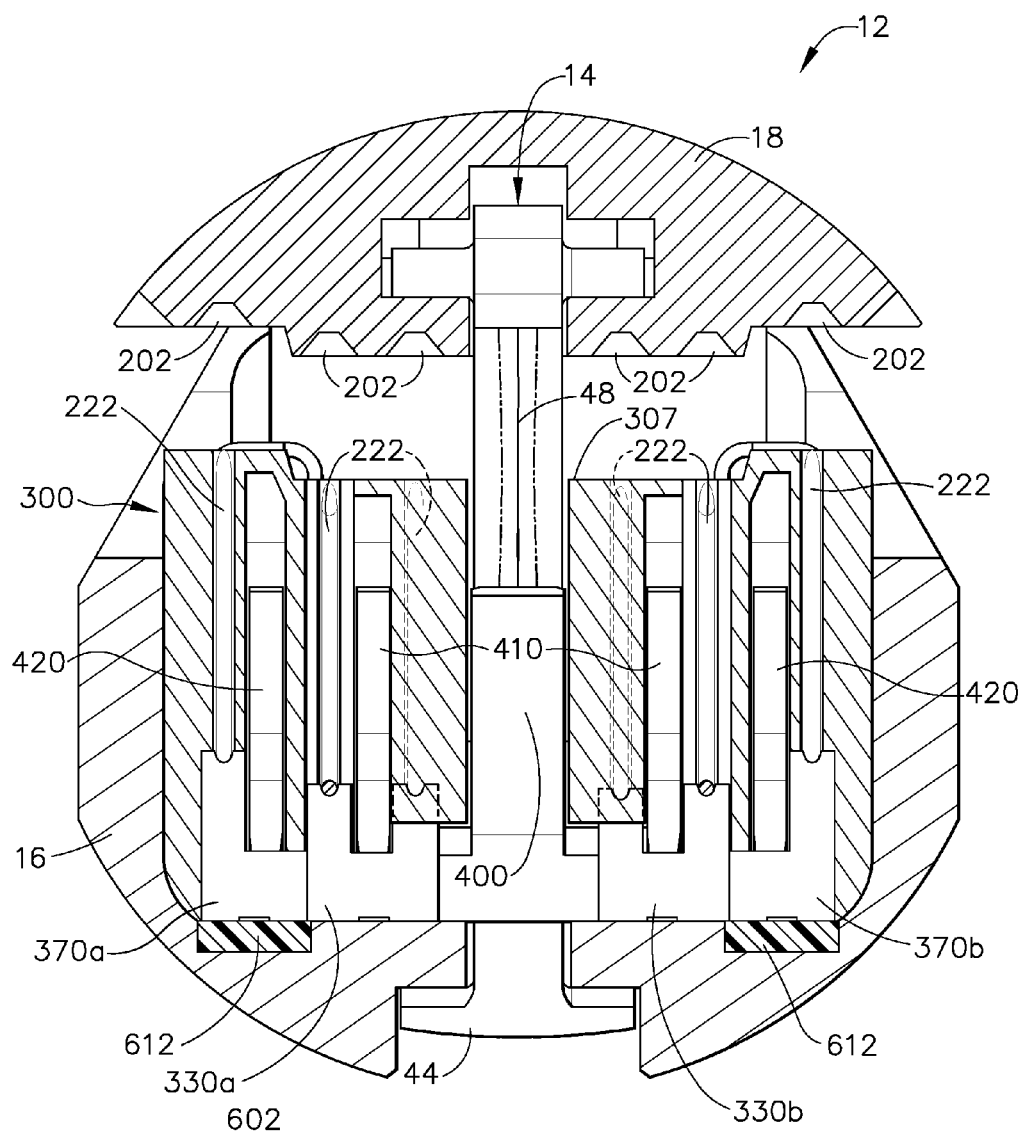
Figure 77:
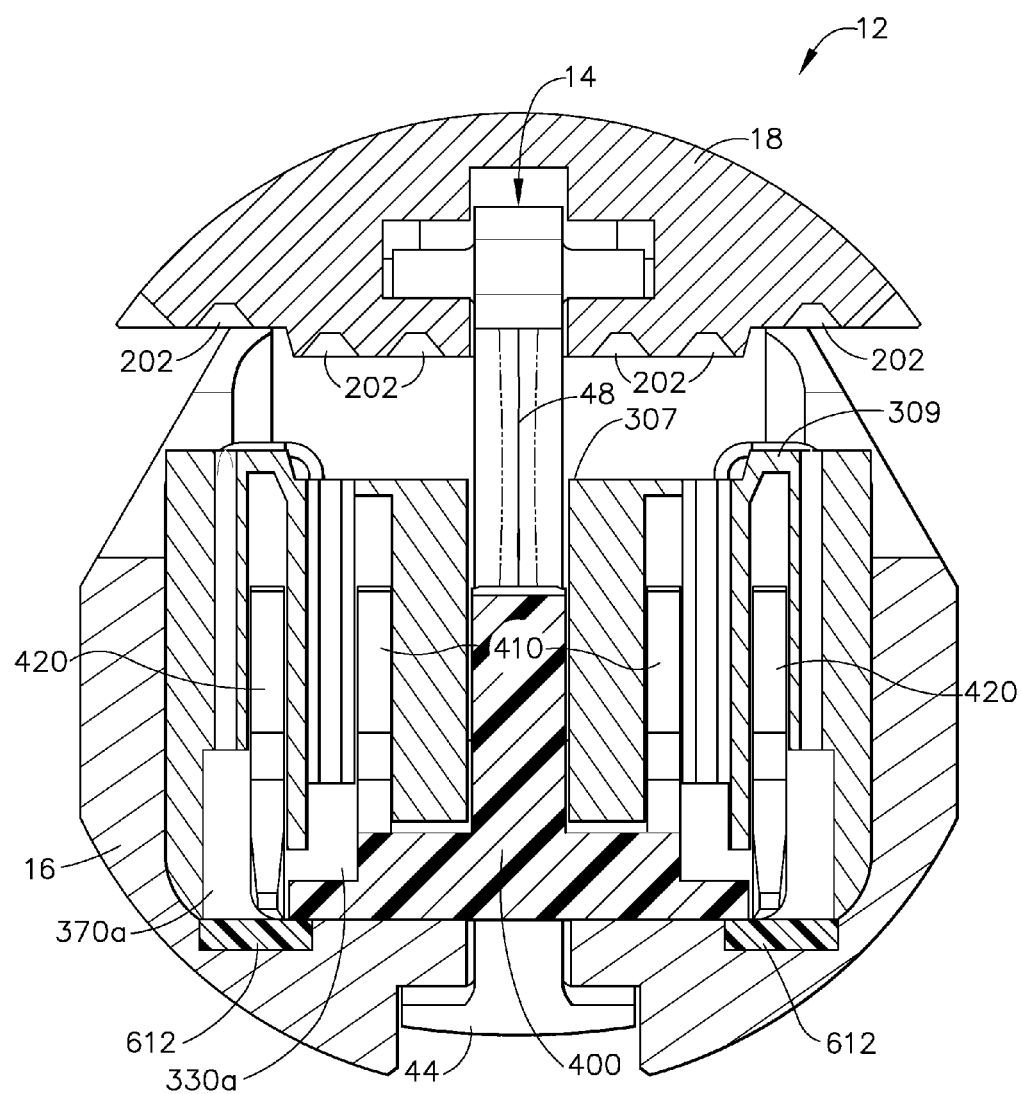
Figure 78:
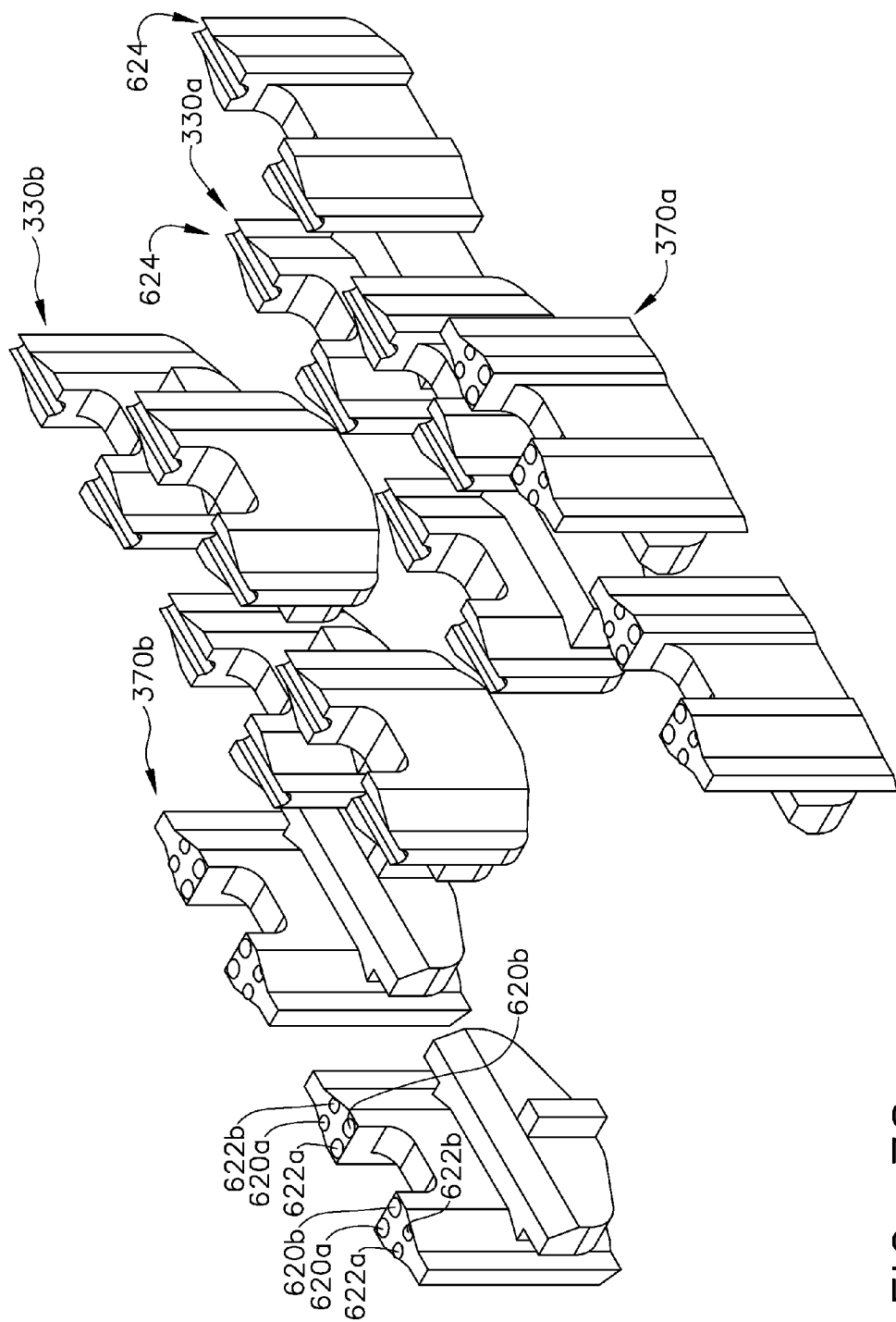
FIGS. 78-83 depict staple drivers that can accommodate staple having different wire diameters according to various embodiments of the present invention.
Figure 79:
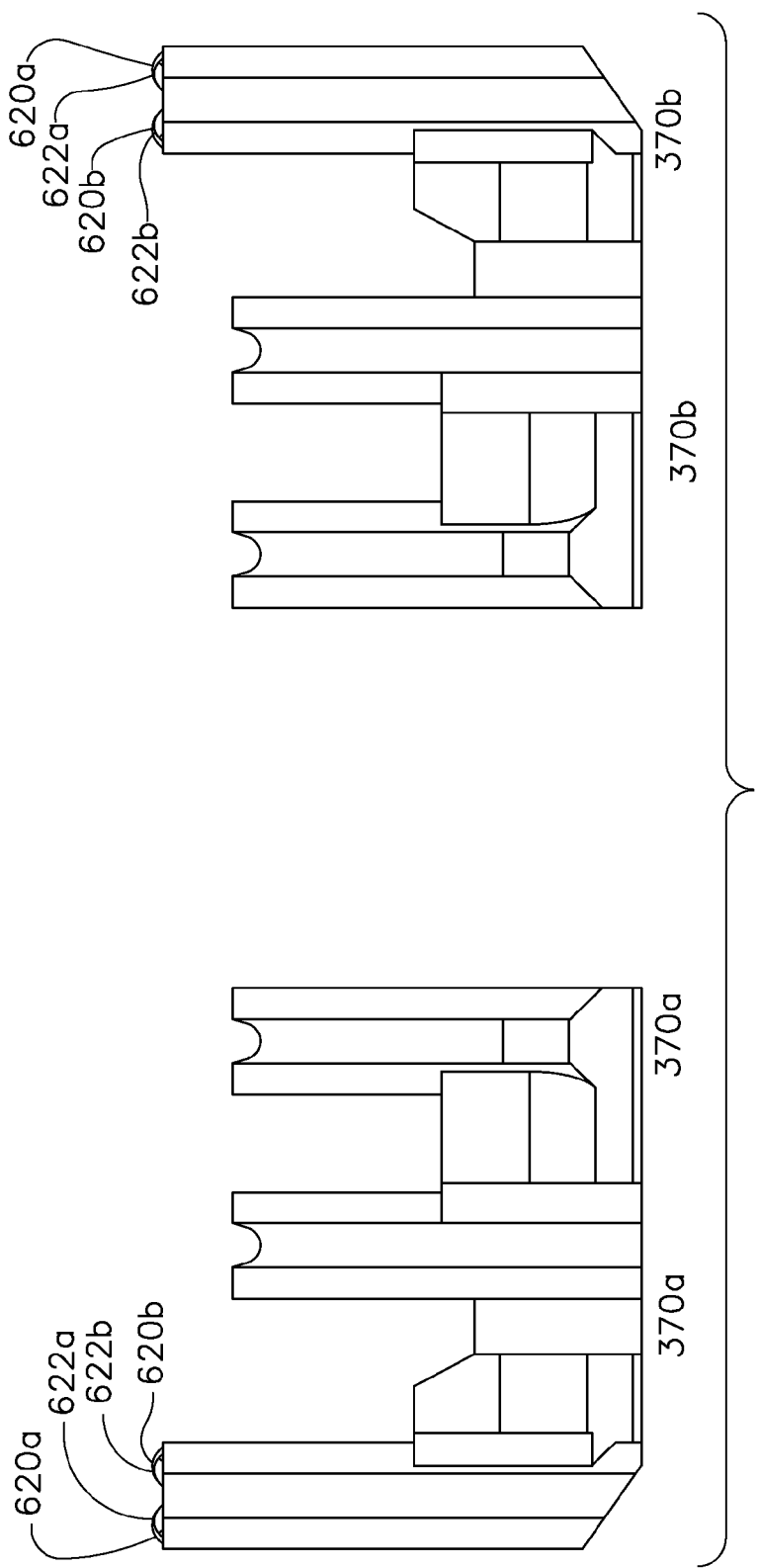
Figure 80:
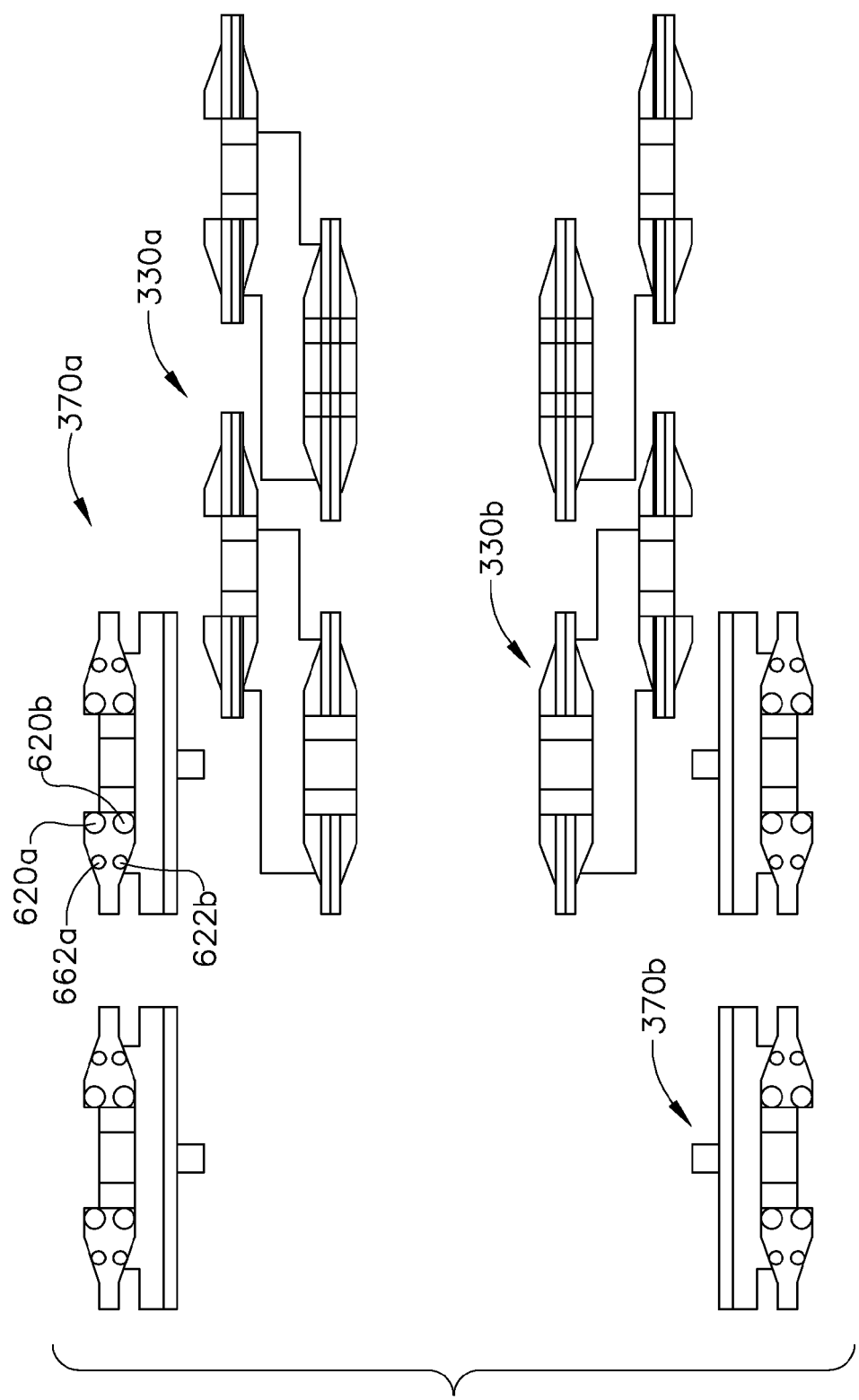

FIGS. 76 and 77 collectively show another embodiment. In this embodiment, the channel 16 includes a compliant material portion 612 under the outside drivers 370. The complaint material portion 612 may be plastic or a composite plastic, for example. The inside drivers 330 may rest on the less-compliant (or "non-compliant") channel 16, which may be made of metal (e.g., stainless steel). The outside sled cam 420 may slightly compress the compliant material portions 612 under the outside drivers 370 when forming the staples in relation to the inside drivers 330 on the channel 16, thereby forming slightly longer staples in the outside rows. In other embodiments, the compliant material portions 612 could be under the inside drivers 330 if it was desired to make the inside staples have a greater formed length.

According to other embodiments, staples of different materials could be used to produce staples of different formed lengths. The different materials may have different modulus of elasticity so that they will be formed differently given the same driving force. Staples having a higher modulus of elasticity will tend to be deformed less given the same driving force, thereby tending to produce staples having a longer formed length. The different materials for the staples 222 may comprise titanium, stainless steel, alloys, etc.

Figure 84:
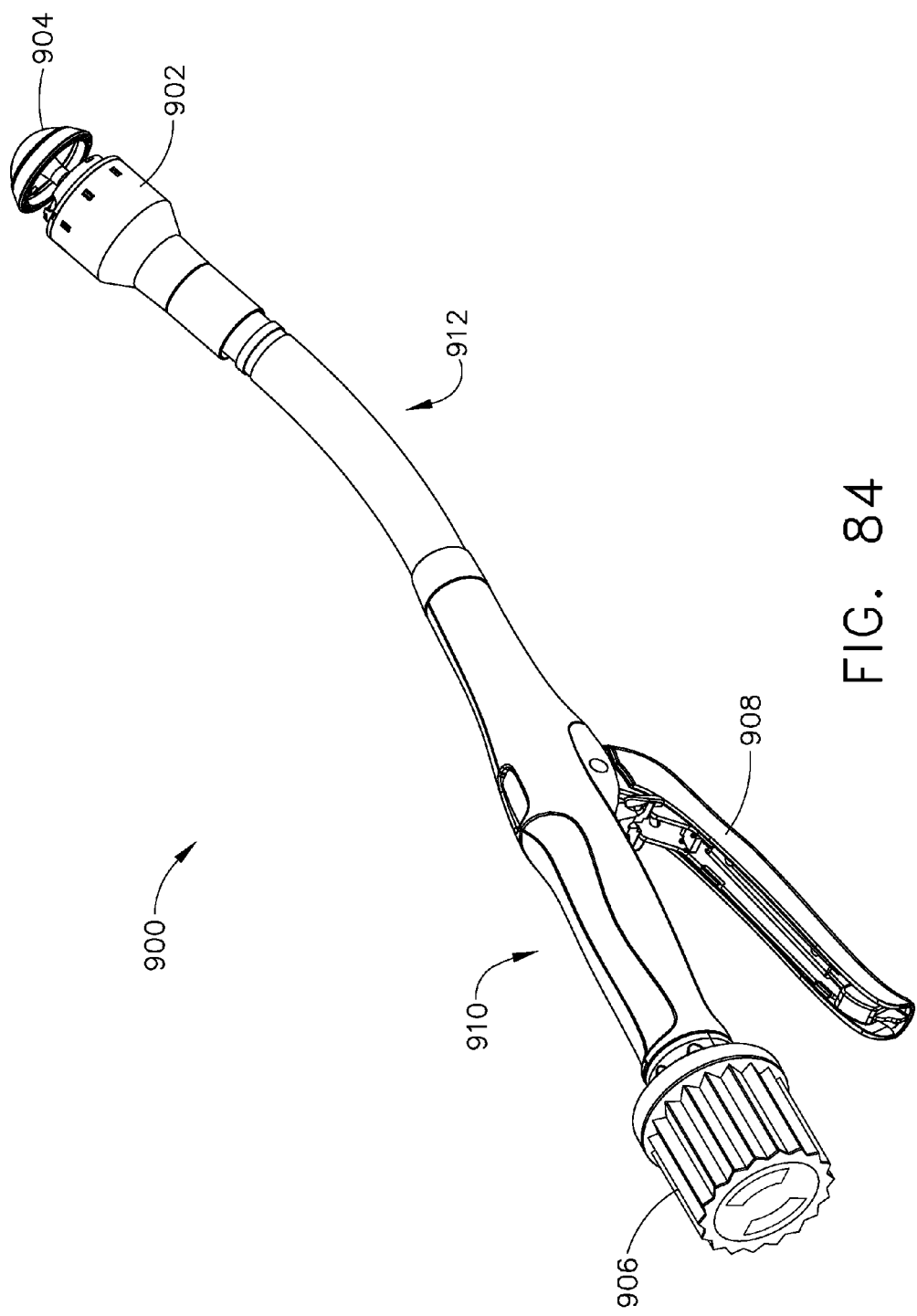
FIGS. 84-89 depict a circular surgical stapling device according to various embodiments of the present invention.

The present invention is also directed to other types of surgical cutting devices that can create formed staples of different heights. For example, FIGS. 84-89 illustrate a circular stapler 900 that is capable of forming staples with different formed heights. As seen in FIG. 84, the circular stapler 900 includes a head 902, an anvil 904, an adjustment knob assembly 906, and a trigger 908. The head 902 is coupled to a handle assembly 910 by an arcuate shaft assembly 912. The trigger 908 is pivotally supported by the handle assembly 910 and acts to operate the stapler 900 when a safety mechanism (not shown) is released. When the trigger 908 is activated, a firing mechanism (not shown in FIG. 84) operates within the shaft assembly 912 so that staples 914 are expelled from the head 902 into forming contact with the anvil 904. Simultaneously, a knife 916 operably supported within the head 902 acts to cut tissue clamped between the head 902 and the anvil 904. The stapler 900 is then pulled through the tissue leaving stapled tissue in its place.

Figure 85:
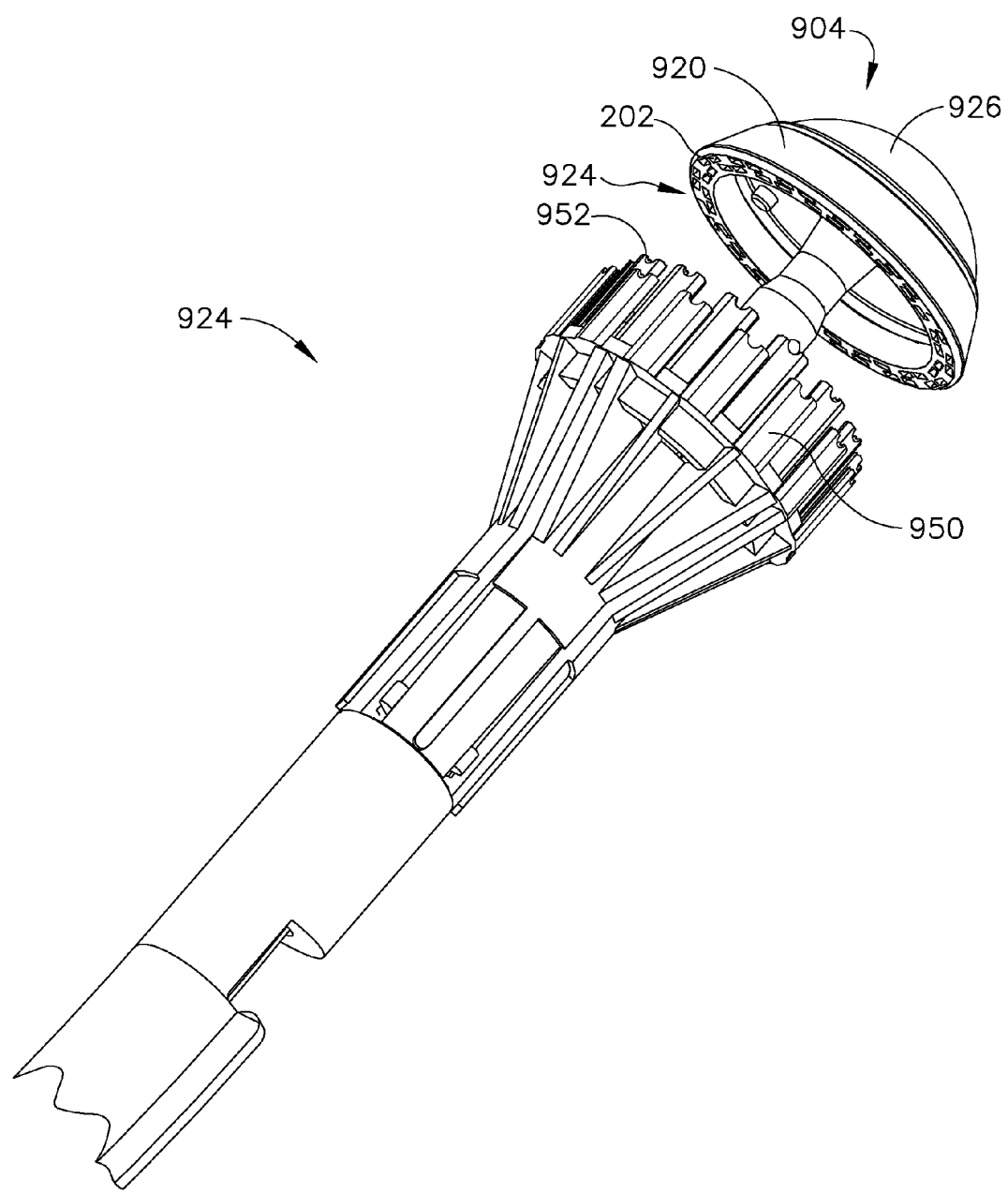
Figure 86:
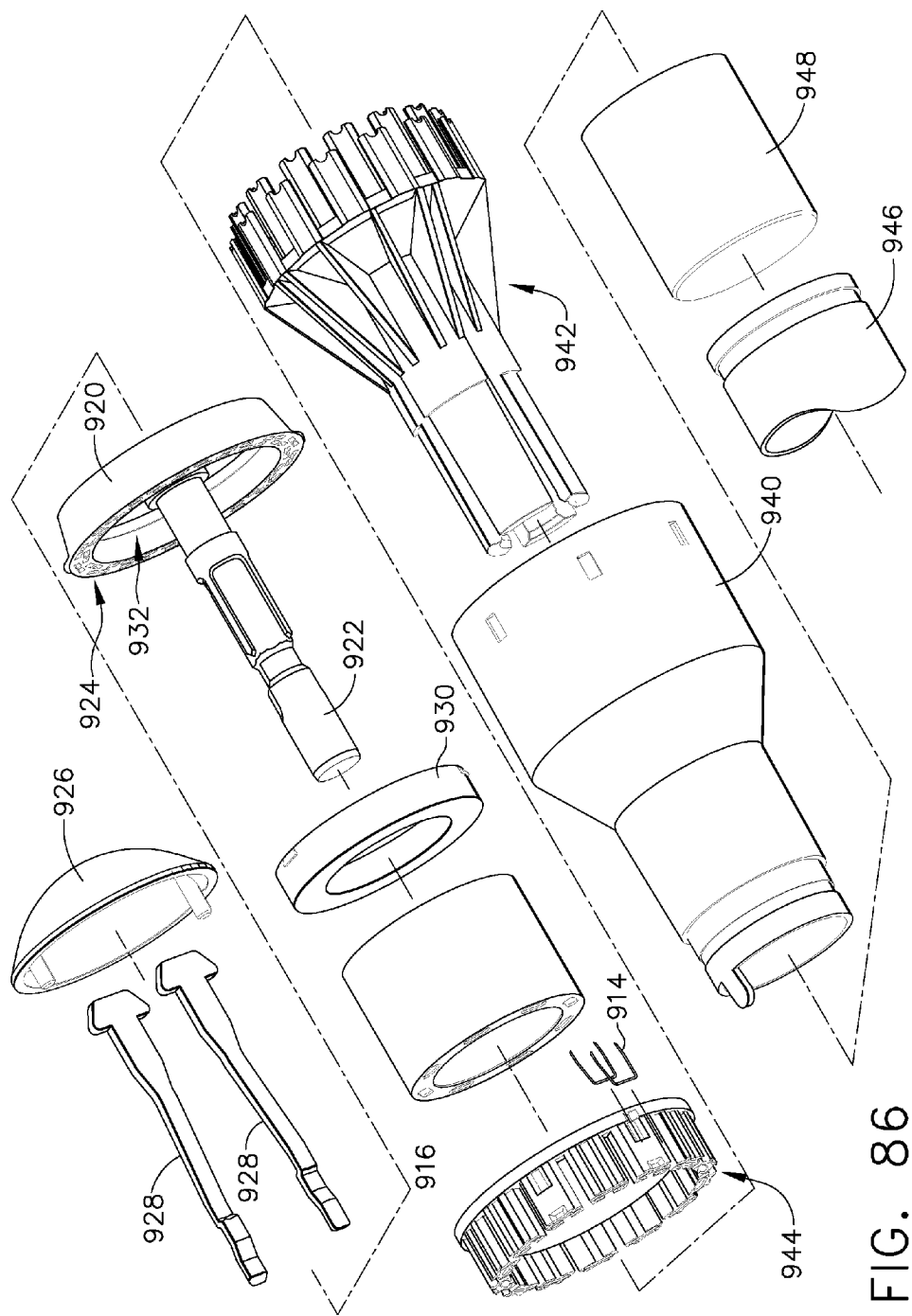
Figure 87:
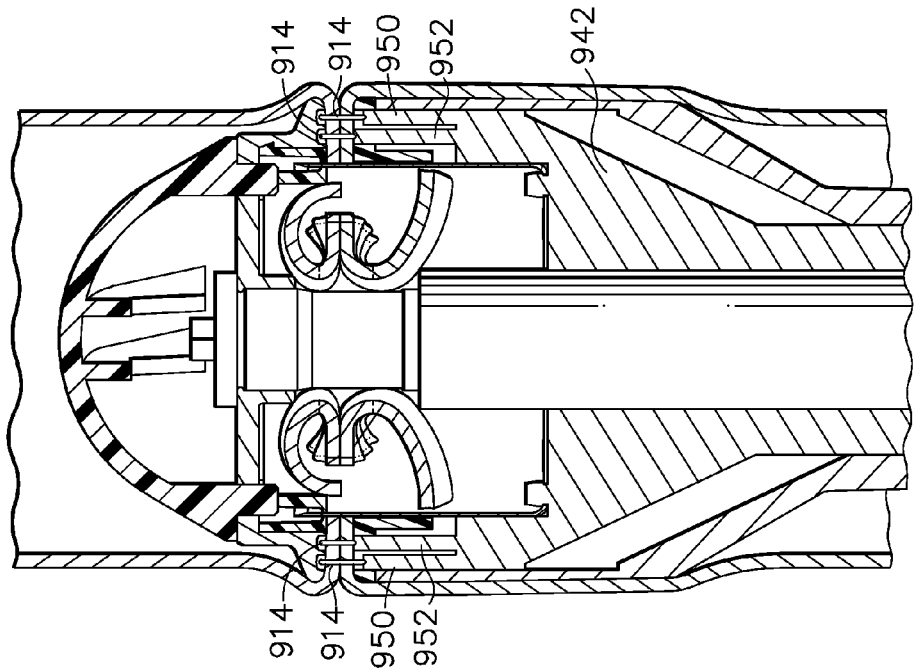

FIGS. 85 and 86 illustrate one form of the anvil 904 and the head 902 that may be employed in connection with various embodiments of the subject invention. As can be seen in these figures, the anvil 904 may have a circular body portion 920 that has an anvil shaft 922 for attaching a trocar (not shown) thereto. The anvil body 920 has a staple forming surface 924 thereon and may also have a shroud 926 attached to the distal end thereof. The anvil 904 may be further provided with a pair of trocar retaining clips or leaf-type springs 928 that serve to releasably retain the trocar in retaining engagement with the anvil shaft 922. A plastic knife board 930 may be fitted into a cavity 932 in the anvil body 904.

The head 902 may comprise a casing member 940 that supports a cartridge supporting assembly in the form of a circular staple driver assembly 942 therein that is adapted to interface with a circular staple cartridge 944 and drive the staples 914 supported therein into forming contact with the staple forming surface 924 of the anvil 904. The circular knife member 916 is also centrally disposed within the staple driver assembly 942. The proximal end of the casing member 940 may be coupled to an outer tubular shroud 946 of the arcuate shaft assembly 912 by a distal ferrule member 948. More details regarding circular staples may be found in U.S. patent application Ser. No. 11/541,151, entitled "Surgical Cutting and Stapling Device with Closure Apparatus for Limiting Maximum Tissue Compression Force," by F. Shelton et al., filed Sep. 29, 2006, which is incorporated herein by reference.

As can be seen in FIGS. 85-89, the staple driver assembly 942 may comprise an outer ring of staple drivers 950 and an inner ring of staple drivers 952. Correspondingly, the anvil 904 may comprise two concentric rings of staple forming pockets 202. Actuation of the firing trigger 908 of the handle assembly 910 cause a compression shaft (not shown) of the shaft assembly 912 to move distally thereby driving the staple driver assembly 942 distally to fire the staples 914 into forming contact with the staple forming surface 924 of the anvil 904. Thus, the outer staple drivers 950, when actuated by the drive mechanism of the stapler 900, drive an outer ring of staples 914 into the clamped tissue and are formed by surface forming surface 924 of the anvil 904. Similarly, the inner staple drivers 952, when actuated by the drive mechanism of the stapler 900, drive an outer ring of staples 914 into the clamped tissue and are formed by surface forming surface 924 of the anvil 904.

Figure 88:
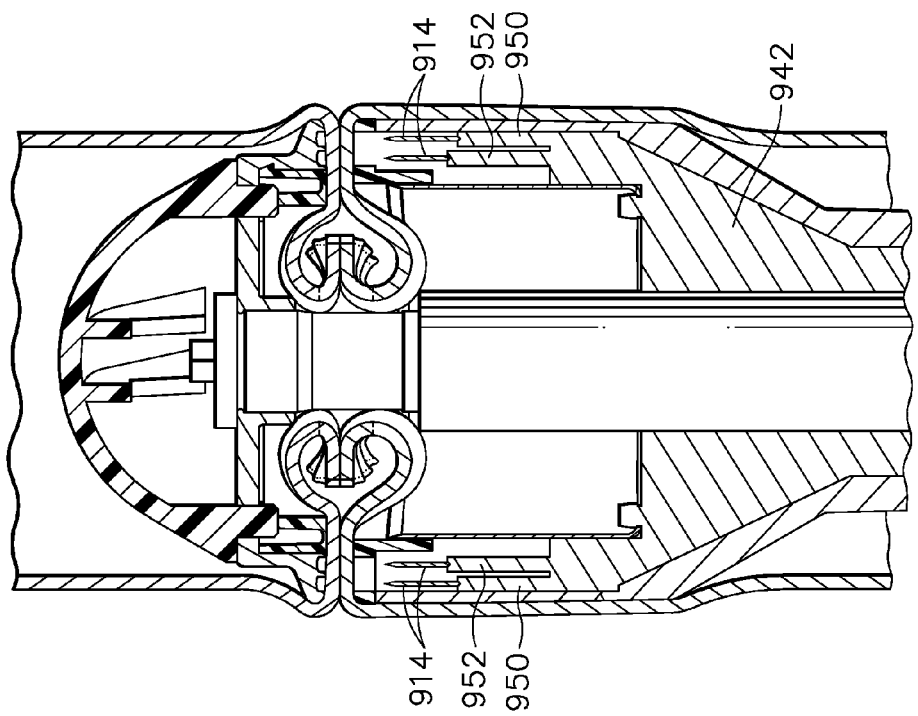
Figure 89:
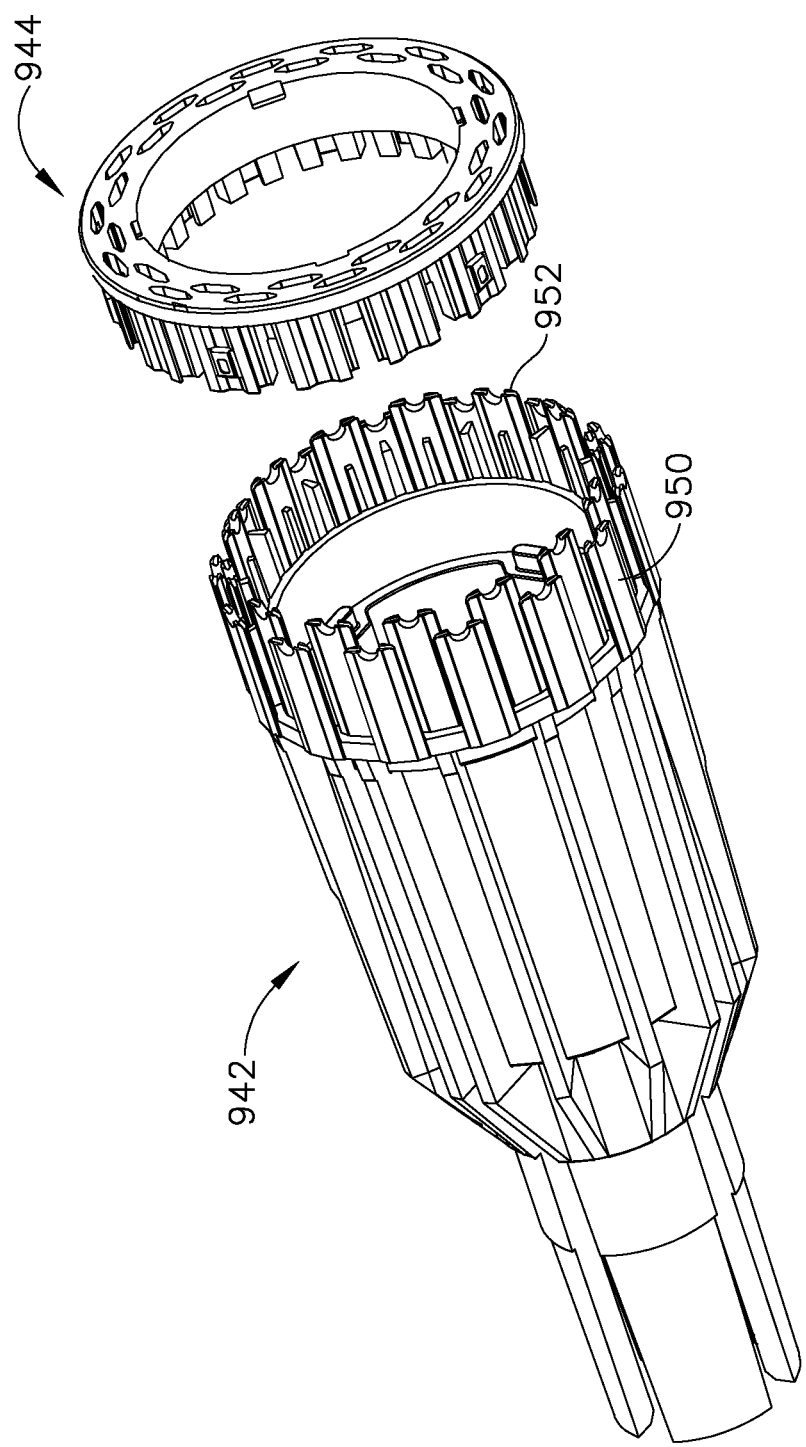
Figure 90:
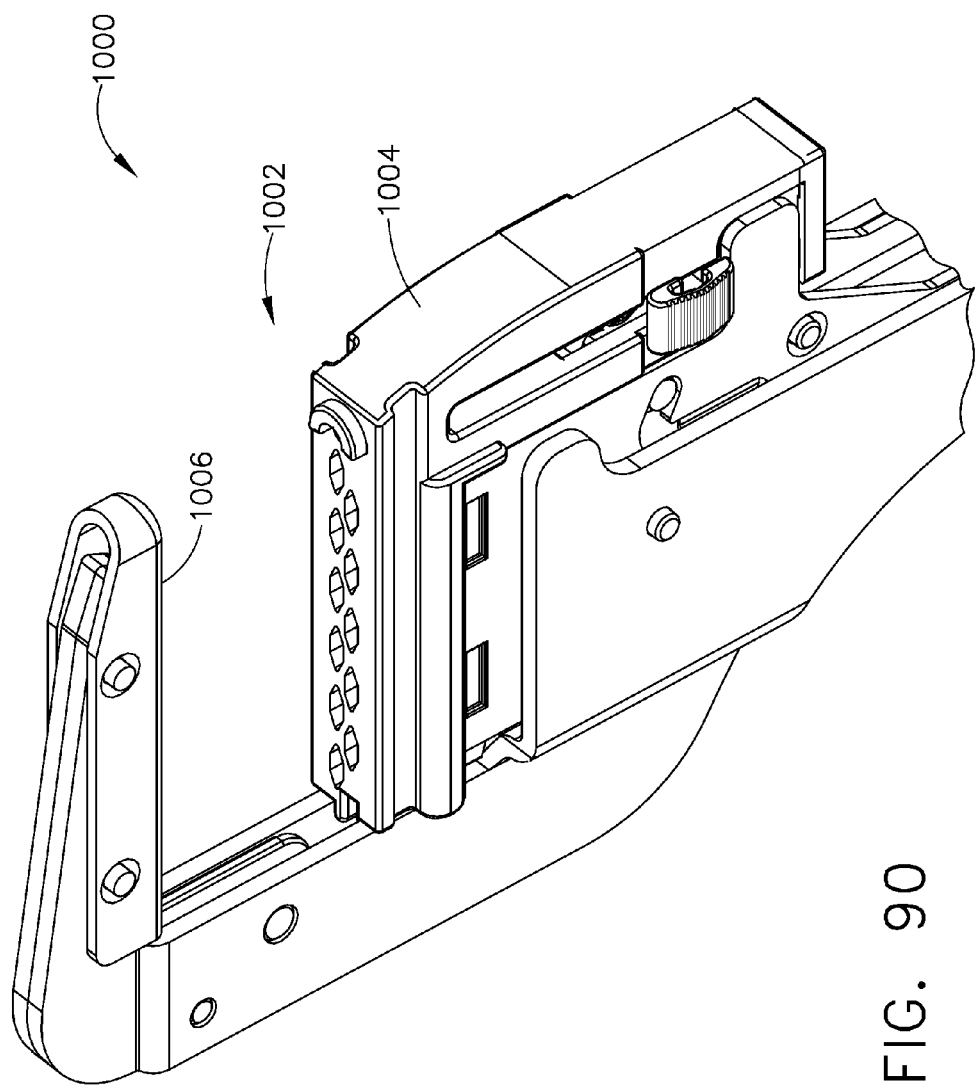
FIGS. 90-95 depict another surgical stapling device according to embodiments of the present invention.
Figure 91:
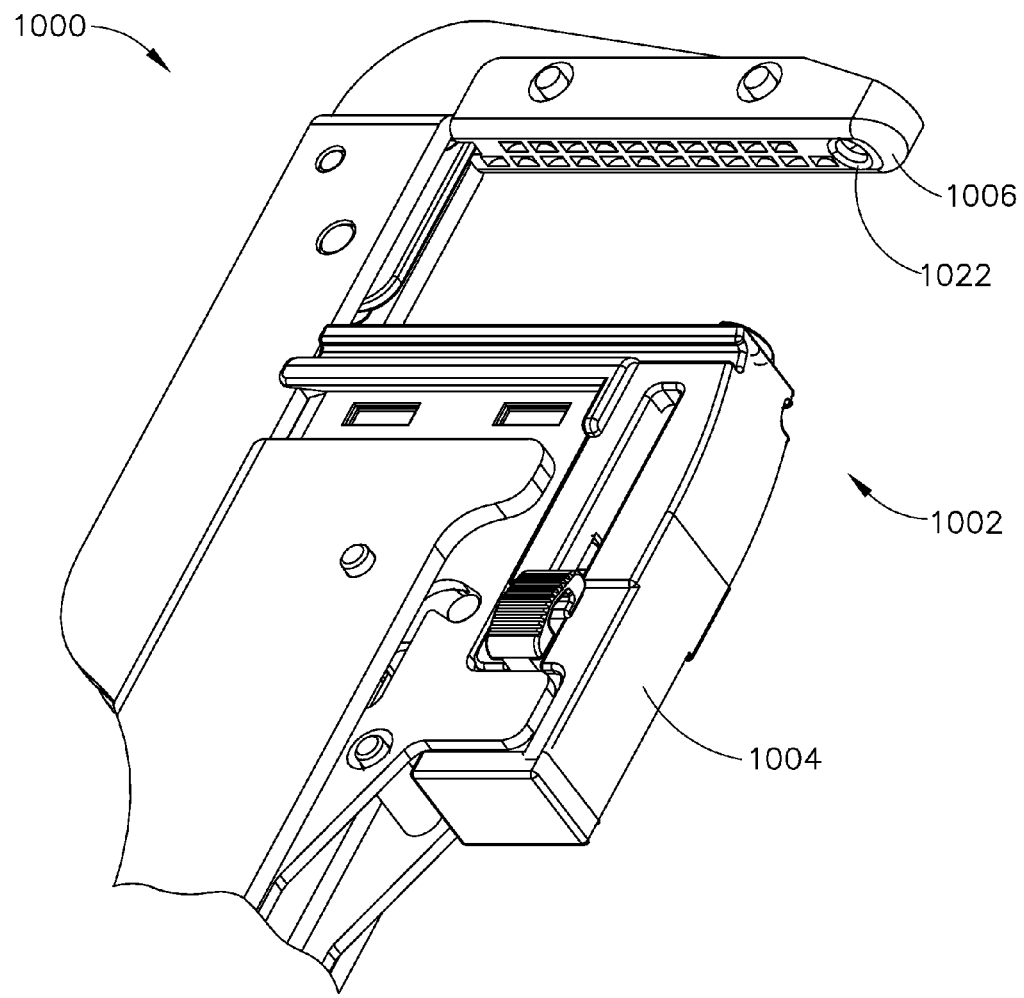

The staple drivers 950, 952 could be of different heights to thereby form different length formed staples (all other things being equal). For example, as shown in the illustrated embodiment, the outer staple drivers 950 may be shorter than the inner staple drivers 952 so that the outer formed staples are longer than the inner formed staples, as shown in FIG. 88. Of course, in other embodiments, the inner staple drivers 952 could be shorter than the outer staple drivers 950. Further, the outer staple drivers 950 may not be a uniform height; there could be height variation among the outer staple drivers 950. Similarly, there could be height variation among the inner staple drivers 952.

In addition, staples with different pre-formation prong heights could be used. Also, the staple forming pockets 202 in the surface forming surface 924 of the anvil 904 may have varying depths to thereby vary the length of the formed staples. Also, as described above, some or all of the staple drivers 950, 952 may have a dimple configuration at their interface with the staples 914 to accommodate staples of different wire diameters or some other configuration that accommodates staples of different wire diameters (e.g., a v-shaped staple channel). Also, some of the pockets 202 in the anvil 1006 may be formed in a compliant material portion of the anvil 1006. Also, the staples 914 could be made of materials that have a different modulus of elasticity.

In other embodiments, as shown in FIGS. 90-95, the present invention is directed to a linear stapler 1000 that is capable of forming staples of different heights. FIGS. 90-95 focus on the end effector 1002 for such a linear stapler 1000. The end effector 1002 may comprise a replaceable staple cartridge 1004 and a linear anvil 1006. The cartridge 1004 comprises staples which are driven into and formed by the anvil 1006 when the device 1000 is actuated. Unlike the endocutters described before, the anvil 1006 may be non-rotatable in the linear stapler 1000. To clamp tissue in the end effector 1002, the user may squeeze a clamping trigger (not shown), which causes the cartridge 1004 to slide distally toward the anvil 1006 from an open position to a closed position. More details regarding the operation and components of a liner stapler may be found in U.S. Pat. No. 5,697,543, entitled "Linear Stapler With Improved Firing Stroke," by M. Burdorff ("the '543 patent"), which is incorporated herein by reference. Typically, such linear staplers do not comprise a cutting instrument.

Figure 92:
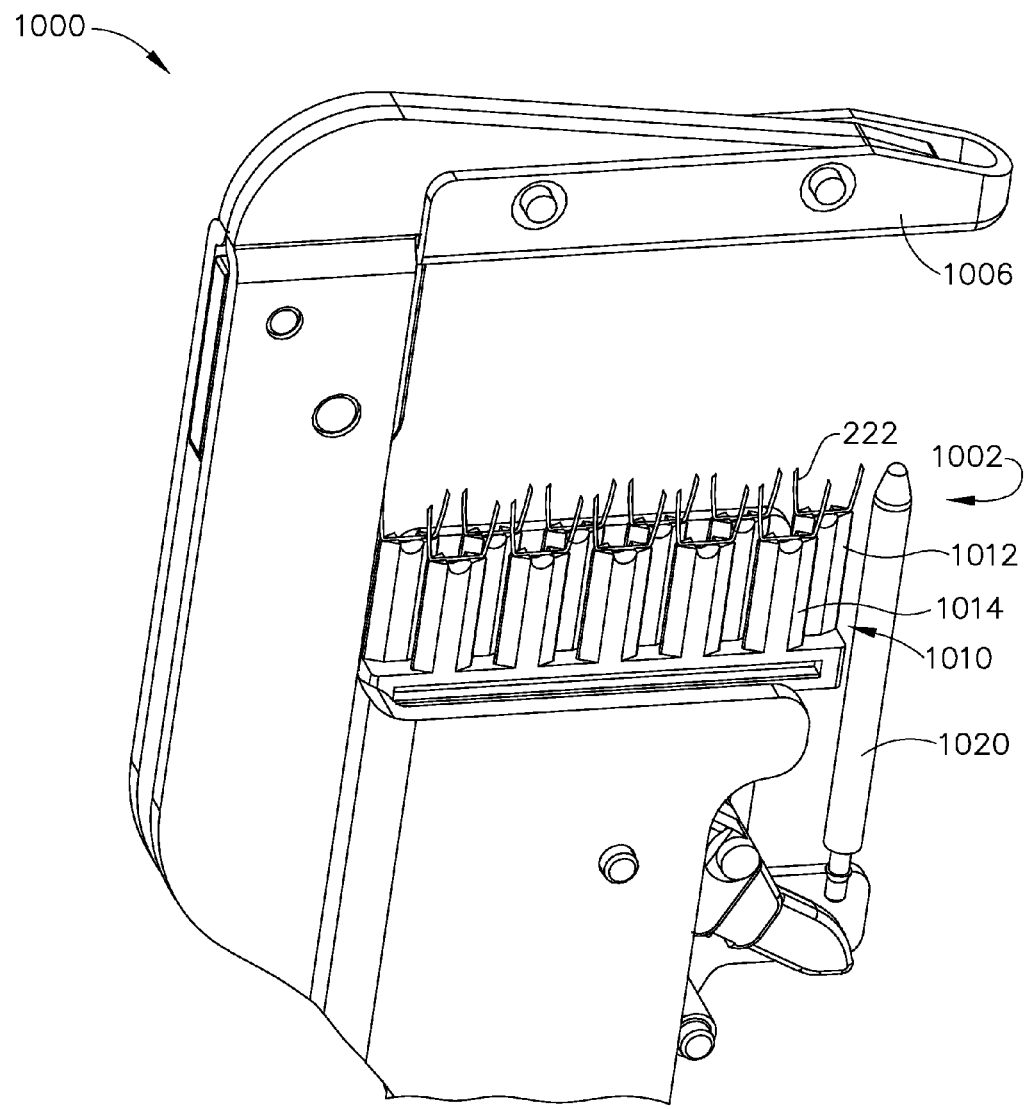
Figure 93:
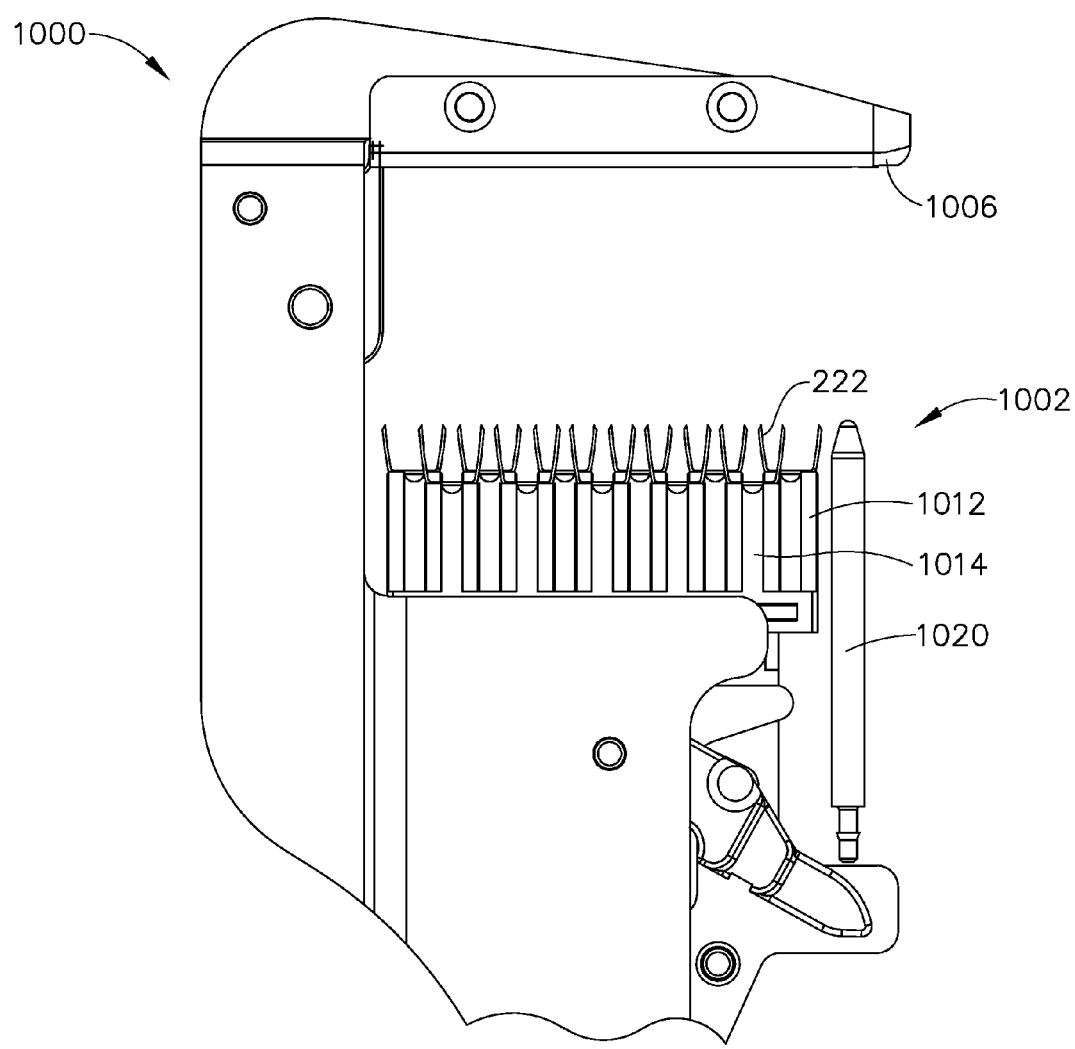
Figure 94:
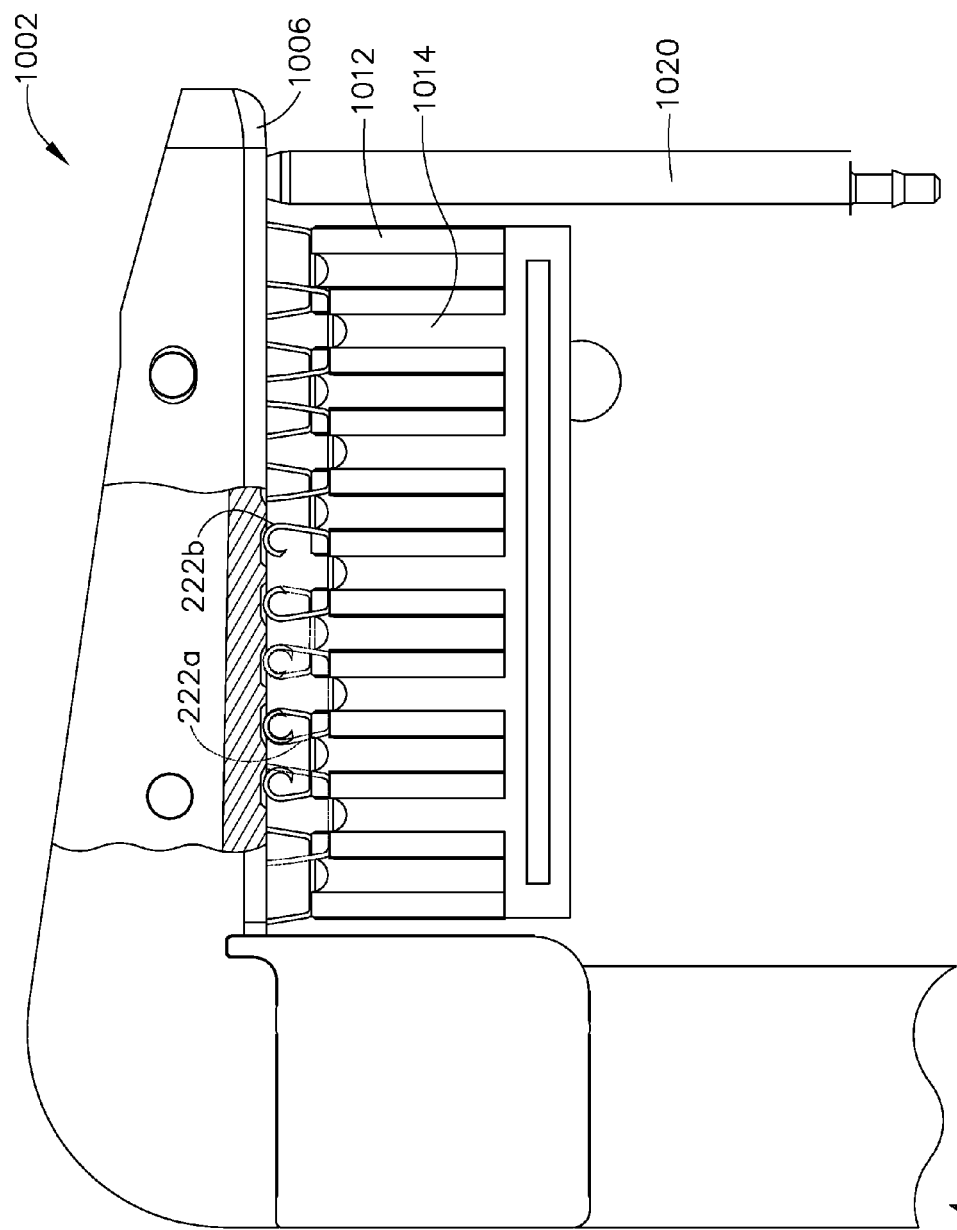
Figure 95:
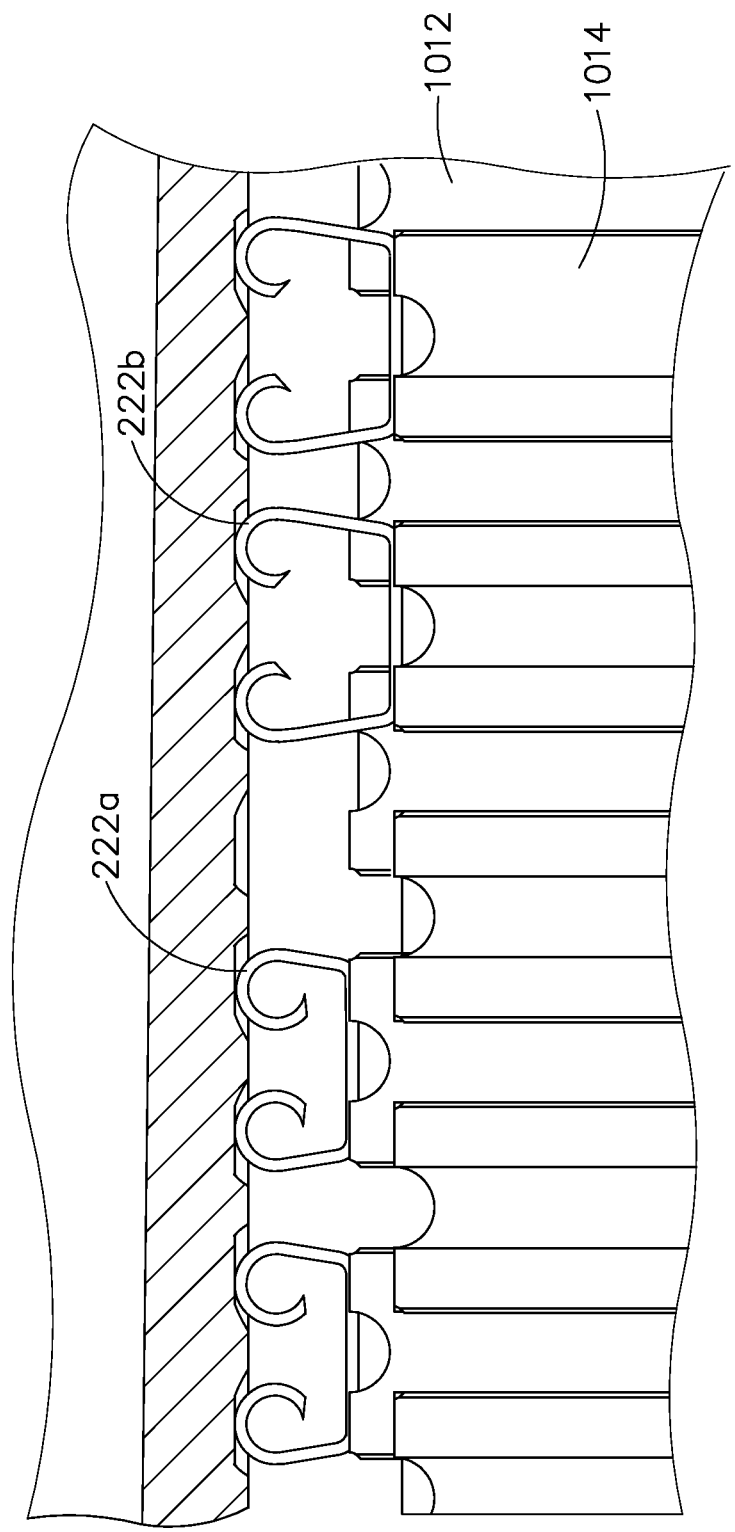

FIGS. 92-93 show the end effector 1002 with the outer cover of the cartridge 1004 removed. As can be seen in these figures, the staple cartridge 1004 may comprise a staple driver assembly 1010 comprising a row of inner staple drivers 1012 and a row of outer staple drivers 1014. The staple drivers 1012, 1014 could be of different heights to thereby form different length formed staples (all other things being equal). For example, as shown in the illustrated embodiment, the outer staple drivers 1014 may be shorter than the inner staple drivers 1012 so that the outer formed staples 222b are longer than the inner formed staples 222a, as shown in FIGS. 94-95. Of course, in other embodiments, the inner staple drivers 1012 could be shorter than the outer staple drivers 1014. Further, the outer staple drivers 1014 may not be a uniform height; there could be height variation among the outer staple drivers 1014. Similarly, there could be height variation among the inner staple drivers 1012. Also, the cartridge 1004 may comprise, for example, three rows of staples, where the outer two rows have shorter staple drivers and the inner row has longer staple drivers.

In addition, staples 1008 having different pre-formation prong heights could be used. Also, the staple forming pockets 202 in the surface forming surface 1016 of the anvil 1006 may have varying depths to thereby vary the length of the formed staples. Also, as described above, some or all of the staple drivers 1012, 1014 may have a dimple configuration at their interface with the staples 1008 to accommodate staples of different wire diameters or some other configuration that accommodates staples of different wire diameters (e.g., a v-shaped staple channel). Also, some of the pockets 202 in the anvil 1006 may be formed in a compliant material portion of the anvil 1006. Also, staples 1008 of different materials could be used.

In operation, as described in more detail in the '543 patent, when the clamping trigger is retracted by the user, the anvil 1006 is cause to slide proximally toward the staple cartridge 1004 into the closed position to clamp tissue in the end effector 102. The cartridge 1004 may comprise a distally-extending tissue retaining pin 1020 that engages an opening 1022 in the anvil when the end effector 1002 is in the closed position to retain the tissue between the cartridge 1004 and the anvil 1002. When the clinician retracts the separate firing trigger (not shown), a distally extending firing bar (not shown) is actuated, which actuates the staple drivers 1010 to drive the staples 1008.

In another embodiment, the linear stapler 1000 could be configured so that the staple cartridge 1004 slides distally toward the anvil when the clamping trigger is actuated.

It should be recognized that stapling devices according to the present invention may combine some of the features described herein for creating staples of different formed lengths. For example, for embodiments having different staple crushing distances, the staples may all have the same pre-formation prong length or some staples may have different pre-formation prong lengths. Also, the staples may all be made out of the same material, or staples made of different materials, with different modulus of elasticity, could be used. Also, the staple wire diameters may all be the same or some of them could be different.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. The various embodiments of the present invention represent vast improvements over prior staple methods that require the use of different sizes of staples in a single cartridge to achieve staples that have differing formed (final) heights.

Accordingly, the present invention has been discussed in terms of endoscopic procedures and apparatus. However, use herein of terms such as "endoscopic" should not be construed to limit the present invention to a surgical stapling and severing instrument for use only in conjunction with an endoscopic tube (i.e., trocar). On the contrary, it is believed that the present invention may find use in any procedure where access is limited to a small incision, including but not limited to laparoscopic procedures, as well as open procedures. Moreover, the unique and novel aspects of the various staple cartridge embodiments of the present invention may find utility when used in connection with other forms of stapling apparatuses without departing from the spirit and scope of the present invention.

Over the years a variety of minimally invasive robotic (or "telesurgical") systems have been developed to increase surgical dexterity as well as to permit a surgeon to operate on a patient in an intuitive manner. Many of such systems are disclosed in the following U.S. patents which are each herein incorporated by reference in their respective entirety: U.S. Pat. No. 5,792,135, entitled "Articulated Surgical Instrument For Performing Minimally Invasive Surgery With Enhanced Dexterity and Sensitivity", U.S. Pat. No. 6,231,565, entitled "Robotic Arm DLUS For Performing Surgical Tasks", U.S. Pat. No. 6,783,524, entitled "Robotic Surgical Tool With Ultrasound Cauterizing and Cutting Instrument", U.S. Pat. No. 6,364,888, entitled "Alignment of Master and Slave In a Minimally Invasive Surgical Apparatus", U.S. Pat. No. 7,524,320, entitled "Mechanical Actuator Interface System For Robotic Surgical Tools", U.S. Pat. No. 7,691,098, entitled Platform Link Wrist Mechanism", U.S. Pat. No. 7,806,891, entitled "Repositioning and Reorientation of Master/Slave Relationship in Minimally Invasive Telesurgery", and U.S. Pat. No. 7,824,401, entitled "Surgical Tool With Writed Monopolar Electrosurgical End Effectors". Many of such systems, however, have in the past been unable to generate the magnitude of forces required to effectively cut and fasten tissue.

Figure 96:
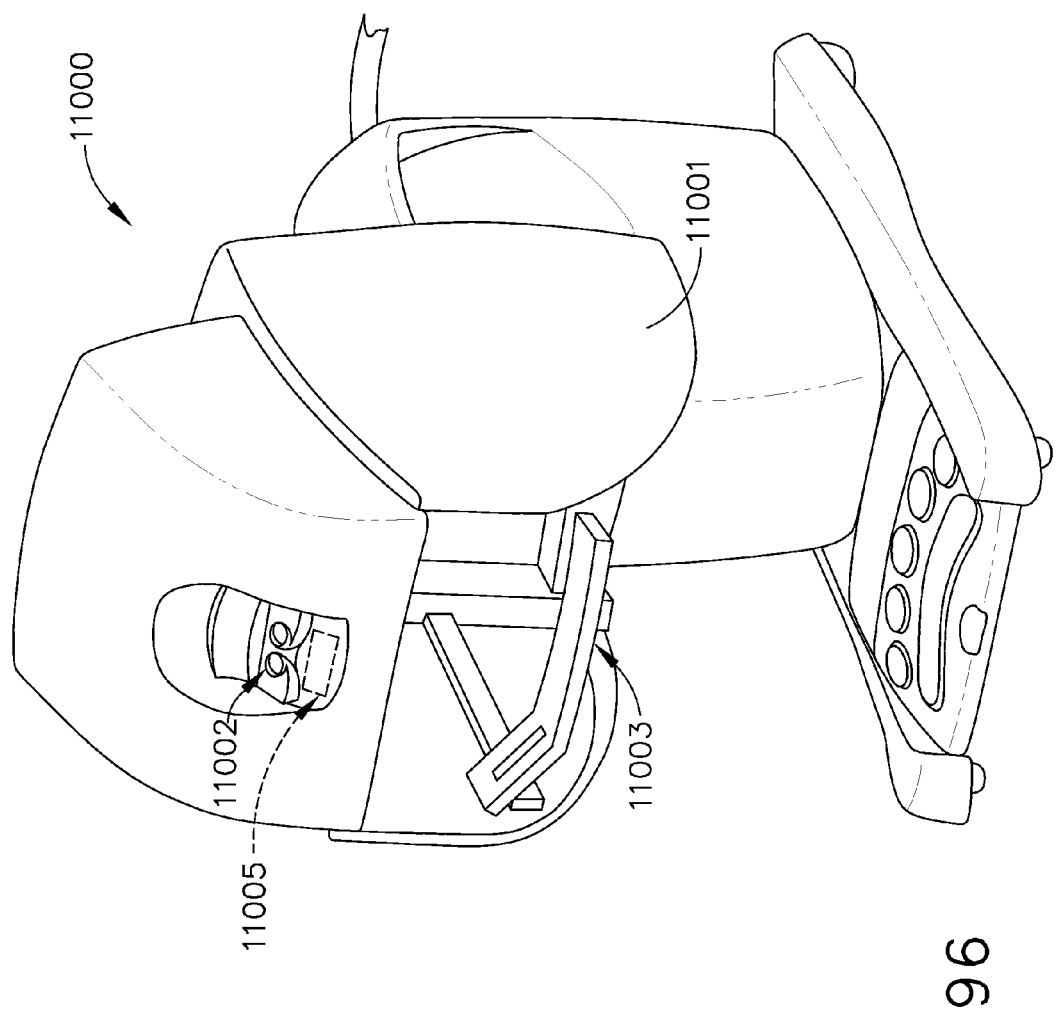
FIG. 96 is a perspective view of one robotic controller embodiment.

FIG. 96 depicts one version of a master controller 11001 that may be used in connection with a robotic arm slave cart 11100 of the type depicted in FIG. 96. Master controller 11001 and robotic arm slave cart 11100, as well as their respective components and control systems are collectively referred to herein as a robotic system 11000. Examples of such systems and devices are disclosed in U.S. Pat. No. 7,524,320 which has been herein incorporated by reference. Thus, various details of such devices will not be described in detail herein beyond that which may be necessary to understand various embodiments and forms of the present invention. As is known, the master controller 11001 generally includes master controllers (generally represented as 11003 in FIG. 96) which are grasped by the surgeon and manipulated in space while the surgeon views the procedure via a stereo display 11002. The master controllers 11001 generally comprise manual input devices which preferably move with multiple degrees of freedom, and which often further have an actuatable handle for actuating tools (for example, for closing grasping saws, applying an electrical potential to an electrode, or the like).

Figure 97:
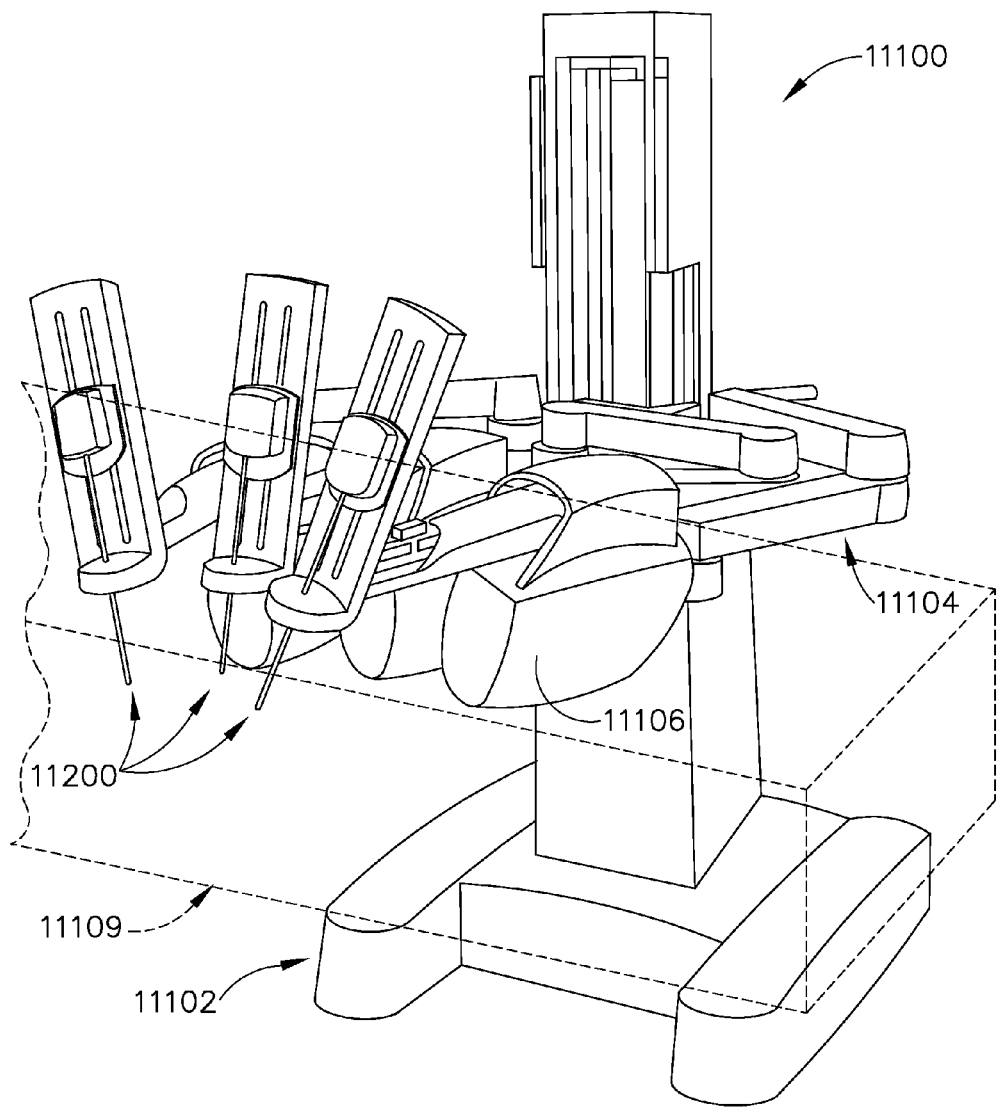
FIG. 97 is a perspective view of one robotic surgical arm cart/manipulator of a robotic system operably supporting a plurality of surgical tool embodiments of the present invention.

As can be seen in FIG. 97, in one form, the robotic arm cart 11100 is configured to actuate a plurality of surgical tools, generally designated as 11200. Various robotic surgery systems and methods employing master controller and robotic arm cart arrangements are disclosed in U.S. Pat. No. 6,132,368, entitled "Multi-Component Telepresence System and Method", the full disclosure of which is incorporated herein by reference. In various forms, the robotic arm cart 11100 includes a base 11002 from which, in the illustrated embodiment, three surgical tools 11200 are supported. In various forms, the surgical tools 11200 are each supported by a series of manually articulatable linkages, generally referred to as set-up joints 11104, and a robotic manipulator 11106. These structures are herein illustrated with protective covers extending over much of the robotic linkage. These protective covers may be optional, and may be limited in size or entirely eliminated in some embodiments to minimize the inertia that is encountered by the servo mechanisms used to manipulate such devices, to limit the volume of moving components so as to avoid collisions, and to limit the overall weight of the cart 11100. Cart 11100 will generally have dimensions suitable for transporting the cart 11100 between operating rooms. The cart 11100 may be configured to typically fit through standard operating room doors and onto standard hospital elevators. In various forms, the cart 11100 would preferably have a weight and include a wheel (or other transportation) system that allows the cart 1100 to be positioned adjacent an operating table by a single attendant.

Figure 98:
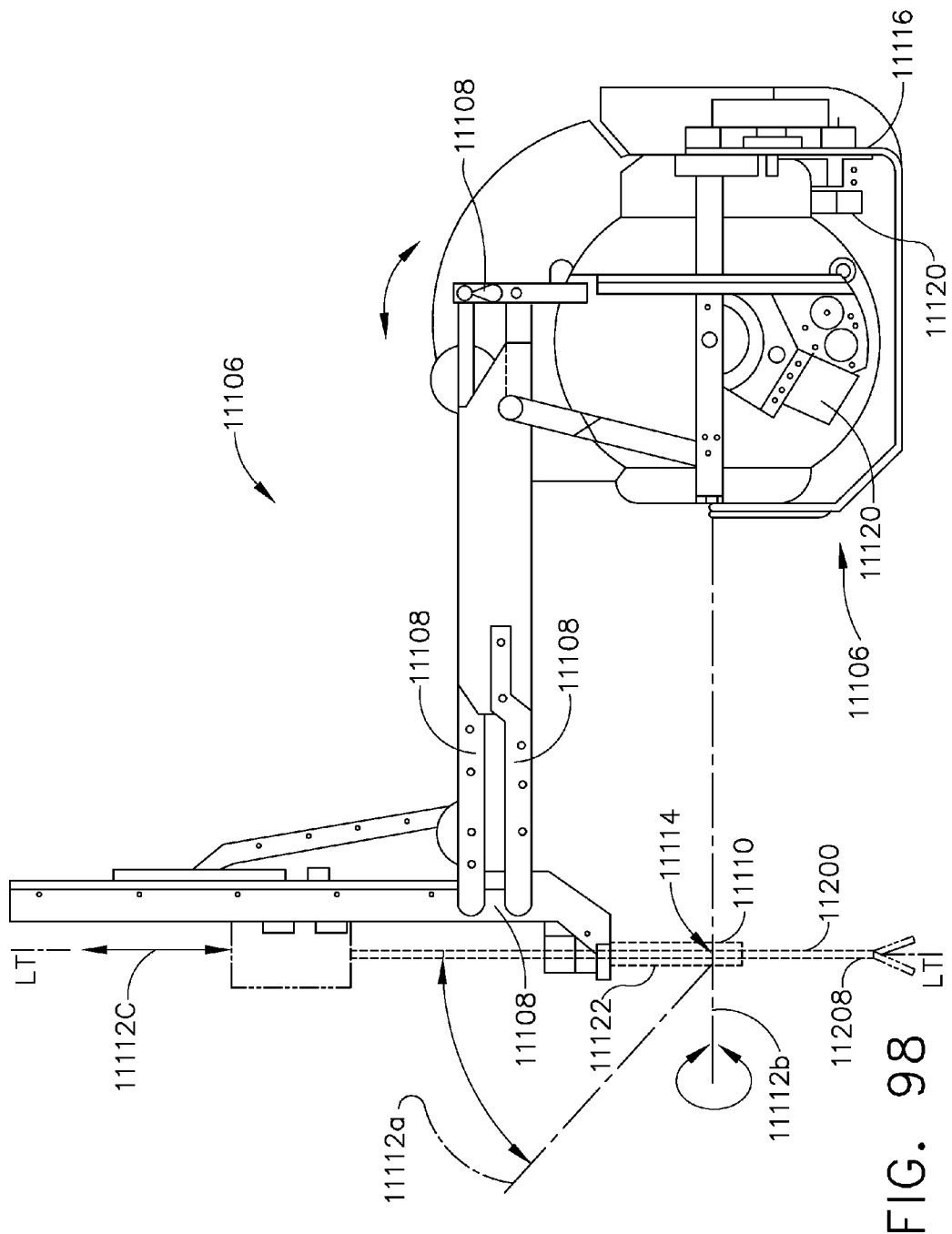
FIG. 98 is a side view of the robotic surgical arm cart/manipulator depicted in FIG. 97.

Referring now to FIG. 98, in at least one form, robotic manipulators 11106 may include a linkage 11108 that constrains movement of the surgical tool 11200. In various embodiments, linkage 11108 includes rigid links coupled together by rotational joints in a parallelogram arrangement so that the surgical tool 11200 rotates around a point in space 11110, as more fully described in issued U.S. Pat. No. 5,817,084, the full disclosure of which is herein incorporated by reference. The parallelogram arrangement constrains rotation to pivoting about an axis 11112a, sometimes called the pitch axis. The links supporting the parallelogram linkage are pivotally mounted to set-up joints 11104 (FIG. 97) so that the surgical tool 11200 further rotates about an axis 11112b, sometimes called the yaw axis. The pitch and yaw axes 11112a, 11112b intersect at the remote center 11114, which is aligned along a shaft 11208 of the surgical tool 11200. The surgical tool 11200 may have further degrees of driven freedom as supported by manipulator 11106, including sliding motion of the surgical tool 11200 along the longitudinal tool axis "LT-LT". As the surgical tool 11200 slides along the tool axis LT-LT relative to manipulator 11106 (arrow 11112c), remote center 11114 remains fixed relative to base 11116 of manipulator 11106. Hence, the entire manipulator is generally moved to re-position remote center 11114. Linkage 11108 of manipulator 11106 is driven by a series of motors 11120. These motors actively move linkage 11108 in response to commands from a processor of a control system. As will be discussed in further detail below, motors 11120 are also employed to manipulate the surgical tool 11200.

Figure 99:
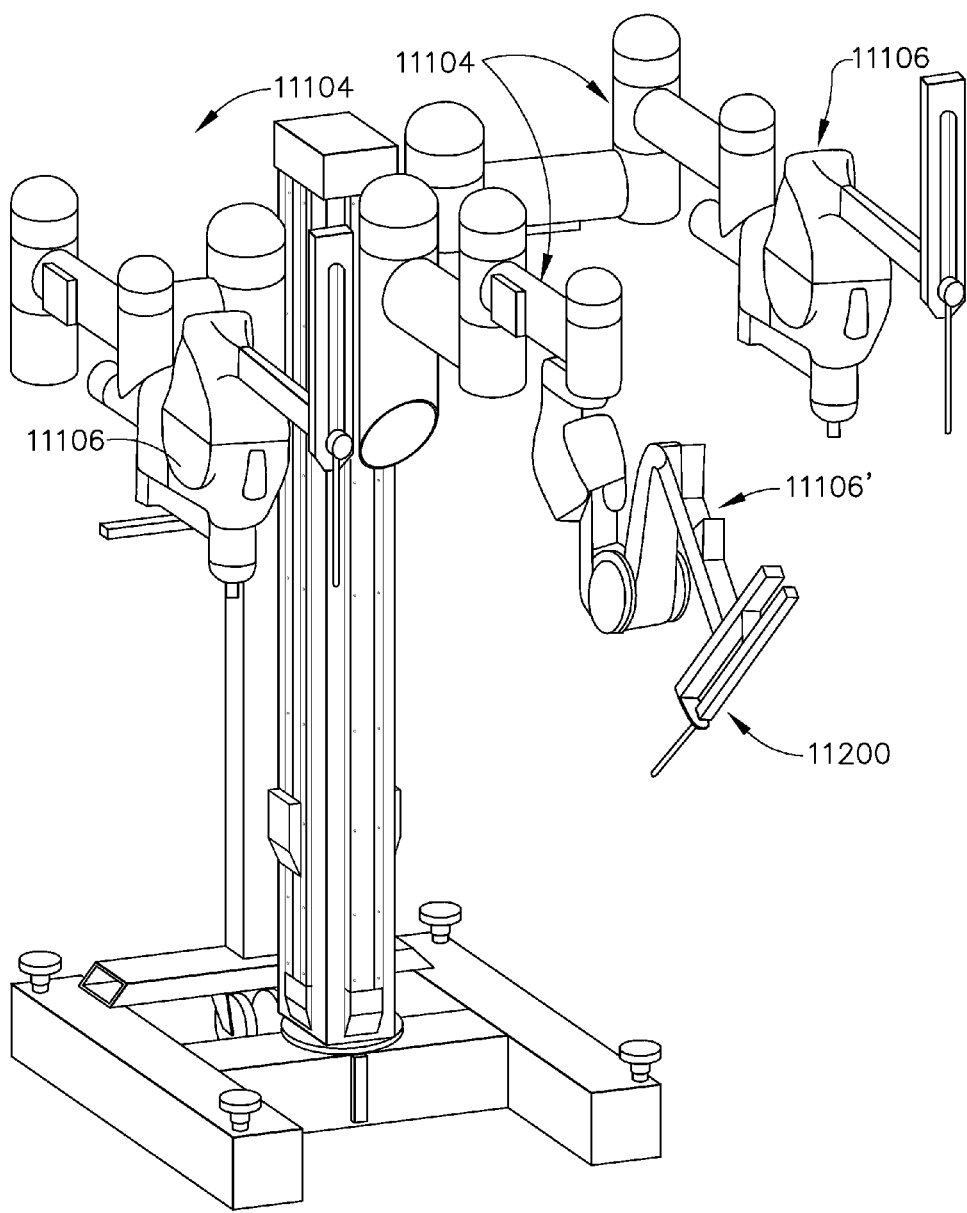
FIG. 99 is a perspective view of an exemplary cart structure with positioning linkages for operably supporting robotic manipulators that may be used with various surgical tool embodiments of the present invention.

An alternative set-up joint structure is illustrated in FIG. 99. In this embodiment, a surgical tool 11200 is supported by an alternative manipulator structure 11106' between two tissue manipulation tools. Those of ordinary skill in the art will appreciate that various embodiments of the present invention may incorporate a wide variety of alternative robotic structures, including those described in U.S. Pat. No. 5,878,193, entitled "Automated Endoscope System For Optimal Positioning", the full disclosure of which is incorporated herein by reference. Additionally, while the data communication between a robotic component and the processor of the robotic surgical system is primarily described herein with reference to communication between the surgical tool 11200 and the master controller 11001, it should be understood that similar communication may take place between circuitry of a manipulator, a set-up joint, an endoscope or other image capture device, or the like, and the processor of the robotic surgical system for component compatibility verification, component-type identification, component calibration (such as off-set or the like) communication, confirmation of coupling of the component to the robotic surgical system, or the like.

Figure 100:
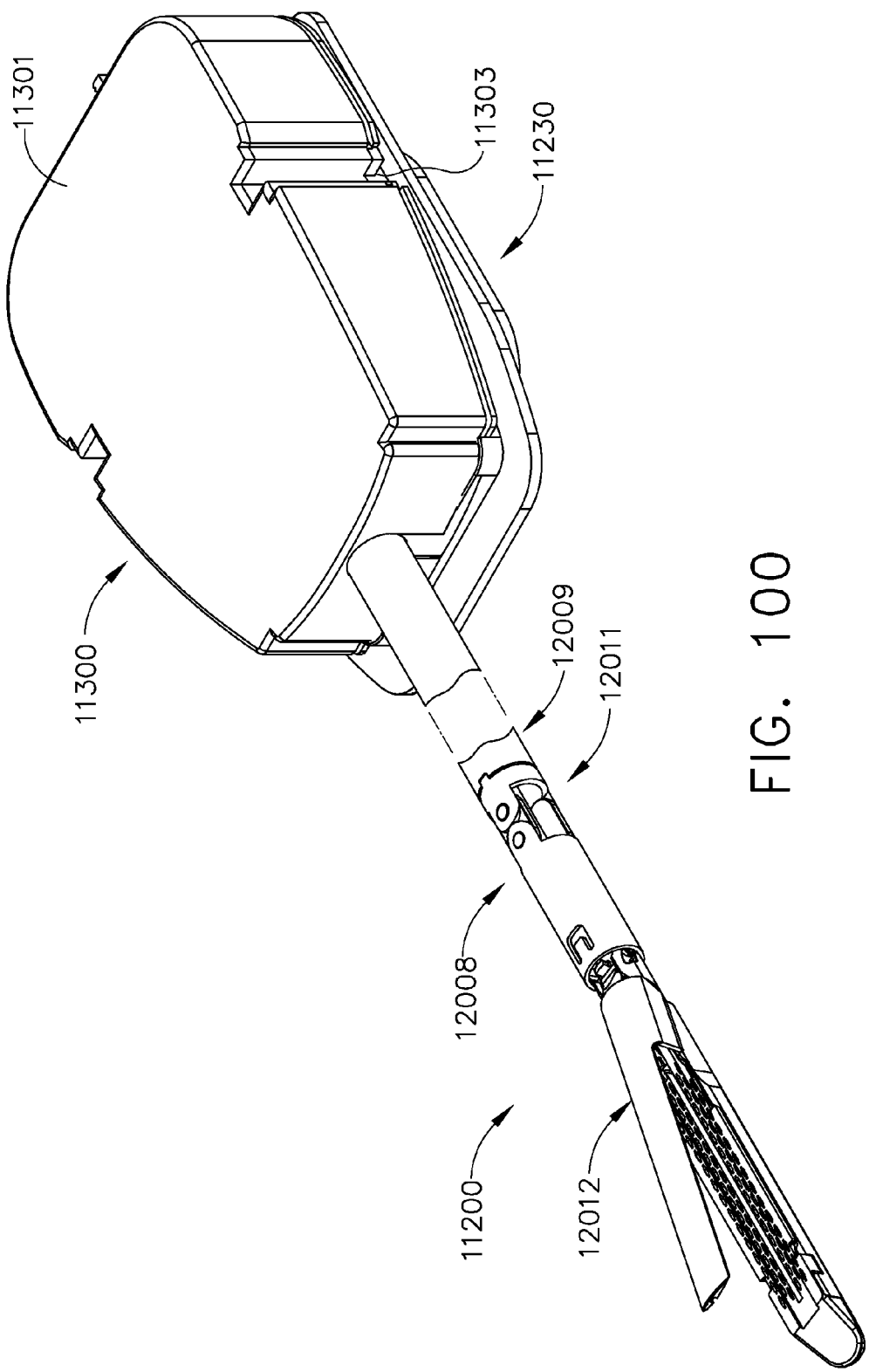
FIG. 100 is a perspective view of a surgical tool embodiment of the present invention.
Figure 105:
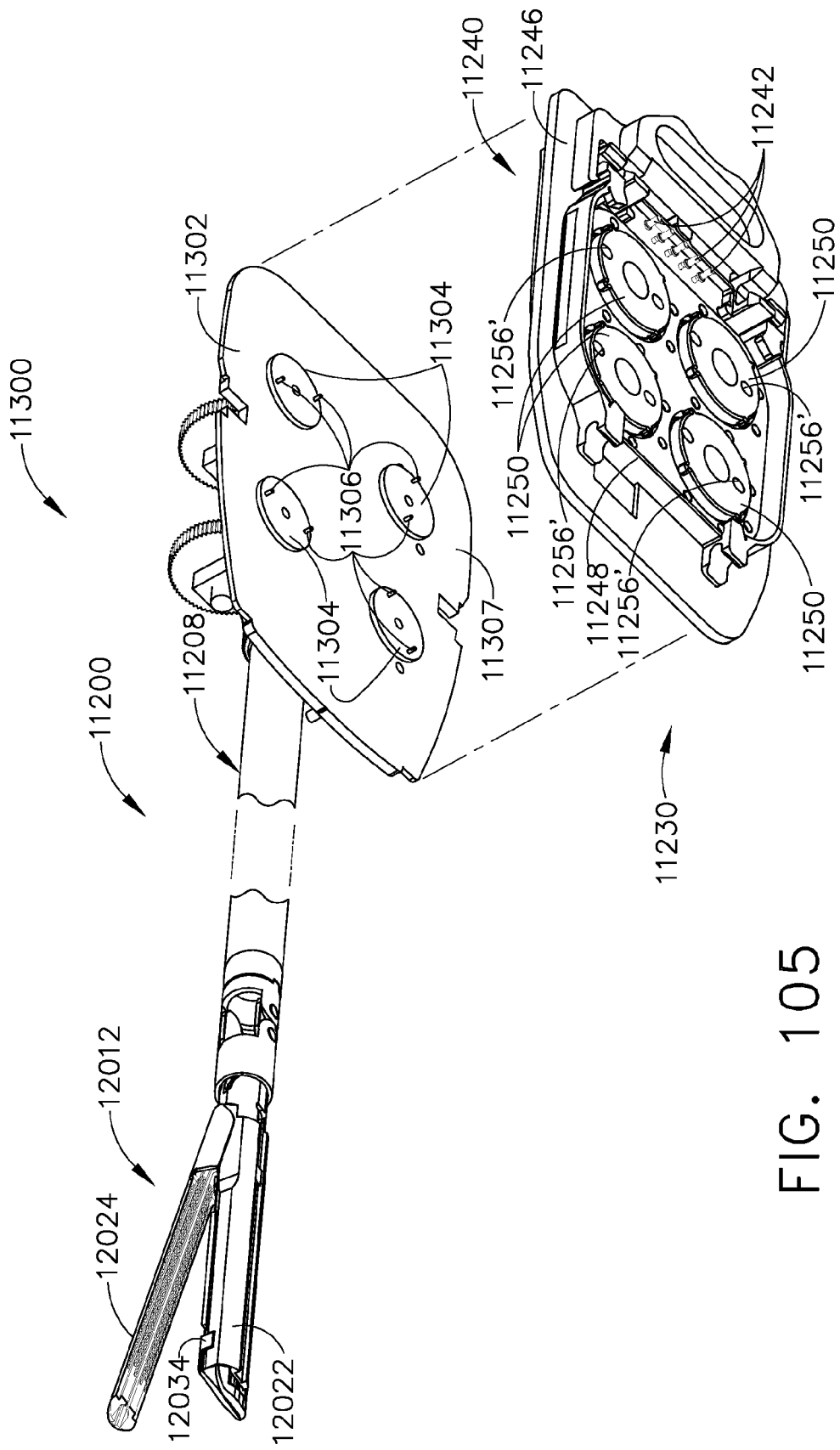
FIG. 105 is a partial bottom perspective view of the surgical tool embodiment of FIG. 100.
Figure 106:
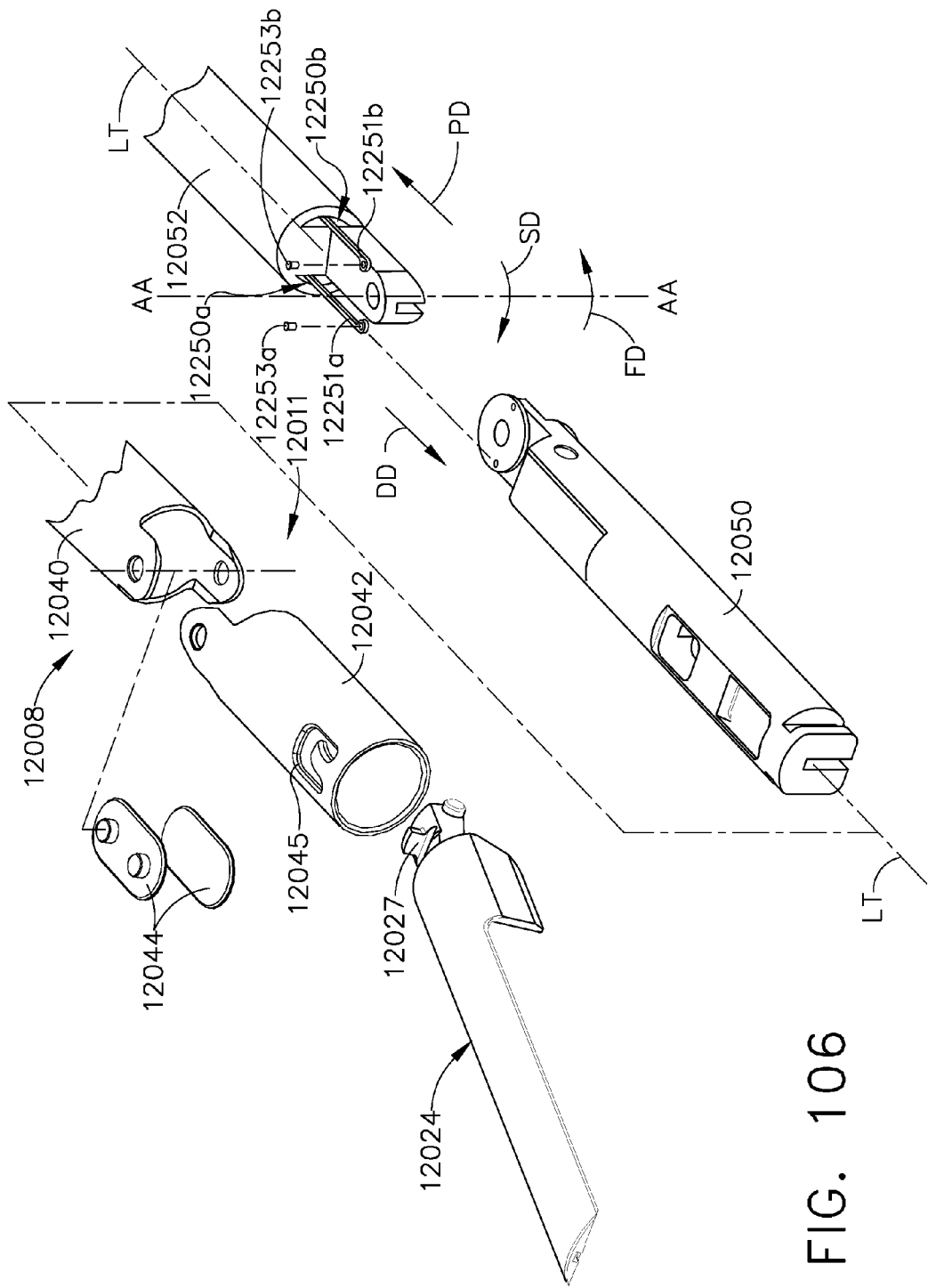
FIG. 106 is a partial exploded view of a portion of an articulatable surgical end effector embodiment of the present invention.
Figure 107:
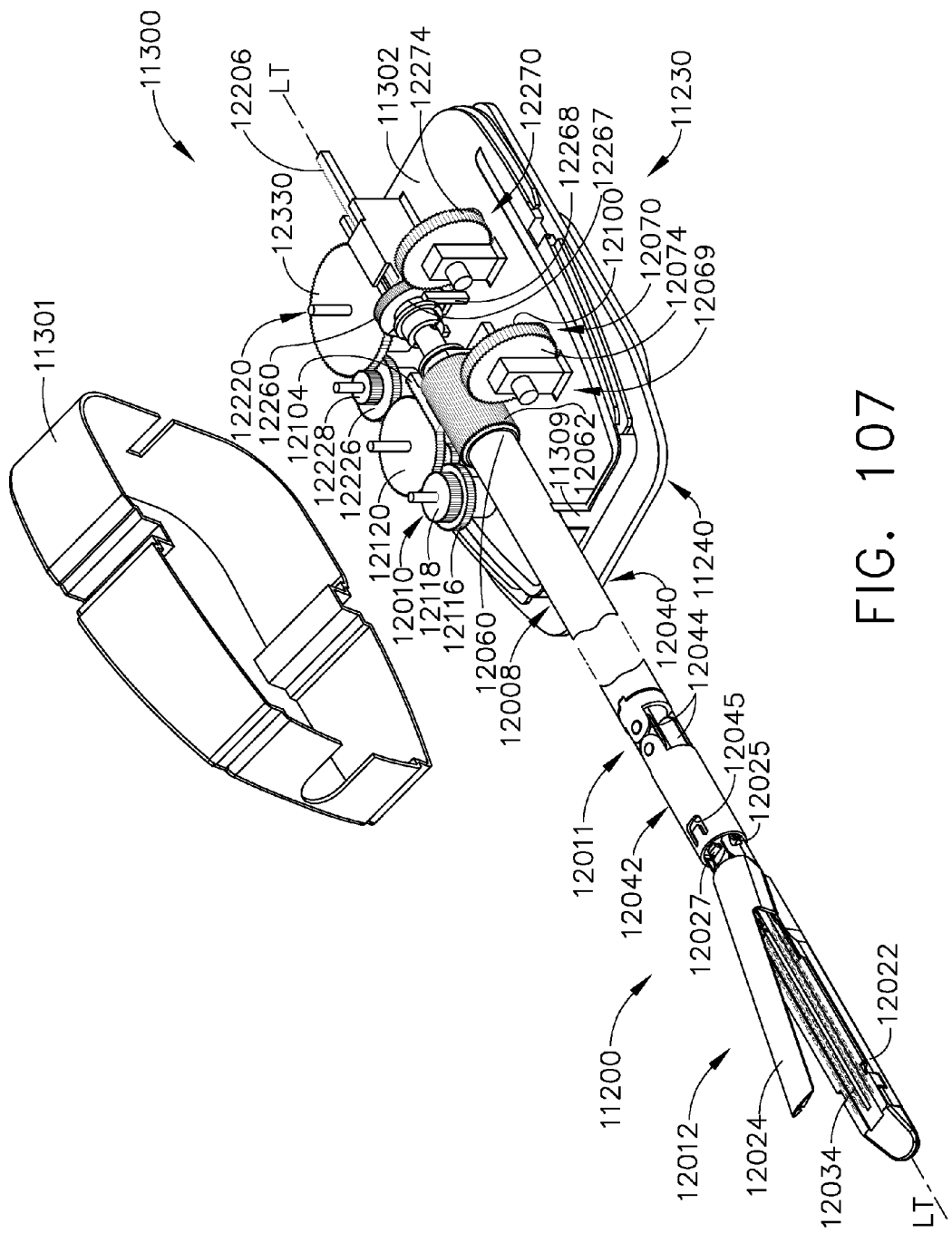
FIG. 107 is a perspective view of the surgical tool embodiment of FIG. 105 with the tool mounting housing removed.

An exemplary non-limiting surgical tool 11200 that is well-adapted for use with a robotic system 11000 that has a tool drive assembly 11010 (FIG. 101) that is operatively coupled to a master controller 11001 that is operable by inputs from an operator (i.e., a surgeon) is depicted in FIG. 100. As can be seen in that Figure, the surgical tool 11200 includes a surgical end effector 12012 that comprises an endocutter. In at least one form, the surgical tool 11200 generally includes an elongated shaft assembly 12008 that has a proximal closure tube 12040 and a distal closure tube 12042 that are coupled together by an articulation joint 12011. The surgical tool 11200 is operably coupled to the manipulator by a tool mounting portion, generally designated as 11300. The surgical tool 11200 further includes an interface 11230 which mechanically and electrically couples the tool mounting portion 11300 to the manipulator. One form of interface 11230 is illustrated in FIGS. 101-105. In various embodiments, the tool mounting portion 11300 includes a tool mounting plate 11302 that operably supports a plurality of (four are shown in FIG. 105) rotatable body portions, driven discs or elements 11304, that each include a pair of pins 11306 that extend from a surface of the driven element 11304. One pin 11306 is closer to an axis of rotation of each driven elements 11304 than the other pin 11306 on the same driven element 11304, which helps to ensure positive angular alignment of the driven element 11304. Interface 11230 includes an adaptor portion 11240 that is configured to mountingly engage the mounting plate 11302 as will be further discussed below. The adaptor portion 11240 may include an array of electrical connecting pins 11242 (FIG. 103) which may be coupled to a memory structure by a circuit board within the tool mounting portion 11300. While interface 11230 is described herein with reference to mechanical, electrical, and magnetic coupling elements, it should be understood that a wide variety of telemetry modalities might be used, including infrared, inductive coupling, or the like.

As can be seen in FIGS. 101-104, the adapter portion 11240 generally includes a tool side 11244 and a holder side 11246. In various forms, a plurality of rotatable bodies 11250 are mounted to a floating plate 11248 which has a limited range of movement relative to the surrounding adaptor structure normal to the major surfaces of the adaptor 11240. Axial movement of the floating plate 11248 helps decouple the rotatable bodies 11250 from the tool mounting portion 11300 when the levers 11303 along the sides of the tool mounting portion housing 11301 are actuated (See FIG. 100). Other mechanisms/arrangements may be employed for releasably coupling the tool mounting portion 11300 to the adaptor 11240. In at least one form, rotatable bodies 11250 are resiliently mounted to floating plate 11248 by resilient radial members which extend into a circumferential indentation about the rotatable bodies 11250. The rotatable bodies 11250 can move axially relative to plate 11248 by deflection of these resilient structures. When disposed in a first axial position (toward tool side 11244) the rotatable bodies 11250 are free to rotate without angular limitation. However, as the rotatable bodies 11250 move axially toward tool side 11244, tabs 11252 (extending radially from the rotatable bodies 11250) laterally engage detents on the floating plates so as to limit angular rotation of the rotatable bodies 11250 about their axes. This limited rotation can be used to help drivingly engage the rotatable bodies 11250 with drive pins 11272 of a corresponding tool holder portion 11270 of the robotic system 11000, as the drive pins 11272 will push the rotatable bodies 11250 into the limited rotation position until the pins 11234 are aligned with (and slide into) openings 11256'. Openings 11256 on the tool side 11244 and openings 11256' on the holder side 11246 of rotatable bodies 11250 are configured to accurately align the driven elements 11304 (FIG. 105) of the tool mounting portion 11300 with the drive elements 11271 of the tool holder 11270. As described above regarding inner and outer pins 11306 of driven elements 11304, the openings 11256, 11256' are at differing distances from the axis of rotation on their respective rotatable bodies 11250 so as to ensure that the alignment is not 180 degrees from its intended position. Additionally, each of the openings 11256 is slightly radially elongated so as to fittingly receive the pins 11306 in the circumferential orientation. This allows the pins 11306 to slide radially within the openings 11256, 11256' and accommodate some axial misalignment between the tool 11200 and tool holder 11270, while minimizing any angular misalignment and backlash between the drive and driven elements. Openings 11256 on the tool side 11244 are offset by about 90 degrees from the openings 11256' (shown in broken lines) on the holder side 11246, as can be seen most clearly in FIG. 104.

Various embodiments may further include an array of electrical connector pins 11242 located on holder side 11246 of adaptor 11240, and the tool side 11244 of the adaptor 11240 may include slots 11258 (FIG. 104) for receiving a pin array (not shown) from the tool mounting portion 11300. In addition to transmitting electrical signals between the surgical tool 11200 and the tool holder 11270, at least some of these electrical connections may be coupled to an adaptor memory device 11260 (FIG. 103) by a circuit board of the adaptor 11240.

Figure 101:
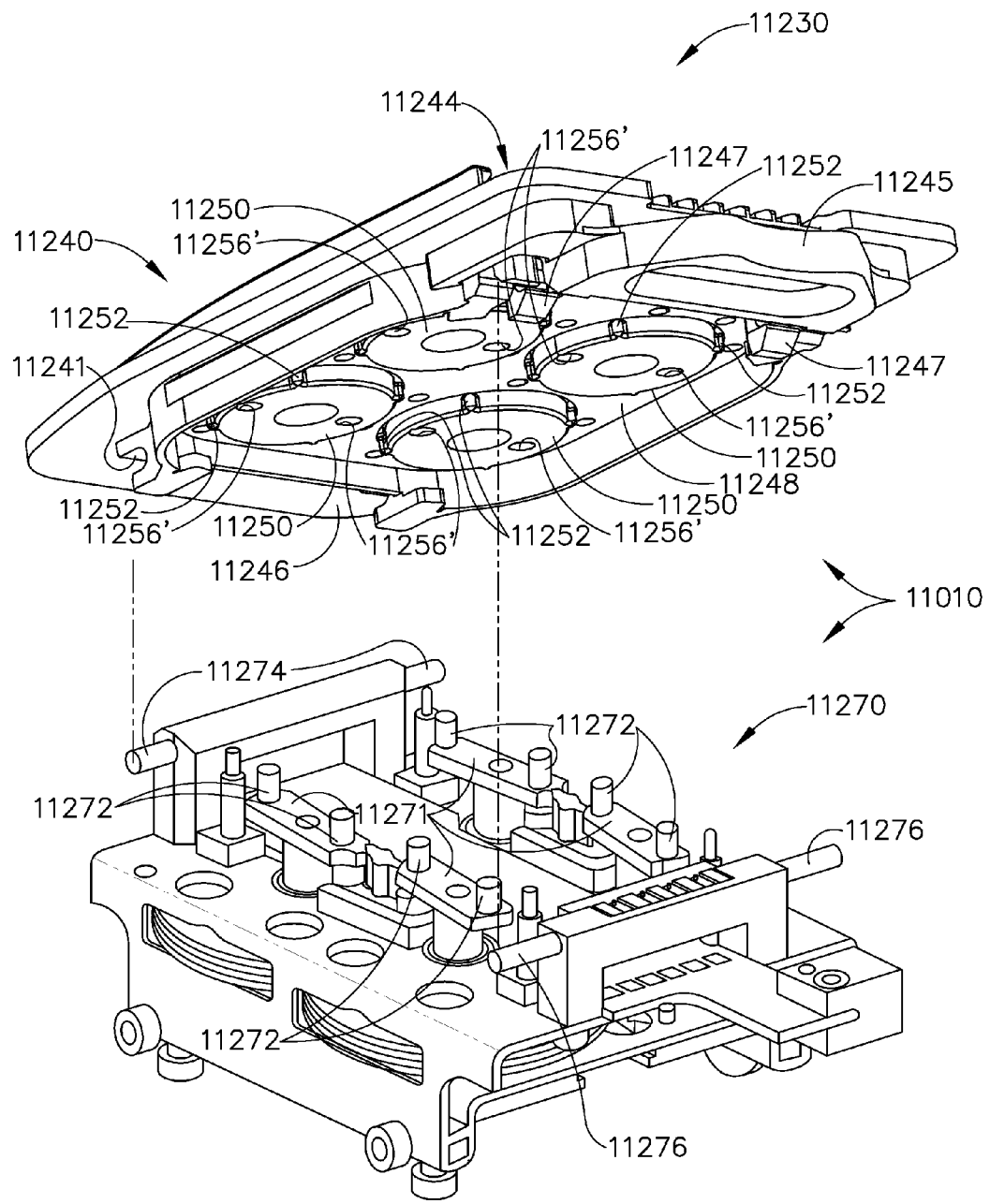
FIG. 101 is an exploded assembly view of an adapter and tool holder arrangement for attaching various surgical tool embodiments to a robotic system.
Figure 102:
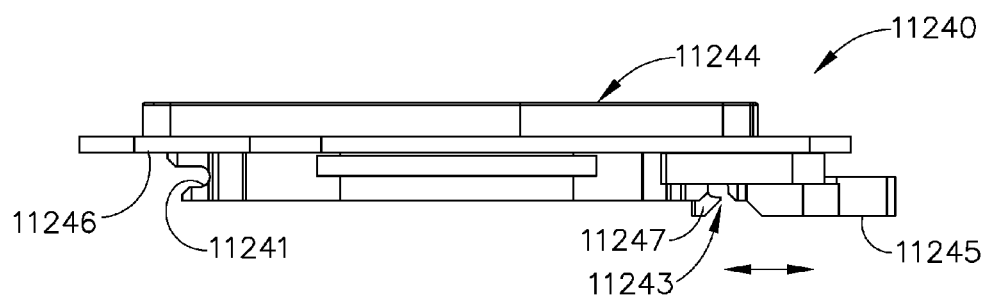
FIG. 102 is a side view of the adapter shown in FIG. 101.
Figure 103:
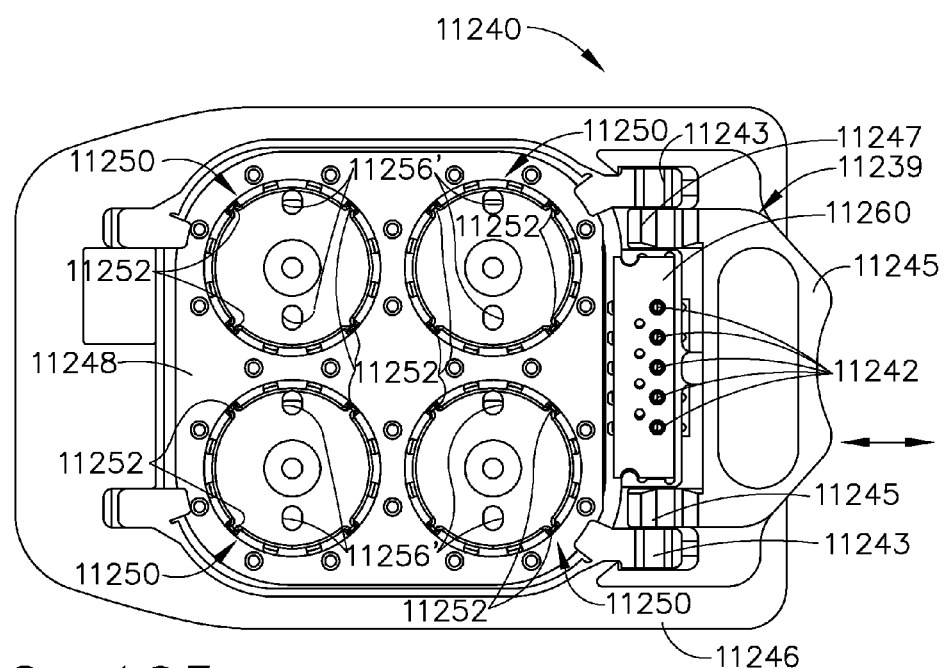
FIG. 103 is a bottom view of the adapter shown in FIG. 101.
Figure 104:
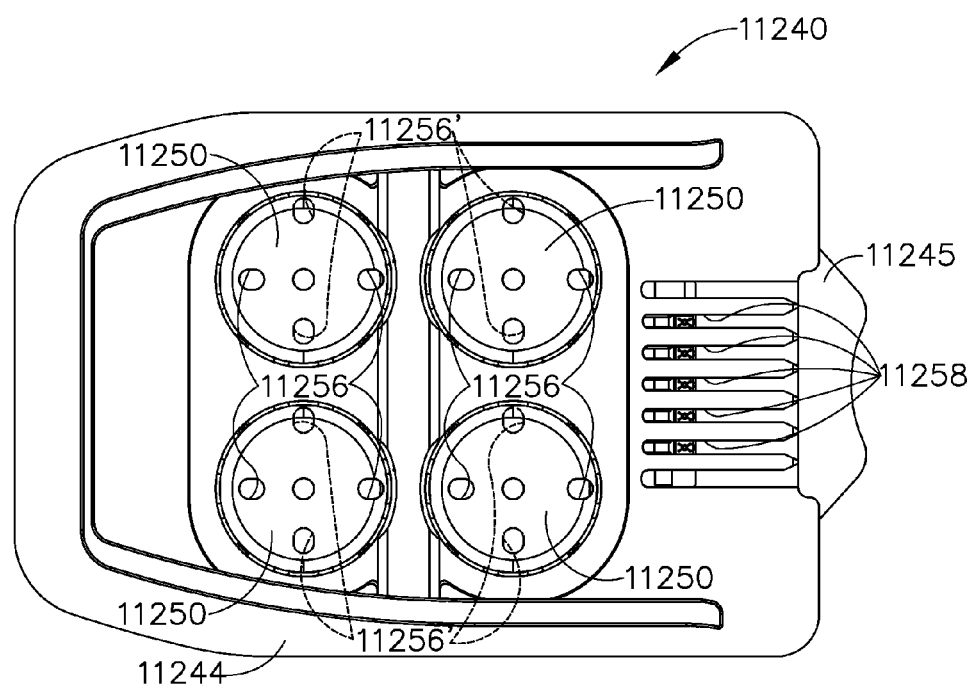
FIG. 104 is a top view of the adapter of FIGS. 101 and 102.

A detachable latch arrangement 11239 may be employed to releasably affix the adaptor 11240 to the tool holder 11270. As used herein, the term "tool drive assembly" when used in the context of the robotic system 11000, at least encompasses various embodiments of the adapter 11240 and tool holder 11270 and which has been generally designated as 11010 in FIG. 101. For example, as can be seen in FIG. 101, the tool holder 11270 may include a first latch pin arrangement 11274 that is sized to be received in corresponding clevis slots 11241 provided in the adaptor 11240. In addition, the tool holder 11270 may further have second latch pins 11276 that are sized to be retained in corresponding latch devises 11243 in the adaptor 11240. See FIG. 103. In at least one form, a latch assembly 11245 is movably supported on the adapter 1240 and is biasable between a first latched position wherein the latch pins 11276 are retained within their respective latch clevis 11243 and an unlatched position wherein the second latch pins 11276 may be into or removed from the latch devises 11243. A spring or springs (not shown) are employed to bias the latch assembly into the latched position. A lip on the tool side 11244 of adaptor 11240 may slidably receive laterally extending tabs of tool mounting housing 11301.

Figure 109:
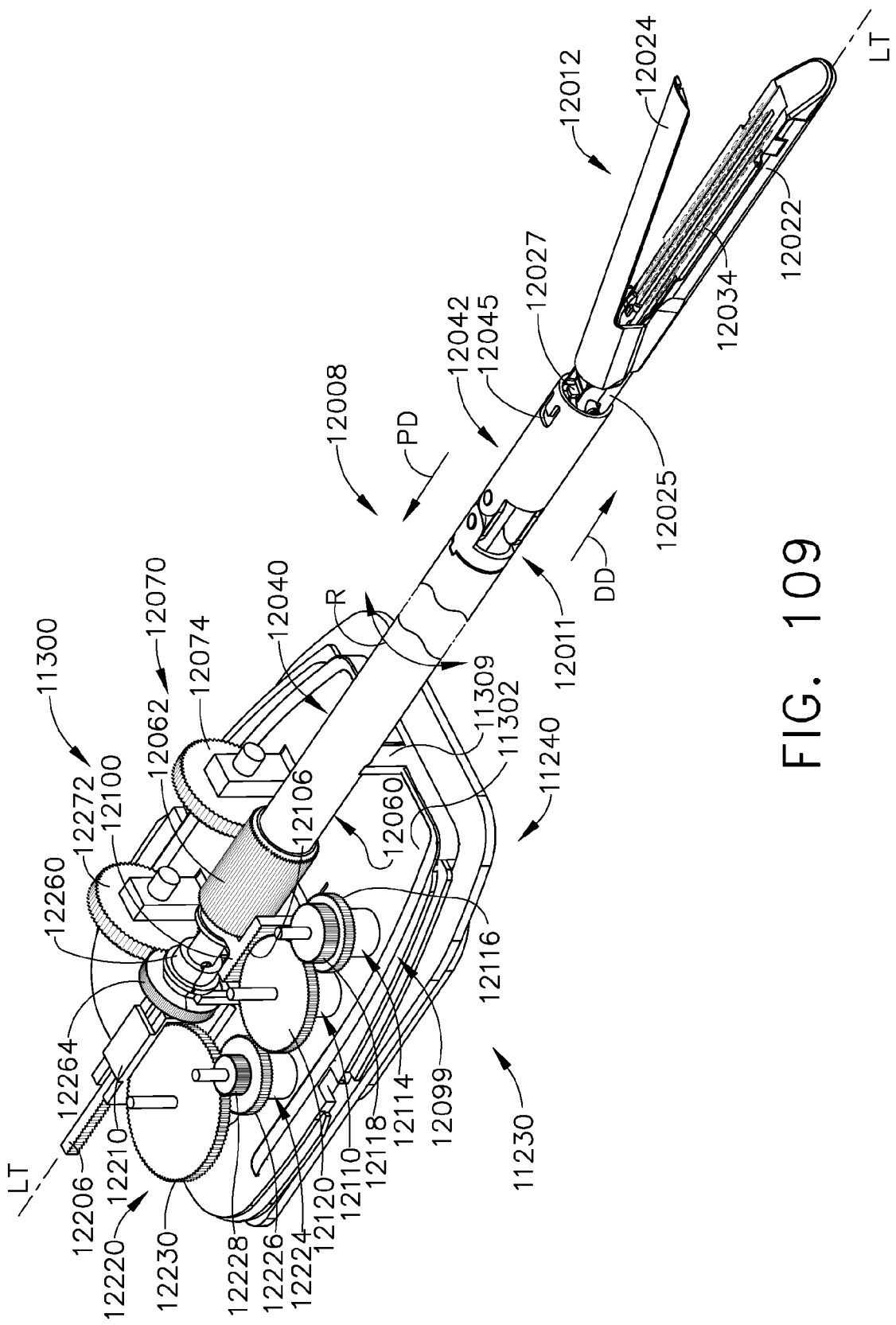
FIG. 109 is a front perspective view of the surgical tool embodiment of FIG. 105 with the tool mounting housing removed.
Figure 110:
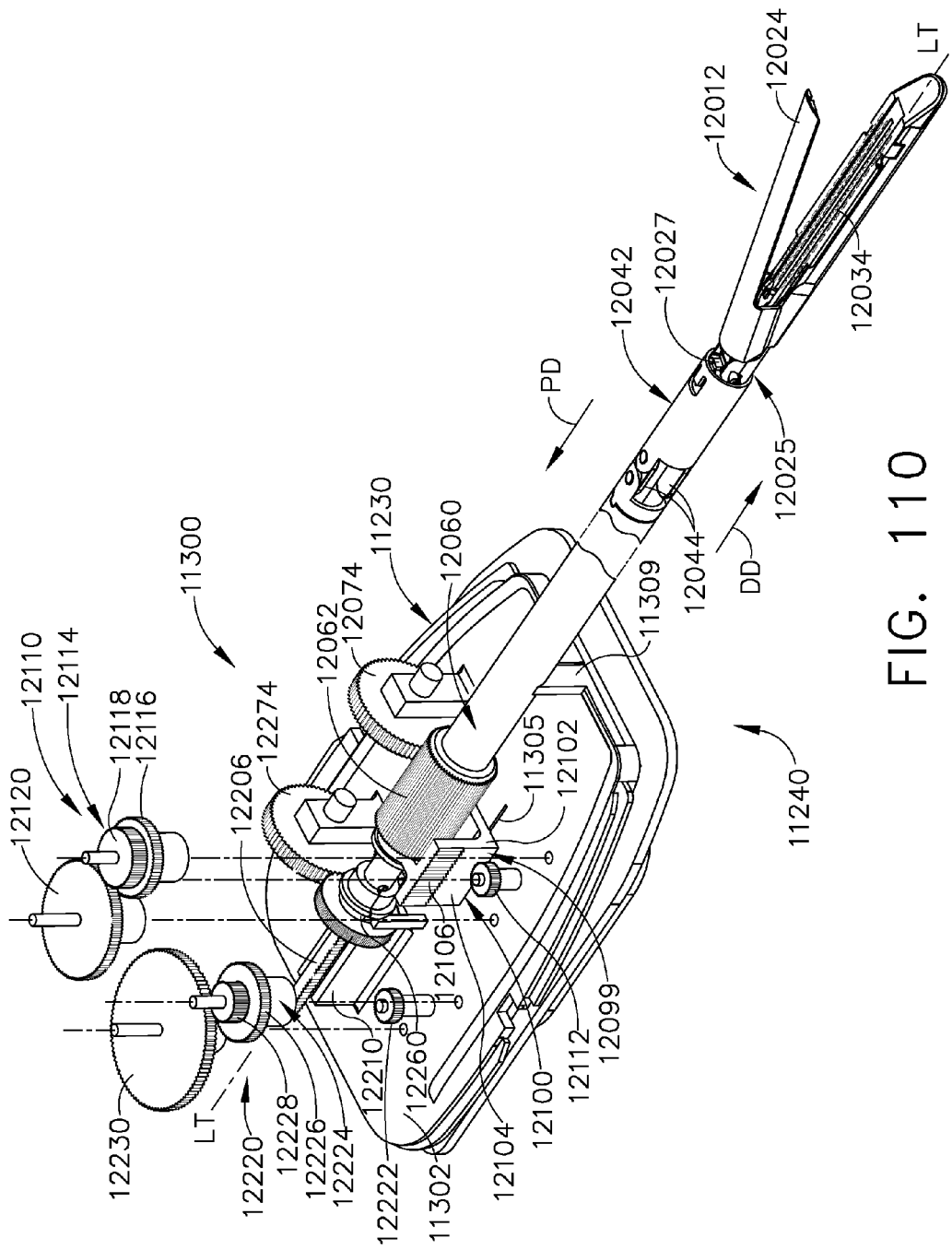
FIG. 110 is a partial exploded perspective view of the surgical tool embodiment of FIG. 105.
Figure 111:
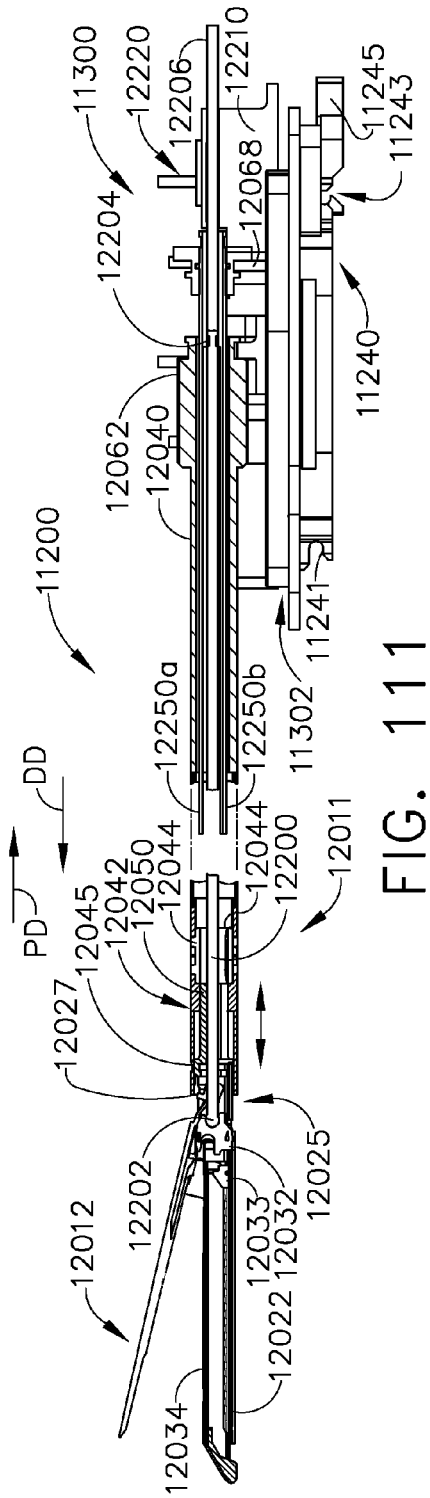
FIG. 111 is a partial cross-sectional side view of the surgical tool embodiment of FIG. 105.
Figure 112:
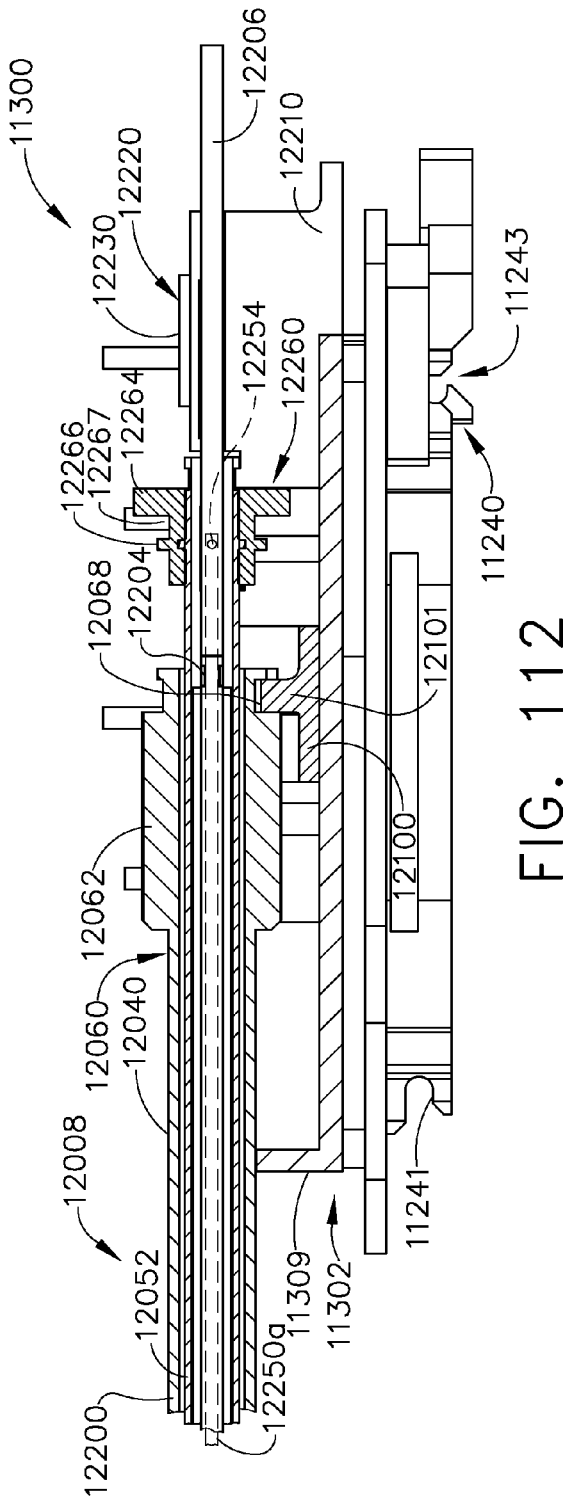
FIG. 112 is an enlarged cross-sectional view of a portion of the surgical tool depicted in FIG. 111.

Turning next to FIGS. 105-112, in at least one embodiment, the surgical tool 11200 includes a surgical end effector 12012 that comprises in this example, among other things, at least one component 12024 that is selectively movable between first and second positions relative to at least one other component 12022 in response to various control motions applied thereto as will be discussed in further detail below. In various embodiments, component 12022 comprises an elongated channel 12022 configured to operably support a surgical staple cartridge 12034 therein and component 12024 comprises a pivotally translatable clamping member, such as an anvil 12024. Various embodiments of the surgical end effector 12012 are configured to maintain the anvil 12024 and elongated channel 12022 at a spacing that assures effective stapling and severing of tissue clamped in the surgical end effector 12012. As can be seen in FIG. 111, the surgical end effector 12012 further includes a cutting instrument 12032 and a sled 12033. The cutting instrument 12032 may be, for example, a knife. The surgical staple cartridge 12034 operably houses a plurality of surgical staples (not show) therein that are supported on movable staple drivers (not shown). As the cutting instrument 12032 is driven distally through a centrally-disposed slot (not shown) in the surgical staple cartridge 12034, it forces the sled 12033 distally as well. As the sled 12033 is driven distally, its "wedge-shaped" configuration contacts the movable staple drivers and drives them vertically toward the closed anvil 12024. The surgical staples are formed as they are driven into the forming surface located on the underside of the anvil 12024. The sled 12033 may be part of the surgical staple cartridge 12034, such that when the cutting instrument 12032 is retracted following the cutting operation, the sled 12033 does not retract. The anvil 12024 may be pivotably opened and closed at a pivot point 12025 located at the proximal end of the elongated channel 12022. The anvil 12024 may also include a tab 12027 at its proximal end that interacts with a component of the mechanical closure system (described further below) to facilitate the opening of the anvil 12024. The elongated channel 12022 and the anvil 12024 may be made of an electrically conductive material (such as metal) so that they may serve as part of an antenna that communicates with sensor(s) in the end effector, as described above. The surgical staple cartridge 12034 could be made of a nonconductive material (such as plastic) and the sensor may be connected to or disposed in the surgical staple cartridge 12034, as was also described above.

As can be seen in FIGS. 105-112, the surgical end effector 12012 is attached to the tool mounting portion 11300 by an elongated shaft assembly 12008 according to various embodiments. As shown in the illustrated embodiment, the shaft assembly 12008 includes an articulation joint generally indicated as 12011 that enables the surgical end effector 12012 to be selectively articulated about an articulation axis AA-AA that is substantially transverse to a longitudinal tool axis LT-LT. See FIG. 106. In other embodiments, the articulation joint is omitted. In various embodiments, the shaft assembly 12008 may include a closure tube assembly 12009 that comprises a proximal closure tube 12040 and a distal closure tube 12042 that are pivotably linked by a pivot links 12044 and operably supported on a spine assembly generally depicted as 12049. In the illustrated embodiment, the spine assembly 12049 comprises a distal spine portion 12050 that is attached to the elongated channel 12022 and is pivotally coupled to the proximal spine portion 12052. The closure tube assembly 12009 is configured to axially slide on the spine assembly 12049 in response to actuation motions applied thereto. The distal closure tube 12042 includes an opening 12045 into which the tab 12027 on the anvil 12024 is inserted in order to facilitate opening of the anvil 12024 as the distal closure tube 12042 is moved axially in the proximal direction "PD". The closure tubes 12040, 12042 may be made of electrically conductive material (such as metal) so that they may serve as part of the antenna, as described above. Components of the main drive shaft assembly (e.g., the drive shafts 12048, 12050) may be made of a nonconductive material (such as plastic).

Figure 108:
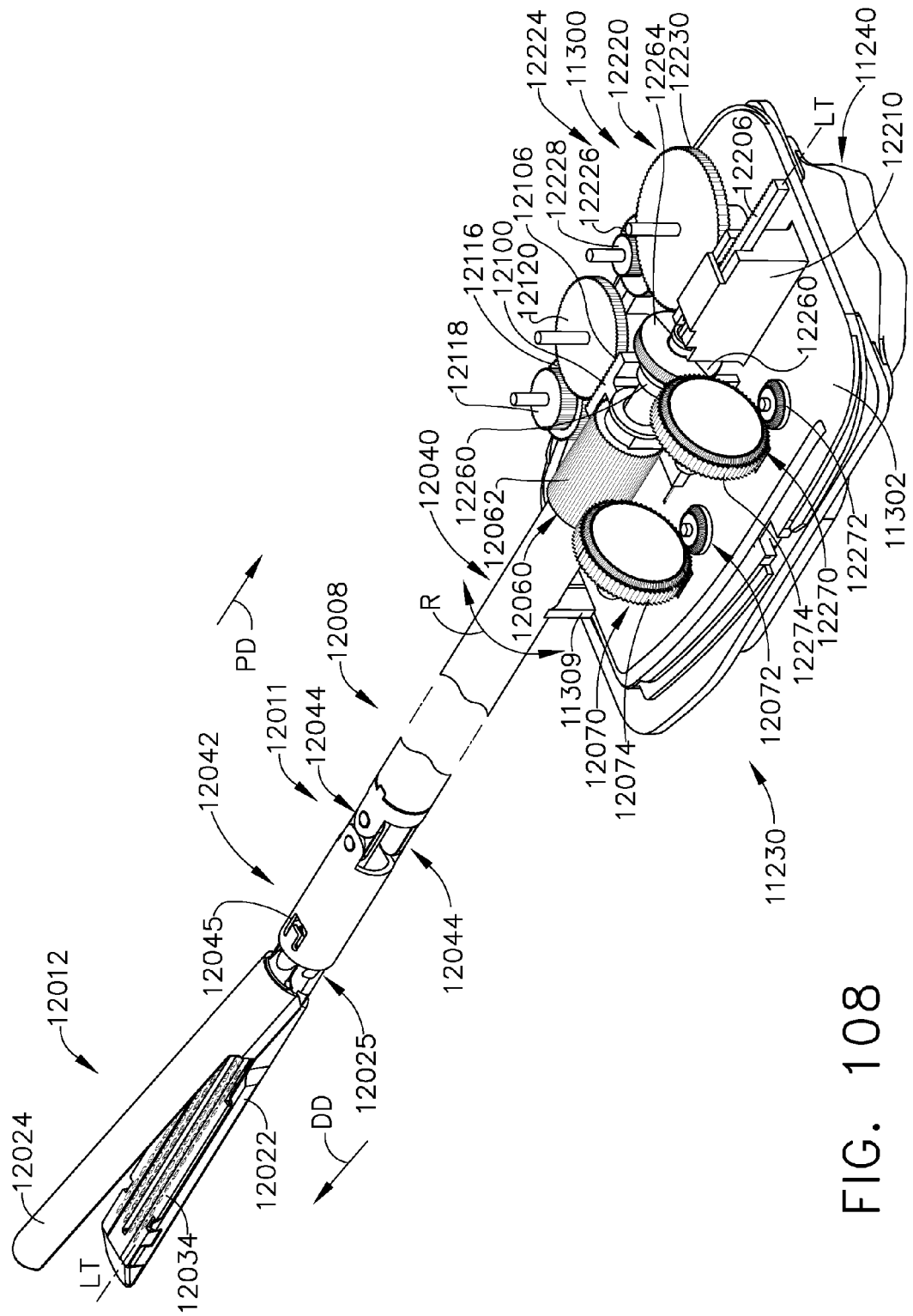
FIG. 108 is a rear perspective view of the surgical tool embodiment of FIG. 105 with the tool mounting housing removed.

In use, it may be desirable to rotate the surgical end effector 12012 about the longitudinal tool axis LT-LT. In at least one embodiment, the tool mounting portion 11300 includes a rotational transmission assembly 12069 that is configured to receive a corresponding rotary output motion from the tool drive assembly 11010 of the robotic system 11000 and convert that rotary output motion to a rotary control motion for rotating the elongated shaft assembly 12008 (and surgical end effector 12012) about the longitudinal tool axis LT-LT. In various embodiments, for example, the proximal end 12060 of the proximal closure tube 12040 is rotatably supported on the tool mounting plate 11302 of the tool mounting portion 11300 by a forward support cradle 11309 and a closure sled 12100 that is also movably supported on the tool mounting plate 11302. In at least one form, the rotational transmission assembly 12069 includes a tube gear segment 12062 that is formed on (or attached to) the proximal end 12060 of the proximal closure tube 12040 for operable engagement by a rotational gear assembly 12070 that is operably supported on the tool mounting plate 11302. As can be seen in FIG. 108, the rotational gear assembly 12070, in at least one embodiment, comprises a rotation drive gear 12072 that is coupled to a corresponding first one of the driven discs or elements 11304 on the adapter side 11307 of the tool mounting plate 11302 when the tool mounting portion 11300 is coupled to the tool drive assembly 11010. See FIG. 105. The rotational gear assembly 12070 further comprises a rotary driven gear 12074 that is rotatably supported on the tool mounting plate 11302 in meshing engagement with the tube gear segment 12062 and the rotation drive gear 12072. Application of a first rotary output motion from the tool drive assembly 11010 of the robotic system 11000 to the corresponding driven element 11304 will thereby cause rotation of the rotation drive gear 12072. Rotation of the rotation drive gear 12072 ultimately results in the rotation of the elongated shaft assembly 12008 (and the surgical end effector 12012) about the longitudinal tool axis LT-LT (represented by arrow "R" in FIG. 108). It will be appreciated that the application of a rotary output motion from the tool drive assembly 11010 in one direction will result in the rotation of the elongated shaft assembly 12008 and surgical end effector 12012 about the longitudinal tool axis LT-LT in a first direction and an application of the rotary output motion in an opposite direction will result in the rotation of the elongated shaft assembly 12008 and surgical end effector 12012 in a second direction that is opposite to the first direction.

Figure 113:
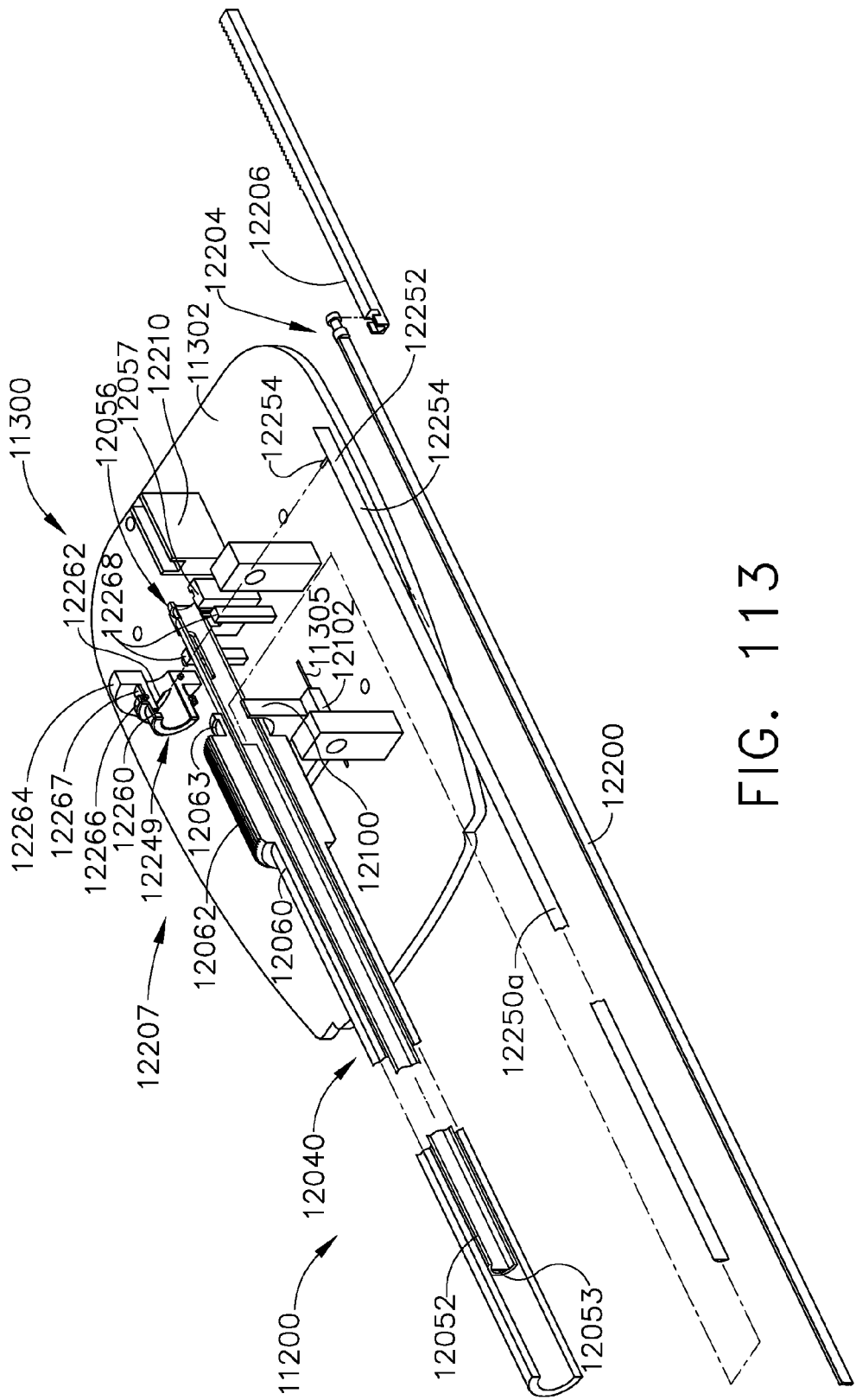
FIG. 113 is an exploded perspective view of a portion of the tool mounting portion of the surgical tool embodiment depicted in FIG. 105.

In at least one embodiment, the closure of the anvil 12024 relative to the staple cartridge 12034 is accomplished by axially moving the closure tube assembly 12009 in the distal direction "DD" on the spine assembly 12049. As indicated above, in various embodiments, the proximal end 12060 of the proximal closure tube 12040 is supported by the closure sled 12100 which comprises a portion of a closure transmission, generally depicted as 12099. In at least one form, the closure sled 12100 is configured to support the closure tube 12009 on the tool mounting plate 11320 such that the proximal closure tube 12040 can rotate relative to the closure sled 12100, yet travel axially with the closure sled 12100. In particular, as can be seen in FIG. 113, the closure sled 12100 has an upstanding tab 12101 that extends into a radial groove 12063 in the proximal end portion of the proximal closure tube 12040. In addition, as can be seen in FIGS. 110 and 113, the closure sled 12100 has a tab portion 12102 that extends through a slot 11305 in the tool mounting plate 11302. The tab portion 12102 is configured to retain the closure sled 12100 in sliding engagement with the tool mounting plate 11302. In various embodiments, the closure sled 12100 has an upstanding portion 12104 that has a closure rack gear 12106 formed thereon. The closure rack gear 12106 is configured for driving engagement with a closure gear assembly 12110. See FIG. 110.

In various forms, the closure gear assembly 12110 includes a closure spur gear 12112 that is coupled to a corresponding second one of the driven discs or elements 11304 on the adapter side 11307 of the tool mounting plate 11302. See FIG.

105. Thus, application of a second rotary output motion from the tool drive assembly 11010 of the robotic system 11000 to the corresponding second driven element 11304 will cause rotation of the closure spur gear 12112 when the tool mounting portion 11300 is coupled to the tool drive assembly 11010. The closure gear assembly 12110 further includes a closure reduction gear set 12114 that is supported in meshing engagement with the closure spur gear 12112. As can be seen in FIGS. 109 and 110, the closure reduction gear set 12114 includes a driven gear 12116 that is rotatably supported in meshing engagement with the closure spur gear 12112. The closure reduction gear set 12114 further includes a first closure drive gear 12118 that is in meshing engagement with a second closure drive gear 12120 that is rotatably supported on the tool mounting plate 11302 in meshing engagement with the closure rack gear 12106. Thus, application of a second rotary output motion from the tool drive assembly 11010 of the robotic system 11000 to the corresponding second driven element 11304 will cause rotation of the closure spur gear 12112 and the closure transmission 12110 and ultimately drive the closure sled 12100 and closure tube assembly 12009 axially. The axial direction in which the closure tube assembly 12009 moves ultimately depends upon the direction in which the second driven element 11304 is rotated. For example, in response to one rotary output motion received from the tool drive assembly 11010 of the robotic system 11000, the closure sled 12100 will be driven in the distal direction "DD" and ultimately drive the closure tube assembly 11009 in the distal direction. As the distal closure tube 12042 is driven distally, the end of the closure tube segment 12042 will engage a portion of the anvil 12024 and cause the anvil 12024 to pivot to a closed position. Upon application of an "opening" out put motion from the tool drive assembly 11010 of the robotic system 11000, the closure sled 12100 and shaft assembly 12008 will be driven in the proximal direction "PD". As the distal closure tube 12042 is driven in the proximal direction, the opening 12045 therein interacts with the tab 12027 on the anvil 12024 to facilitate the opening thereof. In various embodiments, a spring (not shown) may be employed to bias the anvil to the open position when the distal closure tube 12042 has been moved to its starting position. In various embodiments, the various gears of the closure gear assembly 12110 are sized to generate the necessary closure forces needed to satisfactorily close the anvil 12024 onto the tissue to be cut and stapled by the surgical end effector 12012. For example, the gears of the closure transmission 12110 may be sized to generate approximately 70-120 pounds.

Figure 114:
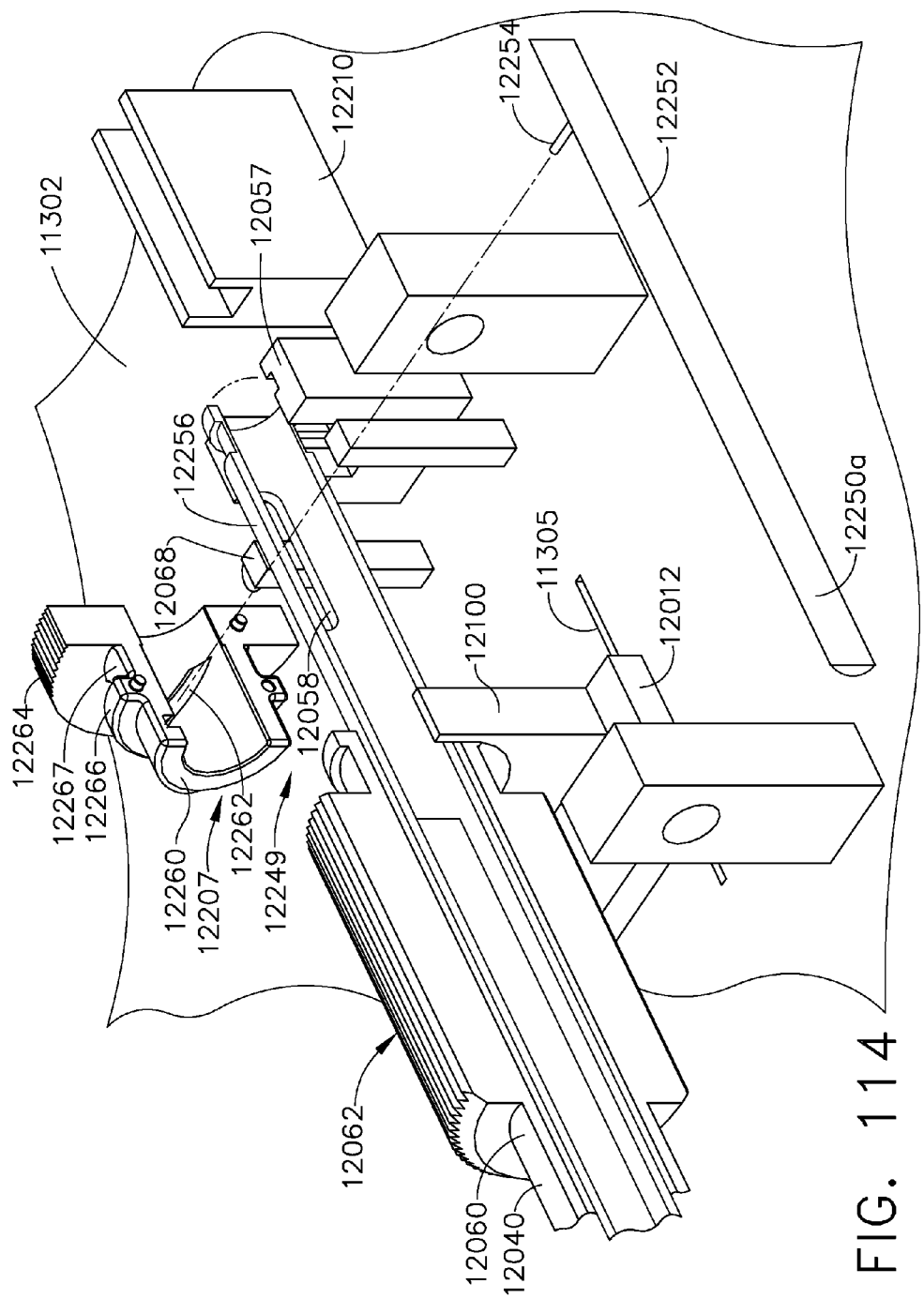
FIG. 114 is an enlarged exploded perspective view of a portion of the tool mounting portion of FIG. 113.
Figure 115:
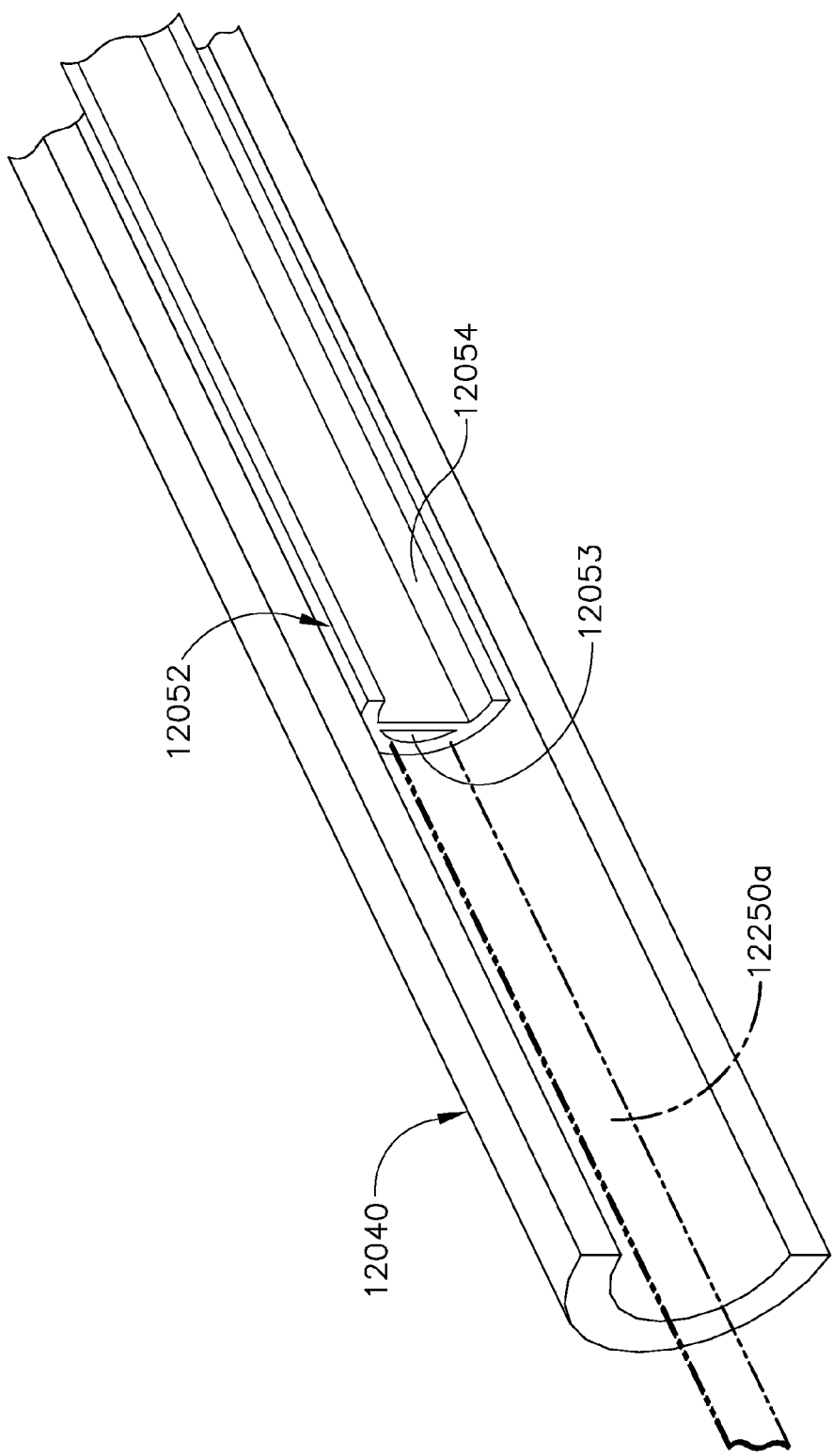
FIG. 115 is a partial cross-sectional view of a portion of the elongated shaft assembly of the surgical tool of FIG. 105.
Figure 116:
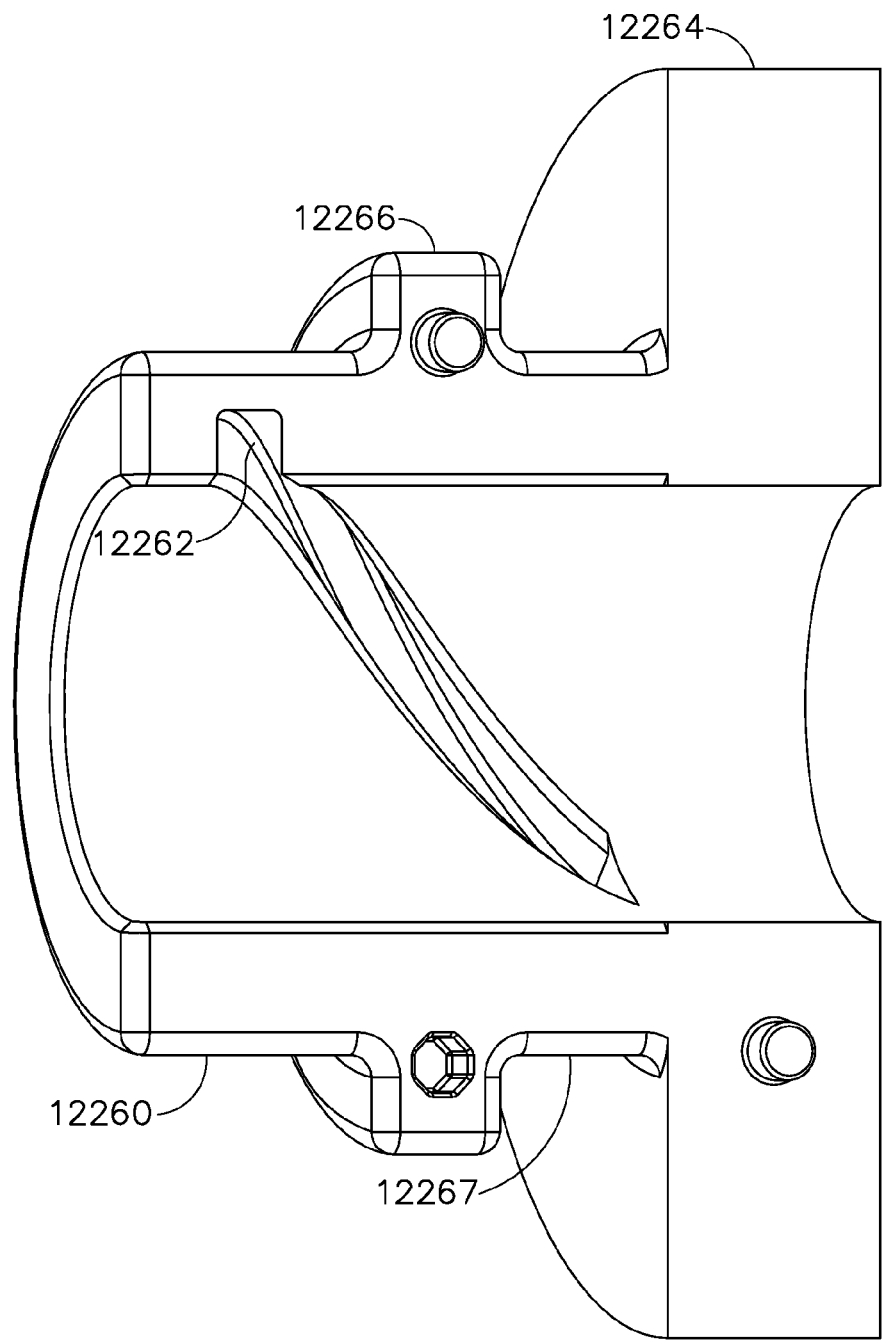
FIG. 116 is a side view of a half portion of a closure nut embodiment of a surgical tool embodiment of the present invention.
Figure 117:
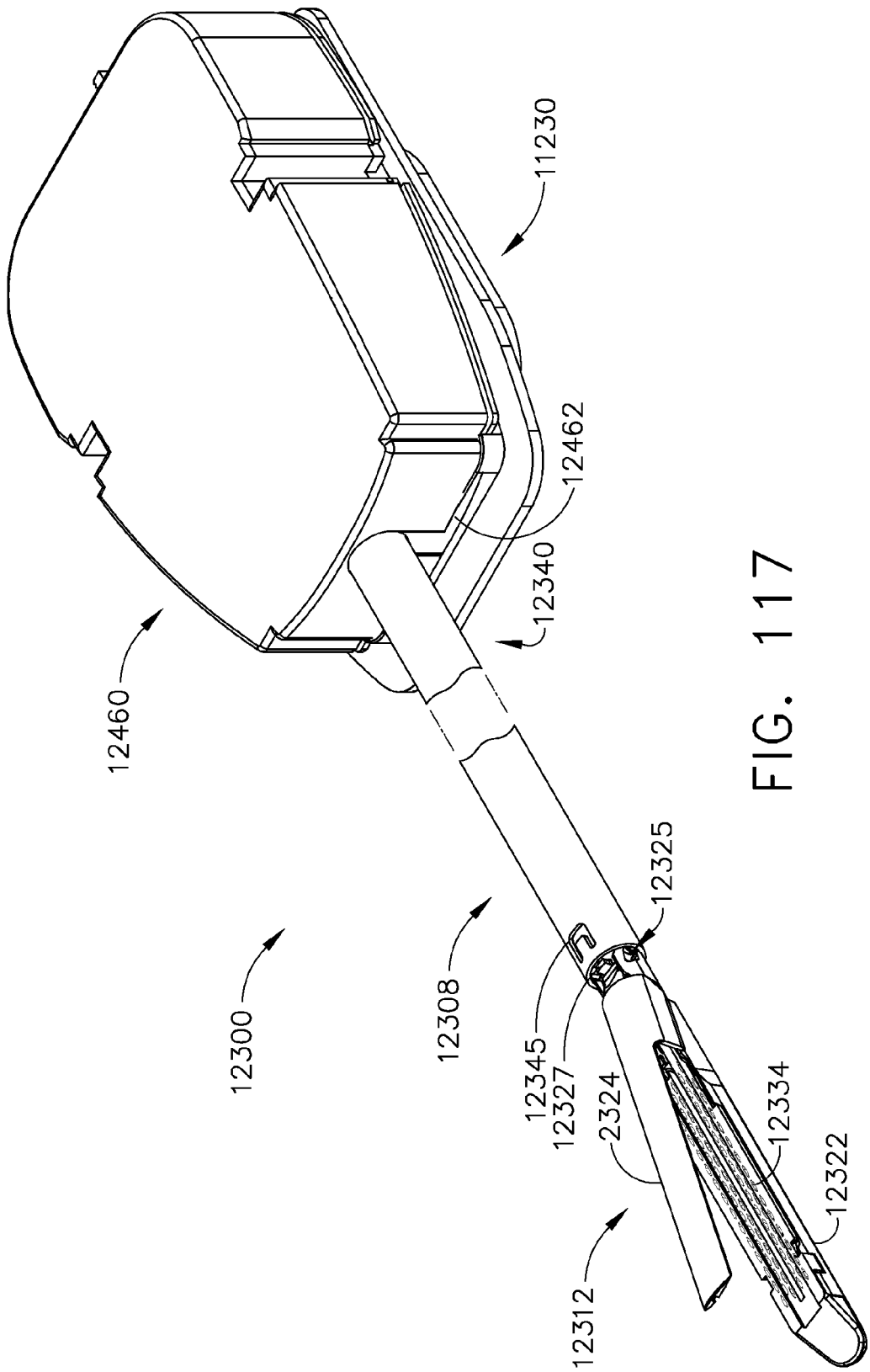
FIG. 117 is a perspective view of another surgical tool embodiment of the present invention.

In various embodiments, the cutting instrument 12032 is driven through the surgical end effector 12012 by a knife bar 12200. See FIGS. 111 and 113. In at least one form, the knife bar 12200 may be fabricated from, for example, stainless steel or other similar material and has a substantially rectangular cross-sectional shape. Such knife bar configuration is sufficiently rigid to push the cutting instrument 12032 through tissue clamped in the surgical end effector 12012, while still being flexible enough to enable the surgical end effector 12012 to articulate relative to the proximal closure tube 12040 and the proximal spine portion 12052 about the articulation axis AA-AA as will be discussed in further detail below. As can be seen in FIGS. 114 and 115, the proximal spine portion 12052 has a rectangular-shaped passage 12054 extending therethrough to provide support to the knife bar 12200 as it is axially pushed therethrough. The proximal spine portion 12052 has a proximal end 12056 that is rotatably mounted to a spine mounting bracket 12057 attached to the tool mounting plate 11032. See FIG. 113. Such arrangement permits the proximal spine portion 12052 to rotate, but not move axially, within the proximal closure tube 12040.

As shown in FIG. 111, the distal end 12202 of the knife bar 12200 is attached to the cutting instrument 12032. The proximal end 12204 of the knife bar 12200 is rotatably affixed to a knife rack gear 12206 such that the knife bar 12200 is free to rotate relative to the knife rack gear 12206. See FIG. 113. As can be seen in FIGS. 107-112, the knife rack gear 12206 is slidably supported within a rack housing 12210 that is attached to the tool mounting plate 11302 such that the knife rack gear 12206 is retained in meshing engagement with a knife gear assembly 12220. More specifically and with reference to FIG. 110, in at least one embodiment, the knife gear assembly 12220 includes a knife spur gear 12222 that is coupled to a corresponding third one of the driven discs or elements 11304 on the adapter side 11307 of the tool mounting plate 11302. See FIG. 105. Thus, application of another rotary output motion from the robotic system 11000 through the tool drive assembly 11010 to the corresponding third driven element 11304 will cause rotation of the knife spur gear 12222. The knife gear assembly 12220 further includes a knife gear reduction set 12224 that includes a first knife driven gear 12226 and a second knife drive gear 12228. The knife gear reduction set 12224 is rotatably mounted to the tool mounting plate 11302 such that the firs knife driven gear 12226 is in meshing engagement with the knife spur gear 12222. Likewise, the second knife drive gear 12228 is in meshing engagement with a third knife drive gear 12230 that is rotatably supported on the tool mounting plate 11302 in meshing engagement with the knife rack gear 12206. In various embodiments, the gears of the knife gear assembly 12220 are sized to generate the forces needed to drive the cutting element 12032 through the tissue clamped in the surgical end effector 12012 and actuate the staples therein. For example, the gears of the knife drive assembly 12230 may be sized to generate approximately 40 to 100 pounds. It will be appreciated that the application of a rotary output motion from the tool drive assembly 11010 in one direction will result in the axial movement of the cutting instrument 12032 in a distal direction and application of the rotary output motion in an opposite direction will result in the axial travel of the cutting instrument 12032 in a proximal direction.

In various embodiments, the surgical tool 11200 employs and articulation system 12007 that includes an articulation joint 12011 that enables the surgical end effector 12012 to be articulated about an articulation axis AA-AA that is substantially transverse to the longitudinal tool axis LT-LT. In at least one embodiment, the surgical tool 11200 includes first and second articulation bars 12250a, 12250b that are slidably supported within corresponding passages 12053 provided through the proximal spine portion 12052. See FIGS. 113 and 115. In at least one form, the first and second articulation bars 12250a, 12250b are actuated by an articulation transmission generally designated as 12249 that is operably supported on the tool mounting plate 11032. Each of the articulation bars 12250a, 12250b has a proximal end 12252 that has a guide rod protruding therefrom which extend laterally through a corresponding slot in the proximal end portion of the proximal spine portion 12052 and into a corresponding arcuate slot in an articulation nut 12260 which comprises a portion of the articulation transmission. FIG. 114 illustrates articulation bar 12250a. It will be understood that articulation bar 12250b is similarly constructed. As can be seen in FIG. 114, for example, the articulation bar 12250a has a guide rod 12254 which extends laterally through a corresponding slot 12058 in the proximal end portion 12056 of the distal spine portion 12050 and into a corresponding arcuate slot 12262 in the articulation nut 12260. In addition, the articulation bar 12250a has a distal end 12251a that is pivotally coupled to the distal spine portion 12050 by, for example, a pin 12253a and articulation bar 12250b has a distal end 12251b that is pivotally coupled to the distal spine portion 12050 by, for example, a pin 12253b. In particular, the articulation bar 12250a is laterally offset in a first lateral direction from the longitudinal tool axis LT-LT and the articulation bar 12250b is laterally offset in a second lateral direction from the longitudinal tool axis LT-LT. Thus, axial movement of the articulation bars 12250a and 12250b in opposing directions will result in the articulation of the distal spine portion 12050 as well as the surgical end effector 12012 attached thereto about the articulation axis AA-AA as will be discussed in further detail below.

Articulation of the surgical end effector 12012 is controlled by rotating the articulation nut 12260 about the longitudinal tool axis LT-LT. The articulation nut 12260 is rotatably journaled on the proximal end portion 12056 of the distal spine portion 12050 and is rotatably driven thereon by an articulation gear assembly 12270. More specifically and with reference to FIG. 108, in at least one embodiment, the articulation gear assembly 12270 includes an articulation spur gear 12272 that is coupled to a corresponding fourth one of the driven discs or elements 11304 on the adapter side 11307 of the tool mounting plate 11302. See FIG. 105. Thus, application of another rotary input motion from the robotic system 11000 through the tool drive assembly 11010 to the corresponding fourth driven element 11304 will cause rotation of the articulation spur gear 12272 when the interface 11230 is coupled to the tool holder 11270. An articulation drive gear 12274 is rotatably supported on the tool mounting plate 11302 in meshing engagement with the articulation spur gear 12272 and a gear portion 12264 of the articulation nut 12260 as shown. As can be seen in FIGS. 113 and 114, the articulation nut 12260 has a shoulder 12266 formed thereon that defines an annular groove 12267 for receiving retaining posts 12268 therein. Retaining posts 12268 are attached to the tool mounting plate 11302 and serve to prevent the articulation nut 12260 from moving axially on the proximal spine portion 12052 while maintaining the ability to be rotated relative thereto. Thus, rotation of the articulation nut 12260 in a first direction, will result in the axial movement of the articulation bar 12250a in a distal direction "DD" and the axial movement of the articulation bar 12250b in a proximal direction "PD" because of the interaction of the guide rods 12254 with the spiral slots 12262 in the articulation gear 12260. Similarly, rotation of the articulation nut 12260 in a second direction that is opposite to the first direction will result in the axial movement of the articulation bar 12250a in the proximal direction "PD" as well as cause articulation bar 12250b to axially move in the distal direction "DD". Thus, the surgical end effector 12012 may be selectively articulated about articulation axis "AA-AA" in a first direction "FD" by simultaneously moving the articulation bar 12250a in the distal direction "DD" and the articulation bar 12250b in the proximal direction "PD". Likewise, the surgical end effector 12012 may be selectively articulated about the articulation axis "AA-AA" in a second direction "SD" by simultaneously moving the articulation bar 12250a in the proximal direction "PD" and the articulation bar 12250b in the distal direction "DD." See FIG. 106.

The tool embodiment described above employs an interface arrangement that is particularly well-suited for mounting the robotically controllable medical tool onto at least one form of robotic arm arrangement that generates at least four different rotary control motions. Those of ordinary skill in the art will appreciate that such rotary output motions may be selectively controlled through the programmable control systems employed by the robotic system/controller. For example, the tool arrangement described above may be well-suited for use with those robotic systems manufactured by Intuitive Surgical, Inc. of Sunnyvale, Calif., U.S.A., many of which may be described in detail in various patents incorporated herein by reference. The unique and novel aspects of various embodiments of the present invention serve to utilize the rotary output motions supplied by the robotic system to generate specific control motions having sufficient magnitudes that enable end effectors to cut and staple tissue. Thus, the unique arrangements and principles of various embodiments of the present invention may enable a variety of different forms of the tool systems disclosed and claimed herein to be effectively employed in connection with other types and forms of robotic systems that supply programmed rotary or other output motions. In addition, as will become further apparent as the present Detailed Description proceeds, various end effector embodiments of the present invention that require other forms of actuation motions may also be effectively actuated utilizing one or more of the control motions generated by the robotic system.

FIGS. 117-121 illustrate yet another surgical tool 12300 that may be effectively employed in connection with the robotic system 11000 that has a tool drive assembly that is operably coupled to a controller of the robotic system that is operable by inputs from an operator and which is configured to provide at least one rotary output motion to at least one rotatable body portion supported on the tool drive assembly. In various forms, the surgical tool 12300 includes a surgical end effector 12312 that includes an elongated channel 12322 and a pivotally translatable clamping member, such as an anvil 12324, which are maintained at a spacing that assures effective stapling and severing of tissue clamped in the surgical end effector 12312. As shown in the illustrated embodiment, the surgical end effector 12312 may include, in addition to the previously-mentioned elongated channel 12322 and anvil 12324, a cutting instrument 12332 that has a sled portion 12333 formed thereon, a surgical staple cartridge 12334 that is seated in the elongated channel 12322, and a rotary end effector drive shaft 12336 that has a helical screw thread formed thereon. The cutting instrument 12332 may be, for example, a knife. As will be discussed in further detail below, rotation of the end effector drive shaft 12336 will cause the cutting instrument 12332 and sled portion 12333 to axially travel through the surgical staple cartridge 12334 to move between a starting position and an ending position. The direction of axial travel of the cutting instrument 12332 depends upon the direction in which the end effector drive shaft 12336 is rotated. The anvil 12324 may be pivotably opened and closed at a pivot point 12325 connected to the proximate end of the elongated channel 12322. The anvil 12324 may also include a tab 12327 at its proximate end that operably interfaces with a component of the mechanical closure system (described further below) to open and close the anvil 12324. When the end effector drive shaft 12336 is rotated, the cutting instrument 12332 and sled 12333 will travel longitudinally through the surgical staple cartridge 12334 from the starting position to the ending position, thereby cutting tissue clamped within the surgical end effector 12312. The movement of the sled 12333 through the surgical staple cartridge 12334 causes the staples therein to be driven through the severed tissue and against the closed anvil 12324, which turns the staples to fasten the severed tissue. In one form, the elongated channel 12322 and the anvil 12324 may be made of an electrically conductive material (such as metal) so that they may serve as part of the antenna that communicates with sensor(s) in the end effector, as described above. The surgical staple cartridge 12334 could be made of a nonconductive material (such as plastic) and the sensor may be connected to or disposed in the surgical staple cartridge 12334, as described above.

It should be noted that although the embodiments of the surgical tool 12300 described herein employ a surgical end effector 12312 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811, now U.S. Pat. No. 7,673,783, to Morgan et al. and U.S. patent application Ser. No. 11/267,383, now U.S. Pat. No. 7,607,557, to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

In the illustrated embodiment, the surgical end effector 12312 is coupled to an elongated shaft assembly 12308 that is coupled to a tool mounting portion 12460 and defines a longitudinal tool axis LT-LT. In this embodiment, the elongated shaft assembly 12308 does not include an articulation joint. Those of ordinary skill in the art will understand that other embodiments may have an articulation joint therein. In at least one embodiment, the elongated shaft assembly 12308 comprises a hollow outer tube 12340 that is rotatably supported on a tool mounting plate 12462 of a tool mounting portion 12460 as will be discussed in further detail below. In various embodiments, the elongated shaft assembly 12308 further includes a distal spine shaft 12350. Distal spine shaft 12350 has a distal end portion 12354 that is coupled to, or otherwise integrally formed with, a distal stationary base portion 12360 that is non-movably coupled to the channel 12322. See FIGS. 118-120.

As shown in FIG. 115, the distal spine shaft 12350 has a proximal end portion 12351 that is slidably received within a slot 12355 in a proximal spine shaft 12353 that is non-movably supported within the hollow outer tube 12340 by at least one support collar 12357. As can be further seen in FIGS. 118 and 119, the surgical tool 12300 includes a closure tube 12370 that is constrained to only move axially relative to the distal stationary base portion 12360. The closure tube 12370 has a proximal end 12372 that has an internal thread 12374 formed therein that is in threaded engagement with a transmission arrangement, generally depicted as 12375 that is operably supported on the tool mounting plate 12462. In various forms, the transmission arrangement 12375 includes a rotary drive shaft assembly, generally designated as 12381. When rotated, the rotary drive shaft assembly 12381 will cause the closure tube 12370 to move axially as will be describe in further detail below. In at least one form, the rotary drive shaft assembly 12381 includes a closure drive nut 12382 of a closure clutch assembly generally designated as 12380. More specifically, the closure drive nut 12382 has a proximal end portion 12384 that is rotatably supported relative to the outer tube 12340 and is in threaded engagement with the closure tube 12370. For assembly purposes, the proximal end portion 12384 may be threadably attached to a retention ring 12386. Retention ring 12386, in cooperation with an end 12387 of the closure drive nut 12382, defines an annular slot 12388 into which a shoulder 12392 of a locking collar 12390 extends. The locking collar 12390 is non-movably attached (e.g., welded, glued, etc.) to the end of the outer tube 12340. Such arrangement serves to affix the closure drive nut 12382 to the outer tube 12340 while enabling the closure drive nut 12382 to rotate relative to the outer tube 12340. The closure drive nut 12382 further has a distal end 12383 that has a threaded portion 12385 that threadably engages the internal thread 12374 of the closure tube 12370. Thus, rotation of the closure drive nut 12382 will cause the closure tube 12370 to move axially as represented by arrow "D" in FIG. 119.

Figure 118:
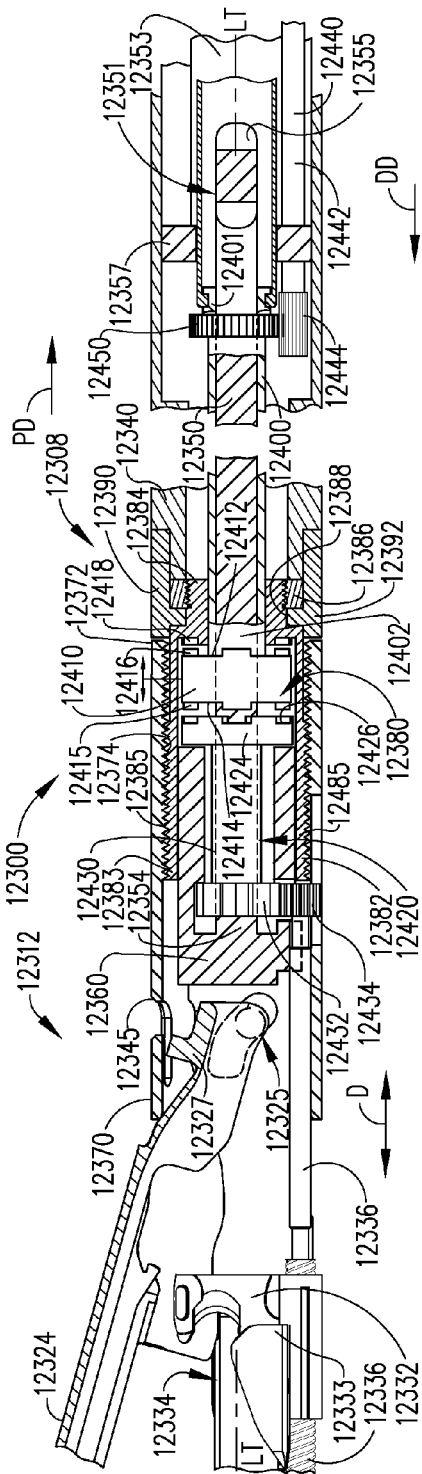
FIG. 118 is a cross-sectional side view of a portion of the surgical end effector and elongated shaft assembly of the surgical tool embodiment of FIG. 117 with the anvil in the open position and the closure clutch assembly in a neutral position.
Figure 119:
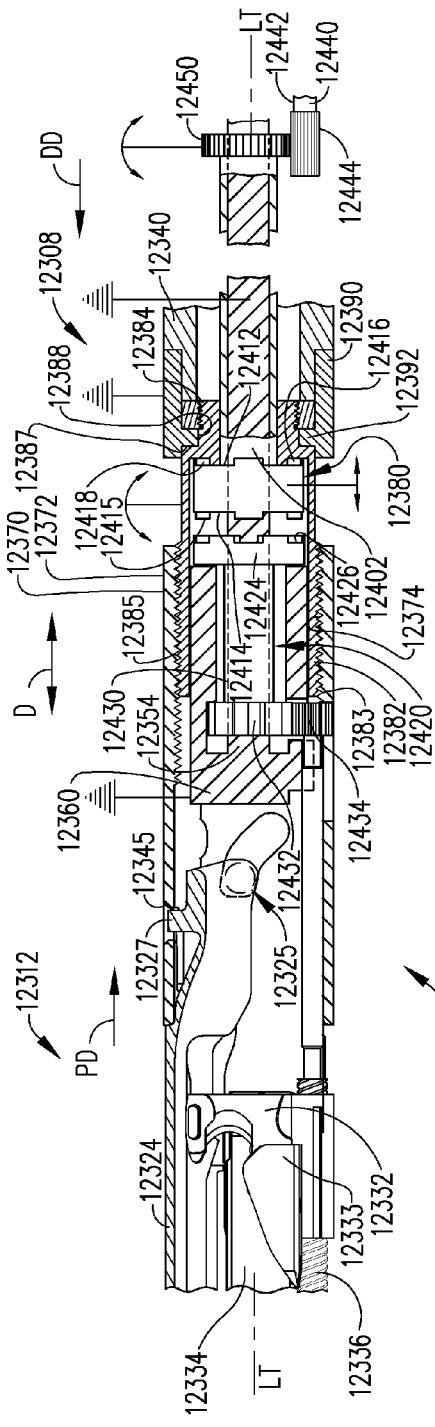
FIG. 119 is another cross-sectional side view of the surgical end effector and elongated shaft assembly shown in FIG. 118 with the clutch assembly engaged in a closure position.

Closure of the anvil 12324 and actuation of the cutting instrument 12332 are accomplished by control motions that are transmitted by a hollow drive sleeve 12400. As can be seen in FIGS. 118 and 119, the hollow drive sleeve 12400 is rotatably and slidably received on the distal spine shaft 12350. The drive sleeve 12400 has a proximal end portion 12401 that is rotatably mounted to the proximal spine shaft 12353 that protrudes from the tool mounting portion 12460 such that the drive sleeve 12400 may rotate relative thereto. See FIG. 118. As can also be seen in FIGS. 118-120, the drive sleeve 12400 is rotated about the longitudinal tool axis "LT-LT" by a drive shaft 12440. The drive shaft 12440 has a drive gear 12444 that is attached to its distal end 12442 and is in meshing engagement with a driven gear 12450 that is attached to the drive sleeve 12400.

The drive sleeve 12400 further has a distal end portion 12402 that is coupled to a closure clutch 12410 portion of the closure clutch assembly 12380 that has a proximal face 12412 and a distal face 12414. The proximal face 12412 has a series of proximal teeth 12416 formed thereon that are adapted for selective engagement with corresponding proximal teeth cavities 12418 formed in the proximal end portion 12384 of the closure drive nut 12382. Thus, when the proximal teeth 12416 are in meshing engagement with the proximal teeth cavities 12418 in the closure drive nut 12382, rotation of the drive sleeve 12400 will result in rotation of the closure drive nut 12382 and ultimately cause the closure tube 12370 to move axially as will be discussed in further detail below.

Figure 120:
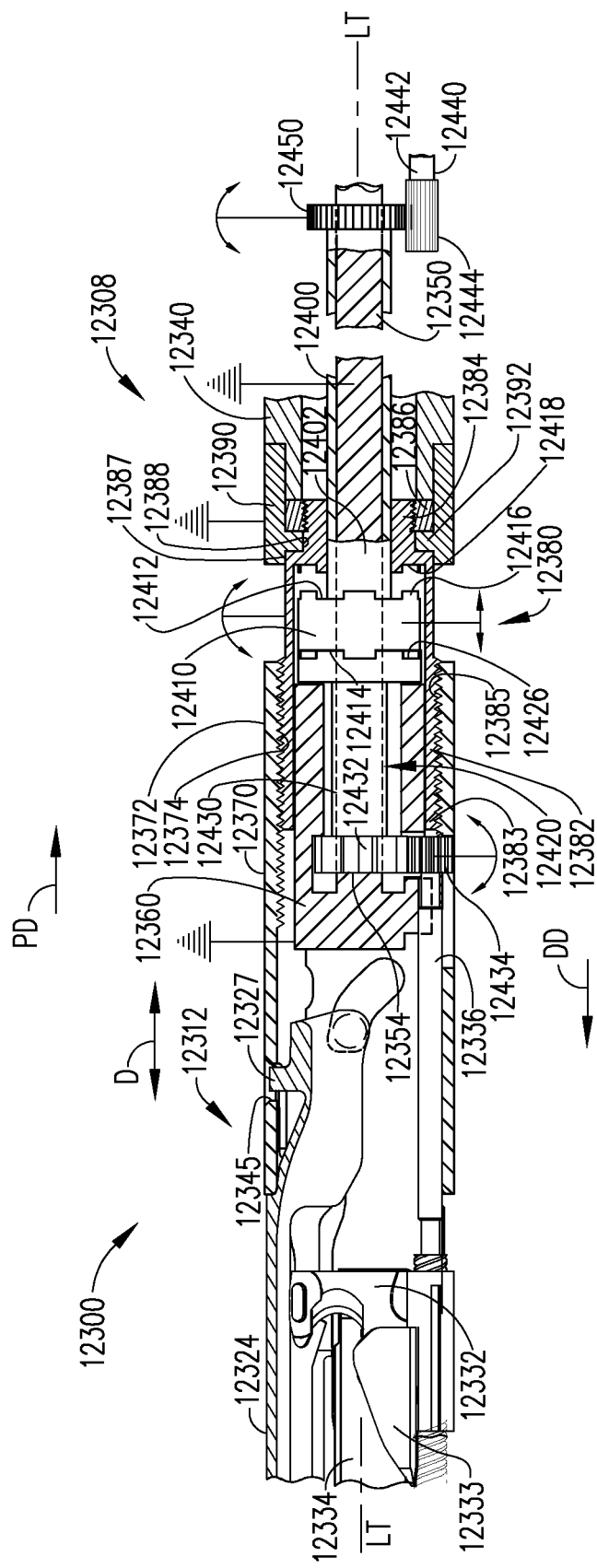
FIG. 120 is another cross-sectional side view of the surgical end effector and elongated shaft assembly shown in FIG. 118 with the clutch assembly engaged in a firing position.

As can be most particularly seen in FIGS. 118 and 119, the distal face 12414 of the drive clutch portion 12410 has a series of distal teeth 12415 formed thereon that are adapted for selective engagement with corresponding distal teeth cavities 12426 formed in a face plate portion 12424 of a knife drive shaft assembly 12420. In various embodiments, the knife drive shaft assembly 12420 comprises a hollow knife shaft segment 12430 that is rotatably received on a corresponding portion of the distal spine shaft 12350 that is attached to or protrudes from the stationary base 12360. When the distal teeth 12415 of the closure clutch portion 12410 are in meshing engagement with the distal teeth cavities 12426 in the face plate portion 12424, rotation of the drive sleeve 12400 will result in rotation of the drive shaft segment 12430 about the stationary shaft 12350. As can be seen in FIGS. 118-120, a knife drive gear 12432 is attached to the drive shaft segment 12430 and is meshing engagement with a drive knife gear 12434 that is attached to the end effector drive shaft 12336. Thus, rotation of the drive shaft segment 12430 will result in the rotation of the end effector drive shaft 12336 to drive the cutting instrument 12332 and sled 12333 distally through the surgical staple cartridge 12334 to cut and staple tissue clamped within the surgical end effector 12312. The sled 12333 may be made of, for example, plastic, and may have a sloped distal surface. As the sled 12333 traverses the elongated channel 12322, the sloped forward surface of the sled 12333 pushes up or "drive" the staples in the surgical staple cartridge 12334 through the clamped tissue and against the anvil 12324. The anvil 12324 turns or "forms" the staples, thereby stapling the severed tissue. As used herein, the term "fire" refers to the initiation of actions required to drive the cutting instrument and sled portion in a distal direction through the surgical staple cartridge to cut the tissue clamped in the surgical end effector and drive the staples through the severed tissue.

Figure 121:
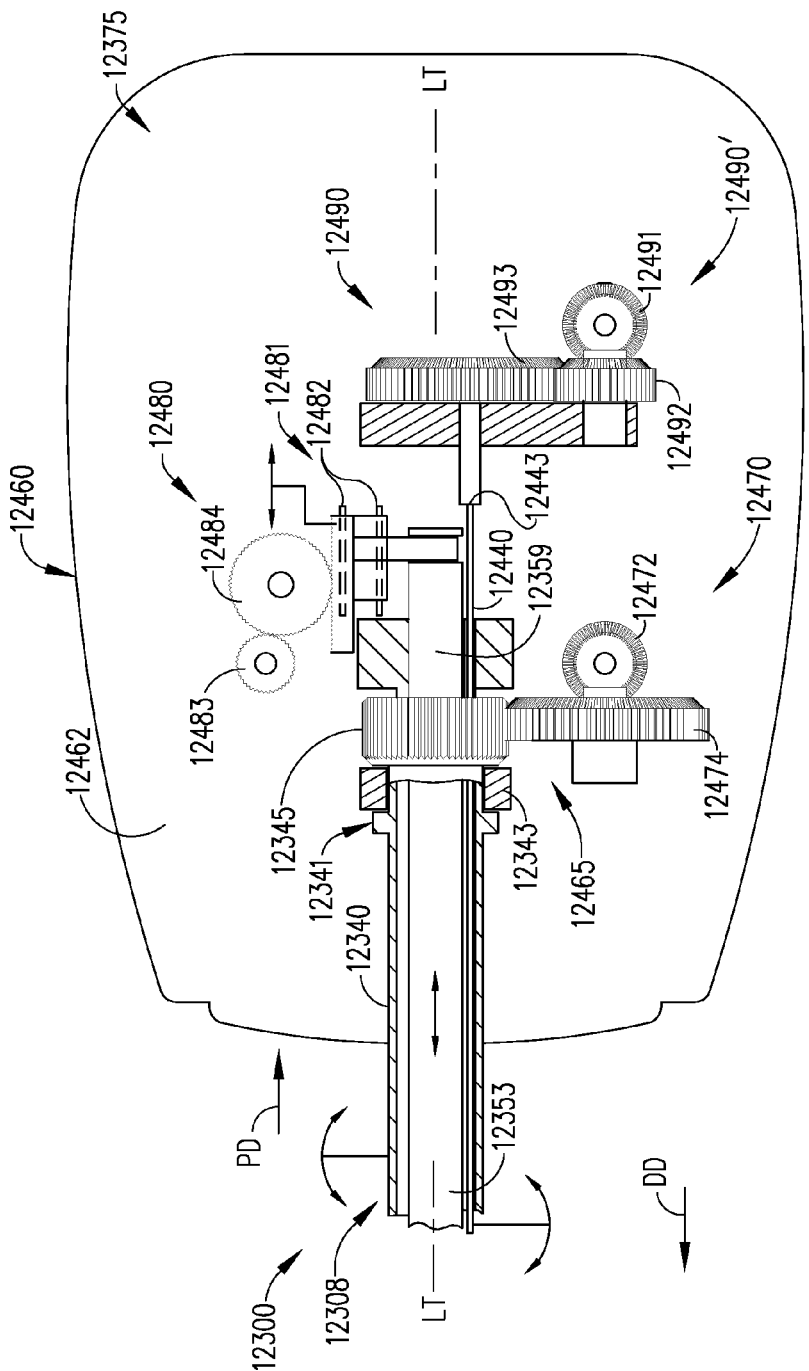
FIG. 121 is a top view of a portion of a tool mounting portion embodiment of the present invention.
Figure 122:
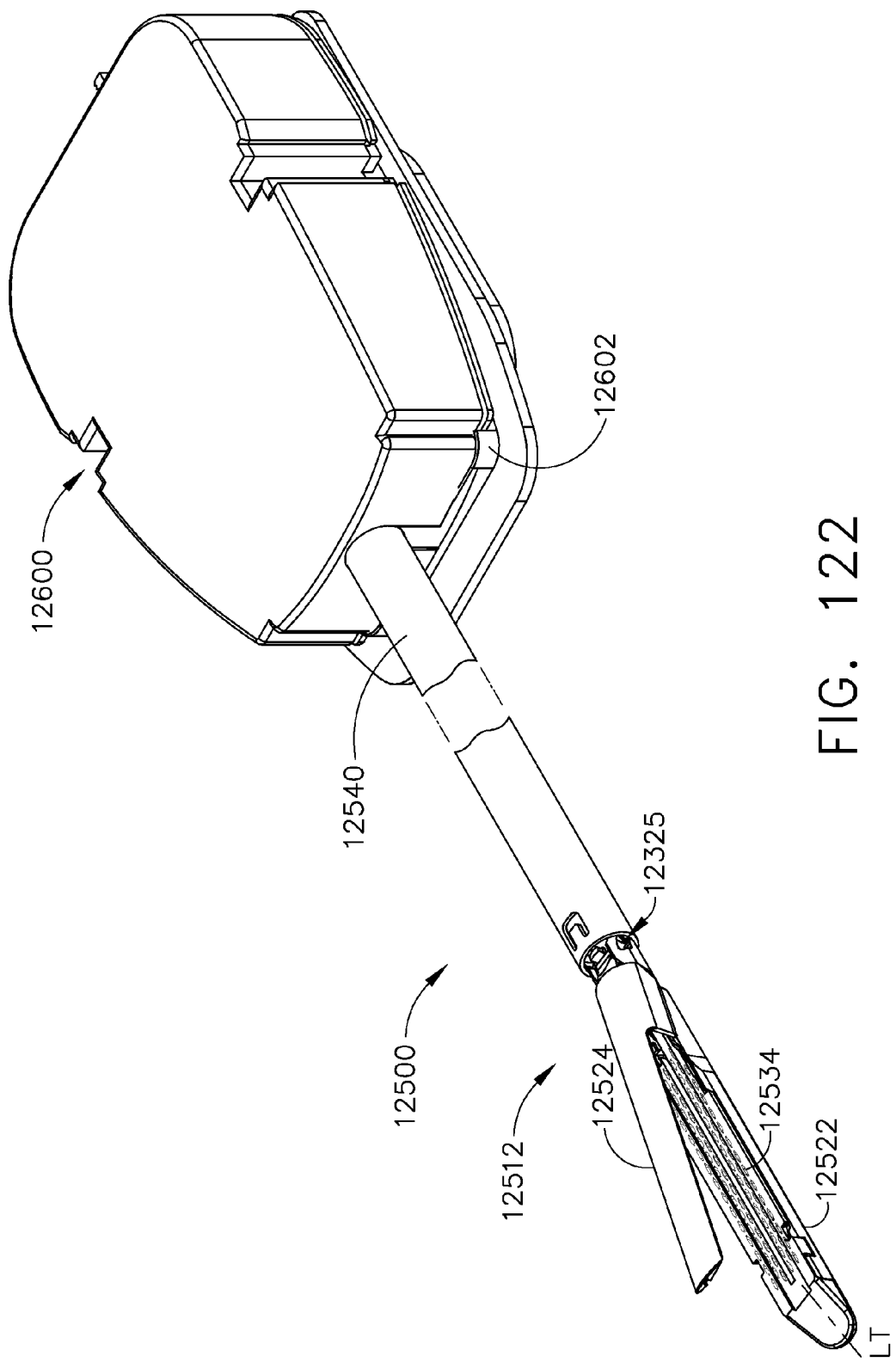
FIG. 122 is a perspective view of another surgical tool embodiment of the present invention.

In use, it may be desirable to rotate the surgical end effector 12312 about the longitudinal tool axis LT-LT. In at least one embodiment, the transmission arrangement 12375 includes a rotational transmission assembly 12465 that is configured to receive a corresponding rotary output motion from the tool drive assembly 11010 of the robotic system 11000 and convert that rotary output motion to a rotary control motion for rotating the elongated shaft assembly 12308 (and surgical end effector 12312) about the longitudinal tool axis LT-LT. As can be seen in FIG. 121, a proximal end 12341 of the outer tube 12340 is rotatably supported within a cradle arrangement 12343 attached to the tool mounting plate 12462 of the tool mounting portion 12460. A rotation gear 12345 is formed in or attached to the proximal end 12341 of the outer tube 12340 of the elongated shaft assembly 12308 for meshing engagement with a rotation gear assembly 12470 operably supported on the tool mounting plate 12462. In at least one embodiment, a rotation drive gear 12472 is coupled to a corresponding first one of the driven discs or elements 11304 on the adapter side of the tool mounting plate 12462 when the tool mounting portion 12460 is coupled to the tool drive assembly 11010. See FIGS. 105 and 121. The rotation drive assembly 12470 further comprises a rotary driven gear 12474 that is rotatably supported on the tool mounting plate 12462 in meshing engagement with the rotation gear 12345 and the rotation drive gear 12472. Application of a first rotary output motion from the robotic system 11000 through the tool drive assembly 11010 to the corresponding driven element 11304 will thereby cause rotation of the rotation drive gear 12472 by virtue of being operably coupled thereto. Rotation of the rotation drive gear 12472 ultimately results in the rotation of the elongated shaft assembly 12308 (and the end effector 12312) about the longitudinal tool axis LT-LT (primary rotary motion).

Closure of the anvil 12324 relative to the staple cartridge 12034 is accomplished by axially moving the closure tube 12370 in the distal direction "DD". Axial movement of the closure tube 12370 in the distal direction "DD" is accomplished by applying a rotary control motion to the closure drive nut 12382. To apply the rotary control motion to the closure drive nut 12382, the closure clutch 12410 must first be brought into meshing engagement with the proximal end portion 12384 of the closure drive nut 12382. In various embodiments, the transmission arrangement 12375 further includes a shifter drive assembly 12480 that is operably supported on the tool mounting plate 12462. More specifically and with reference to FIG. 121, it can be seen that a proximal end portion 12359 of the proximal spine portion 12353 extends through the rotation gear 12345 and is rotatably coupled to a shifter gear rack 12481 that is slidably affixed to the tool mounting plate 12462 through slots 12482. The shifter drive assembly 12480 further comprises a shifter drive gear 12483 that is coupled to a corresponding second one of the driven discs or elements 11304 on the adapter side of the tool mounting plate 12462 when the tool mounting portion 12460 is coupled to the tool holder 11270. See FIGS. 105 and 121. The shifter drive assembly 12480 further comprises a shifter driven gear 12478 that is rotatably supported on the tool mounting plate 12462 in meshing engagement with the shifter drive gear 12483 and the shifter rack gear 12482. Application of a second rotary output motion from the robotic system 11000 through the tool drive assembly 11010 to the corresponding driven element 11304 will thereby cause rotation of the shifter drive gear 12483 by virtue of being operably coupled thereto. Rotation of the shifter drive gear 12483 ultimately results in the axial movement of the shifter gear rack 12482 and the proximal spine portion 12353 as well as the drive sleeve 12400 and the closure clutch 12410 attached thereto. The direction of axial travel of the closure clutch 12410 depends upon the direction in which the shifter drive gear 12483 is rotated by the robotic system 11000. Thus, rotation of the shifter drive gear 12483 in a first rotary direction will result in the axial movement of the closure clutch 12410 in the proximal direction "PD" to bring the proximal teeth 12416 into meshing engagement with the proximal teeth cavities 12418 in the closure drive nut 12382. Conversely, rotation of the shifter drive gear 12483 in a second rotary direction (opposite to the first rotary direction) will result in the axial movement of the closure clutch 12410 in the distal direction "DD" to bring the distal teeth 12415 into meshing engagement with corresponding distal teeth cavities 12426 formed in the face plate portion 12424 of the knife drive shaft assembly 12420.

Once the closure clutch 12410 has been brought into meshing engagement with the closure drive nut 12382, the closure drive nut 12382 is rotated by rotating the closure clutch 12410. Rotation of the closure clutch 12410 is controlled by applying rotary output motions to a rotary drive transmission portion 12490 of transmission arrangement 12375 that is operably supported on the tool mounting plate 12462 as shown in FIG. 121. In at least one embodiment, the rotary drive transmission 12490 includes a rotary drive assembly 12490' that includes a gear 12491 that is coupled to a corresponding third one of the driven discs or elements 11304 on the adapter side of the tool mounting plate 12462 when the tool mounting portion 12460 is coupled to the tool holder 11270. See FIGS. 105 and 121. The rotary drive transmission 12490 further comprises a first rotary driven gear 12492 that is rotatably supported on the tool mounting plate 12462 in meshing engagement with a second rotary driven gear 12493 and the rotary drive gear 12491. The second rotary driven gear 12493 is coupled to a proximal end portion 12443 of the drive shaft 12440.

Rotation of the rotary drive gear 12491 in a first rotary direction will result in the rotation of the drive shaft 12440 in a first direction. Conversely, rotation of the rotary drive gear 12491 in a second rotary direction (opposite to the first rotary direction) will cause the drive shaft 12440 to rotate in a second direction. As indicated above, the drive shaft 12440 has a drive gear 12444 that is attached to its distal end 12442 and is in meshing engagement with a driven gear 12450 that is attached to the drive sleeve 12400. Thus, rotation of the drive shaft 12440 results in rotation of the drive sleeve 12400.

A method of operating the surgical tool 12300 will now be described. Once the tool mounting portion 12462 has been operably coupled to the tool holder 11270 of the robotic system 11000 and oriented into position adjacent the target tissue to be cut and stapled, if the anvil 12334 is not already in the open position (FIG. 118), the robotic system 11000 may apply the first rotary output motion to the shifter drive gear 12483 which results in the axial movement of the closure clutch 12410 into meshing engagement with the closure drive nut 12382 (if it is not already in meshing engagement therewith). See FIG. 119. Once the controller 11001 of the robotic system 11000 has confirmed that the closure clutch 12410 is meshing engagement with the closure drive nut 12382 (e.g., by means of sensor(s)) in the surgical end effector 12312 that are in communication with the robotic control system), the robotic controller 11001 may then apply a second rotary output motion to the rotary drive gear 12492 which, as was described above, ultimately results in the rotation of the rotary drive nut 12382 in the first direction which results in the axial travel of the closure tube 12370 in the distal direction "DD". As the closure tube 12370 moved in the distal direction, it contacts a portion of the anvil 12323 and causes the anvil 12324 to pivot to the closed position to clamp the target tissue between the anvil 12324 and the surgical staple cartridge 12334. Once the robotic controller 11001 determines that the anvil 12334 has been pivoted to the closed position by corresponding sensor(s) in the surgical end effector 12312 in communication therewith, the robotic system 11000 discontinues the application of the second rotary output motion to the rotary drive gear 12491. The robotic controller 11001 may also provide the surgeon with an indication that the anvil 12334 has been fully closed. The surgeon may then initiate the firing procedure. In alternative embodiments, the firing procedure may be automatically initiated by the robotic controller 11001. The robotic controller 11001 then applies the primary rotary control motion 12483 to the shifter drive gear 12483 which results in the axial movement of the closure clutch 12410 into meshing engagement with the face plate portion 12424 of the knife drive shaft assembly 12420. See FIG. 120. Once the controller 11001 of the robotic system 11000 has confirmed that the closure clutch 12410 is meshing engagement with the face plate portion 12424 (by means of sensor(s)) in the end effector 12312 that are in communication with the robotic controller 11001), the robotic controller 11001 may then apply the second rotary output motion to the rotary drive gear 12492 which, as was described above, ultimately results in the axial movement of the cutting instrument 12332 and sled portion 12333 in the distal direction "DD" through the surgical staple cartridge 12334. As the cutting instrument 12332 moves distally through the surgical staple cartridge 12334, the tissue clamped therein is severed. As the sled portion 12333 is driven distally, it causes the staples within the surgical staple cartridge to be driven through the severed tissue into forming contact with the anvil 12324. Once the robotic controller 11001 has determined that the cutting instrument 12324 has reached the end position within the surgical staple cartridge 12334 (by means of sensor(s)) in the end effector 12312 that are in communication with the robotic controller 11001), the robotic controller 11001 discontinues the application of the second rotary output motion to the rotary drive gear 12491. Thereafter, the robotic controller 11001 applies the secondary rotary output motion to the rotary drive gear 12491 which ultimately results in the axial travel of the cutting instrument 12332 and sled portion 12333 in the proximal direction "PD" to the starting position. Once the robotic controller 11001 has determined that the cutting instrument 12324 has reached the staring position by means of sensor(s) in the surgical end effector 12312 that are in communication with the robotic controller 11001, the robotic controller 11001 discontinues the application of the secondary rotary output motion to the rotary drive gear 12491. Thereafter, the robotic controller 11001 applies the primary rotary output motion to the shifter drive gear 12483 to cause the closure clutch 12410 to move into engagement with the rotary drive nut 12382. Once the closure clutch 12410 has been moved into meshing engagement with the rotary drive nut 12382, the robotic controller 11001 then applies the secondary output motion to the rotary drive gear 12491 which ultimately results in the rotation of the rotary drive nut 12382 in the second direction to cause the closure tube 12370 to move in the proximal direction "PD". As can be seen in FIGS. 118-120, the closure tube 12370 has an opening 12345 therein that engages the tab 12327 on the anvil 12324 to cause the anvil 12324 to pivot to the open position. In alternative embodiments, a spring may also be employed to pivot the anvil 12324 to the open position when the closure tube 12370 has been returned to the starting position (FIG. 118).

FIGS. 122-126 illustrate yet another surgical tool 12500 that may be effectively employed in connection with the robotic system 11000. In various forms, the surgical tool 12500 includes a surgical end effector 12512 that includes a "first portion" in the form of an elongated channel 12522 and a "second movable portion" in the form of a pivotally translatable clamping member, such as an anvil 12524, which are maintained at a spacing that assures effective stapling and severing of tissue clamped in the surgical end effector 12512. As shown in the illustrated embodiment, the surgical end effector 12512 may include, in addition to the previously-mentioned elongated channel 12522 and anvil 12524, a "third movable portion" in the form of a cutting instrument 12532, a sled (not shown), and a surgical staple cartridge 12534 that is removably seated in the elongated channel 12522. The cutting instrument 12532 may be, for example, a knife. The anvil 12524 may be pivotably opened and closed at a pivot point 12525 connected to the proximate end of the elongated channel 12522. The anvil 12524 may also include a tab 12527 at its proximate end that is configured to operably interface with a component of the mechanical closure system (described further below) to open and close the anvil 12524. When actuated, the knife 12532 and sled travel longitudinally along the elongated channel 12522, thereby cutting tissue clamped within the surgical end effector 12512. The movement of the sled along the elongated channel 12522 causes the staples of the surgical staple cartridge 12534 to be driven through the severed tissue and against the closed anvil 12524, which turns the staples to fasten the severed tissue. In one form, the elongated channel 12522 and the anvil 12524 may be made of an electrically conductive material (such as metal) so that they may serve as part of the antenna that communicates with sensor(s) in the surgical end effector, as described above. The surgical staple cartridge 12534 could be made of a nonconductive material (such as plastic) and the sensor may be connected to or disposed in the surgical staple cartridge 12534, as described above.

It should be noted that although the embodiments of the surgical tool 12500 described herein employ a surgical end effector 12512 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811, now U.S. Pat. No. 7,673,783, to Morgan et al. and U.S. patent application Ser. No. 11/267,383, now U.S. Pat. No. 7,607,557, to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

In the illustrated embodiment, the elongated channel 12522 of the surgical end effector 12512 is coupled to an elongated shaft assembly 12508 that is coupled to a tool mounting portion 12600. In at least one embodiment, the elongated shaft assembly 12508 comprises a hollow spine tube 12540 that is non-movably coupled to a tool mounting plate 12602 of the tool mounting portion 12600. As can be seen in FIGS. 123 and 124, the proximal end 12523 of the elongated channel 12522 comprises a hollow tubular structure configured to be attached to the distal end 12541 of the spine tube 12540. In one embodiment, for example, the proximal end 12523 of the elongated channel 12522 is welded or glued to the distal end of the spine tube 12540.

As can be further seen in FIGS. 123 and 124, in at least one non-limiting embodiment, the surgical tool 12500 further includes an axially movable actuation member in the form of a closure tube 12550 that is constrained to move axially relative to the elongated channel 12522 and the spine tube 12540. The closure tube 12550 has a proximal end 12552 that has an internal thread 12554 formed therein that is in threaded engagement with a rotatably movable portion in the form of a closure drive nut 12560. More specifically, the closure drive nut 12560 has a proximal end portion 12562 that is rotatably supported relative to the elongated channel 12522 and the spine tube 12540. For assembly purposes, the proximal end portion 12562 is threadably attached to a retention ring 12570. The retention ring 12570 is received in a groove 12529 formed between a shoulder 12527 on the proximal end 12523 of the elongated channel 12522 and the distal end 12541 of the spine tube 12540. Such arrangement serves to rotatably support the closure drive nut 12560 within the elongated channel 12522. Rotation of the closure drive nut 12560 will cause the closure tube 12550 to move axially as represented by arrow "D" in FIG. 123.

Figure 125:
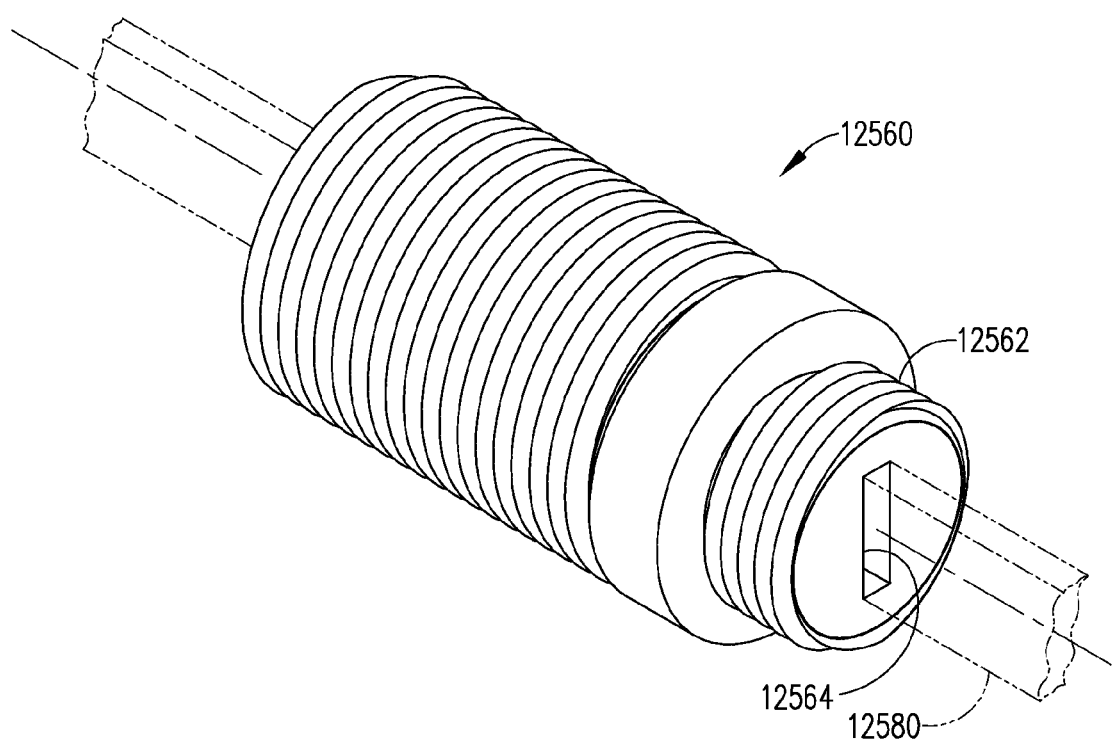
FIG. 125 is a perspective view of a closure drive nut and portion of a knife bar embodiment of the present invention.

Extending through the spine tube 12540 and the closure drive nut 12560 is a drive member which, in at least one embodiment, comprises a knife bar 12580 that has a distal end portion 12582 that is rotatably coupled to the cutting instrument 12532 such that the knife bar 12580 may rotate relative to the cutting instrument 12582. As can be seen in FIG. 123-125, the closure drive nut 12560 has a slot 12564 therein through which the knife bar 12580 can slidably extend. Such arrangement permits the knife bar 12580 to move axially relative to the closure drive nut 12560. However, rotation of the knife bar 12580 about the longitudinal tool axis LT-LT will also result in the rotation of the closure drive nut 12560. The axial direction in which the closure tube 12550 moves ultimately depends upon the direction in which the knife bar 12580 and the closure drive nut 12560 are rotated. As the closure tube 12550 is driven distally, the distal end thereof will contact the anvil 12524 and cause the anvil 12524 to pivot to a closed position. Upon application of an opening rotary output motion from the robotic system 11000, the closure tube 12550 will be driven in the proximal direction "PD" and pivot the anvil 12524 to the open position by virtue of the engagement of the tab 12527 with the opening 12555 in the closure tube 12550.

In use, it may be desirable to rotate the surgical end effector 12512 about the longitudinal tool axis LT-LT. In at least one embodiment, the tool mounting portion 12600 is configured to receive a corresponding first rotary output motion from the robotic system 11000 and convert that first rotary output motion to a rotary control motion for rotating the elongated shaft assembly 12508 about the longitudinal tool axis LT-LT.

As can be seen in FIG. 121, a proximal end 12542 of the hollow spine tube 12540 is rotatably supported within a cradle arrangement 12603 attached to a tool mounting plate 12602 of the tool mounting portion 12600. Various embodiments of the surgical tool 12500 further include a transmission arrangement, generally depicted as 12605, that is operably supported on the tool mounting plate 12602. In various forms the transmission arrangement 12605 include a rotation gear 12544 that is formed on or attached to the proximal end 12542 of the spine tube 12540 for meshing engagement with a rotation drive assembly 12610 that is operably supported on the tool mounting plate 12602. In at least one embodiment, a rotation drive gear 12612 is coupled to a corresponding first one of the rotational bodies, driven discs or elements 11304 on the adapter side of the tool mounting plate 12602 when the tool mounting portion 12600 is coupled to the tool holder 11270. See FIGS. 105 and 126. The rotation drive assembly 12610 further comprises a rotary driven gear 12614 that is rotatably supported on the tool mounting plate 12602 in meshing engagement with the rotation gear 12544 and the rotation drive gear 12612. Application of a first rotary output motion from the robotic system 11000 through the tool drive assembly 11010 to the corresponding driven rotational body 11304 will thereby cause rotation of the rotation drive gear 12612 by virtue of being operably coupled thereto. Rotation of the rotation drive gear 12612 ultimately results in the rotation of the elongated shaft assembly 12508 (and the end effector 12512) about the longitudinal tool axis LT-LT.

Figure 126:
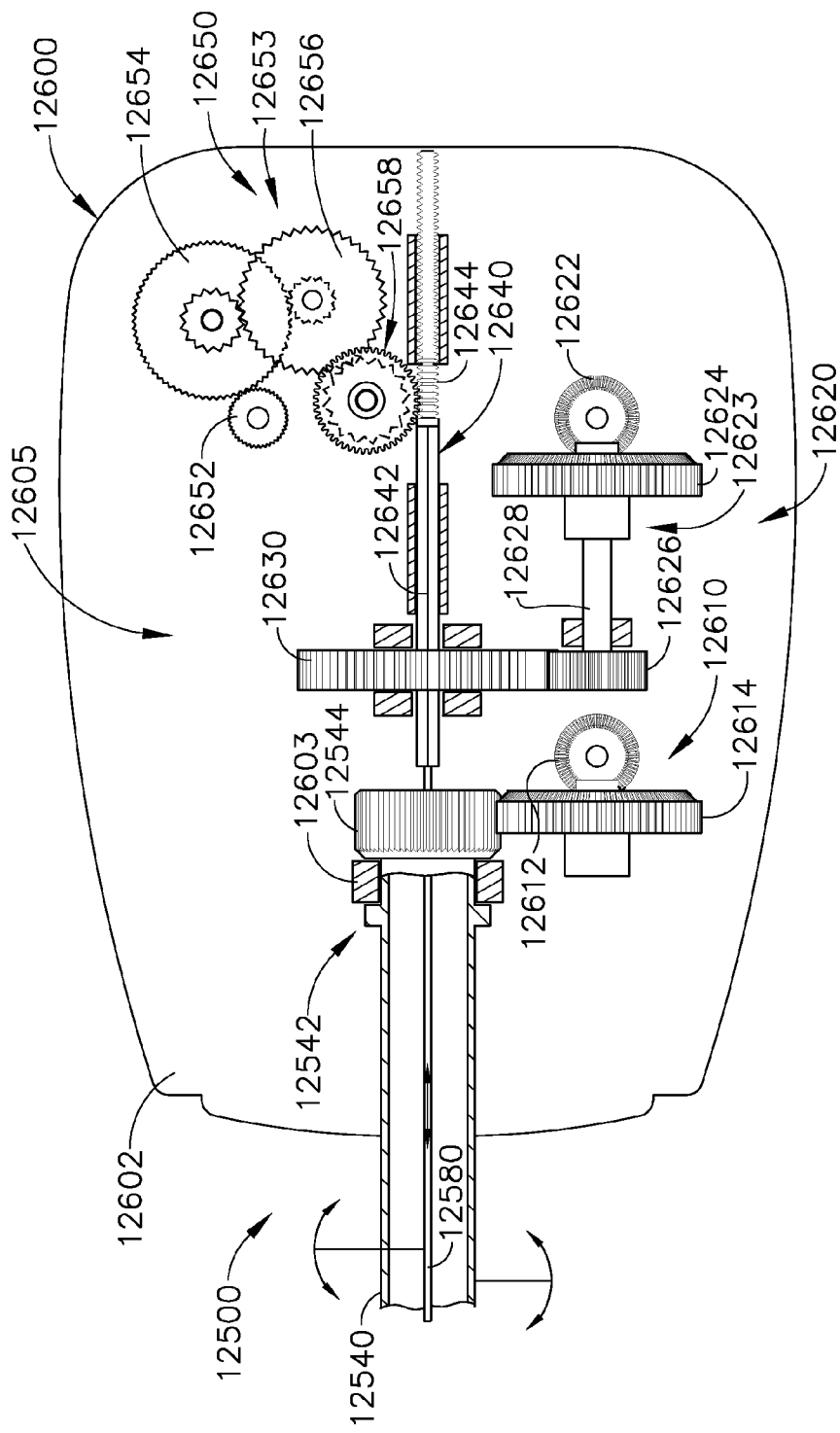
FIG. 126 is a top view of another tool mounting portion embodiment of the present invention.
Figure 127:
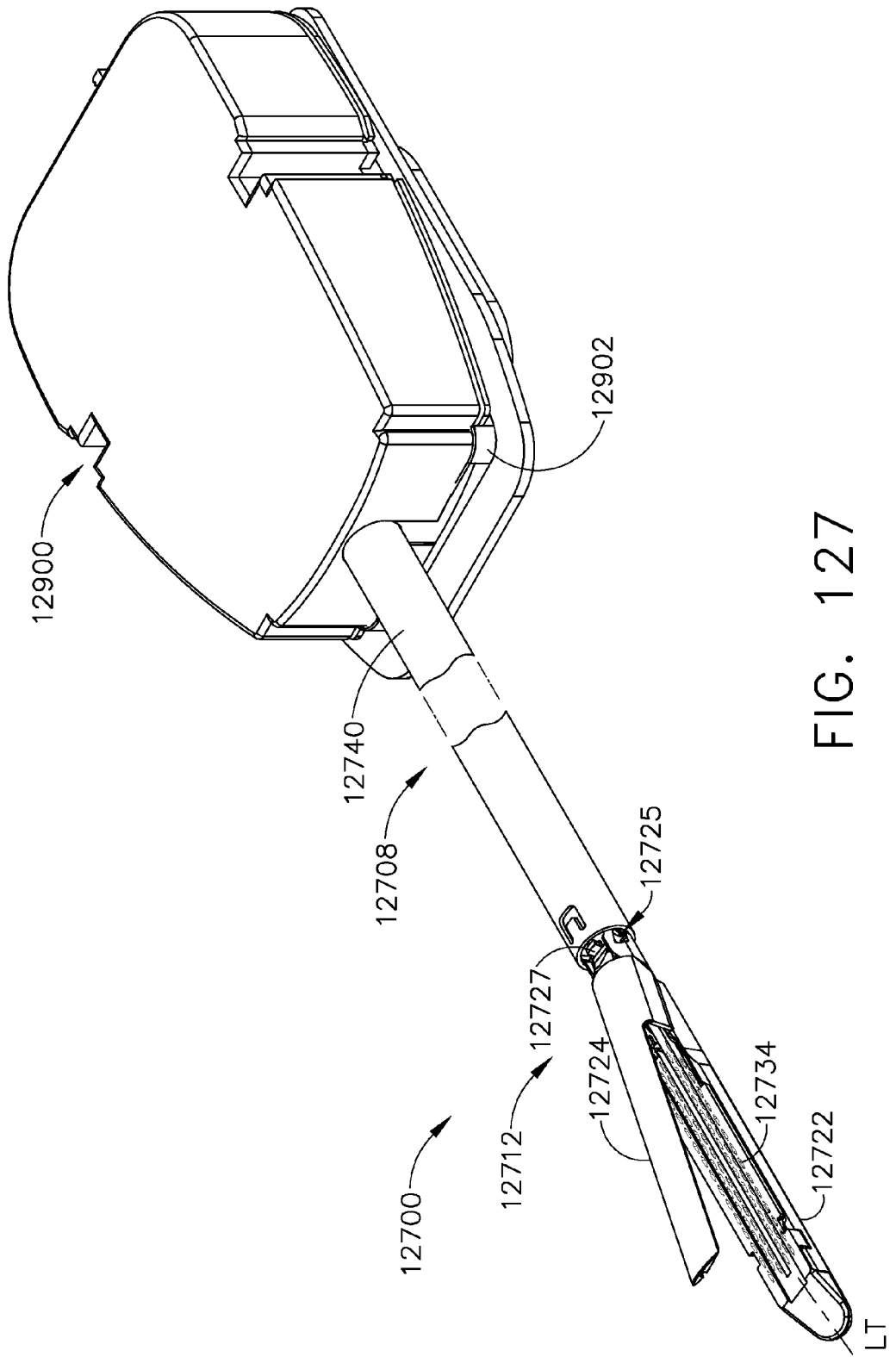
FIG. 127 is a perspective view of another surgical tool embodiment of the present invention.

Closure of the anvil 12524 relative to the surgical staple cartridge 12534 is accomplished by axially moving the closure tube 12550 in the distal direction "DD". Axial movement of the closure tube 12550 in the distal direction "DD" is accomplished by applying a rotary control motion to the closure drive nut 12382. In various embodiments, the closure drive nut 12560 is rotated by applying a rotary output motion to the knife bar 12580. Rotation of the knife bar 12580 is controlled by applying rotary output motions to a rotary closure system 12620 that is operably supported on the tool mounting plate 12602 as shown in FIG. 126. In at least one embodiment, the rotary closure system 12620 includes a closure drive gear 12622 that is coupled to a corresponding second one of the driven rotatable body portions discs or elements 11304 on the adapter side of the tool mounting plate 12462 when the tool mounting portion 12600 is coupled to the tool holder 11270. See FIGS. 105 and 126. The closure drive gear 12622, in at least one embodiment, is in meshing driving engagement with a closure gear train, generally depicted as 12623. The closure gear drive rain 12623 comprises a first driven closure gear 12624 that is rotatably supported on the tool mounting plate 12602. The first closure driven gear 12624 is attached to a second closure driven gear 12626 by a drive shaft 12628. The second closure driven gear 12626 is in meshing engagement with a third closure driven gear 12630 that is rotatably supported on the tool mounting plate 12602. Rotation of the closure drive gear 12622 in a second rotary direction will result in the rotation of the third closure driven gear 12630 in a second direction. Conversely, rotation of the closure drive gear 12483 in a secondary rotary direction (opposite to the second rotary direction) will cause the third closure driven gear 12630 to rotate in a secondary direction.

As can be seen in FIG. 126, a drive shaft assembly 12640 is coupled to a proximal end of the knife bar 12580. In various embodiments, the drive shaft assembly 12640 includes a proximal portion 12642 that has a square cross-sectional shape. The proximal portion 12642 is configured to slidably engage a correspondingly shaped aperture in the third driven gear 12630. Such arrangement results in the rotation of the drive shaft assembly 12640 (and knife bar 12580) when the third driven gear 12630 is rotated. The drive shaft assembly 12640 is axially advanced in the distal and proximal directions by a knife drive assembly 12650. One form of the knife drive assembly 12650 comprises a rotary drive gear 12652 that is coupled to a corresponding third one of the driven rotatable body portions, discs or elements 11304 on the adapter side of the tool mounting plate 12462 when the tool mounting portion 12600 is coupled to the tool holder 11270. See FIGS. 105 and 126. The rotary driven gear 12652 is in meshing driving engagement with a gear train, generally depicted as 12653. In at least one form, the gear train 12653 further comprises a first rotary driven gear assembly 12654 that is rotatably supported on the tool mounting plate 12602. The first rotary driven gear assembly 12654 is in meshing engagement with a third rotary driven gear assembly 12656 that is rotatably supported on the tool mounting plate 12602 and which is in meshing engagement with a fourth rotary driven gear assembly 12658 that is in meshing engagement with a threaded portion 12644 of the drive shaft assembly 12640. Rotation of the rotary drive gear 12652 in a third rotary direction will result in the axial advancement of the drive shaft assembly 12640 and knife bar 12580 in the distal direction "DD". Conversely, rotation of the rotary drive gear 12652 in a tertiary rotary direction (opposite to the third rotary direction) will cause the drive shaft assembly 12640 and the knife bar 12580 to move in the proximal direction.

A method of operating the surgical tool 12500 will now be described. Once the tool mounting portion 12600 has been operably coupled to the tool holder 11270 of the robotic system 11000, the robotic system 11000 can orient the surgical end effector 12512 in position adjacent the target tissue to be cut and stapled. If the anvil 12524 is not already in the open position (FIG. 123), the robotic system 11000 may apply the second rotary output motion to the closure drive gear 12622 which results in the rotation of the knife bar 12580 in a second direction. Rotation of the knife bar 12580 in the second direction results in the rotation of the closure drive nut 12560 in a second direction. As the closure drive nut 12560 rotates in the second direction, the closure tube 12550 moves in the proximal direction "PD". As the closure tube 12550 moves in the proximal direction "PD", the tab 12527 on the anvil 12524 interfaces with the opening 12555 in the closure tube 12550 and causes the anvil 12524 to pivot to the open position. In addition or in alternative embodiments, a spring (not shown) may be employed to pivot the anvil 12354 to the open position when the closure tube 12550 has been returned to the starting position (FIG. 123). The opened surgical end effector 12512 may then be manipulated by the robotic system 11000 to position the target tissue between the open anvil 12524 and the surgical staple cartridge 12534. Thereafter, the surgeon may initiate the closure process by activating the robotic control system 11000 to apply the second rotary output motion to the closure drive gear 12622 which, as was described above, ultimately results in the rotation of the closure drive nut 12382 in the second direction which results in the axial travel of the closure tube 12250 in the distal direction "DD". As the closure tube 12550 moves in the distal direction, it contacts a portion of the anvil 12524 and causes the anvil 12524 to pivot to the closed position to clamp the target tissue between the anvil 12524 and the staple cartridge 12534. Once the robotic controller 11001 determines that the anvil 12524 has been pivoted to the closed position by corresponding sensor(s) in the end effector 12512 that are in communication therewith, the robotic controller 11001 discontinues the application of the second rotary output motion to the closure drive gear 12622. The robotic controller 11001 may also provide the surgeon with an indication that the anvil 12524 has been fully closed. The surgeon may then initiate the firing procedure. In alternative embodiments, the firing procedure may be automatically initiated by the robotic controller 11001.

After the robotic controller 11001 has determined that the anvil 12524 is in the closed position, the robotic controller 11001 then applies the third rotary output motion to the rotary drive gear 12652 which results in the axial movement of the drive shaft assembly 12640 and knife bar 12580 in the distal direction "DD". As the cutting instrument 12532 moves distally through the surgical staple cartridge 12534, the tissue clamped therein is severed. As the sled portion (not shown) is driven distally, it causes the staples within the surgical staple cartridge 12534 to be driven through the severed tissue into forming contact with the anvil 12524. Once the robotic controller 11001 has determined that the cutting instrument 12532 has reached the end position within the surgical staple cartridge 12534 by means of sensor(s) in the surgical end effector 12512 that are in communication with the robotic controller 11001, the robotic controller 11001 discontinues the application of the second rotary output motion to the rotary drive gear 12652. Thereafter, the robotic controller 11001 applies the secondary rotary control motion to the rotary drive gear 12652 which ultimately results in the axial travel of the cutting instrument 12532 and sled portion in the proximal direction "PD" to the starting position. Once the robotic controller 1001 has determined that the cutting instrument 12524 has reached the staring position by means of sensor(s) in the end effector 12512 that are in communication with the robotic controller 11001, the robotic controller 11001 discontinues the application of the secondary rotary output motion to the rotary drive gear 12652. Thereafter, the robotic controller 11001 may apply the secondary rotary output motion to the closure drive gear 12622 which results in the rotation of the knife bar 12580 in a secondary direction. Rotation of the knife bar 12580 in the secondary direction results in the rotation of the closure drive nut 12560 in a secondary direction. As the closure drive nut 12560 rotates in the secondary direction, the closure tube 12550 moves in the proximal direction "PD" to the open position.

FIGS. 127-132B illustrate yet another surgical tool 12700 that may be effectively employed in connection with the robotic system 11000. In various forms, the surgical tool 12700 includes a surgical end effector 12712 that includes a "first portion" in the form of an elongated channel 12722 and a "second movable portion" in on form comprising a pivotally translatable clamping member, such as an anvil 12724, which are maintained at a spacing that assures effective stapling and severing of tissue clamped in the surgical end effector 12712. As shown in the illustrated embodiment, the surgical end effector 12712 may include, in addition to the previously-mentioned channel 12722 and anvil 12724, a "third movable portion" in the form of a cutting instrument 12732, a sled (not shown), and a surgical staple cartridge 12734 that is removably seated in the elongated channel 12722. The cutting instrument 12732 may be, for example, a knife. The anvil 12724 may be pivotably opened and closed at a pivot point 12725 connected to the proximal end of the elongated channel 12722. The anvil 12724 may also include a tab 12727 at its proximal end that interfaces with a component of the mechanical closure system (described further below) to open and close the anvil 12724. When actuated, the knife 12732 and sled to travel longitudinally along the elongated channel 12722, thereby cutting tissue clamped within the surgical end effector 12712. The movement of the sled along the elongated channel 12722 causes the staples of the surgical staple cartridge 12734 to be driven through the severed tissue and against the closed anvil 12724, which turns the staples to fasten the severed tissue. In one form, the elongated channel 12722 and the anvil 12724 may be made of an electrically conductive material (such as metal) so that they may serve as part of the antenna that communicates with sensor(s) in the surgical end effector, as described above. The surgical staple cartridge 12734 could be made of a nonconductive material (such as plastic) and the sensor may be connected to or disposed in the surgical staple cartridge 12734, as described above.

It should be noted that although the embodiments of the surgical tool 12500 described herein employ a surgical end effector 12712 that staples the severed tissue, in other embodiments different techniques for fastening or sealing the severed tissue may be used. For example, end effectors that use RF energy or adhesives to fasten the severed tissue may also be used. U.S. Pat. No. 5,709,680, entitled "Electrosurgical Hemostatic Device" to Yates et al., and U.S. Pat. No. 5,688,270, entitled "Electrosurgical Hemostatic Device With Recessed And/Or Offset Electrodes" to Yates et al., which are incorporated herein by reference, discloses cutting instruments that use RF energy to fasten the severed tissue. U.S. patent application Ser. No. 11/267,811, now U.S. Pat. No. 7,673,783, to Morgan et al. and U.S. patent application Ser. No. 11/267,383, now U.S. Pat. No. 7,607,557, to Shelton et al., which are also incorporated herein by reference, disclose cutting instruments that use adhesives to fasten the severed tissue. Accordingly, although the description herein refers to cutting/stapling operations and the like, it should be recognized that this is an exemplary embodiment and is not meant to be limiting. Other tissue-fastening techniques may also be used.

Figure 130:
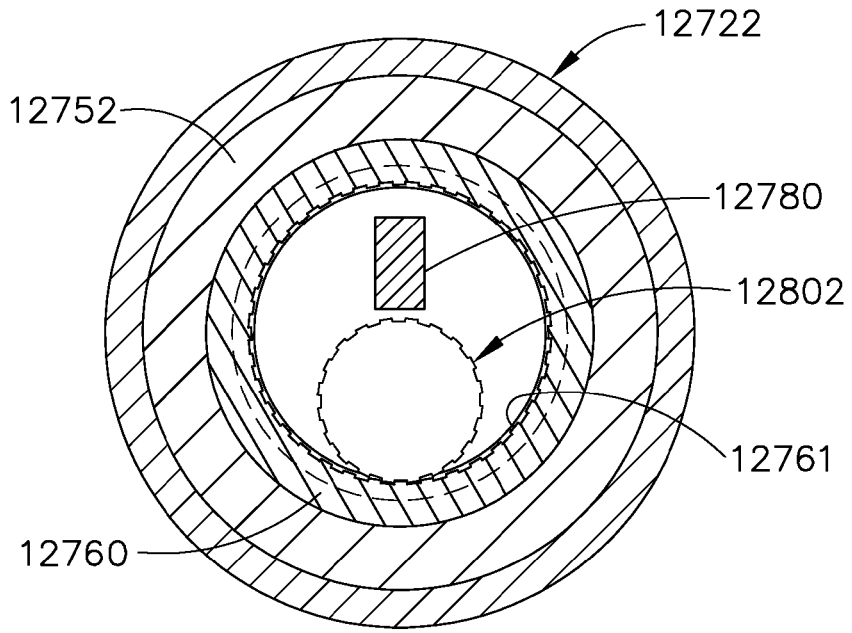
FIG. 130 is a cross-sectional view of a mounting collar embodiment of a surgical tool embodiment of the present invention showing the knife bar and distal end portion of the closure drive shaft.
Figure 131:
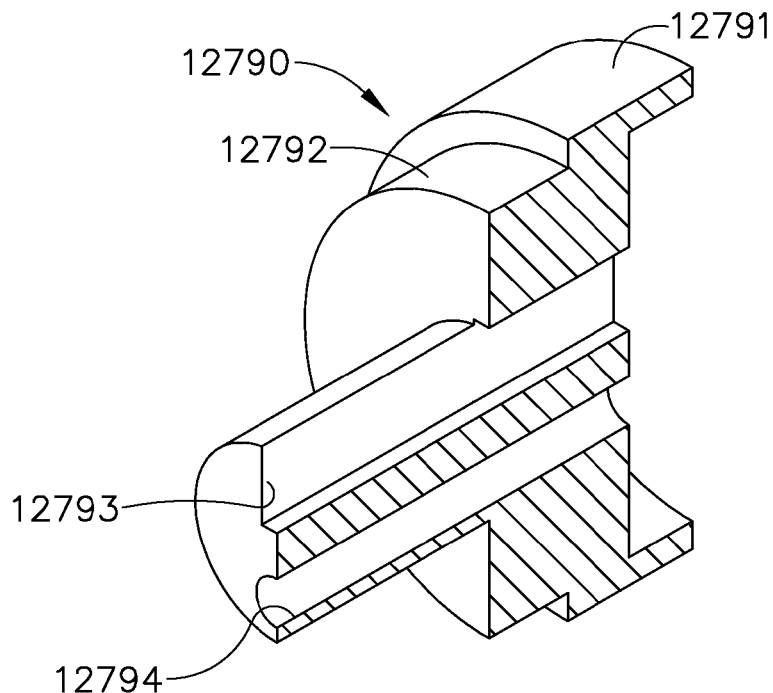
FIG. 131 is a cross-sectional view of the mounting collar embodiment of FIG. 130.

In the illustrated embodiment, the elongated channel 12722 of the surgical end effector 12712 is coupled to an elongated shaft assembly 12708 that is coupled to a tool mounting portion 12900. Although not shown, the elongated shaft assembly 12708 may include an articulation joint to permit the surgical end effector 12712 to be selectively articulated about an axis that is substantially transverse to the tool axis LT-LT. In at least one embodiment, the elongated shaft assembly 12708 comprises a hollow spine tube 12740 that is non-movably coupled to a tool mounting plate 12902 of the tool mounting portion 12900. As can be seen in FIGS. 128 and 129, the proximal end 12723 of the elongated channel 12722 comprises a hollow tubular structure that is attached to the spine tube 12740 by means of a mounting collar 12790. A cross-sectional view of the mounting collar 12790 is shown in FIG. 130. In various embodiments, the mounting collar 12790 has a proximal flanged end 12791 that is configured for attachment to the distal end of the spine tube 12740. In at least one embodiment, for example, the proximal flanged end 12791 of the mounting collar 12790 is welded or glued to the distal end of the spine tube 12740. As can be further seen in FIGS. 128 and 129, the mounting collar 12790 further has a mounting hub portion 12792 that is sized to receive the proximal end 12723 of the elongated channel 12722 thereon. The proximal end 12723 of the elongated channel 12722 is non-movably attached to the mounting hub portion 12792 by, for example, welding, adhesive, etc.

As can be further seen in FIGS. 128 and 129, the surgical tool 12700 further includes an axially movable actuation member in the form of a closure tube 12750 that is constrained to move axially relative to the elongated channel 12722. The closure tube 12750 has a proximal end 12752 that has an internal thread 12754 formed therein that is in threaded engagement with a rotatably movable portion in the form of a closure drive nut 12760. More specifically, the closure drive nut 12760 has a proximal end portion 12762 that is rotatably supported relative to the elongated channel 12722 and the spine tube 12740. For assembly purposes, the proximal end portion 12762 is threadably attached to a retention ring 12770. The retention ring 12770 is received in a groove 12729 formed between a shoulder 12727 on the proximal end 12723 of the channel 12722 and the mounting hub 12729 of the mounting collar 12790. Such arrangement serves to rotatably support the closure drive nut 12760 within the channel 12722. Rotation of the closure drive nut 12760 will cause the closure tube 12750 to move axially as represented by arrow "D" in FIG. 128.

Extending through the spine tube 12740, the mounting collar 12790, and the closure drive nut 12760 is a drive member, which in at least one embodiment, comprises a knife bar 12780 that has a distal end portion 12782 that is coupled to the cutting instrument 12732. As can be seen in FIGS. 128 and 129, the mounting collar 12790 has a passage 12793 therethrough for permitting the knife bar 12780 to slidably pass therethrough. Similarly, the closure drive nut 12760 has a slot 12764 therein through which the knife bar 12780 can slidably extend. Such arrangement permits the knife bar 12780 to move axially relative to the closure drive nut 12760.

Actuation of the anvil 12724 is controlled by a rotary driven closure shaft 12800. As can be seen in FIGS. 128 and 129, a distal end portion 12802 of the closure drive shaft 12800 extends through a passage 12794 in the mounting collar 12790 and a closure gear 12804 is attached thereto. The closure gear 12804 is configured for driving engagement with the inner surface 12761 of the closure drive nut 12760. Thus, rotation of the closure shaft 12800 will also result in the rotation of the closure drive nut 12760. The axial direction in which the closure tube 12750 moves ultimately depends upon the direction in which the closure shaft 12800 and the closure drive nut 12760 are rotated. For example, in response to one rotary closure motion received from the robotic system 11000, the closure tube 12750 will be driven in the distal direction "DD". As the closure tube 12750 is driven distally, the opening 12745 will engage the tab 12727 on the anvil 12724 and cause the anvil 12724 to pivot to a closed position. Upon application of an opening rotary motion from the robotic system 11000, the closure tube 12750 will be driven in the proximal direction "PD" and pivot the anvil 12724 to the open position. In various embodiments, a spring (not shown) may be employed to bias the anvil 12724 to the open position (FIG. 128).

Figure 132:
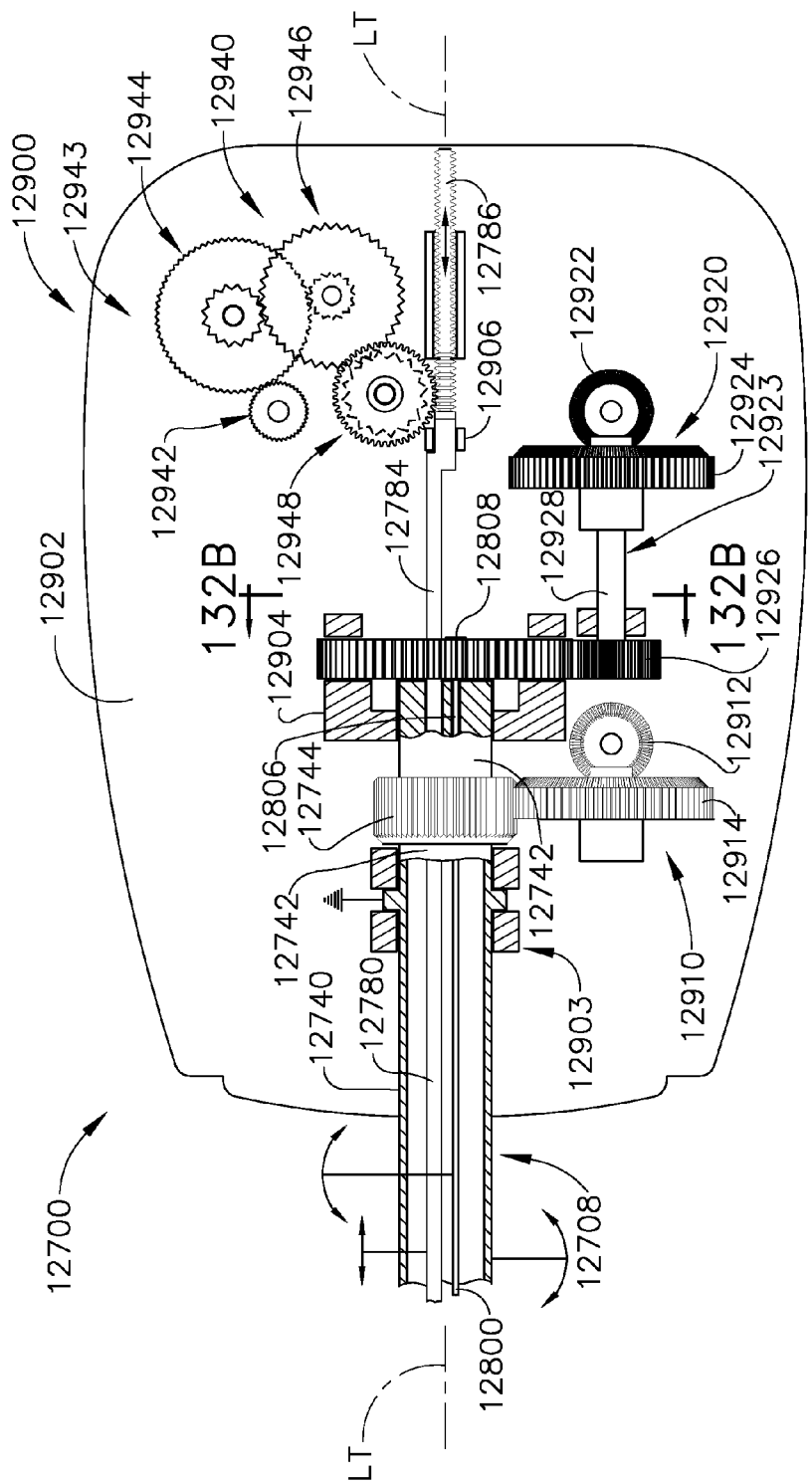
FIG. 132 is a top view of another tool mounting portion embodiment of another surgical tool embodiment of the present invention.

In use, it may be desirable to rotate the surgical end effector 12712 about the longitudinal tool axis LT-LT. In at least one embodiment, the tool mounting portion 12900 is configured to receive a corresponding first rotary output motion from the robotic system 11000 for rotating the elongated shaft assembly 12708 about the tool axis LT-LT. As can be seen in FIG. 132, a proximal end 12742 of the hollow spine tube 12740 is rotatably supported within a cradle arrangement 12903 and a bearing assembly 12904 that are attached to a tool mounting plate 12902 of the tool mounting portion 12900. A rotation gear 12744 is formed on or attached to the proximal end 12742 of the spine tube 12740 for meshing engagement with a rotation drive assembly 12910 that is operably supported on the tool mounting plate 12902. In at least one embodiment, a rotation drive gear 12912 is coupled to a corresponding first one of the driven discs or elements 11304 on the adapter side of the tool mounting plate 12602 when the tool mounting portion 12600 is coupled to the tool holder 11270. See FIGS. 105 and 132. The rotation drive assembly 12910 further comprises a rotary driven gear 12914 that is rotatably supported on the tool mounting plate 12902 in meshing engagement with the rotation gear 12744 and the rotation drive gear 12912. Application of a first rotary control motion from the robotic system 11000 through the tool holder 11270 and the adapter 11240 to the corresponding driven element 11304 will thereby cause rotation of the rotation drive gear 12912 by virtue of being operably coupled thereto. Rotation of the rotation drive gear 12912 ultimately results in the rotation of the elongated shaft assembly 12708 (and the end effector 2712) about the longitudinal tool axis LT-LT (primary rotary motion).

Figure 132A:
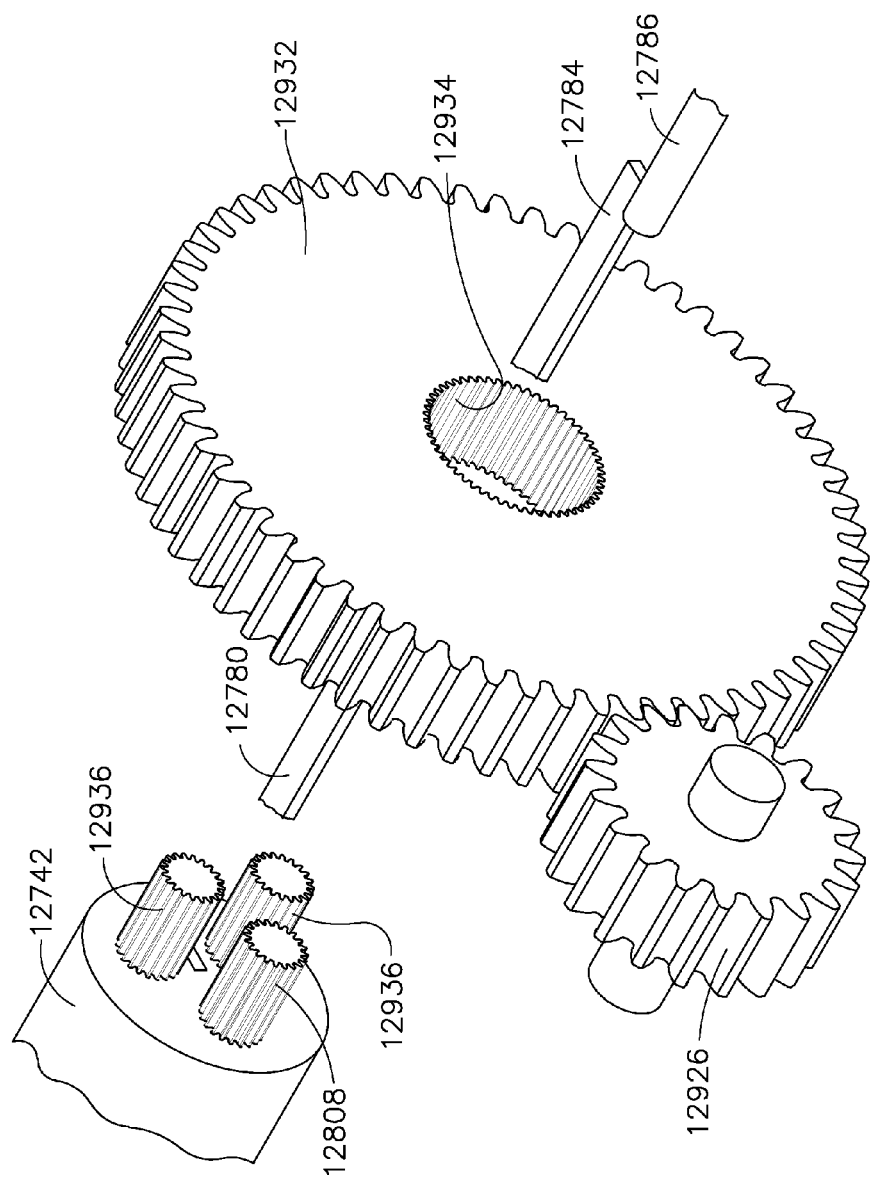
FIG. 132A is an exploded perspective view of a portion of a gear arrangement of another surgical tool embodiment of the present invention.
Figure 132B:
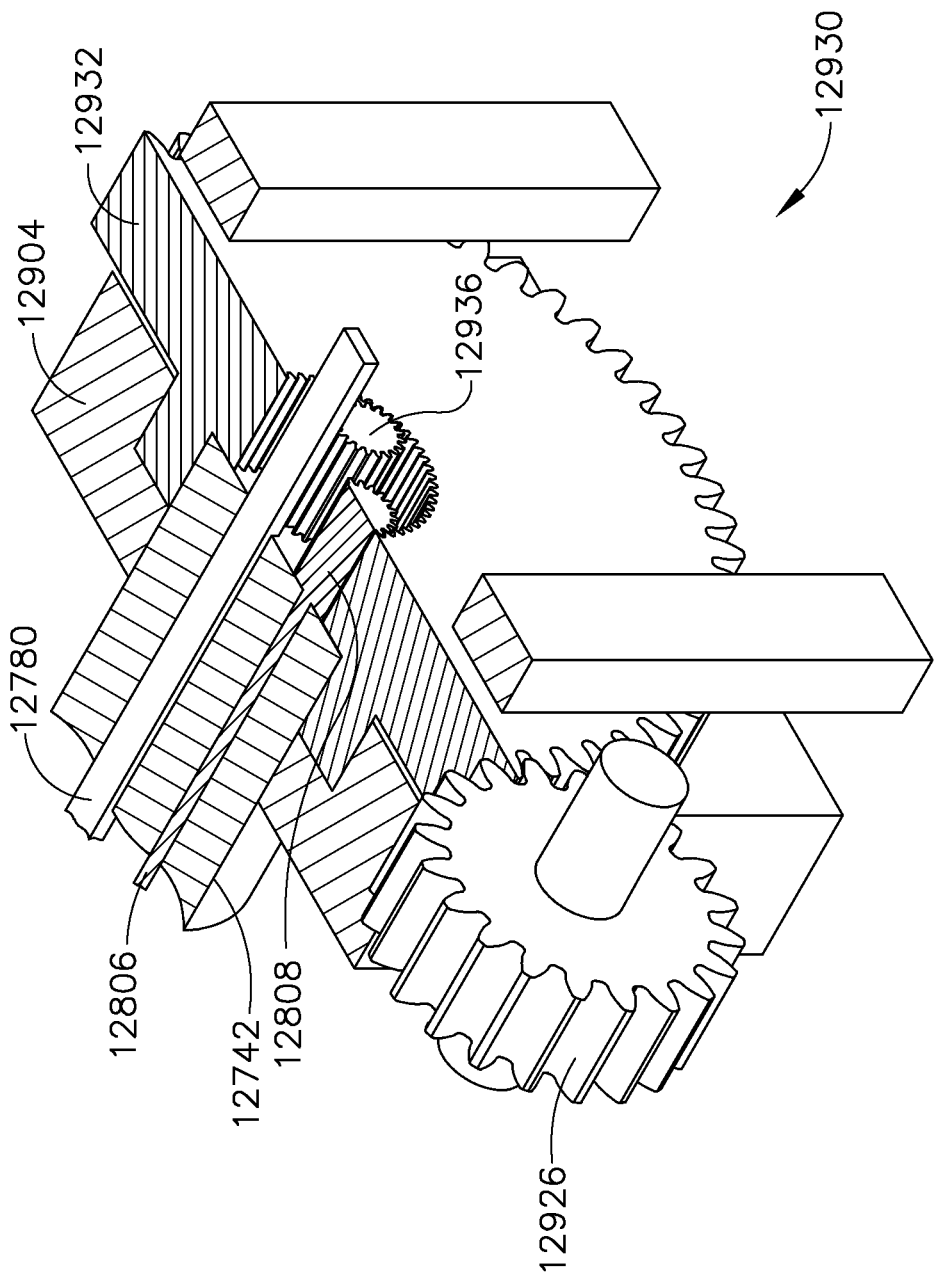
FIG. 132B is a cross-sectional perspective view of the gear arrangement shown in FIG. 132A.

Closure of the anvil 12724 relative to the staple cartridge 12734 is accomplished by axially moving the closure tube 12750 in the distal direction "DD". Axial movement of the closure tube 12750 in the distal direction "DD" is accomplished by applying a rotary control motion to the closure drive nut 12760. In various embodiments, the closure drive nut 12760 is rotated by applying a rotary output motion to the closure drive shaft 12800. As can be seen in FIG. 132, a proximal end portion 12806 of the closure drive shaft 12800 has a driven gear 12808 thereon that is in meshing engagement with a closure drive assembly 12920. In various embodiments, the closure drive system 12920 includes a closure drive gear 12922 that is coupled to a corresponding second one of the driven rotational bodies or elements 11304 on the adapter side of the tool mounting plate 12462 when the tool mounting portion 12900 is coupled to the tool holder 11270. See FIGS. 105 and 132. The closure drive gear 12922 is supported in meshing engagement with a closure gear train, generally depicted as 12923. In at least one form, the closure gear rain 12923 comprises a first driven closure gear 12924 that is rotatably supported on the tool mounting plate 12902. The first closure driven gear 12924 is attached to a second closure driven gear 12926 by a drive shaft 12928. The second closure driven gear 12926 is in meshing engagement with a planetary gear assembly 12930. In various embodiments, the planetary gear assembly 12930 includes a driven planetary closure gear 12932 that is rotatably supported within the bearing assembly 12904 that is mounted on tool mounting plate 12902. As can be seen in FIGS. 132 and 132B, the proximal end portion 12806 of the closure drive shaft 12800 is rotatably supported within the proximal end portion 12742 of the spine tube 12740 such that the driven gear 12808 is in meshing engagement with central gear teeth 12934 formed on the planetary gear 12932. As can also be seen in FIG. 132A, two additional support gears 12936 are attached to or rotatably supported relative to the proximal end portion 12742 of the spine tube 12740 to provide bearing support thereto. Such arrangement with the planetary gear assembly 12930 serves to accommodate rotation of the spine shaft 12740 by the rotation drive assembly 12910 while permitting the closure driven gear 12808 to remain in meshing engagement with the closure drive system 12920. In addition, rotation of the closure drive gear 12922 in a first direction will ultimately result in the rotation of the closure drive shaft 12800 and closure drive nut 12760 which will ultimately result in the closure of the anvil 12724 as described above. Conversely, rotation of the closure drive gear 12922 in a second opposite direction will ultimately result in the rotation of the closure drive nut 12760 in an opposite direction which results in the opening of the anvil 12724.

As can be seen in FIG. 126, the proximal end 12784 of the knife bar 12780 has a threaded shaft portion 12786 attached thereto which is in driving engagement with a knife drive assembly 12940. In various embodiments, the threaded shaft portion 12786 is rotatably supported by a bearing 12906 attached to the tool mounting plate 12902. Such arrangement permits the threaded shaft portion 12786 to rotate and move axially relative to the tool mounting plate 12902. The knife bar 12780 is axially advanced in the distal and proximal directions by the knife drive assembly 12940. One form of the knife drive assembly 12940 comprises a rotary drive gear 12942 that is coupled to a corresponding third one of the rotatable bodies, driven discs or elements 11304 on the adapter side of the tool mounting plate 12902 when the tool mounting portion 12900 is coupled to the tool holder 11270. See FIGS. 105 and 132. The rotary drive gear 12942 is in meshing engagement with a knife gear train, generally depicted as 12943. In various embodiments, the knife gear train 12943 comprises a first rotary driven gear assembly 12944 that is rotatably supported on the tool mounting plate 12902. The first rotary driven gear assembly 12944 is in meshing engagement with a third rotary driven gear assembly 12946 that is rotatably supported on the tool mounting plate 12902 and which is in meshing engagement with a fourth rotary driven gear assembly 12948 that is in meshing engagement with the threaded portion 12786 of the knife bar 12780. Rotation of the rotary drive gear 12942 in one direction will result in the axial advancement of the knife bar 12780 in the distal direction "DD". Conversely, rotation of the rotary drive gear 12942 in an opposite direction will cause the knife bar 12780 to move in the proximal direction. Tool 12700 may otherwise be used as described above.

Figure 133:
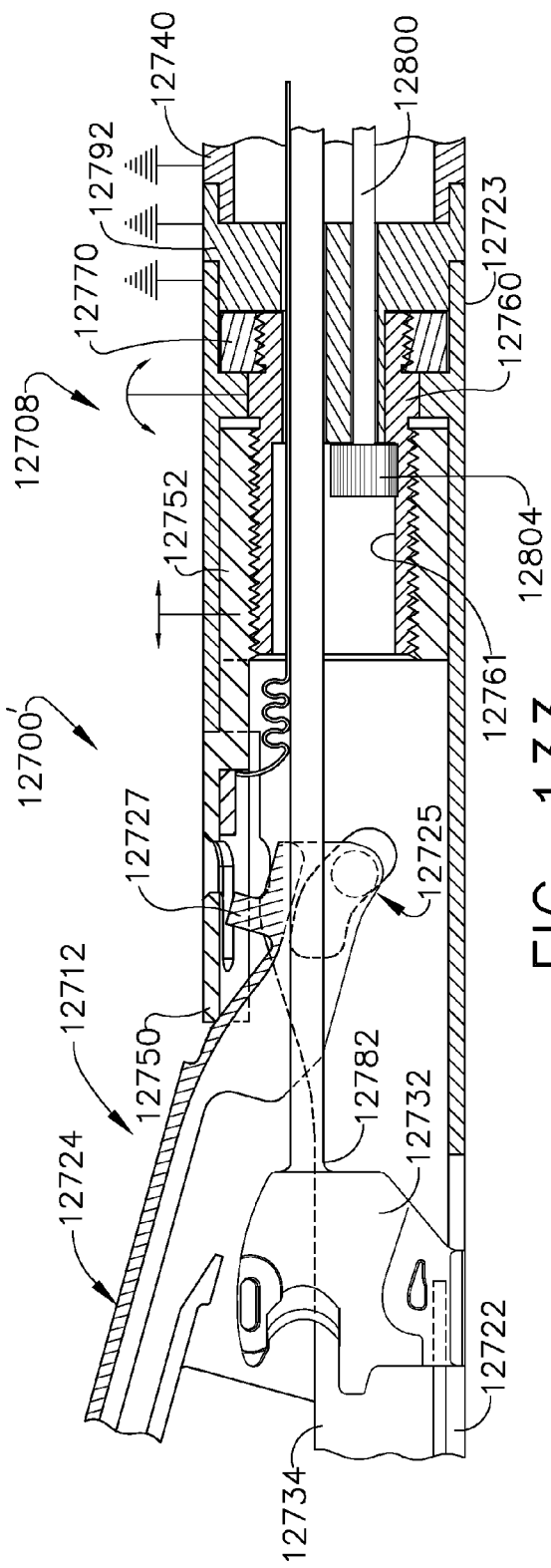
FIG. 133 is a cross-sectional side view of a portion of a surgical end effector and elongated shaft assembly of another surgical tool embodiment of the present invention employing a pressure sensor arrangement with the anvil in the open position.
Figure 134:
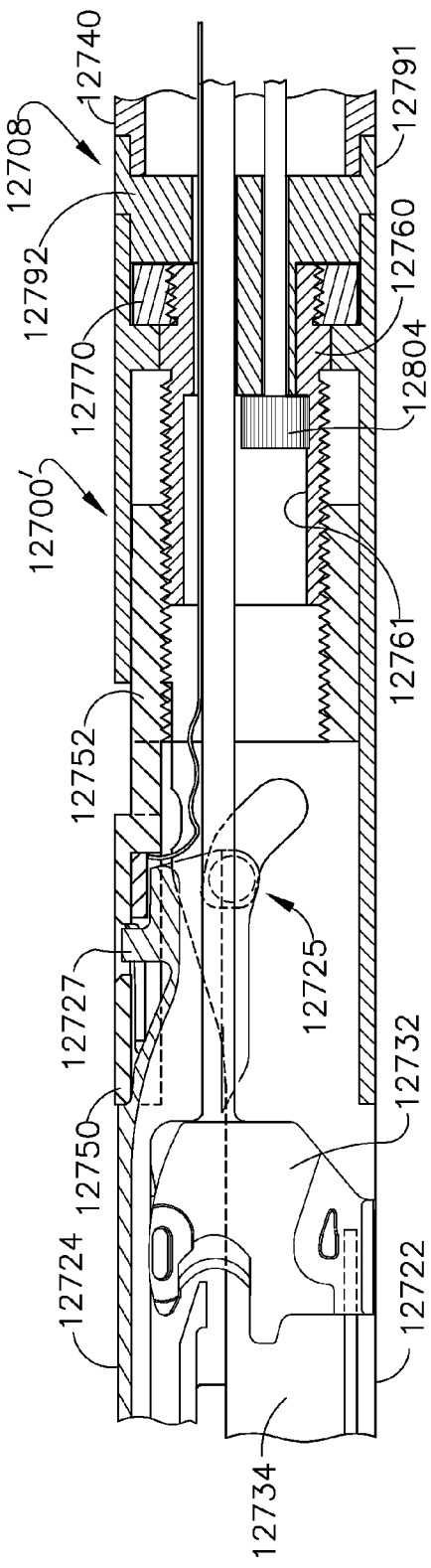
FIG. 134 is another cross-sectional side view of a portion of the surgical end effector and elongated shaft assembly of the surgical tool embodiment of FIG. 133 with the anvil in the closed position.

FIGS. 133 and 134 illustrate a surgical tool embodiment 12700' that is substantially identical to tool 12700 that was described in detail above. However tool 12700' includes a pressure sensor 12950 that is configured to provide feedback to the robotic controller 11001 concerning the amount of clamping pressure experienced by the anvil 12724. In various embodiments, for example, the pressure sensor may comprise a spring biased contact switch. For a continuous signal, it would use either a cantilever beam with a strain gage on it or a dome button top with a strain gage on the inside. Another version may comprise an off switch that contacts only at a known desired load. Such arrangement would include a dome on the based wherein the dome is one electrical pole and the base is the other electrical pole. Such arrangement permits the robotic controller 11001 to adjust the amount of clamping pressure being applied to the tissue within the surgical end effector 12712 by adjusting the amount of closing pressure applied to the anvil 12724. Those of ordinary skill in the art will understand that such pressure sensor arrangement may be effectively employed with several of the surgical tool embodiments described herein as well as their equivalent structures.

Figure 135:
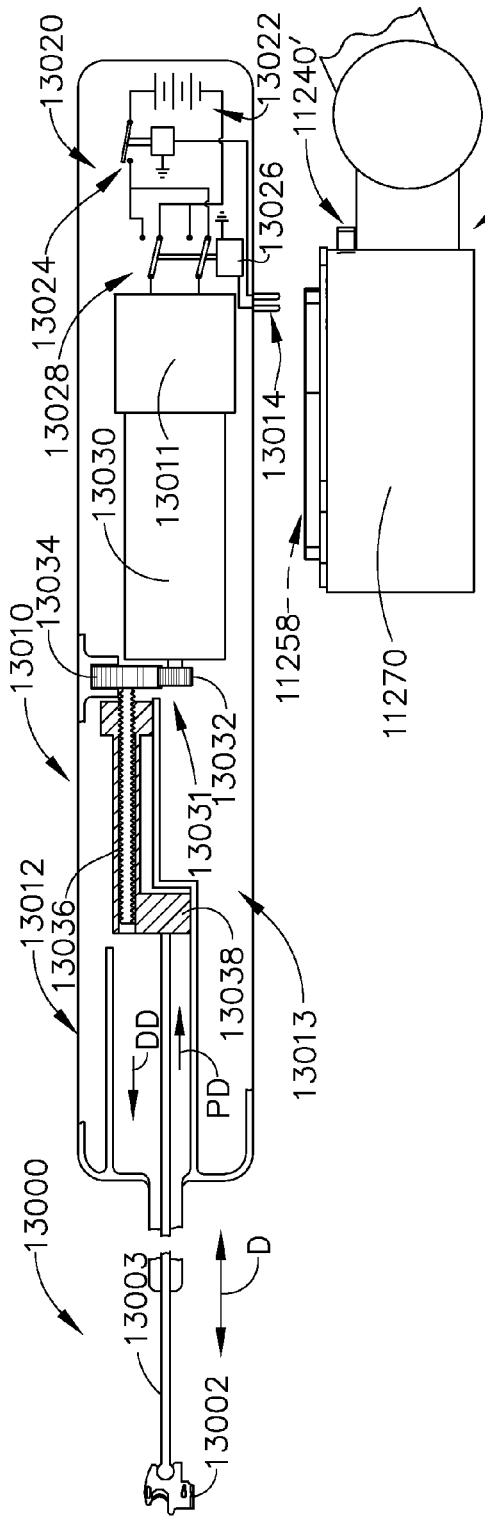
FIG. 135 is a side view of a portion of another surgical tool embodiment of the present invention in relation to a tool holder portion of a robotic system with some of the components thereof shown in cross-section.

FIG. 135 illustrates a portion of another surgical tool 13000 that may be effectively used in connection with a robotic system 11000. The surgical tool 13003 employs on-board motor(s) for powering various components of a surgical end effector cutting instrument. In at least one non-limiting embodiment for example, the surgical tool 13000 includes a surgical end effector in the form of an endocutter (not shown) that has an anvil (not shown) and surgical staple cartridge arrangement (not shown) of the types and constructions described above. The surgical tool 13000 also includes an elongated shaft (not shown) and anvil closure arrangement (not shown) of the types described above. Thus, this portion of the Detailed Description will not repeat the description of those components beyond that which is necessary to appreciate the unique and novel attributes of the various embodiments of surgical tool 13000.

In the depicted embodiment, the end effector includes a cutting instrument 13002 that is coupled to a knife bar 13003. As can be seen in FIG. 135, the surgical tool 13000 includes a tool mounting portion 13010 that includes a tool mounting plate 13012 that is configured to mountingly interface with the adaptor portion 11240' which is coupled to the robotic system 11000 in the various manners described above. The tool mounting portion 13010 is configured to operably support a transmission arrangement 13013 thereon. In at least one embodiment, the adaptor portion 11240' may be identical to the adaptor portion 11240 described in detail above without the powered rotation bodies and disc members employed by adapter 11240. In other embodiments, the adaptor portion 11240' may be identical to adaptor portion 11240. Still other modifications which are considered to be within the spirit and scope of the various forms of the present invention may employ one or more of the mechanical motions (i.e., rotary motion(s)) from the tool holder portion 11270 (as described hereinabove) to power/actuate the transmission arrangement 13013 while also employing one or more motors within the tool mounting portion 13010 to power one or more other components of the surgical end effector. In addition, while the end effector of the depicted embodiment comprises an endocutter, those of ordinary skill in the art will understand that the unique and novel attributes of the depicted embodiment may be effectively employed in connection with other types of surgical end effectors without departing from the spirit and scope of various forms of the present invention.

In various embodiments, the tool mounting plate 13012 is configured to at least house a first firing motor 13011 for supplying firing and retraction motions to the knife bar 13003 which is coupled to or otherwise operably interfaces with the cutting instrument 13002. The tool mounting plate 13012 has an array of electrical connecting pins 13014 which are configured to interface with the slots 11258 (FIG. 104) in the adapter 11240'. Such arrangement permits the controller 11001 of the robotic system 11000 to provide control signals to the electronic control circuit 13020 of the surgical tool 13000. While the interface is described herein with reference to mechanical, electrical, and magnetic coupling elements, it should be understood that a wide variety of telemetry modalities might be used, including infrared, inductive coupling, or the like.

Control circuit 13020 is shown in schematic form in FIG. 135. In one form or embodiment, the control circuit 13020 includes a power supply in the form of a battery 13022 that is coupled to an on-off solenoid powered switch 13024. Control circuit 13020 further includes an on/off firing solenoid 13026 that is coupled to a double pole switch 13028 for controlling the rotational direction of the motor 13011. Thus, when the controller 11001 of the robotic system 11000 supplies an appropriate control signal, switch 13024 will permit battery 13022 to supply power to the double pole switch 13028. The controller 11001 of the robotic system 11000 will also supply an appropriate signal to the double pole switch 13028 to supply power to the motor 13011. When it is desired to fire the surgical end effector (i.e., drive the cutting instrument 13002 distally through tissue clamped in the surgical end effector, the double pole switch 13028 will be in a first position. When it is desired to retract the cutting instrument 13002 to the starting position, the double pole switch 13028 will be moved to the second position by the controller 11001.

Various embodiments of the surgical tool 13000 also employ a gear box 13030 that is sized, in cooperation with a firing gear train 13031 that, in at least one non-limiting embodiment, comprises a firing drive gear 13032 that is in meshing engagement with a firing driven gear 13034 for generating a desired amount of driving force necessary to drive the cutting instrument 13002 through tissue and to drive and form staples in the various manners described herein. In the embodiment depicted in FIG. 135, the driven gear 13034 is coupled to a screw shaft 13036 that is in threaded engagement with a screw nut arrangement 13038 that is constrained to move axially (represented by arrow "D"). The screw nut arrangement 13038 is attached to the firing bar 13003. Thus, by rotating the screw shaft 13036 in a first direction, the cutting instrument 13002 is driven in the distal direction "DD" and rotating the screw shaft in an opposite second direction, the cutting instrument 13002 may be retracted in the proximal direction "PD".

Figure 136:
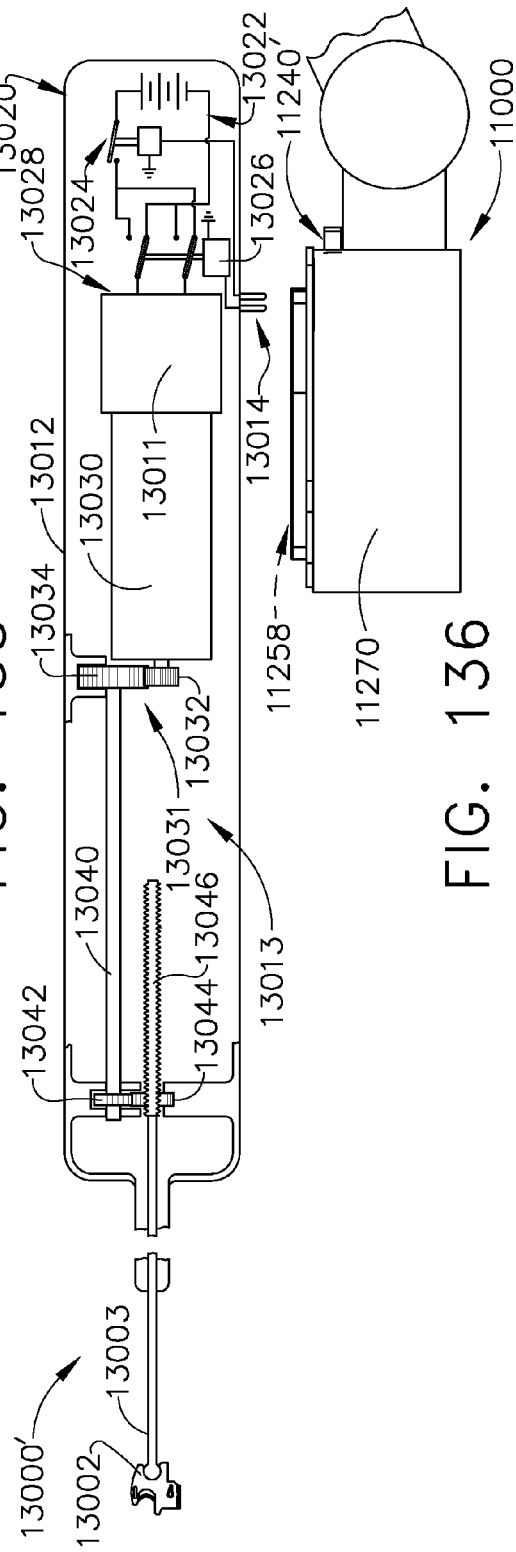
FIG. 136 is a side view of a portion of another surgical tool embodiment of the present invention in relation to a tool holder portion of a robotic system with some of the components thereof shown in cross-section.

FIG. 136 illustrates a portion of another surgical tool 13000' that is substantially identical to tool 13000 described above, except that the driven gear 13034 is attached to a drive shaft 13040. The drive shaft 13040 is attached to a second driver gear 13042 that is in meshing engagement with a third driven gear 13044 that is in meshing engagement with a screw 13046 coupled to the firing bar 13003.

Figure 137:
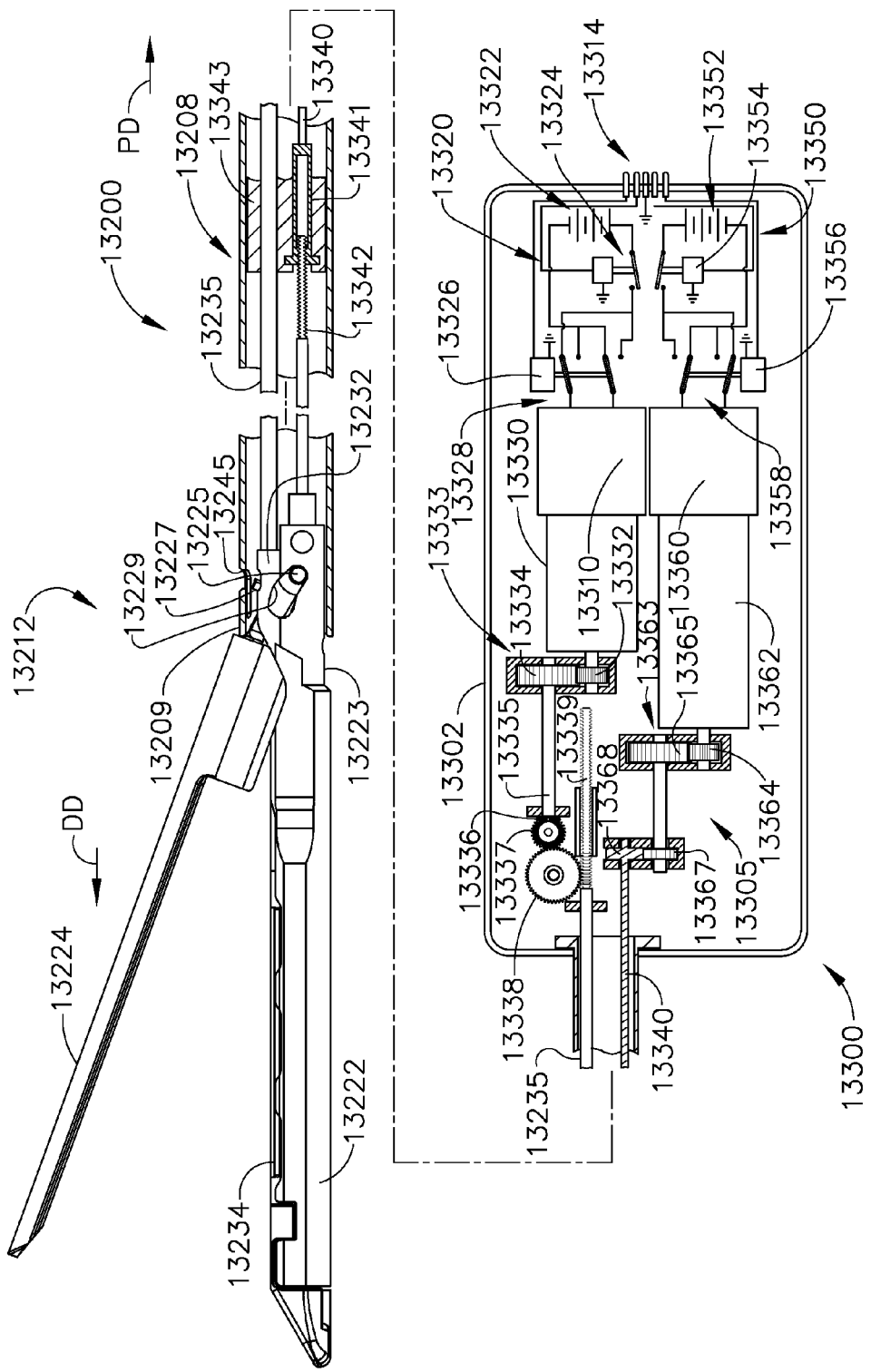
FIG. 137 is a side view of a portion of another surgical tool embodiment of the present invention with some of the components thereof shown in cross-section.

FIG. 137 illustrates another surgical tool 13200 that may be effectively used in connection with a robotic system 11000. In this embodiment, the surgical tool 13200 includes a surgical end effector 13212 that in one non-limiting form, comprises a component portion that is selectively movable between first and second positions relative to at least one other end effector component portion. As will be discussed in further detail below, the surgical tool 13200 employs on-board motors for powering various components of a transmission arrangement 13305. The surgical end effector 13212 includes an elongated channel 13222 that operably supports a surgical staple cartridge 13234. The elongated channel 13222 has a proximal end 13223 that slidably extends into a hollow elongated shaft assembly 13208 that is coupled to a tool mounting portion 13300. In addition, the surgical end effector 13212 includes an anvil 13224 that is pivotally coupled to the elongated channel 13222 by a pair of trunnions 13225 that are received within corresponding openings 13229 in the elongated channel 13222. A distal end portion 13209 of the shaft assembly 13208 includes an opening 13245 into which a tab 13227 on the anvil 13224 is inserted in order to open the anvil 13224 as the elongated channel 13222 is moved axially in the proximal direction "PD" relative to the distal end portion 13209 of the shaft assembly 13208. In various embodiments, a spring (not shown) may be employed to bias the anvil 13224 to the open position.

As indicated above, the surgical tool 13200 includes a tool mounting portion 13300 that includes a tool mounting plate 13302 that is configured to operably support the transmission arrangement 13305 and to mountingly interface with the adaptor portion 11240' which is coupled to the robotic system 11000 in the various manners described above. In at least one embodiment, the adaptor portion 11240' may be identical to the adaptor portion 11240 described in detail above without the powered disc members employed by adapter 11240. In other embodiments, the adaptor portion 11240' may be identical to adaptor portion 11240. However, in such embodiments, because the various components of the surgical end effector 13212 are all powered by motor(s) in the tool mounting portion 13300, the surgical tool 13200 will not employ or require any of the mechanical (i.e., non-electrical) actuation motions from the tool holder portion 11270 to power the surgical end effector 13200 components. Still other modifications which are considered to be within the spirit and scope of the various forms of the present invention may employ one or more of the mechanical motions from the tool holder portion 11270 (as described hereinabove) to power/actuate one or more of the surgical end effector components while also employing one or more motors within the tool mounting portion to power one or more other components of the surgical end effector.

In various embodiments, the tool mounting plate 13302 is configured to support a first firing motor 13310 for supplying firing and retraction motions to the transmission arrangement 13305 to drive a knife bar 13335 that is coupled to a cutting instrument 13332 of the type described above. As can be seen in FIG. 137, the tool mounting plate 13212 has an array of electrical connecting pins 13014 which are configured to interface with the slots 11258 (FIG. 104) in the adapter 11240'. Such arrangement permits the controller 11001 of the robotic system 11000 to provide control signals to the electronic control circuits 13320, 13340 of the surgical tool 13200. While the interface is described herein with reference to mechanical, electrical, and magnetic coupling elements, it should be understood that a wide variety of telemetry modalities might be used, including infrared, inductive coupling, or the like.

In one form or embodiment, the first control circuit 13320 includes a first power supply in the form of a first battery 13322 that is coupled to a first on-off solenoid powered switch 13324. The first firing control circuit 13320 further includes a first on/off firing solenoid 13326 that is coupled to a first double pole switch 13328 for controlling the rotational direction of the first firing motor 13310. Thus, when the robotic controller 11001 supplies an appropriate control signal, the first switch 13324 will permit the first battery 13322 to supply power to the first double pole switch 13328. The robotic controller 11001 will also supply an appropriate signal to the first double pole switch 13328 to supply power to the first firing motor 13310. When it is desired to fire the surgical end effector (i.e., drive the cutting instrument 13232 distally through tissue clamped in the surgical end effector 13212, the first switch 13328 will be positioned in a first position by the robotic controller 11001. When it is desired to retract the cutting instrument 13232 to the starting position, the robotic controller 11001 will send the appropriate control signal to move the first switch 13328 to the second position.

Various embodiments of the surgical tool 13200 also employ a first gear box 13330 that is sized, in cooperation with a firing drive gear 13332 coupled thereto that operably interfaces with a firing gear train 13333. In at least one non-limiting embodiment, the firing gear train 13333 comprises a firing driven gear 13334 that is in meshing engagement with drive gear 13332, for generating a desired amount of driving force necessary to drive the cutting instrument 13232 through tissue and to drive and form staples in the various manners described herein. In the embodiment depicted in FIG. 137, the driven gear 13334 is coupled to a drive shaft 13335 that has a second driven gear 13336 coupled thereto. The second driven gear 13336 is supported in meshing engagement with a third driven gear 13337 that is in meshing engagement with a fourth driven gear 13338. The fourth driven gear 13338 is in meshing engagement with a threaded proximal portion 13339 of the knife bar 13235 that is constrained to move axially. Thus, by rotating the drive shaft 13335 in a first direction, the cutting instrument 13232 is driven in the distal direction "DD" and rotating the drive shaft 13335 in an opposite second direction, the cutting instrument 13232 may be retracted in the proximal direction "PD".

As indicated above, the opening and closing of the anvil 13224 is controlled by axially moving the elongated channel 13222 relative to the elongated shaft assembly 13208. The axial movement of the elongated channel 13222 is controlled by a closure control system 13339. In various embodiments, the closure control system 13339 includes a closure shaft 13340 which has a hollow threaded end portion 13341 that threadably engages a threaded closure rod 13342. The threaded end portion 13341 is rotatably supported in a spine shaft 13343 that operably interfaces with the tool mounting portion 13300 and extends through a portion of the shaft assembly 13208 as shown. The closure system 13339 further comprises a closure control circuit 13350 that includes a second power supply in the form of a second battery 13352 that is coupled to a second on-off solenoid powered switch 13354. Closure control circuit 13350 further includes a second on/off firing solenoid 13356 that is coupled to a second double pole switch 13358 for controlling the rotation of a second closure motor 13360. Thus, when the robotic controller 11001 supplies an appropriate control signal, the second switch 13354 will permit the second battery 13352 to supply power to the second double pole switch 13354. The robotic controller 11001 will also supply an appropriate signal to the second double pole switch 13358 to supply power to the second motor 13360. When it is desired to close the anvil 13224, the second switch 13348 will be in a first position. When it is desired to open the anvil 13224, the second switch 13348 will be moved to a second position.

Various embodiments of tool mounting portion 13300 also employ a second gear box 13362 that is coupled to a closure drive gear 13364. The closure drive gear 13364 is in meshing engagement with a closure gear train 13363. In various non-limiting forms, the closure gear train 13363 includes a closure driven gear 13365 that is attached to a closure drive shaft 13366. Also attached to the closure drive shaft 13366 is a closure drive gear 13367 that is in meshing engagement with a closure shaft gear 13360 attached to the closure shaft 13340. FIG. 137 depicts the end effector 13212 in the open position. As indicated above, when the threaded closure rod 13342 is in the position depicted in FIG. 137, a spring (not shown) biases the anvil 13224 to the open position. When it is desired to close the anvil 13224, the robotic controller 11001 will activate the second motor 13360 to rotate the closure shaft 13340 to draw the threaded closure rod 13342 and the channel 13222 in the proximal direction 'PD'. As the anvil 13224 contacts the distal end portion 13209 of the shaft 13208, the anvil 13224 is pivoted to the closed position.

A method of operating the surgical tool 13200 will now be described. Once the tool mounting portion 13302 has be operably coupled to the tool holder 11270 of the robotic system 11000, the robotic system 11000 can orient the end effector 13212 in position adjacent the target tissue to be cut and stapled. If the anvil 13224 is not already in the open position, the robotic controller 11001 may activate the second closure motor 13360 to drive the channel 13222 in the distal direction to the position depicted in FIG. 137. Once the robotic controller 11001 determines that the surgical end effector 13212 is in the open position by sensor(s) in the and effector and/or the tool mounting portion 13300, the robotic controller 11001 may provide the surgeon with a signal to inform the surgeon that the anvil 13224 may then be closed. Once the target tissue is positioned between the open anvil 13224 and the surgical staple cartridge 13234, the surgeon may then commence the closure process by activating the robotic controller 11001 to apply a closure control signal to the second closure motor 13360. The second closure motor 13360 applies a rotary motion to the closure shaft 13340 to draw the channel 13222 in the proximal direction "PD" until the anvil 13224 has been pivoted to the closed position. Once the robotic controller 11001 determines that the anvil 13224 has been moved to the closed position by sensor(s) in the surgical end effector 13212 and/or in the tool mounting portion 13300 that are in communication with the robotic control system, the motor 13360 may be deactivated. Thereafter, the firing process may be commenced either manually by the surgeon activating a trigger, button, etc. on the controller 11001 or the controller 11001 may automatically commence the firing process.

To commence the firing process, the robotic controller 11001 activates the firing motor 13310 to drive the firing bar 13235 and the cutting instrument 13232 in the distal direction "DD". Once robotic controller 11001 has determined that the cutting instrument 13232 has moved to the ending position within the surgical staple cartridge 13234 by means of sensors in the surgical end effector 13212 and/or the motor drive portion 13300, the robotic controller 11001 may provide the surgeon with an indication signal. Thereafter the surgeon may manually activate the first motor 13310 to retract the cutting instrument 13232 to the starting position or the robotic controller 11001 may automatically activate the first motor 13310 to retract the cutting element 13232.

Figure 138:
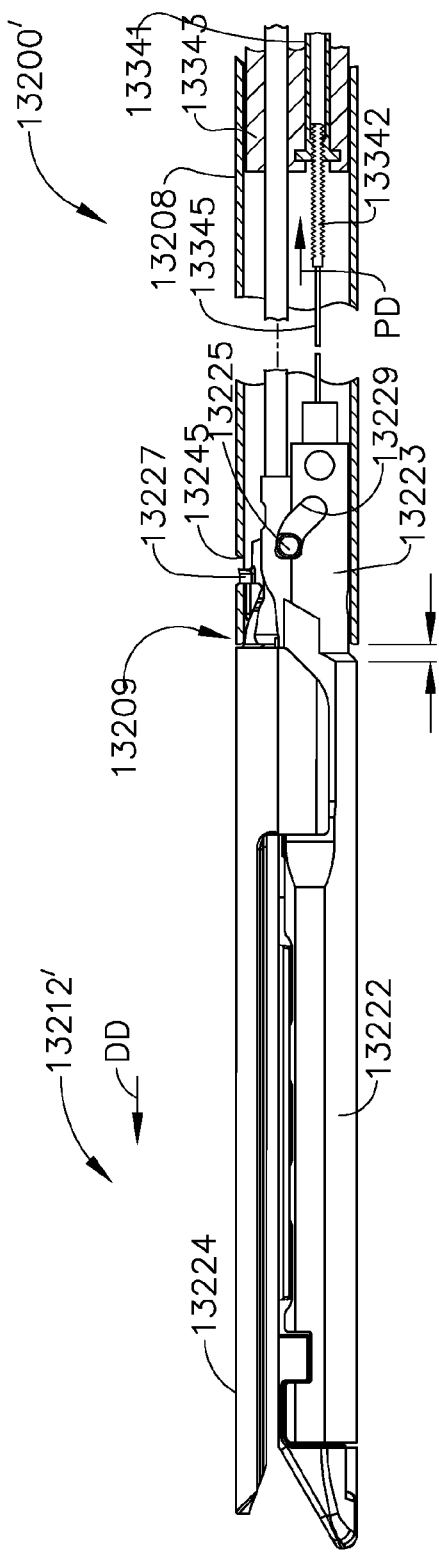
FIG. 138 is a side view of a portion of another surgical end effector embodiment of a portion of a surgical tool embodiment of the present invention with some components thereof shown in cross-section.
Figure 139:
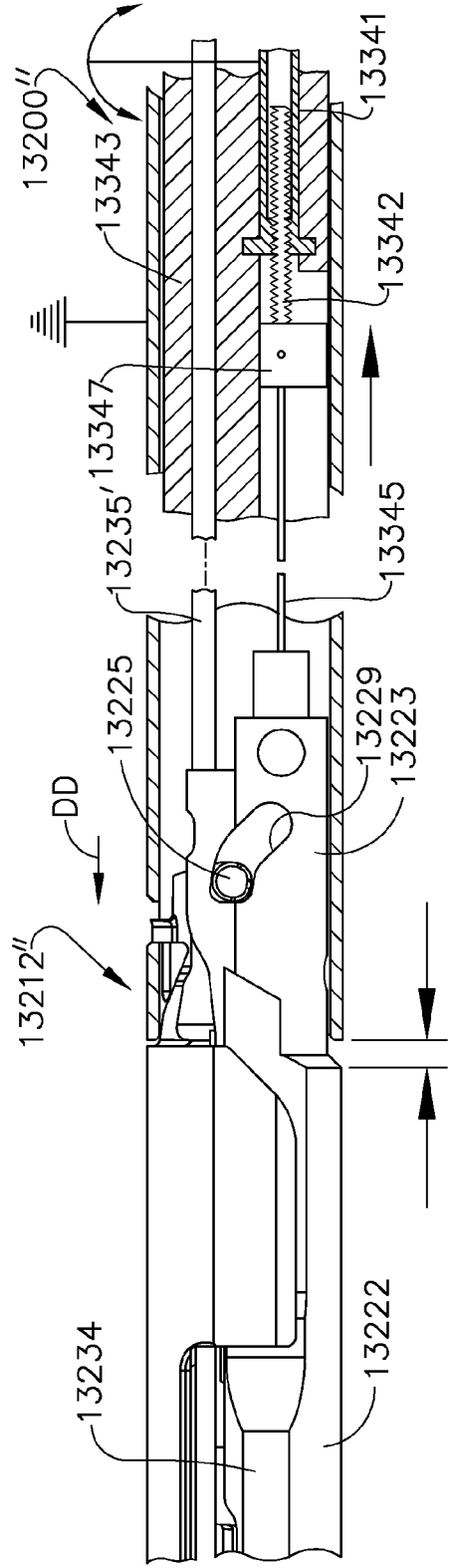
FIG. 139 is a side view of a portion of another surgical end effector embodiment of a portion of a surgical tool embodiment of the present invention with some components thereof shown in cross-section.

The embodiment depicted in FIG. 137 does not include an articulation joint. FIGS. 138 and 139 illustrate surgical tools 13200' and 13200" that have end effectors 13212', 13212", respectively that may be employed with an elongated shaft embodiment that has an articulation joint of the various types disclosed herein. For example, as can be seen in FIG. 138, a threaded closure shaft 13342 is coupled to the proximal end 13223 of the elongated channel 13222 by a flexible cable or other flexible member 13345. The location of an articulation joint (not shown) within the elongated shaft assembly 13208 will coincide with the flexible member 13345 to enable the flexible member 13345 to accommodate such articulation. In addition, in the above-described embodiment, the flexible member 13345 is rotatably affixed to the proximal end portion 13223 of the elongated channel 13222 to enable the flexible member 13345 to rotate relative thereto to prevent the flexible member 13229 from "winding up" relative to the channel 13222. Although not shown, the cutting element may be driven in one of the above described manners by a knife bar that can also accommodate articulation of the elongated shaft assembly. FIG. 139 depicts a surgical end effector 13212" that is substantially identical to the surgical end effector 13212 described above, except that the threaded closure rod 13342 is attached to a closure nut 13347 that is constrained to only move axially within the elongated shaft assembly 13208. The flexible member 13345 is attached to the closure nut 13347. Such arrangement also prevents the threaded closure rod 13342 from winding-up the flexible member 13345. A flexible knife bar 13235' may be employed to facilitate articulation of the surgical end effector 13212".

The surgical tools 13200, 13200', and 13200" described above may also employ anyone of the cutting instrument embodiments described herein. As described above, the anvil of each of the end effectors of these tools is closed by drawing the elongated channel into contact with the distal end of the elongated shaft assembly. Thus, once the target tissue has been located between the staple cartridge 13234 and the anvil 13224, the robotic controller 11001 can start to draw the channel 13222 inward into the shaft assembly 13208. In various embodiments, however, to prevent the end effector 13212, 13212', 13212" from moving the target tissue with the end effector during this closing process, the controller 11001 may simultaneously move the tool holder and ultimately the tool such to compensate for the movement of the elongated channel 13222 so that, in effect, the target tissue is clamped between the anvil and the elongated channel without being otherwise moved.

FIGS. 140-142 depict another surgical tool embodiment 13201 that is substantially identical to surgical tool 13200" described above, except for the differences discussed below. In this embodiment, the threaded closure rod 13342' has variable pitched grooves. More specifically, as can be seen in FIG. 141, the closure rod 13342' has a distal groove section 13380 and a proximal groove section 13382. The distal and proximal groove sections 13380, 13382 are configured for engagement with a lug 13390 supported within the hollow threaded end portion 13341'. As can be seen in FIG. 141, the distal groove section 13380 has a finer pitch than the groove section 13382. Thus, such variable pitch arrangement permits the elongated channel 13222 to be drawn into the shaft 13208 at a first speed or rate by virtue of the engagement between the lug 13390 and the proximal groove segment 13382. When the lug 13390 engages the distal groove segment, the channel 13222 will be drawn into the shaft 13208 at a second speed or rate. Because the proximal groove segment 13382 is coarser than the distal groove segment 13380, the first speed will be greater than the second speed. Such arrangement serves to speed up the initial closing of the end effector for tissue manipulation and then after the tissue has been properly positioned therein, generate the amount of closure forces to properly clamp the tissue for cutting and sealing. Thus, the anvil 13234 initially closes fast with a lower force and then applies a higher closing force as the anvil closes more slowly.

The surgical end effector opening and closing motions are employed to enable the user to use the end effector to grasp and manipulate tissue prior to fully clamping it in the desired location for cutting and sealing. The user may, for example, open and close the surgical end effector numerous times during this process to orient the end effector in a proper position which enables the tissue to be held in a desired location. Thus, in at least some embodiments, to produce the high loading for firing, the fine thread may require as many as 5-10 full rotations to generate the necessary load. In some cases, for example, this action could take as long as 2-5 seconds. If it also took an equally long time to open and close the end effector each time during the positioning/tissue manipulation process, just positioning the end effector may take an undesirably long time. If that happens, it is possible that a user may abandon such use of the end effector for use of a conventional grasper device. Use of graspers, etc. may undesirably increase the costs associated with completing the surgical procedure.

The above-described embodiments employ a battery or batteries to power the motors used to drive the end effector components. Activation of the motors is controlled by the robotic system 11000. In alternative embodiments, the power supply may comprise alternating current "AC" that is supplied to the motors by the robotic system 11000. That is, the AC power would be supplied from the system powering the robotic system 11000 through the tool holder and adapter. In still other embodiments, a power cord or tether may be attached to the tool mounting portion 13300 to supply the requisite power from a separate source of alternating or direct current.

In use, the controller 11001 may apply an initial rotary motion to the closure shaft 13340 (FIG. 137) to draw the elongated channel 13222 axially inwardly into the elongated shaft assembly 13208 and move the anvil from a first position to an intermediate position at a first rate that corresponds with the point wherein the distal groove section 13380 transitions to the proximal groove section 13382. Further application of rotary motion to the closure shaft 13340 will cause the anvil to move from the intermediate position to the closed position relative to the surgical staple cartridge. When in the closed position, the tissue to be cut and stapled is properly clamped between the anvil and the surgical staple cartridge.

FIGS. 143-147 illustrate another surgical tool embodiment 13400 of the present invention. This embodiment includes an elongated shaft assembly 13408 that extends from a tool mounting portion 13500. The elongated shaft assembly 13408 includes a rotatable proximal closure tube segment 13410 that is rotatably journaled on a proximal spine member 13420 that is rigidly coupled to a tool mounting plate 13502 of the tool mounting portion 13500. The proximal spine member 13420 has a distal end 13422 that is coupled to an elongated channel portion 13522 of a surgical end effector 13412. For example, in at least one embodiment, the elongated channel portion 13522 has a distal end portion 13523 that "hookingly engages" the distal end 13422 of the spine member 13420. The elongated channel 13522 is configured to support a surgical staple cartridge 13534 therein. This embodiment may employ one of the various cutting instrument embodiments disclosed herein to sever tissue that is clamped in the surgical end effector 13412 and fire the staples in the staple cartridge 13534 into the severed tissue.

Surgical end effector 13412 has an anvil 13524 that is pivotally coupled to the elongated channel 13522 by a pair of trunnions 13525 that are received in corresponding openings 13529 in the elongated channel 13522. The anvil 13524 is moved between the open (FIG. 143) and closed positions (FIGS. 144-146) by a distal closure tube segment 13430. A distal end portion 13432 of the distal closure tube segment 13430 includes an opening 13445 into which a tab 13527 on the anvil 13524 is inserted in order to open and close the anvil 13524 as the distal closure tube segment 13430 moves axially relative thereto. In various embodiments, the opening 13445 is shaped such that as the closure tube segment 13430 is moved in the proximal direction, the closure tube segment 13430 causes the anvil 13524 to pivot to an open position. In addition or in the alternative, a spring (not shown) may be employed to bias the anvil 13524 to the open position.

As can be seen in FIGS. 143-146, the distal closure tube segment 13430 includes a lug 13442 that extends from its distal end 13440 into threaded engagement with a variable pitch groove/thread 13414 formed in the distal end 13412 of the rotatable proximal closure tube segment 13410. The variable pitch groove/thread 13414 has a distal section 13416 and a proximal section 13418. The pitch of the distal groove/thread section 13416 is finer than the pitch of the proximal groove/thread section 13418. As can also be seen in FIGS. 143-146, the distal closure tube segment 13430 is constrained for axial movement relative to the spine member 13420 by an axial retainer pin 13450 that is received in an axial slot 13424 in the distal end of the spine member 13420.

As indicated above, the anvil 12524 is open and closed by rotating the proximal closure tube segment 13410. The variable pitch thread arrangement permits the distal closure tube segment 13430 to be driven in the distal direction "DD" at a first speed or rate by virtue of the engagement between the lug 13442 and the proximal groove/thread section 13418. When the lug 13442 engages the distal groove/thread section 13416, the distal closure tube segment 13430 will be driven in the distal direction at a second speed or rate. Because the proximal groove/thread section 13418 is coarser than the distal groove/thread segment 13416, the first speed will be greater than the second speed.

Figure 147:
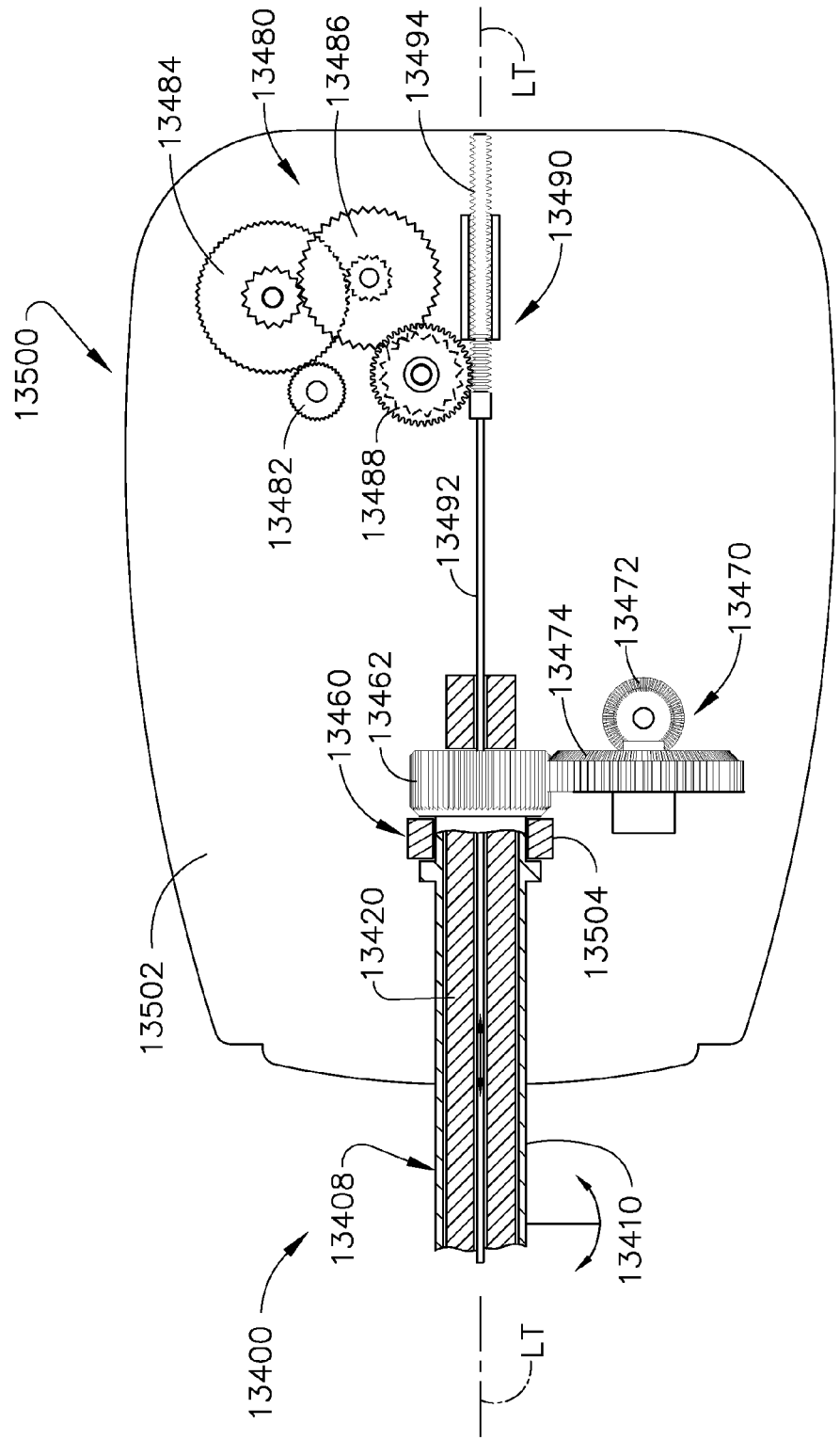
FIG. 147 is a top view of a tool mounting portion embodiment of a surgical tool embodiment of the present invention.

In at least one embodiment, the tool mounting portion 13500 is configured to receive a corresponding first rotary motion from the robotic controller 11001 and convert that first rotary motion to a primary rotary motion for rotating the rotatable proximal closure tube segment 13410 about a longitudinal tool axis LT-LT. As can be seen in FIG. 147, a proximal end 13460 of the proximal closure tube segment 13410 is rotatably supported within a cradle arrangement 13504 attached to a tool mounting plate 13502 of the tool mounting portion 13500. A rotation gear 13462 is formed on or attached to the proximal end 13460 of the closure tube segment 13410 for meshing engagement with a rotation drive assembly 13470 that is operably supported on the tool mounting plate 13502. In at least one embodiment, a rotation drive gear 13472 is coupled to a corresponding first one of the driven discs or elements 11304 on the adapter side of the tool mounting plate 13502 when the tool mounting portion 13500 is coupled to the tool holder 11270. See FIGS. 105 and 146. The rotation drive assembly 13470 further comprises a rotary driven gear 13474 that is rotatably supported on the tool mounting plate 13502 in meshing engagement with the rotation gear 13462 and the rotation drive gear 13472. Application of a first rotary control motion from the robotic controller 11001 through the tool holder 11270 and the adapter 11240 to the corresponding driven element 11304 will thereby cause rotation of the rotation drive gear 13472 by virtue of being operably coupled thereto. Rotation of the rotation drive gear 13472 ultimately results in the rotation of the closure tube segment 13410 to open and close the anvil 13524 as described above.

As indicated above, the surgical end effector 13412 employs a cutting instrument of the type and constructions described above. FIG. 147 illustrates one form of knife drive assembly 13480 for axially advancing a knife bar 13492 that is attached to such cutting instrument. One form of the knife drive assembly 13480 comprises a rotary drive gear 13482 that is coupled to a corresponding third one of the driven discs or elements 11304 on the adapter side of the tool mounting plate 13502 when the tool drive portion 13500 is coupled to the tool holder 11270. See FIGS. 105 and 147. The knife drive assembly 13480 further comprises a first rotary driven gear assembly 13484 that is rotatably supported on the tool mounting plate 15200. The first rotary driven gear assembly 13484 is in meshing engagement with a third rotary driven gear assembly 13486 that is rotatably supported on the tool mounting plate 13502 and which is in meshing engagement with a fourth rotary driven gear assembly 13488 that is in meshing engagement with a threaded portion 13494 of drive shaft assembly 13490 that is coupled to the knife bar 13492. Rotation of the rotary drive gear 13482 in a second rotary direction will result in the axial advancement of the drive shaft assembly 13490 and knife bar 13492 in the distal direction "DD". Conversely, rotation of the rotary drive gear 13482 in a secondary rotary direction (opposite to the second rotary direction) will cause the drive shaft assembly 13490 and the knife bar 13492 to move in the proximal direction.

Figure 148:
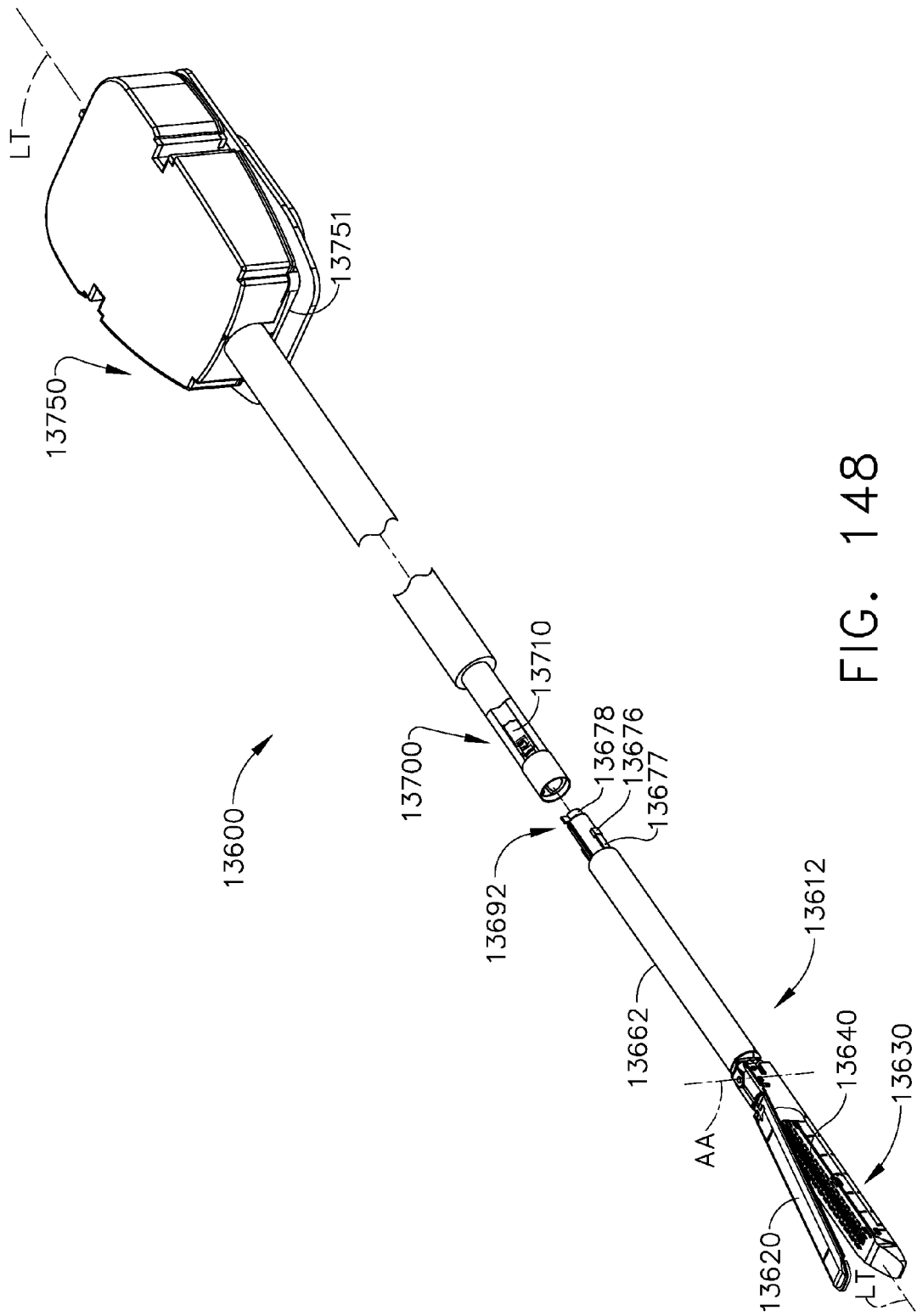
FIG. 148 is a perspective assembly view of another surgical tool embodiment of the present invention.
Figure 151:
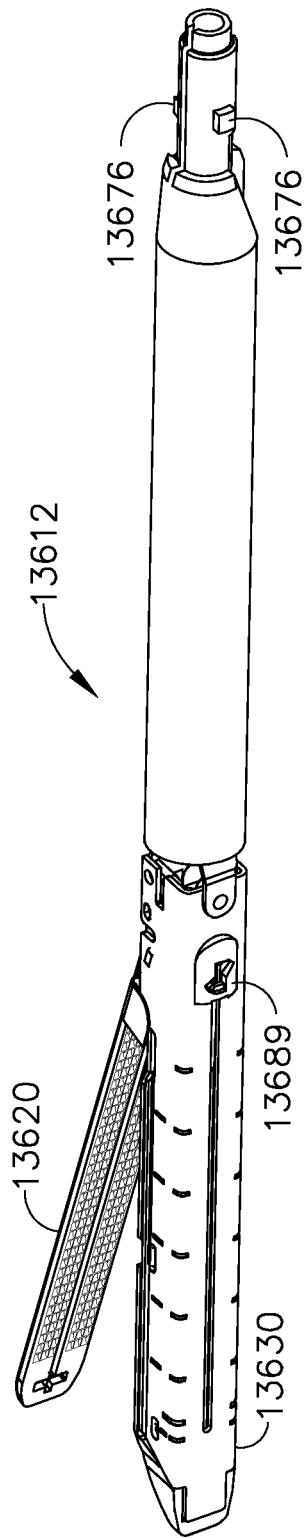
FIG. 151 is a bottom perspective view of the disposable loading unit of FIGS. 149 and 150.
Figure 152:
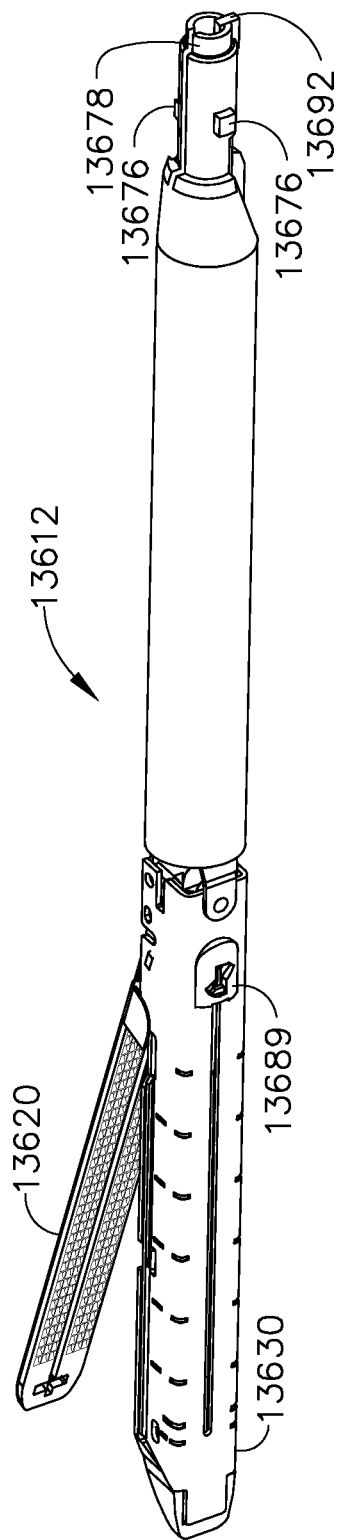
FIG. 152 is a bottom perspective view of another disposable loading unit embodiment that may be employed with various surgical tool embodiments of the present invention.

FIGS. 148-157 illustrate another surgical tool 13600 embodiment of the present invention that may be employed in connection with a robotic system 11000. As can be seen in FIG. 148, the tool 13600 includes an end effector in the form of a disposable loading unit 13612. Various forms of disposable loading units that may be employed in connection with tool 13600 are disclosed, for example, in U.S. Patent Application Publication No. US 2009/0206131 A1, entitled "End Effector Arrangements For a Surgical Cutting and Stapling Instrument", the disclosure of which is herein incorporated by reference in its entirety.

Figure 153:
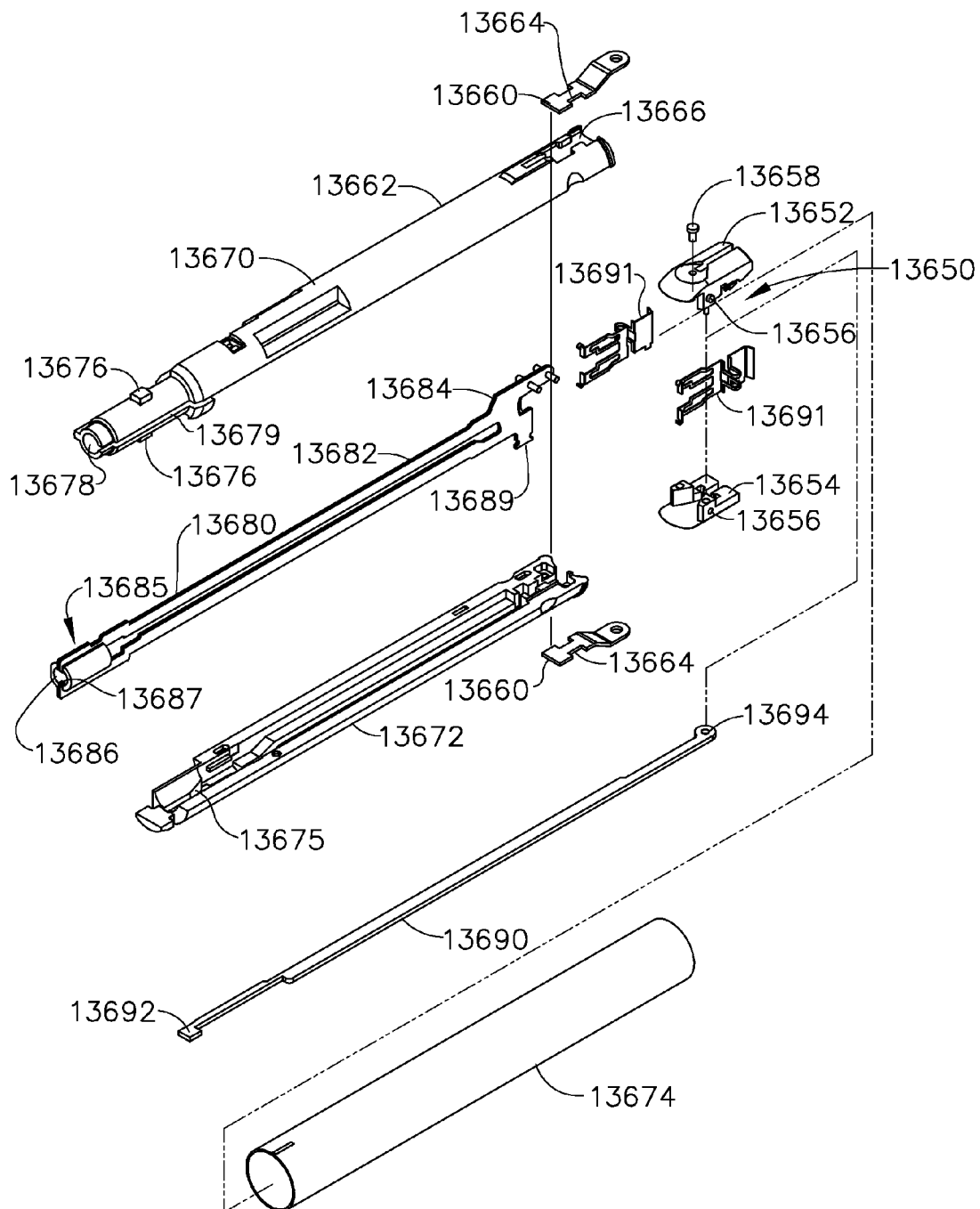
FIG. 153 is an exploded perspective view of a mounting portion of a disposable loading unit depicted in FIGS. 149-151.

In at least one form, the disposable loading unit 13612 includes an anvil assembly 13620 that is supported for pivotal travel relative to a carrier 13630 that operably supports a staple cartridge 13640 therein. A mounting assembly 13650 is pivotally coupled to the cartridge carrier 13630 to enable the carrier 13630 to pivot about an articulation axis AA-AA relative to a longitudinal tool axis LT-LT. Referring to FIG. 153, mounting assembly 13650 includes upper and lower mounting portions 13652 and 13654. Each mounting portion includes a threaded bore 13656 on each side thereof dimensioned to receive threaded bolts (not shown) for securing the proximal end of carrier 13630 thereto. A pair of centrally located pivot members 13658 extends between upper and lower mounting portions via a pair of coupling members 13660 which engage a distal end of a housing portion 13662. Coupling members 13660 each include an interlocking proximal portion 13664 configured to be received in grooves 13666 formed in the proximal end of housing portion 13662 to retain mounting assembly 13650 and housing portion 13662 in a longitudinally fixed position in relation thereto.

In various forms, housing portion 13662 of disposable loading unit 13614 includes an upper housing half 13670 and a lower housing half 13672 contained within an outer casing 13674. The proximal end of housing half 13670 includes engagement nubs 13676 for releasably engaging an elongated shaft 13700 and an insertion tip 13678. Nubs 13676 form a bayonet-type coupling with the distal end of the elongated shaft 13700 which will be discussed in further detail below. Housing halves 13670, 13672 define a channel 13675 for slidably receiving axial drive assembly 13680. A second articulation link 13690 is dimensioned to be slidably positioned within a slot 13679 formed between housing halves 13670, 13672. A pair of blow out plates 13691 are positioned adjacent the distal end of housing portion 13662 adjacent the distal end of axial drive assembly 13680 to prevent outward bulging of drive assembly 13680 during articulation of carrier 13630.

In various embodiments, the second articulation link 13690 includes at least one elongated metallic plate. Preferably, two or more metallic plates are stacked to form link 13690. The proximal end of articulation link 13690 includes a hook portion 13692 configured to engage first articulation link 13710 extending through the elongated shaft 13700. The distal end of the second articulation link 13690 includes a loop 13694 dimensioned to engage a projection formed on mounting assembly 13650. The projection is laterally offset from pivot pin 13658 such that linear movement of second articulation link 13690 causes mounting assembly 13650 to pivot about pivot pins 13658 to articulate the carrier 13630.

In various forms, axial drive assembly 13680 includes an elongated drive beam 13682 including a distal working head 13684 and a proximal engagement section 13685. Drive beam 13682 may be constructed from a single sheet of material or, preferably, multiple stacked sheets. Engagement section 13685 includes a pair of engagement fingers which are dimensioned and configured to mountingly engage a pair of corresponding retention slots formed in drive member 13686. Drive member 13686 includes a proximal porthole 13687 configured to receive the distal end 13722 of control rod 12720 (See FIG. 157) when the proximal end of disposable loading unit 13614 is engaged with elongated shaft 13700 of surgical tool 13600.

Referring to FIGS. 148 and 155-157, to use the surgical tool 13600, a disposable loading unit 13612 is first secured to the distal end of elongated shaft 13700. It will be appreciated that the surgical tool 13600 may include an articulating or a non-articulating disposable loading unit. To secure the disposable loading unit 13612 to the elongated shaft 13700, the distal end 13722 of control rod 13720 is inserted into insertion tip 13678 of disposable loading unit 13612, and insertion tip 13678 is slid longitudinally into the distal end of the elongated shaft 13700 in the direction indicated by arrow "A" in FIG. 155 such that hook portion 13692 of second articulation link 13690 slides within a channel 13702 in the elongated shaft 13700. Nubs 13676 will each be aligned in a respective channel (not shown) in elongated shaft 13700. When hook portion 13692 engages the proximal wall 13704 of channel 13702, disposable loading unit 13612 is rotated in the direction indicated by arrow "B" in FIGS. 154 and 157 to move hook portion 13692 of second articulation link 13690 into engagement with finger 13712 of first articulation link 13710. Nubs 13676 also form a "bayonet-type" coupling within annular channel 13703 in the elongated shaft 13700. During rotation of loading unit 13612, nubs 13676 engage cam surface 13732 (FIG. 155) of block plate 13730 to initially move plate 13730 in the direction indicated by arrow "C" in FIG. 155 to lock engagement member 13734 in recess 13721 of control rod 13720 to prevent longitudinal movement of control rod 13720 during attachment of disposable loading unit 13612. During the final degree of rotation, nubs 13676 disengage from cam surface 13732 to allow blocking plate 13730 to move in the direction indicated by arrow "D" in FIGS. 154 and 157 from behind engagement member 13734 to once again permit longitudinal movement of control rod 13720. While the above-described attachment method reflects that the disposable loading unit 13612 is manipulated relative to the elongated shaft 13700, the person of ordinary skill in the art will appreciate that the disposable loading unit 13612 may be supported in a stationary position and the robotic system 11000 may manipulate the elongated shaft portion 13700 relative to the disposable loading unit 13612 to accomplish the above-described coupling procedure.

Figure 158:
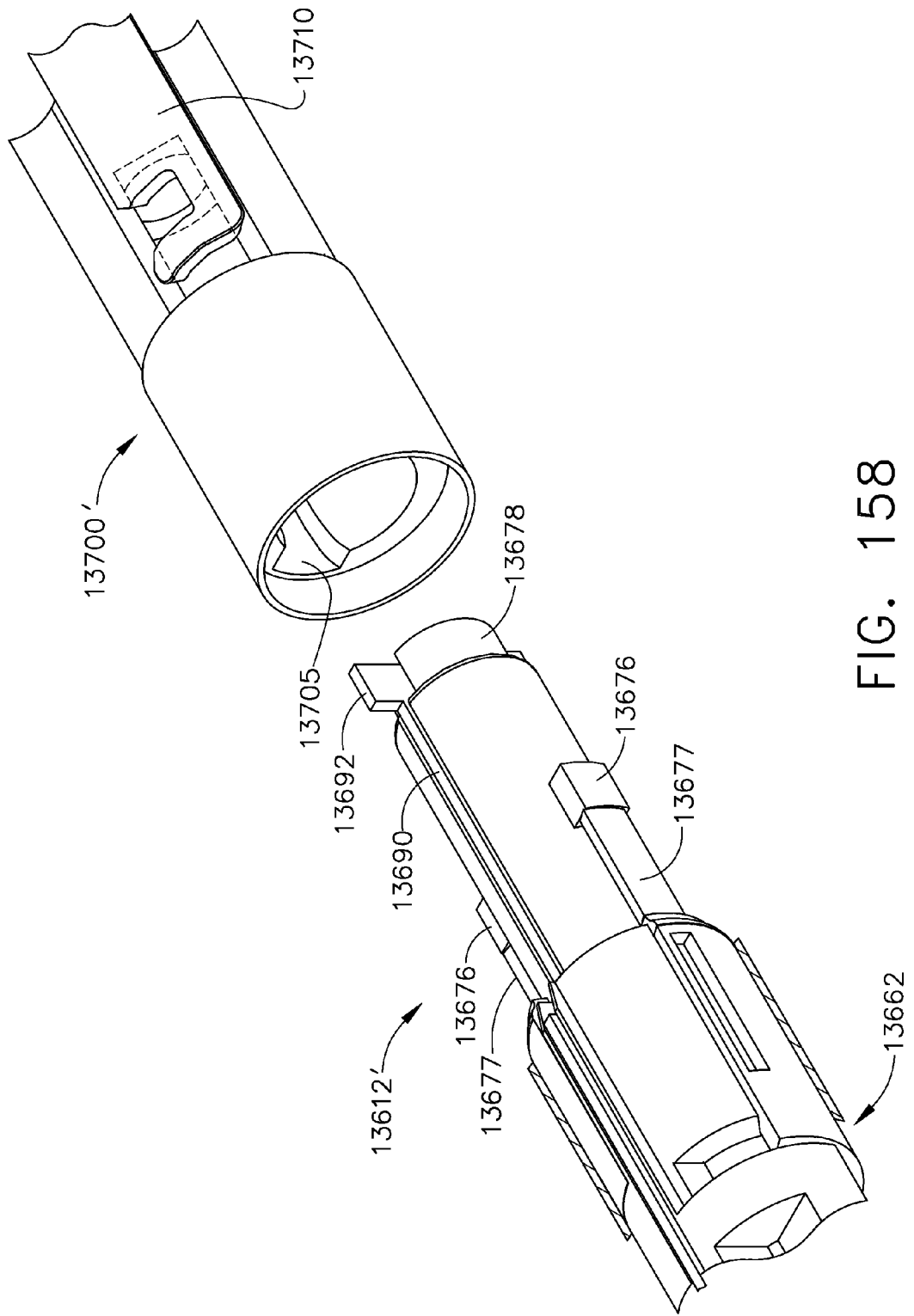

FIG. 158 illustrates another disposable loading unit 13612' that is attachable in a bayonet-type arrangement with the elongated shaft 13700' that is substantially identical to shaft 13700 except for the differences discussed below. As can be seen in FIG. 158, the elongated shaft 13700' has slots 13705 that extend for at least a portion thereof and which are configured to receive nubs 13676 therein. In various embodiments, the disposable loading unit 13612' includes arms 13677 extending therefrom which, prior to the rotation of disposable loading unit 13612', can be aligned, or at least substantially aligned, with nubs 13676 extending from housing portion 13662. In at least one embodiment, arms 13677 and nubs 13676 can be inserted into slots 13705 in elongated shaft 13700', for example, when disposable loading unit 13612' is inserted into elongated shaft 13700'. When disposable loading unit 13612' is rotated, arms 13677 can be sufficiently confined within slots 13705 such that slots 13705 can hold them in position, whereas nubs 13676 can be positioned such that they are not confined within slots 13705 and can be rotated relative to arms 13677. When rotated, the hook portion 13692 of the articulation link 13690 is engaged with the first articulation link 13710 extending through the elongated shaft 13700'.

Figure 159:
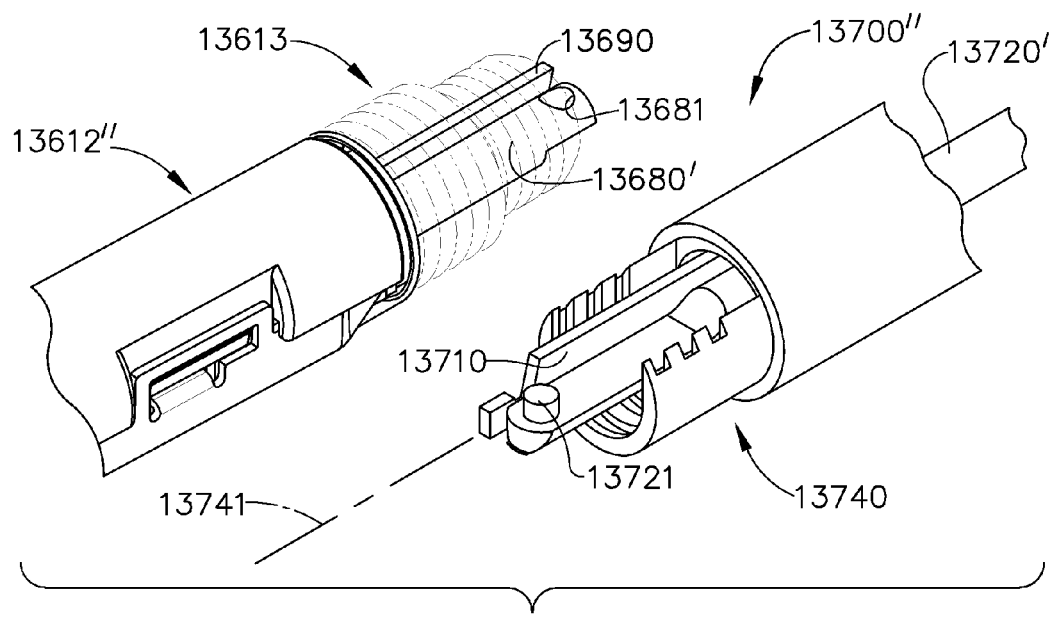
Figure 160:
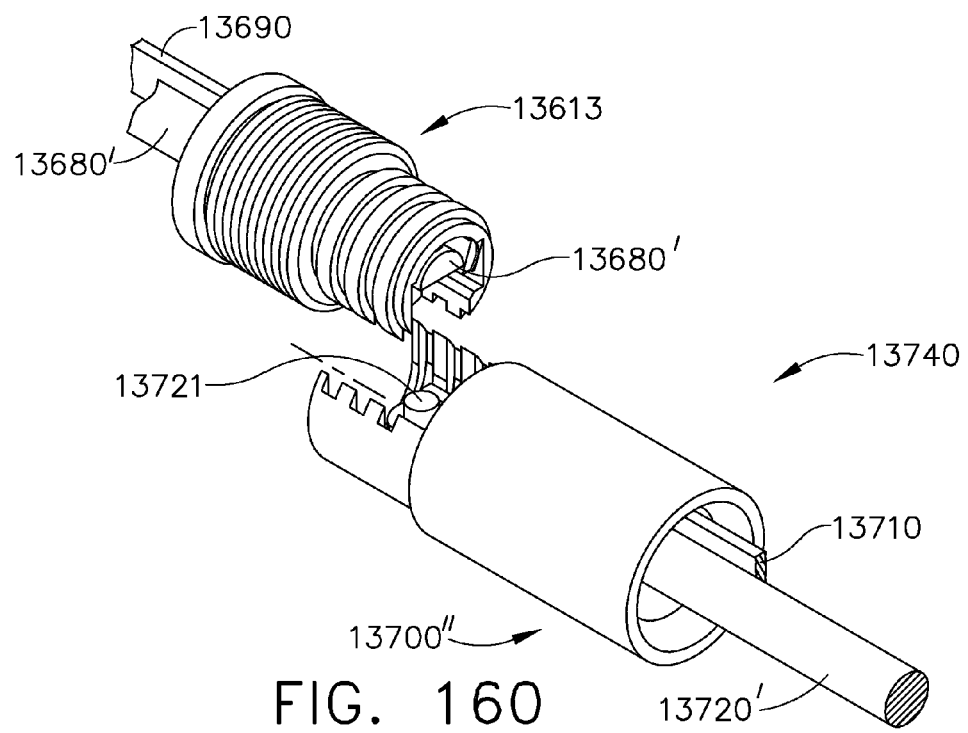

Other methods of coupling the disposable loading units to the end of the elongated shaft may be employed. For example, as shown in FIGS. 159 and 160, disposable loading unit 13612" can include connector portion 13613 which can be configured to be engaged with connector portion 13740 of the elongated shaft 13700". In at least one embodiment, connector portion 13613 can include at least one projection and/or groove which can be mated with at least one projection and/or groove of connector portion 13740. In at least one such embodiment, the connector portions can include co-operating dovetail portions. In various embodiments, the connector portions can be configured to interlock with one another and prevent, or at least inhibit, distal and/or proximal movement of disposable loading unit 13612" along axis 13741. In at least one embodiment, the distal end of the axial drive assembly 13680' can include aperture 13681 which can be configured to receive projection 13721 extending from control rod 13720'. In various embodiments, such an arrangement can allow disposable loading unit 13612" to be assembled to elongated shaft 13700 in a direction which is not collinear with or parallel to axis 13741. Although not illustrated, axial drive assembly 13680' and control rod 13720 can include any other suitable arrangement of projections and apertures to operably connect them to each other. Also in this embodiment, the first articulation link 13710 which can be operably engaged with second articulation link 13690.

Figure 161:
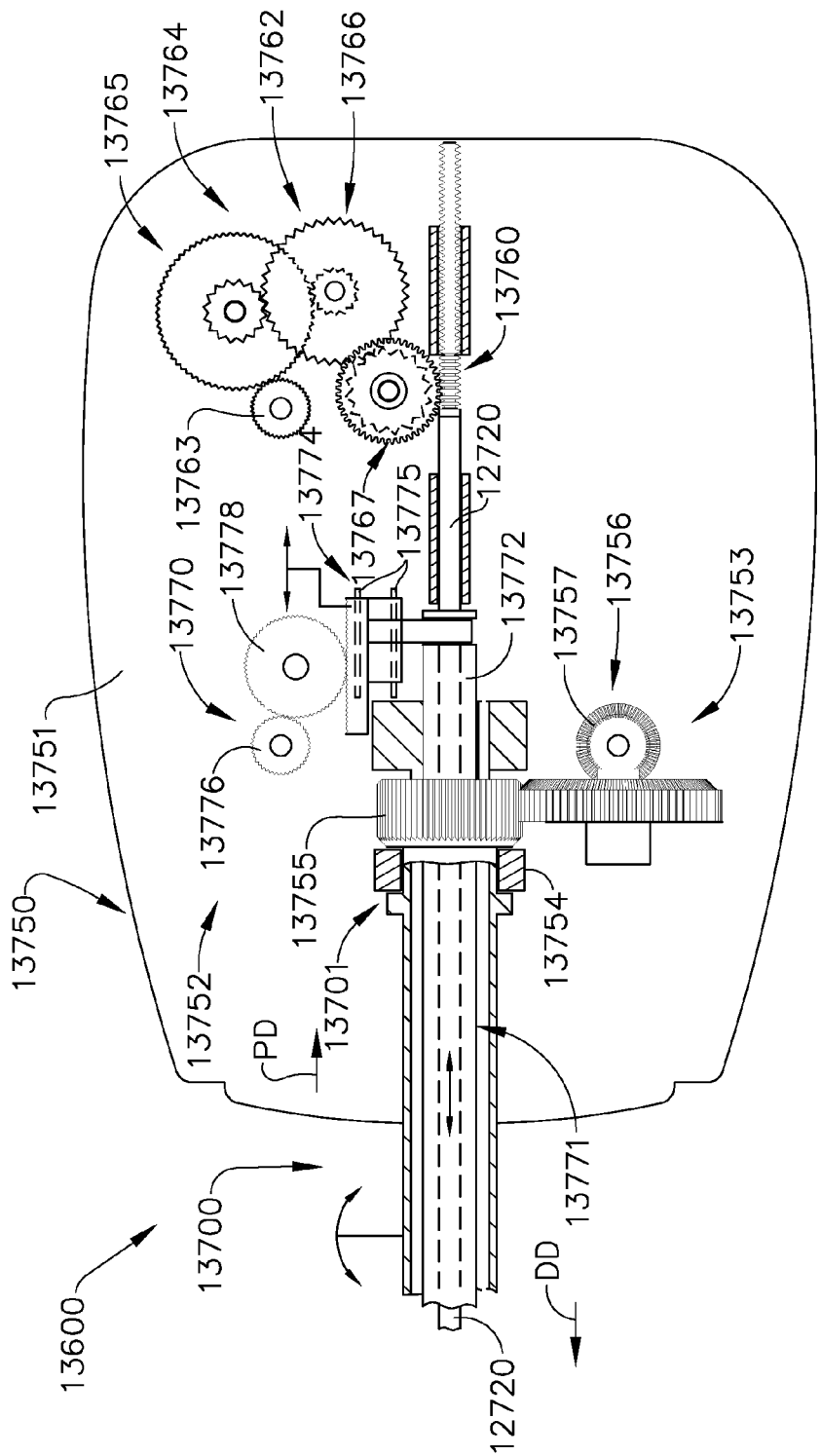

As can be seen in FIGS. 148 and 161, the surgical tool 13600 includes a tool mounting portion 13750. The tool mounting portion 13750 includes a tool mounting plate 13751 that is configured for attachment to the tool drive assembly 11010. The tool mounting portion operably supported a transmission arrangement 13752 thereon. In use, it may be desirable to rotate the disposable loading unit 13612 about the longitudinal tool axis defined by the elongated shaft 13700. In at least one embodiment, the transmission arrangement 13752 includes a rotational transmission assembly 13753 that is configured to receive a corresponding rotary output motion from the tool drive assembly 11010 of the robotic system 11000 and convert that rotary output motion to a rotary control motion for rotating the elongated shaft 13700 (and the disposable loading unit 13612) about the longitudinal tool axis LT-LT. As can be seen in FIG. 161, a proximal end 13701 of the elongated shaft 13700 is rotatably supported within a cradle arrangement 13754 that is attached to the tool mounting plate 13751 of the tool mounting portion 13750. A rotation gear 13755 is formed on or attached to the proximal end 13701 of the elongated shaft 13700 for meshing engagement with a rotation gear assembly 13756 operably supported on the tool mounting plate 13751. In at least one embodiment, a rotation drive gear 13757 drivingly coupled to a corresponding first one of the driven discs or elements 11304 on the adapter side of the tool mounting plate 13751 when the tool mounting portion 13750 is coupled to the tool drive assembly 11010. The rotation transmission assembly 13753 further comprises a rotary driven gear 13758 that is rotatably supported on the tool mounting plate 13751 in meshing engagement with the rotation gear 13755 and the rotation drive gear 13757. Application of a first rotary output motion from the robotic system 11000 through the tool drive assembly 11010 to the corresponding driven element 11304 will thereby cause rotation of the rotation drive gear 13757 by virtue of being operably coupled thereto. Rotation of the rotation drive gear 13757 ultimately results in the rotation of the elongated shaft 13700 (and the disposable loading unit 13612) about the longitudinal tool axis LT-LT (primary rotary motion).

As can be seen in FIG. 161, a drive shaft assembly 13760 is coupled to a proximal end of the control rod 12720. In various embodiments, the control rod 12720 is axially advanced in the distal and proximal directions by a knife/closure drive transmission 13762. One form of the knife/closure drive assembly 13762 comprises a rotary drive gear 13763 that is coupled to a corresponding second one of the driven rotatable body portions, discs or elements 11304 on the adapter side of the tool mounting plate 13751 when the tool mounting portion 13750 is coupled to the tool holder 11270. The rotary driven gear 13763 is in meshing driving engagement with a gear train, generally depicted as 13764. In at least one form, the gear train 13764 further comprises a first rotary driven gear assembly 13765 that is rotatably supported on the tool mounting plate 13751. The first rotary driven gear assembly 13765 is in meshing engagement with a second rotary driven gear assembly 13766 that is rotatably supported on the tool mounting plate 13751 and which is in meshing engagement with a third rotary driven gear assembly 13767 that is in meshing engagement with a threaded portion 13768 of the drive shaft assembly 13760. Rotation of the rotary drive gear 13763 in a second rotary direction will result in the axial advancement of the drive shaft assembly 13760 and control rod 12720 in the distal direction "DD". Conversely, rotation of the rotary drive gear 13763 in a secondary rotary direction which is opposite to the second rotary direction will cause the drive shaft assembly 13760 and the control rod 12720 to move in the proximal direction. When the control rod 12720 moves in the distal direction, it drives the drive beam 13682 and the working head 13684 thereof distally through the surgical staple cartridge 13640. As the working head 13684 is driven distally, it operably engages the anvil 13620 to pivot it to a closed position.

The cartridge carrier 13630 may be selectively articulated about articulation axis AA-AA by applying axial articulation control motions to the first and second articulation links 13710 and 13690. In various embodiments, the transmission arrangement 13752 further includes an articulation drive 13770 that is operably supported on the tool mounting plate 13751. More specifically and with reference to FIG. 161, it can be seen that a proximal end portion 13772 of an articulation drive shaft 13771 configured to operably engage with the first articulation link 13710 extends through the rotation gear 13755 and is rotatably coupled to a shifter rack gear 13774 that is slidably affixed to the tool mounting plate 13751 through slots 13775. The articulation drive 13770 further comprises a shifter drive gear 13776 that is coupled to a corresponding third one of the driven discs or elements 11304 on the adapter side of the tool mounting plate 13751 when the tool mounting portion 13750 is coupled to the tool holder 11270. The articulation drive assembly 13770 further comprises a shifter driven gear 13778 that is rotatably supported on the tool mounting plate 13751 in meshing engagement with the shifter drive gear 13776 and the shifter rack gear 13774. Application of a third rotary output motion from the robotic system 11000 through the tool drive assembly 11010 to the corresponding driven element 11304 will thereby cause rotation of the shifter drive gear 13776 by virtue of being operably coupled thereto. Rotation of the shifter drive gear 13776 ultimately results in the axial movement of the shifter gear rack 13774 and the articulation drive shaft 13771. The direction of axial travel of the articulation drive shaft 13771 depends upon the direction in which the shifter drive gear 13776 is rotated by the robotic system 11000. Thus, rotation of the shifter drive gear 13776 in a first rotary direction will result in the axial movement of the articulation drive shaft 13771 in the proximal direction "PD" and cause the cartridge carrier 13630 to pivot in a first direction about articulation axis AA-AA. Conversely, rotation of the shifter drive gear 13776 in a second rotary direction (opposite to the first rotary direction) will result in the axial movement of the articulation drive shaft 13771 in the distal direction "DD" to thereby cause the cartridge carrier 13630 to pivot about articulation axis AA-AA in an opposite direction.

Figure 162:
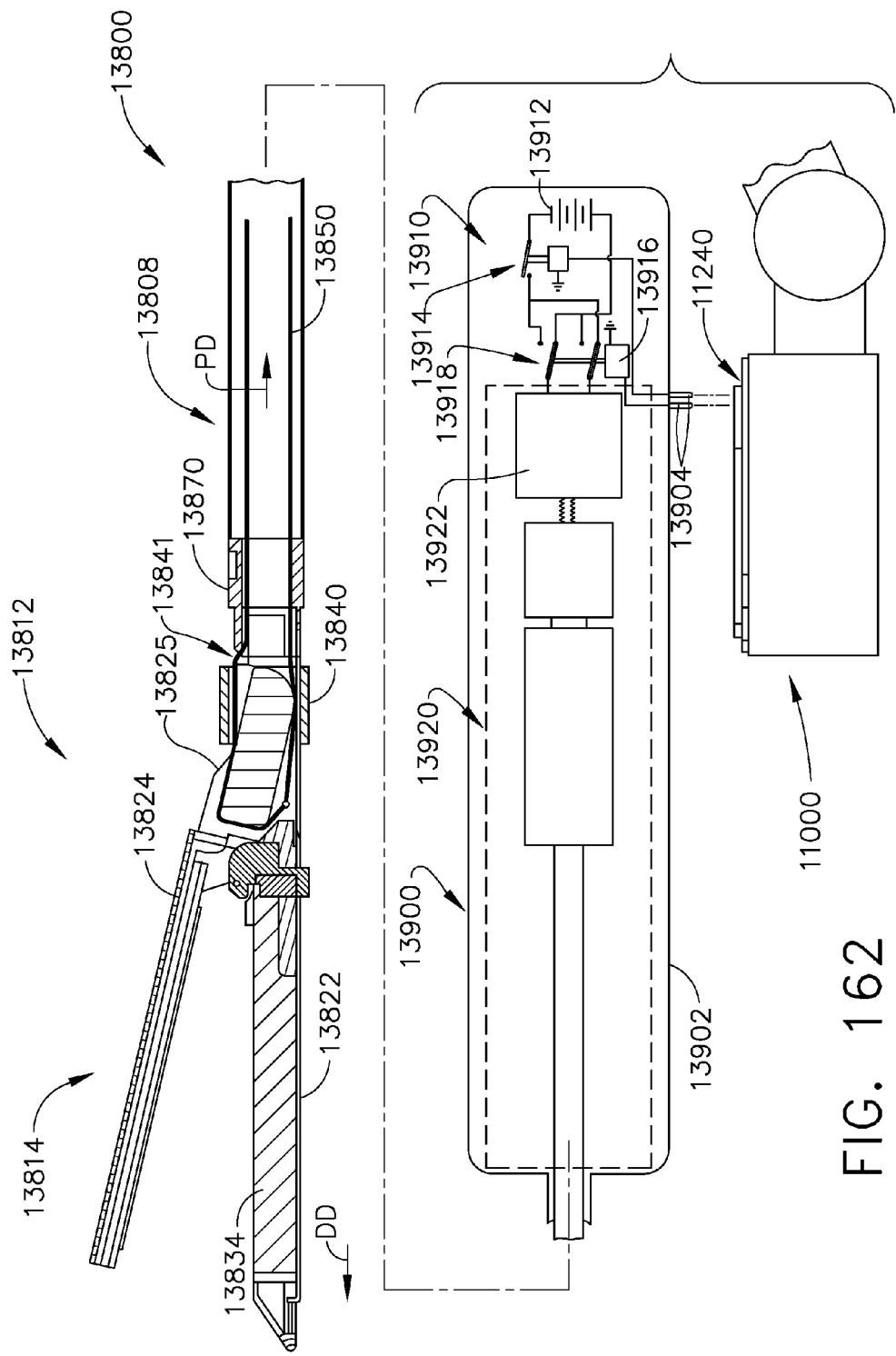

FIG. 162 illustrates yet another surgical tool 13800 embodiment of the present invention that may be employed with a robotic system 11000. As can be seen in FIG. 162, the surgical tool 13800 includes a surgical end effector 13812 in the form of an endocutter 13814 that employs various cable-driven components. Various forms of cable driven endocutters are disclosed, for example, in U.S. Pat. No. 7,726,537, entitled "Surgical Stapler With Universal Articulation and Tissue Pre-Clamp" and U.S. Patent Application Publication No. US 2008/0308603A1, entitled "Cable Driven Surgical Stapling and Cutting Instrument With Improved Cable Attachment Arrangements", the disclosures of each are herein incorporated by reference in their respective entireties. Such endocutters 13814 may be referred to as a "disposable loading unit" because they are designed to be disposed of after a single use. However, the various unique and novel arrangements of various embodiments of the present invention may also be employed in connection with cable driven end effectors that are reusable.

As can be seen in FIG. 163, in at least one form, the endocutter 13814 includes an elongated channel 13822 that operably supports a surgical staple cartridge 13834 therein. An anvil 13824 is pivotally supported for movement relative to the surgical staple cartridge 13834. The anvil 13824 has a cam surface 13825 that is configured for interaction with a preclamping collar 13840 that is supported for axial movement relative thereto. The end effector 13814 is coupled to an elongated shaft assembly 13808 that is attached to a tool mounting portion 13900. In various embodiments, a closure cable 13850 is employed to move pre-clamping collar 13840 distally onto and over cam surface 13825 to close the anvil 13824 relative to the surgical staple cartridge 13834 and compress the tissue therebetween. Preferably, closure cable 13850 attaches to the pre-clamping collar 13840 at or near point 13841 and is fed through a passageway in anvil 13824 (or under a proximal portion of anvil 13824) and fed proximally through shaft 13808. Actuation of closure cable 13850 in the proximal direction "PD" forces pre-clamping collar 13840 distally against cam surface 13825 to close anvil 13824 relative to staple cartridge assembly 13834. A return mechanism, e.g., a spring, cable system or the like, may be employed to return pre-clamping collar 13840 to a pre-clamping orientation which re-opens the anvil 13824.

The elongated shaft assembly 13808 may be cylindrical in shape and define a channel 13811 which may be dimensioned to receive a tube adapter 13870. See FIG. 163. In various embodiments, the tube adapter 13870 may be slidingly received in friction-fit engagement with the internal channel of elongated shaft 13808. The outer surface of the tube adapter 13870 may further include at least one mechanical interface, e.g., a cutout or notch 13871, oriented to mate with a corresponding mechanical interface, e.g., a radially inwardly extending protrusion or detent (not shown), disposed on the inner periphery of internal channel 13811 to lock the tube adapter 13870 to the elongated shaft 13808. In various embodiments, the distal end of tube adapter 13870 may include a pair of opposing flanges 13872*a* and 13872*b* which define a cavity for pivotably receiving a pivot block 13873 therein. Each flange 13872*a* and 13872*b* may include an aperture 13874*a* and 13874*b* that is oriented to receive a pivot pin 13875 that extends through an aperture in pivot block 13873 to allow pivotable movement of pivot block 13873 about an axis that is perpendicular to longitudinal tool axis "LT-LT". The channel 13822 may be formed with two upwardly extending flanges 13823*a*, 13823*b* that have apertures therein, which are dimensioned to receive a pivot pin 13827. In turn, pivot pin 13875 mounts through apertures in pivot block 13873 to permit rotation of the surgical end effector 13814 about the "Y" axis as needed during a given surgical procedure. Rotation of pivot block 13873 about pin 13875 along "Z" axis rotates the surgical end effector 13814 about the "Z" axis. See FIG. 163. Other methods of fastening the elongated channel 13822 to the pivot block 13873 may be effectively employed without departing from the spirit and scope of the present invention.

The surgical staple cartridge 13834 can be assembled and mounted within the elongated channel 13822 during the manufacturing or assembly process and sold as part of the surgical end effector 13812, or the surgical staple cartridge 13834 may be designed for selective mounting within the elongated channel 13822 as needed and sold separately, e.g., as a single use replacement, replaceable or disposable staple cartridge assembly. It is within the scope of this disclosure that the surgical end effector 13812 may be pivotally, operatively, or integrally attached, for example, to distal end 13809 of the elongated shaft assembly 13808 of a disposable surgical stapler. As is known, a used or spent disposable loading unit 13814 can be removed from the elongated shaft assembly 13808 and replaced with an unused disposable unit. The endocutter 13814 may also preferably include an actuator, preferably a dynamic clamping member 13860, a sled 13862, as well as staple pushers (not shown) and staples (not shown) once an unspent or unused cartridge 13834 is mounted in the elongated channel 13822. See FIG. 163.

In various embodiments, the dynamic clamping member 13860 is associated with, e.g., mounted on and rides on, or with or is connected to or integral with and/or rides behind sled 13862. It is envisioned that dynamic clamping member 13860 can have cam wedges or cam surfaces attached or integrally formed or be pushed by a leading distal surface thereof. In various embodiments, dynamic clamping member 13860 may include an upper portion 13863 having a transverse aperture 13864 with a pin 13865 mountable or mounted therein, a central support or upward extension 13866 and substantially T-shaped bottom flange 13867 which cooperate to slidingly retain dynamic clamping member 13860 along an ideal cutting path during longitudinal, distal movement of sled 13862. The leading cutting edge 13868, here, knife blade 13869, is dimensioned to ride within slot 13835 of staple cartridge assembly 13834 and separate tissue once stapled. As used herein, the term "knife assembly" may include the aforementioned dynamic clamping member 13860, knife 13869, and sled 13862 or other knife/beam/sled drive arrangements and cutting instrument arrangements. In addition, the various embodiments of the present invention may be employed with knife assembly/cutting instrument arrangements that may be entirely supported in the staple cartridge 13834 or partially supported in the staple cartridge 13834 and elongated channel 13822 or entirely supported within the elongated channel 13822.

In various embodiments, the dynamic clamping member 13860 may be driven in the proximal and distal directions by a cable drive assembly 13870. In one non-limiting form, the cable drive assembly comprises a pair of advance cables 13880, 13882 and a firing cable 13884. FIGS. 164 and 165 illustrate the cables 13880, 13882, 13884 in diagrammatic form. As can be seen in those Figures, a first advance cable 13880 is operably supported on a first distal cable transition support 13885 which may comprise, for example, a pulley, rod, capstan, etc. that is attached to the distal end of the elongated channel 13822 and a first proximal cable transition support 13886 which may comprise, for example, a pulley, rod, capstan, etc. that is operably supported by the elongated channel 13822. A distal end 13881 of the first advance cable 13880 is affixed to the dynamic clamping assembly 13860. The second advance cable 13882 is operably supported on a second distal cable transition support 13887 which may, for example, comprise a pulley, rod, capstan etc. that is mounted to the distal end of the elongated channel 13822 and a second proximal cable transition support 13888 which may, for example, comprise a pulley, rod, capstan, etc. mounted to the proximal end of the elongated channel 13822. The proximal end 13883 of the second advance cable 13882 may be attached to the dynamic clamping assembly 13860. Also in these embodiments, an endless firing cable 13884 is employed and journaled on a support 13889 that may comprise a pulley, rod, capstan, etc. mounted within the elongated shaft 13808. In one embodiment, the retract cable 13884 may be formed in a loop and coupled to a connector 13889' that is fixedly attached to the first and second advance cables 13880, 13882.

Various non-limiting embodiments of the present invention include a cable drive transmission 13920 that is operably supported on a tool mounting plate 13902 of the tool mounting portion 13900. The tool mounting portion 13900 has an array of electrical connecting pins 13904 which are configured to interface with the slots 11258 (FIG. 104) in the adapter 11240'. Such arrangement permits the robotic system 11000 to provide control signals to a control circuit 13910 of the tool 13800. While the interface is described herein with reference to mechanical, electrical, and magnetic coupling elements, it should be understood that a wide variety of telemetry modalities might be used, including infrared, inductive coupling, or the like.

Control circuit 13910 is shown in schematic form in FIG. 162. In one form or embodiment, the control circuit 13910 includes a power supply in the form of a battery 13912 that is coupled to an on-off solenoid powered switch 13914. In other embodiments, however, the power supply may comprise a source of alternating current. Control circuit 13910 further includes an on/off solenoid 13916 that is coupled to a double pole switch 13918 for controlling motor rotation direction. Thus, when the robotic system 11000 supplies an appropriate control signal, switch 13914 will permit battery 13912 to supply power to the double pole switch 13918. The robotic system 11000 will also supply an appropriate signal to the double pole switch 13918 to supply power to a shifter motor 13922.

Turning to FIGS. 166-171, at least one embodiment of the cable drive transmission 13920 comprises a drive pulley 13930 that is operably mounted to a drive shaft 13932 that is attached to a driven element 11304 of the type and construction described above that is designed to interface with a corresponding drive element 11250 of the adapter 11240. See FIGS. 104 and 169. Thus, when the tool mounting portion 13900 is operably coupled to the tool holder 11270, the robot system 11000 can apply rotary motion to the drive pulley 13930 in a desired direction. A first drive member or belt 13934 drivingly engages the drive pulley 13930 and a second drive shaft 13936 that is rotatably supported on a shifter yoke 13940. The shifter yoke 13940 is operably coupled to the shifter motor 13922 such that rotation of the shaft 13923 of the shifter motor 13922 in a first direction will shift the shifter yoke in a first direction "FD" and rotation of the shifter motor shaft 13923 in a second direction will shift the shifter yoke 13940 in a second direction "SD". Other embodiments of the present invention may employ a shifter solenoid arrangement for shifting the shifter yoke in said first and second directions.

As can be seen in FIGS. 166-169, a closure drive gear 13950 mounted to a second drive shaft 13936 and is configured to selectively mesh with a closure drive assembly, generally designated as 13951. Likewise a firing drive gear 13960 is also mounted to the second drive shaft 13936 and is configured to selectively mesh with a firing drive assembly generally designated as 13961. Rotation of the second drive shaft 13936 causes the closure drive gear 13950 and the firing drive gear 13960 to rotate. In one non-limiting embodiment, the closure drive assembly 13951 comprises a closure driven gear 13952 that is coupled to a first closure pulley 13954 that is rotatably supported on a third drive shaft 13956. The closure cable 13850 is drivingly received on the first closure pulley 13954 such that rotation of the closure driven gear 13952 will drive the closure cable 13850. Likewise, the firing drive assembly 13961 comprises a firing driven gear 13962 that is coupled to a first firing pulley 13964 that is rotatably supported on the third drive shaft 13956. The first and second driving pulleys 13954 and 13964 are independently rotatable on the third drive shaft 13956. The firing cable 13884 is drivingly received on the first firing pulley 13964 such that rotation of the firing driven gear 13962 will drive the firing cable 13884.

Also in various embodiments, the cable drive transmission 13920 further includes a braking assembly 13970. In at least one embodiment, for example, the braking assembly 13970 includes a closure brake 13972 that comprises a spring arm 13973 that is attached to a portion of the transmission housing 13971. The closure brake 13972 has a gear lug 13974 that is sized to engage the teeth of the closure driven gear 13952 as will be discussed in further detail below. The braking assembly 13970 further includes a firing brake 13976 that comprises a spring arm 13977 that is attached to another portion of the transmission housing 13971. The firing brake 13976 has a gear lug 13978 that is sized to engage the teeth of the firing driven gear 13962.

At least one embodiment of the surgical tool 13800 may be used as follows. The tool mounting portion 13900 is operably coupled to the interface 11240 of the robotic system 11000. The controller or control unit of the robotic system is operated to locate the tissue to be cut and stapled between the open anvil 13824 and the staple cartridge 13834. When in that initial position, the braking assembly 13970 has locked the closure driven gear 13952 and the firing driven gear 13962 such that they cannot rotate. That is, as shown in FIG. 167, the gear lug 13974 is in locking engagement with the closure driven gear 13952 and the gear lug 13978 is in locking engagement with the firing driven gear 13962. Once the surgical end effector 13814 has been properly located, the controller 11001 of the robotic system 11000 will provide a control signal to the shifter motor 13922 (or shifter solenoid) to move the shifter yoke 13940 in the first direction. As the shifter yoke 13940 is moved in the first direction, the closure drive gear 13950 moves the gear lug 13974 out of engagement with the closure driven gear 13952 as it moves into meshing engagement with the closure driven gear 13952. As can be seen in FIG. 166, when in that position, the gear lug 13978 remains in locking engagement with the firing driven gear 13962 to prevent actuation of the firing system. Thereafter, the robotic controller 11001 provides a first rotary actuation motion to the drive pulley 13930 through the interface between the driven element 11304 and the corresponding components of the tool holder 11240. As the drive pulley 13930 is rotated in the first direction, the closure cable 13850 is rotated to drive the preclamping collar 13840 into closing engagement with the cam surface 13825 of the anvil 13824 to move it to the closed position thereby clamping the target tissue between the anvil 13824 and the staple cartridge 13834. See FIG. 162. Once the anvil 13824 has been moved to the closed position, the robotic controller 11001 stops the application of the first rotary motion to the drive pulley 13930. Thereafter, the robotic controller 11001 may commence the firing process by sending another control signal to the shifter motor 13922 (or shifter solenoid) to cause the shifter yoke to move in the second direction "SD" as shown in FIG. 168. As the shifter yoke 13940 is moved in the second direction, the firing drive gear 13960 moves the gear lug 13978 out of engagement with the firing driven gear 13962 as it moves into meshing engagement with the firing driven gear 13962. As can be seen in FIG. 168, when in that position, the gear lug 13974 remains in locking engagement with the closure driven gear 13952 to prevent actuation of the closure system. Thereafter, the robotic controller 11001 is activated to provide the first rotary actuation motion to the drive pulley 13930 through the interface between the driven element 11304 and the corresponding components of the tool holder 11240. As the drive pulley 13930 is rotated in the first direction, the firing cable 13884 is rotated to drive the dynamic clamping member 13860 in the distal direction "DD" thereby firing the stapes and cutting the tissue clamped in the end effector 13814. Once the robotic system 11000 determines that the dynamic clamping member 13860 has reached its distal most position—either through sensors or through monitoring the amount of rotary input applied to the drive pulley 13930, the controller 11001 may then apply a second rotary motion to the drive pulley 13930 to rotate the closure cable 13850 in an opposite direction to cause the dynamic clamping member 13860 to be retracted in the proximal direction "PD". Once the dynamic clamping member has been retracted to the starting position, the application of the second rotary motion to the drive pulley 13930 is discontinued. Thereafter, the shifter motor 13922 (or shifter solenoid) is powered to move the shifter yoke 13940 to the closure position (FIG. 166). Once the closure drive gear 13950 is in meshing engagement with the closure driven gear 13952, the robotic controller 11001 may once again apply the second rotary motion to the drive pulley 13930. Rotation of the drive pulley 13930 in the second direction causes the closure cable 13850 to retract the preclamping collar 13840 out of engagement with the cam surface 13825 of the anvil 13824 to permit the anvil 13824 to move to an open position (by a spring or other means) to release the stapled tissue from the surgical end effector 13814.

FIG. 172 illustrates a surgical tool 14000 that employs a gear driven firing bar 14092 as shown in FIGS. 173-175. This embodiment includes an elongated shaft assembly 14008 that extends from a tool mounting portion 14100. The tool mounting portion 14100 includes a tool mounting plate 14102 that operable supports a transmission arrangement 14103 thereon. The elongated shaft assembly 14008 includes a rotatable proximal closure tube 14010 that is rotatably journaled on a proximal spine member 14020 that is rigidly coupled to the tool mounting plate 14102. The proximal spine member 14020 has a distal end that is coupled to an elongated channel portion 14022 of a surgical end effector 14012. The surgical end effector 14012 may be substantially similar to surgical end effector 13412 described above. In addition, the anvil 14024 of the surgical end effector 14012 may be opened and closed by a distal closure tube 14030 that operably interfaces with the proximal closure tube 14010. Distal closure tube 14030 is identical to distal closure tube 13430 described above. Similarly, proximal closure tube 14010 is identical to proximal closure tube segment 13410 described above.

Anvil 14024 is opened and closed by rotating the proximal closure tube 14010 in manner described above with respect to distal closure tube 13410. In at least one embodiment, the transmission arrangement comprises a closure transmission, generally designated as 14011. As will be further discussed below, the closure transmission 14011 is configured to receive a corresponding first rotary motion from the robotic system 11000 and convert that first rotary motion to a primary rotary motion for rotating the rotatable proximal closure tube 14010 about the longitudinal tool axis LT-LT. As can be seen in FIG. 175, a proximal end 14060 of the proximal closure tube 14010 is rotatably supported within a cradle arrangement 14104 that is attached to a tool mounting plate 14102 of the tool mounting portion 14100. A rotation gear 14062 is formed on or attached to the proximal end 14060 of the closure tube segment 14010 for meshing engagement with a rotation drive assembly 14070 that is operably supported on the tool mounting plate 14102. In at least one embodiment, a rotation drive gear 14072 is coupled to a corresponding first one of the driven discs or elements 11304 on the adapter side of the tool mounting plate 14102 when the tool mounting portion 14100 is coupled to the tool holder 11270. See FIGS. 105 and 175. The rotation drive assembly 14070 further comprises a rotary driven gear 14074 that is rotatably supported on the tool mounting plate 14102 in meshing engagement with the rotation gear 14062 and the rotation drive gear 14072. Application of a first rotary control motion from the robotic system 11000 through the tool holder 11270 and the adapter 11240 to the corresponding driven element 11304 will thereby cause rotation of the rotation drive gear 14072 by virtue of being operably coupled thereto. Rotation of the rotation drive gear 14072 ultimately results in the rotation of the closure tube segment 14010 to open and close the anvil 14024 as described above.

As indicated above, the end effector 14012 employs a cutting element 13860 as shown in FIGS. 173 and 174. In at least one non-limiting embodiment, the transmission arrangement 14103 further comprises a knife drive transmission that includes a knife drive assembly 14080. FIG. 175 illustrates one form of knife drive assembly 14080 for axially advancing the knife bar 14092 that is attached to such cutting element using cables as described above with respect to surgical tool 13800. In particular, the knife bar 14092 replaces the firing cable 13884 employed in an embodiment of surgical tool 13800. One form of the knife drive assembly 14080 comprises a rotary drive gear 14082 that is coupled to a corresponding second one of the driven discs or elements 11304 on the adapter side of the tool mounting plate 14102 when the tool mounting portion 14100 is coupled to the tool holder 11270. See FIGS. 105 and 175. The knife drive assembly 14080 further comprises a first rotary driven gear assembly 14084 that is rotatably supported on the tool mounting plate 14102. The first rotary driven gear assembly 14084 is in meshing engagement with a third rotary driven gear assembly 14086 that is rotatably supported on the tool mounting plate 14102 and which is in meshing engagement with a fourth rotary driven gear assembly 14088 that is in meshing engagement with a threaded portion 14094 of drive shaft assembly 14090 that is coupled to the knife bar 14092. Rotation of the rotary drive gear 14082 in a second rotary direction will result in the axial advancement of the drive shaft assembly 14090 and knife bar 14092 in the distal direction "DD". Conversely, rotation of the rotary drive gear 14082 in a secondary rotary direction (opposite to the second rotary direction) will cause the drive shaft assembly 14090 and the knife bar 14092 to move in the proximal direction. Movement of the firing bar 14092 in the proximal direction "PD" will drive the cutting element 31860 in the distal direction "DD". Conversely, movement of the firing bar 41092 in the distal direction "DD" will result in the movement of the cutting element 13860 in the proximal direction "PD".

FIGS. 176-182 illustrate yet another surgical tool 15000 that may be effectively employed in connection with a robotic system 11000. In various forms, the surgical tool 15000 includes a surgical end effector 15012 in the form of a surgical stapling instrument that includes an elongated channel 15020 and a pivotally translatable clamping member, such as an anvil 15070, which are maintained at a spacing that assures effective stapling and severing of tissue clamped in the surgical end effector 15012. As can be seen in FIG. 178, the elongated channel 15020 may be substantially U-shaped in cross-section and be fabricated from, for example, titanium, 203 stainless steel, 304 stainless steel, 416 stainless steel, 17-4 stainless steel, 17-7 stainless steel, 6061 or 7075 aluminum, chromium steel, ceramic, etc. A substantially U-shaped metal channel pan 15022 may be supported in the bottom of the elongated channel 15020 as shown.

Various embodiments include an actuation member in the form of a sled assembly 15030 that is operably supported within the surgical end effector 15012 and axially movable therein between a starting position and an ending position in response to control motions applied thereto. In some forms, the metal channel pan 15022 has a centrally-disposed slot 15024 therein to movably accommodate a base portion 15032 of the sled assembly 15030. The base portion 15032 includes a foot portion 15034 that is sized to be slidably received in a slot 15021 in the elongated channel 15020. See FIG. 178. As can be seen in FIGS. 177, 178, 181, and 182, the base portion 15032 of sled assembly 15030 includes an axially extending threaded bore 15036 that is configured to be threadedly received on a threaded drive shaft 15130 as will be discussed in further detail below. In addition, the sled assembly 15030 includes an upstanding support portion 15038 that supports a tissue cutting blade or tissue cutting instrument 15040. The upstanding support portion 15038 terminates in a top portion 15042 that has a pair of laterally extending retaining fins 15044 protruding therefrom. As shown in FIG. 178, the fins 15044 are positioned to be received within corresponding slots 15072 in anvil 15070. The fins 15044 and the foot 15034 serve to retain the anvil 15070 in a desired spaced closed position as the sled assembly 15030 is driven distally through the tissue clamped within the surgical end effector 15014. As can also be seen in FIGS. 180 and 182, the sled assembly 15030 further includes a reciprocatably or sequentially activatable drive assembly 15050 for driving staple pushers toward the closed anvil 15070.

More specifically and with reference to FIGS. 178 and 179, the elongated channel 15020 is configured to operably support a surgical staple cartridge 15080 therein. In at least one form, the surgical staple cartridge 15080 comprises a body portion 15082 that may be fabricated from, for example, Vectra, Nylon (6/6 or 6/12) and include a centrally disposed slot 15084 for accommodating the upstanding support portion 15038 of the sled assembly 15030. See FIG. 178. These materials could also be filled with glass, carbon, or mineral fill of 10%-40%. The surgical staple cartridge 15080 further includes a plurality of cavities 15086 for movably supporting lines or rows of staple-supporting pushers 15088 therein. The cavities 15086 may be arranged in spaced longitudinally extending lines or rows 15090, 15092, 15094, 15096. For example, the rows 15090 may be referred to herein as first outboard rows. The rows 15092 may be referred to herein as first inboard rows. The rows 15094 may be referred to as second inboard rows and the rows 15096 may be referred to as second outboard rows. The first inboard row 15090 and the first outboard row 15092 are located on a first lateral side of the longitudinal slot 15084 and the second inboard row 15094 and the second outboard row 15096 are located on a second lateral side of the longitudinal slot 15084. The first staple pushers 15088 in the first inboard row 15092 are staggered in relationship to the first staple pushers 15088 in the first outboard row 15090. Similarly, the second staple pushers 15088 in the second outboard row 15096 are staggered in relationship to the second pushers 15088 in the second inboard row 15094. Each pusher 15088 operably supports a surgical staple 15098 thereon.

In various embodiments, the sequentially-activatable or reciprocatably—activatable drive assembly 15050 includes a pair of outboard drivers 15052 and a pair of inboard drivers 15054 that are each attached to a common shaft 15056 that is rotatably mounted within the base 15032 of the sled assembly 15030. The outboard drivers 15052 are oriented to sequentially or reciprocatingly engage a corresponding plurality of outboard activation cavities 15026 provided in the channel pan 15022. Likewise, the inboard drivers 15054 are oriented to sequentially or reciprocatingly engage a corresponding plurality of inboard activation cavities 15028 provided in the channel pan 15022. The inboard activation cavities 15028 are arranged in a staggered relationship relative to the adjacent outboard activation cavities 15026. See FIG. 179. As can also be seen in FIGS. 179 and 181, in at least one embodiment, the sled assembly 15030 further includes distal wedge segments 15060 and intermediate wedge segments 15062 located on each side of the bore 15036 to engage the pushers 15088 as the sled assembly 15030 is driven distally in the distal direction "DD". As indicated above, the sled assembly 15030 is threadedly received on a threaded portion 15132 of a drive shaft 15130 that is rotatably supported within the end effector 15012. In various embodiments, for example, the drive shaft 15130 has a distal end 15134 that is supported in a distal bearing 15136 mounted in the surgical end effector 15012. See FIGS. 178 and 179.

In various embodiments, the surgical end effector 15012 is coupled to a tool mounting portion 15200 by an elongated shaft assembly 15108. In at least one embodiment, the tool mounting portion 15200 operably supports a transmission arrangement generally designated as 15204 that is configured to receive rotary output motions from the robotic system. The elongated shaft assembly 15108 includes an outer closure tube 15110 that is rotatable and axially movable on a spine member 15120 that is rigidly coupled to a tool mounting plate 15201 of the tool mounting portion 15200. The spine member 15120 also has a distal end 15122 that is coupled to the elongated channel portion 15020 of the surgical end effector 15012.

In use, it may be desirable to rotate the surgical end effector 15012 about a longitudinal tool axis LT-LT defined by the elongated shaft assembly 15008. In various embodiments, the outer closure tube 15110 has a proximal end 15112 that is rotatably supported on the tool mounting plate 15201 of the tool drive portion 15200 by a forward support cradle 15203. The proximal end 15112 of the outer closure tube 15110 is configured to operably interface with a rotation transmission portion 15206 of the transmission arrangement 15204. In various embodiments, the proximal end 15112 of the outer closure tube 15110 is also supported on a closure sled 15140 that is also movably supported on the tool mounting plate 15201. A closure tube gear segment 15114 is formed on the proximal end 15112 of the outer closure tube 15110 for meshing engagement with a rotation drive assembly 15150 of the rotation transmission 15206. As can be seen in FIG. 176, the rotation drive assembly 15150, in at least one embodiment, comprises a rotation drive gear 15152 that is coupled to a corresponding first one of the driven discs or elements 11304 on the adapter side 11307 of the tool mounting plate 15201 when the tool drive portion 15200 is coupled to the tool holder 11270. The rotation drive assembly 15150 further comprises a rotary driven gear 15154 that is rotatably supported on the tool mounting plate 15201 in meshing engagement with the closure tube gear segment 15114 and the rotation drive gear 15152. Application of a first rotary control motion from the robotic system 11000 through the tool holder 11270 and the adapter 11240 to the corresponding driven element 11304 will thereby cause rotation of the rotation drive gear 15152. Rotation of the rotation drive gear 15152 ultimately results in the rotation of the elongated shaft assembly 15108 (and the end effector 15012) about the longitudinal tool axis LT-LT (represented by arrow "R" in FIG. 176).

Closure of the anvil 15070 relative to the surgical staple cartridge 15080 is accomplished by axially moving the outer closure tube 15110 in the distal direction "DD". Such axial movement of the outer closure tube 15110 may be accomplished by a closure transmission portion 15144 of the transmission arrangement 15204. As indicated above, in various embodiments, the proximal end 15112 of the outer closure tube 15110 is supported by the closure sled 15140 which enables the proximal end 15112 to rotate relative thereto, yet travel axially with the closure sled 15140. In particular, as can be seen in FIG. 176, the closure sled 15140 has an upstanding tab 15141 that extends into a radial groove 15115 in the proximal end portion 15112 of the outer closure tube 15110. In addition, as was described above, the closure sled 15140 is slidably mounted to the tool mounting plate 15201. In various embodiments, the closure sled 15140 has an upstanding portion 15142 that has a closure rack gear 15143 formed thereon. The closure rack gear 15143 is configured for driving engagement with the closure transmission 15144.

In various forms, the closure transmission 15144 includes a closure spur gear 15145 that is coupled to a corresponding second one of the driven discs or elements 11304 on the adapter side 11307 of the tool mounting plate 15201. Thus, application of a second rotary control motion from the robotic system 11000 through the tool holder 11270 and the adapter 11240 to the corresponding second driven element 11304 will cause rotation of the closure spur gear 15145 when the interface 11230 is coupled to the tool mounting portion 15200. The closure transmission 15144 further includes a driven closure gear set 15146 that is supported in meshing engagement with the closure spur gear 15145 and the closure rack gear 15143. Thus, application of a second rotary control motion from the robotic system 11000 through the tool holder 11270 and the adapter 11240 to the corresponding second driven element 11304 will cause rotation of the closure spur gear 15145 and ultimately drive the closure sled 15140 and the outer closure tube 15110 axially. The axial direction in which the closure tube 15110 moves ultimately depends upon the direction in which the second driven element 11304 is rotated. For example, in response to one rotary closure motion received from the robotic system 11000, the closure sled 15140 will be driven in the distal direction "DD" and ultimately the outer closure tube 15110 will be driven in the distal direction as well. The outer closure tube 15110 has an opening 15117 in the distal end 15116 that is configured for engagement with a tab 15071 on the anvil 15070 in the manners described above. As the outer closure tube 15110 is driven distally, the proximal end 15116 of the closure tube 15110 will contact the anvil 15070 and pivot it closed. Upon application of an "opening" rotary motion from the robotic system 11000, the closure sled 15140 and outer closure tube 15110 will be driven in the proximal direction "PD" and pivot the anvil 15070 to the open position in the manners described above.

In at least one embodiment, the drive shaft 15130 has a proximal end 15137 that has a proximal shaft gear 15138 attached thereto. The proximal shaft gear 15138 is supported in meshing engagement with a distal drive gear 15162 attached to a rotary drive bar 15160 that is rotatably supported with spine member 15120. Rotation of the rotary drive bar 15160 and ultimately rotary drive shaft 15130 is controlled by a rotary knife transmission 15207 which comprises a portion of the transmission arrangement 15204 supported on the tool mounting plate 15210. In various embodiments, the rotary knife transmission 15207 comprises a rotary knife drive system 15170 that is operably supported on the tool mounting plate 15201. In various embodiments, the knife drive system 15170 includes a rotary drive gear 15172 that is coupled to a corresponding third one of the driven discs or elements 11304 on the adapter side of the tool mounting plate 15201 when the tool drive portion 15200 is coupled to the tool holder 11270. The knife drive system 15170 further comprises a first rotary driven gear 15174 that is rotatably supported on the tool mounting plate 15201 in meshing engagement with a second rotary driven gear 15176 and the rotary drive gear 15172. The second rotary driven gear 15176 is coupled to a proximal end portion 15164 of the rotary drive bar 15160.

Rotation of the rotary drive gear 15172 in a first rotary direction will result in the rotation of the rotary drive bar 15160 and rotary drive shaft 15130 in a first direction. Conversely, rotation of the rotary drive gear 15172 in a second rotary direction (opposite to the first rotary direction) will cause the rotary drive bar 15160 and rotary drive shaft 15130 to rotate in a second direction.

One method of operating the surgical tool 15000 will now be described. The tool drive 15200 is operably coupled to the interface 11240 of the robotic system 11000. The controller 11001 of the robotic system 11000 is operated to locate the tissue to be cut and stapled between the open anvil 15070 and the surgical staple cartridge 15080. Once the surgical end effector 15012 has been positioned by the robot system 11000 such that the target tissue is located between the anvil 15070 and the surgical staple cartridge 15080, the controller 11001 of the robotic system 11000 may be activated to apply the second rotary output motion to the second driven element 11304 coupled to the closure spur gear 15145 to drive the closure sled 15140 and the outer closure tube 15110 axially in the distal direction to pivot the anvil 15070 closed in the manner described above. Once the robotic controller 11001 determines that the anvil 15070 has been closed by, for example, sensors in the surgical end effector 15012 and/or the tool drive portion 15200, the robotic controller 11001 system may provide the surgeon with an indication that signifies the closure of the anvil. Such indication may be, for example, in the form of a light and/or audible sound, tactile feedback on the control members, etc. Then the surgeon may initiate the firing process. In alternative embodiments, however, the robotic controller 11001 may automatically commence the firing process.

To commence the firing process, the robotic controller applies a third rotary output motion to the third driven disc or element 11304 coupled to the rotary drive gear 15172. Rotation of the rotary drive gear 15172 results in the rotation of the rotary drive bar 15160 and rotary drive shaft 15130 in the manner described above. Firing and formation of the surgical staples 15098 can be best understood from reference to FIGS. 177, 179, and 180. As the sled assembly 15030 is driven in the distal direction "DD" through the surgical staple cartridge 15080, the distal wedge segments 15060 first contact the staple pushers 15088 and start to move them toward the closed anvil 15070. As the sled assembly 15030 continues to move distally, the outboard drivers 15052 will drop into the corresponding activation cavity 15026 in the channel pan 15022. The opposite end of each outboard driver 15052 will then contact the corresponding outboard pusher 15088 that has moved up the distal and intermediate wedge segments 15060, 15062. Further distal movement of the sled assembly 15030 causes the outboard drivers 15052 to rotate and drive the corresponding pushers 15088 toward the anvil 15070 to cause the staples 15098 supported thereon to be formed as they are driven into the anvil 15070. It will be understood that as the sled assembly 15030 moves distally, the knife blade 15040 cuts through the tissue that is clamped between the anvil and the staple cartridge. Because the inboard drivers 15054 and outboard drivers 15052 are attached to the same shaft 15056 and the inboard drivers 15054 are radially offset from the outboard drivers 15052 on the shaft 15056, as the outboard drivers 15052 are driving their corresponding pushers 15088 toward the anvil 15070, the inboard drivers 15054 drop into their next corresponding activation cavity 15028 to cause them to rotatably or reciprocatingly drive the corresponding inboard pushers 15088 towards the closed anvil 15070 in the same manner. Thus, the laterally corresponding outboard staples 15098 on each side of the centrally disposed slot 15084 are simultaneously formed together and the laterally corresponding inboard staples 15098 on each side of the slot 15084 are simultaneously formed together as the sled assembly 15030 is driven distally. Once the robotic controller 11001 determines that the sled assembly 15030 has reached its distal most position—either through sensors or through monitoring the amount of rotary input applied to the drive shaft 15130 and/or the rotary drive bar 15160, the controller 11001 may then apply a third rotary output motion to the drive shaft 15130 to rotate the drive shaft 15130 in an opposite direction to retract the sled assembly 15030 back to its starting position. Once the sled assembly 15030 has been retracted to the starting position (as signaled by sensors in the end effector 15012 and/or the tool drive portion 15200), the application of the second rotary motion to the drive shaft 15130 is discontinued. Thereafter, the surgeon may manually activate the anvil opening process or it may be automatically commenced by the robotic controller 11001. To open the anvil 15070, the second rotary output motion is applied to the closure spur gear 15145 to drive the closure sled 15140 and the outer closure tube 15110 axially in the proximal direction. As the closure tube 15110 moves proximally, the opening 15117 in the distal end 15116 of the closure tube 15110 contacts the tab 15071 on the anvil 15070 to pivot the anvil 15070 to the open position. A spring may also be employed to bias the anvil 15070 to the open position when the closure tube 15116 has been returned to the starting position. Again, sensors in the surgical end effector 15012 and/or the tool mounting portion 15200 may provide the robotic controller 11001 with a signal indicating that the anvil 15070 is now open. Thereafter, the surgical end effector 15012 may be withdrawn from the surgical site.

Figure 183:
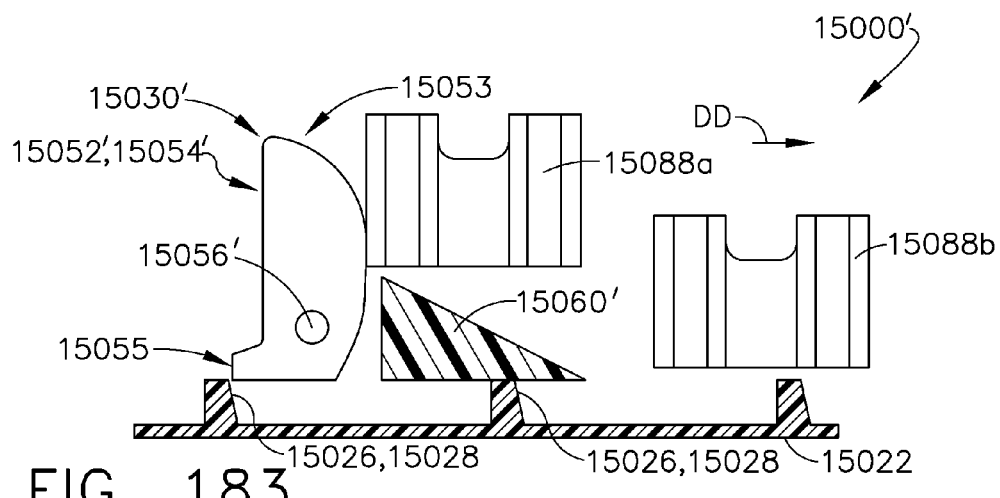
Figure 184:
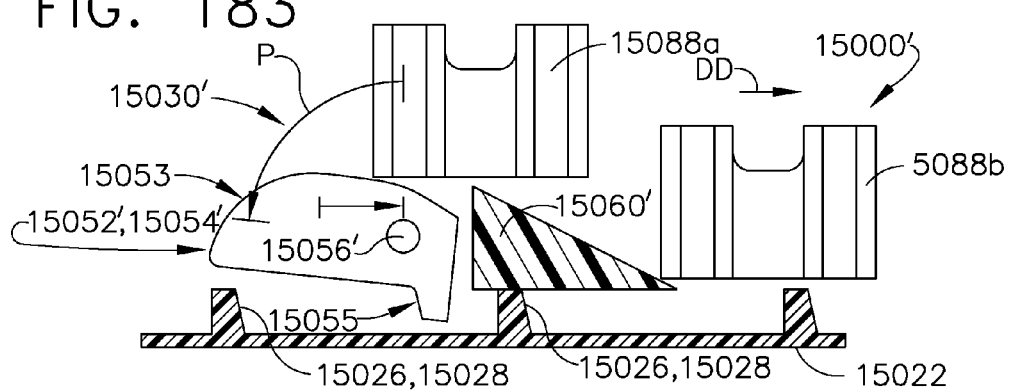
Figure 185:
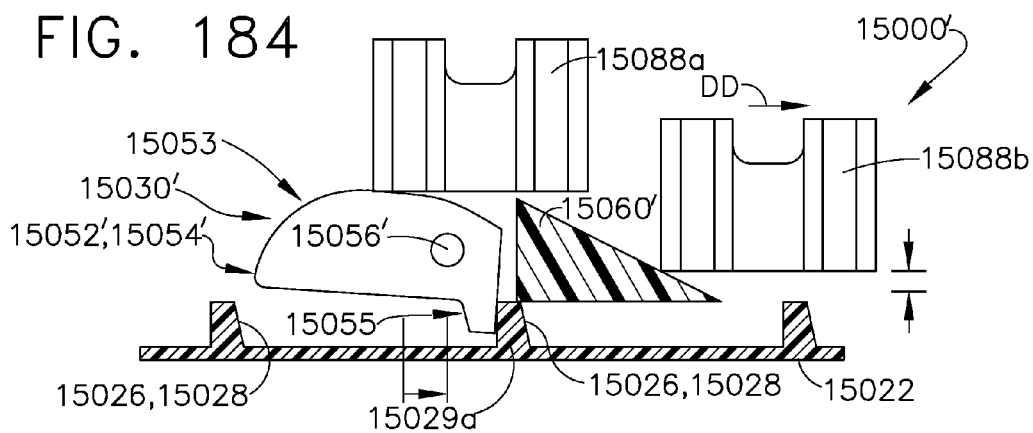
Figure 186:
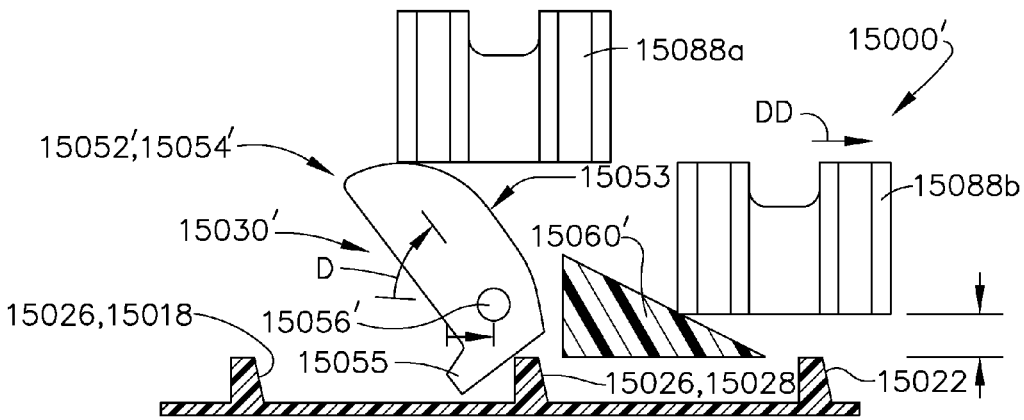
Figure 187:
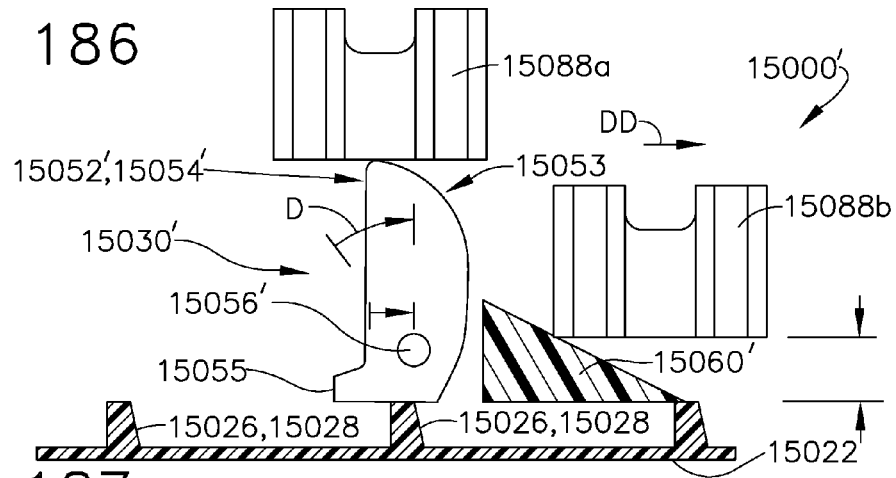
Figure 188:
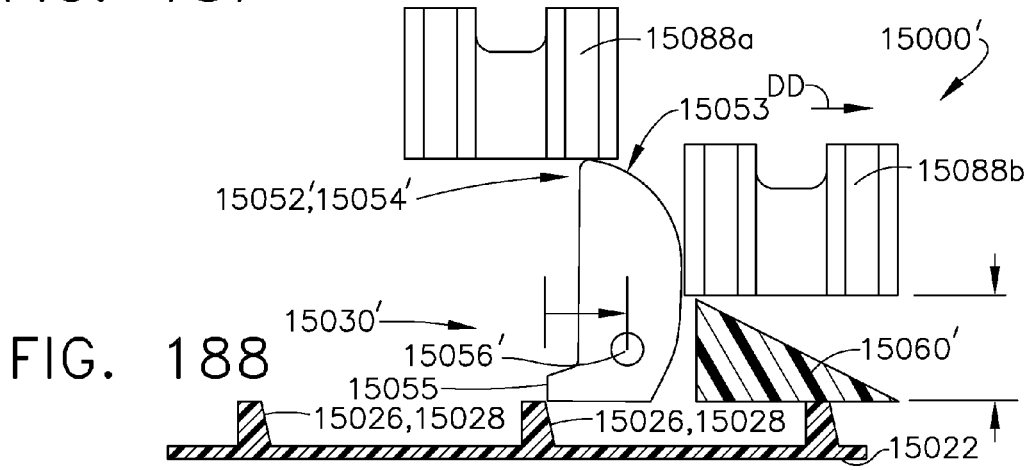

FIGS. 183-188 diagrammatically depict the sequential firing of staples in a surgical tool assembly 15000' that is substantially similar to the surgical tool assembly 15000 described above. In this embodiment, the inboard and outboard drivers 15052', 15054' have a cam-like shape with a cam surface 15053 and an actuator protrusion 15055 as shown in FIGS. 183-189. The drivers 15052', 15054' are journaled on the same shaft 15056' that is rotatably supported by the sled assembly 15030'. In this embodiment, the sled assembly 15030' has distal wedge segments 15060' for engaging the pushers 15088. FIG. 183 illustrates an initial position of two inboard or outboard drivers 15052', 15054' as the sled assembly 15030' is driven in the distal direction "DD". As can be seen in that Figure, the pusher 15088a has advanced up the wedge segment 15060' and has contacted the driver 15052', 15054'. Further travel of the sled assembly 15030' in the distal direction causes the driver 15052', 15054' to pivot in the "P" direction (FIG. 184) until the actuator portion 15055 contacts the end wall 15029a of the activation cavity 15026, 15028 as shown in FIG. 185. Continued advancement of the sled assembly 15030' in the distal direction "DD" causes the driver 15052', 15054' to rotate in the "D" direction as shown in FIG. 186. As the driver 15052', 15054' rotates, the pusher 15088a rides up the cam surface 15053 to the final vertical position shown in FIG. 187. When the pusher 15088a reaches the final vertical position shown in FIGS. 187 and 188, the staple (not shown) supported thereon has been driven into the staple forming surface of the anvil to form the staple.

FIGS. 190-195 illustrate a surgical end effector 15312 that may be employed for example, in connection with the tool mounting portion 11300 and shaft 12008 described in detail above. In various forms, the surgical end effector 15312 includes an elongated channel 15322 that is constructed as described above for supporting a surgical staple cartridge 15330 therein. The surgical staple cartridge 15330 comprises a body portion 15332 that includes a centrally disposed slot 15334 for accommodating an upstanding support portion 15386 of a sled assembly 15380. See FIGS. 190-192. The surgical staple cartridge body portion 15332 further includes a plurality of cavities 15336 for movably supporting staple-supporting pushers 15350 therein. The cavities 15336 may be arranged in spaced longitudinally extending rows 15340, 15342, 15344, 15346. The rows 15340, 15342 are located on one lateral side of the longitudinal slot 15334 and the rows 15344, 15346 are located on the other side of longitudinal slot 15334. In at least one embodiment, the pushers 15350 are configured to support two surgical staples 15352 thereon. In particular, each pusher 15350 located on one side of the elongated slot 15334 supports one staple 15352 in row 15340 and one staple 15352 in row 15342 in a staggered orientation. Likewise, each pusher 15350 located on the other side of the elongated slot 15334 supports one surgical staple 15352 in row 15344 and another surgical staple 15352 in row 15346 in a staggered orientation. Thus, every pusher 15350 supports two surgical staples 15352.

As can be further seen in FIGS. 190, 191, the surgical staple cartridge 15330 includes a plurality of rotary drivers 15360. More particularly, the rotary drivers 15360 on one side of the elongated slot 15334 are arranged in a single line 15370 and correspond to the pushers 15350 in lines 15340, 15342. In addition, the rotary drivers 15360 on the other side of the elongated slot 15334 are arranged in a single line 15372 and correspond to the pushers 15350 in lines 15344, 15346. As can be seen in FIG. 190, each rotary driver 15360 is rotatably supported within the staple cartridge body 15332. More particularly, each rotary driver 15360 is rotatably received on a corresponding driver shaft 15362. Each driver 15360 has an arcuate ramp portion 15364 formed thereon that is configured to engage an arcuate lower surface 15354 formed on each pusher 15350. See FIG. 195. In addition, each driver 15360 has a lower support portion 15366 extend therefrom to slidably support the pusher 15360 on the channel 15322. Each driver 15360 has a downwardly extending actuation rod 15368 that is configured for engagement with a sled assembly 15380.

As can be seen in FIG. 192, in at least one embodiment, the sled assembly 15380 includes a base portion 15382 that has a foot portion 15384 that is sized to be slidably received in a slot 15333 in the channel 15322. See FIG. 190. The sled assembly 15380 includes an upstanding support portion 15386 that supports a tissue cutting blade or tissue cutting instrument 15388. The upstanding support portion 15386 terminates in a top portion 15390 that has a pair of laterally extending retaining fins 15392 protruding therefrom. The fins 15392 are positioned to be received within corresponding slots (not shown) in the anvil (not shown). As with the above-described embodiments, the fins 15392 and the foot portion 15384 serve to retain the anvil (not shown) in a desired spaced closed position as the sled assembly 15380 is driven distally through the tissue clamped within the surgical end effector 15312. The upstanding support portion 15386 is configured for attachment to a knife bar 12200 (FIG. 111). The sled assembly 15380 further has a horizontally-extending actuator plate 15394 that is shaped for actuating engagement with each of the actuation rods 15368 on the pushers 15360.

Operation of the surgical end effector 15312 will now be explained with reference to FIGS. 190 and 191. As the sled assembly 15380 is driven in the distal direction "DD" through the staple cartridge 15330, the actuator plate 15394 sequentially contacts the actuation rods 15368 on the pushers 15360. As the sled assembly 15380 continues to move distally, the actuator plate 15394 sequentially contacts the actuator rods 15368 of the drivers 15360 on each side of the elongated slot 15334. Such action causes the drivers 15360 to rotate from a first unactuated position to an actuated portion wherein the pushers 15350 are driven towards the closed anvil. As the pushers 15350 are driven toward the anvil, the surgical staples 15352 thereon are driven into forming contact with the underside of the anvil. Once the robotic system 11000 determines that the sled assembly 15080 has reached its distal most position through sensors or other means, the control system of the robotic system 11000 may then retract the knife bar and sled assembly 15380 back to the starting position. Thereafter, the robotic control system may then activate the procedure for returning the anvil to the open position to release the stapled tissue.

FIGS. 196-200 depict one form of an automated reloading system embodiment of the present invention, generally designated as 15500. In one form, the automated reloading system 15500 is configured to replace a "spent" surgical end effector component in a manipulatable surgical tool portion of a robotic surgical system with a "new" surgical end effector component. As used herein, the term "surgical end effector component" may comprise, for example, a surgical staple cartridge, a disposable loading unit or other end effector components that, when used, are spent and must be replaced with a new component. Furthermore, the term "spent" means that the end effector component has been activated and is no longer useable for its intended purpose in its present state. For example, in the context of a surgical staple cartridge or disposable loading unit, the term "spent" means that at least some of the unformed staples that were previously supported therein have been "fired" therefrom. As used herein, the term "new" surgical end effector component refers to an end effector component that is in condition for its intended use. In the context of a surgical staple cartridge or disposable loading unit, for example, the term "new" refers to such a component that has unformed staples therein and which is otherwise ready for use.

In various embodiments, the automated reloading system 15500 includes a base portion 15502 that may be strategically located within a work envelope 11109 of a robotic arm cart 11100 (FIG. 97) of a robotic system 11000. As used herein, the term "manipulatable surgical tool portion" collectively refers to a surgical tool of the various types disclosed herein and other forms of surgical robotically-actuated tools that are operably attached to, for example, a robotic arm cart 11100 or similar device that is configured to automatically manipulate and actuate the surgical tool. The term "work envelope" as used herein refers to the range of movement of the manipulatable surgical tool portion of the robotic system. FIG. 97 generally depicts an area that may comprise a work envelope of the robotic arm cart 11100. Those of ordinary skill in the art will understand that the shape and size of the work envelope depicted therein is merely illustrative. The ultimate size, shape and location of a work envelope will ultimately depend upon the construction, range of travel limitations, and location of the manipulatable surgical tool portion. Thus, the term "work envelope" as used herein is intended to cover a variety of different sizes and shapes of work envelopes and should not be limited to the specific size and shape of the sample work envelope depicted in FIG. 97.

As can be seen in FIG. 196, the base portion 15502 includes a new component support section or arrangement 15510 that is configured to operably support at least one new surgical end effector component in a "loading orientation". As used herein, the term "loading orientation" means that the new end effector component is supported in such away so as to permit the corresponding component support portion of the manipulatable surgical tool portion to be brought into loading engagement with (i.e., operably seated or operably attached to) the new end effector component (or the new end effector component to be brought into loading engagement with the corresponding component support portion of the manipulatable surgical tool portion) without human intervention beyond that which may be necessary to actuate the robotic system. As will be further appreciated as the present Detailed Description proceeds, in at least one embodiment, the preparation nurse will load the new component support section before the surgery with the appropriate length and color cartridges (some surgical staple cartridges may support certain sizes of staples the size of which may be indicated by the color of the cartridge body) required for completing the surgical procedure. However, no direct human interaction is necessary during the surgery to reload the robotic endocutter. In one form, the surgical end effector component comprises a staple cartridge 12034 that is configured to be operably seated within a component support portion (elongated channel) of any of the various other end effector arrangements described above. For explanation purposes, new (unused) cartridges will be designated as "12034*a*" and spent cartridges will be designated as "12034*b*". The Figures depict cartridges 12034*a*, 12034*b* designed for use with a surgical end effector 12012 that includes a channel 12022 and an anvil 12024, the construction and operation of which were discussed in detail above. Cartridges 12034*a*, 12034*b* are identical to cartridges 12034 described above. In various embodiments, the cartridges 12034*a*, 12034*b* are configured to be snappingly retained (i.e., loading engagement) within the channel 12022 of a surgical end effector 12012. As the present Detailed Description proceeds, however, those of ordinary skill in the art will appreciate that the unique and novel features of the automated cartridge reloading system 15500 may be effectively employed in connection with the automated removal and installation of other cartridge arrangements without departing from the spirit and scope of the present invention.

In the depicted embodiment, the term "loading orientation" means that the distal tip portion 12035*a* of the a new surgical staple cartridge 12034*a* is inserted into a corresponding support cavity 15512 in the new cartridge support section 15510 such that the proximal end portion 12037*a* of the new surgical staple cartridge 12034*a* is located in a convenient orientation for enabling the arm cart 11100 to manipulate the surgical end effector 12012 into a position wherein the new cartridge 12034*a* may be automatically loaded into the channel 12022 of the surgical end effector 12012. In various embodiments, the base 15502 includes at least one sensor 15504 which communicates with the control system 11003 of the robotic controller 11001 to provide the control system 11003 with the location of the base 15502 and/or the reload length and color doe each staged or new cartridge 12034*a*.

As can also be seen in the Figures, the base 15502 further includes a collection receptacle 15520 that is configured to collect spent cartridges 12034*b* that have been removed or disengaged from the surgical end effector 12012 that is operably attached to the robotic system 11000. In addition, in one form, the automated reloading system 15500 includes an extraction system 15530 for automatically removing the spent end effector component from the corresponding support portion of the end effector or manipulatable surgical tool portion without specific human intervention beyond that which may be necessary to activate the robotic system. In various embodiments, the extraction system 15530 includes an extraction hook member 15532. In one form, for example, the extraction hook member 15532 is rigidly supported on the base portion 15502. In one embodiment, the extraction hook member has at least one hook 5534 formed thereon that is configured to hookingly engage the distal end 12035 of a spent cartridge 12034*b* when it is supported in the elongated channel 12022 of the surgical end effector 12012. In various forms, the extraction hook member 15532 is conveniently located within a portion of the collection receptacle 15520 such that when the spent end effector component (cartridge 12034*b*) is brought into extractive engagement with the extraction hook member 15532, the spent end effector component (cartridge 12034*b*) is dislodged from the corresponding component support portion (elongated channel 12022), and falls into the collection receptacle 15020. Thus, to use this embodiment, the manipulatable surgical tool portion manipulates the end effector attached thereto to bring the distal end 12035 of the spent cartridge 12034*b* therein into hooking engagement with the hook 15534 and then moves the end effector in such a way to dislodge the spent cartridge 12034*b* from the elongated channel 12022.

In other arrangements, the extraction hook member 15532 comprises a rotatable wheel configuration that has a pair of diametrically-opposed hooks 15334 protruding therefrom. See FIGS. 196 and 199. The extraction hook member 15532 is rotatably supported within the collection receptacle 15520 and is coupled to an extraction motor 15540 that is controlled by the controller 11001 of the robotic system. This form of the automated reloading system 15500 may be used as follows. FIG. 198 illustrates the introduction of the surgical end effector 12012 that is operably attached to the manipulatable surgical tool portion 11200. As can be seen in that Figure, the arm cart 11100 of the robotic system 11000 locates the surgical end effector 12012 in the shown position wherein the hook end 15534 of the extraction member 15532 hookingly engages the distal end 12035 of the spent cartridge 12034*b* in the surgical end effector 12012. The anvil 12024 of the surgical end effector 12012 is in the open position. After the distal end 12035 of the spent cartridge 12034*b* is engaged with the hook end 15532, the extraction motor 15540 is actuated to rotate the extraction wheel 15532 to disengage the spent cartridge 12034*b* from the channel 12022. To assist with the disengagement of the spent cartridge 12034*b* from the channel 12022 (or if the extraction member 15530 is stationary), the robotic system 11000 may move the surgical end effector 12012 in an upward direction (arrow "U" in FIG. 199). As the spent cartridge 12034*b* is dislodged from the channel 12022, the spent cartridge 12034*b* falls into the collection receptacle 15520. Once the spent cartridge 12034*b* has been removed from the surgical end effector 12012, the robotic system 11000 moves the surgical end effector 12012 to the position shown in FIG. 200.

In various embodiments, a sensor arrangement 15533 is located adjacent to the extraction member 15532 that is in communication with the controller 11001 of the robotic system 11000. The sensor arrangement 15533 may comprise a sensor that is configured to sense the presence of the surgical end effector 12012 and, more particularly the tip 12035*b* of the spent surgical staple cartridge 12034*b* thereof as the distal tip portion 12035*b* is brought into engagement with the extraction member 15532. In some embodiments, the sensor arrangement 15533 may comprise, for example, a light curtain arrangement. However, other forms of proximity sensors may be employed. In such arrangement, when the surgical end effector 12012 with the spent surgical staple cartridge 12034*b* is brought into extractive engagement with the extraction member 15532, the sensor senses the distal tip 12035*b* of the surgical staple cartridge 12034*b* (e.g., the light curtain is broken). When the extraction member 15532 spins and pops the surgical staple cartridge 12034*b* loose and it falls into the collection receptacle 15520, the light curtain is again unbroken. Because the surgical end effector 12012 was not moved during this procedure, the robotic controller 11001 is assured that the spent surgical staple cartridge 12034*b* has been removed therefrom. Other sensor arrangements may also be successfully employed to provide the robotic controller 11001 with an indication that the spent surgical staple cartridge 12034*b* has been removed from the surgical end effector 12012.

As can be seen in FIG. 200, the surgical end effector 12012 is positioned to grasp a new surgical staple cartridge 12034*a* between the channel 12022 and the anvil 12024. More specifically, as shown in FIGS. 197 and 200, each cavity 11512 has a corresponding upstanding pressure pad 15514 associated with it. The surgical end effector 12012 is located such that the pressure pad 15514 is located between the new cartridge 12034*a* and the anvil 12024. Once in that position, the robotic system 11000 closes the anvil 12024 onto the pressure pad 15514 which serves to push the new cartridge 12034*a* into snapping engagement with the channel 12022 of the surgical end effector 12012. Once the new cartridge 12034*a* has been snapped into position within the elongated channel 12022, the robotic system 11000 then withdraws the surgical end effector 12012 from the automated cartridge reloading system 15500 for use in connection with performing another surgical procedure.

FIGS. 201-205 depict another automated reloading system 15600 that may be used to remove a spent disposable loading unit 13612 from a manipulatable surgical tool arrangement 13600 (FIGS. 148-161) that is operably attached to an arm cart 11100 or other portion of a robotic system 11000 and reload a new disposable loading unit 13612 therein. As can be seen in FIGS. 201 and 202, one form of the automated reloading system 15600 includes a housing 15610 that has a movable support assembly in the form of a rotary carrousel top plate 15620 supported thereon which cooperates with the housing 15610 to form a hollow enclosed area 15612. The automated reloading system 15600 is configured to be operably supported within the work envelop of the manipulatable surgical tool portion of a robotic system as was described above. In various embodiments, the rotary carrousel plate 15620 has a plurality of holes 15622 for supporting a plurality of orientation tubes 15660 therein. As can be seen in FIGS. 202 and 203, the rotary carrousel plate 15620 is affixed to a spindle shaft 15624. The spindle shaft 15624 is centrally disposed within the enclosed area 15612 and has a spindle gear 15626 attached thereto. The spindle gear 15626 is in meshing engagement with a carrousel drive gear 15628 that is coupled to a carrousel drive motor 15630 that is in operative communication with the robotic controller 11001 of the robotic system 11000.

Various embodiments of the automated reloading system 15600 may also include a carrousel locking assembly, generally designated as 15640. In various forms, the carrousel locking assembly 15640 includes a cam disc 15642 that is affixed to the spindle shaft 15624. The spindle gear 15626 may be attached to the underside of the cam disc 15642 and the cam disc 15642 may be keyed onto the spindle shaft 15624. In alternative arrangements, the spindle gear 15626 and the cam disc 15642 may be independently non-rotatably affixed to the spindle shaft 15624. As can be seen in FIGS. 202 and 203, a plurality of notches 15644 are spaced around the perimeter of the cam disc 15642. A locking arm 15648 is pivotally mounted within the housing 15610 and is biased into engagement with the perimeter of the cam disc 15642 by a locking spring 15649. As can be seen in FIG. 201, the outer perimeter of the cam disc 15642 is rounded to facilitate rotation of the cam disc 15642 relative to the locking arm 15648. The edges of each notch 15644 are also rounded such that when the cam disc 15642 is rotated, the locking arm 15648 is cammed out of engagement with the notches 15644 by the perimeter of the cam disc 15642.

Various forms of the automated reloading system 15600 are configured to support a portable/replaceable tray assembly 15650 that is configured to support a plurality of disposable loading units 13612 in individual orientation tubes 15660. More specifically and with reference to FIGS. 202 and 203, the replaceable tray assembly 15650 comprises a tray 15652 that has a centrally-disposed locator spindle 15654 protruding from the underside thereof. The locator spindle 15654 is sized to be received within a hollow end 15625 of spindle shaft 15624. The tray 15652 has a plurality of holes 15656 therein that are configured to support an orientation tube 15660 therein. Each orientation tube 15660 is oriented within a corresponding hole 15656 in the replaceable tray assembly 15650 in a desired orientation by a locating fin 15666 on the orientation tube 15660 that is designed to be received within a corresponding locating slot 15658 in the tray assembly 15650. In at least one embodiment, the locating fin 15666 has a substantially V-shaped cross-sectional shape that is sized to fit within a V-shaped locating slot 15658. Such arrangement serves to orient the orientation tube 15660 in a desired starting position while enabling it to rotate within the hole 15656 when a rotary motion is applied thereto. That is, when a rotary motion is applied to the orientation tube 15660 the V-shaped locating fin 15666 will pop out of its corresponding locating slot enabling the tube 15660 to rotate relative to the tray 15652 as will be discussed in further detail below. As can also be seen in FIGS. 201-203, the replaceable tray 15652 may be provided with one or more handle portions 15653 to facilitate transport of the tray assembly 15652 when loaded with orientation tubes 15660.

As can be seen in FIG. 205, each orientation tube 15660 comprises a body portion 15662 that has a flanged open end 15664. The body portion 15662 defines a cavity 15668 that is sized to receive a portion of a disposable loading unit 13612 therein. To properly orient the disposable loading unit 13612 within the orientation tube 15660, the cavity 15668 has a flat locating surface 15670 formed therein. As can be seen in FIG. 205, the flat locating surface 15670 is configured to facilitate the insertion of the disposable loading unit into the cavity 15668 in a desired or predetermined non-rotatable orientation. In addition, the end 15669 of the cavity 15668 may include a foam or cushion material 15672 that is designed to cushion the distal end of the disposable loading unit 13612 within the cavity 15668. Also, the length of the locating surface may cooperate with a sliding support member 13689 of the axial drive assembly 13680 of the disposable loading unit 13612 to further locate the disposable loading unit 13612 at a desired position within the orientation tube 15660.

The orientation tubes 15660 may be fabricated from Nylon, polycarbonate, polyethylene, liquid crystal polymer, 6061 or 7075 aluminum, titanium, 300 or 400 series stainless steel, coated or painted steel, plated steel, etc. and, when loaded in the replaceable tray 15662 and the locator spindle 15654 is inserted into the hollow end 15625 of spindle shaft 15624, the orientation tubes 15660 extend through corresponding holes 15662 in the carrousel top plate 15620. Each replaceable tray 15662 is equipped with a location sensor 15663 that communicates with the control system 11003 of the controller 11001 of the robotic system 11000. The sensor 15663 serves to identify the location of the reload system, and the number, length, color and fired status of each reload housed in the tray. In addition, an optical sensor or sensors 15665 that communicate with the robotic controller 11001 may be employed to sense the type/size/length of disposable loading units that are loaded within the tray 15662.

Various embodiments of the automated reloading system 15600 further include a drive assembly 15680 for applying a rotary motion to the orientation tube 15660 holding the disposable loading unit 13612 to be attached to the shaft 13700 of the surgical tool 13600 (collectively the "manipulatable surgical tool portion") that is operably coupled to the robotic system. The drive assembly 15680 includes a support yoke 15682 that is attached to the locking arm 15648. Thus, the support yoke 15682 pivots with the locking arm 15648. The support yoke 15682 rotatably supports a tube idler wheel 15684 and a tube drive wheel 15686 that is driven by a tube motor 15688 attached thereto. Tube motor 15688 communicates with the control system 11003 and is controlled thereby. The tube idler wheel 15684 and tube drive wheel 15686 are fabricated from, for example, natural rubber, sanoprene, isoplast, etc. such that the outer surfaces thereof create sufficient amount of friction to result in the rotation of an orientation tube 15660 in contact therewith upon activation of the tube motor 15688. The idler wheel 15684 and tube drive wheel 15686 are oriented relative to each other to create a cradle area 15687 therebetween for receiving an orientation tube 15060 in driving engagement therein.

In use, one or more of the orientation tubes 15660 loaded in the automated reloading system 15600 are left empty, while the other orientation tubes 15660 may operably support a corresponding new disposable loading unit 13612 therein. As will be discussed in further detail below, the empty orientation tubes 15660 are employed to receive a spent disposable loading unit 13612 therein.

The automated reloading system 15600 may be employed as follows after the system 15600 is located within the work envelope of the manipulatable surgical tool portion of a robotic system. If the manipulatable surgical tool portion has a spent disposable loading unit 13612 operably coupled thereto, one of the orientation tubes 15660 that are supported on the replaceable tray 15662 is left empty to receive the spent disposable loading unit 13612 therein. If, however, the manipulatable surgical tool portion does not have a disposable loading unit 13612 operably coupled thereto, each of the orientation tubes 15660 may be provided with a properly oriented new disposable loading unit 13612.

As described hereinabove, the disposable loading unit 13612 employs a rotary "bayonet-type" coupling arrangement for operably coupling the disposable loading unit 13612 to a corresponding portion of the manipulatable surgical tool portion. That is, to attach a disposable loading unit 13612 to the corresponding portion of the manipulatable surgical tool portion (13700—see FIG. 154, 155), a rotary installation motion must be applied to the disposable loading unit 13612 and/or the corresponding portion of the manipulatable surgical tool portion when those components have been moved into loading engagement with each other. Such installation motions are collectively referred to herein as "loading motions". Likewise, to decouple a spent disposable loading unit 13612 from the corresponding portion of the manipulatable surgical tool, a rotary decoupling motion must be applied to the spent disposable loading unit 13612 and/or the corresponding portion of the manipulatable surgical tool portion while simultaneously moving the spent disposable loading unit and the corresponding portion of the manipulatable surgical tool away from each other. Such decoupling motions are collectively referred to herein as "extraction motions".

To commence the loading process, the robotic system 11000 is activated to manipulate the manipulatable surgical tool portion and/or the automated reloading system 15600 to bring the manipulatable surgical tool portion into loading engagement with the new disposable loading unit 13612 that is supported in the orientation tube 15660 that is in driving engagement with the drive assembly 15680. Once the robotic controller 11001 (FIG. 96) of the robotic control system 11000 has located the manipulatable surgical tool portion in loading engagement with the new disposable loading unit 13612, the robotic controller 11001 activates the drive assembly 15680 to apply a rotary loading motion to the orientation tube 15660 in which the new disposable loading unit 13612 is supported and/or applies another rotary loading motion to the corresponding portion of the manipulatable surgical tool portion. Upon application of such rotary loading motions(s), the robotic controller 11001 also causes the corresponding portion of the manipulatable surgical tool portion to be moved towards the new disposable loading unit 13612 into loading engagement therewith. Once the disposable loading unit 13612 is in loading engagement with the corresponding portion of the manipulatable tool portion, the loading motions are discontinued and the manipulatable surgical tool portion may be moved away from the automated reloading system 15600 carrying with it the new disposable loading unit 13612 that has been operably coupled thereto.

To decouple a spent disposable loading unit 13612 from a corresponding manipulatable surgical tool portion, the robotic controller 11001 of the robotic system manipulates the manipulatable surgical tool portion so as to insert the distal end of the spent disposable loading unit 13612 into the empty orientation tube 15660 that remains in driving engagement with the drive assembly 15680. Thereafter, the robotic controller 11001 activates the drive assembly 15680 to apply a rotary extraction motion to the orientation tube 15660 in which the spent disposable loading unit 13612 is supported and/or applies a rotary extraction motion to the corresponding portion of the manipulatable surgical tool portion. The robotic controller 11001 also causes the manipulatable surgical tool portion to withdraw away from the spent rotary disposable loading unit 13612. Thereafter the rotary extraction motion(s) are discontinued.

After the spent disposable loading unit 13612 has been removed from the manipulatable surgical tool portion, the robotic controller 11001 may activate the carrousel drive motor 15630 to index the carrousel top plate 15620 to bring another orientation tube 15660 that supports a new disposable loading unit 13612 therein into driving engagement with the drive assembly 15680. Thereafter, the loading process may be repeated to attach the new disposable loading unit 13612 therein to the portion of the manipulatable surgical tool portion. The robotic controller 11001 may record the number of disposable loading units that have been used from a particular replaceable tray 15652. Once the controller 11001 determines that all of the new disposable loading units 13612 have been used from that tray, the controller 11001 may provide the surgeon with a signal (visual and/or audible) indicating that the tray 15652 supporting all of the spent disposable loading units 13612 must be replaced with a new tray 15652 containing new disposable loading units 13612.

FIGS. 206-211 depict another non-limiting embodiment of a surgical tool 16000 of the present invention that is well-adapted for use with a robotic system 11000 that has a tool drive assembly 11010 (FIG. 101) that is operatively coupled to a master controller 11001 that is operable by inputs from an operator (i.e., a surgeon). As can be seen in FIG. 206, the surgical tool 16000 includes a surgical end effector 16012 that comprises an endocutter. In at least one form, the surgical tool 16000 generally includes an elongated shaft assembly 16008 that has a proximal closure tube 16040 and a distal closure tube 16042 that are coupled together by an articulation joint 16100. The surgical tool 16000 is operably coupled to the manipulator by a tool mounting portion, generally designated as 16200. The surgical tool 16000 further includes an interface 16030 which may mechanically and electrically couple the tool mounting portion 16200 to the manipulator in the various manners described in detail above.

In at least one embodiment, the surgical tool 16000 includes a surgical end effector 16012 that comprises, among other things, at least one component 16024 that is selectively movable between first and second positions relative to at least one other component 16022 in response to various control motions applied to component 16024 as will be discussed in further detail below to perform a surgical procedure. In various embodiments, component 16022 comprises an elongated channel 16022 configured to operably support a surgical staple cartridge 16034 therein and component 16024 comprises a pivotally translatable clamping member, such as an anvil 16024. Various embodiments of the surgical end effector 16012 are configured to maintain the anvil 16024 and elongated channel 16022 at a spacing that assures effective stapling and severing of tissue clamped in the surgical end effector 16012. Unless otherwise stated, the end effector 16012 is similar to the surgical end effector 12012 described above and includes a cutting instrument (not shown) and a sled (not shown). The anvil 16024 may include a tab 16027 at its proximal end that interacts with a component of the mechanical closure system (described further below) to facilitate the opening of the anvil 16024. The elongated channel 16022 and the anvil 16024 may be made of an electrically conductive material (such as metal) so that they may serve as part of an antenna that communicates with sensor(s) in the end effector, as described above. The surgical staple cartridge 16034 could be made of a nonconductive material (such as plastic) and the sensor may be connected to or disposed in the surgical staple cartridge 16034, as was also described above.

As can be seen in FIG. 206, the surgical end effector 16012 is attached to the tool mounting portion 16200 by the elongated shaft assembly 16008 according to various embodiments. As shown in the illustrated embodiment, the elongated shaft assembly 16008 includes an articulation joint generally designated as 16100 that enables the surgical end effector 16012 to be selectively articulated about a first tool articulation axis AA1-AA1 that is substantially transverse to a longitudinal tool axis LT-LT and a second tool articulation axis AA2-AA2 that is substantially transverse to the longitudinal tool axis LT-LT as well as the first articulation axis AA1-AA1. See FIG. 207. In various embodiments, the elongated shaft assembly 16008 includes a closure tube assembly 16009 that comprises a proximal closure tube 16040 and a distal closure tube 16042 that are pivotably linked by a pivot links 16044 and 16046. The closure tube assembly 16009 is movably supported on a spine assembly generally designated as 16102.

As can be seen in FIG. 208, the proximal closure tube 16040 is pivotally linked to an intermediate closure tube joint 16043 by an upper pivot link 16044U and a lower pivot link 16044L such that the intermediate closure tube joint 16043 is pivotable relative to the proximal closure tube 16040 about a first closure axis CA1-CA1 and a second closure axis CA2-CA2. In various embodiments, the first closure axis CA1-CA1 is substantially parallel to the second closure axis CA2-CA2 and both closure axes CA1-CA1, CA2-CA2 are substantially transverse to the longitudinal tool axis LT-LT. As can be further seen in FIG. 208, the intermediate closure tube joint 16043 is pivotally linked to the distal closure tube 16042 by a left pivot link 16046L and a right pivot link 16046R such that the intermediate closure tube joint 16043 is pivotable relative to the distal closure tube 16042 about a third closure axis CA3-CA3 and a fourth closure axis CA4-CA4. In various embodiments, the third closure axis CA3-CA3 is substantially parallel to the fourth closure axis CA4-CA4 and both closure axes CA3-CA3, CA4-CA4 are substantially transverse to the first and second closure axes CA1-CA1, CA2-CA2 as well as to longitudinal tool axis LT-LT.

The closure tube assembly 16009 is configured to axially slide on the spine assembly 16102 in response to actuation motions applied thereto. The distal closure tube 16042 includes an opening 16045 which interfaces with the tab 16027 on the anvil 16024 to facilitate opening of the anvil 16024 as the distal closure tube 16042 is moved axially in the proximal direction "PD". The closure tubes 16040, 16042 may be made of electrically conductive material (such as metal) so that they may serve as part of the antenna, as described above. Components of the spine assembly 16102 may be made of a nonconductive material (such as plastic).

As indicated above, the surgical tool 16000 includes a tool mounting portion 16200 that is configured for operable attachment to the tool mounting assembly 11010 of the robotic system 11000 in the various manners described in detail above. As can be seen in FIG. 210, the tool mounting portion 16200 comprises a tool mounting plate 16202 that operably supports a transmission arrangement 16204 thereon. In various embodiments, the transmission arrangement 16204 includes an articulation transmission 16142 that comprises a portion of an articulation system 16140 for articulating the surgical end effector 16012 about a first tool articulation axis TA1-TA1 and a second tool articulation axis TA2-TA2. The first tool articulation axis TA1-TA1 is substantially transverse to the second tool articulation axis TA2-TA2 and both of the first and second tool articulation axes are substantially transverse to the longitudinal tool axis LT-LT. See FIG. 207.

To facilitate selective articulation of the surgical end effector 16012 about the first and second tool articulation axes TA1-TA1, TA2-TA2, the spine assembly 16102 comprises a proximal spine portion 16110 that is pivotally coupled to a distal spine portion 16120 by pivot pins 16122 for selective pivotal travel about TA1-TA1. Similarly, the distal spine portion 16120 is pivotally attached to the elongated channel 16022 of the surgical end effector 16012 by pivot pins 16124 to enable the surgical end effector 16012 to selectively pivot about the second tool axis TA2-TA2 relative to the distal spine portion 16120.

In various embodiments, the articulation system 16140 further includes a plurality of articulation elements that operably interface with the surgical end effector 16012 and an articulation control arrangement 16160 that is operably supported in the tool mounting member 16200 as will described in further detail below. In at least one embodiment, the articulation elements comprise a first pair of first articulation cables 16144 and 16146. The first articulation cables are located on a first or right side of the longitudinal tool axis. Thus, the first articulation cables are referred to herein as a right upper cable 16144 and a right lower cable 16146. The right upper cable 16144 and the right lower cable 16146 extend through corresponding passages 16147, 16148, respectively along the right side of the proximal spine portion 16110. See FIG. 211. The articulation system 16140 further includes a second pair of second articulation cables 16150, 16152. The second articulation cables are located on a second or left side of the longitudinal tool axis. Thus, the second articulation cables are referred to herein as a left upper articulation cable 16150 and a left articulation cable 16152. The left upper articulation cable 16150 and the left lower articulation cable 16152 extend through passages 16153, 16154, respectively in the proximal spine portion 16110.

As can be seen in FIG. 207, the right upper cable 16144 extends around an upper pivot joint 16123 and is attached to a left upper side of the elongated channel 16022 at a left pivot joint 16125. The right lower cable 16146 extends around a lower pivot joint 16126 and is attached to a left lower side of the elongated channel 16022 at left pivot joint 16125. The left upper cable 16150 extends around the upper pivot joint 16123 and is attached to a right upper side of the elongated channel 16022 at a right pivot joint 16127. The left lower cable 16152 extends around the lower pivot joint 16126 and is attached to a right lower side of the elongated channel 16022 at right pivot joint 16127. Thus, to pivot the surgical end effector 16012 about the first tool articulation axis TA1-TA1 to the left (arrow "L"), the right upper cable 16144 and the right lower cable 16146 must be pulled in the proximal direction "PD". To articulate the surgical end effector 16012 to the right (arrow "R") about the first tool articulation axis TA1-TA1, the left upper cable 16150 and the left lower cable 16152 must be pulled in the proximal direction "PD". To articulate the surgical end effector 16012 about the second tool articulation axis TA2-TA2, in an upward direction (arrow "U"), the right upper cable 16144 and the left upper cable 16150 must be pulled in the proximal direction "PD". To articulate the surgical end effector 16012 in the downward direction (arrow "DW") about the second tool articulation axis TA2-TA2, the right lower cable 16146 and the left lower cable 16152 must be pulled in the proximal direction "PD".

The proximal ends of the articulation cables 16144, 16146, 16150, 16152 are coupled to the articulation control arrangement 16160 which comprises a ball joint assembly that is a part of the articulation transmission 16142. More specifically and with reference to FIG. 211, the ball joint assembly 16160 includes a ball-shaped member 16162 that is formed on a proximal portion of the proximal spine 16110. Movably supported on the ball-shaped member 16162 is an articulation control ring 16164. As can be further seen in FIG. 211, the proximal ends of the articulation cables 16144, 16146, 16150, 16152 are coupled to the articulation control ring 16164 by corresponding ball joint arrangements 16166. The articulation control ring 16164 is controlled by an articulation drive assembly 16170. As can be most particularly seen in FIG. 211, the proximal ends of the first articulation cables 16144, 16146 are attached to the articulation control ring 16164 at corresponding spaced first points 16149, 16151 that are located on plane 16159. Likewise, the proximal ends of the second articulation cables 16150, 16152 are attached to the articulation control ring 16164 at corresponding spaced second points 16153, 16155 that are also located along plane 16159. As the present Detailed Description proceeds, those of ordinary skill in the art will appreciate that such cable attachment configuration on the articulation control ring 16164 facilitates the desired range of articulation motions as the articulation control ring 16164 is manipulated by the articulation drive assembly 16170.

In various forms, the articulation drive assembly 16170 comprises a horizontal articulation assembly generally designated as 16171. In at least one form, the horizontal articulation assembly 16171 comprises a horizontal push cable 16172 that is attached to a horizontal gear arrangement 16180. The articulation drive assembly 16170 further comprises a vertically articulation assembly generally designated as 16173. In at least one form, the vertical articulation assembly 16173 comprises a vertical push cable 16174 that is attached to a vertical gear arrangement 16190. As can be seen in FIGS. 210 and 211, the horizontal push cable 16172 extends through a support plate 16167 that is attached to the proximal spine portion 16110. The distal end of the horizontal push cable 16174 is attached to the articulation control ring 16164 by a corresponding ball/pivot joint 16168. The vertical push cable 16174 extends through the support plate 16167 and the distal end thereof is attached to the articulation control ring 16164 by a corresponding ball/pivot joint 16169.

The horizontal gear arrangement 16180 includes a horizontal driven gear 16182 that is pivotally mounted on a horizontal shaft 16181 that is attached to a proximal portion of the proximal spine portion 16110. The proximal end of the horizontal push cable 16172 is pivotally attached to the horizontal driven gear 16182 such that, as the horizontal driven gear 16172 is rotated about horizontal pivot axis HA, the horizontal push cable 16172 applies a first pivot motion to the articulation control ring 16164. Likewise, the vertical gear arrangement 16190 includes a vertical driven gear 16192 that is pivotally supported on a vertical shaft 16191 attached to the proximal portion of the proximal spine portion 16110 for pivotal travel about a vertical pivot axis VA. The proximal end of the vertical push cable 16174 is pivotally attached to the vertical driven gear 16192 such that as the vertical driven gear 16192 is rotated about vertical pivot axis VA, the vertical push cable 16174 applies a second pivot motion to the articulation control ring 16164.

The horizontal driven gear 16182 and the vertical driven gear 16192 are driven by an articulation gear train 16300 that operably interfaces with an articulation shifter assembly 16320. In at least one form, the articulation shifter assembly comprises an articulation drive gear 16322 that is coupled to a corresponding one of the driven discs or elements 11304 on the adapter side 11307 of the tool mounting plate 16202. See FIG. 210. Thus, application of a rotary input motion from the robotic system 11000 through the tool drive assembly 11010 to the corresponding driven element 11304 will cause rotation of the articulation drive gear 16322 when the interface 11230 is coupled to the tool holder 11270. An articulation driven gear 16324 is attached to a splined shifter shaft 16330 that is rotatably supported on the tool mounting plate 16202. The articulation driven gear 16324 is in meshing engagement with the articulation drive gear 16322 as shown. Thus, rotation of the articulation drive gear 16322 will result in the rotation of the shaft 16330. In various forms, a shifter driven gear assembly 16340 is movably supported on the splined portion 16332 of the shifter shaft 16330.

In various embodiments, the shifter driven gear assembly 16340 includes a driven shifter gear 16342 that is attached to a shifter plate 16344. The shifter plate 16344 operably interfaces with a shifter solenoid assembly 16350. The shifter solenoid assembly 16350 is coupled to corresponding pins 16352 by conductors 16352. See FIG. 210. Pins 16352 are oriented to electrically communicate with slots 11258 (FIG. 104) on the tool side 11244 of the adaptor 11240. Such arrangement serves to electrically couple the shifter solenoid assembly 16350 to the robotic controller 11001. Thus, activation of the shifter solenoid 16350 will shift the shifter driven gear assembly 16340 on the splined portion 16332 of the shifter shaft 16330 as represented by arrow "S" in FIGS. 210 and 211. Various embodiments of the articulation gear train 16300 further include a horizontal gear assembly 16360 that includes a first horizontal drive gear 16362 that is mounted on a shaft 16361 that is rotatably attached to the tool mounting plate 16202. The first horizontal drive gear 16362 is supported in meshing engagement with a second horizontal drive gear 16364. As can be seen in FIG. 211, the horizontal driven gear 16182 is in meshing engagement with the distal face portion 16365 of the second horizontal driven gear 16364.

Various embodiments of the articulation gear train 16300 further include a vertical gear assembly 16370 that includes a first vertical drive gear 16372 that is mounted on a shaft 16371 that is rotatably supported on the tool mounting plate 16202. The first vertical drive gear 16372 is supported in meshing engagement with a second vertical drive gear 16374 that is concentrically supported with the second horizontal drive gear 16364. The second vertical drive gear 16374 is rotatably supported on the proximal spine portion 16110 for travel therearound. The second horizontal drive gear 16364 is rotatably supported on a portion of said second vertical drive gear 16374 for independent rotatable travel thereon. As can be seen in FIG. 211, the vertical driven gear 16192 is in meshing engagement with the distal face portion 16375 of the second vertical driven gear 16374.

In various forms, the first horizontal drive gear 16362 has a first diameter and the first vertical drive gear 16372 has a second diameter. As can be seen in FIGS. 210 and 211, the shaft 16361 is not on a common axis with shaft 16371. That is, the first horizontal driven gear 16362 and the first vertical driven gear 16372 do not rotate about a common axis. Thus, when the shifter gear 16342 is positioned in a center "locking" position such that the shifter gear 16342 is in meshing engagement with both the first horizontal driven gear 16362 and the first vertical drive gear 16372, the components of the articulation system 16140 are locked in position. Thus, the shiftable shifter gear 16342 and the arrangement of first horizontal and vertical drive gears 16362, 16372 as well as the articulation shifter assembly 16320 collectively may be referred to as an articulation locking system, generally designated as 16380.

In use, the robotic controller 11001 of the robotic system 11000 may control the articulation system 16140 as follows. To articulate the end effector 16012 to the left about the first tool articulation axis TA1-TA1, the robotic controller 11001 activates the shifter solenoid assembly 16350 to bring the shifter gear 16342 into meshing engagement with the first horizontal drive gear 16362. Thereafter, the controller 11001 causes a first rotary output motion to be applied to the articulation drive gear 16322 to drive the shifter gear in a first direction to ultimately drive the horizontal driven gear 16182 in another first direction. The horizontal driven gear 16182 is driven to pivot the articulation ring 16164 on the ball-shaped portion 16162 to thereby pull right upper cable 16144 and the right lower cable 16146 in the proximal direction "PD". To articulate the end effector 16012 to the right about the first tool articulation axis TA1-TA1, the robotic controller 11001 activates the shifter solenoid assembly 16350 to bring the shifter gear 16342 into meshing engagement with the first horizontal drive gear 16362. Thereafter, the controller 11001 causes the first rotary output motion in an opposite direction to be applied to the articulation drive gear 16322 to drive the shifter gear 16342 in a second direction to ultimately drive the horizontal driven gear 16182 in another second direction. Such actions result in the articulation control ring 16164 moving in such a manner as to pull the left upper cable 16150 and the left lower cable 16152 in the proximal direction "PD". In various embodiments the gear ratios and frictional forces generated between the gears of the vertical gear assembly 16370 serve to prevent rotation of the vertical driven gear 16192 as the horizontal gear assembly 16360 is actuated.

To articulate the end effector 16012 in the upper direction about the second tool articulation axis TA2-TA2, the robotic controller 11001 activates the shifter solenoid assembly 16350 to bring the shifter gear 16342 into meshing engagement with the first vertical drive gear 16372. Thereafter, the controller 11001 causes the first rotary output motion to be applied to the articulation drive gear 16322 to drive the shifter gear 16342 in a first direction to ultimately drive the vertical driven gear 16192 in another first direction. The vertical driven gear 16192 is driven to pivot the articulation ring 16164 on the ball-shaped portion 16162 of the proximal spine portion 16110 to thereby pull right upper cable 16144 and the left upper cable 16150 in the proximal direction "PD". To articulate the end effector 16012 in the downward direction about the second tool articulation axis TA2-TA2, the robotic controller 11001 activates the shifter solenoid assembly 16350 to bring the shifter gear 16342 into meshing engagement with the first vertical drive gear 16372. Thereafter, the controller 11001 causes the first rotary output motion to be applied in an opposite direction to the articulation drive gear 16322 to drive the shifter gear 16342 in a second direction to ultimately drive the vertical driven gear 16192 in another second direction. Such actions thereby cause the articulation control ring 16164 to pull the right lower cable 16146 and the left lower cable 16152 in the proximal direction "PD". In various embodiments, the gear ratios and frictional forces generated between the gears of the horizontal gear assembly 16360 serve to prevent rotation of the horizontal driven gear 16182 as the vertical gear assembly 16370 is actuated.

In various embodiments, a variety of sensors may communicate with the robotic controller 11001 to determine the articulated position of the end effector 16012. Such sensors may interface with, for example, the articulation joint 16100 or be located within the tool mounting portion 16200. For example, sensors may be employed to detect the position of the articulation control ring 16164 on the ball-shaped portion 16162 of the proximal spine portion 16110. Such feedback from the sensors to the controller 11001 permits the controller 11001 to adjust the amount of rotation and the direction of the rotary output to the articulation drive gear 16322. Further, as indicated above, when the shifter drive gear 16342 is centrally positioned in meshing engagement with the first horizontal drive gear 16362 and the first vertical drive gear 16372, the end effector 16012 is locked in the articulated position. Thus, after the desired amount of articulation has been attained, the controller 11001 may activate the shifter solenoid assembly 16350 to bring the shifter gear 16342 into meshing engagement with the first horizontal drive gear 16362 and the first vertical drive gear 16372. In alternative embodiments, the shifter solenoid assembly 16350 may be spring activated to the central locked position.

In use, it may be desirable to rotate the surgical end effector 16012 about the longitudinal tool axis LT-LT. In at least one embodiment, the transmission arrangement 16204 on the tool mounting portion includes a rotational transmission assembly 16400 that is configured to receive a corresponding rotary output motion from the tool drive assembly 11010 of the robotic system 11000 and convert that rotary output motion to a rotary control motion for rotating the elongated shaft assembly 16008 (and surgical end effector 16012) about the longitudinal tool axis LT-LT. In various embodiments, for example, a proximal end portion 16041 of the proximal closure tube 16040 is rotatably supported on the tool mounting plate 16202 of the tool mounting portion 16200 by a forward support cradle 16205 and a closure sled 16510 that is also movably supported on the tool mounting plate 16202. In at least one form, the rotational transmission assembly 16400 includes a tube gear segment 16402 that is formed on (or attached to) the proximal end 16041 of the proximal closure tube 16040 for operable engagement by a rotational gear assembly 16410 that is operably supported on the tool mounting plate 16202. As can be seen in FIG. 210, the rotational gear assembly 16410, in at least one embodiment, comprises a rotation drive gear 16412 that is coupled to a corresponding second one of the driven discs or elements 11304 on the adapter side 11307 of the tool mounting plate 16202 when the tool mounting portion 16200 is coupled to the tool drive assembly 11010. See FIG. 105. The rotational gear assembly 16410 further comprises a first rotary driven gear 16414 that is rotatably supported on the tool mounting plate 16202 in meshing engagement with the rotation drive gear 16412. The first rotary driven gear 16414 is attached to a drive shaft 16416 that is rotatably supported on the tool mounting plate 16202. A second rotary driven gear 16418 is attached to the drive shaft 16416 and is in meshing engagement with tube gear segment 16402 on the proximal closure tube 16040. Application of a second rotary output motion from the tool drive assembly 11010 of the robotic system 11000 to the corresponding driven element 11304 will thereby cause rotation of the rotation drive gear 16412. Rotation of the rotation drive gear 16412 ultimately results in the rotation of the elongated shaft assembly 16008 (and the surgical end effector 16012) about the longitudinal tool axis LT-LT. It will be appreciated that the application of a rotary output motion from the tool drive assembly 11010 in one direction will result in the rotation of the elongated shaft assembly 16008 and surgical end effector 16012 about the longitudinal tool axis LT-LT in a first direction and an application of the rotary output motion in an opposite direction will result in the rotation of the elongated shaft assembly 16008 and surgical end effector 16012 in a second direction that is opposite to the first direction.

In at least one embodiment, the closure of the anvil 12024 relative to the staple cartridge 12034 is accomplished by axially moving a closure portion of the elongated shaft assembly 12008 in the distal direction "DD" on the spine assembly 12049. As indicated above, in various embodiments, the proximal end portion 16041 of the proximal closure tube 16040 is supported by the closure sled 16510 which comprises a portion of a closure transmission, generally depicted as 16512. As can be seen in FIG. 210, the proximal end portion 16041 of the proximal closure tube portion 16040 has a collar 6048 formed thereon. The closure sled 16510 is coupled to the collar 16048 by a yoke 16514 that engages an annular groove 16049 in the collar 16048. Such arrangement serves to enable the collar 16048 to rotate about the longitudinal tool axis LT-LT while still being coupled to the closure transmission 16512. In various embodiments, the closure sled 16510 has an upstanding portion 16516 that has a closure rack gear 16518 formed thereon. The closure rack gear 16518 is configured for driving engagement with a closure gear assembly 16520. See FIG. 210.

In various forms, the closure gear assembly 16520 includes a closure spur gear 16522 that is coupled to a corresponding second one of the driven discs or elements 11304 on the adapter side 11307 of the tool mounting plate 16202. See FIG. 210. Thus, application of a third rotary output motion from the tool drive assembly 11010 of the robotic system 11000 to the corresponding second driven element 11304 will cause rotation of the closure spur gear 16522 when the tool mounting portion 16202 is coupled to the tool drive assembly 11010. The closure gear assembly 16520 further includes a closure reduction gear set 16524 that is supported in meshing engagement with the closure spur gear 16522 and the closure rack gear 12106. Thus, application of a third rotary output motion from the tool drive assembly 11010 of the robotic system 11000 to the corresponding second driven element 11304 will cause rotation of the closure spur gear 16522 and the closure transmission 16512 and ultimately drive the closure sled 16510 and the proximal closure tube 16040 axially on the proximal spine portion 16110. The axial direction in which the proximal closure tube 16040 moves ultimately depends upon the direction in which the third driven element 11304 is rotated. For example, in response to one rotary output motion received from the tool drive assembly 11010 of the robotic system 11000, the closure sled 16510 will be driven in the distal direction "DD" and ultimately drive the proximal closure tube 16040 in the distal direction "DD". As the proximal closure tube 16040 is driven distally, the distal closure tube 16042 is also driven distally by virtue of it connection with the proximal closure tube 16040. As the distal closure tube 16042 is driven distally, the end of the closure tube 16042 will engage a portion of the anvil 16024 and cause the anvil 16024 to pivot to a closed position. Upon application of an "opening" output motion from the tool drive assembly 11010 of the robotic system 11000, the closure sled 16510 and the proximal closure tube 16040 will be driven in the proximal direction "PD" on the proximal spine portion 16110. As the proximal closure tube 16040 is driven in the proximal direction "PD", the distal closure tube 16042 will also be driven in the proximal direction "PD". As the distal closure tube 16042 is driven in the proximal direction "PD", the opening 16045 therein interacts with the tab 16027 on the anvil 16024 to facilitate the opening thereof. In various embodiments, a spring (not shown) may be employed to bias the anvil 16024 to the open position when the distal closure tube 16042 has been moved to its starting position. In various embodiments, the various gears of the closure gear assembly 16520 are sized to generate the necessary closure forces needed to satisfactorily close the anvil 16024 onto the tissue to be cut and stapled by the surgical end effector 16012. For example, the gears of the closure transmission 16520 may be sized to generate approximately 70-120 pounds of closure forces.

In various embodiments, the cutting instrument is driven through the surgical end effector 16012 by a knife bar 16530. See FIG. 210. In at least one form, the knife bar 16530 is fabricated with a joint arrangement (not shown) and/or is fabricated from material that can accommodate the articulation of the surgical end effector 16102 about the first and second tool articulation axes while remaining sufficiently rigid so as to push the cutting instrument through tissue clamped in the surgical end effector 16012. The knife bar 16530 extends through a hollow passage 16532 in the proximal spine portion 16110.

In various embodiments, a proximal end 16534 of the knife bar 16530 is rotatably affixed to a knife rack gear 16540 such that the knife bar 16530 is free to rotate relative to the knife rack gear 16540. The distal end of the knife bar 16530 is attached to the cutting instrument in the various manners described above. As can be seen in FIG. 210, the knife rack gear 16540 is slidably supported within a rack housing 16542 that is attached to the tool mounting plate 16202 such that the knife rack gear 16540 is retained in meshing engagement with a knife drive transmission portion 16550 of the transmission arrangement 16204. In various embodiments, the knife drive transmission portion 16550 comprises a knife gear assembly 16560. More specifically and with reference to FIG. 210, in at least one embodiment, the knife gear assembly 16560 includes a knife spur gear 16562 that is coupled to a corresponding fourth one of the driven discs or elements 11304 on the adapter side 11307 of the tool mounting plate 16202. See FIG. 105. Thus, application of another rotary output motion from the robotic system 11000 through the tool drive assembly 11010 to the corresponding fourth driven element 11304 will cause rotation of the knife spur gear 16562. The knife gear assembly 16560 further includes a knife gear reduction set 16564 that includes a first knife driven gear 16566 and a second knife drive gear 16568. The knife gear reduction set 16564 is rotatably mounted to the tool mounting plate 16202 such that the firs knife driven gear 16566 is in meshing engagement with the knife spur gear 16562. Likewise, the second knife drive gear 16568 is in meshing engagement with a third knife drive gear assembly 16570. As shown in FIG. 210, the second knife driven gear 16568 is in meshing engagement with a fourth knife driven gear 16572 of the third knife drive gear assembly 16570. The fourth knife driven gear 16572 is in meshing engagement with a fifth knife driven gear assembly 16574 that is in meshing engagement with the knife rack gear 16540. In various embodiments, the gears of the knife gear assembly 16560 are sized to generate the forces needed to drive the cutting instrument through the tissue clamped in the surgical end effector 16012 and actuate the staples therein. For example, the gears of the knife gear assembly 16560 may be sized to generate approximately 40 to 100 pounds of driving force. It will be appreciated that the application of a rotary output motion from the tool drive assembly 11010 in one direction will result in the axial movement of the cutting instrument in a distal direction and application of the rotary output motion in an opposite direction will result in the axial travel of the cutting instrument in a proximal direction.

As can be appreciated from the foregoing description, the surgical tool 16000 represents a vast improvement over prior robotic tool arrangements. The unique and novel transmission arrangement employed by the surgical tool 16000 enables the tool to be operably coupled to a tool holder portion 11010 of a robotic system that only has four rotary output bodies, yet obtain the rotary output motions therefrom to: (i) articulate the end effector about two different articulation axes that are substantially transverse to each other as well as the longitudinal tool axis; (ii) rotate the end effector 16012 about the longitudinal tool axis; (iii) close the anvil 16024 relative to the surgical staple cartridge 16034 to varying degrees to enable the end effector 16012 to be used to manipulate tissue and then clamp it into position for cutting and stapling; and (iv) firing the cutting instrument to cut through the tissue clamped within the end effector 16012. The unique and novel shifter arrangements of various embodiments of the present invention described above enable two different articulation actions to be powered from a single rotatable body portion of the robotic system.

The various embodiments of the present invention have been described above in connection with cutting-type surgical instruments. It should be noted, however, that in other embodiments, the inventive surgical instrument disclosed herein need not be a cutting-type surgical instrument, but rather could be used in any type of surgical instrument including remote sensor transponders. For example, it could be a non-cutting endoscopic instrument, a grasper, a stapler, a clip applier, an access device, a drug/gene therapy delivery device, an energy device using ultrasound, RF, laser, etc. In addition, the present invention may be in laparoscopic instruments, for example. The present invention also has application in conventional endoscopic and open surgical instrumentation as well as robotic-assisted surgery.

FIG. 211 depicts use of various aspects of certain embodiments of the present invention in connection with a surgical tool 17000 that has an ultrasonically powered end effector 17012. The end effector 17012 is operably attached to a tool mounting portion 17100 by an elongated shaft assembly 17008. The tool mounting portion 17100 may be substantially similar to the various tool mounting portions described hereinabove. In one embodiment, the end effector 17012 includes an ultrasonically powered jaw portion 17014 that is powered by alternating current or direct current in a known manner. Such ultrasonically-powered devices are disclosed, for example, in U.S. Pat. No. 6,783,524, entitled "Robotic Surgical Tool With Ultrasound Cauterizing and Cutting Instrument", the entire disclosure of which is herein incorporated by reference. In the illustrated embodiment, a separate power cord 17020 is shown. It will be understood, however, that the power may be supplied thereto from the robotic controller 1001 through the tool mounting portion 17100. The surgical end effector 17012 further includes a movable jaw 17016 that may be used to clamp tissue onto the ultrasonic jaw portion 17014. The movable jaw portion 17016 may be selectively actuated by the robotic controller 11001 through the tool mounting portion 17100 in anyone of the various manners herein described.

FIG. 213 illustrates use of various aspects of certain embodiments of the present invention in connection with a surgical tool 18000 that has an end effector 18012 that comprises a linear stapling device. The end effector 18012 is operably attached to a tool mounting portion 18100 by an elongated shaft assembly 13700 of the type and construction describe above. However, the end effector 18012 may be attached to the tool mounting portion 18100 by a variety of other elongated shaft assemblies described herein. In one embodiment, the tool mounting portion 18100 may be substantially similar to tool mounting portion 13750. However, various other tool mounting portions and their respective transmission arrangements describe in detail herein may also be employed. Such linear stapling head portions are also disclosed, for example, in U.S. Pat. No. 7,673,781, entitled "Surgical Stapling Device With Staple Driver That Supports Multiple Wire Diameter Staples", the entire disclosure of which is herein incorporated by reference.

Various sensor embodiments described in U.S. Patent Publication No. 2011/0062212 A1 to Shelton, IV et al., the disclosure of which is herein incorporated by reference in its entirety, may be employed with many of the surgical tool embodiments disclosed herein. As was indicated above, the master controller 11001 generally includes master controllers (generally represented by 11003) which are grasped by the surgeon and manipulated in space while the surgeon views the procedure via a stereo display 11002. See FIG. 96. The master controllers 11001 are manual input devices which preferably move with multiple degrees of freedom, and which often further have an actuatable handle for actuating the surgical tools. Some of the surgical tool embodiments disclosed herein employ a motor or motors in their tool drive portion to supply various control motions to the tool's end effector. Such embodiments may also obtain additional control motion(s) from the motor arrangement employed in the robotic system components. Other embodiments disclosed herein obtain all of the control motions from motor arrangements within the robotic system.

Such motor powered arrangements may employ various sensor arrangements that are disclosed in the published US patent application cited above to provide the surgeon with a variety of forms of feedback without departing from the spirit and scope of the present invention. For example, those master controller arrangements 11003 that employ a manually actuatable firing trigger can employ run motor sensor(s) to provide the surgeon with feedback relating to the amount of force applied to or being experienced by the cutting member. The run motor sensor(s) may be configured for communication with the firing trigger portion to detect when the firing trigger portion has been actuated to commence the cutting/stapling operation by the end effector. The run motor sensor may be a proportional sensor such as, for example, a rheostat or variable resistor. When the firing trigger is drawn in, the sensor detects the movement, and sends an electrical signal indicative of the voltage (or power) to be supplied to the corresponding motor. When the sensor is a variable resistor or the like, the rotation of the motor may be generally proportional to the amount of movement of the firing trigger. That is, if the operator only draws or closes the firing trigger in a small amount, the rotation of the motor is relatively low. When the firing trigger is fully drawn in (or in the fully closed position), the rotation of the motor is at its maximum. In other words, the harder the surgeon pulls on the firing trigger, the more voltage is applied to the motor causing greater rates of rotation. Other arrangements may provide the surgeon with a feed back meter 11005 that may be viewed through the display 1002 and provide the surgeon with a visual indication of the amount of force being applied to the cutting instrument or dynamic clamping member. Other sensor arrangements may be employed to provide the master controller 11001 with an indication as to whether a staple cartridge has been loaded into the end effector, whether the anvil has been moved to a closed position prior to firing, etc.

In alternative embodiments, a motor-controlled interface may be employed in connection with the controller 11001 that limit the maximum trigger pull based on the amount of loading (e.g., clamping force, cutting force, etc.) experienced by the surgical end effector. For example, the harder it is to drive the cutting instrument through the tissue clamped within the end effector, the harder it would be to pull/actuate the activation trigger. In still other embodiments, the trigger on the controller 11001 is arranged such that the trigger pull location is proportionate to the end effector-location/condition. For example, the trigger is only fully depressed when the end effector is fully fired.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Although the present invention has been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical tool for use with a robotic system that has a tool drive assembly that is operatively coupled to a control unit of the robotic system that is operable by inputs from an operator and is configured to provide at least one rotary output motion to at least one rotatable body portion supported on the tool drive assembly, said surgical tool comprising:
   a surgical end effector comprising an anvil that is selectively movable between first and second positions relative to a surgical staple cartridge;
   a cable drive assembly configured to apply at least one control motion to said anvil, said cable drive assembly comprising:
      a closure cable operably interfacing with said anvil to apply a closing motion and an opening motion thereto; and
      a cable drive transmission configured to operably interface with at least one of the rotary body portions of the tool drive assembly, said surgical tool further comprising:
   a tool mounting portion operably interfacing with said cable drive assembly and the at least one rotary body portion of the tool drive assembly of the robotic system such that application of at least one of the rotary output motions to the rotatable body portion causes said cable drive assembly to apply at least one of said closing and opening motions to said anvil;
   an elongated shaft assembly extending between said surgical end effector and said cable drive transmission; and
   a preclamping collar axially movable on said elongated shaft assembly and interfacing with said anvil and said closure cable such that said application of said rotary output motion to the rotatable body portion in a first rotary direction causes said preclamping collar to apply said closing motion to said anvil and upon another application of said rotary output motion to the rotatable body portion in a second rotary direction causes said preclamping collar to apply said opening motion to said anvil.

2. The surgical tool of claim 1 further comprising a tissue cutting member that is axially movable within said surgical staple cartridge between a starting position and an ending position in response to a firing motion applied thereto by said cable drive assembly.

3. The surgical tool of claim 2 further comprising a firing cable operably interfacing with said tissue cutting member and said cable drive transmission and wherein said cable drive transmission is selectively shiftable between a closure position wherein said application of said rotary output motion to the rotatable body portion in said first rotary direction causes said closure cable to apply said closing motion to said anvil and upon said another rotary output motion to the rotatable body portion in said second rotary direction causes said closure cable to apply said opening motion to said anvil and a firing position wherein said application of said rotary output motion to the rotatable body portion in said first rotary direction causes said firing cable to apply a firing motion to said tissue cutting member and upon said another application of said rotary output motion to the rotatable body portion in said second rotary direction causes said firing cable to apply a retraction motion to said tissue cutting member.

4. The surgical tool of claim 3 further comprising a shifter motor operably interfacing with said cable drive transmission for moving said cable drive transmission between said closure position and said firing position in response to corresponding control signals applied thereto from the control unit of the robotic system.

5. The surgical tool of claim 3 further comprising:
   a firing brake engageable with said cable drive transmission to prevent said firing cable from applying said firing motion to said tissue cutting member when said cable drive transmission is in said closure position; and
   a closure brake engageable with said cable drive transmission to prevent said closure cable from applying said opening motion to said anvil when said cable drive transmission is in said firing position.

6. The surgical tool of claim 1 further comprising a tissue cutting member that is axially movable within said surgical staple cartridge between a starting position and an ending position in response to a firing motion applied thereto by said cable drive assembly and wherein said surgical tool further comprises a knife bar operably interfacing with said cable drive assembly and the at least one rotary body portion of the tool drive assembly of the robotic system such that application of said at least one of the rotary output motions to the rotatable body portion causes said knife bar to apply a firing control motion to said cable drive assembly.

7. A surgical tool for use with a robotic system that has a tool drive assembly that is operatively coupled to a control unit of the robotic system that is operable by inputs from an operator and is configured to provide at least one rotary output motion to at least one rotatable body portion supported on the tool drive assembly, said surgical tool comprising:
   a surgical end effector comprising:
      a non-movable portion;
      a first movable component portion that is selectively movable between first and second positions relative to said non-movable portion;
      a second movable component portion that is selectively movable between third and fourth positions relative to said non-movable portion and wherein said surgical tool further comprises:
   an elongated shaft assembly operably coupled to said non-movable portion, said elongated shaft assembly at least partially operably supporting a cable drive assembly comprising:
      a first cable operably interfacing with said first movable component portion; and a second cable operably interfacing with said second movable component portion and wherein said surgical tool further comprises:
a tool mounting portion operably coupled to said elongated shaft assembly, said tool mounting portion being configured to operably interface with the tool drive assembly when coupled thereto, said tool mounting portion comprising:
a driven element rotatably supported on said tool mounting portion and configured for driving engagement with a corresponding one of said at least one rotatable body portions of the tool drive assembly to receive corresponding rotary output motions therefrom; and
a cable drive transmission assembly operably interfacing with said driven element and being selectively shiftable in response to control signals from the control unit of the robotic system between a first actuation position wherein an application of one of said rotary output motions to the corresponding rotatable body portion causes said first cable to move said first movable component portion between said first and second positions and a second actuation position wherein said application of said one of said rotary output motions to the corresponding rotatable body portion causes said second cable to move said second movable component portion between said third and fourth positions.

8. The surgical tool of claim 7 wherein an application of said one of said rotary output motions in a first rotary direction causes said first movable component portion to move from said first position to said second position when said cable drive transmission assembly is in said first actuation position and another application of said one of said rotary output motions in said first rotary direction causes said second movable component portion to move from said third position to said fourth position when said cable drive transmission assembly is in said second actuation position.

9. The surgical tool of claim 7 further comprising:
a first brake engageable with said cable drive transmission assembly to prevent said first cable from moving said first movable component portion between said first and second positions when said cable drive transmission assembly is in said second actuation position; and
a second brake engageable with said cable drive transmission assembly to prevent said second cable from moving said second movable component portion between said third and fourth positions when said cable drive transmission assembly is in said first actuation position.

10. The surgical tool of claim 9 wherein said cable drive transmission assembly is movable between said first and second actuation positions and a neutral position and wherein when said cable drive transmission assembly is in said neutral position, said first brake prevents said first cable from moving said first movable component portion between said first and second positions and said second brake prevents said second cable from moving said second movable component portion between said third and fourth positions.

11. The surgical tool of claim 7 further comprising a shifter motor operably supported by said tool mounting portion and interfacing with said cable drive transmission assembly and the control unit of the robotic system.

12. The surgical tool of claim 11 wherein said shifter motor is powered by at least one battery.

13. A surgical tool for use with a robotic system that has a tool drive assembly that is operatively coupled to a control unit of the robotic system that is operable by inputs from an operator and is configured to provide at least one rotary output motion to at least one rotatable body portion supported on the tool drive assembly, said surgical tool comprising:
a surgical end effector comprising:
an elongated channel configured to support a surgical staple cartridge;
an anvil movably supported relative to the elongated channel and being selectively movable between open and closed positions relative to said elongated channel; and
a tissue cutting member selectively axially movable between unfired and fired positions and wherein said surgical tool further comprises:
an elongated shaft assembly operably coupled to said elongated channel;
a preclamping collar axially movable on said elongated shaft assembly for selective operable engagement with said anvil;
a closure cable operably interfacing with said preclamping collar; and
a firing cable operably interfacing with said tissue cutting member;
a tool mounting portion operably coupled to said elongated shaft assembly, said tool mounting portion being configured to operably interface with the tool drive assembly when coupled thereto, said tool mounting portion comprising:
a driven element rotatably supported on said tool mounting portion and configured for driving engagement with a corresponding one of said at least one rotatable body portions of the tool drive assembly to receive corresponding rotary output motions therefrom; and
a cable drive transmission assembly operably interfacing with said driven element and being selectively shiftable in response to control signals from the control unit of the robotic system between a closure position wherein an application of one of said rotary output motions to the corresponding rotatable body portion in a first rotary direction causes said closure cable to move said preclamping collar into closing engagement with said anvil and a firing position wherein said application of said one of said rotary output motions in said first rotary direction to the corresponding rotatable body portion causes said firing cable to move said tissue cutting member from a starting position to an ending position within said elongated channel.

14. The surgical tool of claim 13 wherein said application of one of said rotary output motions in a second rotary direction when said cable drive transmission assembly is in said closure position causes said closure cable to move said preclamping collar to move out of said closing engagement with said anvil and when said cable drive transmission assembly is in said firing position, said application of said one of said rotary output motions in said second rotary directions causes said firing cable to move said tissue cutting member from said ending position to said starting position.

15. The surgical tool of claim 14 further comprising:
a closure brake engageable with said cable drive transmission assembly to prevent said closure cable from moving said anvil between said open and closed positions when said cable drive transmission assembly is in said firing position; and
a firing brake engageable with said cable drive transmission assembly to prevent said firing cable from moving said tissue cutting member between said starting and ending positions when said cable drive transmission assembly is in said closure position.

16. The surgical tool of claim 15 wherein said cable drive transmission assembly is movable between said closure and firing positions and a neutral position and wherein when said cable drive transmission assembly is in said neutral position, said closure brake prevents said closure cable from moving said anvil between said open and closed positions and said firing brake prevents said firing cable from moving said tissue cutting member between said starting and ending positions.

17. The surgical tool of claim 16 further comprising a shifter motor operably supported by said tool mounting portion and interfacing with said cable drive transmission assembly and the control unit of the robotic system.

* * * * *